(12) United States Patent
Ogawa et al.

(10) Patent No.: US 8,039,514 B2
(45) Date of Patent: Oct. 18, 2011

(54) SULFONAMIDE COMPOUNDS AND USE THEREOF

(75) Inventors: Masami Ogawa, Tokyo (JP); Kazuhiko Kitagawa, Tokyo (JP); Hiromitsu Shirahashi, Tokyo (JP); Satomi Kuribayashi, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 12/476,585

(22) Filed: Jun. 2, 2009

(65) Prior Publication Data

US 2010/0022601 A1 Jan. 28, 2010

Related U.S. Application Data

(60) Provisional application No. 61/058,985, filed on Jun. 5, 2008.

(51) Int. Cl.
- A61K 31/18 (2006.01)
- A01N 41/12 (2006.01)
- C07D 213/00 (2006.01)

(52) U.S. Cl. .................................. 514/602; 546/293
(58) Field of Classification Search .................. None
See application file for complete search history.

(56) References Cited

U.S. PATENT DOCUMENTS

| | | |
|---|---|---|
| 4,330,542 A | 5/1982 | Descamps et al. |
| 6,022,894 A | 2/2000 | Del Mar et al. |
| 6,127,372 A | 10/2000 | Tung et al. |
| 6,291,459 B1 | 9/2001 | Bhatnagar et al. |
| 6,335,338 B1 | 1/2002 | Bhatnagar et al. |
| 6,417,215 B1 | 7/2002 | Lago |
| 6,432,656 B1 | 8/2002 | Del Mar et al. |
| 6,521,667 B1 | 2/2003 | Del Mar et al. |
| 6,818,660 B2 | 11/2004 | Del Mar et al. |
| 6,864,267 B2 | 3/2005 | Bhatnagar et al. |
| 6,916,956 B2 | 7/2005 | Shinagawa et al. |
| 7,105,537 B2 | 9/2006 | Gavai et al. |
| 7,109,238 B2 | 9/2006 | Lago et al. |
| 7,202,261 B2 | 4/2007 | Del Mar et al. |
| 7,205,322 B2 | 4/2007 | Gungor et al. |
| 7,211,685 B2 | 5/2007 | Shinagawa et al. |
| 7,285,572 B2 | 10/2007 | Shinagawa et al. |
| 7,304,174 B2 | 12/2007 | Shinagawa et al. |
| 7,459,460 B2 | 12/2008 | Yang et al. |
| 7,514,441 B2 | 4/2009 | Yasuma et al. |
| 7,514,473 B2 | 4/2009 | Marquis et al. |
| 2002/0099220 A1 | 7/2002 | Del Mar et al. |
| 2003/0018203 A1 | 1/2003 | Lago et al. |
| 2003/0212110 A1 | 11/2003 | Bhatnagar et al. |
| 2004/0006130 A1 | 1/2004 | Shinegawa et al. |
| 2004/0009980 A1 | 1/2004 | Bhatnagar et al. |
| 2004/0014723 A1 | 1/2004 | Bhatnagar et al. |
| 2004/0192741 A1 | 9/2004 | Lago et al. |
| 2004/0229860 A1 | 11/2004 | Gavai et al. |
| 2004/0242602 A1 | 12/2004 | Gungor et al. |
| 2005/0004151 A1 | 1/2005 | Yang et al. |
| 2005/0032796 A1 | 2/2005 | Shinagawa et al. |
| 2005/0032850 A1 | 2/2005 | Del Mar et al. |
| 2005/0107448 A1 | 5/2005 | Shinegawa et al. |
| 2005/0267152 A1 | 12/2005 | Bloomfield et al. |
| 2006/0058391 A1 | 3/2006 | Marquis et al. |
| 2006/0079536 A1 | 4/2006 | Yasuma et al. |
| 2006/0128786 A1 | 6/2006 | Hom et al. |
| 2006/0135572 A1 | 6/2006 | Shinagawa et al. |
| 2007/0155819 A1 | 7/2007 | Marquis, Jr. et al. |
| 2007/0203226 A1 | 8/2007 | Marquis, Jr. |
| 2007/0249702 A1 | 10/2007 | Del Mar et al. |
| 2008/0234370 A1 | 9/2008 | Marquis et al. |
| 2008/0255042 A1 | 10/2008 | Shinagawa et al. |
| 2009/0163589 A1 | 6/2009 | Marquis et al. |
| 2009/0215746 A1 | 8/2009 | Yasuma et al. |

FOREIGN PATENT DOCUMENTS

| | | |
|---|---|---|
| JP | 10-500938 | 1/1998 |
| WO | 95/24385 | 9/1995 |
| WO | 97/37967 | 10/1997 |
| WO | 00/09132 | 2/2000 |
| WO | 00/09491 | 2/2000 |
| WO | 00/45816 | 8/2000 |
| WO | 01/53254 | 7/2001 |
| WO | 02/07673 | 1/2002 |
| WO | 02/14259 | 2/2002 |
| WO | 02/34204 | 5/2002 |
| WO | 02/38106 | 5/2002 |

(Continued)

OTHER PUBLICATIONS

R. Neer et al., "Effect of Parathyroid Hormone (1-34) on Fractures and Bone Mineral Density in Postmenopausal Women with Osteoporosis," The New England Journal of Medicine, vol. 344, No. 19, pp. 1434-1441, 2001.

(Continued)

*Primary Examiner* — Brandon Fetterolf
*Assistant Examiner* — Anna Pagonakis
(74) *Attorney, Agent, or Firm* — Greenblum & Bernstein, PLC

(57) ABSTRACT

The sulfoneamide compounds having the following Formula (1), which can be used as an effective component of a CaSR antagonizing agent useful for prophylaxis and/or treatment of bone disorders including osteoporosis and etc., are provided. The compounds have an excellent activity of promoting PTH secretion. In addition, the compounds are useful as an effective component of a medicament for the prophylaxis and/or treatment of bone disorders such as osteoporosis, bone fracture, hypoparathyroidism and the like.

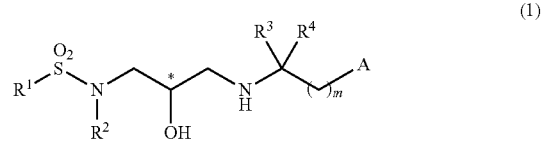

(1)

9 Claims, No Drawings

FOREIGN PATENT DOCUMENTS

| WO | 03/055478 | 7/2003 |
|---|---|---|
| WO | 2004/017908 | 3/2004 |
| WO | 2004/029019 | 4/2004 |
| WO | 2004/047751 | 6/2004 |
| WO | 2004/069793 | 8/2004 |
| WO | 2004/094362 | 11/2004 |
| WO | 2004/106280 | 12/2004 |
| WO | 2004/106296 | 12/2004 |
| WO | 2004/113280 | 12/2004 |
| WO | 2005/030746 | 4/2005 |
| WO | 2005/030749 | 4/2005 |
| WO | 2005/077886 | 8/2005 |
| WO | 2005/077892 | 8/2005 |
| WO | 2008/077009 | 6/2008 |
| WO | 2008/089933 | 7/2008 |
| WO | 2009/055631 | 4/2009 |

OTHER PUBLICATIONS

M. McClung et al., "Opposite Bone Remodeling Effects of Teriparatide and Alendronate in Increasing Bone Mass," Arch. Intern. Med., vol. 165, pp. 1762-1768, 2005.

T. Miki et al., "Effect and Safety of Intermittent Weekly Administration of Human Parathyroid Hormone 1-34 in Patients with Primary Osteoporosis Evaluated by Histomorphometry and Microstructural Analysis of Iliac Trabecular Bone Before and After 1 Year of Treatment," J. Bone Miner. Metab., vol. 22, pp. 569-576, 2004.

T. Matsumoto et al., "Daily Nasal Spray of hPTH(1-34) for 3 Months Increases Bone Mass in Osteoporotic Subjects: A Pilot Study", Osteoporos. Int., vol. 17, pp. 1532-1538, 2006.

E. Brown et al., "Cloning and Characterization of an Extracellular $Ca^{2+}$-Sensing Receptor from Bovine Parathyroid," Nature, vol. 366, pp. 575-580, 1993.

M. Gowen et al., "Antagonizing the Parathyroid Calcium Receptor Stimulates Parathyroid Hormone Secretion and Bone Formation in Osteopenic Rats," The Journal of Clinical Investigation, vol. 105, No. 11, pp. 1595-1604, 2000.

T. Uzawa et al., "Comparison of the Effects of Intermittent and Continuous Administration of Human Parathyroid Hormone(1-34) on Rat Bone," Bone, vol. 16, No. 4, pp. 477-484, 1995.

International Search Report for PCT/JP2009/060060, Sep. 1, 2009.

Information Disclosure Statement and Examiner Interview Summary filed in U.S. Appl. No. 12/476,585 on APr. 20, 2011 (5 pages).

Extended Search Report from E.P.O. that issued with respect to patent family member European Patent Application No. 09758319.9, mail date Jul. 26, 2011.

SULFONAMIDE COMPOUNDS AND USE THEREOF

CROSS REFERENCE TO RELATED APPLICATIONS

This application claims the benefit of U.S. Provisional Application No. 61/058,985, filed Jun. 5, 2008.

TECHNICAL FIELD

The present invention is directed to novel sulfonamide compounds. More specifically, the present invention is directed to use of sulfonamide compounds that are useful as an effective component of a medicament.

BACKGROUND ART

Osteoporosis is defined as a "disorder characterized by decreased bone strength and high risk for bone fracture". Bone fracture often occurs at metaphyseal region of limb bones or at spine. In particular, femoral neck fracture, vertebral fracture, distal radial fracture, and proximal humeral fracture are the four major fractures caused by osteoporosis. In general, due to fragile nature of a bone, bone fracture accompanied with osteoporosis cannot be completely cured by a treatment. In addition, there is other problem that a sufficient level of fixation cannot be obtained even when osteosynthesis is carried out. Further, a various kind of serious complications such as muscle weakness, articular contracture, decubitus ulcer, dementia, urinary tract infection, impaired cardiopulmonary function and the like may easily occur due to disuse of a human body which follows the fracture. Still further, an unfavorable cycle in which simultaneous occurrence of disuse bone atrophy causes further progress in osteoporosis may not be avoided.

As described in the above, bone fracture that is accompanied with osteoporosis impairs quality of life (QOL) of patients, and also has a significant effect on prognosis. At the same time, it imposes significant social problems relating to attending patients and high medical cost, etc. Therefore, object of treating osteoporosis is to accelerate bone formation so that bone mass is increased and bone fracture is prevented.

Until now, as a prophylactic and/or therapeutic agent for osteoporosis, estrogen preparation, a selective estrogen receptor modulator (SERM) like raloxifen, etc., a calcitonin preparation like elcatonin, etc., and a bisphosphonate preparation like alendronate, etc., have been clinically used. Most of these preparations contribute to increasing bone mineral density during bone remodeling process by inhibiting bone resorption. Recently, excellent efficacy of a parathyroid hormone (PTH) preparation, which restores a lost bone dimension by actively stimulating bone formation, is getting new attention.

To a patient having postmenopausal osteoporosis who had been already suffering from vertebral body fracture, PTH (20 μg) was administered subcutaneously everyday for 19 months in average. As a result, bone mineral density was increased as much as 9.7% in lumbar spine (1.1% for placebo administration group), and 2.8% in neck of femur (−0.7% for placebo administration group). In addition, frequency of occurrence of new vertebral body fracture was inhibited as much as 65% and frequency of occurrence of non-vertebral body fracture was also inhibited as much as 53% [Non-patent Document No. 1]. Considering that the inhibitory effect of an agent for inhibiting bone resorption, such as bisphosphonate, raloxifen and the like, on vertebral body fracture is about 50% when it is administered for 3 to 4 years, bone fracture inhibiting effect of PTH is believed to be very potent. In fact, from a comparative test in which PTH (20 μg, subcutaneous injection everyday) or alendronate (ALN; 10 mg, oral administration everyday) was administered to a patient having postmenopausal osteoporosis, it was found that bone mineral density of lumbar spine was increased up to 10.3% for PTH administration group 18 months after the administration, while only 5.5% increase was recognized for the ALN administration group [Non-patent Document No. 2], thus indicating potent efficacy which has not been obtained from previous drug compounds. However, the PTH preparation is a peptide preparation and needs to be subcutaneously injected to a subject every day. Thus, as an administration method for patients suffering from osteoporosis, who are predominantly elderly people, it is not necessarily a convenient method. For such reasons, several attempts are made to provide compliance of dosing and convenience for patients, such as developing a preparation which can be administered once a week (Non-patent Document No. 3), developing an intranasal dosage preparation (Non-patent Document No. 4), etc. A study relating to an antagonist for a calcium-sensing receptor is one of such attempts.

Calcium-sensing receptor (CaSR) is a G protein coupled receptor which was cloned in 1993, and it plays an essential role for the control of PTH secretion in parathyroid gland. Activation of CaSR by extracellular calcium (Ca) inhibits secretion of PTH via activation of Gq protein [Non-patent Document No. 5]. In this connection, an idea of producing a preparation that can promote secretion of PTH by inhibiting CaSR function was presented. In fact, the first antagonist for CaSR was reported by Gowen et al. (Non-patent Document No. 6). As a result of single oral administration of an antagonist for CaSR referred to as NPS2143 to a rat, Gowen et al. confirmed that PTH concentration in blood is continuously increased. Further, after the oral administration of NPS2143 to a model rat having osteoporosis (rat with removed ovary) everyday for eight weeks, they also learned that bone formation evaluated by bone morphometry is increased but bone mineral density remained almost the same. Meanwhile, when NPS2143 and estrogen are administered together, increase in bone resorption that was found for administration of NPS2143 only was inhibited, and even compared to a group administered with estrogen only, a significant increase in bone mineral density was found. In general, it is believed that intermittent administration of PTH increases bone mineral density while continuous administration of PTH decreases it [Non-patent Document No. 7]. As such, it was considered that the reason why no activity of increasing bone mineral density was found when only NPS2143 was administered is due to the persistent activity of increasing the PTH concentration in blood by the compounds. Therefore, unlike NPS2143, an ideal antagonist for CaSR preferably has a transient activity of increasing PTH concentration in blood. Further, an essential requirement for an ideal antagonist for CaSR includes excellent safety having no cell toxicity, mutagenicity, drug interaction, etc. However, at the present moment there is no antagonist for CaSR that is approved as a pharmaceutical preparation by authorities.

Meanwhile, as a compound which has a similar function as the compounds of the present invention, those disclosed in the following Patent Documents have been known. However, they are all different from the compounds of the present invention in terms of characteristics of a chemical structure.

[Prior Art Literatures]
[Non-Patent Document]
[Non-patent Document No. 1] Neer R M., et al., N. Engl. J. Med. 344. 1434-1441. 2001.

[Non-patent Document No. 2] McClung M R., et al., Arch. Intern. Med. 165. 1762-1768. 2005.
[Non-patent Document No. 3] Miki T., et al., J. Bone Mineral Metab. 22. 569-576. 2004.
[Non-patent Document No. 4] Matsumoto T., et al., Osteoporosis Int. 17. 1532-1538. 2006.
[Non-patent Document No. 5] Brown E M., et al., Nature. 366. 575-580. 1993.
[Non-patent Document No. 6] Gowen M., et al., J. Clin. Invest. 105. 1595-1604. 2000.
[Non-patent Document No. 7] Uzawa T., et al., Bone 16. 477-484. 1995.
[Patent Document]
[Patent Document No. 1] International Publication No. WO97/37967 pamphlet
[Patent Document No. 2] International Publication No. WO02/14259 pamphlet
[Patent Document No. 3] International Publication No. WO04/69793 pamphlet
[Patent Document No. 4] International Publication No. WO04/106296 pamphlet
[Patent Document No. 5] International Publication No. WO04/047751 pamphlet
[Patent Document No. 6] International Publication No. WO04/017908 pamphlet

SUMMARY OF THE INVENTION

Problems to be Solved by the Invention

Object of the present invention is to provide novel compounds which can be used as an effective component of a CaSR antagonist that is very useful for prophylaxis and/or treatment of a bone disorder including osteoporosis, etc. In addition, the other object of the present invention is to provide a medicament which comprises the compound as an effective component.

Means to Solve the Problems

In order to solve the problems described in the above, inventors of the present invention extensively studied to find out material which can inhibit CaSR function. As a result, it was found that the sulfoneamide compounds that are novel compounds and represented by the following formula (1) have an excellent activity of promoting PTH secretion and are useful as an effective component for a medicament for the prophylaxis and/or treatment of a bone disorder including osteoporosis, bone fracture, hypoparathyroidism, etc. The present invention is completed based on such findings.

Specifically, the present invention is directed to the followings.

<1> A Compound represented by Formula (1) or a salt thereof:

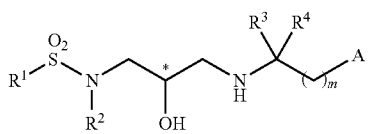

wherein,
A represents an optionally substituted aryl group;
$R^1$ represents the following Formula ($R^{1a}$) or ($R^{1b}$):

[in the Formulae ($R^{1a}$) and ($R^{1b}$),
$Ar^1$ represents the following Formula ($Ar^{1a}$), ($Ar^{1b}$) or ($Ar^{1c}$):

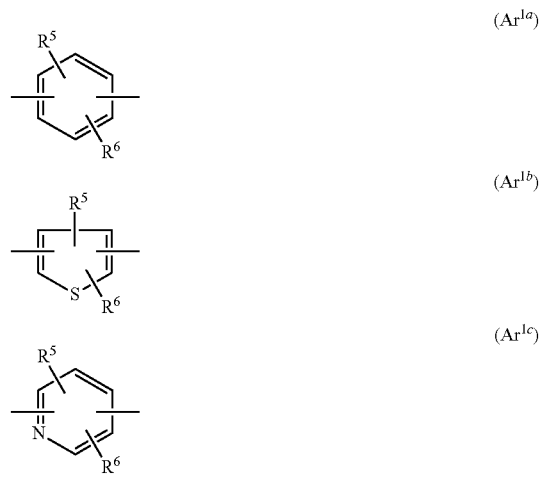

($R^5$ and $R^6$ each independently represents a hydrogen atom, a halogen atom, an optionally substituted lower alkyl group, an optionally substituted lower alkoxy group, or a cyano group);
$Ar^2$ represents the following Formula ($Ar^{2a}$), ($Ar^{2b}$), or ($Ar^{2c}$):

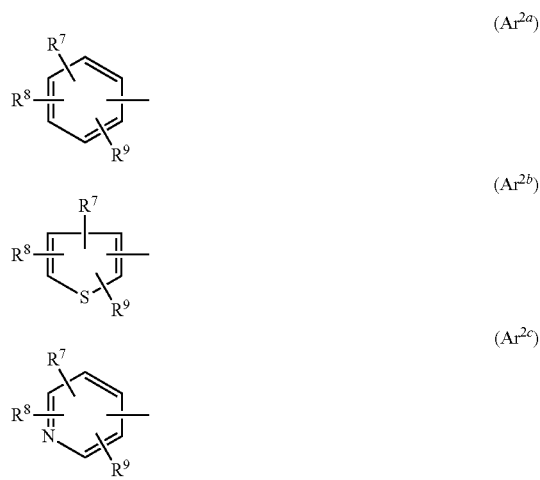

($R^7$ and $R^8$ each independently represents a hydrogen atom, a hydroxyl group, a halogen atom, an optionally substituted lower alkyl group, an optionally substituted lower alkoxy group, an optionally substituted amino group, a nitro group, a cyano group, $SOCH_3$ group, $SO_2CH_3$ group, a lower acyl group, or $R^7$ and $R^8$ together form —$COOCH_2$— or —$CH_2CH_2O$—;

$R^9$ represents a hydrogen atom or $-J-COOR^{10}$;

J represents a covalent bond, an optionally substituted alkylene having 1 to 5 carbon atoms, an optionally substituted alkenylene having 2 to 5 carbon atoms, or an optionally substituted alkynylene having 2 to 5 carbon atoms, wherein one carbon atom in said alkylene, alkenylene and alkynylene groups may be replaced by an oxygen atom, a sulfur atom, $NR^1$, $CONR^{11}$, or $NR^{11}CO$ at any chemically allowable position;

$R^{11}$ represents a hydrogen atom or a lower alkyl group; and $R^{10}$ represents a hydrogen atom or a lower alkyl group); and p represents 0 or 1];

$R^2$ represents a hydrogen atom or a lower alkyl group:

$R^3$ and $R^4$ each independently represents a lower alkyl group or $R^3$ and $R^4$ may together form alkylene having 2 to 6 carbon atoms;

* indicates an asymmetric carbon; and m represents an integer of 1 to 3.

<2> The compound described in <1> or a salt thereof, wherein A is optionally substituted phenyl, optionally substituted thiophen-yl, naphthalen-2-yl, or 2,3-dihydroinden-2-yl; $R^2$, $R^3$ and $R^4$ are a methyl group; and m=1.

<3> The compound described in <1> or a salt thereof, wherein A is phenyl, optionally substituted phenyl, optionally substituted thiophen-yl, or optionally substituted pyridin-yl; $R^2$, $R^3$ and $R^4$ are a methyl group; and m=3.

<4> The compound described in any of <1> to <3> or a salt thereof, wherein $R^7$ and $R^8$ each independently represent a hydrogen atom, a fluorine atom, a chlorine atom, a methyl group, an ethyl group, a trifluoromethyl group, a methoxy group or a trifluoromethoxy group.

<5> The compound described in any of <1> to <4> or a salt thereof, wherein $R^9$ is $CH_2CH_2COOR^{10}$, $CH_2CH_2CH_2COOR^{10}$ or $CH=CHCOOR^{10}$.

<6> The compound described in any of <1> to <5> or a salt thereof, wherein $R^1$ is $(R^{1a})$; p=0; $Ar^1$ is $(Ar^{1a})$ or $(Ar^{1b})$; $R^5$ is a hydrogen atom or a chlorine atom; and $R^6$ is a fluorine atom, a chlorine atom, a methyl group, an ethyl group, a trifluoromethyl group, or a trifluoromethoxy group.

<7> The compound described in any of <1> to <5> or a salt thereof, wherein $R^1$ is $(R^{1b})$; p=0; $Ar^2$ is $(Ar^{2a})$ or $(Ar^{2b})$; $R^7$ is a hydrogen atom, a chlorine atom, or a fluorine atom; and $R^8$ is a fluorine atom, a chlorine atom, a methyl group, an ethyl group, a trifluoromethyl group, or a trifluoromethoxy group.

<8> Compound represented by the following Formula (A) or (B) or a salt thereof.

(A)

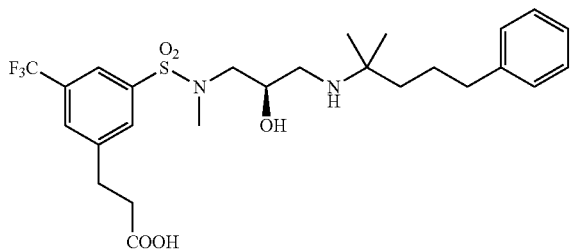

(B)

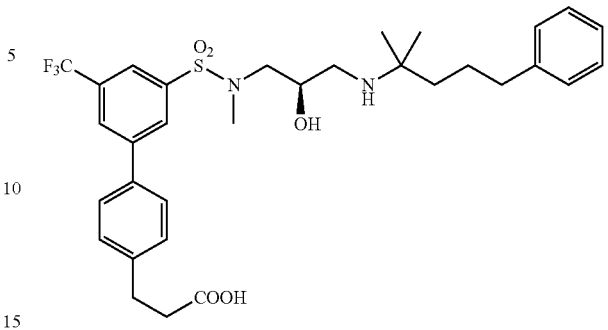

According to another aspect of the present invention, <9> A medicament comprising, as an effective component, a compound represented by the above Formula (1) or a pharmaceutically acceptable salt thereof is provided. The above described medicament can be used as an agent for promoting PTH secretion. The medicament of the present invention can be adopted for the prophylaxis and/or treatment of a bone disorder, and is useful as a prophylactic and/or therapeutic agent for osteoporosis, osteomalacia, osteitis fibrosa, bone aplasia, dialyitic bone disorder, hypoparathyroidism, osteopenia due to tumors such as multiple myeloma and etc., osteopenia due to administration of drugs such as steroids and etc., osteopenia and arthritis due to inflammation, periodontal disease, bone metastasis of cancer, hypercalcemia, Paget's disease of bone, ankylosing spondylitis, osteogenesis imperfecta, bone defect (alveolar bone defect, mandibular defect, childhood paroxysmal bone defect and etc.), bone fracture, refracture, rheumatoid arthritis, and osteoarthritis, for example. In addition, the medicament of the present invention is also useful for the prophylaxis and/or treatment of rupture in joint tissues which occurs in the disorders that are similar to the above described disorders.

Further, the medicament of the present invention can be used as an agent for promoting bone regeneration during surgical procedures. Specifically, the medicament can be adopted as an agent for promoting bone regeneration during surgical procedures including joint replacement, spinal canal restoration (spinal fusion, intervertebral fusion, posterior lumbar interbody fusion (PLIF), posterior lumbar fusion (PLF), transforaminal lumbar interbody fusion (TLIF) and etc.), spinal canal expansion, osteotomy, bone extension, dental reconstruction, skull defect restoration, skull formation, iliac bone spacer fusion using a bony support, bone transplantation between heterogeneous species, bone transplantation between homogenous species, autogenous bone transplantation, or bone transplantation replacement therapy, and bone restoration and/or bone reconstruction after surgical removal of primary malignant tumor or bone metastasis, for example.

Still further, the medicament of the present invention can be adopted for various disorders that can be improved by increasing PTH concentration in blood, and therefore is useful as a prophylactic and/or therapeutic agent for idiopathic hypoparathyroidism, spondylosis deformans, neutropenia, thrombocytopenia, scabies or alopecia, for example.

According to another aspect of the present invention, the followings are provided.

<10> The medicament described in <9>, which is an agent for promoting PTH secretion.

<11> The medicament described in <9>, which is used for the prophylaxis and/or treatment of a bone disorder.

<12> The medicament described in <11>, wherein the bone disorder is primary osteoporosis and/or secondary osteoporosis.

<13> The medicament described in <11>, wherein the bone disorder is bone fracture and/or refracture.

<14> The medicament described in <11>, wherein the bone disorder is osteomalacia, osteitis fibrosa, bone aplasia, dialyitic bone disorder, hypoparathyroidism, osteopenia due to tumors such as multiple myeloma and etc., osteopenia due to administration of drugs such as steroids and etc., osteopenia and arthritis due to inflammation, periodontal disease, bone metastasis of cancer, hypercalcemia, Paget's disease of bone, ankylosing spondylitis, osteogenesis imperfecta, bone defect (alveolar bone defect, mandibular defect, childhood paroxysmal bone defect and etc.), rheumatoid arthritis, osteoarthritis, or rupture in joint tissues.

<15> The medicament described in <9>, which is used for promotion of bone regeneration during surgical procedures.

<16> The medicament described in <15>, wherein the surgical procedures are bone restoration and/or bone reconstruction.

<17> The medicament described in <15>, wherein the surgical procedures are joint replacement, spinal canal restoration (spinal fusion, intervertebral fusion, posterior lumbar interbody fusion (PLIF), posterior lumbar fusion (PLF), transforaminal lumbar interbody fusion (TLIF) and etc.), spinal canal expansion, osteotomy, bone extension, dental reconstruction, skull defect restoration, skull formation, iliac bone spacer fusion using a bony support, bone transplantation between heterogeneous species, bone transplantation between homogenous species, autogenous bone transplantation, bone transplantation replacement therapy, bone restoration or bone reconstruction after surgical removal of primary malignant tumor or bone metastasis.

<18> The medicament described in <10>, which is used for the prophylaxis and/or treatment of a disorder that can be improved by increasing PTH concentration in blood.

<19> The medicament described in <18>, wherein the disorder that can be improved by increasing PTH concentration in blood is idiopathic hypoparathyroidism, spondylosis deformans, neutropenia, thrombocytopenia, scabies or alopecia.

<20> A calcium-sensing receptor antagonizing agent which comprises, as an effective component, the compound described in any one of <1> to <8> or a pharmaceutically acceptable salt thereof.

EFFECT OF THE INVENTION

When the compound of the present invention in free form or a salt thereof is administered to human or an animal, a potent activity of promoting PTH secretion is obtained. Thus, the compound and the salt of the invention are useful as an effective component of a medicament for the prophylaxis and/or treatment of bone disorders such as osteoporosis, bone fracture, hypoparathyroidism and the like, or for a medicament for promoting bone regeneration during surgical procedures and etc.

BEST MODE TO CARRY OUT THE INVENTION

Hereinbelow, the present invention will be explained in greater detail.

According to the present specification, a carbon atom is sometimes expressed simply as "C", a hydrogen atom is sometimes expressed simply as "H", an oxygen atom is sometimes expressed simply as "O", a sulfur atom is sometimes expressed simply as "S", a nitrogen atom is sometimes expressed simply as "N", and a boron atom is sometimes expressed simply as "B". In addition, a carbonyl group is sometimes expressed simply as "—CO—", carboxyl group is sometimes expressed simply as "—COO—", a sulfinyl group is sometimes expressed simply as "—SO—", a sulfonyl group is sometimes expressed simply as "—SO$_2$-", an ether bond is sometimes expressed simply as "—O—", and a thioether bond is sometimes expressed simply as "—S-" (in this case, "-" represents a bond).

In the present specification, unless specifically described otherwise, a fluorine atom, a chlorine atom, a bromine atom or an iodine atom is exemplified as a halogen atom. Preferred examples of a halogen atom include a fluorine atom, a chlorine atom, a bromine atom or an iodine atom, and more preferred examples include a fluorine atom or a chlorine atom. Still more preferable example is a fluorine atom. There is other embodiment in which a chlorine atom is still more preferred.

Examples of an alkyl group include a linear, branched, or cyclic saturated hydrocarbon group, or a combination thereof. A lower alkyl group is preferred. In the present specification, the term "lower" indicates that there are 1 to 6 carbon atoms as an atom which constitutes a functional group. Examples thereof include an alkyl group having 1 to 6 carbon atoms, and preferred examples thereof include an alkyl group having 1 to 3 carbon atoms. It is the same for an alkyl moiety which is comprised in other substituents (e.g., an alkoxy group, etc.).

Preferred examples of an alkyl group having 1 to 3 carbon atoms include methyl group, ethyl group, n-propyl group, isopropyl group, or cyclopropyl group and the like. In addition, preferred examples of an alkyl group having 4 to 6 carbon atoms include n-butyl group, isobutyl group, s-butyl group, t-butyl group, cyclobutyl group, cyclopropylmethyl group, n-pentyl group, cyclopentyl group, cyclopropylethyl group, cyclobutylmethyl group, n-hexyl group, cyclohexyl group, cyclopropylpropyl group, cyclobutylethyl group, or cyclopentylmethyl group and the like. As an alkyl group, methyl group, ethyl group, n-propyl group, or isopropyl group is more preferred.

Examples of an alkenyl group include a lower alkenyl group which has one or at least two double bonds. A lower alkenyl group comprising one double bond is preferred. As a lower alkenyl group, an alkenyl group having 2 to 5 carbon atoms is preferred and an alkenyl group having 2 to 4 carbon atoms is more preferred. Preferred examples of an alkenyl group having 2 to 4 carbon atoms include vinyl group, allyl group, propenyl group, butylidene group, but-1-enyl group, but-2-enyl group, or but-3-enyl group and the like. In addition, preferred examples of an alkenyl group having 5 carbon atoms include pentylidene group, pent-1-enyl group, pent-2-enyl group, pent-3-enyl group, or pent-4-enyl group and the like. More preferred examples of an alkenyl group include vinyl group, allyl group, or propenyl group, and even more preferred examples of an alkenyl group include vinyl group, or allyl group. Allyl group is still even more preferred. There is other embodiment in which a vinyl group is even more preferred.

Examples of an alkynyl group include a lower alkynyl group which has one or at least two triple bonds. A lower alkynyl group comprising one triple bond is preferred. The alkynyl group having 2 to 5 carbon atoms is preferred as a lower alkynyl group. Specifically, preferred examples include ethynyl group, prop-1-ynyl group, prop-2-ynyl group, but-1-ynyl group, but-2-ynyl group, but-3-ynyl group, pent-1-ynyl group, pent-2-ynyl group, pent-3-ynyl group, or pent-4-ynyl group and the like. Ethynyl group, prop-2-ynyl group, or but-3-ynyl group is more preferred. Ethynyl group, or prop-1-ynyl group is still more preferred. Ethynyl group is even still more preferred.

As for an alkoxy group, a linear, branched, cyclic saturated alkyloxy group, or a saturated alkyloxy group having combination thereof can be mentioned. A lower alkoxy group is preferred. As for a lower alkoxy group, an alkoxy group having 1 to 6 carbon atoms can be mentioned. An alkoxy group having 1 to 4 carbon atoms is preferred. Preferred examples of an alkoxy group having 1 to 4 carbon atoms include methoxy group, ethoxy group, n-propoxy group, isopropoxy group, cyclopropoxy group, n-butoxy group, isobutoxy group, s-butoxy group, t-butoxy group, cyclobutoxy group, or cyclopropylmethoxy and the like. In addition, preferred examples of an alkoxy group comprising 5 or 6 carbon atoms include n-pentyloxy group, cyclopentyloxy group, cyclopropylethyloxy group, cyclobutylmethyloxy group, n-hexyloxy group, cyclohexyloxy group, cyclopropylpropyloxy group, cyclobutylethyloxy group, or cyclopentylmethyloxy group and the like.

As for a substituent for an optionally substituted alkyl group, a hydroxyl group, a halogen atom, an alkoxy group, a carboxy group, a cyano group, a saturated heterocyclic group, an alkylsulfonylamino group, an aminocarbonylamino group and the like can be mentioned as a preferred example. A hydroxyl group or a halogen atom can be mentioned as a more preferred example. A hydroxyl group, a methoxy group, or a fluorine atom can be mentioned as a still more preferred example. A hydroxyl group can be mentioned as a particularly more preferred example. In addition, there is other embodiment in which a fluorine atom is particularly more preferred.

As for an optionally substituted alkyl group, one group selected from a group consisting of the above described preferred examples of an alkyl group further including a trifluoromethyl group, a difluoromethyl group, a hydroxymethyl group, 2-hydroxyethyl group, and a methoxymethyl group, is preferred. A methyl group, an ethyl group, a n-propyl group, an isopropyl group, a cyclopropyl group, a trifluoromethyl group, a difluoromethyl group, a hydroxymethyl group, a 2-hydroxyethyl group or a methoxymethyl group are more preferred as an optionally substituted alkyl group. A methyl group is still more preferred.

As for a substituent for an optionally substituted alkenyl group, and a substituent for an optionally substituted alkynyl group, a substituent for an optionally substituted alkyl group as described in the above can be also mentioned.

As for an optionally substituted alkenyl group, the preferred example of an alkenyl group as described in the above is also preferred. In addition, as an optionally substituted alkynyl group, the preferred example of an alkynyl group as described in the above is also preferred.

As for a substituent for an optionally substituted alkoxy group, a substituent for an optionally substituted alkyl group as described in the above can be also mentioned. In particular, one or more halogen atom is preferred.

As for a substituted alkoxy group, an alkoxy group optionally substituted with one or more halogen atoms is preferred, and an alkoxy group having 1 to 4 carbon atoms which is optionally substituted with one or more halogen atoms is preferred. When the substitution is made with two or more halogen atoms, such halogen atoms can be the same or different to each other.

As for an optionally substituted alkoxy group, in addition to the above described preferred examples of an alkoxy group having 1 to 6 carbon atoms, a group selected from a group consisting of a monofluoromethoxy group, a difluoromethoxy group, a trifluoromethoxy group, or 2,2,2-trifluoroethoxy group is preferred. Further, in addition to the above described preferred examples of an alkoxy group having 1 to 6 carbon atoms, a group selected from a group further consisting of a trifluoromethoxy group and 2,2,2-trifluoroethoxy group is more preferred.

As for an aryl ring, a monocyclic aromatic ring or a fused polycyclic aromatic ring and the like can be mentioned. The monocyclic aromatic ring or the fused polycyclic aromatic ring defined herein include a partially unsaturated monocyclic or a fused bicyclic carbon ring and heterocyclic ring. The aryl ring can be a hydrocarbon ring or it may comprise at least one, for example 1 to 3, of one or more kinds of heteroatoms that are selected from a group consisting of a nitrogen atom, a sulfur atom and an oxygen atom as a ring-forming atom other than a carbon atom.

Examples of a monocyclic aromatic ring include a monocyclic aromatic hydrocarbon or a monocyclic aromatic heterocycle which comprises one or at least two heteroatoms. For example, a benzene ring or a 5- or 6-membered aromatic heterocycle comprising one or at least two heteroatoms can be mentioned. Specifically, preferred examples of a 5- or 6-membered aromatic heterocycle include thiophene, pyridine, furan, thiazole, oxazole, pyrazole, pyrazine, pyrimidine, pyrrole, imidazole, pyridazine, isothiazole, isoxazole, 1,2,4-oxadiazole, 1,3,4-oxadiazole, 1,2,4-thiadiazole, 1,3,4-thiadiazole or furazane and the like.

Examples of a fused polycyclic aromatic ring include a fused polycyclic aromatic hydrocarbon or a fused polycyclic aromatic heterocycle which comprises one or at least two heteroatoms. As for a fused polycyclic aromatic hydrocarbon, a fused polycyclic aromatic hydrocarbon comprising any one of 9 to 14 carbon atoms, i.e., two- or three-ring aromatic hydrocarbon can be mentioned. Specifically, preferred examples include naphthalene, 1,2,3,4-tetrahydronaphthalene, azulene, indene, indane, 2,3-dihydroindene, fluorene, phenanthrene, 9,10-dihydrophenanthrene, or anthracene and the like. As for a fused polycyclic aromatic heterocycle, a 9- to 14-membered, preferably 9- or 10-membered, fused polycyclic aromatic heterocycle comprising at least one heteroatom, for example 1 to 4 heteroatoms, can be mentioned. Specifically, preferred examples include benzofuran, 2,3-dihydrobenzofuran, benzothiophene, 2,3-dihydrobenzothiophene, benzimidazole, benzoxazole, benzisoxazole, benzothiazole, benzisothiazole, naphtho[2,3-b]thiophene, quinoline, isoquinoline, 1,2-dihydroisoquinoline, 3,4-dihydroisoquinoline, 1,2-dihydroquinoline, 3,4-dihydroquinoline, 1,2,3,4-tetrahydroisoquinoline, 1,2,3,4-tetrahydroquinoline, indole, indoline, isoindoline, quinoxaline, phenanthridine, phenothiazine, phenoxazine, phthalazine, naphthyridine, quinazoline, cinnoline, carbazole, β-carboline, acridine, phenazine, phthalimide, or thioxanthene and the like.

As for an aryl group, a monocyclic aromatic group or a fused polycyclic aromatic group and the like can be mentioned, for example. In addition, a monovalent residue that is produced by removing any single hydrogen atom from the above described aryl ring can be exemplified.

As for a monocyclic aromatic group, a monovalent residue that is produced by removing any single hydrogen atom from a monocyclic aromatic ring can be exemplified. Preferred examples of a monocyclic aromatic group include phenyl group, thienyl group (2- or 3-thienyl group), pyridyl group (2-, 3- or 4-pyridyl group), furyl group (2- or 3-furyl group), thiazolyl group (2-, 4- or 5-thiazolyl group), oxazolyl group (2-, 4- or 5-oxazolyl group), pyrazolyl group (1-, 3- or 4-pyrazolyl group), 2-pyrazinyl group, pyrimidinyl group (2-, 4- or 5-pyrimidinyl group), pyrrolyl group (1-, 2- or 3-pyrrolyl group), imidazolyl group (1-, 2- or 4-imidazolyl group), pyridazinyl group (3- or 4-pyridazinyl group), 3-isothiazolyl group, 3-isoxazolyl group, 1,2,4-oxadiazol-5-yl group, or 1,2,4-oxadiazol-3-yl group and the like.

As for a fused polycyclic aromatic group, a monovalent residue that is produced by removing any single hydrogen atom from a fused polycyclic aromatic ring comprising 2 to 4, preferably 2 or 3, rings can be exemplified.

Specifically, preferred examples of a fused polycyclic aromatic group include 1-naphthyl group, 2-naphthyl group, azulen-1-yl group, azulen-5-yl group, tetrahydronaphthyl group (substitution position is 1, 2, 5 or 6), 1-indenyl group, 2-indenyl group, 2,3-dihydroinden-1-yl group, 2,3-dihydroinden-2-yl group, 2,3-dihydroinden-5-yl group, 2-anthryl group, quinolyl group (2-, 3-, 4-, 5-, 6-, 7- or 8-quinolyl group), isoquinolyl group (1-, 3-, 4-, 5-, 6-, 7- or 8-isoquinolyl group), 1,2-dihydroisoquinolyl group or 1,2,3,4-tetrahydroisoquinolyl group (substitution position is the same as the isoquinolyl group), indolyl group (1-, 2-, 3-, 4-, 5-, 6- or 7-indolyl group), isoindolyl group (1-, 2-, 4- or 5-isoindolyl group), phthalazinyl group (1-, 5- or 6-phthalazinyl group), quinoxalinyl group (2-, 3- or 5-quinoxalinyl group), benzofuranyl group (2-, 3-, 4-, 5- or 6-benzofuranyl group), 2,3-dihydrobenzofuran-1-yl group, 2,3-dihydrobenzofuran-2-yl group, 2,3-dihydrobenzothiophen-1-yl group, 2,3-dihydrobenzothiophen-2-yl group, benzothiazolyl group (2-, 4-, 5- or 6-benzothiazolyl group), benzimidazolyl group (1-, 2-, 4-, 5- or 6-benzimidazolyl group), fluorenyl group (1-, 2-, 3- or 4-fluorenyl group), or thioxanthenyl group and the like.

As for a substituent for an optionally substituted aryl group, a hydroxyl group, a halogen atom, an alkyl group, an alkoxy group, a carboxy group, an alkoxycarbonyl group, a cyano group, an alkylsulfonylamino group, an aminocarbonylamino group and the like can be mentioned as a preferred example. A hydroxyl group, a halogen atom, an alkyl group or an alkoxy group are more preferred. A hydroxyl group, a fluorine atom, a chlorine atom, a methyl group or a methoxy group are still more preferred. A fluorine atom, a chlorine atom, or a methyl group are even still more preferred. When the substitution is made with two or more substituents, they can be the same or different to each other. The number of a substituent for an optionally substituted aryl group is 1 to 3, for example. Preferably it is 1 or 2.

As for an alkylene, a linear, branched, or cyclic saturated divalent hydrocarbon group having 1 to 6 carbon atoms, or combination thereof can be mentioned. An alkylene having 1 to 3 carbon atoms is more preferred. There is other embodiment in which an alkylene having 4 to 6 carbon atoms is more preferred. A linear alkylene or a branched alkylene is more preferred. A linear alkylene is still more preferred. Specific examples include methylene, ethylene, propan-1,3-diyl, n-butan-1,4-diyl, n-butan-2,4-diyl, n-pentan-1,5-diyl, n-pentan-2,5-diyl, n-hexan-1,6-diyl and the like. Preferred examples include methylene, ethylene, or propan-1,3-diyl and still more preferred examples include methylene or ethylene.

As for a substituent for an optionally substituted alkylene, in addition to the above described preferred examples of an alkyl group, a group selected from a group consisting of a trifluoromethyl group, a difluoromethyl group, a hydroxymethyl group, and 2-hydroxyethyl group is preferred. More preferably, it is a methyl group, an ethyl group, n-propyl group, an isopropyl group, a cyclopropyl group, a trifluoromethyl group, a difluoromethyl group, a hydroxymethyl group, or 2-hydroxyethyl group, and still more preferably it is a methyl group.

An alkenylene is a divalent radical which comprises one or at least two double bonds in the alkylene group described above. A lower alkenylene comprising one double bond is preferred. An alkenylene having 2 to 5 carbon atoms is preferred as a lower alkenylene. An alkenylene having 2 to 4 carbon atoms is more preferred. As for a preferred example of alkenylene having 2 to 4 carbon atoms, ethylene-diyl, propendiyl, buten-diyl, 1,3-butadien-diyl and the like can be mentioned. Specific examples include ethylene-1,2-diyl, propen-1,2-diyl, propen-1,3-diyl, 1-buten-1,2-diyl, 1-buten-1,3-diyl, 1-buten-1,4-diyl, 2-buten-2,4-diyl, 1,3-butadien-1,4-diyl, 1-penten-1,2-diyl, 1-penten-1,3-diyl, 1-penten-1,4-diyl, 1-penten-1,5-diyl, 2-penten-2,5-diyl and the like. With respect to stereochemistry relating to a double bond, any of cis and trans is acceptable. Preferred stereochemistry is trans.

As for a substituent for an optionally substituted alkenylene, the substituents for an optionally substituted alkylene as described above are also included. A methyl group and a trifluoromethyl group are preferred, and a methyl group is still more preferred. There is other embodiment in which a trifluoromethyl group is preferred.

Alkynylene is a divalent radical which comprises one or more triple bond in the alkylene described above, for example. A lower alkynylene comprising one triple bond is preferred. As for a lower alkynylene, alkynylene having 2 to 5 carbon atoms is preferred, for example. An alkynylene having 2 carbon atoms is more preferred. Specifically, acetylen-diyl, propyn-diyl, 1-butyn-1,4-diyl, 2-butyn-1,4-diyl, 1-pentyn-1,5-diyl, 2-pentyn-1,5-diyl, 3-pentyn-1,5-diyl and the like can be mentioned.

As for a substituent for an optionally substituted alkynylene, an alkyl and the like can be mentioned, for example. An alkynylene can be independently substituted with one or two substituents.

As for an acyl group, an alkylcabonyl group can be mentioned, for example. Further, as for the alkyl moiety of an alkylcarbonyl group, the alkyl group same as those described above can be exemplified. A lower acyl group indicates an acyl group having 2 to 6 carbon atoms. An acyl group having 2 to 4 carbon atoms is preferred. Specifically, examples of an alkylcarbonyl group include an acetyl group, a propanoyl group, 1-methylpropanoyl group, a cyclopropanecarbonyl group, a butanoyl group, 1-methylpropanoyl group, 2-methylpropanoyl group, 1,1-dimethylpropanoyl group, a cyclobutanecarbonyl group, a pentanoyl group, and the like. An acetyl group and a propanoyl group are mentioned as a preferred example.

As for a substituent for an optionally substituted amino group, a hydrogen atom, an alkyl group, an alkenyl group, an alkynyl group, an acyl group, an alkylsulfonyl group, or an arylsulfonyl group can be exemplified. With respect to an optionally substituted amino group, an amino group, a methylamino group, a dimethylamino group, an ethylamino group, a diethylamino group, an acetylamino group, a methanesulfonylamino group, a benzenesulfonylamino group, or p-toluenesulfonylamino group and the like can be mentioned. Among these, an amino group, a methylamino group, or a dimethylamino group is preferred. An amino group is still more preferred.

A is defined as an optionally substituted aryl group and examples thereof are the same as the aryl group described above. A is preferably phenyl, optionally substituted phenyl, naphthalen-2-yl, 2,3-dihydro-1H-inden-2-yl, 2,3-dihydro-1H-inden-5-yl, thiophen-2-yl, thiophen-3-yl, 5-fluorothiophen-2-yl, 1,2,3,4-tetrahydroisoquinolin-2-yl, 2,3-dihydroisoindol-2-yl, pyridin-2-yl, pyridin-3-yl, pyridin-4-yl, 2-fluoropyridin-4-yl, or 3-fluoropyridin-4-yl. Optionally substituted phenyl is more preferred. There are other embodiments in which a phenyl group is more preferred, naphthalen-2-yl is more preferred, 2-fluorophenyl is more preferred, thiophen-2-yl is more preferred, thiophen-3-yl is more preferred, or 2,3-dihydro-1H-inden-2-yl is more preferred. As for a substituent for an optionally substituted phenyl group, the substituent for an optionally substituted aryl group described above can be also mentioned. A methyl group, a fluorine atom, a chlorine atom, a bromine atom, and a methoxy group are preferred. A methyl group, a fluorine atom, and a chlorine atom are more preferred. There are other embodiments in which fluorine atom is more preferred, a chlorine atom is more preferred, or a methyl group is more preferred. The number of a substituent is not specifically limited. Preferably, it is 1 to 3, and more preferably it is 1 or 2. When there are two or more substituents, they can be the same or different to each other. Position for substitution is not specifically limited. Preferably, it is meta or para position relative to the binding position with —$(CH_2)_m$—. More preferably, substitution is made at both positions. There is other embodiment in which meta position is more preferred. There is other embodiment in which para position is more preferred. There is still other embodiment in which ortho position is more preferred. With respect to the optionally substituted-phenyl group, preferred examples include 3-fluoro-4-methylphenyl, 4-chloro-3-fluorophenyl, 2-chlorophenyl, 2-fluorophenyl, 3-fluorophenyl, 4-fluorophenyl, 4-isopropylphenyl, and 4-isopropyl-3-fluorophenyl. There are other embodiments in which 3-fluoro-4-methylphenyl is more preferred, 4-chloro-3-fluorophenyl is more preferred, 2-chlorophenyl is more preferred, 2-fluorophenyl is more preferred, 3-fluorophenyl is more preferred, 4-fluorophenyl is more preferred, 4-isopropylphenyl is more preferred, or 4-isopropyl-3-fluorophenyl is more preferred.

$R^1$ is defined as the above described Formula ($R^{1a}$) or ($R^{1b}$), and the Formula ($R^{1a}$) is more preferred. There is other embodiment in which the Formula ($R^{1b}$) is more preferred.

$Ar^1$ in the Formula ($R^{1a}$) is defined as the above described Formulae ($Ar^{1a}$), ($Ar^{1b}$) or ($Ar^{1c}$). The Formula ($Ar^{1a}$) is more preferred. There is other embodiment in which the Formula ($Ar^{1b}$) is preferred. There is other embodiment in which the Formula ($Ar^{1c}$) is preferred. Position for binding of the Formula (Aria) to $(CH_2)_p$ and $Ar^2$, respectively, is not specifically limited. Preferably, $Ar^2$ binds to meta or para position relative to the binding position with $(CH_2)_p$. More preferably, binding is made at meta position. There is other embodiment in which para position is more preferred. There is other embodiment in which ortho position is more preferred. With respect to the Formula ($Ar^{1b}$), position for binding with $(CH_2)_p$ and $Ar^2$, respectively, is not specifically limited. Preferably, $(CH_2)_p$ is bonded to position 2 of ($Ar^{1b}$) while $Ar^2$ is bonded to position 5 of ($Ar^{1b}$). Further, there is other embodiment in which $(CH_2)_p$ is preferably bonded to position 2 of ($Ar^{1b}$) while $Ar^2$ is bonded to position 4 of ($Ar^{1b}$). With respect to the Formula ($Ar^{1c}$), position for binding with $(CH_2)_p$ and $Ar^2$, respectively, is not specifically limited. Preferably, $(CH_2)_p$ is bonded to position 3 for the nitrogen atom of ($Ar^{1c}$) while $Ar^2$ is bonded to position 5.

$Ar^2$ in the Formulae ($R^{1a}$) or ($R^{1b}$) is defined as the above described Formulae ($Ar^{2a}$), ($Ar^{2b}$) or ($Ar^{2c}$). The Formula ($Ar^{2a}$) is more preferred. There is other embodiment in which the Formula ($Ar^{2b}$) is preferred. There is other embodiment in which the Formula ($Ar^{2c}$) is preferred. Position for binding of ($Ar^{2b}$) with $(CH_2)_p$ or $Ar^1$, respectively, is not specifically limited. However, position 2 is preferred. Position for binding of ($Ar^{2c}$) with $(CH_2)_p$ or $Ar^1$, respectively, is not specifically limited. Position 2 or Position 3 is more preferred. Position 2 is still more preferred. p in the Formulae ($R^{1a}$) or ($R^{1b}$) is defined as 0 or 1. It is preferably 0.

Examples of the Formula ($R^{1a}$) include 3-(2-carboxyvinyl)biphenyl-2'-yl, 3-carboxybiphenyl-2'-yl, 3-carboxy-5-nitrobiphenyl-2'-yl, 2-carboxybiphenyl-3'-yl, 3-carboxybiphenyl-3'-yl, 4-carboxybiphenyl-3'-yl, 3-carboxy-4-methylbiphenyl-3'-yl, 3-methyl-4-carboxybiphenyl-3'-yl, 3-fluoro-4-carboxybiphenyl-3'-yl, 3-amino-4-carboxybiphenyl-3'-yl, 3-chloro-4-carboxybiphenyl-3'-yl, 2-fluoro-4-carboxybiphenyl-3'-yl, 3-(2,3-dihydro-7-carboxybenzofuran-5-yl)phenyl, 4-(2-carboxyvinyl)biphenyl-3'-yl, 4-carboxyethylbiphenyl-3'-yl, 3-(2-carboxyvinyl)biphenyl-3'-yl, 5-amino-3-carboxybiphenyl-3'-yl, 3-carboxy-5-nitrobiphenyl-3'-yl, 2-amino-4-carboxybiphenyl-3'-yl, 4-carboxy-2-nitrobiphenyl-3'-yl, 3-(N-(3-carboxypropionyl)anilin-4-yl)phenyl, 3-methoxymethyl-4-carboxybiphenyl-3'-yl, 3-carboxy-6-fluorobiphenyl-3'-yl, 3-hydroxy-4-carboxybiphenyl-3'-yl, 3,5-difluoro-4-carboxybiphenyl-3'-yl, 3-(2-carboxythiophen-5-yl)phenyl, 3-(N-(2-carboxyethyl)benzoic acid amide-4-yl)phenyl, 3-(N-carboxymethylanilin-4-yl)phenyl, 2-carboxybiphenyl-4'-yl, 3-carboxybiphenyl-4'-yl, 4-carboxybiphenyl-4'-yl, 3-carboxy-4-methylbiphenyl-4'-yl, 3-methyl-4-carboxybiphenyl-4'-yl, 3-amino-4-carboxybiphenyl-4'-yl, 4-carboxy-2-fluoro-biphenyl-4'-yl, 4-(2,3-dihydro-7-carboxybenzofuran-5-yl)phenyl, 4-(2-carboxyvinyl)biphenyl-4'-yl, 4-(2-carboxyethyl)biphenyl-4'-yl, 3-(2-carboxyvinyl)biphenyl-4'-yl, 3-carboxy-5-nitrobiphenyl-4'-yl, 2-amino-4-carboxybiphenyl-4'-yl, 2-nitro-4-carboxybiphenyl-4'-yl, 4-(N-(3-carboxypropionyl)anilin-4-yl)phenyl, 2-(2-carboxyvinyl)biphenyl-4'-yl, 3-fluoro-4-(2-carboxyvinyl)biphenyl-4'-yl, 3-hydroxy-4-carboxybiphenyl-4'-yl, 4-carboxymethylthiobiphenyl-4'-yl, 3,5-difluoro-4-carboxybiphenyl-4'-yl, 4-carboxymethylbiphenyl-3'-yl, 3-carboxymethylbiphenyl-3'-yl, ((4-carboxy-3-methyl)biphenyl-2'-yl)methyl, (4-(2-carboxyvinyl)biphenyl-2'-yl)methyl, (4-(2-carboxyethyl)biphenyl-2'-yl)methyl, (3-(2-carboxyvinyl)biphenyl-2'-yl)methyl, (3-fluoro-5-carboxybiphenyl-2'-yl)methyl, (4-(2-carboxyvinyl)biphenyl-3'-yl)methyl, (4-(2-carboxyethyl)biphenyl-3'-yl)methyl, (3-(2-carboxyvinyl)biphenyl-3'-yl)methyl, (4-(2-carboxyvinyl)biphenyl-4'-yl)methyl, (4-(2-carboxyethyl)biphenyl-4'-yl)methyl, (3-(2-carboxyvinyl)biphenyl-4'-yl)methyl, 2-ethoxycarbonylbiphenyl-3'-yl, 3-methyl-4-methoxycarbonylbiphenyl-3'-yl, 3-ethoxycarbonyl-5-fluorobiphenyl-3'-yl, 4-(N-(3-ethoxycarbonylpropionyl)benzoic acid amide-4-yl)phenyl, 3-(N-ethoxycarbonylmethylanilin-4-yl)phenyl, 3-ethoxycarbonylbiphenyl-3'-yl, 4-(2-ethoxycarbonylethyl)biphenyl-3'-yl, 4-ethoxycarbonylmethylbiphenyl-3'-yl, 3-(2-carboxyethyl)biphenyl-5-trifluoromethyl-3'-yl, 4-(2-carboxyethyl)biphenyl-5-trifluoromethyl-3'-yl, 3-(2-carboxyethyl)biphenyl-5-fluoro-3'-yl, 4-(2-carboxyethyl)biphenyl-5-fluoro-3'-yl, 3-(2-carboxyethyl)biphenyl-5-chloro-3'-yl, 4-(2-carboxyethyl)biphenyl-5-chloro-3'-yl, 3-(2-carboxyethyl)biphenyl-5-ethyl-3'-yl, 4-(2-carboxyethyl)biphenyl-5-ethyl-3'-yl.

Examples of the Formula ($R^{1b}$) include 2-carboxyphenyl, 3-carboxyphenyl, 4-carboxyphenyl, 2-(2-carboxyethyl)phenyl, 3-(2-carboxyethyl)phenyl, 4-(2-carboxyethyl)phenyl, 2-(2-carboxyvinyl)phenyl, 3-(2-carboxyvinyl)phenyl, 4-(2-carboxyvinyl)phenyl, 3-carboxy-5-trifluorophenyl, 3-carboxymethyl-5-trifluoromethylphenyl, 3-(2-carboxyethyl)-5-trifluoromethylphenyl, 3-(2-carboxyvinyl)-5-trifluoromethylphenyl, 3-(2-carboxyethyl)-5-chlorophenyl, 3-(2-carboxyvinyl)-5-chlorophenyl, 3-(2-carboxyethyl)-5-fluorophenyl, 3-(2-carboxyvinyl)-5-fluorophenyl, 3-(2-carboxyethyl)-5-methylphenyl, 3-(2-carboxyvinyl)-5-methylphenyl, 3-(2-carboxyethyl)-5-ethylphenyl, 3-(2-carboxyvinyl)-5-ethylphenyl, 3-(2-carboxyethyl)-5-trifluoromethoxyphenyl, 3-(2-carboxyvinyl)-5-trifluoromethoxyphenyl, 4-(2-carboxyethyl)-3-trifluoromethylphenyl, 4-(2-carboxyvinyl)-3-trifluoromethylphenyl, 4-(2-carboxyethyl)-3-fluorophenyl, 4-(2-carboxyvinyl)-3-fluorophenyl, 4-(2-carboxyethyl)-3-chlorophenyl, 4-(2-carboxyvinyl)-3-chlorophenyl, 4-(2-carboxyethyl)-3-methylphenyl, 4-(2-carboxyvinyl)-3-methylphenyl, 4-(2-carboxyethyl)-2-trifluoromethylphenyl, 4-(2-carboxyvinyl)-2-trifluoromethylphenyl, 4-(2-carboxyethyl)-2-fluorophenyl, 4-(2-carboxyvinyl)-2-fluorophenyl, 4-(2-carboxyethyl)-2-chlorophenyl, 4-(2-carboxyvinyl)-2-chlorophenyl, 4-(2-carboxyethyl)-2-methylphenyl, 4-(2-carboxyvinyl)-2-methylphenyl, 4-(2-carboxyethyl)-2-ethylphenyl, 4-(2-carboxyvinyl)-2-ethylphenyl, 4-(2-carboxyethyl)-2-trifluoromethoxyphenyl, 4-(2-carboxyvinyl)-2-trifluoromethoxyphenyl, 4-(2-carboxyethyl)-2,6-dichlorophenyl, 4-(2-carboxyethyl)-2,5-difluorophenyl, 2-(2-carboxyethyl)-4-trifluorophenyl, 2-(2-carboxyethyl)-5-trifluorophenyl, 5-(2-carboxyethyl)-2-methoxyphenyl, 5-(2-carboxyvinyl)-2-methoxyphenyl, 4-(2-carboxyethyl)-5-chlorothiophen-2-yl, 4-(3-carboxypropyl)-5-chlorothiophen-2-yl, 3-carboxymethylthio-5-trifluorophenyl, 3-(2-carboxyethyl)thio-5-trifluorophenyl, 3-(2-carboxy-1-methylethyl)-5-trifluoromethylphenyl, 3-(2-carboxy-1-methylvinyl)-5-trifluoromethylphenyl, 3-(3-carboxy-1-methylpropyl)-5-trifluoromethylphenyl, 3-[(2-carboxyethyl)ethynyl]-5-trifluoromethylphenyl, 3-[(3-carboxypropyl)ethynyl]-5-trifluoromethylphenyl, 4-(3-carboxypropyl)-3-trifluoromethylphenyl, 4-(3-carboxymethylvinyl)-3-trifluoromethylphenyl, 3-(3-carboxypropyl)-5-trifluoromethylphenyl, 3-(3-carboxypropyl)-5-fluorophenyl, 3-(3-carboxypropyl)-5-chlorophenyl, 3-(3-carboxypropyl)-5-methylphenyl, 3-(3-carboxypropyl)-5-ethylphenyl, 3-(3-carboxypropyl)-5-trifluoromethoxyphenyl, 4-(3-carboxypropyl)-3-fluorophenyl, 4-(3-carboxypropyl)-3-chlorophenyl, 4-(3-carboxypropyl)-3-ethylphenyl, 4-(3-carboxypropyl)-2-ethylphenyl, 4-[(2-carboxyethyl)vinyl]-3-trifluoromethylphenyl, 4-(2-carboxybutynyl)-3-trifluoromethylphenyl, and 4-[(2-carboxyethyl-1,1-dimethyl)vinyl]-3-trifluoromethylphenyl.

$R^5$ and $R^6$ in the Formula ($Ar^{1a}$), the Formula ($Ar^{1b}$) or the Formula ($Ar^{1c}$) are each independently defined as a hydrogen atom, a halogen atom, an optionally substituted lower alkyl group, an optionally substituted lower alkoxy group, or a cyano group. A hydrogen atom, a halogen atom, a methyl group, an ethyl group, a trifluoromethyl group, and a trifluoromethoxy group are preferred, and a hydrogen atom, a methyl group, an ethyl group, a trifluoromethyl group are more preferred. As for a halogen atom, a fluorine atom, a chlorine atom, a bromine atom, and an iodine atom are preferred. A fluorine atom is more preferred. There is other embodiment in which a chlorine atom is more preferred. As for a combination of $R^5$ and $R^6$, combinations in which $R^5$ and $R^6$ are both hydrogen atom, $R^5$ is a hydrogen atom and $R^6$ is a halogen atom, or $R^5$ is a hydrogen atom and $R^6$ is a methyl group are preferred. A combination in which $R^5$ and $R^6$ are both a hydrogen atom is more preferred. There is other preferred embodiment in which $R^5$ is a hydrogen atom and $R^6$ is a methyl group. There is other preferred embodiment in which $R^5$ is a hydrogen atom and $R^6$ is a fluorine atom. There is other preferred embodiment in which $R^6$ is a hydrogen atom and $R^6$ is a chlorine atom. There is other preferred embodiment in which $R^5$ is a hydrogen atom and $R^6$ is an ethyl group. There is other preferred embodiment in which $R^5$ is a hydrogen atom and $R^6$ is a trifluoromethyl group. There is other preferred embodiment in which $R^5$ is a hydrogen atom and $R^6$ is a trifluoromethoxy group. There is other preferred embodiment in which both $R^5$ and $R^6$ are a chloro atom. When the carbon atom bonded to $(CH_2)_p$ is position 1, examples of the Formula ($Ar^{1a}$) include phenyl-1,2-diyl, phenyl-1,3-diyl, phenyl-1,4-diyl, 2-methylphenyl-1,4-diyl, 2-methylphenyl-1,5-diyl, 3-methylphenyl-1,4-diyl, 3-methylphenyl-1,5-diyl, 2-ethylphenyl-1,4-diyl, 2-ethylphenyl-1,5-diyl, 3-ethylphenyl-1,4-diyl, 3-ethylphenyl-1,5-diyl, 2-trifluoromethylphenyl-1,4-diyl, 2-trifluoromethylphenyl-1,5-diyl, 3-trifluoromethylphenyl-1,4-diyl, 3-trifluoromethylphenyl-1,5-diyl, 2-fluorophenyl-1,4-diyl, 2-fluorophenyl-1,5-diyl, 3-fluorophenyl-1,4-diyl, 3-fluorophenyl-1,5-diyl, 2-chlorophenyl-1,4-diyl, 2-chlorophenyl-1,5-diyl, 3-chlorophenyl-1,4-diyl, 3-chlorophenyl-1,5-diyl, 2,4-difluorophenyl-1,5-diyl, 2-trifluoromethoxyphenyl-1,4-diyl, 2,6-dichlorophenyl-1,4-diyl, 2,5-difluorophenyl-1,4-diyl, 3-trifluoromethyl-1,6-diyl, 4-trifluoromethyl-1,6-diyl, and 2,4-dichloromethyl-1,6-diyl. When the carbon atom bonded to $(CH_2)_p$ is position 2, examples of the Formula ($Ar^{1b}$) include thiophen-2,5-diyl, 5-chlorothiophen-2,4-diyl, and 5-trifluoromethylthiophen-2,4-diyl. As for the Formula ($Ar^{1c}$), pyridin-3,5-diyl is exemplified.

$R^7$ and $R^8$ in the Formula ($Ar^{2a}$), the Formula ($Ar^{2b}$) or the Formula ($Ar^{2c}$) are each independently defined as a hydrogen atom, a hydroxyl group, a halogen atom, an optionally substituted lower alkyl group, an optionally substituted lower alkoxy group, an optionally substituted amino group, a nitro group, a cyano group, $SOCH_3$ group, $SO_2CH_3$ group, a lower acyl group, or $R^7$ and $R^8$ may together form —COOCH$_2$— and —CH$_2$CH$_2$O—. Preferred examples include a hydrogen atom, a hydroxyl group, a halogen atom, a methyl group, an ethyl group, a trifluoromethyl group, a trifluoromethoxy group, a methoxy group, a nitro group, or an amino group, and more preferred examples include a hydrogen atom, a fluorine atom, a chlorine atom, a methyl group, and an ethyl group. As for a halogen atom, a fluorine atom, a chlorine atom, a bromine atom, and an iodine atom are preferred, and a fluorine atom is still more preferred. There is other embodiment in which a chlorine atom is still more preferred. There is other embodiment in which a bromine atom is still more preferred. As for a preferred combination of $R^7$ and $R^8$, a combination in which they are both a hydrogen atom, or $R^7$ is a hydrogen atom and $R^8$ is any one of a hydroxyl group, a halogen atom, a methyl group, an ethyl group, a trifluoromethyl group, a trifluoromethoxy group, a methoxy group, a nitro group, or an amino group is preferred. More preferred is combination in which both $R^7$ and $R^8$ are a hydrogen atom. There is other preferred embodiment in which $R^7$ is a hydrogen atom and $R^8$ is a hydroxyl group. There is other preferred embodiment in which $R^7$ is a hydrogen atom and $R^8$ is a fluorine atom. There is other preferred embodiment in which $R^7$ is a hydrogen atom and $R^8$ is a chlorine atom. There is other preferred embodiment in which $R^7$ is a hydrogen atom and $R^8$ is a methyl group. There is other preferred embodiment in which $R^7$ is a hydrogen atom and $R^8$ is an ethyl group. There is other preferred embodiment in which $R^7$ is a hydrogen atom and $R^8$ is a trifluoromethyl group. There is other preferred embodiment in which $R^7$ is a hydrogen atom and $R^8$ is a trifluoromethoxy group. There is other preferred embodiment in which both $R^7$ and $R^8$ are a fluorine atom. There is other preferred embodiment in which both $R^7$ and $R^8$ are a chlorine atom.

$R^9$ in the Formula ($Ar^{2a}$) or the Formula ($Ar^{2b}$) is defined as a hydrogen atom, -J-COOR$^{10}$. Preferably, it is -J-COOR$^{10}$.

J is a covalent bond, an optionally substituted alkylene having 1 to 5 carbon atoms, an optionally substituted alkenylene having 2 to 5 carbon atoms, or an optionally substituted alkynylene having 2 to 5 carbon atoms, and any one of the chemically allowed carbon atoms of the alkylene, alkenylene and alkynylene may be substituted with an oxygen atom, a sulfur atom, $NR^{11}$, $CONR^{11}$, or $NR^{11}CO$; J is preferably a covalent bond, methylene, ethylene, propan-1,3-diyl, n-butane-1,4-diyl, n-pentane-1,5-diyl, —CH$_2$CH$_2$C(CH$_3$)$_2$CH$_2$—, —CH═CH—, —CH═CHCH$_2$—, —CH═CHCH$_2$CH$_2$—, —CH═CHC(CH$_3$)$_2$CH$_2$—, —CH═CHCH$_2$CH$_2$CH$_2$—, —OCH$_2$—, —OCH$_2$CH$_2$—, —OCH$_2$CH$_2$CH$_2$—, —C≡CCH$_2$—, —C≡CCH$_2$CH$_2$—, —C≡CCH$_2$CH$_2$CH$_2$—, —SCH$_2$—, —SCH$_2$CH$_2$—, —SCH$_2$CH$_2$CH$_2$—, —NHCH$_2$—, —NHCH$_2$CH$_2$—, —NHCH$_2$CH$_2$CH$_2$—, —NHCOCH$_2$—, —NHCOCH$_2$CH$_2$—, —CONHCH$_2$—, —CONHCH$_2$CH$_2$—C(CH$_3$)═CH—, —C(CH$_3$)═CHCH$_2$—, —CH(CH$_3$)CH$_2$— or —CH(CH$_3$)CH$_2$CH$_2$—, and more preferably a covalent bond, methylene, ethylene. There is other embodiment in which J is more preferably a covalent bond. There is other embodiment in which J is more preferably methylene. There is other embodiment in which J is more preferably ethylene.

There is other embodiment in which J is more preferably propan-1,3-diyl.

$R^{11}$ is defined as a hydrogen atom, or a lower alkyl group. A hydrogen atom, a methyl group, an ethyl group, a propyl group, an isopropyl group, or a t-butyl group is preferred and a hydrogen atom, a methyl group, or an ethyl group is still more preferred. There is other embodiment in which $R^{11}$ is more preferably a methyl group. There is other embodiment in which $R^{11}$ is more preferably an ethyl group.

$R^{10}$ is defined as a hydrogen atom, or a lower alkyl group. A hydrogen atom, a methyl group, an ethyl group, a propyl group, an isopropyl group, or a t-butyl group is preferred and a hydrogen atom, a methyl group, and an ethyl group is still more preferred. There is other embodiment in which $R^{10}$ is more preferably a hydrogen atom. There is other embodiment in which $R^{10}$ is more preferably a methyl group. There is other embodiment in which $R^{10}$ is more preferably an ethyl group.

$R^2$ is defined as hydrogen atom or a lower alkyl group, and a lower alkyl group is preferred. Among the lower alkyl groups, a methyl group or an ethyl group is more preferred, and a methyl group is still more preferred. There is other embodiment in which a hydrogen atom is preferred.

With respect to a combination of $R^1$ and $R^2$, preferred combinations include the Formula ($R^{1a}$) and a hydrogen atom, the Formula ($R^{1b}$) and a hydrogen atom, the Formula ($R^{1a}$) and a lower alkyl group, the Formula ($R^{1b}$) and a lower alkyl group, the Formula ($R^{1a}$) and a methyl group, the Formula ($R^{1b}$) and a methyl group, the Formula ($R^{1a}$) and an ethyl group, or the Formula ($R^{1b}$) and an ethyl group. The combination of the Formula ($R^{1a}$) and a methyl group is more preferred. Further, the combination of the Formula ($R^{1b}$) and a methyl group is also more preferred. There is other embodiment in which combination of the Formula ($R^{1a}$) and a hydrogen atom, or combination of the Formula ($R^{1b}$) and a hydrogen atom is preferred.

$R^3$ and $R^4$ are independently defined as a lower alkylene group, or they together form alkylene having 2 to 6 carbon atoms. A combination in which R and $R^4$ both are a methyl group is preferred. There is other embodiment in which $R^3$ and $R^4$ together form ethylene. There is other embodiment in which $R^3$ and $R^4$ together form propan-1,3-diyl.

m is defined as any integer of 1 to 3. Preferably, it is 1 or 3, and more preferably 1. There is other embodiment in which it is more preferably 3.

The carbon atom indicated with the symbol "*" for the compounds represented by the Formula (1) is an asymmetric carbon. Regarding a stereoconfiguration of such asymmetric carbon, S configuration and R configuration are exemplified. R configuration is preferred. The compounds of the present invention include any optically pure optical isomers, any mixture comprising the optical isomers, or racemate thereof that are originated from an asymmetric carbon. In addition, according to types of a substituent, the compounds of the present invention may have one or more asymmetric carbon. Stereoconfiguration other than the asymmetric carbon specified above is not specifically limited and any stereoconfiguration can be exemplified. The compounds of the present invention include stereoisomers originated from such one or more asymmetric carbon, including stereoisomers such as optical isomers in pure form, diastereoisomers, etc., any mixture comprising the stereoisomers, or racemate thereof, etc. Further, when the compounds of the present invention have an olefinic double bond or a cyclic structure, two or more stereoisomers may be present. Still, any stereoisomers in pure form or any mixture comprising the stereoisomers all falls within the scope of the compounds of the present invention. Still further, some compounds of the present invention that are represented by the Formula (1) may be present as a tautomer. Presence of such tautomer will be obvious to a skilled person in the pertinent art and the tautomer also falls within the scope of the compounds of the present invention.

A prodrug is a compound which can reproduce the compounds of the present invention in accordance with its chemical or biochemical hydrolysis in a living body. For example, when the compounds of the Formula (1) have a carboxyl group, examples of a prodrug include a compound in which the carboxyl group is converted to a suitable ester. Specific examples of an ester include methyl ester, ethyl ester, n-propyl ester, isopropyl ester, n-butyl ester, n-pentyl ester, n-hexyl ester, pivaloyloxymethyl ester, acetyloxymethyl ester, cyclohexylacetyloxymethyl ester, 1-methylcyclohexylcarbonyloxymethyl ester, ethyloxycarbonyloxy-1-ethyl ester, or cyclohexyloxycarbonyloxy-1-ethyl ester and the like.

The compounds represented by the Formula (1) may be also present as a salt. With respect to a salt of the compounds of the present invention, their type is not specifically limited. It can be any of an acid addition salt or a base addition salt. It can be also present in counter ion form in a molecule. Pharmaceutically acceptable salts are particularly preferable. Type of an acid and a base which can form a pharmaceutically acceptable salt is well known to a skilled person in the pertinent art, and examples include those described in J. Pharm. Sci., 1-19 (1977) written by Berge et al. Examples of an acid addition salt include a mineral acid salt such as hydrochloric acid salt, hydrobromic acid salt, hydroiodic acid salt, nitric acid salt, sulfuric acid salt, hydrogen sulfate salt, phosphate salt, or hydrogen phosphate salt, and an organic acid salt such as acetic acid salt, trifluoroacetic acid salt, gluconic acid salt, lactic acid salt, salicylic acid salt, citric acid salt, tartaric acid salt, ascorbic acid salt, succinic acid salt, maleic acid salt, fumaric acid salt, formic acid salt, benzoic acid salt, methanesulfonic acid salt, ethanesulfonic acid salt, or p-toluenesulfonic acid salt and the like. When one or more substituent comprises an acidic moiety, examples of a base addition salt include an alkali metal salt such as sodium salt, or potassium salt and the like, an alkaline earth metal salt such as magnesium salt, or calcium salt and the like, an organic amine salt such as triethylamine salt, pyridine salt, procaine salt, picoline salt, dicyclohexylamine salt, diethanolamine salt, triethanolamine salt, or tris(hydroxymethyl)aminomethane salt and the like, or an amino acid addition salt such as arginine salt, lysine salt, ornithine salt, serine salt, glycine salt, aspartic acid salt, or glutamic acid salt and the like.

Combination of a substituent for the compounds represented by the Formula (1) is not specifically limited and preferred examples include the followings.

(a-1) A compound in which $R^2$ is a hydrogen atom, and each of $R^3$ and $R^4$ is methyl
(a-2) A compound in which each of $R^2$, $R^3$ and $R^4$ is methyl
(a-3) A compound in which $R^2$ is methyl, and $R^3$ and $R^4$ together form ethylene
(a-4) A compound in which $R^2$ is methyl and $R^3$ and $R^4$ together form propan-1,3-diyl
(b-1) A compound according to any of (a-1) to (a-4) in which A is phenyl
(b-2) A compound according to any of (a-1) to (a-4) in which A is naphthalen-2-yl
(b-3) A compound according to any of (a-1) to (a-4) in which A is 2,3-dihydroinden-2-yl
(b-4) A compound according to any of (a-1) to (a-4) in which A is 3-fluoro-4-methylphenyl
(b-5) A compound according to any of (a-1) to (a-4) in which A is 4-chloro3-fluorophenyl
(b-5) A compound according to any of (a-1) to (a-4) in which A is 3-fluoro-4-isopropylphenyl
(b-6) A compound according to any of (a-1) to (a-4) in which A is thiophen-2-yl
(b-7) A compound according to any of (a-1) to (a-4) in which A is thiophen-3-yl
(b-8) A compound according to any of (a-1) to (a-4) in which A is 2-fluorophenyl
(b-9) A compound according to any of (a-1) to (a-4) in which A is 3-fluorophenyl
(b-10) A compound according to any of (a-1) to (a-4) in which A is 4-fluorophenyl
(b-11) A compound according to any of (a-1) to (a-4) in which A is difluorophenyl
(c-1) A compound according to any of (b-1) to (b-11) in which $Ar^2$ is $Ar^{2a}$
(c-2) A compound according to any of (b-1) to (b-11) in which $Ar^2$ is $Ar^{2b}$
(c-3) A compound according to any of (b-1) to (b-11) in which $Ar^2$ is $Ar^{2c}$
(d-1) A compound according to any of (c-1) to (c-3) in which each of $R^7$ and $R^8$ is a hydrogen atom
(d-2) A compound according to any of (c-1) to (c-3) in which $R^7$ is a hydrogen atom and $R^8$ is a fluorine atom
(d-3) A compound according to any of (c-1) to (c-3) in which $R^7$ is a hydrogen atom and $R^8$ is a chlorine atom (d-4) A compound according to any of (c-1) to (c-3) in which $R^7$ is a hydrogen atom and $R^8$ is a methyl group
(d-5) A compound according to any of (c-1) to (c-3) in which $R^7$ is a hydrogen atom and $R^8$ is an ethyl group
(d-6) A compound according to any of (c-1) to (c-3) in which $R^7$ is a hydrogen atom and $R^8$ is a trifluoromethyl group
(d-7) A compound according to any of (c-1) to (c-3) in which $R^7$ is a hydrogen atom and $R^8$ is a trifluoromethoxy group
(e) A compound according to any of (d-1) to (d-7) in which $R^9$ is -J-COOR$^{10}$
(f-1) A compound according to (e) in which $R^{10}$ is a hydrogen atom
(f-2) A compound according to (e) in which $R^{10}$ is a lower alkyl group
(g-1) A compound according to (f-1) or (f-2) in which J is a covalent bond
(g-2) A compound according to (f-1) or (f-2) in which J is —CH$_2$—
(g-3) A compound according to (f-1) or (f-2) in which J is —CH$_2$CH$_2$—
(g-4) A compound according to (f-1) or (f-2) in which J is —CH=CH—
(g-5) A compound according to (f-1) or (f-2) in which J is —CH$_2$CH$_2$CH$_2$—
(g-6) A compound according to (f-1) or (f-2) in which J is —OCH$_2$—
(g-7) A compound according to (f-1) or (f-2) in which J is —OCH$_2$CH$_2$—
(g-8) A compound according to (f-1) or (f-2) in which J is —NHCH$_2$—
(g-9) A compound according to (f-1) or (f-2) in which J is —NHCH$_2$CH$_2$—
(g-10) A compound according to (f-1) or (f-2) in which J is —C≡CCH$_2$CH$_2$—
(g-11) A compound according to (f-1) or (f-2) in which J is —C≡CCH$_2$CH$_2$CH$_2$—
(h-1) A compound according to any of (g-1) to (g-11) in which p=0
(h-2) A compound according to any of (g-1) to (g-11) in which p=1
(i-1) A compound according to (h-1) or (h-2) in which m=1
(i-2) A compound according to (h-1) or (h-2) in which r=3
(j-1) A compound according to (i-1) or (i-2) in which $R^1$ is $R^{1a}$
(j-2) A compound according to (i-1) or (i-2) in which $R^1$ is $R^{1b}$
(k-1) A compound according to (j-1) in which $Ar^1$ is $Ar^{1a}$
(k-2) A compound according to (j-1) in which $Ar^1$ is $Ar^{1b}$
(k-3) A compound according to (j-1) in which $Ar^1$ is $Ar^{1c}$
(l-1) A compound according to any of (k-1) to (k-3) in which each of $R^5$ and $R^6$ is a hydrogen atom
(l-2) A compound according to any of (k-1) to (k-3) in which $R^5$ is a hydrogen atom and $R^6$ is a fluorine atom
(l-3) A compound according to any of (k-1) to (k-3) in which $R^5$ is a hydrogen atom and $R^6$ is a chlorine atom
(l-4) A compound according to any of (k-1) to (k-3) in which $R^5$ is a hydrogen atom and $R^6$ is a methyl group
(l-5) A compound according to any of (k-1) to (k-3) in which $R^5$ is a hydrogen atom and $R^6$ is an ethyl group
(l-6) A compound according to any of (k-1) to (k-3) in which $R^5$ is a hydrogen atom and $R^6$ is a trifluoromethyl group
(l-7) A compound according to any of (k-1) to (k-3) in which $R^5$ is a hydrogen atom and $R^6$ is a trifluoromethoxy group
(l-8) A compound according to any of (k-1) to (k-3) in which each of $R^5$ and $R^6$ is a fluorine atom
(l-9) A compound according to any of (k-1) to (k-3) in which each of $R^5$ and $R^6$ is a chlorine atom.

(Preparation Method)

Compounds of the present invention are novel compound that have never been disclosed in any literature. Although the compounds of the present invention represented by the Formula (1) can be prepared according to the method described below, for example, a method of preparing the compounds of the present invention is not limited thereto.

For respective reaction, reaction time is not specifically limited. Since the progress of a reaction can be easily monitored using an analytical means that is described below, each reaction can be terminated when the amount of a target compound is highest. Further, each reaction may be carried out under inert gas atmosphere such as nitrogen stream or argon stream, etc., if required. Further, for each reaction, a protective group can be introduced and also deprotection can be carried out, if required. A protective group and a method for protection and deprotection that can be used for each reaction are not specifically limited if they belong to a protective group and a method for protection and deprotection that is usually used for organic synthesis. For example, a publicly known protecting group and a method for protection and deprotection that are known in the literatures (e.g., Protective Groups in Organic Synthesis, Fourth Edition, 2007, John Wiley & Sons, Inc.) can be appropriately selected and used. Further, if required, any number of protection and deprotection can be carried out during any stage of the reaction process for preparing the compounds that are represented by the Formula (1).

Examples of a functional group which can be protected and/or deprotected during the reaction process for preparing the compounds that are represented by the Formula (1) include a carboxyl group (—COOH), a hydroxyl group (—OH), a carbonyl group (—CO—), a primary amino group (—NH$_2$), and a secondary amino group (—NH—) and the like. In addition, for a heterocycle like indole and indazole, etc., for example, an atom group including a nitrogen to which a hydrogen atom binds among the ring-constituting nitrogen atoms (i.e., —NH—) is also a functional group that can be protected and/or deprotected.

As for a protecting group for a carboxyl group, an alkyl group having 1 to 4 carbon atoms, an alkenyl group having 2 to 4 carbon atoms, an alkyl group having 1 to 4 carbon atoms that is substituted with an alkoxy group having 1 to 4 carbon atoms, or an alkyl group having 1 to 4 carbon atoms that is substituted with 1 to 3 halogen atoms, etc. can be mentioned. Specific examples include a methyl group, an ethyl group, a t-butyl group, an allyl group, a methoxyethyl group, or trichloroethyl group, etc.

As for a protecting group for a hydroxyl group, an alkyl group having 1 to 4 carbon atoms, an alkenyl group having 2 to 4 carbon atoms, an alkyl group having 1 to 4 carbon atoms that is substituted with an alkoxy group having 1 to 4 carbon atoms, an alkyl group having 1 to 4 carbon atoms that is substituted with 1 to 3 halogen atoms, a silyl group which is substituted with three different or the same alkyl groups having 1 to 4 carbon atoms or phenyl groups, a tetrahydropyranyl group, a tetrahydrofuryl group, a propargyl group, or a trimethylsilylethyl group, etc. can be mentioned. Specific examples include a methyl group, an ethyl group, a t-butyl group, an allyl group, a methoxymethyl (MOM) group, a methoxyethyl (MEM) group, a trichloroethyl group, phenyl group, a methylphenyl group, a chlorophenyl group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, a N-methylaminobenzyl group, a N,N-dimethylaminobenzyl group, a phenacyl group, a trityl group, a 1-ethoxyethyl (EE) group, a tetrahydropyranyl (THP) group, a tetrahydrofuryl group, a propargyl group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, an allyloxycarbonyl (Alloc) group, or a 2,2,2-trichloroethoxycarbonyl (Troc) group, etc.

As for a protecting group for a carbonyl group, an acetal group can be mentioned, for example. Specific examples include dimethyl acetal, diethyl acetal, or ethylene acetal, etc.

As for a protecting group for an amino group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, a N-methylaminobenzyl group, a N,N-dimethylaminobenzyl group, a phenacyl group, an acetyl group, a trifluoroacetyl group, a pivaloyl group, a benzoyl group, an allyloxycarbonyl group, a 2,2,2-trichloroethoxycarbonyl group, a benzyloxycarbonyl group, a t-butoxycarbonyl (Boc) group, a 1-methyl-1-(4-biphenyl)ethoxycarbonyl (Bpoc) group, a 9-fluorenylmethoxycarbonyl group, a benzyloxymethyl (BOM) group, or a 2-(trimethylsilyl)ethoxymethyl (SEM) group, etc. can be mentioned.

Further, with regard to a deprotection method that is generally used in the present invention, deprotection method 1 to 6 that will be described below can be exemplified.

Deprotection method 1. Deprotection reaction based on alkali hydrolysis is carried out, for example, by the reaction with a base in a polar solvent. Examples of a base include, for example, an alkali metal base such as sodium hydroxide, potassium hydroxide, lithium hydroxide, barium hydroxide, calcium hydroxide, sodium carbonate, potassium carbonate, sodium methoxide, or potassium t-butoxide, etc., and an organic base such as triethyl amine, etc. Use amount of these bases is generally 1 to 20 times, preferably 1 to 10 times the molar amount of a reaction compound for an alkali metal base, and 1 mole to excess molar amount for an organic base. The reaction solvent is generally an inert medium which does not interfere with a reaction. Preferably, the reaction is carried out in a polar solvent. Examples of the polar solvent include water, methanol, ethanol, tetrahydrofuran (THF), or dioxane and the like. A mixture thereof can be also used, if necessary. The reaction temperature is appropriately chosen between −10° C. to reflux temperature of a solvent, for example. The reaction time is generally 0.5 to 72 hours, preferably 1 to 48 hours when an alkali metal base is used. When an organic base is used, it is generally 5 hours to 14 days. Since the progress of reaction can be monitored by thin layer chromatography (TLC), high performance liquid chromatography (HPLC), etc., the reaction normally can be appropriately terminated when the amount of a target compound is highest.

Deprotection method 2. Deprotection reaction under acidic condition is carried out, for example, in an organic solvent such as dichloromethane, chloroform, dioxane, ethyl acetate, or anisole, etc. in the presence of an organic acid such as acetic acid, trifluoroacetic acid, methanesulfonic acid, or p-toluenesulfonic acid, etc., Lewis acid such as boron tribromide, boron trifluoride, aluminum bromide, or aluminum chloride and the like, or an inorganic acid such as hydrochloric acid, or sulfuric acid and the like or a mixture thereof at the temperature of −10 to 100° C. In addition, there is another method in which ethanethiol, or 1,2-ethanedithiol, etc. are added as an additive.

Deprotection method 3. Deprotection reaction based on hydrogenation can be carried out, for example, in an ether solvent such as tetrahydrofuran, dioxane, dimethoxy ethane, or diethyl ether, and the like, an alcohol solvent such as methanol, or ethanol, and the like, an aromatic solvent such as benzene, or toluene and the like, a ketone solvent such as acetone, or methyl ethyl ketone and the like, a nitrile solvent such as acetonitrile and the like, an amide solvent such as dimethylformamide, and the like, an ester solvent such as ethyl acetate and the like, water, acetic acid, or a mixed solvent comprising two or more of them in the presence of a catalyst such as palladium on carbon powder, platinum oxide, activated nickel and the like and hydrogen source such as atmospheric or pressurized hydrogen gas, ammonium formate, or hydrazine hydrate and the like at the temperature of −10 to 60° C.

Deprotection method 4. Deprotection reaction of a silyl group is carried out, for example, by using tetra-n-butyl ammonium fluoride and the like in an organic solvent which is miscible with water (e.g., tetrahydrofuran, or acetonitrile and the like) at the temperature of −10 to 60° C.

Deprotection method 5. Deprotection reaction using a metal is carried out in an acidic solvent, for example, in acetic acid, a buffer solution having pH 4.2-7.2, or a mixture solvent comprising them and an organic solvent such as tetrahydrofuran and the like in the presence of zinc powder with or without ultrasonication at the temperature of −10 to 60° C.

Deprotection method 6. Deprotection reaction using a metal complex is carried out, for example, in an organic solvent such as dichloromethane, dimethylformamide, tetrahydrofuran, ethyl acetate, acetonitrile, dioxane, or ethanol and the like, water, or a mixture solvent thereof, in the presence of a trapping agent such as tributyltin hydride, triethylsilane, dimedone, morpholine, diethylamine, or pyrrolidine and the like, an organic acid such as acetic acid, formic acid, or 2-ethylhexanoic acid and the like and/or an organic acid salt such as sodium 2-ethyl hexanoate, or potassium 2-ethylhexanoate, and the like, with or without a phosphine reagent such as triphenylphsophine and the like by using a metal complex such as tetrakis(triphenylphosphine)palladium(0), 2-chlorobis(triphenylphosphine)palladium(II), palladium(II) acetate, or chlorotris(triphenylphosphine)rhodium(I) and the like, at the temperature of −10 to 60° C.

The compounds that are represented by the Formula (1) can be produced according to reaction steps described in the following figures, for example. In the following figures, "Scheme" is "reaction scheme", "STEP" is "reaction step" and "OR" indicates "or". Thus, for example, "Scheme 1" indicates "scheme 1" and "STEP 1-1" indicates "Step 1-1".

Deprotection of the protecting group comprised in the Formula (2) can be easily carried out, for example, by using an established known method such as the above described Deprotection method 1 to 6 with reference to the literatures described above.

For example, for a conversion reaction from the compounds having the Formula (2) to the compounds having the Formula (1), when a deprotection is carried out based on ester hydrolysis, the hydrolysis is preferably carried out under basic or acidic condition. When an ester is a primary alkyl ester such as methyl ester, or ethyl ester and the like, hydrolysis is preferably carried out under basic condition. As for a base which is used for hydrolysis under basic condition, examples include alkali metal hydroxides such as sodium hydroxide, potassium hydroxide, or lithium hydroxide and the like, alkali earth metal hydroxides such as barium hydroxide, or calcium hydroxide and the like, alkali carbonates such as sodium carbonate, or potassium carbonate and the like, and alkali metal alkoxides such as sodium methoxide, or potassium t-butoxide and the like. Use amount of a base is preferably 1 to 20 moles, more preferably 1 to 10 moles compared to the compounds having the Formula (2). An inert solvent that can be used for hydrolysis reaction includes water, methanol, ethanol, tetrahydrofuran, dioxane and the like, and a mixture solvent thereof can be also used, if required. Reaction temperature varies depending on a starting compound, a base, a solvent and the like, and it can be in the range of a room temperature to reflux temperature of a solvent.

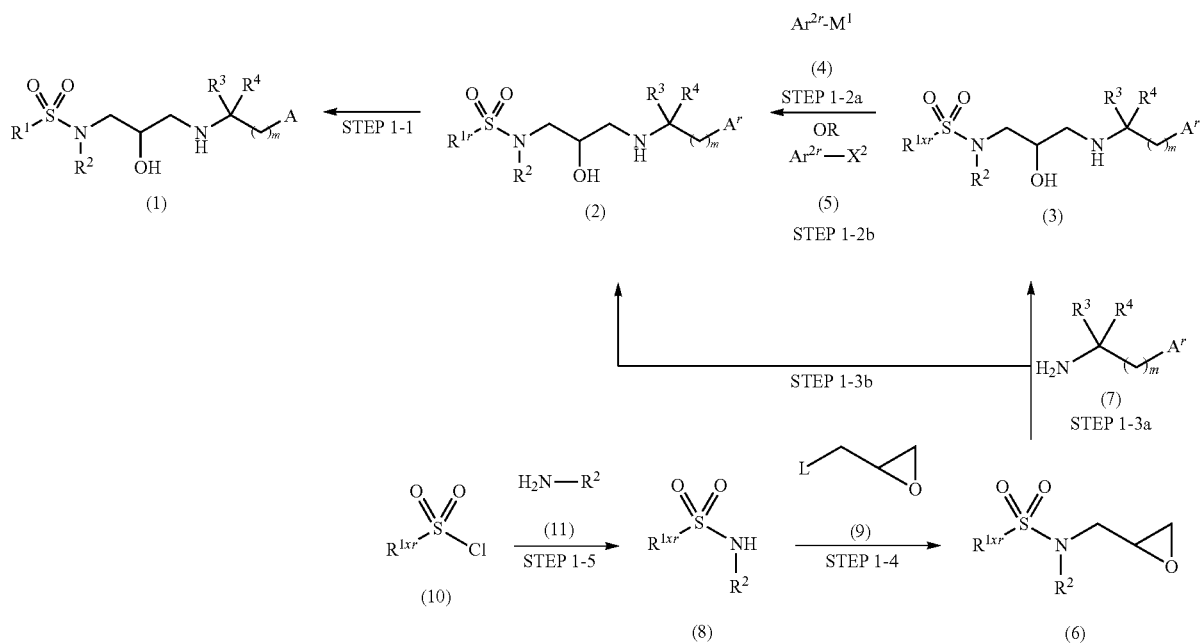

Scheme 1

For example, the compounds that are represented by the above described Formula (1) can be produced by deprotecting a protecting group of the compounds that are represented by the above described Formula (2) [wherein, $R^{1r}$ and $R^{2r}$ respectively have the same meaning as $R^1$ and $R^2$, or at least one of these groups may be protected; $A^r$ has the same meaning as A or at least one group may be protected; $R^3$, $R^4$, and m have the meanings same as the above.] (Step 1-1)

When an ester is a tertiary alkyl ester such as t-butyl ester and the like, it is preferable that a hydrolysis reaction is carried out under acidic condition. Examples of an acid which can be used for hydrolysis reaction under acidic condition include an inorganic acid such as hydrochloric acid, hydrogen chloride, or sulfuric acid, etc. and an organic acid such as trifluoroacetic acid and the like. Use amount of an acid is preferably 0.1 to excess moles, still preferably 1 to excess moles compared to the compounds having the Formula (2).

Examples of a solvent which can be used for the hydrolysis reaction include water, ethyl acetate, or dioxane and the like. A mixture solvent thereof can be also used, if necessary. Further, the reaction can be carried out without any solvent. Reaction temperature varies depending on a starting compound, an acid, a solvent and the like, and it can be in the range of −50° C. to reflux temperature of a solvent, preferably in the range of −20° C. to 50° C.

Further, when the compound having the Formula (2) comprises no protecting group, a skilled person in the pertinent art would easily understand that the compound having the Formula (2) corresponds to the compounds having the Formula (1).

When compounds having the Formula (1) comprise an alkoxycarbonyl group in part of the chemical structure of $R^1$, for example, a corresponding carboxylic acid and a corresponding alcohol can be used for an esterification reaction to provide the compounds having the Formula (2).

For an esterification reaction, a method in which dehydration is carried out in the presence of an acid catalyst, if required, and a reaction between carboxylic acid and alcohol is carried out can be mentioned. Examples of an acid catalyst which can be used for the reaction include an inorganic acid such as hydrochloric acid, hydrogen chloride, or sulfuric acid and the like, an organic acid such as p-toluenesulfonic acid and the like, and Lewis acid such as boron trifluoride diethyl ether complex, and the like. Use amount of an acid catalyst is 0.1 to excess moles compared to the carboxylic acid used. Use amount of an alcohol is 1 mole to excess moles compared to the carboxylic acid used. Example of an inert solvent which can be used for the reaction include a halogenated hydrocarbon solvent such as dichloromethane, chloroform, or 1,2-dichloroethane and the like, an ether solvent such as tetrahydrofuran, or dioxane and the like, and an aromatic hydrocarbon solvent such as benzene, toluene, xylene, or chlorobenzene and the like, and a mixture solvent comprising two or more of them can be also used. In addition, an alcohol which is used for the reaction can be also used as a solvent, and the reaction can be carried out without any solvent. With respect to a dehydration method which is employed for the esterification reaction, if required, a method in which a solvent such as benzene, toluene and the like which forms an azeotropic mixture with water are used and azeotropic water is removed by using Dean-Stark apparatus, etc. can be exemplified. Reaction temperature varies depending on a starting compound, a catalyst, a solvent and the like, and it normally can be in the range of −20° C. to reflux temperature of a solvent.

Carrying out an esterification reaction is not limited to the method described above. It can be carried out, for example, in view of "Esterification using an alcohol" (New Experimental Chemistry Series, Vol. 14, page 1002, The Chemical Society of Japan, Maruzen publishing company), "Esterification using an O-alkylating agent" (ibid, page 1002), "Esterification using a alkyl halide" (ibid, page 1008), and "Esterification reaction using a dehydrating agent" (ibid, Vol. 22, page 45), and the like.

Compounds having the Formula (2) in which $R^{1r}$ corresponds to $R^{1ar}$ [$R^{1ar}$ may have the same meaning as $R^{1a}$, or correspond to $R^{1a}$ of which one or more groups are protected.] can be produced by reacting the compounds having the Formula (3) in which $R^{1xr}$ corresponds to $Ar^{1xr}$—$(CH_2)_p$— [in the Formula, $R^{1xr}$ has the same meaning as $R^{1r}$ or represents $Ar^{1xr}$—$(CH_2)_p$— (provided that, $Ar^{1xr}$ corresponds to $Ar^1$ of which any one of hydrogen atoms which binds to carbon atom is replaced with a leaving group $X^1$, and one or more groups may be protected), $R^2$, $A^r$, $R^3$, $R^4$, and m have the same meanings as defined above.] with the compounds having the Formula (4) [in the Formula, $Ar^{2r}$ has the same meaning as $Ar^2$ or corresponds to $Ar^2$ of which at least one group is protected, and $M^1$ is a group represented by the Formula B $(OR^{B1})(OR^{B2})$ (provided that, $R^{B1}$ and $R^{B2}$ can be the same or different to each other and represent a hydrogen atom, or a lower alkyl group, or $R^{B1}$ and $R^{B2}$ may together form 1,1,2,2-tetramethylethylene group).] based on Suzuki reaction in the presence of a palladium catalyst (Step 1-2a).

With respect to the compounds having the Formula (3) that are used for the Suzuki reaction, examples of the leaving groups $X^1$ include a halogen group such as a chloro group, a bromo group, or an iodine group, or an optionally substituted alkylsulfonyloxy group such as a trifluoromethanesulfonyloxy group, etc. A bromo group, an iodine group, or a trifluoromethanesulfonyloxy group are preferred.

With respect to the compounds having the Formula (4) that are used for the Suzuki reaction, both $R^{B1}$ and $R^{B2}$ are preferably a hydrogen atom. In addition, according to other embodiment, it is preferable that $R^{B1}$ and $R^{B2}$ together form 1,1,2,2-tetramethylethylene group.

In addition, the compounds represented by the Formula (2) can be also produced by the method of Step 1-2b. Specifically, when the compounds represented by the Formula (3) have a bromine atom for a substituent of $R^{1xr}$, a known boration reaction with boronic ester is carried out for the compounds of the Formula (3) and the resulting compound is reacted with the compounds represented by the Formula (5) $Ar^{2r}$-$X^2$ [in the formula, $Ar^{2r}$ is as defined above and $X^2$ is a leaving group] according to the above described Suzuki reaction to give the compounds of the Formula (2) (Step 1-2b).

Examples of a palladium catalyst which can be used for the Suzuki reaction include tetrakis(triphenylphosphine)palladium, tetrakis(methyldiphenylphosphine)palladium, dichlorobis(triphenylphosphine)palladium, dichlorobis(tri-o-tolylphosphine)palladium, dichlorobis(tricyclohexylphosphine)palladium, dichlorobis(triethylphosphine)palladium, palladium acetate, palladium chloride, chlorobis(acetonitrile)palladium, tris(dibenzylideneacetone)dipalladium, or chlorobis(diphenylphosphinoferrocene)palladium and the like. Further, a catalyst that is prepared from palladium acetate, tris(dibenzylideneacetone)dipalladium, etc. and a certain ligand can be also used. Valency of palladium is 0 or +2, for example. Examples of a ligand for palladium include a phosphine ligand such as trifurylphosphine, tri(o-tolyl)phosphine, tri(cyclohexyl)phosphine, tri(t-butyl)phosphine, dicyclohexylphenylphosphine, 1,1'-bis(di-t-butylphosphino)ferrocene, 2-dicyclohexylphosphino-2'-dimethylamino-1,1'-biphenyl, or 2-(di-t-butylphosphino)biphenyl, etc. or a non-phosphine ligand such as imidazol-2-ylidene carbene and the like.

Amount of the palladium catalyst used for the Suzuki reaction is preferably 0.01-20 mol %, and more preferably 0.1-10 mol %. A base which can be used for the Suzuki reaction include, for example, sodium carbonate, potassium carbonate, cesium carbonate, cesium fluoride, potassium fluoride, potassium phosphate, potassium acetate, triethylamine, potassium hydroxide, sodium hydroxide, sodium methoxide, or lithium methoxide and the like.

An inert solvent used for the Suzuki reaction includes a hydrocarbon solvent such as toluene, xylene, or hexane and the like, a halogenated hydrocarbon solvent such as dichloromethane, or chloroform and the like, a sulfoxide solvent such as dimethylsulfoxide and the like, an amide solvent such as dimethylformamide and the like, an ether solvent such as tetrahydrofuran, dioxane, or diglyme and the like, an alcohol solvent such as methanol, or ethanol and the like, a nitrile solvent such as acetonitrile and the like, a ketone solvent such as acetone, or cyclohexanone and the like, an ester solvent such as ethyl acetate and the like, or a heterocyclic solvent such as pyridine and the like. Two or more of these organic solvents can be used as a mixture. In addition, with respect to a solvent system, any one of two-phase system comprising water and an organic solvent, water-comprising organic solvent, or homogeneous organic solvent system can be used.

Reaction temperature may vary depending on starting compounds, a catalyst, a base, a solvent, and the like. In general, the reaction is preferably carried out in the temperature range of 0° C. to 150° C. Preferably, it is in the temperature range of room temperature to 120° C.

Compounds having the Formula (3) can be produced by reacting the compounds having the Formula (6) [in the Formula, $R^{1xr}$ and $R^2$ are the same as defined above.] with the compounds having the Formula (7) [in the Formula, $A^r$, $R^3$, $R^4$, and m are the same as defined above.] based on an alkylation reaction (Step 1-3a).

The alkylation reaction can be carried out in the presence of an acid catalyst, if necessary. As an acid catalyst, a Lewis acid catalyst such as lithium perchlorate and the like is preferred.

The amount of an acid catalyst used for the alkylation reaction is preferably 0.01 to 10 equivalents, more preferably 0.1 to 2 equivalents compared to the compounds having the Formula (7).

A solvent which can be used for the alkylation reaction is not specifically limited if it is inert to the alkylation reaction. Examples thereof include a hydrocarbon solvent such as toluene, or xylene and the like, an ether solvent such as tetrahydrofuran, dioxane, or diglyme and the like, an alcohol solvent such as methanol, ethanol, 1-propanol, or 2-propanol and the like or a nitrile solvent such as acetonitrile and the like. In addition, two or more organic solvents can be used as a mixture. Preferably, it is toluene, ethanol, tetrahydrofuran, dioxane, acetonitrile and the like.

Reaction temperature varies depending on a starting compound, a catalyst, a solvent and the like, and it normally can be in the range of 0° C. to reflux temperature of a solvent, preferably in the range of room temperature to reflux temperature of a solvent.

The compounds having Formula (2) in which $R^{1r}$ is not $R^{1ar}$ can be produced by reacting the compounds having the Formula (6) in which $R^{1r}$ is not $R^{1ar}$ with the compounds having the Formula (7) in the same manner as Step 1-3a described above (Step 1-3b).

Compounds having the Formula (6) can be produced by reacting the compounds having the Formula (8) [in the Formula, $R^{1xr}$ and $R^2$ are the same as defined above.] with the compounds having the Formula (9) [in the Formula, L represents a leaving group.] based on an alkylation reaction (Step 1-4).

With respect to a stereoconfiguration of an asymmetric carbon that is present in a compound having the Formula (9) used for the alkylation reaction, R configuration or S configuration are exemplified. Any of optically pure optical isomers of the compounds having the Formula (9), any mixture of the optical isomer, or racemate thereof can be used.

As for a leaving group L, a halogen group such as a chloro group, a bromo group or an iodine group, etc., an optionally substituted alkylsulfonyloxy group such as a trifluoromethanesulfonyloxy group, or a methanesulfonyloxy group and the like, and an optionally substituted arylsulfonyloxy group such as a benzenesulfonyloxy group, a p-toluenesulfonyloxy group, or 3-nitrobenzenesulfonyloxy group and the like are exemplified. More preferred examples include a chloro group, p-toluenesulfonyloxy group, or 3-nitrobenzenesulfonyloxy group and the like and 3-nitrobenzenesulfonyloxy group is still more preferred.

As for a base which can be used for the alkylation reaction, alkali carbonate such as potassium carbonate, sodium carbonate, or cesium carbonate and the like are exemplified.

The use amount of the compounds having the Formula (9) for the alkylation reaction is preferably 0.5 to 10 times, more preferably 1 to 5 times the molar amount of the compounds having the Formula (8).

An inert solvent which can be used for the alkylation reaction includes a ketone solvent such as acetone and the like, a nitrile solvent such as acetonitrile and the like, an amide solvent such as dimethylformamide and the like. Dimethylformamide and the like is preferred.

Reaction temperature varies depending on a starting compound, a base, a solvent and the like, and it normally can be in the range of 0° C. to reflux temperature of a solvent, preferably in the range of room temperature to reflux temperature of a solvent.

Compounds having the Formula (8) can be produced by reacting the compounds having the Formula (10) [in the Formula, $R^{1xr}$ is the same as defined above.] with the compounds having the Formula (11) [in the Formula, $R^2$ is the same as defined above.] based on a sulfonylation reaction in the presence of a base, if necessary (Step 1-5).

As for a base which can be used if necessary for the sulfonylation reaction, an organic base such as triethylamine, or diisopropylethylamine and the like, and an inorganic base such as potassium carbonate, sodium carbonate and the like are exemplified. The use amount of the base is preferably 1 to 10 times, preferably 1 to 5 times the molar amount of the compounds having the Formula (10).

The use amount of the compounds having the Formula (11) for the sulfonylation reaction is preferably 0.1 to 20 times, more preferably 0.5 to 10 times the molar amount of the compounds having the Formula (10).

Most of the compounds that are represented by the Formula (10) are publicly known and commercially available. In addition, they can be easily produced from a commercially available compound according to an established known method for synthesizing sulfonyl halides as described in the literature (Experimental Chemistry Series, 4$^{th}$ Edition, Vol. 24, Chapter 7, Maruzen), etc.

Most of the compounds that are represented by the Formula (4) which are used for the above described Step 1-2a are publicly known and commercially available. In addition, they can be produced according to an established known method as described in the literature (Organic Syntheses Via Boranes, Volume 3 Suzuki Coupling, 2003, Aldrich Chemical Company, Inc.), etc.

Compounds having the Formula (4) in which $R^{B1}$ and $R^{B2}$ are a lower alkyl group, for example, can be produced by reacting the compounds that are represented by the Formula $Ar^{2r}$-$M^2$ [in the Formula, $Ar^{2r}$ is the same as defined above, and $M^2$ represents an alkali metal atom such as lithium and the like, or a monohalogenated alkali earth metal group such as monochloromagnesium group, monobromomagnesium group, or monoiodomagnesium group and the like.] with trialkyl borate. Examples of a lower alkyl group for trialkyl borate which is used for the reaction include a methyl group, an ethyl group, or an isopropyl group and the like, and an isopropyl group is preferred. Examples of an inert solvent which can be used for the reaction include a hydrocarbon solvent such as pentane, hexane, heptane, cyclohexane, benzene, or toluene and the like, and an ether solvent such as diethyl ether, tetrahydrofuran, 1,4-dioxane, 1,2-dimethoxyethane, or 1,2-diethoxyethane and the like. In addition, a mixture solvent comprising two or more of them can be also used. The amount of the trialkyl borate that is used for the reaction is 0.5 to 1.5 times the molar amount of the compounds that are represented by the Formula $Ar^{2r}$-$M^2$. Reaction temperature varies depending on a starting compound, a solvent and the like, and it normally can be in the range of −100° C. to room temperature, for example. The compounds represented by the Formula $Ar^{2r}$-M can be commercially obtained, or can be easily prepared according to a known preparation method.

For the compounds represented by the Formula (4) in which $R^{B1}$ and $R^{B2}$ are a hydrogen atom, they can be produced by hydrolysis of the compounds represented by the Formula (4) in which $R^{B1}$ and $R^{B2}$ are a lower alkyl group with mineral acid. Examples of mineral acids for the hydrolysis reaction include hydrochloric acid, sulfuric acid, phosphoric acid, and the like. With respect to a solvent which is used for the hydrolysis reaction, the solvent which is used for the method for producing the compound represented by the Formula (4) in which $R^{B1}$ and $R^{B2}$ are a lower alkyl group can be exemplified. The reaction temperature varies depending on a reacting compound, a solvent, and the like. In general, it can be −20° C. to 50° C.

Most of the compounds having the Formula (4) in which $R^{B1}$ and $R^{B2}$ together form 1,1,2,2-tetramethylethylene group are commercially obtainable. In addition, they can be produced by reacting the compounds that are represented by the Formula $Ar^{2r}$-$X^2$ [in the Formula, $Ar^{2r}$ and $X^2$ are the same as defined above.] with a boron compound in the presence of a palladium catalyst. As for a palladium catalyst which can be used for the reaction, those described for the above Step 1-2 can be exemplified. Further, a catalyst that is prepared from palladium acetate, tris(dibenzylideneacetone)dipalladium, etc. and a certain ligand can be also used. Valency of palladium is 0 or +2, for example. As for a ligand for palladium, those described for the above Step 1-2 can be exemplified.

As for a leaving group $X^2$, a halogen group such as a chloro group, a bromo group or an iodine group, etc., or an optionally substituted alkylsulfonyloxy group such as a trifluoromethanesulfonyloxy group and the like are exemplified. Preferred examples include a bromo group, an iodine group, or a trifluoromethanesulfonyloxy group and the like.

Amount of the palladium catalyst used for the reaction is preferably 0.01-20 mol %, and more preferably 0.1-10 mol %.

A boron compound used for the reaction includes 4,4,5,5-tetramethyl-1,3,2-dioxaborolane, or bis(pinacolato)diboron and the like.

A base which can be used for the reaction includes, for example, sodium carbonate, potassium carbonate, cesium carbonate, cesium fluoride, potassium fluoride, potassium phosphate, potassium acetate, triethylamine, potassium hydroxide, sodium hydroxide, sodium methoxide, or lithium methoxide and the like.

Examples of an inert solvent used for the reaction include a hydrocarbon solvent such as toluene, xylene, or hexane and the like, a halogenated hydrocarbon solvent such as dichloromethane, or chloroform and the like, a sulfoxide solvent such as dimethylsulfoxide and the like, an amide solvent such as dimethylformamide and the like, an ether solvent such as tetrahydrofuran, dioxane, or diglyme and the like, an alcohol solvent such as methanol, or ethanol and the like, a nitrile solvent such as acetonitrile and the like, a ketone solvent such as acetone, or cyclohexanone and the like, an ester solvent such as ethyl acetate and the like, or a heterocyclic solvent such as pyridine and the like. Two or more of these organic solvent can be used as a mixture. In addition, with respect to a solvent system, any one of two-phase system comprising water and an organic solvent, water-comprising organic solvent, or homogeneous organic solvent system can be used.

Reaction temperature may vary depending on starting compounds, a catalyst, a base, a solvent, and the like. In general, the reaction is preferably carried out in the temperature range of 0° C. to 150° C. Preferably, it is in the temperature range of room temperature to 120° C.

Most of the compounds that are represented by the Formula (5) and used for the above Step 1-2b are well known and commercially obtainable, or can be easily prepared according to a known preparation method.

In addition, for the Formulae (2), (3), (6), and (8), substituents can be converted within the scope of $R^{1xr}$ described above based on a method known for each Formula.

Most of the compounds having the Formula (7) that are used for the above Step 1-3a or Step 1-3b are well known, commercially available or can be produced according to established known methods, for example, by following reaction steps described in the following figures. In the following figures, "Scheme" is "reaction scheme". For example, "Scheme 2" indicates "scheme 2". Further, "STEP" is "reaction step" and "STEP 2-1" indicates "step 2-1".

Scheme 2

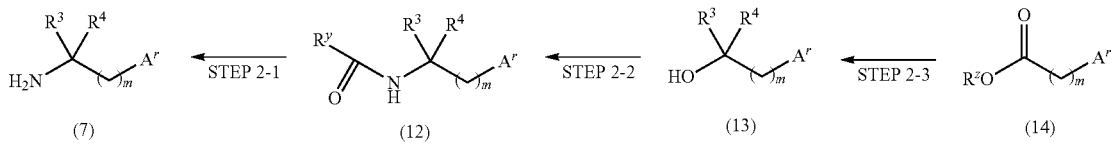

(7) (12) (13) (14)

For example, the compounds that are represented by the above described Formula (7) can be produced by hydrolysis reaction of the compounds that are represented by the above described Formula (12) [wherein, $R^y$ represents a hydrogen atom, or a lower alkyl group and $R^3$, $R^4$, $A^r$ and m have the meanings same as the above.] (Step 2-1).

As for a base which is used for the hydrolysis reaction, an alkali hydroxide such as sodium hydroxide, potassium hydroxide, lithium hydroxide, or barium hydroxide and the like is exemplified. The use amount of a base is preferably 1 to 30 times, preferably 5 to 15 times the molar amount of the compounds having the Formula (12). Examples of $R^y$ include a hydrogen atom, or a methyl group and the like.

A solvent which can be used for the hydrolysis reaction is not specifically limited if it is inert to the hydrolysis reaction. Examples thereof include an alcohol solvent such as methanol, ethanol, 1-propanol, 2-propanol, or ethylene glycol and the like, or a mixture solvent comprising them and water.

Reaction temperature may vary depending on starting compounds, a base, a solvent, and the like. In general, the reaction is preferably carried out in the temperature range of room temperature to reflux temperature of a solvent.

Further, for preparing the compounds represented by the Formula (7), a method of heating the compounds of the Formula (12) which have a chloromethyl group as $R^y$ with thiourea in acetic acid can be exemplified. In addition, for preparing the compounds represented by the Formula (7), a method of treating the compounds of the Formula (12) which have a 2-nitrobenzyl group as $R^y$ with palladium on carbon in acetic acid under hydrogen atmosphere and then heating them in acetic acid can be exemplified.

The compounds that are represented by the above described Formula (12) can be produced by Ritter reaction of the compounds that are represented by the Formula (13) [wherein, $R^3$, $R^4$, $A^r$ and m have the meanings same as the above.] (Step 2-2).

As for a cyano compound used for the Ritter reaction, hydrogen cyanide, acetonitrile, chloroacetonitrile, 2-nitrophenylacetonitrile, and the like are exemplified. In addition, hydrogen cyanide which is produced in a reaction system by adding mineral acid such as sulfuric acid to an alkali cyanide such as sodium cyanide, potassium cyanide and the like can be used without isolation.

The cyano compound for the Ritter reaction is used in an amount of 1 to 10 times, preferably 1 to 5 times the molar amount of the compounds represented by the Formula (13).

As for an acid used for the Ritter reaction, sulfuric acid and the like is exemplified. The acid for the Ritter reaction is used in an amount of 1 to 10 times, preferably 1 to 5 times the molar amount of the compounds represented by the Formula (13).

As for a solvent used for the Ritter reaction, acetic acid and the like is exemplified.

Reaction temperature may vary depending on starting compounds, an acid, a solvent, and the like. In general, the reaction is preferably carried out in the temperature range of $-100°$ C. to $100°$ C. Preferably, it is in the temperature range of $-50°$ C. to $50°$ C.

The compounds that are represented by the Formula (13) can be produced by treating the compounds that are represented by the Formula (14) [wherein, $R^z$ is a lower alkyl group and Ar and m have the meanings same as the above.] with an organometallic reagent such as alkyllithium or alkylmagnesium halide and the like (Step 2-3). Examples of $R^z$ include a methyl group, or an ethyl group and the like.

The amount of an organometallic reagent used for the reaction is preferably 2 to 20 times, preferably 2 to 10 times the molar amount of the compounds having the Formula (14).

Examples of an inert solvent which can be used for the reaction include a hydrocarbon solvent such as pentane, hexane, heptane, cyclohexane, benzene, or toluene and the like, and an ether solvent such as diethyl ether, tetrahydrofuran, 1,4-dioxane, 1,2-dimethoxyethane, or 1,2-diethoxyethane and the like. In addition, a mixture solvent comprising two or more of the organic solvents can be also used.

Reaction temperature may vary depending on starting compounds, a solvent, and the like. In general, the reaction is preferably carried out in the temperature range of $-100°$ C. to $100°$ C. Preferably, it is in the temperature range of $-50°$ C. to $50°$ C.

Most of the compounds that are represented by the Formula (14) are publicly known and commercially available. In addition, they can be easily produced from commercially available compounds according to a known method for synthesizing esters as described in the literature (Experimental Chemistry Series, $4^{th}$ Edition, Vol. 22, Chapter 1, Maruzen), etc.

The compounds of the present invention that are obtained according to the descriptions above, starting compounds and intermediates thereof can be isolated and purified by a general method such as extraction, distillation, and chromatography, etc.

With respect to a method of producing an optically active material of the compounds that are represented by the Formula (1), a method using an optically active material of the compounds that are represented by the Formula (9) for the above Step 1-4 can be exemplified. Optically active material of the compounds that are represented by the Formula (9) are mostly known, commercially available or can be easily produced according to an established known method. In addition, there is a method by which the racemates or mixture comprising the optical isomers of the compounds having the Formula (1) or reaction intermediates thereof are resolved into optically active isomers by following a generally known method. Such method includes a high performance liquid chromatography (HPLC) method using an optically active column, and a method of resolving and purifying diastereomers that are produced by condensing with an optically active reagent, followed by dissociating them, etc. When a reaction intermediate is separated to give an optically active form, the preparation method as described in the above can be carried out to produce the optically active compounds that are represented by the Formula (1).

Since the compounds that are represented by the Formula (1) have an amino group in the chemical structure, an acid addition salt can be prepared by an established known method such as mixing the compounds that are represented by the Formula (1) with an acid in a solvent, for example. Types of an acid addition salt are the same as those described above. The amount of an acid used for producing an acid addition salt is, for example, 0.1 to 10 equivalents compared to the compounds that are represented by the Formula (1). As for a solvent which can be used for the reaction, water and a water-miscible inert organic solvent such as methanol, ethanol, acetone, dioxane, and the like are exemplified. A mixture comprising two or more of them can be also used.

In addition, when the compounds that are represented by the Formula (1) comprise an acidic functional group such as a carboxyl group, or a phenolic hydroxyl group and the like, a base addition salt can be produced by an established known method, for example, mixing the compounds that are represented by the Formula (1) with a base in a solvent; etc. Types of a base addition salt are the same as those described above. The amount of a base used for producing a base addition salt is, for example, 0.1 to 10 equivalents compared to the compounds that are represented by the Formula (1). As for a solvent which can be used for the reaction, water and a water-miscible inert organic solvent such as methanol, ethanol, acetone, dioxane, and the like are exemplified. A mixture comprising two or more of them can be also used.

A solution comprising the acid addition salt or the base addition salt obtained by the above described method can be concentrated or further added with a water-miscible organic solvent which lowers solubility of dissolved salts (e.g., butanol, ethylmethyl ketone and the like) to obtain a solid salt.

As shown in the following Examples, the compounds of the present invention and the pharmaceutically acceptable salts thereof show no toxicity while exhibiting the CaSR function suppressing activity. Therefore, the compounds and the salts are useful as an effective component for a medicament.

The compounds of the present invention or pharmaceutically acceptable salt are expected to have an activity of promoting secretion of PTH by acting on CaSR of parathyroid gland. Further, the compounds of the present invention or pharmaceutically acceptable salt are expected to have an activity of systemically increasing bone mineral density and bone strength. The activity of promoting secretion of PTH by the compounds of the present invention or pharmaceutically acceptable salt can be evaluated by following PTH concentration in culture, using parathyroid cells that are harvested from animals like a bovine, a monkey and the like and then cultured. In addition, for the evaluation, change in concentration of PTH in blood can be also followed by using an experimental animal such as a rat, a monkey and the like. Further, the activity of increasing bone mineral density and bone strength by the compounds of the present invention or pharmaceutically acceptable salt thereof can be evaluated by, for example, following bone mineral density or bone strength of limb bones or vertebrae using a disease-model animal such as a model rat having reduced bone mass after oophorectomy.

A medicament of the present invention which comprises a compound represented by the Formula (1) or a pharmaceutically acceptable salt as an effective component can promote bone formation in vertebrates including human, preferably mammals. For example, the medicament of the present invention is useful for the prophylaxis and/or treatment of a bone disorder such as osteoporosis, etc. Further, the medicament of the present invention is useful as a medicament for promoting regeneration of bone.

As for a bone disorder, a disorder showing reduced bone mineral density and/or deterioration in bone tissues, and/or reduced bone strength, etc. that is caused by uncoupling between bone resorption and bone formation in bone remodeling due to various reasons can be mentioned. As a representative example of such bone disorder, osteoporosis can be mentioned.

Osteoporosis is a skeletal disorder characterized by decreased bone strength and high risk for bone fracture, and it indicates the disorder defined by American National Institute of Health (NIH) Consensus Conference in 2000 ("Guidelines of Prevention and Treatment of Osteoporosis, 2006 edition", by Committee for Establishing Guidelines of Prevention and Treatment of Osteoporosis, published by Life Science, 2006, Japan). Osteoporosis is generally classified into primary osteoporosis having no basic disorder, and secondary osteoporosis which follows other disorders such as endocrine disorder and blood dyscrasia, etc.

Primary osteoporosis includes juvenile osteoporosis and degenerative osteoporosis. Examples of degenerative osteoporosis include postmenopausal or post oophorectomy osteoporosis, and senile osteoporosis.

Secondary osteoporosis includes immobile osteoporosis due to prolonged immobility, weightless condition, etc., drug-related osteoporosis due to long-term administration of corticosteroid and the like, osteoporosis due to endocrine disorders such as Cushing's disease due to over-secretion of endogenous steroids, hypogonadism, or primary hyperparathyroidism, secondary hyperparathyroidism, hyperthyroidism, hypoparathyroidism, renal osteodystrophy, diabetes, etc., osteoporosis due to blood dyscrasia such as multiple myeloma, malignant lymphoid and the like, osteoporosis due to inflammatory disorders such as rheumatoid arthritis, etc., and osteoporosis due to genetic disorders such as osteogenesis imperfecta, homocystinuria, Marfan's syndrome, and the like.

Bone disorders other than osteoporosis include osteomalacia, osteitis fibrosa, bone aplasia, dialyitic bone disorder, hypoparathyroidism, osteopenia due to tumors such as multiple myeloma, etc., osteopenia due to administration of drugs such as steroids, etc., osteopenia and arthritis due to inflammation, periodontal disease, bone metastasis of cancer, hypercalcemia, Paget's disease of bone, ankylosing spondylitis, osteogenesis imperfecta, bone defect (alveolar bone defect, mandibular defect, childhood paroxysmal bone defect, etc.), reumatoid arthritis, and osteoarthritis, rupture in joint tissues, for example.

Further, abnormality in bone tissues that is caused by physical load is also included as other bone disorders. Examples of such bone disorder include, for example, bone fracture, refracture, and the like. In addition, femoral neck fracture, vertebral fracture, distal radial fracture, and proximal humeral fracture, all originating from osteoporosis, are also included in the scope of other bone disorders.

In addition to the above described disorders, any disorder showing reduced bone mineral density and/or deterioration in bone tissues, and/or reduced bone strength and the like due to uncoupling between bone resorption and bone formation in bone remodeling is included in the term "bone disorder" described in the present specification, and it is a subject for the prophylaxis and/or treatment with the medicament of the present invention.

In addition to the prophylaxis and/or treatment of the bone disorders described above, the medicament of the present invention can be used for promoting bone regeneration during various surgical procedures, including bone restoration and/or bone reconstruction after surgical removal of primary malignant tumors such as myeloma, osteosarcoma, chondrosarcoma, Ewing's sarcoma, malignant fibrous histiocytoma, fibrosarcoma and etc., or of focus in bone having metastatic lung cancer, stomach cancer, breast cancer, liver cancer and the like.

Further, examples of surgical procedures include joint replacement, spinal canal restoration (spinal fusion, intervertebral fusion, posterior lumbar interbody fusion (PLIF), posterior lumbar fusion (PLF), transforaminal lumbar interbody fusion (TLIF), etc.), spinal canal expansion, osteotomy, bone extension, dental reconstruction, skull defect restoration, skull formation, iliac bone spacer fusion using a bony support, bone transplantation between heterogeneous species, bone transplantation between homogenous species, autogenous bone transplantation and the like. In addition, bone transplantation replacement therapy is also included as a surgical procedure. The term "surgical procedure" used in the present specification should be understood in the broadest sense including open surgery that is practiced in surgical areas including brain surgery, thoracic surgery, or abdominal surgery, etc., orthopedic surgery, plastic surgery and the like (e.g., open chest operation, or operation for replacing artificial joint, etc.) and closed surgery (e.g., fixation of a fracture site using a plaster bandage, etc.) and the like, and in no case it is understood in limited ways.

Further, in addition to medical procedures described above, any procedures expected to have improvement in QOL, ADL and life prognosis of a patient by promoting generation of bone are a subject for the application of the medicament of the present invention.

The medicament of the present invention can be also used, in addition to the prophylaxis and/or treatment of the disorders described above, as a pharmaceutical agent for treating various disorders that can be improved by increasing PTH concentration in blood. Examples of such disorders include idiopathic hypoparathyroidism, spondylosis deformans, neutropenia, thrombocytopenia, psoriasisscabies, alopecia and the like.

The medicament of the present invention is preferably used as an agent for promoting secretion of PTH. In addition, the medicament of the present invention is more preferably used for the prophylaxis and/or treatment of bone disorders. The medicament of the present invention is still more preferably used for the prophylaxis and/or treatment of osteoporosis and/or bone fracture and/or hypoparathyroidism. Further, it would be easily understood by a skilled person in the pertinent art that the medicament for the prophylaxis and/or treatment of the present invention may include a medicament used for preventing or inhibiting progress of symptoms of diseases.

The medicament of the present invention can be prepared as a pharmaceutical composition comprising a compound of the present invention represented by the Formula (1) or pharmaceutically acceptable salts thereof as an effective component. Moreover, a prodrug which is metabolized in vivo to yield a compound represented by the Formula (1) or a pharmaceutically acceptable salt thereof, may also be included in the scope of the present invention.

Regarding the medicament of the present invention, a compound represented by the Formula (1) or a pharmaceutically acceptable salt thereof can be used alone. However, for the administration, it is preferable to prepare a pharmaceutical composition comprising a compound represented by the Formula (1) or a pharmaceutically acceptable salt thereof and one or more pharmaceutically acceptable carriers. In addition, as an effective component for the pharmaceutical composition of the present invention, a hydrate and a solvate of the compound represented by the Formula (1) or a pharmaceutically acceptable salt thereof may also be used.

When using as a pharmaceutical agent, a pharmaceutical composition may be prepared. The pharmaceutical composition contains an effective amount of a compound represented by formula (1) of the present invention or a pharmaceutically acceptable salt alone, or together with a pharmaceutically acceptable carrier. Examples of such carrier include, a suspending agent such as carboxymethylcellulose and the like, or purified water, physiological saline and the like, depending on the case. Further, other known carriers can also be used. For example, the compound of the present invention or pharmaceutically acceptable salt can be suspended or dissolved in purified water containing 0.5% carboxymethylcellulose. As a formulation type for formulating the above described pharmaceutical composition, a tablet, powder, granules, syrup, suspension, a capsule, an injection solution and the like can be mentioned. For such preparation, various carriers are used depending on each type of the formulation. For example, as a carrier for an orally administered formulation, a vehicle, a binding agent, a lubricant, an agent for promoting flowability, and a colorant can be mentioned. When the compounds of the present invention are used for preparing a parenteral formulation such as an injection solution, etc., distilled water for an injection solution, physiological saline, glucose solution, vegetable oil for an injection solution, propylene glycol, polyethylene glycol and the like can be used as a diluent. In addition, if required, a sterilizing agent, a preservative, a stabilizing agent, an isotonic agent, a pain killer and the like can be added.

When the compounds of the present invention are administered to a mammal, for example, a human, they can be administered by selecting suitable dosage form and suitable pathway. For example, they can be orally administered in form of a tablet, powder, granules, syrup, suspension, or a capsule. Further, they can be administered via airway in form of an inhaling agent. Further, they can be administered subcutaneously, intradermally, intravenously, intramuscularly, or intraperitoneally in form of an injection solution including a drop, etc. Still further, they can be administered intramucosally in form of a suppository, or a sublingual agent, etc. and also intradermally in form of a gel, a lotion, an ointment, a cream or a spray and the like.

The medicament of the present invention shows very low toxicity and can be safely administered to vertebrates including human, preferably mammals including human.

Administration period of the medicament of the present invention is not specifically limited. However, when it is administered under the purpose of treatment, a period during clinical signs of a disorder is found to be present can be taken as a time period for the administration. In general, the administration is continued from several weeks to two years. However, depending on symptoms, it can be further administered, or can be continuously administered even after recovery from clinical symptoms. In addition, even when no clinical signs are observed, it can be administered for a prophylactic purpose based on clinician's judgment. Dosage of the medicament of the present invention is not specifically limited. For oral administration, for example, it can be generally administered in an effective amount of 0.01 to 2000 mg per day for an adult, in a single dose or divided in several doses. In such a case, administration frequency can be from once a month to everyday. Preferably, it is once a week to three times a week, or five times a week, or can be administered everyday. Single day and/or single time dosage, administration period, and administration frequency, etc. may be either increased or decreased according to age, body weight, overall health of a subject, type of disorder to be treated and severeness of the disorder, administration route, a formulation type (i.e., a carrier's property of slowly releasing an effective component, etc.) and the like.

When prophylaxis and/or treatment of a bone disorder is carried out by using the medicament of the present invention, the medicament of the present invention can be used at the same time or at different time in combination with one or more drugs that are selected from a group consisting of a drug for bone activation, a drug for promoting bone formation, a drug for inhibiting bone resorption, a drug for improving bone metabolism, a gonadal hormone preparation and a calcium preparation. In addition, the medicament of the present invention can be also prepared and administered in a form of so-called combination drugs to be administered together with the above-exemplified drugs.

Examples of a drug for bone activation include calcitriol, alfacalcidol, OCT, or ED-71 and the like. Examples of a drug for promoting bone formation include menatetrenone, somatropin, insulin-like growth factor-I (IGF-I), Bone Morphogenetic Proteins (BMPs), basic Fibroblast growth factor (bFGF), Transforming growth factor-$\beta$ (TGF-$\beta$), growth hormone secretagogues, EP2 agonist, EP4 agonist, anti-Sclerostin antibody, or an agent for blocking activin type II receptor A such as ACE-011 and the like. Examples of a drug for inhibiting bone resorption include elcatonin, calcitonin salmon, etidronate, pamidronate, clodronate, alendronate, incadronate, risedronate, minodronate, ibandronate, zoledronate, cathepsin K inhibitor, or a RANKL signal blocking agent such as Denosumab, OPG and the like. Examples of a drug for improving bone metabolism include fluoride, strontium ranelate, or ipriflavone and the like. Examples of a gonadal hormone preparation include estriol, estradiol, conjugated estrogen, progesterone, medroxyprogesterone, testosterone, methyltestosterone, mestanolone, stanozolol, metenolone, nandrolone, selective estrogen receptor modulator (SERM: raloxifen, lasofoxifene, bazedoxifene, ospemifene, arzoxifene, CHF4227, PSK-3471, etc.), or selective androgen receptor modulator (SARM) and the like. Examples of a calcium preparation include calcium carbonate, calcium lactate, calcium gluconate, calcium acetate, calcium chloride, calcium citrate, calcium hydrogen phosphate, or calcium L-asparagine acid and the like.

It is evident that the medicament of the present invention can be administered with other prophylactic or curative agent that are used against various symptoms or disorders, aside from the prophylactic and/or curative purpose of the medicament of the present invention.

When using as a medicament, a pharmaceutical composition may be prepared. The pharmaceutical composition contains an effective amount of a compound represented by formula (1) of the present invention or a pharmaceutically acceptable salt-alone, or together with a pharmaceutically acceptable carrier. Examples of such carrier include, a suspending agent such as carboxymethylcellulose and the like, or purified water, physiological saline and the like, depending on the case. Further, other known carriers can be also used. For example, the compound of the present invention or pharmaceutically acceptable salt can be suspended or dissolved in purified water containing 0.5% carboxymethylcellulose.

As a formulation type for formulating the above described pharmaceutical composition, a tablet, powder, granules, syrup, suspension, a capsule, an injection solution and the like can be mentioned. For preparing such formulation, various types of carriers are used for each formulation. For example, as a carrier for an orally administered formulation, a vehicle, a binding agent, a lubricant, an agent for promoting flowability, and a colorant can be mentioned.

When the compounds of the present invention are used for preparing a parenteral formulation such as an injection solution, etc., distilled water for an injection solution, physiological saline, glucose solution, vegetable oil for an injection solution, propylene glycol, polyethylene glycol and the like can be used as a diluent. In addition, if required, a sterilizing agent, a preservative, a stabilizing agent, an isotonic agent, a pain killer and the like can be also added.

When the compounds of the present invention are administered to a mammal, for example, a human, they can be orally administered in the form of a tablet, powder, granules, suspension, or a capsule, for example. Further, they can be administered parenterally in the form of an injection solution including a drop, a suppository, a gel, a lotion, an ointment, a cream or a spray and the like. Dosage of the medicament of the present invention varies depending on symptoms to be treated, dosage form, age and body weight of a patient, and severeness of symptom and the like. For example, an amount of 1 to 1000 mg can be generally administered in a single dose or two or three divided doses per day for an adult. Administration is generally carried out everyday from several days to two months. However, depending on symptom of a patient, single day dosage and administration period can be all increased or decreased appropriately.

Further, the compounds of the present invention, or salts thereof or derivatives thereof that are useful as a prodrug have excellent safety (i.e., having favorable pharmacology regarding various toxicity and also safety), pharmacokinetics of a drug, and a dissolution property and etc., thus usefulness as an effective component for a medicament is confirmed.

Regarding a test related to safety, the followings can be mentioned but not limited thereto. Specifically, pharmacology safety test relating to a cardiovascular system (hERG inhibition evaluation test, etc.), general toxicology test and the like are included.

In addition, regarding a test for pharmacokinetics of a drug, the followings are included, but not limited thereto. Inhibition test regarding cytochrome P450 enzyme, blood concentration time profile test, solubility test (i.e., solubility test based on turbidity, etc.) and the like are included.

Usefulness of the compounds of the present invention that are represented by the above Formula (1), salts thereof or derivatives thereof that are useful as a prodrug (1) as an effective component for a medicament can be confirmed by carrying out a safety pharmacology test regarding cardiovascular system. Examples of safety pharmacology test regarding cardiovascular system include an evaluation method of hERG inhibition (patch clamp method (Chachin, M. et al., Nippon Yakurigaku Zasshi, 119, pp. 345-351, 2002), Binding assay method (Gilbert, J. D. et al., J. Pharm. Tox. Methods, 50, pp. 187-199, 2004), $Rb^+$ efflex assay method (Cheng, C. S. et al., Drug Develop. Indust. Pharm., 28, pp. 177-191, 2002), Membrane potential assay method (Dorn, A. et al., J. Biomol. Screen., 10, pp. 339-347, 2005) etc.) etc. By running one, two or more tests based on these methods, effect of the compounds of the present invention on a cardiovascular system can be clearly identified so that their usefulness as an effective component of a medicament can be confirmed.

Usefulness of the compounds of the present invention that are represented by the above Formula (1), salts thereof or derivatives thereof that are useful as a prodrug as an effective component for a medicament can be confirmed by carrying out a general toxicity test. Specifically, according to a general toxicity test, a compound which is either dissolved or suspended in an appropriate solvent is orally administered or intravenously administered of a single time or multiple times (several days) to rodents such as rat, mouse, and the like or non-rodents such as monkey, dog and the like as a subject animal, and then animal's general state is observed and any change in clinical chemistry or tissue in terms of pathology, etc. are evaluated. By identifying general toxicity of a compound of the present invention based on these methods, usefulness of the compounds of the present invention as an effective component for a medicament can be confirmed.

Usefulness of the compounds of the present invention that are represented by the above Formula (1), salts thereof or derivatives thereof that are useful as a prodrug as an effective component for a medicament can be confirmed by carrying out an inhibition test of cytochrome P450 enzyme (Gomez-Lechon, M. J. et al., Curr. Drug Metab. 5(5), pp. 443-462, 2004). Examples of the test include a method of determining in vitro an inhibitory effect of a compound on an enzyme activity by using cytochrome P450 enzyme of each molecular species that is either purified from a cell or prepared using a genetic recombinant, or a microsome as a human P450 expression system (Miller, V. P. et al., Ann. N.Y. Acad. Sci., 919, pp. 26-32, 2000), a method of determining expression of cytochrome P450 enzyme for each molecular species or variation in enzyme activity by using a human liver microsome or cell homogenate (Hengstler, J. G. et al., Drug Metab. Rev., 32, pp. 81-118, 2000). By running one, two or more tests based on these methods, effect of the compounds of the present invention on inhibition of cytochrome P450 enzyme can be clearly identified so that their usefulness as an effective component of a medicament can be confirmed.

Usefulness of the compounds of the present invention that are represented by the above Formula (1), salts thereof or derivatives useful as a prodrug as an effective component of a medicament can be confirmed by, for example, measuring concentration of the compounds in blood over time or by measuring concentration of PTH in blood of animal which has been administered orally or parenterally with the compounds. Examples of the test include a method of determining blood concentration profile of a compound using LC-MS/MS method (Harada Kenichi et al., eds. "Newest aspects in mass spectrometry for biological sciences", 2002, Kodansha Scientific, etc.) by orally or parenterally (e.g., intravenous, intramuscular, intraperitoneal, subcutaneous, or trans-dermal administration, or administration into an eye or via nose, etc.)

administering the compound to a rodent, a monkey or a dog. As for a test to measure PTH concentration in blood, a method by which the compounds are administered orally or parenterally (e.g., intravenous, intramuscular, intraperitoneal, subcutaneous, or trans-dermal administration, or administration into an eye or via nose, etc.) to a rodent, a monkey, etc., and concentration of intact PTH in blood after the administration is measured by an immunological method such as ELISA, etc. can be mentioned. Based on these methods, change in concentration of the compound or PTH concentration in blood over time can be compared with the change in concentration of a compound having no or weak activity of increasing bone mineral density (e.g., NPS-2143) or with the change in PTH concentration in blood over time to confirm the usefulness of the compound as an effective component for a medicament.

Usefulness of the compounds of the present invention that are represented by the above Formula (1), salts thereof or derivatives thereof that are useful as a prodrug as an effective component for a medicament can be confirmed by carrying out a solubility test, for example. Examples of the test include a method of determining solubility based on turbidity (Lipinski, C. A. et al., Adv. Drug Deliv. Rev., 23, pp. 3-26, 1997; Bevan, C. D. et al., Anal. Chem., 72, pp. 1781-1787, 2000), etc. By identifying compound's dissolution property based on this method, usefulness of the compounds of the present invention as an effective component for a medicament can be confirmed.

Hereinbelow, the present invention will be explained in view of the Examples, Reference examples, Preparation examples and Experimental examples. However, scope of the present invention is not limited to them. Hereinbelow, the present invention will be explained in greater detail in view of the examples. However, scope of the present invention is not limited to them.

Regarding the Examples described below, various analysis was carried out according to the following descriptions.

In the Examples, for a microwave generator, Discover (manufactured by CEM) was used. For thin layer chromatography (TLC) in the Examples, TLC plate manufactured by Merck Co., Germany was used (Precoated Silica Gel 60 F254, Product No. 5715-1M). After development using chloroform:methanol (1:0-1:1), acetonitrile:acetic acid:water (200:1-100:4:4), or ethyl acetate:hexane (1:0-0:1), UV ray (254 nm or 365 nm) illumination was carried out, followed by chromogenic reaction using iodide solution, potassium permanganate solution, phosphorousmolybdenum acid (ethanol solution), ninhydrin, or dinitrophenylhydrazine hydrochloride solution for identification. For drying of an organic solvent, anhydrous magnesium sulfate or anhydrous sodium sulfate was used. Regarding the "Quad" described for column chromatography, Quad 1 fractionation system (manufactured by Biotage Co.) was used and one or several cartridge columns selected from KP-Sil-12M, 40S, or 40M, all manufactured by Biotage Co., are used depending on the amount of a sample. In addition, with respect to the "Yamazen" described for column chromatography, a multiprep YFLC (manufactured by Yamazen) was used and one of the Ultrapack Si-40A, 40B or 40D (manufactured by Yamazen) was also used as a column. For silica gel column chromatography, silica gel 60N (gloubule, neutral, 40-100 µm, manufactured by Kanto Chemical Co., Inc., Japan), BONDE SIL-SAX, 40UM (manufactured by VARIAN), BONDESIL-SCX, 40UM (manufactured by VARIAN), or Megabond Elute SI (manufactured by VARIAN) was used. For preparative thin layer chromatography (hereinbelow, abbreviated as "PTLC"), one or multiple PLC plates of silica gel 60 F254 (20×20 cm, layer thickness 2 mm, having concentration zone (4 cm)); manufactured by Merck Co., Product No. 13793-1M) were used depending on the amount of a sample. For HPLC purification, LCMS fractionation system (manufactured by Waters Company) was used in conjunction with Develosil C-30-UG-5 (manufactured by NOMURA CHEMICAL CO., LTD) or ODS column. For an elution solution, water-acetonitrile solvent comprising 0.1% acetic acid was used. For the HPLC purification, a target compound was obtained using a molecular weight as a trigger, unless specifically described otherwise. Solvent was removed by freeze-drying. For nuclear magnetic resonance (NMR) spectrum measurement, AL-300 (FT-NMR, manufactured by JEOL Co.) or LA-400 (FT-NMR, manufactured by JEOL Co.) was used. As a solvent, $CDCl_3$ or DMSO-$d_6$ was used, unless specifically described otherwise. For measurement of chemical shift, tetramethylsilane (TMS) was taken as an internal standard. The chemical shift value was expressed in δ (ppm). In addition, a coupling constant was expressed in J (Hz). Furthermore, symbols for a splitting pattern are as follows: s; singlet, d; doublet, t; triplet, q; quartet, qu; quintet, dd; doublet doublet, td; triplet doublet, m; multiplet, brs; broad singlet, brd; broad doublet, brdd; broad doublet doublet, brddd; broad doublet doublet doublet.

As for "LCMS", liquid chromatography mass analysis spectrum (LC-MS) was used to obtain mass spectrum. For the analysis, two apparatuses (A) and (B) described below were used separately.

(A) As a mass spectrometer, Platform-LC type mass spectrometer (manufactured by Micromass, England) was used (ionization was carried out based on an electrospray method (ESI)). The liquid chromatography instrument manufactured by GILSON, France was used. As a separation column, Develosil C30-UG-5 (50×4.6 mm, manufactured by NOMURA CHEMICAL CO., LTD) was used. General condition for elution was as follows—flow rate: 2 mL/minute, solvent: liquid A=water containing 0.1% (v/v) acetic acid, liquid B=acetonitrile containing 0.1% (v/v) acetic acid, and from minute 0 to minute 4, liquid B with linear gradient of 5-98% (v/v) was applied followed by elution with 98% of liquid B until minute 6.

(B) As an apparatus for mass analysis, an apparatus for single quadrupole mass analysis, i.e., HPLC/SQD system (manufactured by Waters Company), was used based on an electrospray (ESI) method. As for an apparatus for liquid chromatography, Acquity Ultra Performance LC systems (manufactured by Waters Company) was used. As for a separation column, ACQUITY HPLC BEH C18 (2.1×50 mm 1.7 µm, manufactured by Waters Company) was used. General condition for elution was as follows—flow rate: 0.6 mL/minute, solvent: liquid A=water containing 0.1% (v/v) acetic acid, liquid B=acetonitrile containing 0.1% (v/v) acetic acid, and from minute 0 to minute 2.0, liquid B with linear gradient of 5-90% (v/v) was applied followed by linear gradient of 90-98% (v/v) of liquid B from minute 2.0 to minute 2.5.

For the entire examples, data related to the instruments are described in the Table 1 to 15 below. In addition, meanings of the symbols described in the Table 1 to 15 are as follows.

"Exp"; Example number;
"Str"; Structure shown in the tables;
"AM"; am in the Table 1, 2, 8 and 9;
"BA"; ba in the Table 3 to 6;
"ES"; es in the Table 10 and 11;
"SM1" "SM2": Example number of a starting material or intermediate number (provided that, in case of example number, it is indicated as "Exp. Example number". For example, "Exp. 1-1" indicates Example 1-1. In addition, a reference example number is described as "IM Reference example number". For example, "IM 1-1" indicates the Reference example 1-1).

"LCMS"; data for liquid chromatography mass analysis spectrum (m/z);

"method"; condition for liquid chromatography. The condition "A" means that for the above described "LCMS" apparatus, condition (A) was used. Similarly, condition "B" means that for the above described "LCMS" apparatus, condition (B) was used. In addition, for the symbol "C" described for the condition, mass spectrum data that are measured by Fast Atom Bombardment Mass Spectrometry (FAB-MS) using JEOL-JMS-SX102 (manufactured by JEOL LTD.) are described;

"RTime"; retention time in LCMS.;

"MASS"; mass spectrum data.; (provided that, the term "N.D." indicates that molecular ion peak was impossible to detect);

"Spl": a manufacturer of a reagent used.

In addition, meanings of the abbreviations in the tables are as follows.

The number that is described before each substituent indicates substitution position. In addition, the number given with '- (hyphen)' before abbreviation of an aromatic ring indicates substitution position of the aromatic ring. The term '(S)' described in compound name or structure indicates that the corresponding asymmetric carbon has S configuration while (R) indicates R configuration.

In addition, regarding the manufacturers of the reagents used, they are sometimes described as the following abbreviations in the present specification. "TCI"; manufactured by Tokyo Chemical Industry, Co., Ltd., "Ald"; manufactured by Aldrich Company, "KANTO"; manufactured by Kanto Chemical Co., Inc., "WAKO"; manufactured by Wako Pure Chemicals, "LANC"; manufactured by Lancaster, "MAYB"; manufactured by Maybridge Company, "Frontier"; manufactured by Frontier Scientific INC, "Combi"; manufactured by Combi-blocks Inc.

EXAMPLE 1-1

Synthesis of (S)-2-bromo-N-methyl-N-(oxiran-2-ylmethyl)benzenesulfonamide (Step A) Synthesis of 2-bromo-N-methylbenzenesulfonamide 2-Bromobenzenesulfonyl chloride (manufactured by Fluorochem Co., 25 g) was dissolved in tetrahydrofuran (40 mL), and under stirring at 0° C., 40% methylamine aqueous solution (TCI, 25 mL) was added dropwise thereto over ten minutes. After stirring the mixture at room temperature for 2 hours and 40 minutes, water was added to the reaction solution, followed by extraction with ethyl acetate. The organic layer was washed with brine, dried over anhydrous sodium sulfate, and the solvent was removed by distillation under reduced pressure. To the residues, hexane and a small amount of ethyl acetate were added, followed by stirring. Solids were filtered to obtain the target compound (23.26 g).

(Step B) Synthesis of (S)-2-bromo-N-methyl-N-(oxiran-2-ylmethyl)benzenesulfonamide 2-Bromo-N-methylbenzenesulfonamide (10 g) obtained from above Example 1-1 Step A was dissolved in dimethylformamide (100 mL), and (R)-glycidyl 3-nitrobenzenesulfonate (WAKO, 11.4 g), and potassium carbonate (KANTO, 11.05 g) were added thereto, followed by stirring at 80° C. for 3 hours and 10 minutes. After cooling to room temperature, water was added to the reaction solution and extraction was carried out with ether. The organic layer was washed with water and brine in order, dried over anhydrous sodium sulfate, and the solvent was removed by distillation under reduced pressure. The residue was purified by silica gel column chromatography to obtain the target compound (8.63 g).

EXAMPLES 1-2 TO 6

By using 3-bromobenzenesulfonyl chloride (Fluorochem), 4-bromobenzenesulfonyl chloride (TCI), (2-bromophenyl)methanesulfonyl chloride (MAYB), (3-bromophenyl)methanesulfonyl chloride (MAYB), or (4-bromophenyl)methanesulfonyl chloride (MAYB) instead of 2-bromobenzenesulfonyl chloride, the target compounds were obtained according to Step A and Step B of Example 1-1. Each structure of the compounds of the above Example 1-1 to Example 1-6 is described as the following Exp. 1-1 to Exp. 1-6.

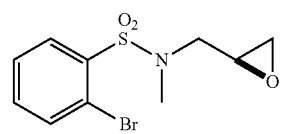

Exp. 1-1

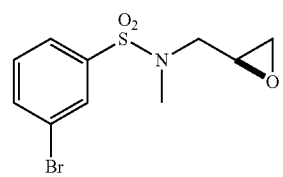

Exp. 1-2

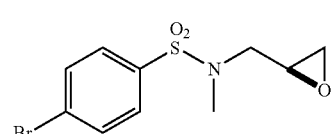

Exp. 1-3

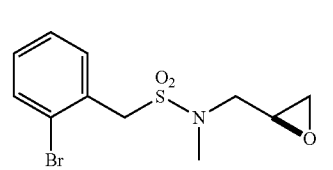

Exp. 1-4

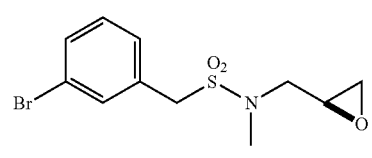

Exp. 1-5

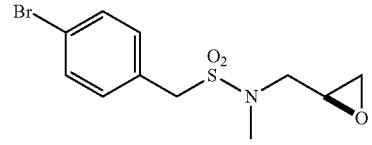

Exp. 1-6

EXAMPLE 1-2

(S)-3-bromo-N-methyl-N-(oxiran-2-ylmethyl)benzenesulfonamide

EXAMPLE 1-3

(S)-4-bromo-N-methyl-N-(oxiran-2-ylmethyl)benzenesulfonamide

EXAMPLE 1-4

(S)-1-(2-bromophenyl)-N-methyl-N-(oxiran-2-ylmethyl)methanesulfonamide

EXAMPLE 1-5

(S)-1-(3-bromophenyl)-N-methyl-N-(oxiran-2-ylmethyl)methanesulfonamide

EXAMPLE 1-6

(S)-1-(4-bromophenyl)-N-methyl-N-(oxiran-2-ylmethyl)methanesulfonamide

EXAMPLES 1-7 TO 15

Target compounds were obtained according to Example 1-1 except that 4-bromo-2-ethylbenzenesulfonyl chloride (MAYB), 4-bromo-2,6-dichlorobenzenesulfonyl chloride (Ald), 4-bromo-2-methylbenzenesulfonyl chloride (MAYB), 4-bromo-3-methylbenzenesulfonyl chloride (Fluorochem), 4-bromo-2-chlorobenzenesulfonyl chloride (WAKO), 4-bromo-3-chlorobenzenesulfonyl chloride. (Oakwood), 4-bromo-2-trifluoromethylbenzenesulfonyl chloride (Ald), 4-bromo-3-trifluoromethylbenzenesulfonyl chloride (Fluorochem), or 4-bromo-2-trifluoromethoxybenzenesulfonyl chloride (WAKO) was used instead of 2-bromobenzenesulfonyl chloride.

EXAMPLE 1-7

(S)-4-bromo-2-ethyl-N-methyl-N-(oxiran-2-ylmethyl)benzenesulfoneamide

EXAMPLE 1-8

(S)-4-bromo-2,6-dichloro-N-methyl-N-(oxiran-2-ylmethyl)benzenesulfoneamide

EXAMPLE 1-9

(S)-4-bromo-N,2-dimethyl-N-(oxiran-2-ylmethyl)benzenesulfoneamide

EXAMPLE 1-10

(S)-4-bromo-N,3-dimethyl-N-(oxiran-2-ylmethyl)benzenesulfoneamide

EXAMPLE 1-11

(S)-4-bromo-2-chloro-N-methyl-N-(oxiran-2-ylmethyl)benzenesulfoneamide

EXAMPLE 1-12

(S)-4-bromo-3-chloro-N-methyl-N-(oxiran-2-ylmethyl)benzenesulfoneamide

EXAMPLE 1-13

(S)-4-bromo-N-methyl-N-(oxiran-2-ylmethyl)-2-(trifluoromethyl)benzenesulfoneamide

EXAMPLE 1-14

(S)-4-bromo-N-methyl-N-(oxiran-2-ylmethyl)-3-(trifluoromethyl)benzenesulfoneamide

EXAMPLE 1-15

(S)-4-bromo-N-methyl-N-(oxiran-2-ylmethyl)-2-(trifluoromethoxy)benzenesulfoneamide

EXAMPLE 1-16

(S)-4-Bromo-2,5-difluoro-N-methyl-N-(oxiran-2-ylmethyl)benzenesulfoneamide (Step A) Synthesis of tert-butyl 4-bromo-2,5-difluorophenylsulfonyl carbamate 4-Bromo-2,5-difluorobenzenesulfoneamide (Fluorochem, 1.0 g) was dissolved in tetrahydrofuran (30 mL), and added with di-tert-butyl bicarbonate (WAKO, 1.0 g), 4-dimethylaminopyridine (WAKO, 48 mg), and triethylamine (WAKO, 1.1 mL) under ice cooling followed by stirring for 5 minutes. Ice bath was removed and the mixture was further stirred for 4 hours. Saturated ammonium chloride solution was added, and the extraction was carried out with ethyl acetate. The organic layer was washed with brine, dried over anhydrous sodium sulfate, and the solvent was distilled off under reduced pressure. The residue was purified by silica gel column chromatography to obtain the target compound (1.4 g).

(Step B) Synthesis of tert-butyl 4-bromo-2,5-difluorophenylsulfonyl(methyl)carbamate The compound synthesized from the Example 1-16 Step A (1.4 g) was dissolved in dimethylformamide (15 mL), and added with sodium hydride (WAKO, 249 mg) and methyl iodide (TCI, 0.26 mL) under ice cooling followed by stirring for 5 minutes. Ice bath was removed and the mixture was further stirred for 2 hours. Saturated ammonium chloride solution was added, and the extraction was carried out with ether. The organic layer was washed with brine, dried over anhydrous sodium sulfate, and the solvent was distilled off under reduced pressure. The residue was purified by silica gel column chromatography to obtain the target compound (450.7 mg).

(Step C) Synthesis of 4-bromo-2,5-difluoro-N-methylbenzenesulfoneamide

The compound synthesized from the Example 1-16 Step B (1.4 g) was dissolved in dichloromethane (5 mL), and added with trifluoroacetic acid (WAKO, 1 mL) under ice cooling followed by stirring for 5 minutes. Ice bath was removed and the mixture was further stirred for 5 hours. Sodium bicarbonate solution was added, and the extraction was carried out with dichloromethane. The organic layer was washed with brine, dried over anhydrous sodium sulfate, and the solvent was distilled off under reduced pressure. The residue was purified by silica gel column chromatography to obtain the target compound (315.3 mg).

EXAMPLES 1-17 TO 18

The target compounds were obtained according to Example 1-16 except that 4-bromo-2-fluorobenzenesulfoneamide or 4-bromo-3-fluorobenzenesulfoneamide was used instead of 4-bromo-2,5-difluorobenzenesulfoneamide.

EXAMPLE 1-17

(S)-4-bromo-2-fluoro-N-methyl-N-(oxiran-2-ylmethyl)benzenesulfoneamide

EXAMPLE 1-18

(S)-4-bromo-3-fluoro-N-methyl-N-(oxiran-2-ylmethyl)benzenesulfoneamide

EXAMPLES 1-19 TO 26

Target compounds were obtained according to Example 1-1 by using 2-bromo-4,6-dichlorobenzenesulfonyl chloride (Oakwood), 2-bromo-5-trifluoromethylbenzenesulfonyl chloride (WAKO), 2-bromo-4-trifluoromethylbenzenesulfonyl chloride (WAKO), 3-bromo-5-trifluoromethylbenzenesulfonyl chloride (Matrix Scientific), 5-bromo-2-methoxybenzenesulfonyl chloride (WAKO), 4-bromo-5-chlorothiophenesulfonyl chloride (MAYB), 5-bromothiophenesulfonyl chloride (MAYB), or 5-bromopyridin-3-sulfonyl chloride (MAYB).

EXAMPLE 1-19

(S)-2-bromo-4,6-dichloro-N-methyl-N-(oxiran-2-ylmethyl)benzenesulfoneamide

EXAMPLE 1-20

(S)-2-bromo-N-methyl-N-(oxiran-2-ylmethyl)-5-(trifluoromethyl)benzenesulfoneamide

EXAMPLE 1-21

(S)-2-bromo-N-methyl-N-(oxiran-2-ylmethyl)-4-(trifluoromethyl)benzenesulfoneamide

EXAMPLE 1-22

(S)-3-bromo-N-methyl-N-(oxiran-2-ylmethyl)-5-(trifluoromethyl)benzenesulfoneamide

EXAMPLE 1-23

(S)-5-bromo-2-methoxy-N-methyl-N-(oxiran-2-ylmethyl)benzenesulfoneamide

EXAMPLE 1-24

(S)-4-bromo-5-chloro-2-(N-methyl-N-(oxiran-2-ylmethyl)sulfamoyl)thiophene

EXAMPLE 1-25

(S)-5-bromo-2-(N-methyl-N-(oxiran-2-ylmethyl)sulfamoyl)thiophene

EXAMPLE 1-26

(S)-5-bromo-N-methyl-N-(oxiran-2-ylmethyl)pyridin-3-sulfoneamide

EXAMPLE 1-27

Ethyl (S)-3-(N-methyl-N-(oxiran-2-ylmethyl)sulfamoyl)-5-(trifluoromethyl)benzoate (Step A) Synthesis of 3-cyano-N-methyl-5-trifluoromethylbenzenesulfoneamide 3-Bromo-N-methyl-5-trifluoromethylbenzenesulfoneamide (synthesized according to Example 1-22 Step A; 1.82 g) was dissolved in dimethylformamide (20 mL), and added with zinc cyanide (Ald, 0.80 g) and tetrakistriphenylphosphine palladium (Ald, 1.32 g) followed by stirring for 9 hours at 100° C. After cooling to room temperature, sodium bicarbonate solution was added to the reaction solution, and the extraction was carried out with ether. The organic layer was washed with brine, dried over anhydrous sodium sulfate, and the solvent was distilled off under reduced pressure. The residue was purified by silica gel column chromatography to obtain the target compound (1.05 g).

(Step B) Synthesis of 3-(N-methylsulfamoyl)-5-trifluoromethylbenzoic acid

The compound synthesized from the Example 1-27 Step A (1.05 g) was dissolved in ethylene glycol (15 mL), and added with potassium hydroxide (ten granules) followed by stirring for 15 hours at 110° C. After cooling to room temperature, 5N hydrochloric acid was added to acidify the reaction solution, and the extraction was carried out with ether. The organic layer was washed with brine, dried over anhydrous sodium sulfate, and the solvent was distilled off under reduced pressure to obtain the target compound as a crude product (1.12 g).

(Step C) Synthesis of ethyl 3-(N-methylsulfamoyl)-5-trifluoromethylbenzoate

The compound synthesized from the Example 1-27 Step B (98.7 mg) was dissolved in ethanol (3 mL), and added with conc. sulfuric acid (0.5 mL) followed by reflux for 15 hours. After cooling to room temperature, potassium carbonate and sodium bicarbonate solutions were added to the reaction solution, and the extraction was carried out with ether. The organic layer was washed with brine, dried over anhydrous sodium sulfate, and the solvent was distilled off under reduced pressure. The residue was purified by silica gel column chromatography to obtain the target compound (100.8 mg).

(Step D) Synthesis of ethyl (S)-3-(N-methyl-N-(oxiran-2-ylmethyl)sulfamoyl)-5-(trifluoromethyl)benzoate According to the method of Example 1-1 Step B, the target compound was obtained from the compound synthesized from Example 1-27 Step C.

EXAMPLE 1-28

Ethyl (S)-2-(3-(N-methyl-N-(oxiran-2-ylmethyl) sulfamoyl)-5-(trifluoromethyl)phenyl)acetate (Step A) Synthesis of 3-hydroxymethyl-N-methyl-5-trifluoromethylbenzenesulfoneamide The compound synthesized from the Example 1-27 Step B (488.1 mg) was dissolved in tetrahydrofuran (15 mL), and added with borane dimethylsulfide complex (TCI, 0.33 mL) followed by reflux for 3.5 hours. After cooling to 0° C., methanol and brine were added to the reaction solution, and the extraction was carried out with ethyl acetate. The organic layer was washed with brine, dried over anhydrous sodium sulfate, and the solvent was distilled off under reduced pressure. The residue was purified by silica gel column chromatography to obtain the target compound (404.2 mg).

(Step B) Synthesis of 3-bromomethyl-N-methyl-5-trifluoromethylbenzenesulfoneamide The compound synthesized from the Example 1-28 Step A (840.7 mg) was dissolved in dichloromethane (20 mL), and added with carbon tetrabromide (WAKO, 1.29 g) and triphenylphosphine (WAKO, 1.23 g) under ice cooling followed by stirring for 1 hour. Ice bath was removed and the mixture was further stirred for 8 hours. The solvent was distilled off under reduced pressure. The residue was purified by silica gel column chromatography to obtain the target compound (282.1 mg).

(Step C) Synthesis of 3-cyanomethyl-N-methyl-5-trifluoromethylbenzenesulfoneamide The compound synthesized from the Example 1-28 Step B (282.1 mg) was dissolved in dimethylformamide (5 mL), and added with potassium cyanide (KANTO, 66.4 mg) under ice cooling followed by stirring for 1 hour. Ice bath was removed and the mixture was further stirred for 4 hours. Sodium bicarbonate solution was added, and the extraction was carried out with ether. The organic layer was washed with brine, dried over anhydrous sodium sulfate, and the solvent was distilled off under reduced pressure. The residue was purified by silica gel column chromatography to obtain the target compound (176.9 mg).

(Step D) Synthesis of 2-(3-(N-methylsulfamoyl)-5-(trifluoromethyl)phenyl)acetic acid The compound synthesized from the Example 1-28 Step C (176.9 mg) was dissolved in ethylene glycol (10 mL), and added with potassium hydroxide (10 granules) followed by stirring at 110° C. for 7 hours. After cooling to room temperature, 5N hydrochloric acid was added to acidify the reaction solution, and the extraction was carried out with ether. The organic layer was washed with brine, dried over anhydrous sodium sulfate, and the solvent was distilled off under reduced pressure to obtain the target compound as a crude product (200 mg).

(Step E) Synthesis of ethyl 2-(3-(N-methylsulfamoyl)-5-(trifluoromethyl)phenyl)acetate The compound synthesized from the Example 1-28 Step D (200 mg) was dissolved in ethanol (5 mL), and added with conc. sulfuric acid (0.5 mL) followed by reflux for 9 hours. After cooling to room temperature, potassium carbonate and sodium bicarbonate solutions were added to the reaction solution, and the extraction was carried out with ether. The organic layer was washed with brine, dried over anhydrous sodium sulfate, and the solvent was distilled off under reduced pressure. The residue was purified by silica gel column chromatography to obtain the target compound (125.5 mg).

(Step F) Synthesis of ethyl (S)-2-(3-(N-methyl-N-(oxiran-2-ylmethyl)sulfamoyl)-5-(trifluoromethyl) phenyl)acetate According to the method of Example 1-1 Step B, the target compound was obtained from the compound synthesized from Example 1-28 Step E.

EXAMPLE 1-29

Ethyl (S)-3-(3-chloro-5-(N-methyl-N-(oxiran-2-ylmethyl)sulfamoyl)phenyl)propionate (Step A) Synthesis of 1-bromo-3-chloro-5-hydroxysulfonylbenzene 1,3-Dibromo-5-chlorobenzene (WAKO, 5.98 g) was dissolved in ether (200 mL), and added with 1.6M n-butyl lithium n-hexane solution (KANTO, 15.2 mL) and liquefied sulfur dioxide (9.7 mL) at −70° C. After being allowed to warm to room temperature, the mixture was stirred for 5 hours. The solvent was distilled off under reduced pressure to obtain the target compound as a crude product. LCMS Method B, retention time 0.83 minutes, (ES−) 254.9

(Step B) Synthesis of 3-bromo-5-chlorobenzene-1-sulfonyl chloride

The compound synthesized from the Example 1-29 Step A was dissolved in dichloromethane (150 mL), and added with N-chlorosuccinic imide (TCI, 5.9 g) and the mixture was stirred for 13 hours at room temperature. The solvent was distilled off under reduced pressure to obtain the target compound as a crude product.

(Step C) Synthesis of 3-bromo-5-chloro-N-methylbenzenesulfoneamide

The compound synthesized from the Example 1-29 Step B was dissolved in tetrahydrofuran (150 mL), and added with 40% methylamine aqueous solution (TCI, 7.4 mL) under ice cooling followed by stirring for 4 hours. Saturated ammonium chloride solution was added, and the extraction was carried out with ethyl acetate. The organic layer was washed with brine, dried over anhydrous sodium sulfate, and the solvent was distilled off under reduced pressure. The residue was purified by silica gel column chromatography to obtain the target compound (4.0 g).

(Step D) Synthesis of ethyl 3-(3-chloro-5-(N-methylsulfamoyl)phenyl)acrylate

The compound synthesized from the Example 1-29 Step C (3.1 g) was dissolved in propionitrile (WAKO, 22 mL), and added with palladium acetate (Sigma-Ald, 244.7 mg), tri-o-tolylphosphine (KANTO, 1327.1 mg), ethyl acrylate (Ald, 4.37 mL), and N-ethyldiisopropylamine (WAKO, 7.5 mL) followed by stirring at 120° C. for 4 hours. After subjecting the mixture to a ChemElute column (manufactured by VARIAN), the solvent was distilled off under reduced pressure. The residue was purified by silica gel column chromatography to obtain the target compound (2.7 g).

(Step E) Synthesis of ethyl 3-(3-chloro-5-(N-methylsulfamoyl)phenyl)propionate

The compound synthesized from the Example 1-29 Step D (2.7 g) was dissolved in tetrahydrofuran (15 mL), and added with 5 wt % rhodium-activated carbon (Ald, 200 mg) and iron acetate(II) (WAKO, 76.1 mg) and the mixture was stirred for 3 days at room temperature under hydrogen atmosphere. With purification by filtering, the target compound (2.4 g) was obtained.

(Step F) Synthesis of ethyl (S)-3-(3-chloro-5-(N-methyl-N-(oxiran-2-ylmethyl)sulfamoyl)phenyl)propionate According to the method of Example 1-1 Step B, the target compound was obtained from the compound synthesized from Example 1-29 Step E.

EXAMPLE 1-30

Isobutyl (S)-4-(3-chloro-5-(N-methyl-N-(oxiran-2-ylmethyl)sulfamoyl)phenyl)butanoate (Step A) Synthesis of isobutyl 4-(3-chloro-5-(N-methylsulfamoyl)phenyl)but-3-enoate The target compound was obtained in the same manner as Example 1-29 Step D except that isobutyl but-3-enoate (Alfa Eesar) was used instead of ethyl acrylate.

(Step B) Synthesis of isobutyl 4-(3-chloro-5-(N-methylsulfamoyl)phenyl)butanoate According to the method of Example 1-29 Step E, the target compound was obtained from the compound synthesized from Example 1-30 Step A.

(Step C) Synthesis of isobutyl (S)-4-(3-chloro-5-(N-methyl-N-(oxiran-2-ylmethyl)sulfamoyl)phenyl)butanoate According to the method of Example 1-1 Step B, the target compound was obtained from the compound synthesized from Example 1-30 Step B.

EXAMPLE 1-31

Ethyl (S)-3-(3-fluoro-5-(N-methyl-N-(oxiran-2-ylmethyl)sulfamoyl)phenyl)propionate (Step A) Synthesis of ethyl 3-(3-fluoro-5-(N-methylsulfamoyl)phenyl)acrylate 3-Bromo-5-fluoro-N-methylbenzenesulfoneamide (synthesized from 1,3-dibromo-5-fluorobenzene in view of Example 1-29 Step A, B, and C) (1.4 g) was dissolved in dioxane (15 mL) and toluene (15 mL), and added with tris-dibenzylideneacetonepalladium(0) (Ald, 0.7 g), tri-tert-butylphosphinetetrafluoroborate (Aid, 0.6 g), cesium carbonate (WAKO, 4.2 g) and ethyl acrylate (Ald, 2.19 mL) followed by stirring at 100° C. for 6 hours. After subjecting the mixture to a ChemElute column (manufactured by VARIAN), the solvent was distilled off under reduced pressure. The residue was purified by silica gel column chromatography to obtain the target compound (213.4 mg).

(Step B) Synthesis of ethyl 3-(3-fluoro-5-(N-methylsulfamoyl)phenyl)propionate

The compound synthesized from the Example 1-31 Step A (213.4 mg) was dissolved in methanol (3 mL), and added with 10% palladium—activated carbon (MERCK, 20 mg) and the mixture was stirred under hydrogen atmosphere for 1 day at room temperature. With purification by filtering, the target compound (199.5 mg) was obtained.

(Step C) Synthesis of ethyl (S)-3-(3-fluoro-5-(N-methyl-N-(oxiran-2-ylmethyl)sulfamoyl)phenyl)propionate According to the method of Example 1-1 Step B, the target compound was obtained from the compound synthesized from Example 1-31 Step B.

EXAMPLE 1-32

Ethyl (S)-3-(3-(N-methyl-N-(oxiran-2-ylmethyl)sulfamoyl)-5-(trifluoromethoxy)phenyl)propionate According to the method of Example 1-29, the target compound was obtained from 3-bromo-5-trifluoromethoxy-N-methylbenzenesulfoneamide (synthesized from 1,3-dibromo-5-trifluoromethoxybenzene according to the method of Example 1-29 Step A, B and C).

EXAMPLE 1-33

Ethyl (S)-3-(3-(N-methyl-N-(oxiran-2-ylmethyl)sulfamoyl)-5-(trifluoromethyl)phenyl)propionic acid According to the method of Example 1-31, the target compound was obtained from 3-bromo-5-trifluoromethyl-N-methylbenzenesulfoneamide (synthesized according to Example 1-22 Step A).

EXAMPLE 1-34

Ethyl (S)-3-(3-(N-methyl-N-(oxiran-2-ylmethyl)sulfamoyl)-5-(trifluoromethyl)phenyl)acrylate According to the method of Example 1-31 Step A and Step C, the target compound was obtained from 3-bromo-5-trifluoromethyl-N-methylbenzenesulfoneamide (synthesized according to Example 1-22 Step A).

EXAMPLE 1-35

Isobutyl (S)-4-(3-fluoro-5-(N-methyl-N-(oxiran-2-ylmethyl)sulfamoyl)phenyl)butanoate The target compound was obtained in the same manner as Example 1-29 Step D except that isobutyl but-3-enoate was used instead of ethyl acrylate.

EXAMPLES 1-36 TO 39

The target compounds were obtained in the same manner as Example 1-35 except that 3-bromo-5-trifluoromethoxy-N- methylbenzenesulfoneamide, 4-bromo-2-ethyl-N-methylbenzenesulfoneamide, 3-bromo-5-trifluoromethyl-N-methylbenzenesulfoneamide, or 4-bromo-5-chloro-2-(N-methylsulfamoyl)thiophene was used instead of 3-bromo-5-fluoro-N-methylbenzenesulfoneamide.

EXAMPLE 1-36

Isobutyl (S)-4-(3-(N-methyl-N-(oxiran-2-ylmethyl)sulfamoyl)-5-(trifluoromethoxy)phenyl)butanoate

EXAMPLE 1-37

Isobutyl (S)-4-(3-ethyl-4-(N-methyl-N-(oxiran-2-ylmethyl)sulfamoyl)phenyl)butanoate

EXAMPLE 1-38

Isobutyl (S)-4-(3-(N-methyl-N-(oxiran-2-ylmethyl)sulfamoyl)-5-(trifluoromethyl)phenyl)butanoate

EXAMPLE 1-39

Isobutyl (S)-4-(2-chloro-5-(N-methyl-N-(oxiran-2-ylmethyl)sulfamoyl)thiophen-3-yl)butanoate

EXAMPLE 1-40

Isobutyl (S)-4-(5-(N-methyl-N-(oxiran-2-ylmethyl)sulfamoyl)-2-(trifluoromethyl)thiophen-3-yl)butanoate (Step A) Synthesis of isobutyl 4-(5-(N-methylsulfamoyl)thiophen-3-yl)buta-3-enoate 4-Bromo-5-chloro-N-methylthiophen-2-sulfoneamide (synthesized from Example 1-24 Step A) (3.0 g) was dissolved in propionitrile (WAKO, 20 mL), and added with palladium acetate (Sigma-Ald, 228.6 mg), tri-o-tolylphosphine (KANTO, 1239.4 mg), isobutyl 3-butenoate (Alfa Aesar, 4.3 g), and N-ethyldiisopropylamine (WAKO, 7 mL) followed by stirring at 120° C. for 7 hours. After subjecting the mixture to a ChemElute column (manufactured by VARIAN), the solvent was distilled off under reduced pressure. The residue was purified by silica gel column chromatography to obtain the target compound (404.1 mg).

(Step B) Synthesis of isobutyl 4-(5-(N-methylsulfamoyl)thiophen-3-yl)butanoate

The compound synthesized from the Example 1-40 Step A mg) was dissolved in methanol (5 mL), and added with 10% palladium—activated carbon (MERCK, 20 mg) and the mixture was stirred under hydrogen atmosphere for 1 day at room temperature. With purification by filtering, the target compound (364.6 mg) was obtained.

(Step C) Synthesis of isobutyl 4-(2-iodo-5-(N-methylsulfamoyl)thiophen-3-yl)butanoate The compound synthesized from the Example 1-40 Step B mg) was dissolved in carbon tetrachloride (3 mL), and added with iodide (KANTO, 226.4 mg), bistrifluoroacetoxyiodobenzene (Ald, 383.6 mg) under ice cooling followed by stirring for 2 hours. Ice bath was removed and the mixture was further stirred for 2 hours. Sodium thiosulfate solution was added, and the extraction was carried out with dichloromethane. The organic layer was washed with brine, dried over anhydrous sodium sulfate, and the solvent was distilled off under reduced pressure. The residue was purified by silica gel column chromatography to obtain the target compound (111.2 mg).

(Step D) Synthesis of isobutyl 4-(5-(N-methylsulfamoyl-2-trifluoromethylthiophen-3-yl)butanoate The compound synthesized from the Example 1-40 Step C (177.9 mg) was dissolved in dimethylformamide (6 mL), and added with copper iodide(I) (WAKO, 19 mg) and methyl 2,2-difluoro-2-(fluorosulfonyl)acetate (TCI, 0.127 mL) followed by stirring at 100° C. for 9 hours. Sodium bicarbonate solution was added to the reaction solution, and the extraction was carried out with ether. The organic layer was washed with brine, dried over anhydrous sodium sulfate, and the solvent was distilled off under reduced pressure. The residue was purified by silica gel column chromatography to obtain the target compound (72.9 mg).

(Step E) Synthesis of isobutyl (S)-4-(5-(N-methyl-N-(oxiran-2-ylmethyl)sulfamoyl)-2-(trifluoromethyl)thiophen-3-yl)butanoate According to the method of Example 1-1 Step B, the target compound was obtained from the compound synthesized from Example 1-40 Step D.

EXAMPLE 1-41

Ethyl (S)-3-(3-(N-methyl-N-(oxiran-2-ylmethyl)sulfamoyl)-5-(trifluoromethyl)phenyl)butanoate (Step A) Synthesis of ethyl 3-(3-(N-methylsulfamoyl)-5-(trifluoromethyl)phenyl)but-2-enoate According to the literature (J. Org. Chem., Vol. 41, No. 2, 1976, 265-272), the target compound (150 mg) was obtained from 3-bromo-N-methyl-5-(trifluoromethyl)benzenesulfoneamide (synthesized according to Example 1-22 Step A) (311 mg) and ethyl crotonate (TCI, 0.62 mL).

(Step B) Synthesis of ethyl 3-(3-(N-methylsulfamoyl)-5-(trifluoromethyl)phenyl)butanoate The compound synthesized from the Example 1-41 Step A (150 mg) was added with 10% palladium carbon (MERCK, 15 mg) and ethanol (WAKO, 4.3 mL) and the mixture was stirred under hydrogen atmosphere for 17 hours at room temperature. With filtration, the target compound was obtained as a crude product.

(Step C) Synthesis of ethyl (S)-3-(3-(N-methyl-N-(oxiran-2-ylmethyl)sulfamoyl)-5-(trifluoromethyl)phenyl)butanoate According to the method of Example 1-1 Step B, the target compound (123 mg) was obtained from the crude compound synthesized from Example 1-41 Step B.

EXAMPLE 1-42

Methyl (S)-4-(3-(N-methyl-N-(oxiran-2-ylmethyl)sulfamoyl)-5-(trifluoromethyl)phenyl)pentanoate The target compound was obtained in the same manner as Example 1-41 except that methyl 3-pentenoate (TCI) was used instead of ethyl crotonate.

EXAMPLE 1-43

Ethyl (S)-3-(3'-ethyl-6-fluoro-4'-(N-methyl-N-(oxiran-2-ylmethyl)sulfamoyl)biphenyl-2-yl)acrylate The compound described in Example 1-7 (Exp. 1-7, 843.6 mg) was dissolved in ethanol (10 mL) and toluene (10 mL), and added with ethyl 3-(3-fluoro o-2-(4,4,5,5-tetramethyl-1,3,2-dioxaboran-2-yl)phenyl)acrylate (ba42, 1050.5 mg), b is 1,1'-bis(diphenylphosphinoferrocene)palladium(II) dichloride-dichloromethane complex (Ald, 412.2 mg) and potassium carbonate (WAKO, 697.7 mg) followed by stirring at 80° C. for 4 hours. After subjecting the mixture to a ChemElute column (manufactured by VARIAN), the solvent was distilled off under reduced pressure. The residue was purified by silica gel column chromatography to obtain the target compound (832.4 mg).

EXAMPLES 1-44 TO 51

The target compounds were obtained in the same manner as Example 1-43 except that Exp. 1-2 and ba29, Exp. 1-7 and ba12, Exp. 1-2 and Ba12, Exp. 1-22 and ba46, Exp. 1-2 and ba46, Exp. 1-22 and 4-(2-ethoxycarbonylethyl)phenylboronic acid (Combi-Blocks), Exp. 1-8 and ba42, or Exp. 1-2 and 3-methoxycarbonylphenylboronic acid (WAKO) was respectively used instead of Exp. 1-7 and ba42.

EXAMPLE 1-44

Ethyl (S)-2-(3'-(N-methyl-N-(oxiran-2-ylmethyl)sulfamoyl)biphenyl-4-yl)acetate

EXAMPLE 1-45

Ethyl (S)-3-(3'-ethyl-4'-(N-methyl-N-(oxiran-2-ylmethyl)sulfamoyl)biphenyl-4-yl)propionate

EXAMPLE 1-46

Ethyl (S)-3-(3'-(N-methyl-N-(oxiran-2-ylmethyl)sulfamoyl)biphenyl-4-yl)propionate

EXAMPLE 1-47

Methyl (S)-3-(3'-(N-methyl-N-(oxiran-2-ylmethyl)sulfamoyl)-5'-(trifluoromethyl)biphenyl-3-yl)propionate

EXAMPLE 1-48

Methyl (S)-3-(3'-(N-methyl-N-(oxiran-2-ylmethyl)sulfamoyl)biphenyl-3-yl)propionate

EXAMPLE 1-49

Methyl (S)-3-(3'-(N-methyl-N-(oxiran-2-ylmethyl)sulfamoyl)-5'-(trifluoromethyl)biphenyl-4-yl)propionate

EXAMPLE 1-50

Ethyl (S)-3-(3',5'-dichloro-6-fluoro-4'-(N-methyl-N-(oxiran-2-ylmethyl)sulfamoyl)biphenyl-2-yl)acrylate

EXAMPLE 1-51

Methyl (S)-3'-(N-methyl-N-(oxiran-2-ylmethyl)sulfamoyl)biphenyl-3-carboxylate

EXAMPLE 1-52

Ethyl (S)-3-(6-(3-(N-methyl-N-(oxiran-2-ylmethyl)sulfamoyl)-5-(trifluoromethyl)phenyl)pyridin-2-yl)acrylate (Step A) Synthesis of ethyl 3-(6-(3-(N-methylsulfamoyl)-5-trifluoromethylphenyl)pyridin-2-yl)acrylate According to the method described in the patent document (WO03/070686), the target compound (141 mg) was obtained from 3-bromo-N-methyl-5-(trifluoromethyl)benzenesulfoneamide (synthesized from Example 1-22 Step A; 191 mg).

(Step B) Synthesis of ethyl (S)-3-(6-(3-(N-methyl-N-(oxiran-2-ylmethyl)sulfamoyl)-5-(trifluoromethyl)phenyl)pyridin-2-yl)acrylate According to the method of Example 1-1 Step B, the target compound (92 mg) was obtained from the compound synthesized from Example 1-52 Step A (116 mg).

EXAMPLES 1-53 TO 54

According to the method of Example 1-52, the target compound was obtained.

EXAMPLE 1-53

Methyl (S)-6-(3-(N-methyl-N-(oxiran-2-ylmethyl)sulfamoyl)-5-(trifluoromethyl)phenyl)picolinate

EXAMPLE 1-54

Ethyl (S)-3-(2-(3-(N-methyl-N-(oxiran-2-ylmethyl)sulfamoyl)-5-(trifluoromethyl)phenyl)pyridin-3-yl)acrylate

EXAMPLE 1-55

Ethyl (S)-2-(5-trifluoromethyl-3-(N-methyl-N-(oxiran-2-ylmethyl)sulfamoyl)phenyloxy)acetate (Step A) Synthesis of tert-butyl 3-bromo-5-(trifluoromethyl)phenylsulfonyl(methyl)carbamate 3-Bromo-N-methyl-5-(trifluoromethyl)benzenesulfoneamide synthesized from the Example 1-22 Step A (3.0 g) was dissolved in tetrahydrofuran (KANTO, 18 mL), and added with di-tert-butyl bicarbonate (PEPTIDE INSTITUTE, INC.; 6.2 g), N,N-4-dimethylaminopyridine (WAKO, 1.4 g) and triethylamine (WAKO, 3.9 mL) followed by stirring at room temperature for 30 minutes. Water was added to the reaction mixture, and the extraction was carried out with ethyl acetate. The organic layer was washed with saturated sodium hydrogen carbonate solution and brine, dried over anhydrous magnesium sulfate, and the reaction solution was concentrated under reduced pressure to obtain a crude product, which was then purified by silica gel column chromatography to obtain the target compound (3.2 g).

(Step B) Synthesis of 3-hydroxy-N-methyl-5-(trifluoromethyl)benzenesulfoneamide

The compound obtained from the Step A (1.0 g) was dissolved in tetrahydrofuran (KANTO, 2.4 mL) under nitrogen atmosphere. After cooling to 0° C., isopropylmagnesium chloride (Ald, 1.25 mL) was added thereto followed by stirring at room temperature for 2 hours and 15 minutes. Subsequently, triisopropyl borate (TCI, 0.6 mL) was added and stirred overnight. To the reaction mixture, 2N NaOH aqueous solution (2.8 mL) and 30% hydrogen peroxide (0.46 mL) were added and the mixture was stirred at room temperature for 4 hours. 1N HCl solution was added to the reaction mixture, and the extraction was carried out with ethyl acetate. The organic layer was dried over anhydrous magnesium sulfate, and the reaction solution was concentrated under reduced pressure to obtain a crude product, which was then purified by silica gel column chromatography to obtain the target compound (139.3 mg).

(Step C) Synthesis of ethyl 2-(3-(N-methylsulfamoyl)-5-(trifluoromethyl)phenoxy)acetate The compound obtained from the Example 1-55 Step B (102.5 mg) was dissolved in dimethylformamide (2.0 mL) under nitrogen atmosphere, and added with potassium carbonate (KOKUSAN CHEMICAL Co., Ltd.; 60.8 mg) and ethyl bromoacetate (WAKO, 44 µL) followed by stirring overnight at 70° C. The reaction mixture was filtered and concentrated under reduced pressure to obtain a crude product, which was then purified by silica gel column chromatography to obtain the target compound (103.7 mg).

(Step D) Synthesis of ethyl (S)-2-(3-(N-methyl-N-(oxiran-2-ylmethyl)sulfamoyl)-5-(trifluoromethyl)phenoxy)acetate According to the method of Reference example 1-1 Step B, the target compound was obtained from the compound obtained from Example 1-55 Step C under nitrogen atmosphere.

EXAMPLES 1-56 TO 57

According to the method of Example 1-52, the target compound was obtained.

EXAMPLE 1-56

Ethyl (S)-3-(5-(3-(N-methyl-N-(oxiran-2-ylmethyl)sulfamoyl)-5-(trifluoromethyl)phenyl)thiophen-2-yl)acrylate

EXAMPLE 1-57

Ethyl (S)-3-(5-(3-(N-methyl-N-(oxiran-2-ylmethyl)sulfamoyl)phenyl)thiophen-2-yl)acrylate

EXAMPLE 1-58

Ethyl (S)-3-(6-(3-ethyl-4-(N-methyl-N-(oxiran-2-ylmethyl)sulfamoyl)phenyl)pyridin-2-yl)propionate (Step A) Synthesis of ethyl 3-(6-(3-ethyl-4-(N-methylsulfamoyl)phenyl)pyridin-2-yl)acrylate According to the method of the patent document (WO03/070686), the target compound was obtained from the compound (351 mg) synthesized from Example 1-7 Step A.

(Step B) Synthesis of ethyl 3-(6-(3-ethyl-4-(N-methylsulfamoyl)phenyl)pyridin-2-yl)propionate The compound synthesized from the Example 1-58 Step A (327 mg) was added with palladium carbon (MERCK, 32 mg) and ethanol (WAKO, 8.7 mL) and the mixture was stirred under hydrogen atmosphere for 16 hours at room temperature. After filtration and concentration under reduced pressure, the target compound was obtained as a crude product.

(Step C) Synthesis of ethyl (S)-3-(6-(3-ethyl-4-(N-methyl-N-(oxiran-2-ylmethyl)sulfamoyl)phenyl)pyridin-2-yl)propionate According to the method of Example 1-1 Step B, the target compound (88 mg) was obtained from the compound synthesized from Example 1-58 Step B.

EXAMPLES 1-59 TO 60

According to the method of Example 1-58, the target compound was obtained.

EXAMPLE 1-59

Ethyl (S)-3-(3-(3-(N-methyl-N-(oxiran-2-ylmethyl)sulfamoyl)-5-(trifluoromethyl)phenyl)thiophen-2-yl)propionate

EXAMPLE 1-60

Ethyl (S)-3-(2-(3-(N-methyl-N-(oxiran-2-ylmethyl)sulfamoyl)-5-(trifluoromethyl)phenyl)thiophen-3-yl)propionate

EXAMPLE 1-61

Ethyl (S)-3-(6-(3,5-dichloro-4-(N-methyl-N-(oxiran-2-ylmethyl)sulfamoyl)phenyl)pyridin-2-yl)propionate (Step A) Synthesis of ethyl 3-(6-bromopyridin-2-yl)propionate According to the method of the literature (J. Org. Chem., 1987, 52, 4665-4673), the target compound (650 mg) was obtained from ethyl 3-(6-bromopyridin-2-yl)acrylate (1.071 g)

(Step B) Synthesis of ethyl 3-(6-(3,5-dichloro-4-(N-methylsulfamoyl)phenyl)pyridin-2-yl)propionate According to the method of the patent document (WO03/070686), the target compound (120 mg) was obtained from the compound synthesized from Example 1-8 Step A (319 mg) and the compound synthesized from Example 1-61 Step A (264 mg).

(Step C) Synthesis of ethyl (S)-3-(6-(3,5-dichloro-4-(N-methyl-N-(oxiran-2-ylmethyl)sulfamoyl)phenyl)pyridin-2-yl)propionate According to the method of Example 1-1 Step B, the target compound (102 mg) was obtained from the compound synthesized from Example 1-61 Step B.

EXAMPLE 1-62

Ethyl (S)-3-(6-(2-chloro-4-(N-methyl-N-(oxiran-2-ylmethyl)sulfamoyl)phenyl)pyridin-2-yl)propionate The target compound was obtained in the same manner as Example 1-61 except that 4-bromo-3-chloro-N-methylbenzenesulfoneamide was used instead of 4-bromo-2,6-dichloro-N-methylbenzenesulfoneamide used in Step B.

EXAMPLE 1-63

Ethyl (S)-3-(5-(3-(N-methyl-N-(oxiran-2-ylmethyl)sulfamoyl)-5-(trifluoromethyl)phenyl)pyridin-2-yl)propionate (Step A) Synthesis of 5-bromopicoline aldehyde According to the literature (Tetrahedron Letters, 41, 2000, 4335-4338), the target compound (2.00 g) was obtained from 2,5-dibromopyridine (10.01 g).

(Step B) Synthesis of ethyl 3-(5-bromopyridin-2-yl)acrylate

The compound synthesized from the Example 1-63 Step A (0.50 g) was dissolved in ethanol (WAKO, 6 mL), and added with ethyl diethylphosphonoacetate (TCI, 0.64 mL) and sodium ethoxide (1.25 mL) followed by stirring at room temperature for 1 hour under nitrogen atmosphere. Water was added to the reaction solution, and the extraction was carried out with ethyl acetate. The organic layer was washed with brine, dried over anhydrous sodium sulfate, and the solvent was distilled off under reduced pressure. The residue was purified by silica gel column chromatography to obtain the target compound (0.66 g).

(Step C) Synthesis of ethyl 3-(5-(3-(N-methylsulfamoyl)-5-(trifluoromethyl)phenyl)pyridin-2-yl)acrylate According to the method of the patent document (WO03/070686), the target compound (229 mg) was obtained from the compound synthesized from Example 1-22 Step A (191 mg) and the compound synthesized from Example 1-63 Step B (256 mg).

(Step D) Synthesis of ethyl 3-(5-(3-(N-methylsulfamoyl)-5-(trifluoromethyl)phenyl)pyridin-2-yl)propionate The compound synthesized from the Example 1-63 Step C (224 mg) was added with palladium carbon (MERCK, 22 mg) and methanol (WAKO, 5 mL) and the mixture was stirred under hydrogen atmosphere for 3.5 hours at room temperature. After filtration and concentration under reduced pressure, the target compound was obtained as a crude product.

(Step E) Synthesis of ethyl (S)-3-(5-(3-(N-methyl-N-(oxiran-2-ylmethyl)sulfamoyl)-5-(trifluoromethyl)phenyl)pyridin-2-yl)propionate According to the method of Example 1-1 Step B, the target compound (101 mg) was obtained from the compound synthesized from Example 1-63 Step D.

EXAMPLE 1-64

Ethyl (S)-3-(6-(3-(N-methyl-N-(oxiran-2-ylmethyl)sulfamoyl)-5-(trifluoromethyl)phenyl)pyridin-3-yl)propionate The target compound was obtained in the same manner as Example 1-63 except that 6-bromopyridine aldehyde was used instead of 5-bromopicoline aldehyde.

EXAMPLE 1-65

Ethyl (S)-3-(5-(3,5-dichloro-4-(N-methyl-N-(oxiran-2-ylmethyl)sulfamoyl)phenyl)pyridin-2-yl)propionate (Step A) Synthesis of ethyl 3-(5-(3,5-dichloro-4-(N-methylsulfamoyl)phenyl)pyridin-2-yl)acrylate According to the method described in the patent document (WO03/070686), the target compound (130 mg) was obtained from 4-bromo-2,6-dichloro-N-methylbenzenesulfoneamide (synthesized from Example 1-8 Step A, 319 mg).

(Step B) Synthesis of ethyl 3-(5-(3,5-dichloro-4-(N-methylsulfamoyl)phenyl)pyridin-2-yl)propionate According to the method described in the literature (J. Org. Chem., 1987, 52, 4665-4673), the target compound (59 mg) was obtained from the compound synthesized from Example 1-65 Step A (130 mg).

(Step C) Synthesis of ethyl (S)-3-(5-(3,5-dichloro-4-(N-methyl-N-(oxiran-2-ylmethyl)sulfamoyl)phenyl)pyridin-2-yl)propionate According to the method of Example 1-1 Step B, the target compound (57 mg) was obtained from the compound synthesized from Example 1-65 Step B.

EXAMPLE 1-66

(S)-3-bromo-N-ethyl-N-(oxiran-2-ylmethyl)benzenesulfoneamide

The target compound was obtained in the same manner as Example 1-2 except that ethylamine was used instead of methylamine.

EXAMPLE 1-67

Ethyl (S)-3-(2-chloro-5-fluoro-3-(N-methyl-N-(oxiran-2-ylmethyl)sulfamoyl)phenyl)propionate According to the method of Example 1-29, the target compound was obtained from 1,3-dibromo-2-chloro-5-fluorobenzene.

EXAMPLE 1-68

Ethyl (S)-2-(3-(N-methyl-N-(oxiran-2-ylmethyl)sulfamoyl)-5-(trifluoromethyl)phenylamino)propionate (Step A) Synthesis of 3-fluoro-N-methyl-5-(trifluoromethyl)benzenesulfoneamide The target compound (0.568 g) was obtained in the same manner as Example 1-1 Step A except that 3-fluoro-5-(trifluoromethyl)benzenesulfonyl chloride (Alfa Aesar, 0.544 g) was used instead of 2-bromobenzenesulfonyl chloride.

(Step B) Synthesis of 2-(3-(N-methylsulfamoyl)-5-(trifluoromethyl)phenylamino)propionic acid The compound synthesized from the Example 1-68 Step A (0.568 g) was dissolved in dimethylsulfoxide (6.3 mL), and added with glycine (WAKO, 0.262 g) and potassium carbonate (0.991 g), followed by stirring at 150° C. for 1 hour by using a microwave generator. After air-cooling to room temperature, the mixture was again stirred at 150° C. for 1 hour by using a microwave generator, and then air-cooled to room temperature. Water and hydrochloric acid solution were added to the reaction solution, and the extraction was carried out with ethyl acetate. The organic layer was washed with brine, dried over anhydrous sodium sulfate, and the solvent was distilled off under reduced pressure. The residue was purified by silica gel column chromatography to obtain the target compound as a crude product.

(Step C) Synthesis of ethyl 2-(3-(N-methylsulfamoyl)-5-(trifluoromethyl)phenylamino)propionate The crude product synthesized from the Example 1-68 Step B was dissolved in ethanol (20 mL), and added with a catalytic amount of sulfuric acid, followed by reflux at 85° C. for 10 hours. After air-cooling to room temperature, water was added to the reaction solution, and the extraction was carried out with ethyl acetate. The organic layer was washed with brine, dried over anhydrous sodium sulfate, and the solvent was distilled off under reduced pressure to obtain the target compound as a crude product.

(Step D) Synthesis of ethyl (S)-2-(3-(N-methyl-N-(oxiran-2-ylmethyl)sulfamoyl)-5-(trifluoromethyl)phenylamino)propionate According to the method of Example 1-1 Step B, the target compound (0.061 g) was obtained by using the crude product synthesized from Example 1-68 Step C.

Hereinbelow, structures of the compounds of Example to 1-68 (Exp. 1-7 to Exp. 1-68) are shown.

Exp. 1-7

Exp. 1-8

Exp. 1-9

Exp. 1-10

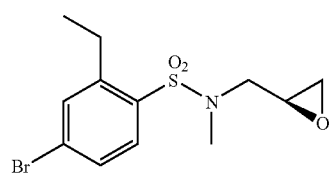

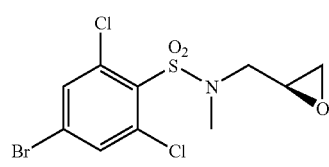

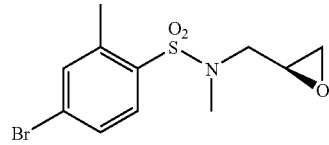

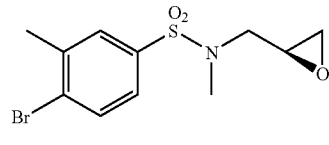

-continued

Exp. 1-11

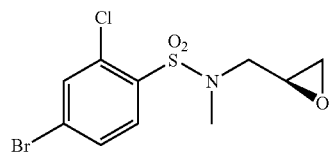

Exp. 1-12

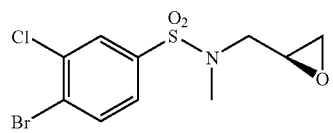

Exp. 1-13

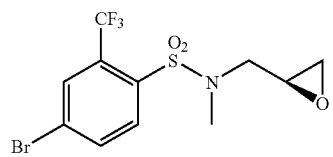

Exp. 1-14

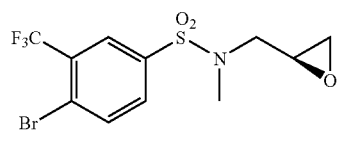

Exp. 1-15

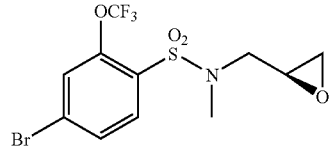

Exp. 1-16

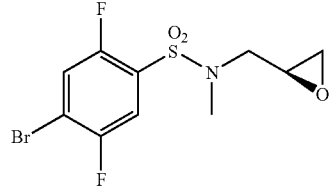

Exp. 1-17

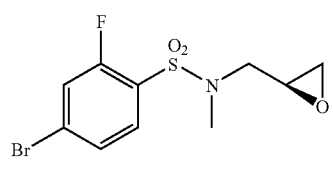

Exp. 1-18

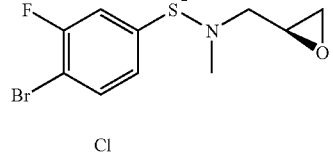

Exp. 1-19

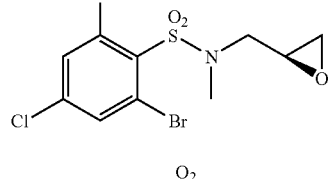

Exp. 1-20

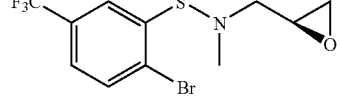

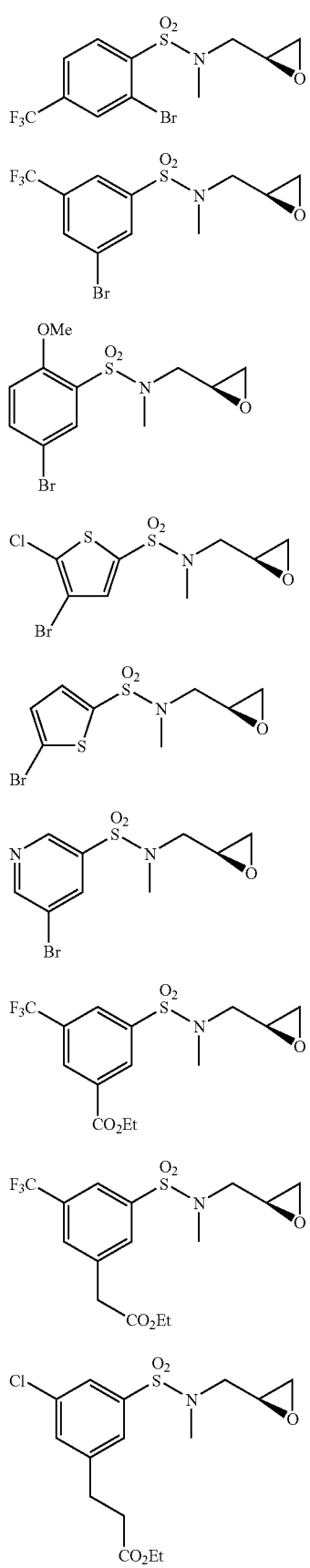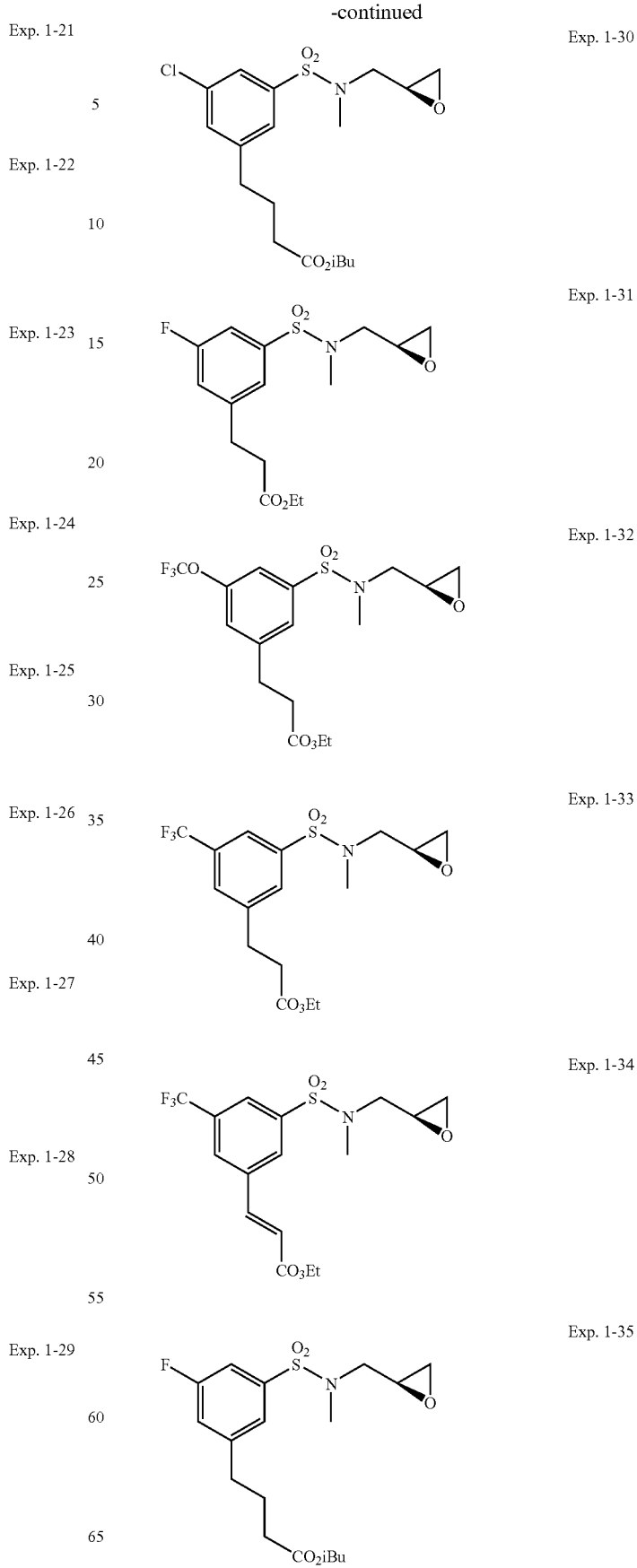

Exp. 1-36
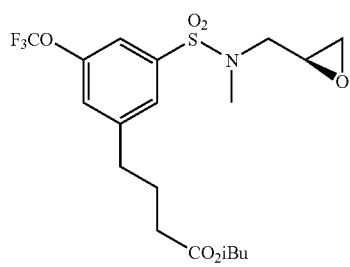
Exp. 1-42
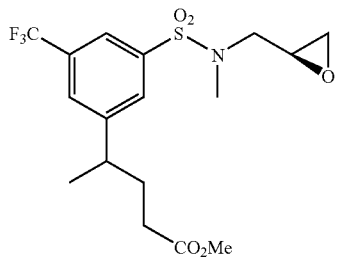
Exp. 1-37
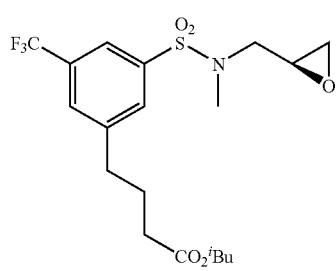
Exp. 1-43
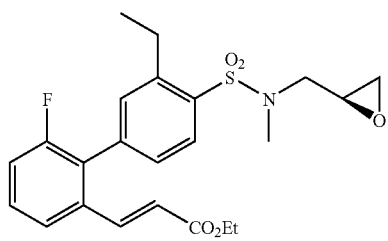
Exp. 1-38
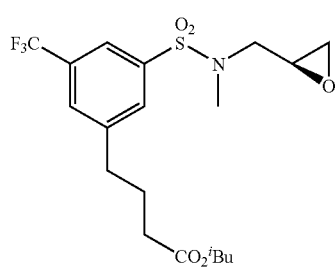
Exp. 1-44
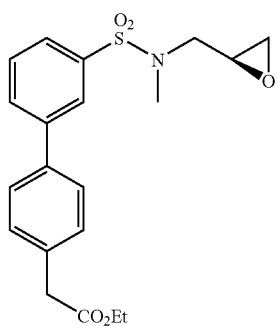
Exp. 1-39
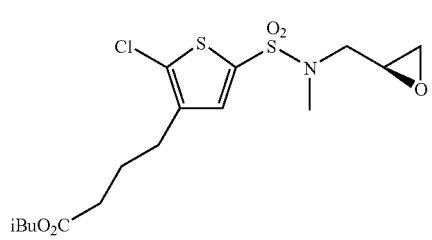
Exp. 1-45
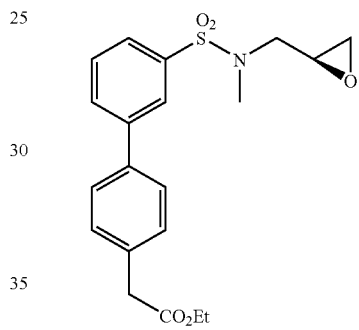
Exp. 1-40
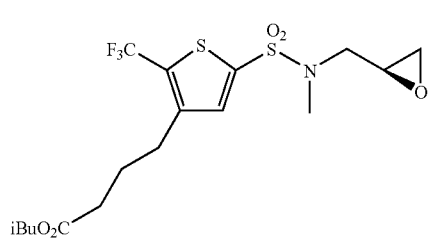
Exp. 1-46
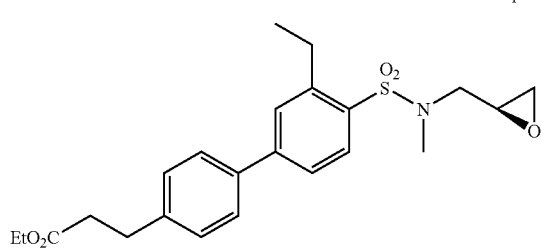
Exp. 1-41
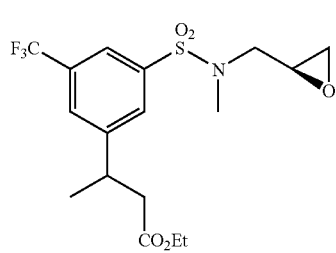
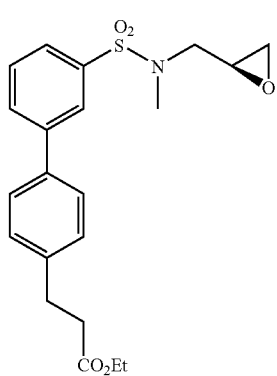

Exp. 1-47
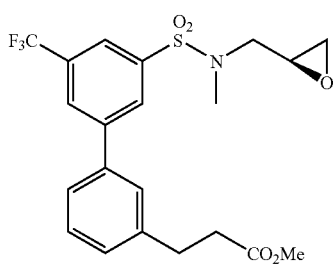
Exp. 1-48
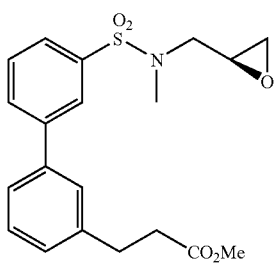
Exp. 1-49
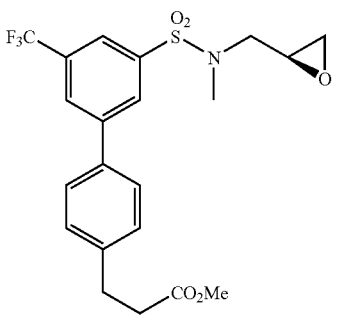
Exp. 1-50
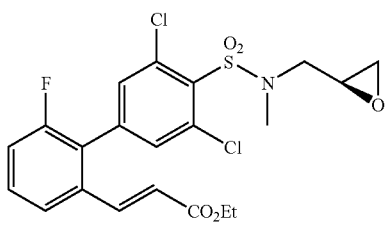
Exp. 1-51
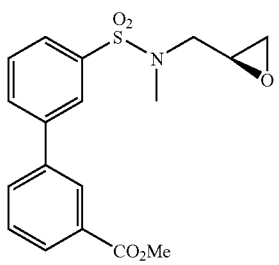
Exp. 1-52
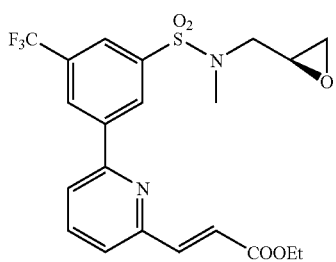
Exp. 1-53
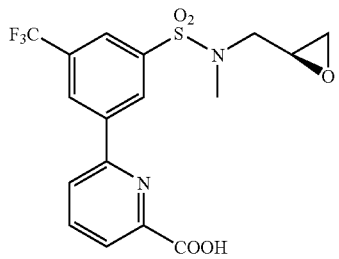
Exp. 1-54
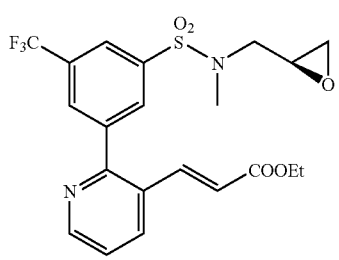
Exp. 1-55
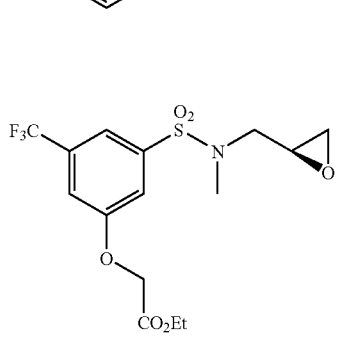
Exp. 1-56
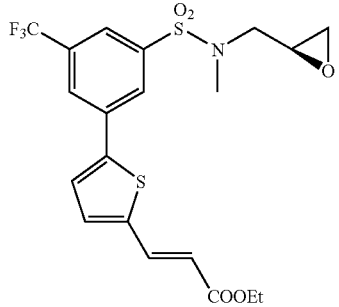
Exp. 1-57
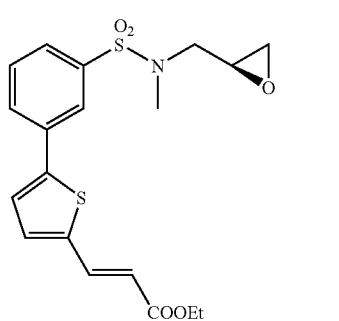

Exp. 1-58
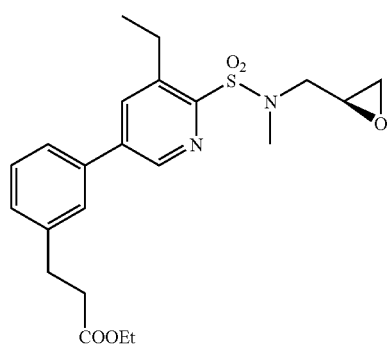
Exp. 1-59
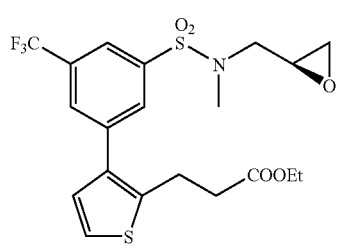
Exp. 1-60
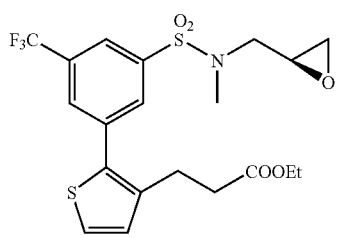
Exp. 1-61
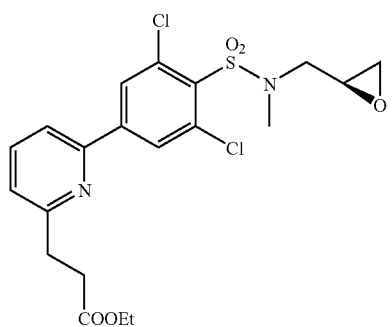
Exp. 1-62
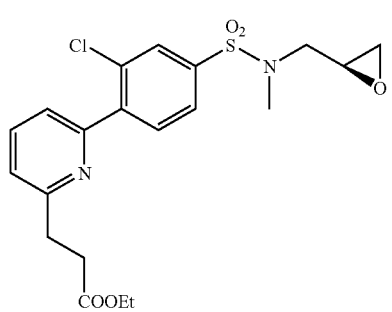
Exp. 1-63
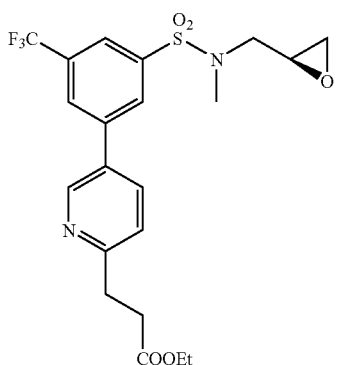
Exp. 1-64
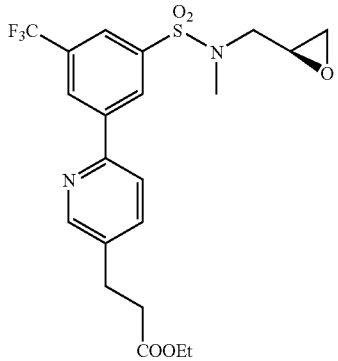
Exp. 1-65
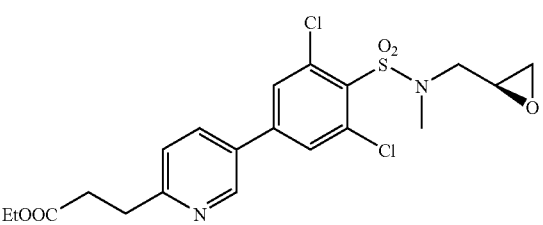
Exp. 1-66
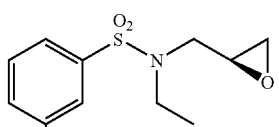
Exp. 1-67
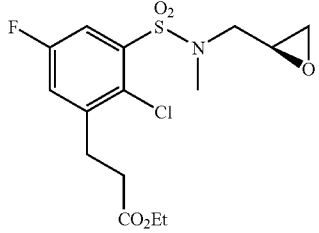

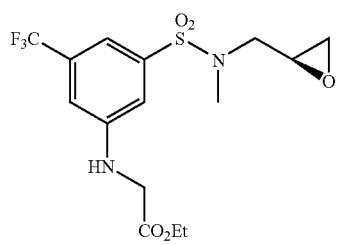

Exp. 1-68

EXAMPLE 2-1

Synthesis of (R)-2-bromo-N-(2-hydroxy-3-(2-methyl-1-(naphthalen-2-yl)propan-2-ylamino)propyl)-N-methylbenzenesulfonamide (S)-2-Bromo-N-methyl-N-(oxiran-2-ylmethyl)benzenesulfonamide (Exp. 1-1, 3.06 g) was dissolved in acetonitrile (25 mL), 2-methyl-1-(naphthalen-2-yl)propan-2-amine (am1, 1.99 g) and lithium perchlorate (KANTO, 1.06 g) were added thereto followed by reflux for 6 hours and 35 minutes. After cooling to room temperature, same amount of water and brine was added to the reaction solution and extraction was carried out with ethyl acetate. The organic layer was washed with brine, dried over anhydrous sodium sulfate, and the solvent was removed by distillation under reduced pressure. The residue was purified by silica gel column chromatography to obtain the target compound (3.97 g).

EXAMPLES 2-2 TO 15

By using SM1 instead of Exp. 1-1 and using AM instead of am1 in combination as shown in the Table 1, the reaction was carried out according to Example 2-1 to obtain the target compounds.

TABLE 1

| Exp. | SM1 | AM | LCMS method | RTime | Mass |
|---|---|---|---|---|---|
| 2-1 | Exp. 1-1 | am1 | A | 3.08 | 507 |
| 2-2 | Exp. 1-2 | am1 | A | 3.32 | 507 |
| 2-3 | Exp. 1-3 | am1 | A | 3.27 | 507 |
| 2-4 | Exp. 1-1 | am2 | A | 3.04 | 497 |
| 2-5 | Exp. 1-2 | am2 | A | 3.13 | 497 |
| 2-6 | Exp. 1-3 | am2 | A | 3.18 | 497 |
| 2-7 | Exp. 1-1 | am3 | A | 2.90 | 489 |
| 2-8 | Exp. 1-2 | am3 | A | 3.18 | 489 |
| 2-9 | Exp. 1-3 | am3 | A | 3.04 | 489 |
| 2-10 | Exp. 1-1 | am4 | A | 2.94 | 509 |
| 2-11 | Exp. 1-2 | am4 | A | 3.13 | 509 |
| 2-12 | Exp. 1-3 | am4 | A | 3.13 | 509 |
| 2-13 | Exp. 1-4 | am1 | A | 3.23 | 521 |
| 2-14 | Exp. 1-5 | am1 | A | 3.19 | 521 |
| 2-15 | Exp. 1-6 | am1 | A | 3.20 | 521 |

Further, structures of the compounds of the Example to Example 2-15 (Exp. 2-1 to Exp. 2-15) are described below.

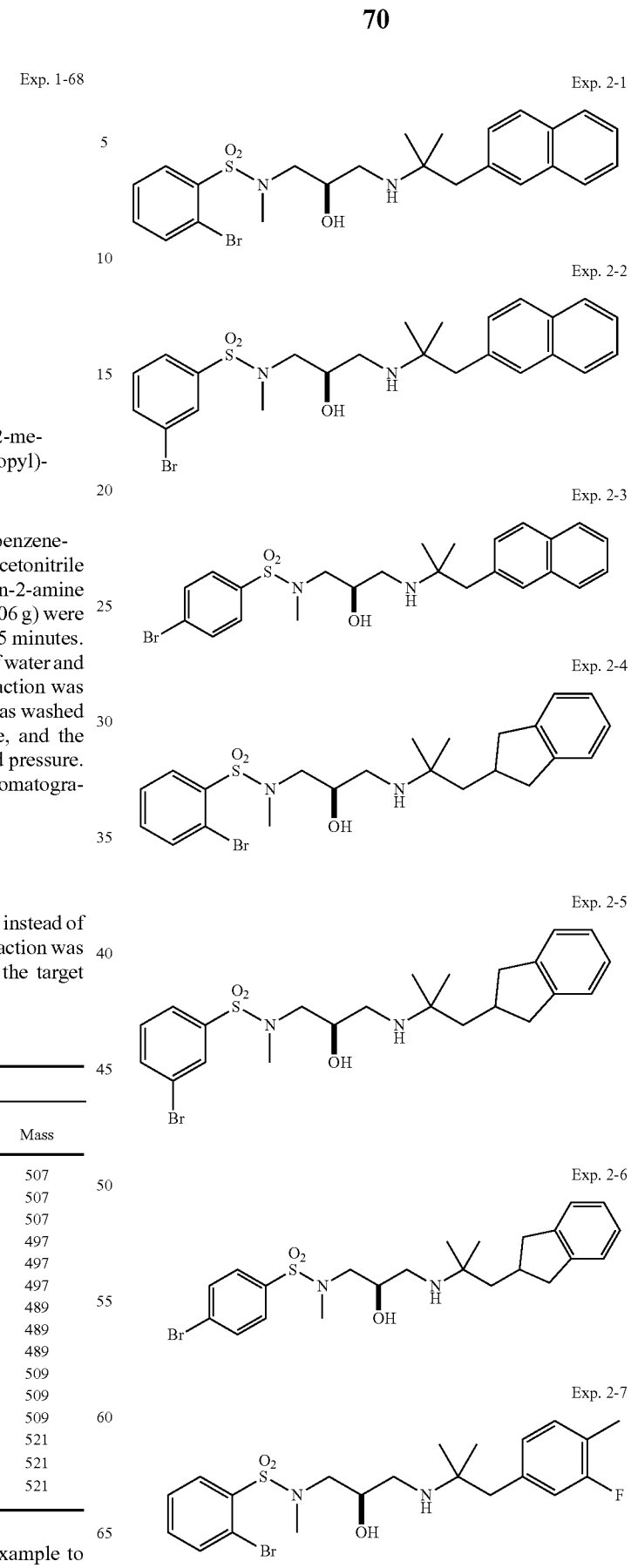

-continued

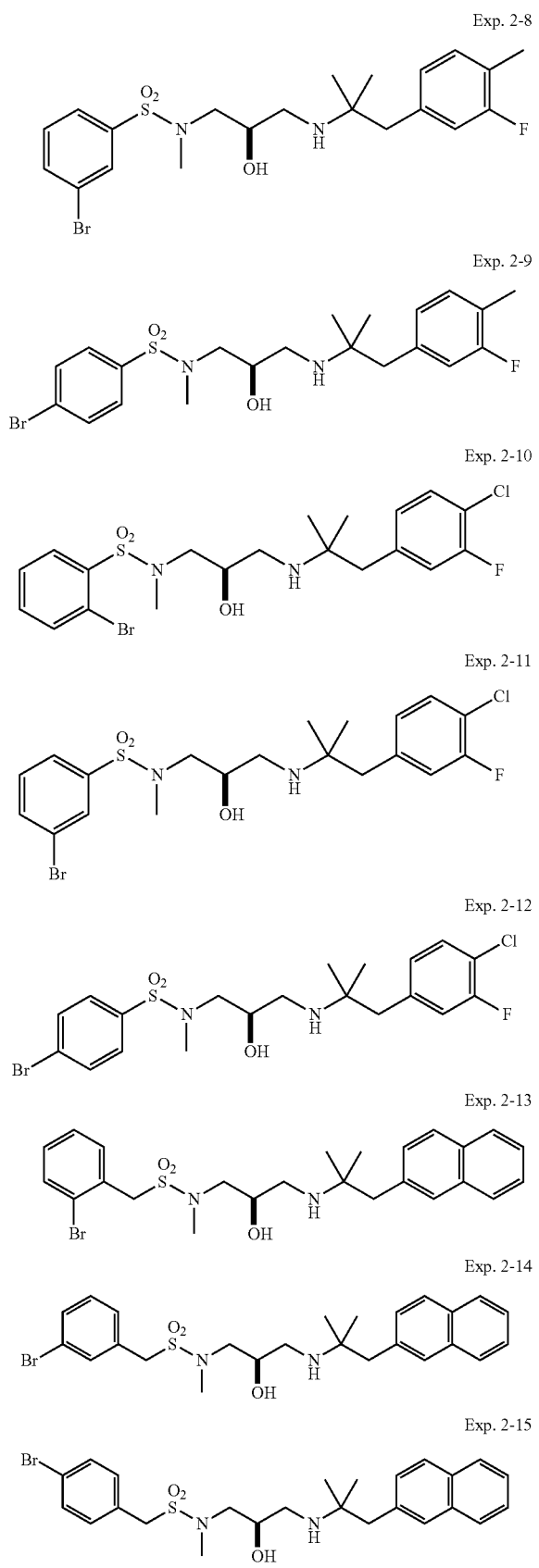

EXAMPLE 2-2

(R)-3-bromo-N-(2-hydroxy-3-(2-methyl-1-(naphthalen-2-yl)propan-2-ylamino)propyl)-N-methylbenzenesulfonamide

EXAMPLE 2-3

(R)-4-bromo-N-(2-hydroxy-3-(2-methyl-1-(naphthalen-2-yl)propan-2-ylamino)propyl)-N-methylbenzenesulfonamide

EXAMPLE 2-4

(R)-2-bromo-N-(3-(1-(2,3-dihydro-1H-inden-2-yl)-2-methylpropan-2-ylamino)-2-hydroxypropyl)-N-methylbenzenesulfonamide

EXAMPLE 2-5

(R)-3-bromo-N-(3-(1-(2,3-dihydro-1H-inden-2-yl)-2-methylpropan-2-ylamino)-2-hydroxypropyl)-N-methylbenzenesulfonamide

EXAMPLE 2-6

(R)-4-bromo-N-(3-(1-(2,3-dihydro-1H-inden-2-yl)-2-methylpropan-2-ylamino)-2-hydroxypropyl)-N-methylbenzenesulfonamide

EXAMPLE 2-7

(R)-2-bromo-N-(3-(1-(3-fluoro-4-methylphenyl)-2-methylpropan-2-ylamino)-2-hydroxypropyl)-N-methylbenzenesulfonamide

EXAMPLE 2-8

(R)-3-bromo-N-(3-(1-(3-fluoro-4-methylphenyl)-2-methylpropan-2-ylamino)-2-hydroxypropyl)-N-methylbenzenesulfonamide

EXAMPLE 2-9

(R)-4-bromo-N-(3-(1-(3-fluoro-4-methylphenyl)-2-methylpropan-2-ylamino)-2-hydroxypropyl)-N-methylbenzenesulfonamide

EXAMPLE 2-10

(R)-2-bromo-N-(3-(1-(4-chloro-3-fluorophenyl)-2-methylpropan-2-ylamino)-2-hydroxypropyl)-N-methylbenzenesulfonamide

EXAMPLE 2-11

(R)-3-bromo-N-(3-(1-(4-chloro-3-fluorophenyl)-2-methylpropan-2-ylamino)-2-hydroxypropyl)-N-methylbenzenesulfonamide

EXAMPLE 2-12

(R)-4-bromo-N-(3-(1-(4-chloro-3-fluorophenyl)-2-methylpropan-2-ylamino)-2-hydroxypropyl)-N-methylbenzenesulfonamide

EXAMPLE 2-13

(R)-1-(2-bromophenyl)-N-(2-hydroxy-3-(2-methyl-1-(naphthalen-2-yl)propan-2-ylamino)propyl)-N-methyl-methanesulfonamide

EXAMPLE 2-14

(R)-1-(3-bromophenyl)-N-(2-hydroxy-3-(2-methyl-1-(naphthalen-2-yl)propan-2-ylamino)propyl)-N-methyl-methanesulfonamide

EXAMPLE 2-15

(R)-1-(4-bromophenyl)-N-(2-hydroxy-3-(2-methyl-1-(naphthalen-2-yl)propan-2-ylamino)propyl)-N-methyl-methanesulfonamide

EXAMPLES 2-16 TO 43

The target compounds were obtained in the same manner as Example 2-1 with combinations shown in Table 2, except that SM1 and AM were used instead of Exp. 1-1 and am1, respectively.

TABLE 2

| Exp. | SM1 | AM | LCMS method | RTime | Mass |
|---|---|---|---|---|---|
| 2-16 | Exp. 1-7 | am2 | B | 1.4 | 523 |
| 2-17 | Exp. 1-7 | am5 | B | 1.46 | 511 |
| 2-18 | Exp. 1-8 | am2 | B | 1.38 | 565 |
| 2-19 | Exp. 1-8 | am5 | B | 1.56 | 553 |
| 2-20 | Exp. 1-9 | am2 | B | 1.37 | 511 |
| 2-21 | Exp. 1-10 | am2 | B | 1.4 | 509 |
| 2-22 | Exp. 1-10 | am5 | B | 1.34 | 497 |
| 2-23 | Exp. 1-11 | am2 | B | 1.31 | 529 |
| 2-24 | Exp. 1-12 | am2 | B | 1.37 | 529 |
| 2-25 | Exp. 1-12 | am5 | B | 1.43 | 517 |
| 2-26 | Exp. 1-13 | am2 | B | 1.43 | 563 |
| 2-27 | Exp. 1-14 | am2 | B | 1.37 | 563 |
| 2-28 | Exp. 1-15 | am2 | B | 1.46 | 579 |
| 2-29 | Exp. 1-16 | am2 | B | 1.45 | 531 |
| 2-30 | Exp. 1-17 | am5 | B | 1.4 | 501 |
| 2-31 | Exp. 1-18 | am2 | B | 1.31 | 513 |
| 2-32 | Exp. 1-19 | am5 | B | 1.39 | 553 |
| 2-33 | Exp. 1-20 | am5 | B | 1.43 | 551 |
| 2-34 | Exp. 1-21 | am5 | B | 1.48 | 551 |
| 2-35 | Exp. 1-22 | am2 | B | 1.32 | 565 |
| 2-36 | Exp. 1-22 | am4 | B | 1.38 | 575 |
| 2-37 | Exp. 1-22 | am5 | B | 1.37 | 551 |
| 2-38 | Exp. 1-23 | am2 | B | 1.26 | 527 |
| 2-39 | Exp. 1-24 | am2 | B | 1.36 | 535 |
| 2-40 | Exp. 1-25 | am2 | B | 1.29 | 501 |
| 2-41 | Exp. 1-26 | am2 | B | 1.18 | 496 |
| 2-42 | Exp. 1-24 | am5 | B | 1.46 | 525 |
| 2-43 | Exp. 1-66 | am2 | B | 1.46 | 525 |

EXAMPLE 2-16

(R)-4-bromo-N-(3-(1-(2,3-dihydro-1H-inden-2-yl)-2-methylpropan-2-ylamino)-2-hydroxypropyl)-2-ethyl-N-methylbenzenesulfoneamide

EXAMPLE 2-17

(R)-4-bromo-2-ethyl-N-(2-hydroxy-3-(2-methyl-5-phenylpentan-2-ylamino)propyl)-N-methylbenzenesulfoneamide

EXAMPLE 2-18

(R)-4-bromo-2,6-dichloro-N-(3-(1-(2,3-dihydro-1H-inden-2-yl)-2-methylpropan-2-ylamino)-2-hydroxypropyl)-N-methylbenzenesulfoneamide

EXAMPLE 2-19

(R)-4-bromo-2,6-dichloro-N-(2-hydroxy-3-(2-methyl-5-phenylpentan-2-ylamino)propyl)-N-methylbenzenesulfoneamide

EXAMPLE 2-20

(R)-4-bromo-N-(3-(1-(2,3-dihydro-1H-inden-2-yl)-2-methylpropan-2-ylamino)-2-hydroxypropyl)-N,2-dimethylbenzenesulfoneamide

EXAMPLE 2-21

(R)-4-bromo-N-(3-(1-(2,3-dihydro-1H-inden-2-yl)-2-methylpropan-2-ylamino)-2-hydroxypropyl)-N,3-dimethylbenzenesulfoneamide

EXAMPLE 2-22

(R)-4-bromo-N-(2-hydroxy-3-(2-methyl-5-phenylpentan-2-ylamino)propyl)-N,3-dimethylbenzenesulfoneamide

EXAMPLE 2-23

(R)-4-bromo-2-chloro-N-(3-(1-(2,3-dihydro-1H-inden-2-yl)-2-methylpropan-2-ylamino)-2-hydroxypropyl)-N-methylbenzenesulfoneamide

EXAMPLE 2-24

(R)-4-bromo-3-chloro-N-(3-(1-(2,3-dihydro-1H-inden-2-yl)-2-methylpropan-2-ylamino)-2-hydroxypropyl)-N-methylbenzenesulfoneamide

EXAMPLE 2-25

(R)-4-bromo-3-chloro-N-(2-hydroxy-3-(2-methyl-5-phenylpentan-2-ylamino)propyl)-N-methylbenzenesulfoneamide

EXAMPLE 2-26

(R)-4-bromo-N-(3-(1-(2,3-dihydro-1H-inden-2-yl)-2-methylpropan-2-ylamino)-2-hydroxypropyl)-N-methyl-2-(trifluoromethyl)benzenesulfoneamide

EXAMPLE 2-27

(R)-4-bromo-N-(3-(1-(2,3-dihydro-1H-inden-2-yl)-2-methylpropan-2-ylamino)-2-hydroxypropyl)-N-methyl-3-(trifluoromethyl)benzenesulfoneamide

EXAMPLE 2-28

(R)-4-bromo-N-(3-(1-(2,3-dihydro-1H-inden-2-yl)-2-methylpropan-2-ylamino)-2-hydroxypropyl)-N-methyl-2-(trifluoromethoxy)benzenesulfoneamide

EXAMPLE 2-29

(R)-4-bromo-N-(3-(1-(2,3-dihydro-1H-inden-2-yl)-2-methylpropan-2-ylamino)-2-hydroxypropyl)-2,5-difluoro-N-methylbenzenesulfoneamide

EXAMPLE 2-30

(R)-4-bromo-2-fluoro-N-(2-hydroxy-3-(2-methyl-5-phenylpentan-2-ylamino)propyl)-N-methylbenzenesulfoneamide

EXAMPLE 2-31

(R)-4-bromo-N-(3-(1-(2,3-dihydro-1H-inden-2-yl)-2-methylpropan-2-ylamino)-2-hydroxypropyl)-3-fluoro-N-methylbenzenesulfoneamide

EXAMPLE 2-32

(R)-2-bromo-4,6-dichloro-N-(2-hydroxy-3-(2-methyl-5-phenylpentan-2-ylamino)propyl)-N-methylbenzenesulfoneamide

EXAMPLE 2-33

(R)-2-bromo-N-(2-hydroxy-3-(2-methyl-5-phenylpentan-2-ylamino)propyl)-N-methyl-5-(trifluoromethyl)benzenesulfoneamide

EXAMPLE 2-34

(R)-2-bromo-N-(2-hydroxy-3-(2-methyl-5-phenylpentan-2-ylamino)propyl)-N-methyl-4-(trifluoromethyl)benzenesulfoneamide

EXAMPLE 2-35

(R)-3-bromo-N-(3-(1-(2,3-dihydro-1H-inden-2-yl)-2-methylpropan-2-ylamino)-2-hydroxypropyl)-N-methyl-5-(trifluoromethyl)benzenesulfoneamide

EXAMPLE 2-36

(R)-3-bromo-N-(3-(1-(4-chloro-3-fluorophenyl)-2-methylpropan-2-ylamino)-2-hydroxypropyl)-N-methyl-5-(trifluoromethyl)benzenesulfoneamide

EXAMPLE 2-37

(R)-3-bromo-N-(2-hydroxy-3-(2-methyl-5-phenylpentan-2-ylamino)propyl)-N-methyl-5-(trifluoromethyl)benzenesulfoneamide

EXAMPLE 2-38

(R)-5-bromo-N-(3-(1-(2,3-dihydro-1H-inden-2-yl)-2-methylpropan-2-ylamino)-2-hydroxypropyl)-2-methoxy-N-methylbenzenesulfoneamide

EXAMPLE 2-39

(R)-4-bromo-5-chloro-N-(3-(1-(2,3-dihydro-1H-inden-2-yl)-2-methylpropan-2-ylamino)-2-hydroxypropyl)-N-methylthiophen-2-sulfoneamide

EXAMPLE 2-40

(R)-5-bromo-N-(3-(1-(2,3-dihydro-1H-inden-2-yl)-2-methylpropan-2-ylamino)-2-hydroxypropyl)-N-methylthiophen-2-sulfoneamide

EXAMPLE 2-41

(R)-5-bromo-N-(3-(1-(2,3-dihydro-1H-inden-2-yl)-2-methylpropan-2-ylamino)-2-hydroxypropyl)-N-methylpyridin-3-sulfoneamide

EXAMPLE 2-42

(R)-4-bromo-5-chloro-N-(2-hydroxy-3-(2-methyl-5-phenylpentan-2-ylamino)propyl)-N-methylthiophen-2-sulfoneamide

EXAMPLE 2-43

(R)-3-bromo-N-(3-(1-(2,3-dihydro-1H-inden-2-yl)-2-methylpropan-2-ylamino)-2-hydroxypropyl)-N-ethylbenzenesulfoneamide Hereinbelow, structures of the compounds of Example to 2-43 (Exp. 2-16 to Exp. 2-43) are shown.

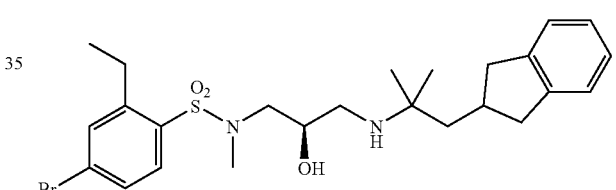

Exp. 2-16

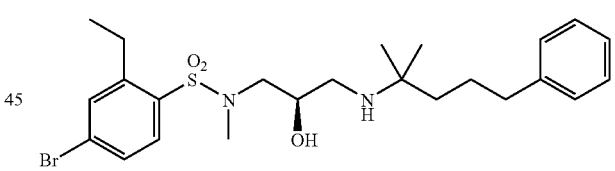

Exp. 2-17

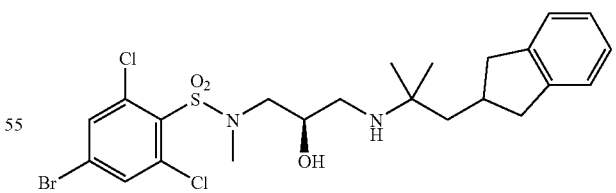

Exp. 2-18

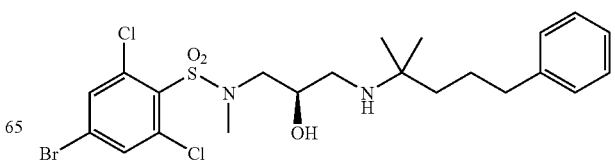

Exp. 2-19

-continued
Exp. 2-20
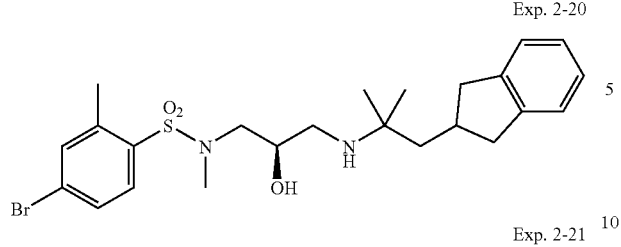
Exp. 2-21
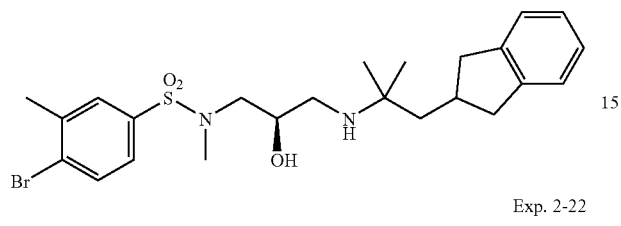
Exp. 2-22
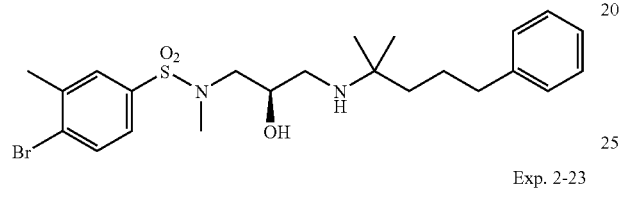
Exp. 2-23
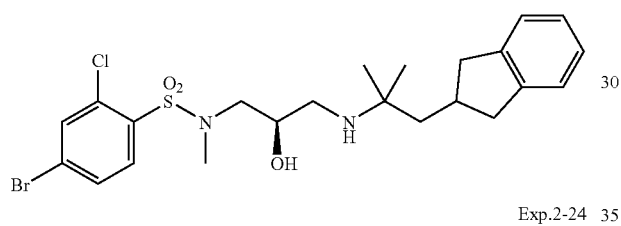
Exp.2-24
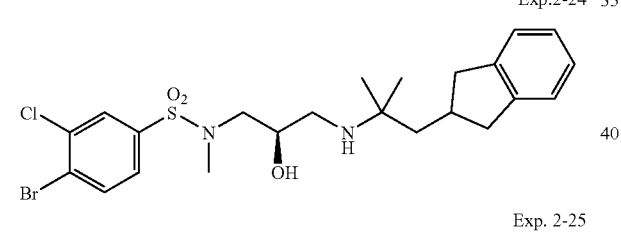
Exp. 2-25
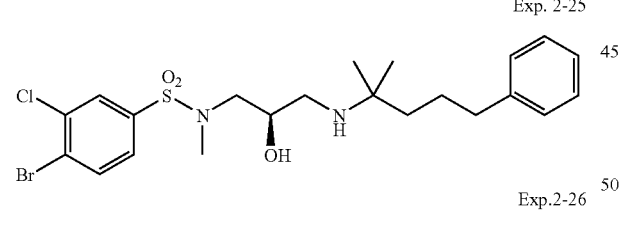
Exp.2-26
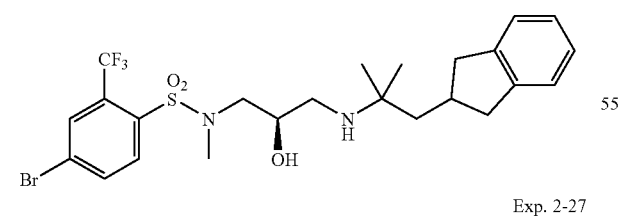
Exp. 2-27
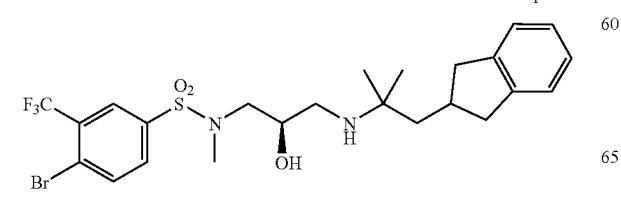
-continued
Exp. 2-28
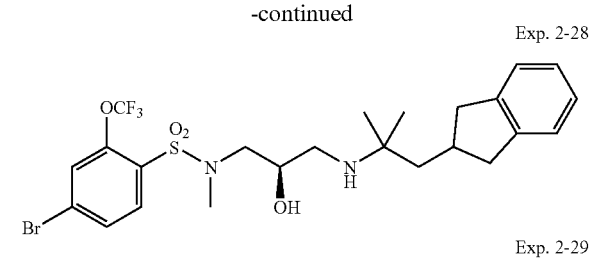
Exp. 2-29
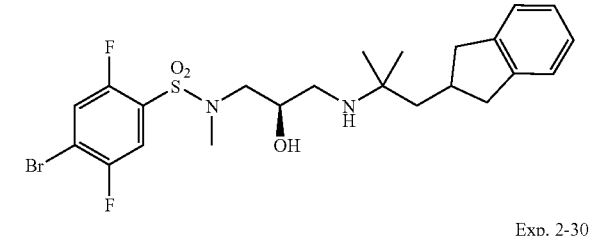
Exp. 2-30
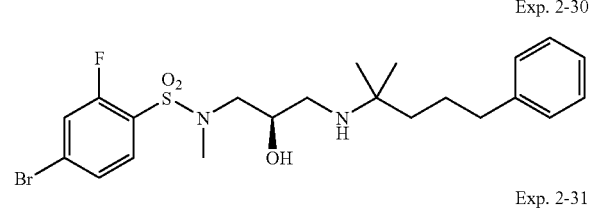
Exp. 2-31
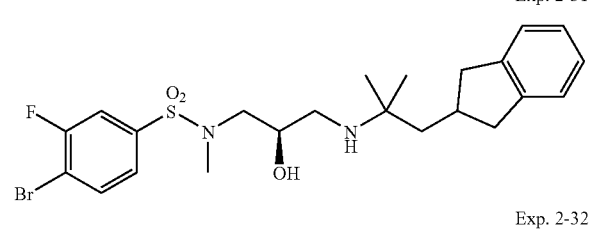
Exp. 2-32
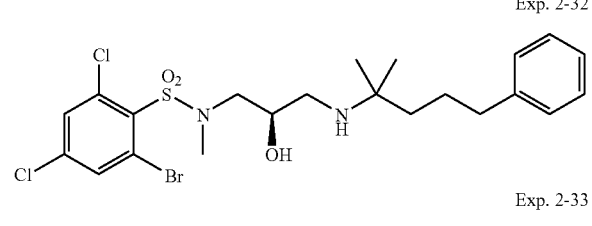
Exp. 2-33
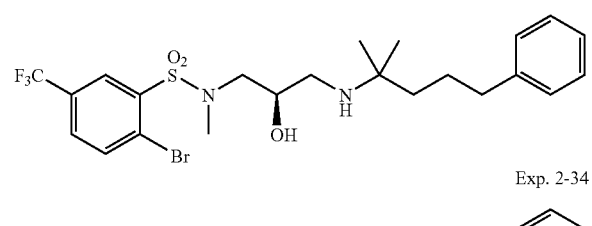
Exp. 2-34
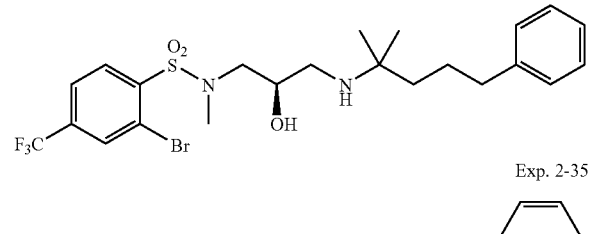
Exp. 2-35
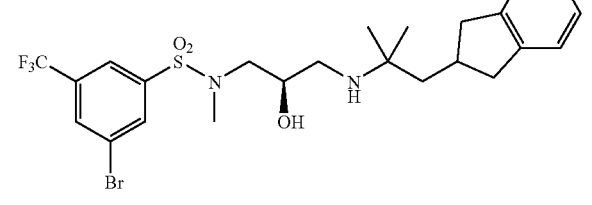

Exp. 2-36
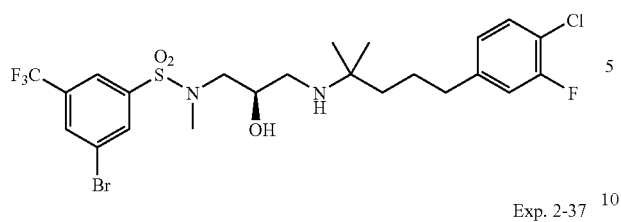

Exp. 2-37
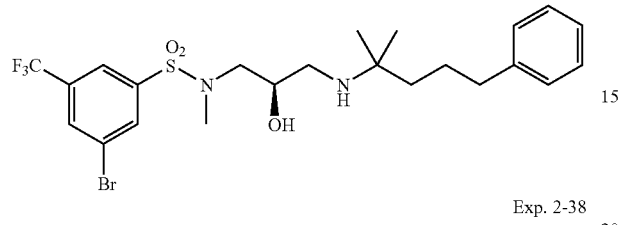

Exp. 2-38
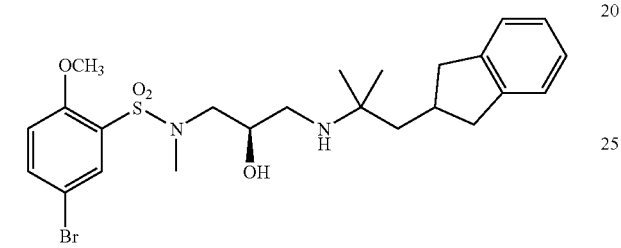

Exp. 2-39
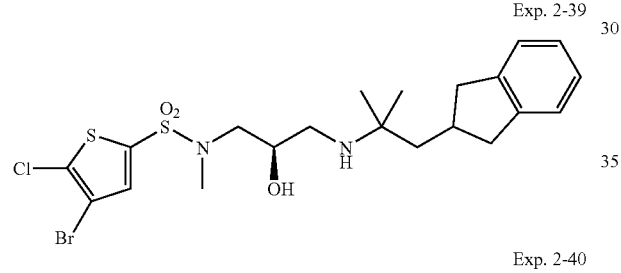

Exp. 2-40
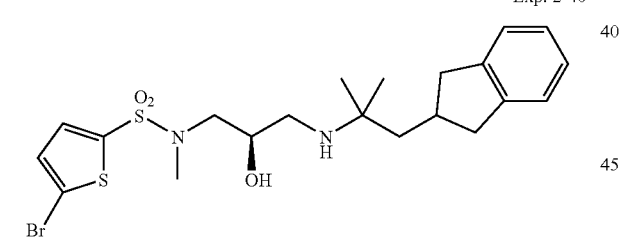

Exp. 2-41
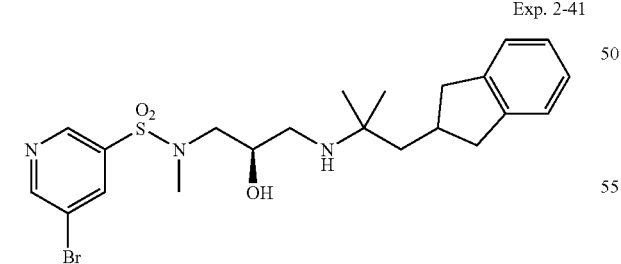

Exp. 2-42
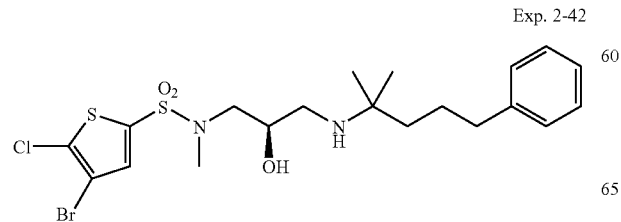

Exp. 2-43
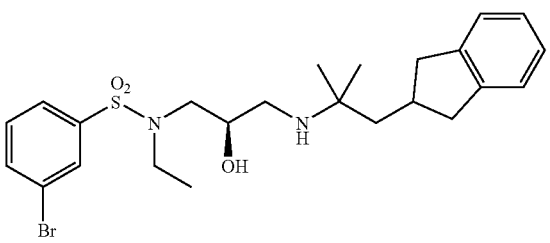

EXAMPLE 3-1

Synthesis of (R)-3-(2'-(N-(2-hydroxy-3-(2-methyl-1-(naphthalen-2-yl)propan-2-ylamino)propyl)-N-methylsulfamoyl)biphenyl-3-yl)acrylic acid (Step A) Synthesis of ethyl (R)-3-(2'-(N-(2-hydroxy-3-(2-methyl-1-(naphthalen-2-yl)propan-2-ylamino)propyl)-N-methylsulfamoyl)biphenyl-3-yl)acrylate Under nitrogen atmosphere, (R)-2-bromo-N-(2-hydroxy-3-(2-methyl-1-naphthalen-2-yl)propan-2-ylamino)propyl)-N-methylbenzenesulfonamide (Exp. 2-1, 25.4 mg) was dissolved in toluene (2 mL), potassium carbonate (WAKO, 22.8 mg), 3-(2-carboxyvinyl)benzeneboronic acid (ba13, LANC, 15.8 mg), bis1,1'-bis(diphenylphosphinoferrocene)palladium(II) dichloride-dichloromethane complex (Ald, 9 mg) and ethanol (1 mL) were added thereto followed by stirring at 80° C. for four hours. The reaction solution was charged in a diatomaceous earth column, and then eluted with chloroform and ethyl acetate. The solvent was distilled off under reduced pressure. The residue was used for the next Step B. without further purification.

(Step B) Synthesis of (R)-3-(2'-(N-(2-hydroxy-3-(2-methyl-1-(naphthalen-2-yl)propan-2-ylamino)propyl)-N-methylsulfamoyl)biphenyl-3-yl)acrylic acid Ethyl (R)-3-(2'-(N-(2-hydroxy-3-(2-methyl-1-(naphthalen-2-yl)propan-2-ylamino)propyl)-N-methylsulfamoyl)biphenyl-3-yl)acrylate synthesized from Example 3-1 Step A was dissolved in tetrahydrofuran (4 mL), water (1 mL) and potassium hydroxide (five granules) were added thereto followed by stirring at 50° C. for 1 day. The residue was neutralized with 2N hydrochloric acid, and extracted with diethyl ether. The organic layer was washed with brine, dried over anhydrous sodium sulfate and the solvent was distilled off under reduced pressure. Thus obtained residue was purified by HPLC to obtain the target compound (3.7 mg).

EXAMPLES 3-2 TO 91

By using SM2 instead of Exp. 2-1 and using BA instead of ba13, the reaction was carried out in combination described in the Table 3 according to Step A and Step B of Example 3-1 to obtain the target compounds.

TABLE 3

| Exp. | SM2 | BA | LCMS method | RTime | Mass |
|---|---|---|---|---|---|
| 3-1 | Exp. 2-1 | ba13 | B | 1.43 | 573 |
| 3-2 | Exp. 2-1 | ba2 | A | 3.34 | 547 |
| 3-3 | Exp. 2-1 | ba15 | A | 3.84 | 547 |
| 3-4 | Exp. 2-2 | ba1 | B | 1.40 | 592 |
| 3-5 | Exp. 2-2 | ba2 | A | 3.72 | 547 |
| 3-6 | Exp. 2-2 | ba3 | A | 3.36 | 547 |
| 3-7 | Exp. 2-2 | ba4 | B | 1.37 | 561 |
| 3-8 | Exp. 2-2 | ba5 | A | 3.60 | 561 |
| 3-9 | Exp. 2-2 | ba6 | B | 1.28 | 565 |
| 3-10 | Exp. 2-2 | ba7 | A | 3.14 | 562 |
| 3-11 | Exp. 2-2 | ba8 | A | 3.22 | 583 |
| 3-12 | Exp. 2-2 | ba9 | A | 3.36 | 565 |
| 3-13 | Exp. 2-2 | ba10 | A | 3.06 | 589 |
| 3-14 | Exp. 2-2 | ba11 | B | 1.22 | 573 |
| 3-15 | Exp. 2-2 | ba12 | B | 1.33 | 575 |
| 3-16 | Exp. 2-2 | ba13 | B | 1.36 | 573 |
| 3-17 | Exp. 2-2 | ba14 | B | 1.14 | 562 |
| 3-18 | Exp. 2-2 | ba15 | B | 1.33 | 592 |
| 3-19 | Exp. 2-2 | ba16 | B | 1.27 | 562 |
| 3-20 | Exp. 2-2 | ba17 | B | 1.32 | 592 |
| 3-21 | Exp. 2-2 | ba18 | B | 1.27 | 618 |
| 3-22 | Exp. 2-2 | ba19 | B | 1.43 | 591 |
| 3-23 | Exp. 2-2 | ba20 | B | 1.44 | 565 |
| 3-24 | Exp. 2-2 | ba23 | B | 1.37 | 563 |
| 3-25 | Exp. 2-2 | ba25 | B | 1.31 | 583 |
| 3-26 | Exp. 2-2 | ba26 | B | 1.29 | 553 |
| 3-27 | Exp. 2-2 | ba27 | B | 1.28 | 618 |
| 3-28 | Exp. 2-2 | ba28 | B | 1.38 | 576 |
| 3-29 | Exp. 2-3 | ba1 | A | 3.46 | 547 |
| 3-30 | Exp. 2-3 | ba2 | A | 3.42 | 547 |
| 3-31 | Exp. 2-3 | ba3 | A | 3.19 | 547 |
| 3-32 | Exp. 2-3 | ba4 | B | 1.36 | 561 |
| 3-33 | Exp. 2-3 | ba5 | A | 3.42 | 561 |
| 3-34 | Exp. 2-3 | ba7 | A | 3.16 | 562 |
| 3-35 | Exp. 2-3 | ba9 | A | 3.26 | 565 |
| 3-36 | Exp. 2-3 | ba10 | A | 3.09 | 589 |
| 3-37 | Exp. 2-3 | ba11 | B | 1.26 | 573 |
| 3-38 | Exp. 2-3 | ba12 | B | 1.33 | 575 |
| 3-39 | Exp. 2-3 | ba13 | B | 1.36 | 573 |
| 3-40 | Exp. 2-3 | ba15 | B | 1.31 | 592 |
| 3-41 | Exp. 2-3 | ba16 | B | 1.27 | 562 |
| 3-42 | Exp. 2-3 | ba17 | B | 1.32 | 592 |
| 3-43 | Exp. 2-3 | ba18 | B | 1.26 | 618 |
| 3-44 | Exp. 2-3 | ba21 | B | 1.49 | 573 |
| 3-45 | Exp. 2-3 | ba22 | B | 1.40 | 591 |
| 3-46 | Exp. 2-3 | ba23 | B | 1.33 | 563 |
| 3-47 | Exp. 2-3 | ba24 | B | 1.39 | 593 |
| 3-48 | Exp. 2-3 | ba25 | B | 1.29 | 583 |
| 3-49 | Exp. 2-5 | ba2 | B | 1.33 | 537 |
| 3-50 | Exp. 2-5 | ba3 | B | 1.35 | 537 |
| 3-51 | Exp. 2-5 | ba4 | A | 3.39 | 551 |
| 3-52 | Exp. 2-5 | ba5 | A | 3.29 | 551 |
| 3-53 | Exp. 2-5 | ba6 | B | 1.32 | 555 |
| 3-54 | Exp. 2-5 | ba8 | B | 1.37 | 573 |
| 3-55 | Exp. 2-5 | ba9 | B | 1.40 | 555 |
| 3-56 | Exp. 2-5 | ba11 | B | 1.30 | 563 |
| 3-57 | Exp. 2-5 | ba12 | B | 1.17 | 565 |
| 3-58 | Exp. 2-5 | ba13 | B | 1.32 | 563 |
| 3-59 | Exp. 2-5 | ba18 | B | 1.08 | 608 |
| 3-60 | Exp. 2-5 | ba20 | B | 1.41 | 555 |
| 3-61 | Exp. 2-5 | ba29 | B | 1.48 | 551 |
| 3-62 | Exp. 2-5 | ba30 | B | 1.34 | 551 |
| 3-63 | Exp. 2-8 | ba2 | B | 1.30 | 529 |
| 3-64 | Exp. 2-8 | ba3 | B | 1.29 | 529 |
| 3-65 | Exp. 2-8 | ba6 | B | 1.29 | 547 |
| 3-66 | Exp. 2-8 | ba8 | B | 1.31 | 563 |
| 3-67 | Exp. 2-8 | ba9 | B | 1.36 | 547 |
| 3-68 | Exp. 2-8 | ba11 | B | 1.23 | 555 |
| 3-69 | Exp. 2-8 | ba12 | B | 1.18 | 557 |
| 3-70 | Exp. 2-8 | ba13 | B | 1.18 | 555 |
| 3-71 | Exp. 2-8 | ba20 | B | 1.36 | 547 |
| 3-72 | Exp. 2-11 | ba2 | B | 1.35 | 551 |
| 3-73 | Exp. 2-11 | ba3 | B | 1.33 | 551 |
| 3-74 | Exp. 2-11 | ba6 | B | 1.31 | 569 |
| 3-75 | Exp. 2-11 | ba8 | B | 1.33 | 585 |
| 3-76 | Exp. 2-11 | ba9 | B | 1.38 | 569 |
| 3-77 | Exp. 2-11 | ba11 | B | 1.24 | 577 |
| 3-78 | Exp. 2-11 | ba12 | B | 1.26 | 577 |
| 3-79 | Exp. 2-11 | ba13 | B | 1.30 | 577 |
| 3-80 | Exp. 2-11 | ba20 | B | 1.39 | 569 |
| 3-81 | Exp. 2-13 | ba5 | A | 3.26 | 575 |
| 3-82 | Exp. 2-13 | ba11 | B | 1.36 | 587 |
| 3-83 | Exp. 2-13 | ba12 | B | 1.34 | 589 |
| 3-84 | Exp. 2-13 | ba13 | B | 1.33 | 587 |
| 3-85 | Exp. 2-13 | ba20 | A | 3.40 | 579 |
| 3-86 | Exp. 2-14 | ba11 | B | 1.26 | 587 |
| 3-87 | Exp. 2-14 | ba12 | B | 1.28 | 589 |
| 3-88 | Exp. 2-14 | ba13 | B | 1.31 | 587 |
| 3-89 | Exp. 2-15 | ba11 | B | 1.33 | 587 |
| 3-90 | Exp. 2-15 | ba12 | B | 1.28 | 589 |
| 3-91 | Exp. 2-15 | ba13 | B | 1.27 | 587 |

Hereinbelow, structures of the compounds of Example to 91 (Exp. 3-1 to Exp. 3-91) are shown.

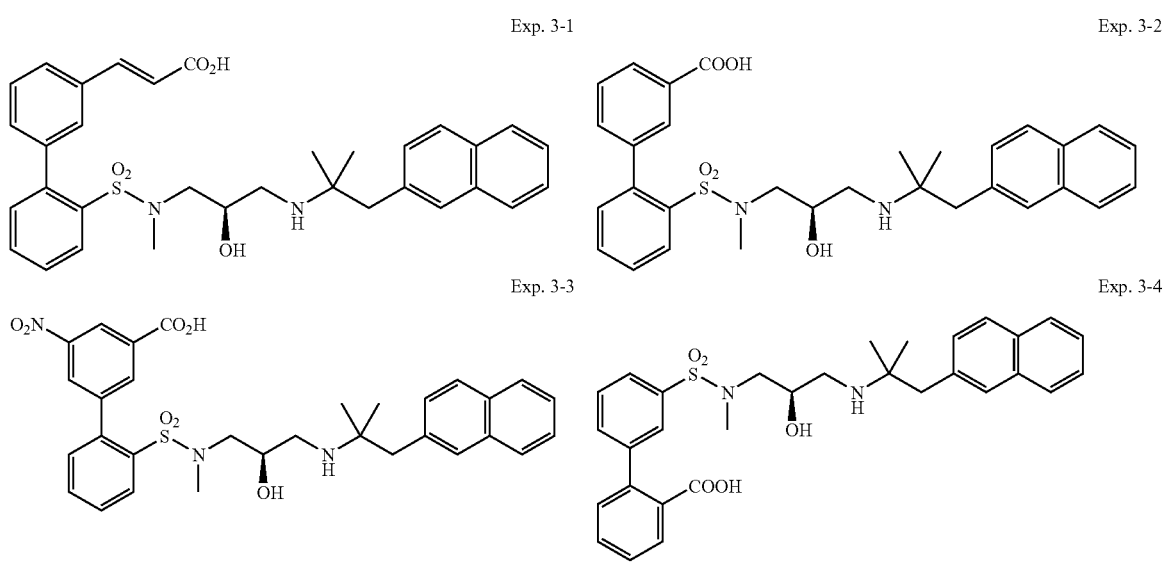

-continued
Exp. 3-5
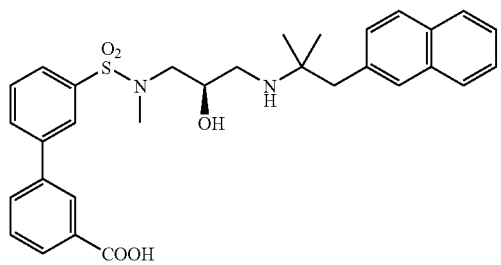
Exp. 3-6
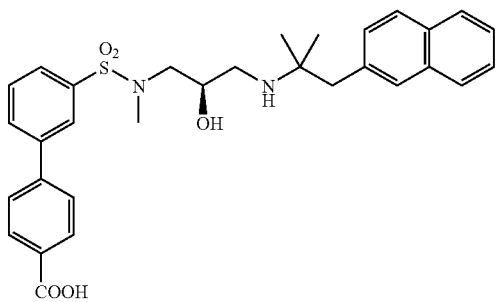
Exp. 3-7
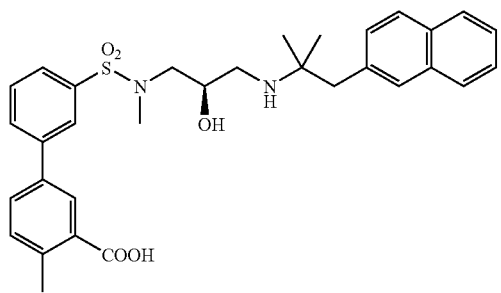
Exp. 3-8
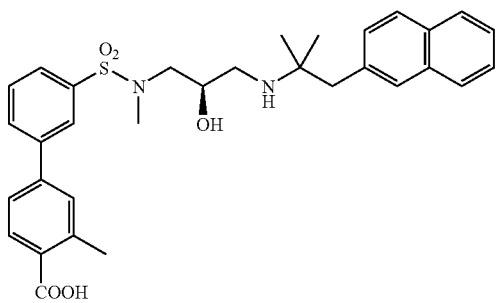
Exp. 3-9
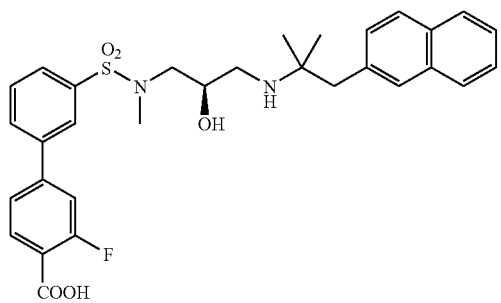
Exp. 3-10
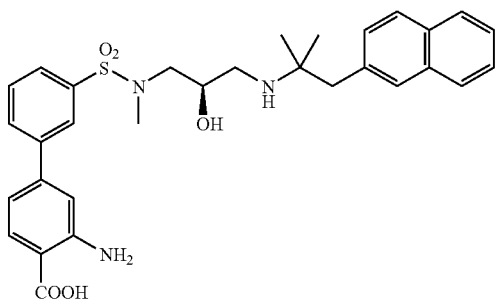
Exp. 3-11
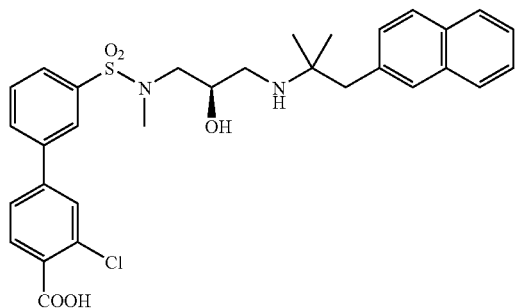
Exp. 3-12
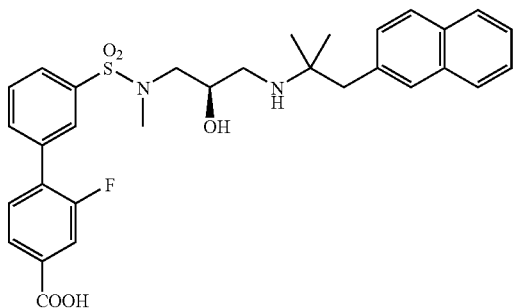

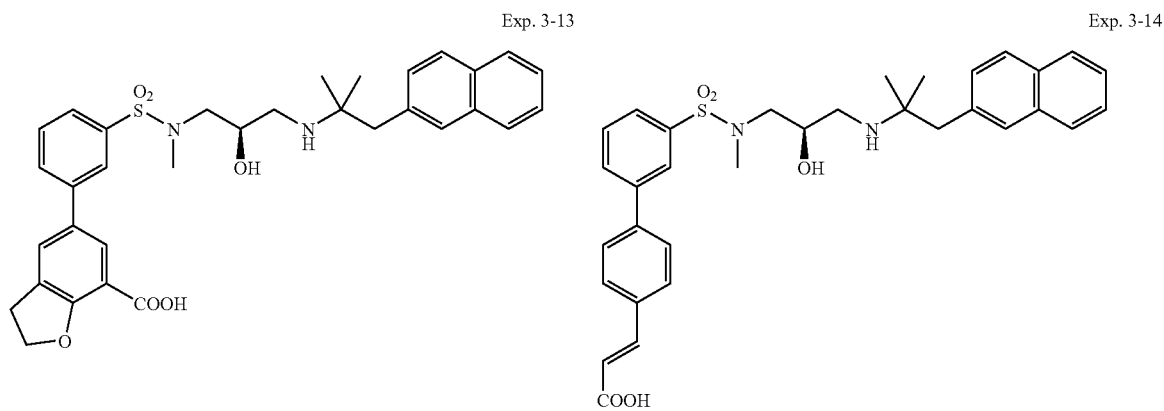
Exp. 3-13
Exp. 3-14
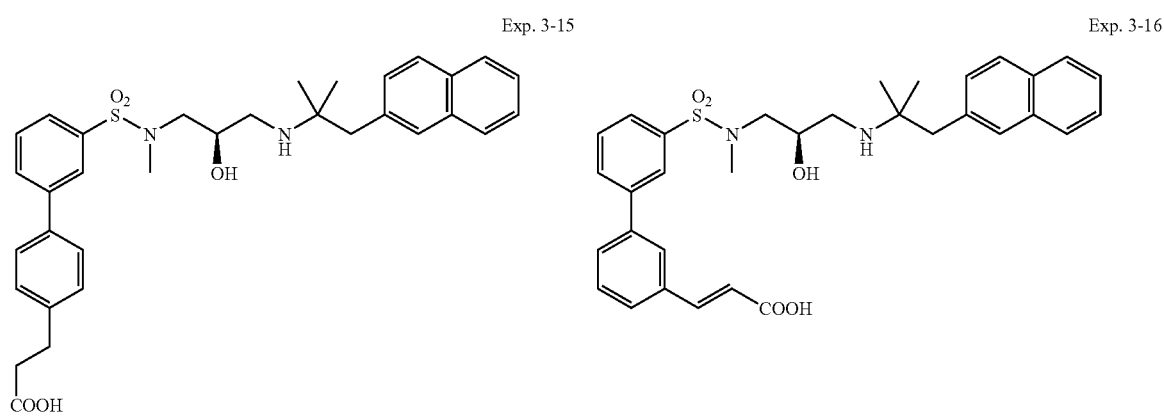
Exp. 3-15
Exp. 3-16
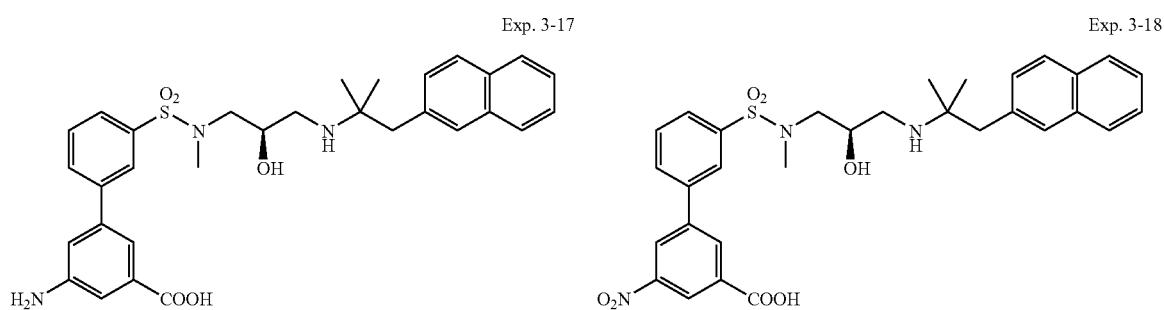
Exp. 3-17
Exp. 3-18
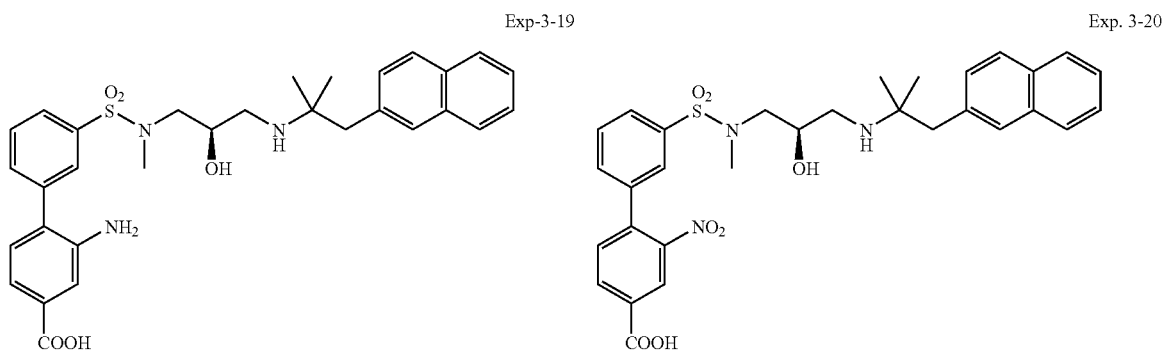
Exp-3-19
Exp-3-20

-continued
Exp. 3-21
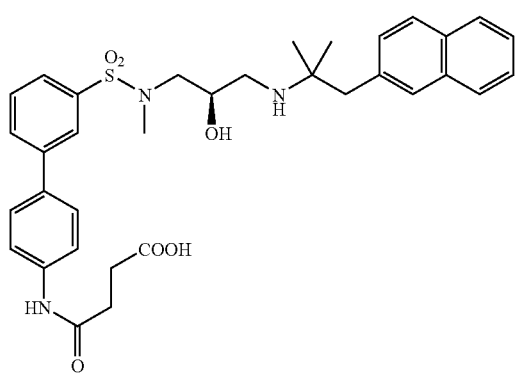
Exp. 3-22
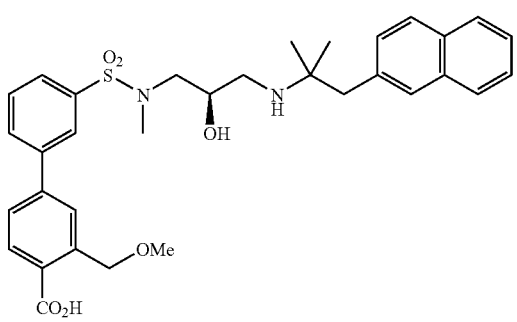
Exp. 3-23
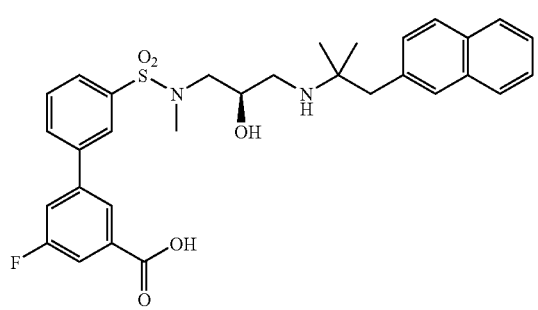
Exp. 3-24
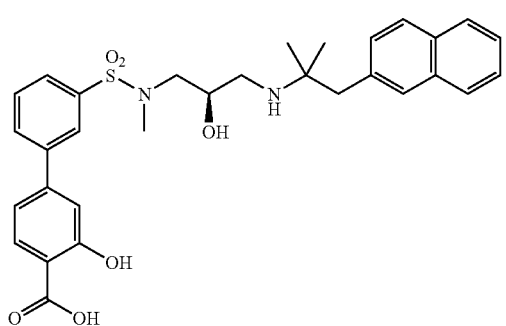
Exp. 3-25
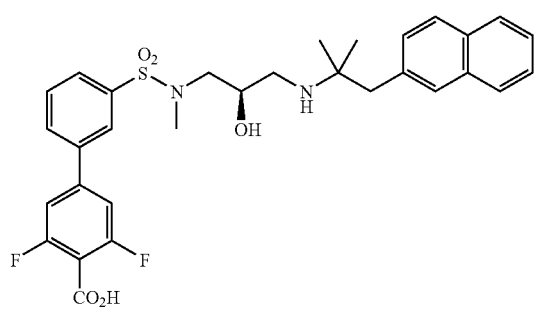
Exp. 3-26
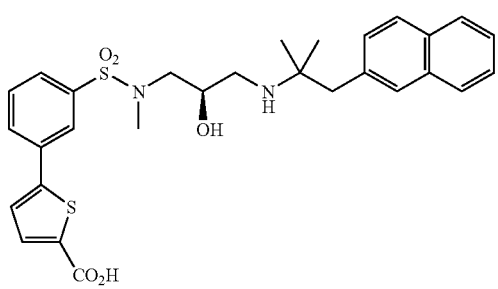
Exp. 3-27
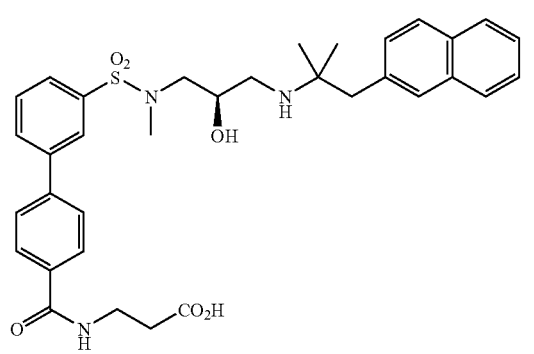
Exp. 3-28
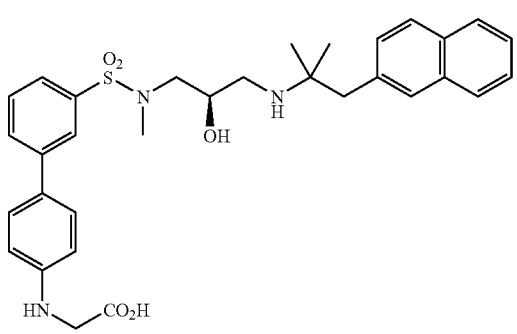
Exp. 3-29
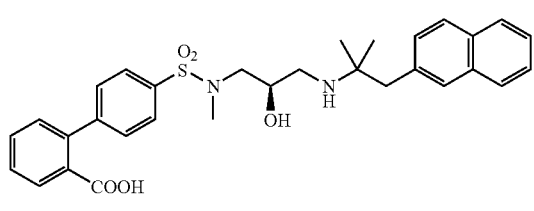
Exp. 3-30
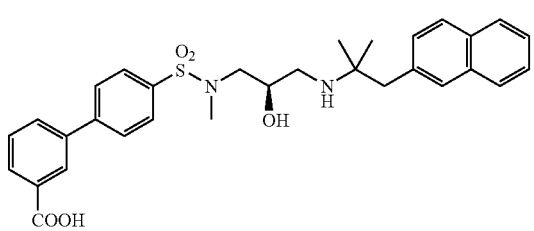

-continued
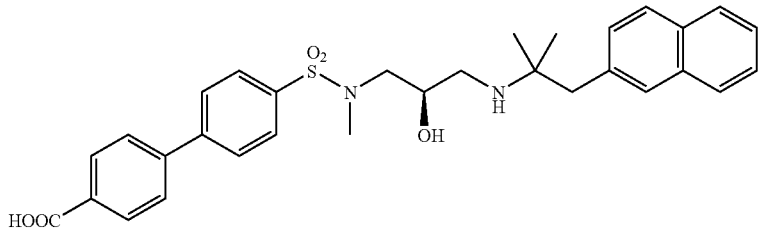
Exp. 3-31
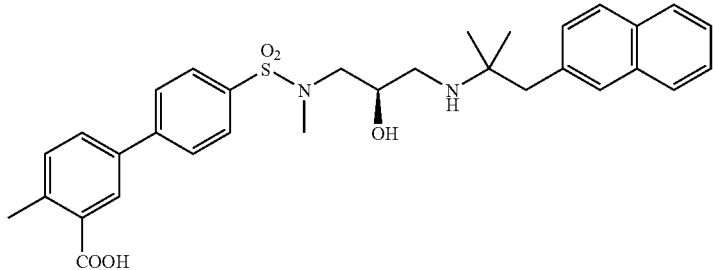
Exp. 3-32
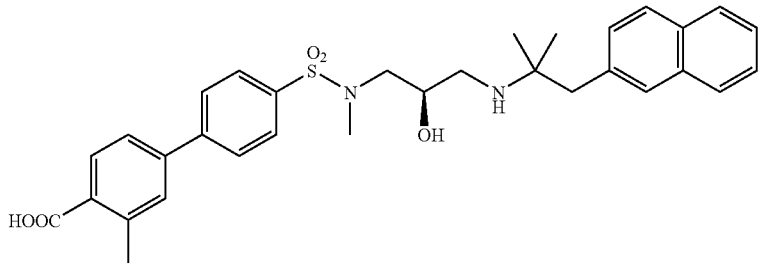
Exp. 3-33
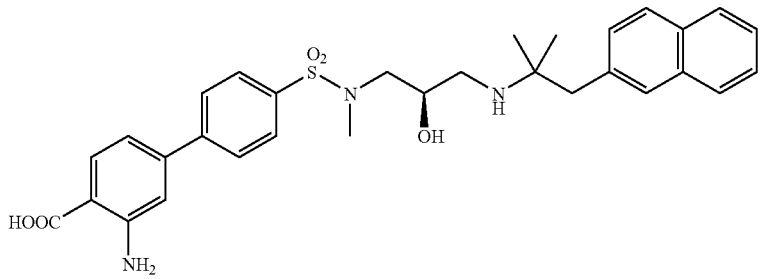
Exp. 3-34
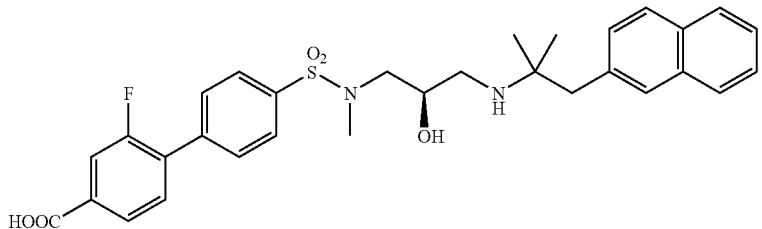
Exp. 3-35
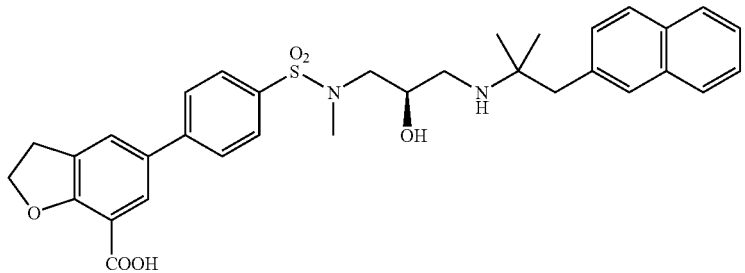
Exp. 3-36

-continued
Exp. 3-37
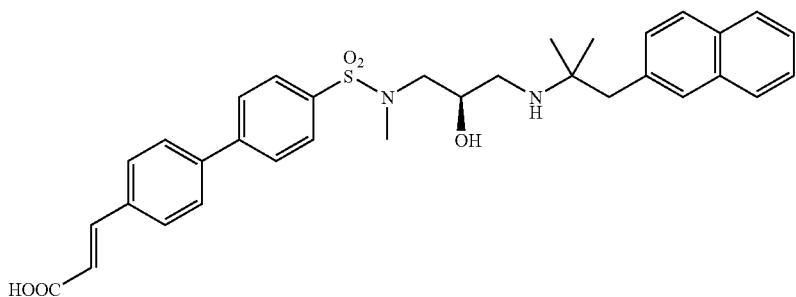
Exp. 3-38
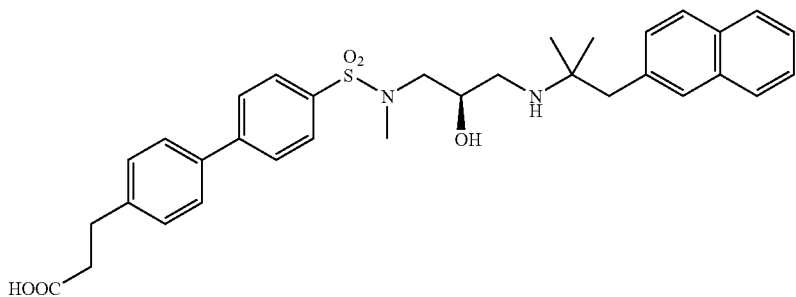
Exp. 3-39
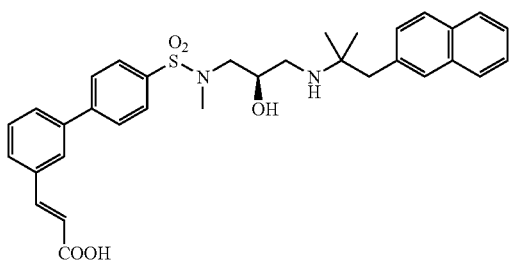
Exp. 3-40
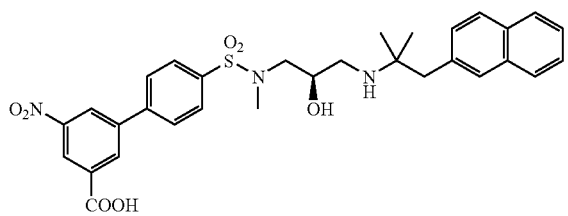
Exp. 3-41
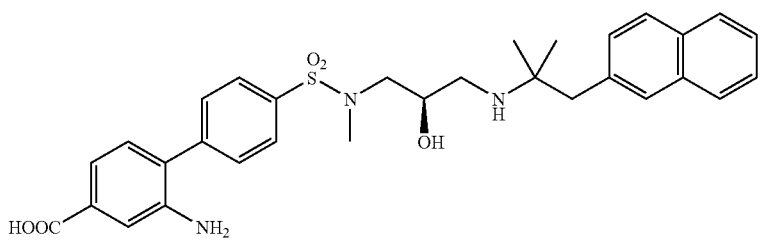
Exp. 3-42
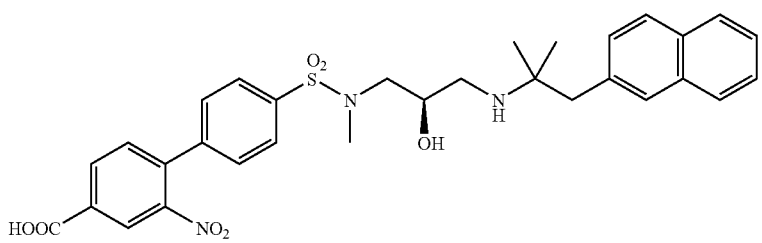
Exp. 3-43
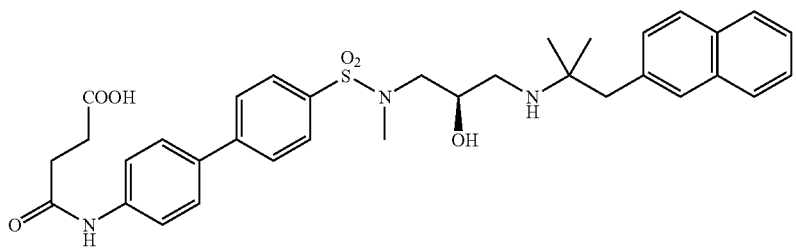

-continued
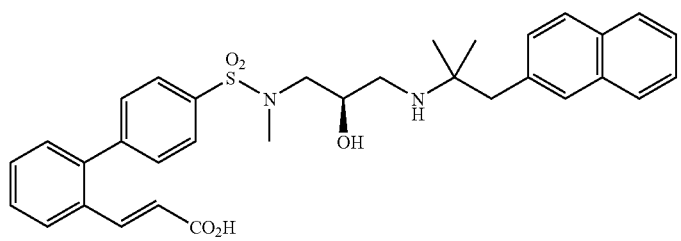
Exp. 3-44
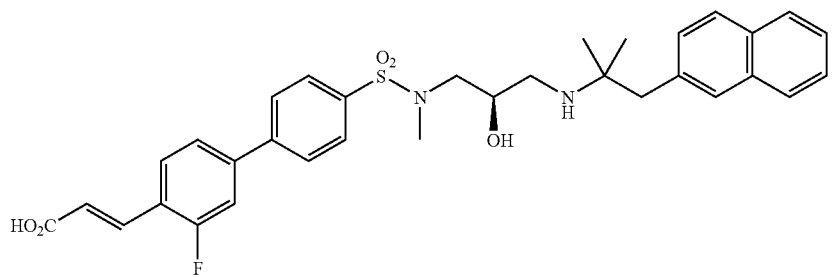
Exp. 3-45
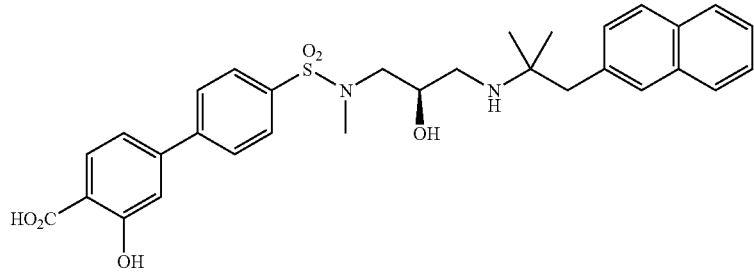
Exp. 3-46
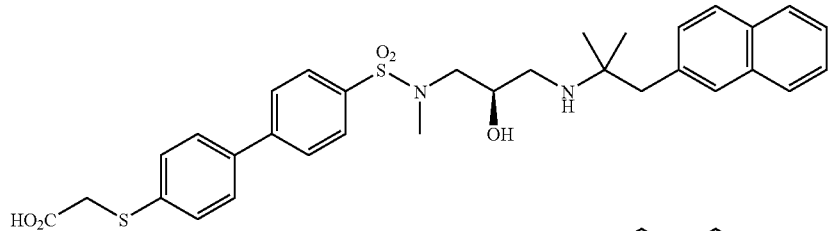
Exp. 3-47
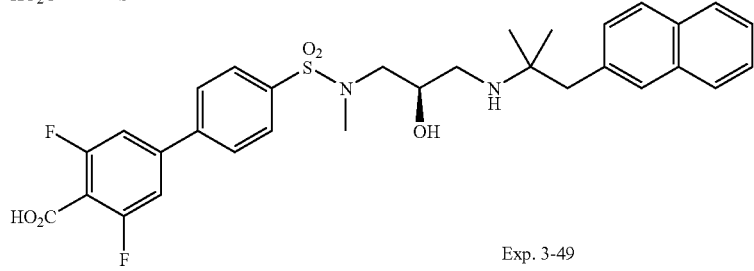
Exp. 3-48
Exp. 3-49
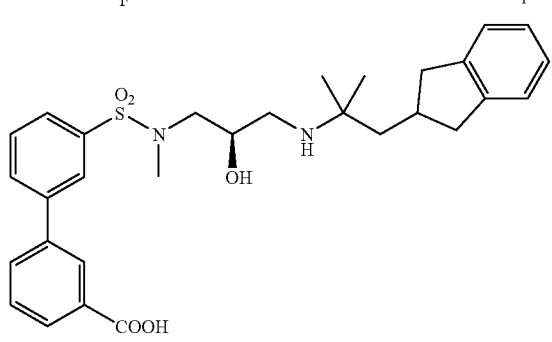
Exp. 3-50
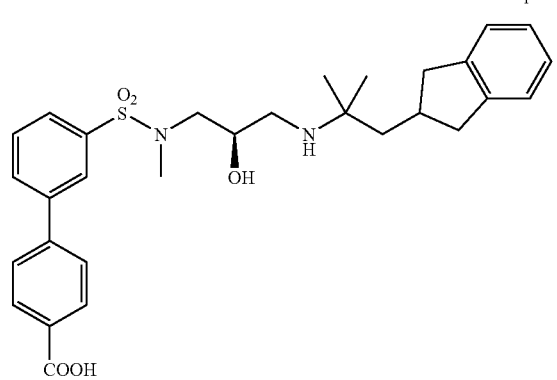

-continued
Exp. 3-51
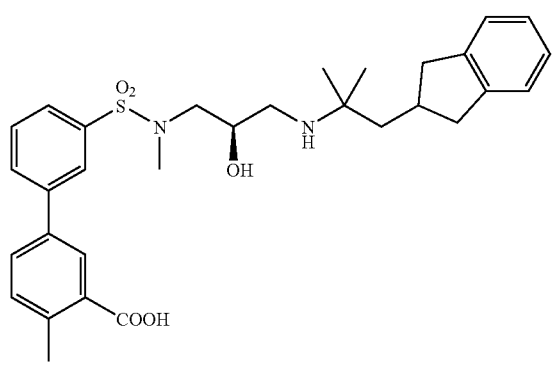
Exp. 3-52
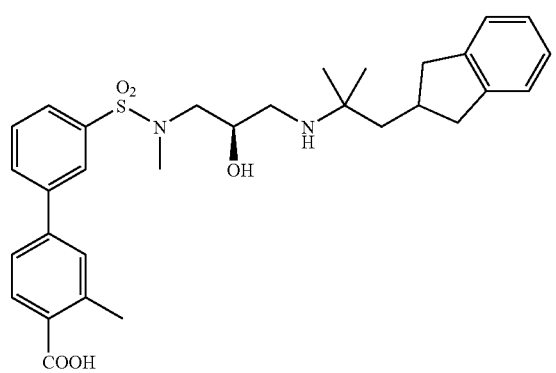
Exp. 3-53
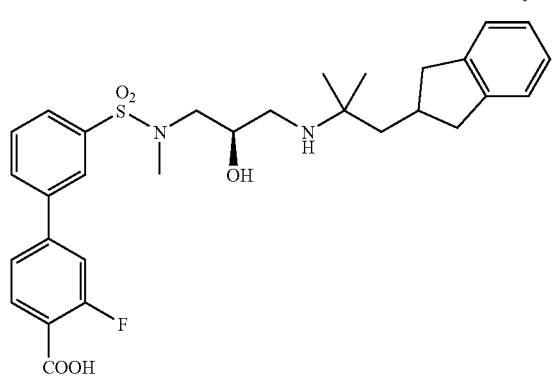
Exp. 3-54
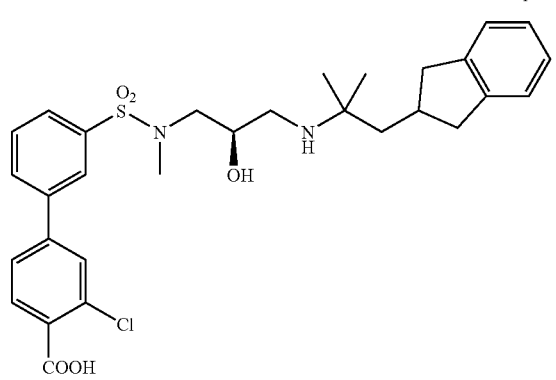
Exp. 3-55
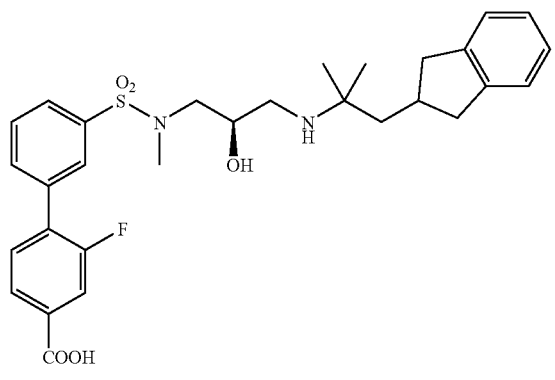
Exp. 3-56
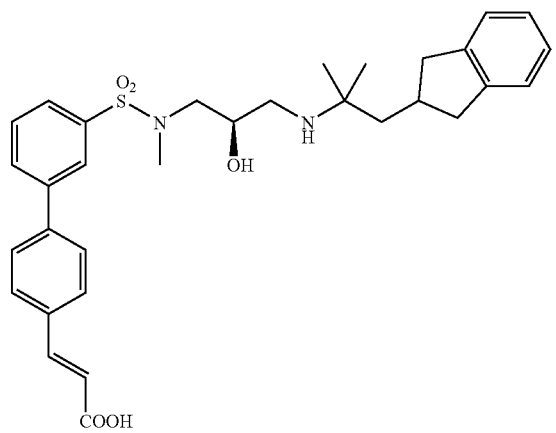
Exp. 3-57
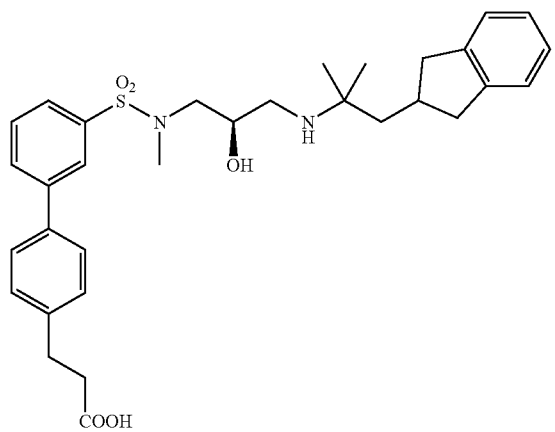
Exp. 3-58
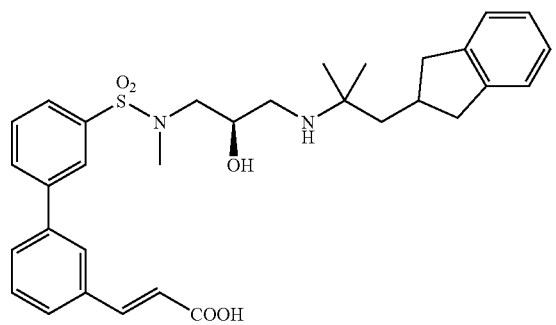

-continued
Exp. 3-59
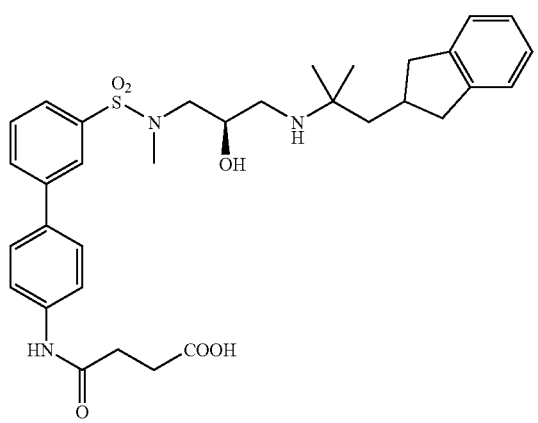
Exp. 3-60
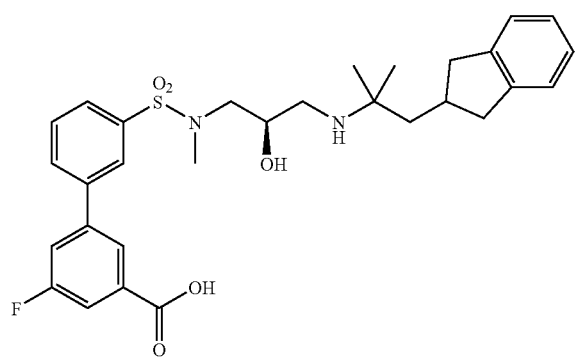
Exp. 3-61
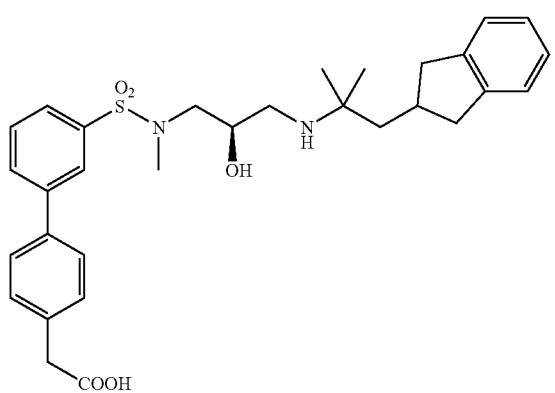
Exp. 3-62
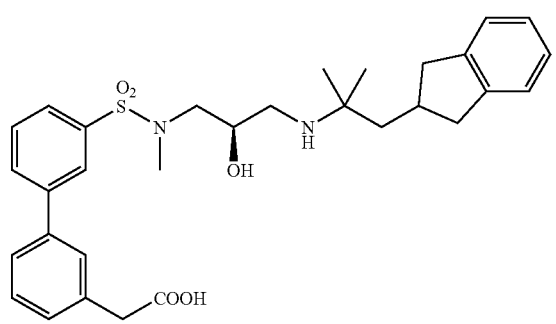
Exp. 3-63
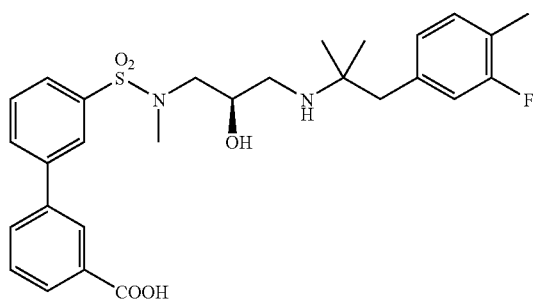
Exp. 3-64
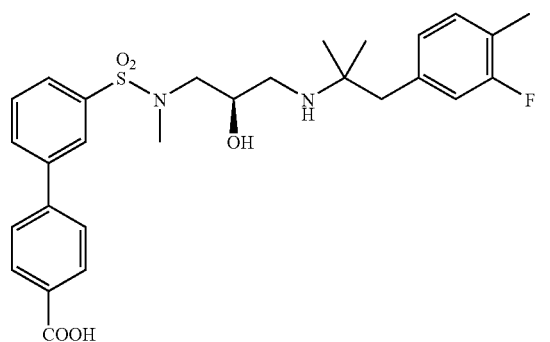
Exp. 3-65
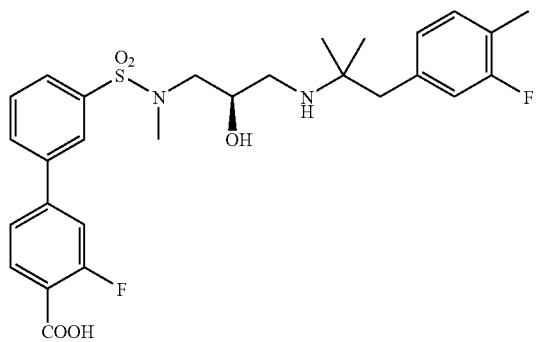
Exp. 3-66
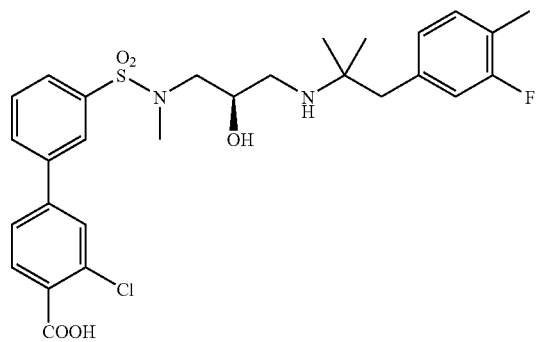

-continued
Exp. 3-67
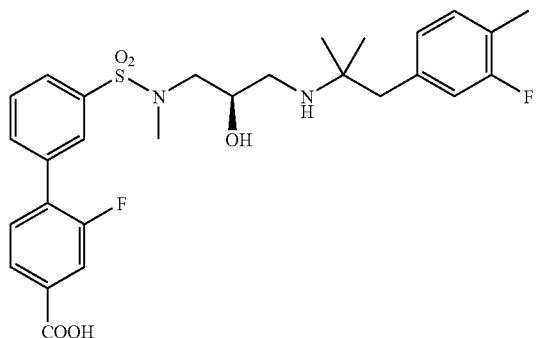
Exp. 3-68
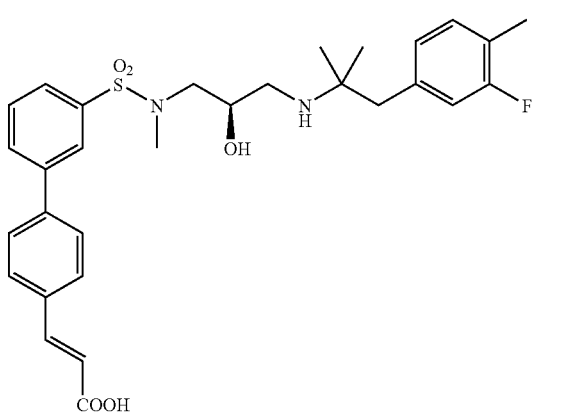
Exp. 3-69
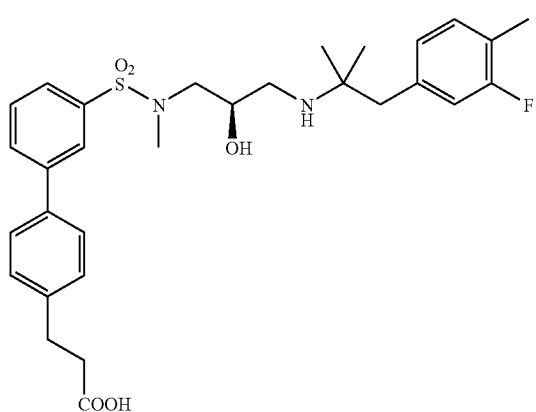
Exp. 3-70
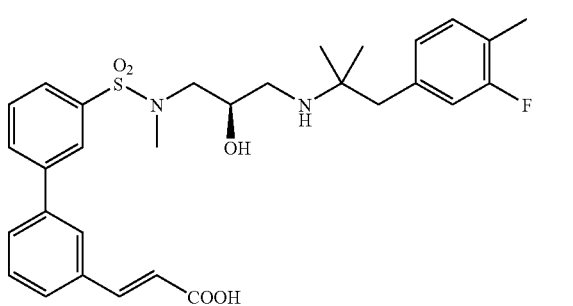
Exp. 3-71
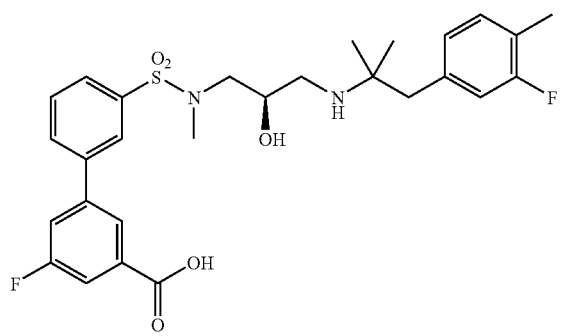
Exp. 3-72
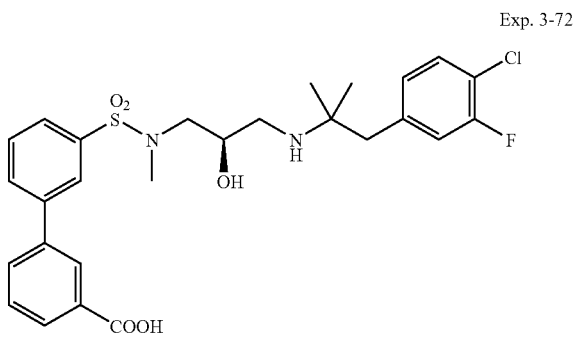
Exp. 3-73
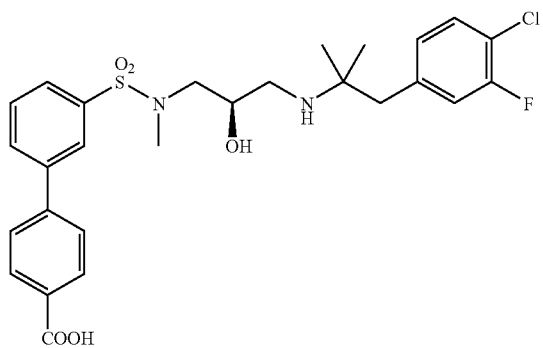
Exp. 3-74
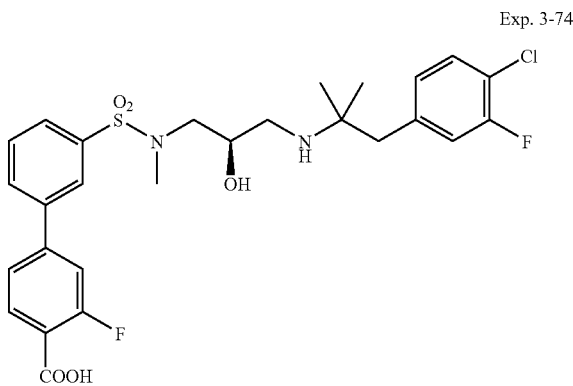

Exp. 3-75 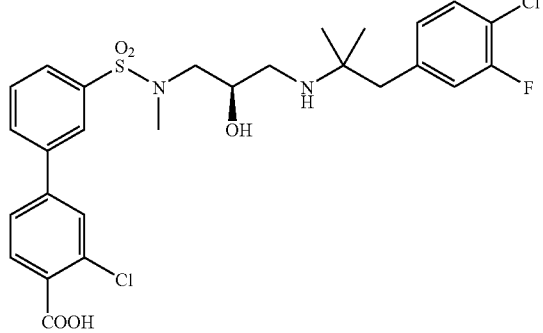
Exp. 3-76 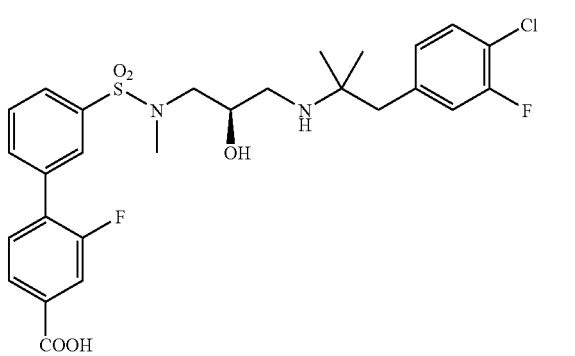
Exp. 3-77 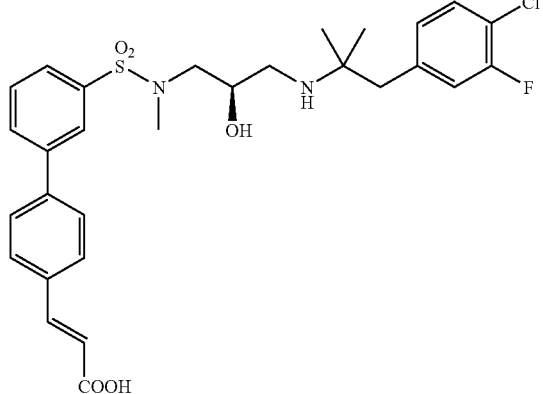
Exp. 3-78 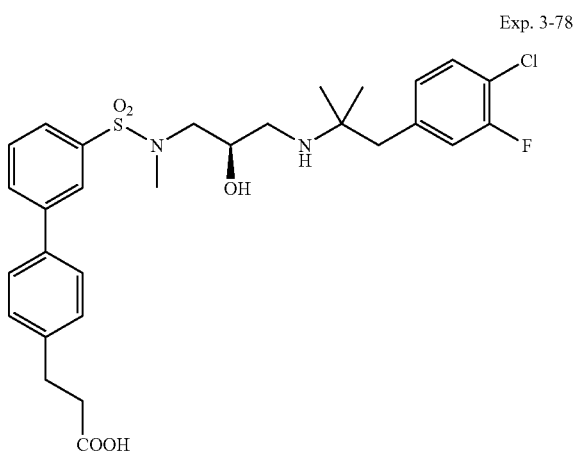
Exp. 3-79 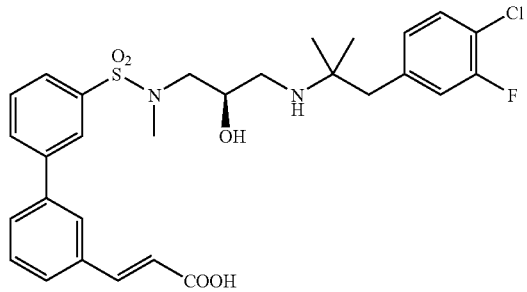
Exp. 3-80 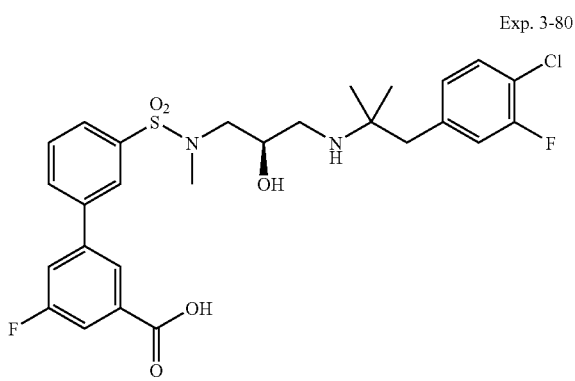
Exp. 3-81 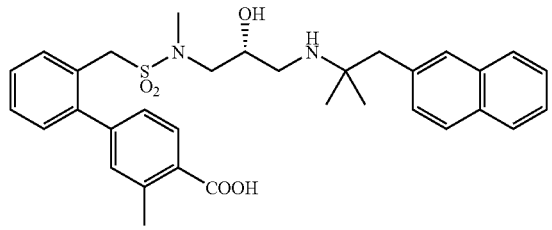
Exp. 3-82 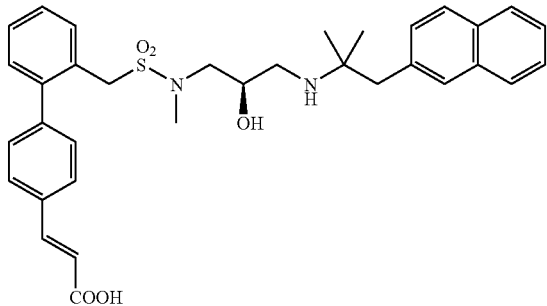

-continued
Exp. 3-83
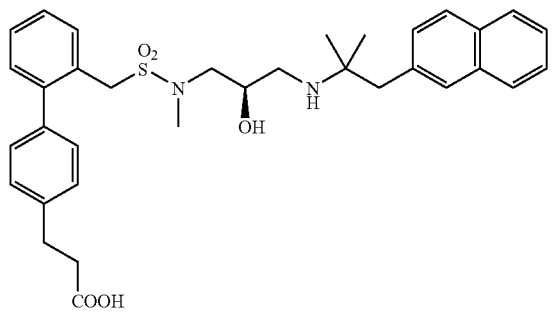
Exp. 3-84
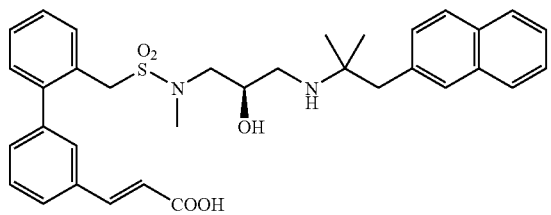
Exp. 3-85
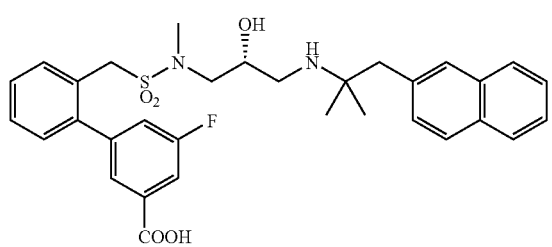
Exp. 3-86
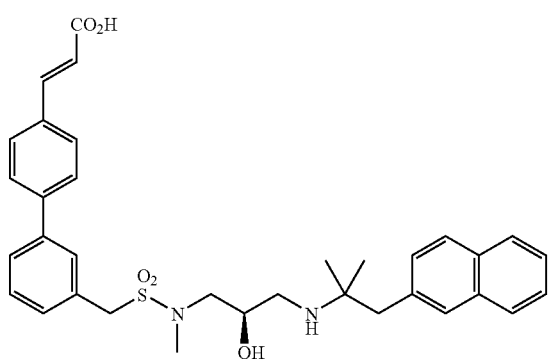
Exp. 3-87
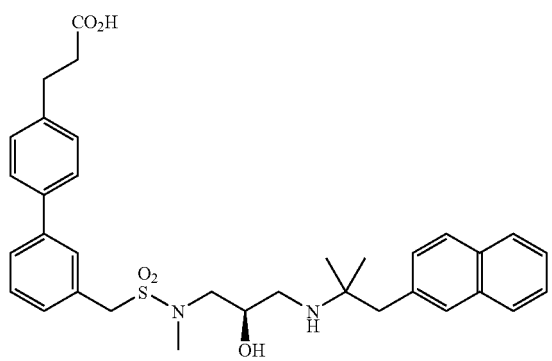
Exp. 3-88
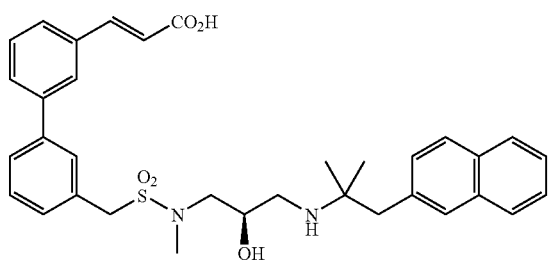
Exp. 3-89
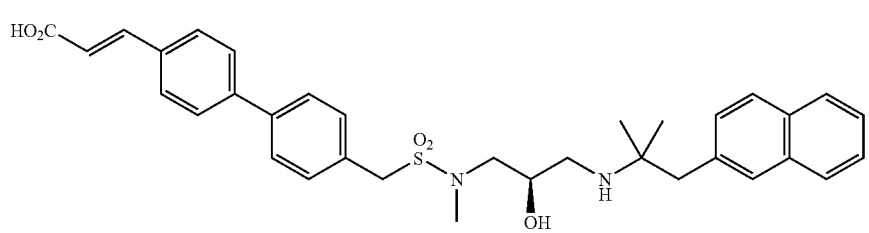
Exp. 3-90
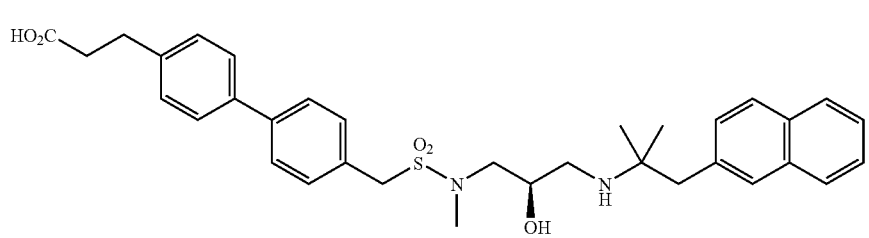

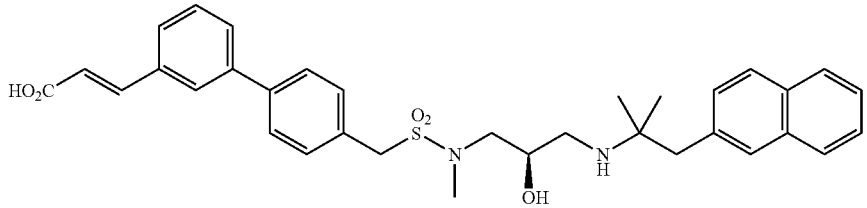

Exp. 3-91

EXAMPLE 3-2

(R)-2'-(N-(2-hydroxy-3-(2-methyl-1-(naphthalen-2-yl)propan-2-ylamino)propyl)-N-methylsulfamoyl)biphenyl-3-carboxylic acid

EXAMPLE 3-3

(R)-2'-(N-(2-hydroxy-3-(2-methyl-1-(naphthalen-2-yl)propan-2-ylamino)propyl)-N-methylsulfamoyl)-5-nitrobiphenyl-3-carboxylic acid

EXAMPLE 3-4

(R)-3'-(N-(2-hydroxy-3-(2-methyl-1-(naphthalen-2-yl)propan-2-ylamino)propyl)-N-methylsulfamoyl)biphenyl-2-carboxylic acid

EXAMPLE 3-5

(R)-3'-(N-(2-hydroxy-3-(2-methyl-1-(naphthalen-2-yl)propan-2-ylamino)propyl)-N-methylsulfamoyl)biphenyl-3-carboxylic acid

EXAMPLE 3-6

(R)-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-7

(R)-3'-(N-(2-hydroxy-3-(2-methyl-1-(naphthalen-2-yl)propan-2-ylamino)propyl)-N-methylsulfamoyl)-4-methylbiphenyl-3-carboxylic acid

EXAMPLE 3-8

(R)-3'-(N-(2-hydroxy-3-(2-methyl-1-(naphthalen-2-yl)propan-2-ylamino)propyl)-N-methylsulfamoyl)-3-methylbiphenyl-4-carboxylic acid

EXAMPLE 3-9

(R)-3-fluoro-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-10

(R)-3-amino-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-11

(R)-3-chloro-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-12

(R)-2-fluoro-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-13

(R)-5-(3-(N-(2-hydroxy-3-(2-methyl-1-(naphthalen-2-yl)propan-2-ylamino)propyl)-N-methylsulfamoyl)phenyl)-2,3-dihydrobenzofuran-7-carboxylic acid

EXAMPLE 3-14

(R)-3-(3'-(N-(2-hydroxy-3-(2-methyl-1-(naphthalen-2-yl)propan-2-ylamino)propyl)-N-methylsulfamoyl)biphenyl-4-yl)acrylic acid

EXAMPLE 3-15

(R)-3-(3'-(N-(2-hydroxy-3-(2-methyl-1-(naphthalen-2-yl)propan-2-ylamino)propyl)-N-methylsulfamoyl)biphenyl-4-yl)propionic acid

EXAMPLE 3-16

(R)-3-(3'-(N-(2-hydroxy-3-(2-methyl-1-(naphthalen-2-yl)propan-2-ylamino)propyl)-N-methylsulfamoyl)biphenyl-3-yl)acrylic acid

EXAMPLE 3-17

(R)-5-amino-3'-(N-(2-hydroxy-3-(2-methyl-1-(naphthalen-2-yl)propan-2-ylamino)propyl)-N-methylsulfamoyl)biphenyl-3-carboxylic acid

EXAMPLE 3-18

(R)-3'-(N-(2-hydroxy-3-(2-methyl-1-(naphthalen-2-yl)propan-2-ylamino)propyl)-N-methylsulfamoyl)-5-nitrobiphenyl-3-carboxylic acid

EXAMPLE 3-19

(R)-2-amino-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-20

(R)-3'-(N-(2-hydroxy-3-(2-methyl-1-(naphthalen-2-yl)propan-2-ylamino)propyl)-N-methylsulfamoyl)-2-nitrobiphenyl-4-carboxylic acid

EXAMPLE 3-21

(R)-4-(3'-(N-(2-hydroxy-3-(2-methyl-1-(naphthalen-2-yl)propan-2-ylamino)propyl)-N-methylsulfamoyl)biphenyl-4-ylamino)-4-oxobutanoic acid

EXAMPLE 3-22

(R)-3'-(N-(2-hydroxy-3-(2-methyl-1-(naphthalen-2-yl)propan-2-ylamino)propyl)-N-methylsulfamoyl)-3-(methoxymethyl)biphenyl-4-carboxylic acid

EXAMPLE 3-23

(R)-5-fluoro-3'-(N-(2-hydroxy-3-(2-methyl-1-(naphthalen-2-yl)propan-2-ylamino)propyl)-N-methylsulfamoyl)biphenyl-3-carboxylic acid

EXAMPLE 3-24

(R)-3-hydroxy-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-25

(R)-3,5-difluoro-3'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-26

(R)-5-(3-(N-(2-hydroxy-3-(2-methyl-1-(naphthalen-2-yl)propan-2-ylamino)propyl)-N-methylsulfamoyl)phenyl)thiophen-2-carboxylic acid

EXAMPLE 3-27

(R)-3-(3'-(N-(2-hydroxy-3-(2-methyl-1-(naphthalen-2-yl)propan-2-ylamino)propyl)-N-methylsulfamoyl)biphenyl-4-ylcarboxamide)propionic acid

EXAMPLE 3-28

(R)-2-(3'-(N-(2-hydroxy-3-(2-methyl-1-(naphthalen-2-yl)propan-2-ylamino)propyl)-N-methylsulfamoyl)biphenyl-4-ylamino)acetic acid

EXAMPLE 3-29

(R)-4'-(N-(2-hydroxy-3-(2-methyl-1-(naphthalen-2-yl)propan-2-ylamino)propyl)-N-methylsulfamoyl)biphenyl-2-carboxylic acid

EXAMPLE 3-30

(R)-4'-(N-(2-hydroxy-3-(2-methyl-1-(naphthalen-2-yl)propan-2-ylamino)propyl)-N-methylsulfamoyl)biphenyl-3-carboxylic acid

EXAMPLE 3-31

(R)-4'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-32

(R)-4'-(N-(2-hydroxy-3-(2-methyl-1-(naphthalen-2-yl)propan-2-ylamino)propyl)-N-methylsulfamoyl)-4-methylbiphenyl-3-carboxylic acid

EXAMPLE 3-33

(R)-4'-(N-(2-hydroxy-3-(2-methyl-1-(naphthalen-2-yl)propan-2-ylamino)propyl)-N-methylsulfamoyl)-3-methylbiphenyl-4-carboxylic acid

EXAMPLE 3-34

(R)-3-amino-4'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-35

(R)-2-fluoro-4'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-36

(R)-5-(4-(N-(2-hydroxy-3-(2-methyl-1-(naphthalen-2-yl)propan-2-ylamino)propyl)-N-methylsulfamoyl)phenyl)-2,3-dihydrobenzofuran-7-carboxylic acid

EXAMPLE 3-37

(R)-3-(4'-(N-(2-hydroxy-3-(2-methyl-1-(naphthalen-2-yl)propan-2-ylamino)propyl)-N-methylsulfamoyl)biphenyl-4-yl)acrylic acid

EXAMPLE 3-38

(R)-3-(4'-(N-(2-hydroxy-3-(2-methyl-1-(naphthalen-2-yl)propan-2-ylamino)propyl)-N-methylsulfamoyl)biphenyl-4-yl)propionic acid

EXAMPLE 3-39

(R)-3-(4'-(N-(2-hydroxy-3-(2-methyl-1-(naphthalen 2-yl)propan-2-ylamino)propyl)-N-methylsulfamoyl)biphenyl-3-yl)acrylic acid

EXAMPLE 3-40

(R)-4'-(N-(2-hydroxy-3-(2-methyl-1-(naphthalen-2-yl)propan-2-ylamino)propyl)-N-methylsulfamoyl)-5-nitrobiphenyl-3-carboxylic acid

EXAMPLE 3-41

(R)-2-amino-4'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-42

(R)-4'-(N-(2-hydroxy-3-(2-methyl-1-(naphthalen-2-yl)propan-2-ylamino)propyl)-N-methylsulfamoyl)-2-nitrobiphenyl-4-carboxylic acid

EXAMPLE 3-43

(R)-4-(4'-(N-(2-hydroxy-3-(2-methyl-1-(naphthalen-2-yl)propan-2-ylamino)propyl)-N-methylsulfamoyl)biphenyl-4-ylamino)-4-oxobutanoic acid

EXAMPLE 3-44

(R)-3-(4'-(N-(2-hydroxy-3-(2-methyl-1-(naphthalen-2-yl)propan-2-ylamino)propyl)-N-methylsulfamoyl)biphenyl-2-yl)acrylic acid

EXAMPLE 3-45

(R)-3-(3-fluoro-4'-(N-(2-hydroxy-3-(2-methyl-1-(naphthalen-2-yl)propan-2-ylamino)propyl)-N-methylsulfamoyl)biphenyl-4-yl)acrylic acid

EXAMPLE 3-46

(R)-3-hydroxy-4'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-47

(R)-2-(4'-(N-(2-hydroxy-3-(2-methyl-1-(naphthalen-2-yl)propan-2-ylamino)propyl)-N-methylsulfamoyl)biphenyl-4-ylthio)acetic acid

EXAMPLE 3-48

(R)-3,5-difluoro-4'-(N-(2-hydroxy-3-(2-methyl-1-(naphthalen-2-yl)propan-2-ylamino)propyl)-N-methylsulfamoyl)biphenyl-4-carboxylic acid

EXAMPLE 3-49

(R)-3'-(N-(3-(1-(2,3-dihydro-1H-inden-2-yl)-2-methylpropan-2-ylamino)-2-hydroxypropyl)-N-methylsulfamoyl)biphenyl-3-carboxylic acid

EXAMPLE 3-50

(R)-3'-(N-(3-(1-(2,3-dihydro-1H-inden-2-yl)-2-methylpropan-2-ylamino)-2-hydroxypropyl)-N-methylsulfamoyl)biphenyl-4-carboxylic acid

EXAMPLE 3-51

(R)-3'-(N-(3-(1-(2,3-dihydro-1H-inden-2-yl)-2-methylpropan-2-ylamino)-2-hydroxypropyl)-N-methylsulfamoyl)-4-methylbiphenyl-3-carboxylic acid

EXAMPLE 3-52

(R)-3'-(N-(3-(1-(2,3-dihydro-1H-inden-2-yl)-2-methylpropan-2-ylamino)-2-hydroxypropyl)-N-methylsulfamoyl)-3-methylbiphenyl-4-carboxylic acid

EXAMPLE 3-53

(R)-3'-(N-(3-(1-(2,3-dihydro-1H-inden-2-yl)-2-methylpropan-2-ylamino)-2-hydroxypropyl)-N-methylsulfamoyl)-3-fluorobiphenyl-4-carboxylic acid

EXAMPLE 3-54

(R)-3-chloro-3'-(N-(3-(1-(2,3-dihydro-1H-inden-2-yl)-2-methylpropan-2-ylamino)-2-hydroxypropyl)-N-methylsulfamoyl)biphenyl-4-carboxylic acid

EXAMPLE 3-55

(R)-3'-(N-(3-(1-(2,3-dihydro-1H-inden-2-yl)-2-methylpropan-2-ylamino)-2-hydroxypropyl)-N-methylsulfamoyl)-2-fluorobiphenyl-4-carboxylic acid

EXAMPLE 3-56

(R)-3-(3'-(N-(3-(1-(2,3-dihydro-1H-inden-2-yl)-2-methylpropan-2-ylamino)-2-hydroxypropyl)-N-methylsulfamoyl)biphenyl-4-yl)acrylic acid

EXAMPLE 3-57

(R)-3-(3' (N-(3-(1-(2,3-dihydro-1H-inden-2-yl)-2-methylpropan-2-ylamino)-2-hydroxypropyl)-N-methylsulfamoyl)biphenyl-4-yl)propionic acid

EXAMPLE 3-58

(R)-3-(3'-(N-(3-(1-(2,3-dihydro-1H-inden-2-yl)-2-methylpropan-2-ylamino)-2-hydroxypropyl)-N-methylsulfamoyl)biphenyl-3-yl)acrylic acid

EXAMPLE 3-59

(R)-4-(3'-(N-(3-(1-(2,3-dihydro-1H-inden-2-yl)-2-methylpropan-2-ylamino)-2-hydroxypropyl)-N-methylsulfamoyl)biphenyl-4-ylamino)-4-oxobutanoic acid

EXAMPLE 3-60

(R)-3'-(N-(3-(1-(2,3-dihydro-1H-inden-2-yl)-2-methylpropan-2-ylamino)-2-hydroxypropyl)-N-methylsulfamoyl)-5-fluorobiphenyl-3-carboxylic acid

EXAMPLE 3-61

(R)-2-(3'-(N-(3-(1-(2,3-dihydro-1H-inden-2-yl)-2-methylpropan-2-ylamino)-2-hydroxypropyl)-N-methylsulfamoyl)biphenyl-4-yl)acetic acid

EXAMPLE 3-62

(R)-2-(3'-(N-(3-(1-(2,3-dihydro-1H-inden-2-yl)-2-methylpropan-2-ylamino)-2-hydroxypropyl)-N-methylsulfamoyl)biphenyl-3-yl)acetic acid

EXAMPLE 3-63

(R)-3'-(N-(3-(1-(3-fluoro-4-methylphenyl)-2-methylpropan-2-ylamino)-2-hydroxypropyl)-N-methylsulfamoyl)biphenyl-3-carboxylic acid

EXAMPLE 3-64

(R)-3'-(N-(3-(1-(3-fluoro-4-methylphenyl)-2-methylpropan-2-ylamino)-2-hydroxypropyl)-N-methylsulfamoyl)biphenyl-4-carboxylic acid

EXAMPLE 3-65

(R)-3-fluoro-3'-(N-(3-(1-(3-fluoro-4-methylphenyl)-2-methylpropan-2-ylamino)-2-hydroxypropyl)-N-methylsulfamoyl)biphenyl-4-carboxylic acid

EXAMPLE 3-66

(R)-3-chloro-3'-(N-(3-(1-(3-fluoro-4-methylphenyl)-2-methylpropan-2-ylamino)-2-hydroxypropyl)-N-methylsulfamoyl)biphenyl-4-carboxylic acid

EXAMPLE 3-67

(R)-2-fluoro-3'-(N-(3-(1-(3-fluoro-4-methylphenyl)-2-methylpropan-2-ylamino)-2-hydroxypropyl)-N-methylsulfamoyl)biphenyl-4-carboxylic acid

EXAMPLE 3-68

(R)-3-(3'-(N-(3-(1-(3-fluoro-4-methylphenyl)-2-methylpropan-2-ylamino)-2-hydroxypropyl)-N-methylsulfamoyl)biphenyl-4-yl)acrylic acid

EXAMPLE 3-69

(R)-3-(3'-(N-(3-(1-(3-fluoro-4-methylphenyl)-2-methylpropan-2-ylamino)-2-hydroxypropyl)-N-methylsulfamoyl)biphenyl-4-yl)propionic acid

EXAMPLE 3-70

(R)-3-(3'-(N-(3-(1-(3-fluoro-4-methylphenyl)-2-methylpropan-2-ylamino)-2-hydroxypropyl)-N-methylsulfamoyl)biphenyl-3-yl)acrylic acid

EXAMPLE 3-71

(R)-5-fluoro-3'-(N-(3-(1-(3-fluoro-4-methylphenyl)-2-methylpropan-2-ylamino)-2-hydroxypropyl)-N-methylsulfamoyl)biphenyl-3-carboxylic acid

EXAMPLE 3-72

(R)-3'-(N-(3-(1-(4-chloro-3-fluorophenyl)-2-methylpropan-2-ylamino)-2-hydroxypropyl)-N-methylsulfamoyl)biphenyl-3-carboxylic acid

EXAMPLE 3-73

(R)-3'-(N-(3-(1-(4-chloro-3-fluorophenyl)-2-methylpropan-2-ylamino)-2-hydroxypropyl)-N-methylsulfamoyl)biphenyl-4-carboxylic acid

EXAMPLE 3-74

(R)-3'-(N-(3-(1-(4-chloro-3-fluorophenyl)-2-methylpropan-2-ylamino)-2-hydroxypropyl)-N-methylsulfamoyl)-3-fluorobiphenyl-4-carboxylic acid

EXAMPLE 3-75

(R)-3-chloro-3'-(N-(3-(1-(4-chloro-3-fluorophenyl)-2-methylpropan-2-ylamino)-2-hydroxypropyl)-N-methylsulfamoyl)biphenyl-4-carboxylic acid

EXAMPLE 3-76

(R)-3'-(N-(3-(1-(4-chloro-3-fluorophenyl)-2-methylpropan-2-ylamino)-2-hydroxypropyl)-N-methylsulfamoyl)-2-fluorobiphenyl-4-carboxylic acid

EXAMPLE 3-77

(R)-3-(3'-(N-(3-(1-(4-chloro-3-fluorophenyl)-2-methylpropan-2-ylamino)-2-hydroxypropyl)-N-methylsulfamoyl)biphenyl-4-yl)acrylic acid

EXAMPLE 3-78

(R)-3-(3'-(N-(3-(1-(4-chloro-3-fluorophenyl)-2-methylpropan-2-ylamino)-2-hydroxypropyl)-N-methylsulfamoyl)biphenyl-4-yl)propionic acid

EXAMPLE 3-79

(R)-3-(3'-(N-(3-(1-(4-chloro-3-fluorophenyl)-2-methylpropan-2-ylamino)-2-hydroxypropyl)-N-methylsulfamoyl)biphenyl-3-yl)acrylic acid

EXAMPLE 3-80

(R)-3'-(N-(3-(1-(4-chloro-3-fluorophenyl)-2-methylpropan-2-ylamino)-2-hydroxypropyl)-N-methylsulfamoyl)-5-fluorobiphenyl-3-carboxylic acid

EXAMPLE 3-81

(R)-2'-((N-(2-hydroxy-3-(2-methyl-1-(naphthalen-2-yl)propan-2-ylamino)propyl)-N-methylsulfamoyl)methyl)-3-methylbiphenyl-4-carboxylic acid

EXAMPLE 3-82

(R)-3-(2'-((N-(2-hydroxy-3-(2-methyl-1-(naphthalen-2-yl)propan-2-ylamino)propyl)-N-methylsulfamoyl)methyl)biphenyl-4-yl)acrylic acid

EXAMPLE 3-83

(R)-3-(2'-((N-(2-hydroxy-3-(2-methyl-1-(naphthalen-2-yl)propan-2-ylamino)propyl)-N-methylsulfamoyl)methyl)biphenyl-4-yl)propionic acid

EXAMPLE 3-84

(R)-3-(2'-((N-(2-hydroxy-3-(2-methyl-1-(naphthalen-2-yl)propan-2-ylamino)propyl)-N-methylsulfamoyl)methyl)biphenyl-3-yl)acrylic acid

EXAMPLE 3-85

(R)-5-fluoro-2'-((N-(2-hydroxy-3-(2-methyl-1-(naphthalen-2-yl)propan-2-ylamino)propyl)-N-methylsulfamoyl)methyl)biphenyl-3-carboxylic acid

EXAMPLE 3-86

(R)-3-(3'-((N-(2-hydroxy-3-(2-methyl-1-(naphthalen-2-yl)propan-2-ylamino)propyl)-N-methylsulfamoyl)methyl)biphenyl-4-yl)acrylic acid

EXAMPLE 3-87

(R)-3-(3'-((N-(2-hydroxy-3-(2-methyl-1-(naphthalen-2-yl)propan-2-ylamino)propyl)-N-methylsulfamoyl)methyl)biphenyl-4-yl)propionic acid

EXAMPLE 3-88

(R)-3-(3'-((N-(2-hydroxy-3-(2-methyl-1-(naphthalen-2-yl)propan-2-ylamino)propyl)-N-methylsulfamoyl)methyl)biphenyl-3-yl)acrylic acid

EXAMPLE 3-89

(R)-3-(4'-((N-(2-hydroxy-3-(2-methyl-1-(naphthalen-2-yl)propan-2-ylamino)propyl)-N-methylsulfamoyl)methyl)biphenyl-4-yl)acrylic acid

EXAMPLE 3-90

(R)-3-(4'-((N-(2-hydroxy-3-(2-methyl-1-(naphthalen-2-yl)propan-2-ylamino)propyl)-N-methylsulfamoyl)methyl)biphenyl-4-yl)propionic acid

EXAMPLE 3-91

(R)-3-(4'-((N-(2-hydroxy-3-(2-methyl-1-(naphthalen-2-yl)propan-2-ylamino)propyl)-N-methylsulfamoyl)methyl)biphenyl-3-yl)acrylic acid

EXAMPLES 3-92 TO 232

Reaction was carried out in the same manner as Example 3-1 with combinations shown in Table 4, except that and BA were used instead of Exp. 2-1 and ba13, respectively, to obtain a crude product, which was then purified according to the above described purification method to give a target compound.

TABLE 4

| Exp. | SM2 | BA | method | Rtime | Mass |
|---|---|---|---|---|---|
| | | | | LCMS | |
| 3-92 | Exp. 2-5 | ba56 | B | 1.32 | 551 |
| 3-93 | Exp. 2-35 | ba12 | B | 1.45 | 633 |
| 3-94 | Exp. 2-38 | ba12 | B | 1.29 | 595 |
| 3-95 | Exp. 2-36 | ba12 | B | 1.45 | 645 |
| 3-96 | Exp. 2-40 | ba12 | B | 1.37 | 571 |
| 3-97 | Exp. 2-18 | ba12 | B | 1.42 | 633 |
| 3-98 | Exp. 2-26 | ba12 | B | 1.42 | 633 |
| 3-99 | Exp. 2-39 | ba12 | B | 1.37 | 605 |
| 3-100 | Exp. 2-28 | ba12 | B | 1.43 | 649 |
| 3-101 | Exp. 2-20 | ba12 | B | 1.37 | 579 |
| 3-102 | Exp. 2-16 | ba12 | B | 1.37 | 593 |
| 3-103 | Exp. 2-41 | ba12 | B | 1.20 | 566 |
| 3-104 | Exp. 2-23 | ba12 | B | 1.37 | 599 |
| 3-105 | Exp. 2-27 | ba12 | B | 1.44 | 633 |
| 3-106 | Exp. 2-24 | ba12 | B | 1.43 | 599 |
| 3-107 | Exp. 2-21 | ba12 | B | 1.36 | 579 |
| 3-108 | Exp. 2-29 | ba12 | B | 1.48 | 601 |
| 3-109 | Exp. 2-31 | ba12 | B | 1.48 | 583 |
| 3-110 | Exp. 2-30 | ba12 | B | 1.34 | 571 |
| 3-111 | Exp. 2-33 | ba12 | B | 1.53 | 621 |

TABLE 4-continued

| Exp. | SM2 | BA | method | Rtime | Mass |
|---|---|---|---|---|---|
| | | | | LCMS | |
| 3-112 | Exp. 2-32 | ba12 | B | 1.73 | 621 |
| 3-113 | Exp. 2-34 | ba12 | B | 1.48 | 621 |
| 3-114 | Exp. 2-25 | ba12 | B | 1.54 | 587 |
| 3-115 | Exp. 2-22 | ba12 | B | 1.40 | 567 |
| 3-116 | Exp. 2-17 | ba12 | B | 1.43 | 581 |
| 3-117 | Exp. 2-6 | ba13 | B | 1.40 | 563 |
| 3-118 | Exp. 2-35 | ba2 | B | 1.43 | 605 |
| 3-119 | Exp. 2-38 | ba2 | B | 1.26 | 567 |
| 3-120 | Exp. 2-6 | ba2 | B | 1.32 | 537 |
| 3-121 | Exp. 2-41 | ba2 | B | 1.25 | 538 |
| 3-122 | Exp. 2-40 | ba2 | B | 1.35 | 543 |
| 3-123 | Exp. 2-21 | ba2 | B | 1.41 | 551 |
| 3-124 | Exp. 2-26 | ba2 | B | 1.41 | 605 |
| 3-125 | Exp. 2-36 | ba2 | B | 1.48 | 617 |
| 3-126 | Exp. 2-18 | ba2 | B | 1.47 | 605 |
| 3-127 | Exp. 2-38 | ba20 | B | 1.27 | 585 |
| 3-128 | Exp. 2-35 | ba20 | B | 1.48 | 623 |
| 3-129 | Exp. 2-5 | ba22 | B | 1.34 | 581 |
| 3-130 | Exp. 2-5 | ba26 | B | 1.25 | 543 |
| 3-131 | Exp. 2-38 | ba29 | B | 1.26 | 581 |
| 3-132 | Exp. 2-40 | ba29 | B | 1.34 | 557 |
| 3-133 | Exp. 2-35 | ba29 | B | 1.45 | 619 |
| 3-134 | Exp. 2-6 | ba29 | B | 1.32 | 551 |
| 3-135 | Exp. 2-21 | ba29 | B | 1.37 | 565 |
| 3-136 | Exp. 2-36 | ba29 | B | 1.44 | 631 |
| 3-137 | Exp. 2-26 | ba29 | B | 1.51 | 619 |
| 3-138 | Exp. 2-41 | ba29 | B | 1.29 | 552 |
| 3-139 | Exp. 2-40 | ba29 | B | 1.39 | 557 |
| 3-140 | Exp. 2-18 | ba29 | B | 1.47 | 619 |
| 3-141 | Exp. 2-27 | ba29 | B | 1.35 | 619 |
| 3-142 | Exp. 2-24 | ba29 | B | 1.30 | 585 |
| 3-143 | Exp. 2-39 | ba29 | B | 1.41 | 591 |
| 3-144 | Exp. 2-28 | ba29 | B | 1.39 | 635 |
| 3-145 | Exp. 2-20 | ba29 | B | 1.32 | 565 |
| 3-146 | Exp. 2-23 | ba29 | B | 1.33 | 585 |
| 3-147 | Exp. 2-16 | ba29 | B | 1.42 | 579 |
| 3-148 | Exp. 2-31 | ba29 | B | 1.43 | 569 |
| 3-149 | Exp. 2-29 | ba29 | B | 1.43 | 587 |
| 3-150 | Exp. 2-35 | ba3 | B | 1.42 | 605 |
| 3-151 | Exp. 2-38 | ba3 | B | 1.23 | 567 |
| 3-152 | Exp. 2-6 | ba3 | B | 1.33 | 537 |
| 3-153 | Exp. 2-38 | ba30 | B | 1.35 | 581 |
| 3-154 | Exp. 2-35 | ba30 | B | 1.45 | 619 |
| 3-155 | Exp. 2-41 | ba30 | B | 1.29 | 552 |
| 3-156 | Exp. 2-6 | ba30 | B | 1.32 | 551 |
| 3-157 | Exp. 2-35 | ba33 | B | 1.48 | 661 |
| 3-158 | Exp. 2-38 | ba33 | B | 1.32 | 623 |
| 3-159 | Exp. 2-35 | ba36 | B | 1.51 | 649 |
| 3-160 | Exp. 2-38 | ba38 | B | 1.35 | 611 |
| 3-161 | Exp. 2-6 | ba38 | B | 1.38 | 581 |
| 3-162 | Exp. 2-35 | ba43 | B | 1.51 | 645 |
| 3-163 | Exp. 2-35 | ba46 | B | 1.48 | 633 |
| 3-164 | Exp. 2-38 | ba46 | B | 1.29 | 595 |
| 3-165 | Exp. 2-6 | ba46 | B | 1.40 | 565 |
| 3-166 | Exp. 2-26 | ba46 | B | 1.45 | 633 |
| 3-167 | Exp. 2-36 | ba46 | B | 1.48 | 645 |
| 3-168 | Exp. 2-40 | ba46 | B | 1.32 | 571 |
| 3-169 | Exp. 2-18 | ba46 | B | 1.48 | 633 |
| 3-170 | Exp. 2-39 | ba46 | B | 1.39 | 605 |
| 3-171 | Exp. 2-28 | ba46 | B | 1.48 | 649 |
| 3-172 | Exp. 2-20 | ba46 | B | 1.38 | 579 |
| 3-173 | Exp. 2-23 | ba46 | B | 1.39 | 599 |
| 3-174 | Exp. 2-27 | ba46 | B | 1.37 | 633 |
| 3-175 | Exp. 2-16 | ba46 | B | 1.36 | 593 |
| 3-176 | Exp. 2-24 | ba46 | B | 1.35 | 599 |
| 3-177 | Exp. 2-41 | ba46 | B | 1.23 | 566 |
| 3-178 | Exp. 2-21 | ba46 | B | 1.38 | 579 |
| 3-179 | Exp. 2-31 | ba46 | B | 1.40 | 583 |
| 3-180 | Exp. 2-29 | ba46 | B | 1.43 | 601 |
| 3-181 | Exp. 2-30 | ba46 | B | 1.29 | 571 |
| 3-182 | Exp. 2-33 | ba46 | B | 1.51 | 621 |
| 3-183 | Exp. 2-34 | ba46 | B | 1.45 | 621 |
| 3-184 | Exp. 2-32 | ba46 | B | 1.79 | 621 |
| 3-185 | Exp. 2-25 | ba46 | B | 1.54 | 587 |
| 3-186 | Exp. 2-22 | ba46 | B | 1.45 | 567 |
| 3-187 | Exp. 2-17 | ba46 | B | 1.50 | 581 |

TABLE 4-continued

| Exp. | SM2 | BA | LCMS method | Rtime | Mass |
|---|---|---|---|---|---|
| 3-188 | Exp. 2-30 | ba47 | B | 1.42 | 571 |
| 3-189 | Exp. 2-29 | ba47 | B | 1.48 | 601 |
| 3-190 | Exp. 2-25 | ba47 | B | 1.67 | 587 |
| 3-191 | Exp. 2-22 | ba47 | B | 1.59 | 567 |
| 3-192 | Exp. 2-17 | ba47 | B | 1.65 | 581 |
| 3-193 | Exp. 2-35 | ba48 | B | 1.42 | 623 |
| 3-194 | Exp. 2-38 | ba48 | B | 1.26 | 585 |
| 3-195 | Exp. 2-6 | ba48 | B | 1.32 | 555 |
| 3-196 | Exp. 2-43 | ba46 | B | 1.46 | 579 |
| 3-197 | Exp. 2-35 | ba5 | B | 1.45 | 619 |
| 3-198 | Exp. 2-38 | ba5 | B | 1.26 | 581 |
| 3-199 | Exp. 2-43 | ba29 | B | 1.39 | 565 |
| 3-200 | Exp. 2-38 | ba51 | B | 1.26 | 585 |
| 3-201 | Exp. 2-5 | ba52 | B | 1.35 | 555 |
| 3-202 | Exp. 2-5 | ba53 | B | 1.34 | 571 |
| 3-203 | Exp. 2-5 | ba54 | B | 1.26 | 552 |
| 3-204 | Exp. 2-5 | ba55 | B | 1.32 | 551 |
| 3-205 | Exp. 2-35 | ba8 | B | 1.43 | 639 |
| 3-206 | Exp. 2-38 | ba8 | B | 1.26 | 601 |
| 3-207 | Exp. 2-41 | ba8 | B | 1.24 | 572 |
| 3-208 | Exp. 2-6 | ba8 | B | 1.36 | 571 |
| 3-209 | Exp. 2-40 | ba8 | B | 1.36 | 577 |
| 3-210 | Exp. 2-36 | ba8 | B | 1.44 | 651 |
| 3-211 | Exp. 2-21 | ba8 | B | 1.44 | 585 |
| 3-212 | Exp. 2-18 | ba8 | B | 1.46 | 641 |
| 3-213 | Exp. 2-26 | ba8 | B | 1.47 | 639 |
| 3-214 | Exp. 2-5 | ba57 | B | 1.32 | 569 |
| 3-215 | Exp. 2-5 | ba58 | B | 1.31 | 569 |
| 3-216 | Exp. 2-5 | ba59 | B | 1.29 | 581 |
| 3-217 | Exp. 2-5 | ba60 | B | 1.42 | 579 |
| 3-218 | Exp. 2-5 | ba61 | B | 1.31 | 596 |
| 3-219 | Exp. 2-5 | ba62 | B | 1.37 | 569 |
| 3-220 | Exp. 2-5 | ba63 | B | 1.32 | 551 |
| 3-221 | Exp. 2-5 | ba64 | B | 1.32 | 566 |
| 3-222 | Exp. 2-5 | ba49 | B | 1.18 | 538 |
| 3-223 | Exp. 2-5 | ba66 | B | 1.37 | 601 |
| 3-224 | Exp. 2-5 | ba67 | B | 1.40 | 600 |
| 3-225 | Exp. 2-5 | ba68 | B | 1.39 | 569 |
| 3-226 | Exp. 2-5 | ba69 | B | 1.36 | 571 |
| 3-227 | Exp. 2-5 | ba70 | B | 1.32 | 567 |
| 3-228 | Exp. 2-5 | ba71 | B | 1.43 | 605 |
| 3-229 | Exp. 2-27 | ba49 | B | 1.35 | 606 |
| 3-230 | Exp. 2-24 | ba49 | B | 1.26 | 572 |
| 3-231 | Exp. 2-27 | ba50 | A | 3.08 | 606 |
| 3-232 | Exp. 2-43 | ba12 | B | 1.43 | 579 |

Hereinbelow, structures of the compounds of Example to 3-232 (Exp. 3-92 to Exp. 3-232) are shown.

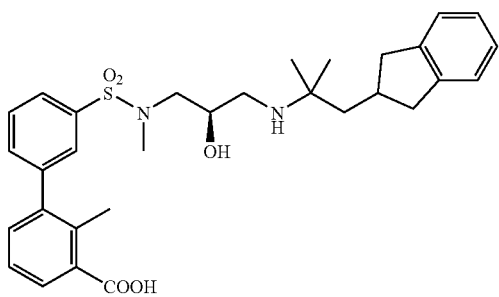

-continued
Exp. 3-96
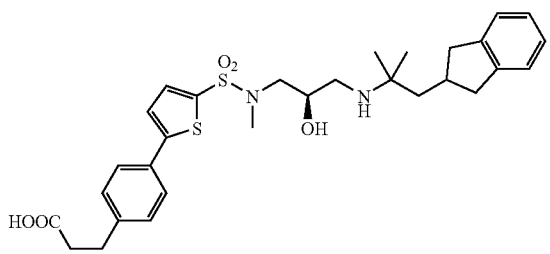
Exp. 3-97
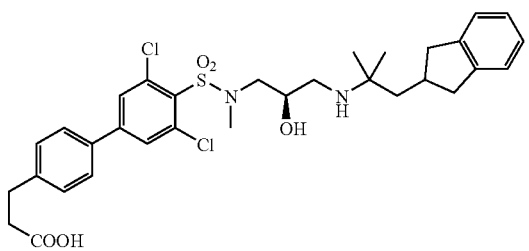
Exp. 3-98
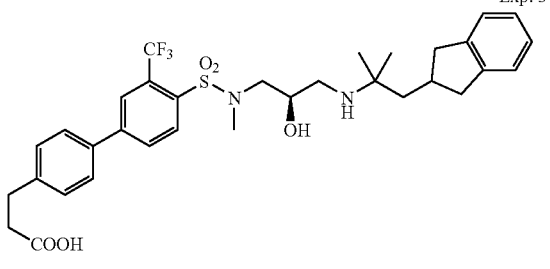
Exp. 3-99
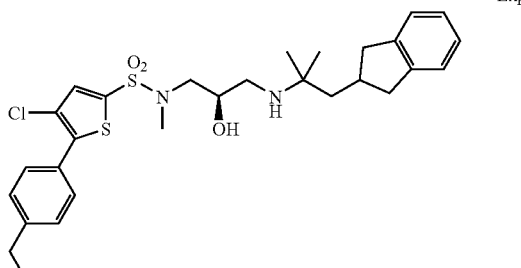
Exp. 3-100
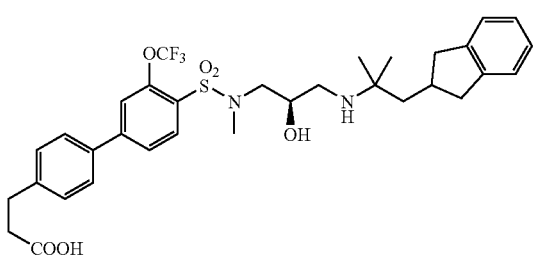
Exp. 3-101
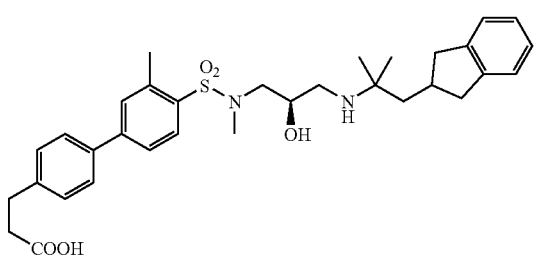
Exp. 3-102
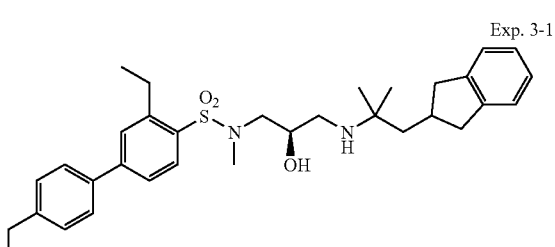
Exp. 3-103
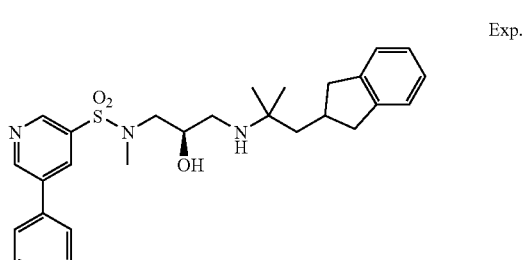
Exp. 3-104
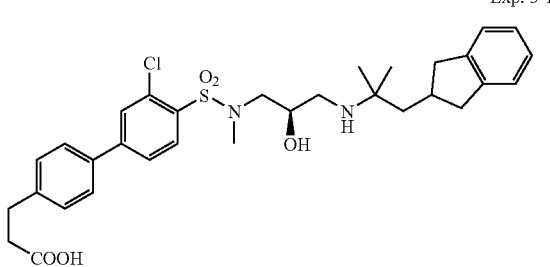
Exp. 3-105
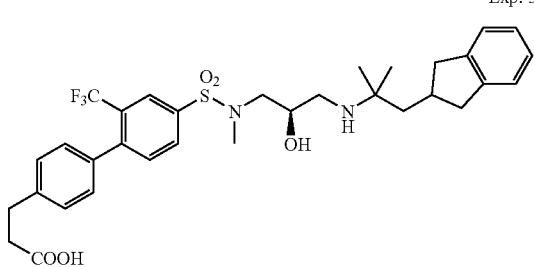

-continued
Exp. 3-106
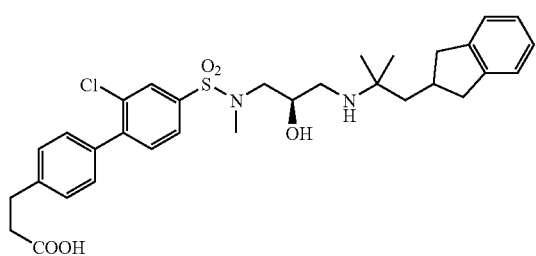
Exp. 3-107
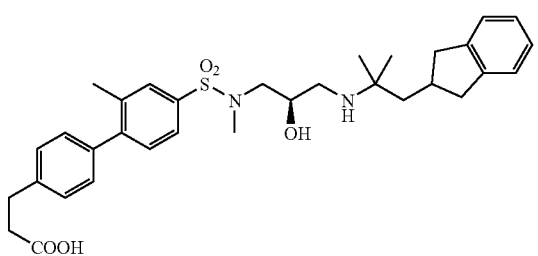
Exp. 3-108
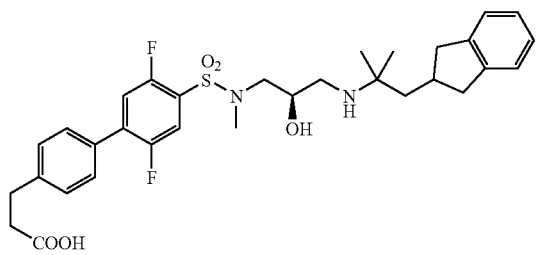
Exp. 3-109
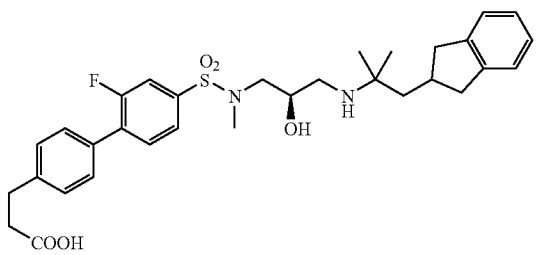
Exp. 3-110
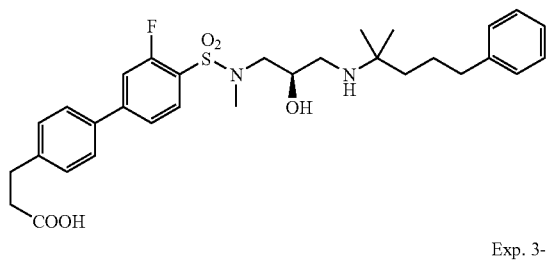
Exp. 3-111
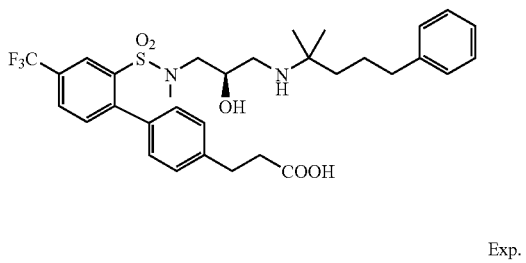
Exp. 3-112
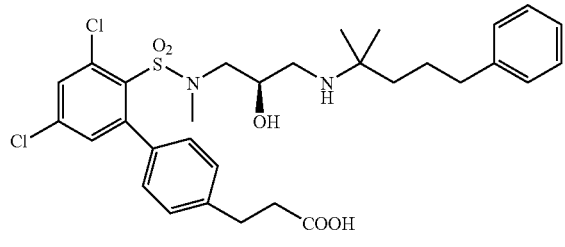
Exp. 3-113
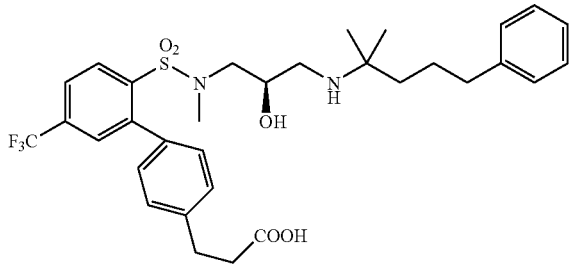
Exp. 3-114
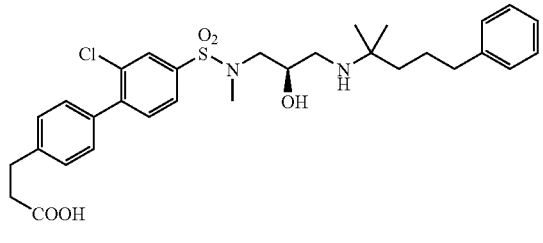
Exp. 3-115
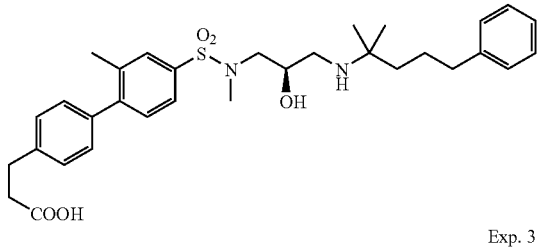
Exp. 3-116
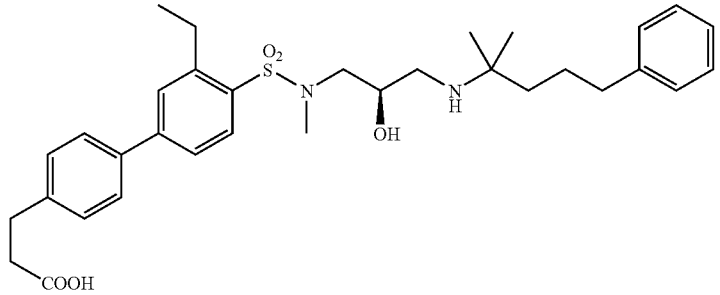

-continued
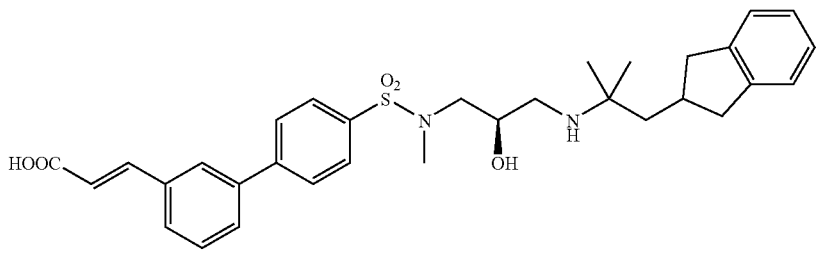
Exp. 3-117
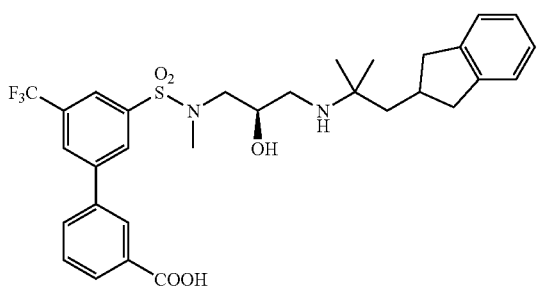
Exp. 3-118
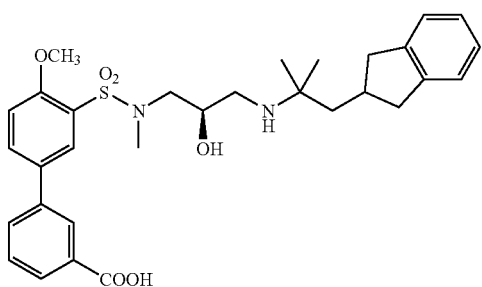
Exp. 3-119
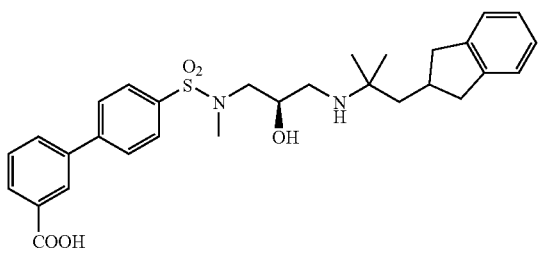
Exp. 3-120
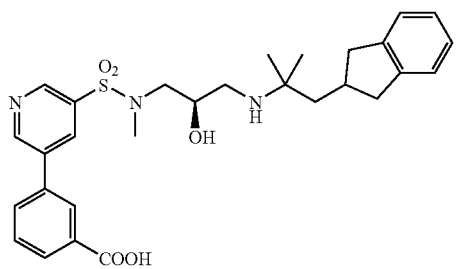
Exp. 3-121
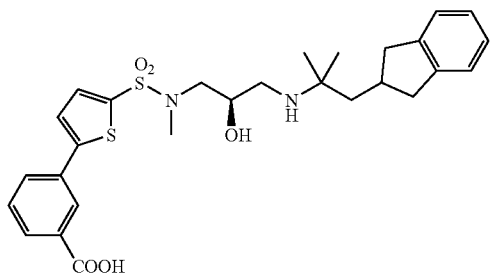
Exp. 3-122
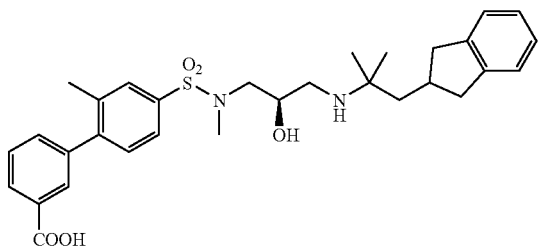
Exp. 3-123
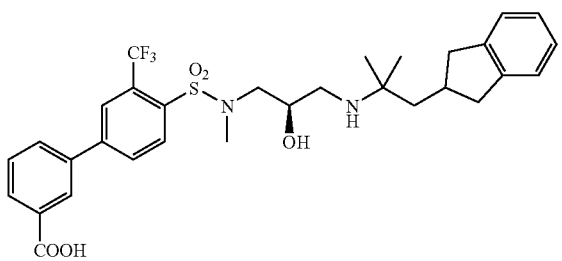
Exp. 3-124
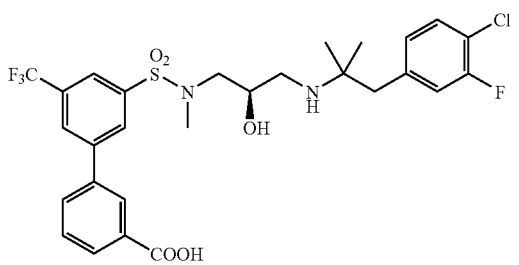
Exp. 3-125

-continued
Exp. 3-126
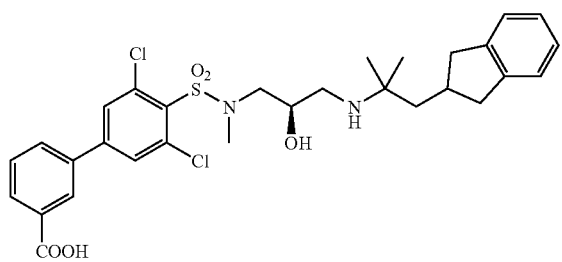
Exp. 3-127
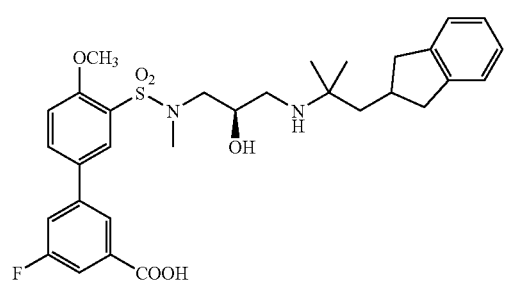
Exp. 3-128
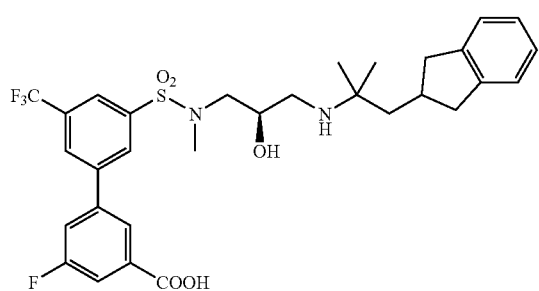
Exp. 3-129
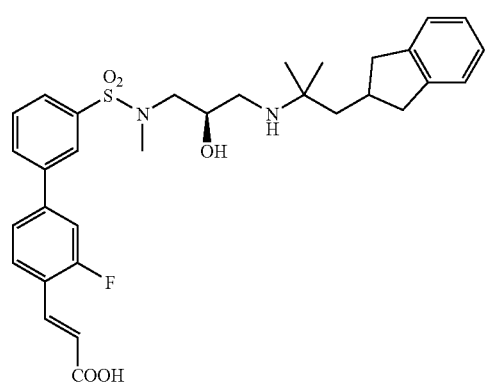
Exp. 3-130
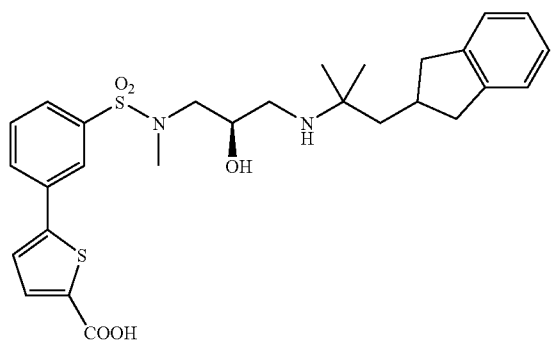
Exp. 3-131
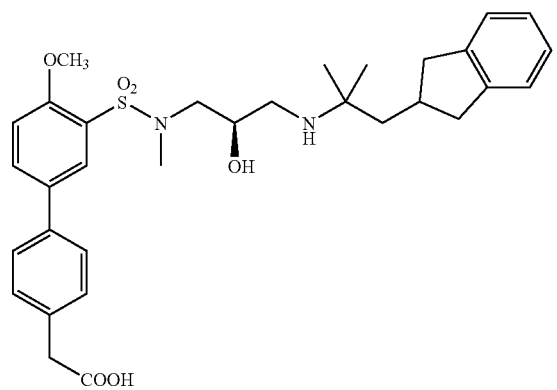
Exp. 3-132
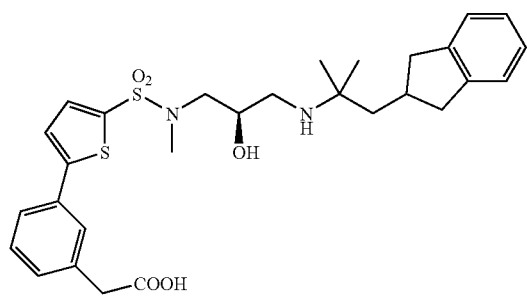
Exp. 3-133
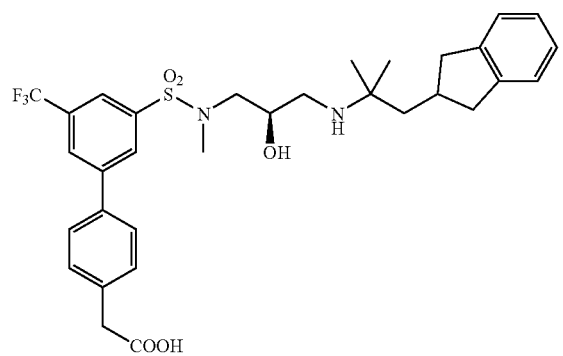

-continued
Exp. 3-134
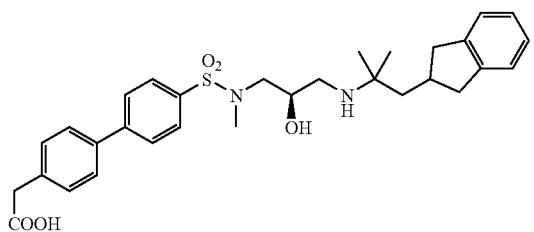
Exp. 3-135
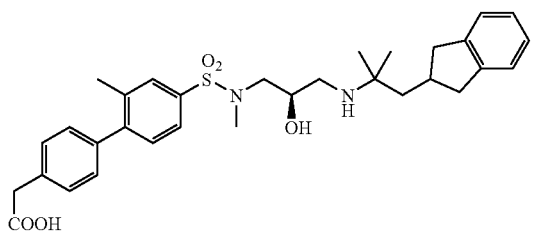
Exp. 3-136
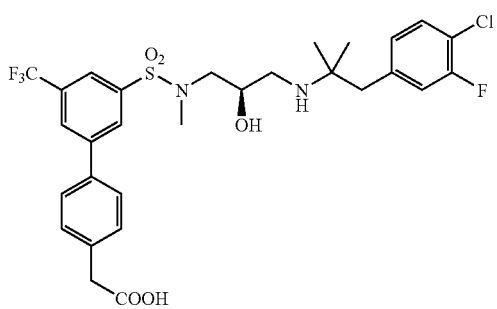
Exp. 3-137
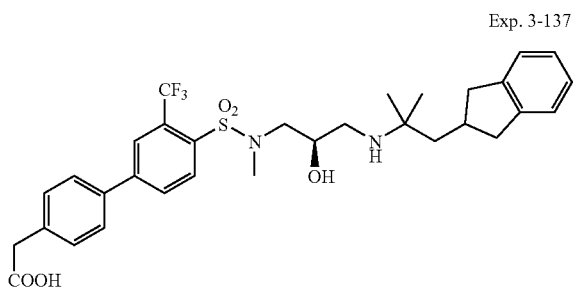
Exp. 3-138
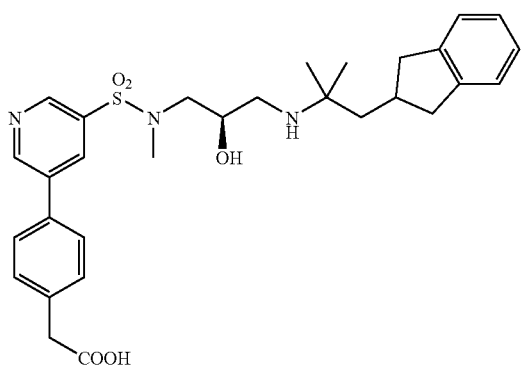
Exp. 3-139
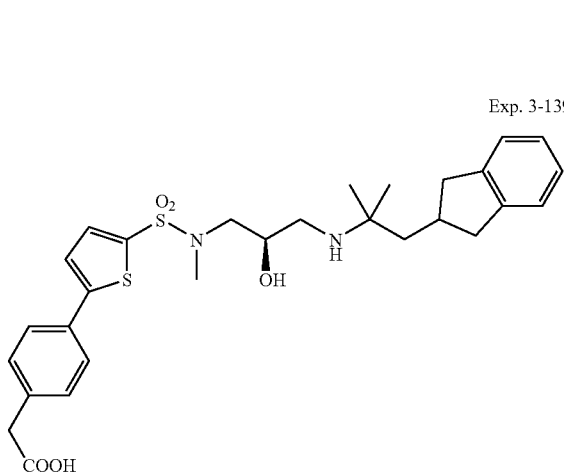
Exp. 3-140
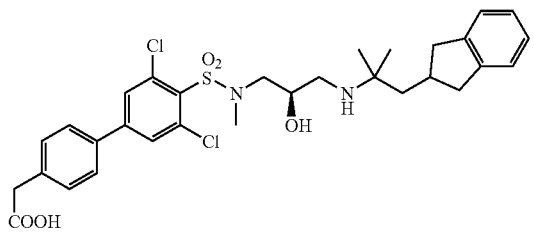
Exp. 3-141
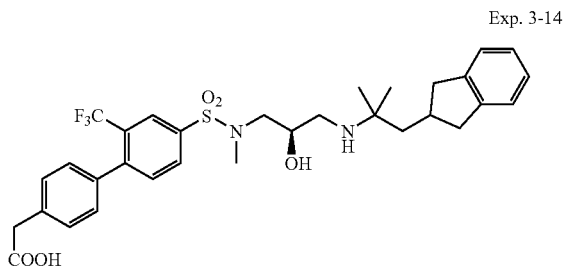
Exp. 3-142
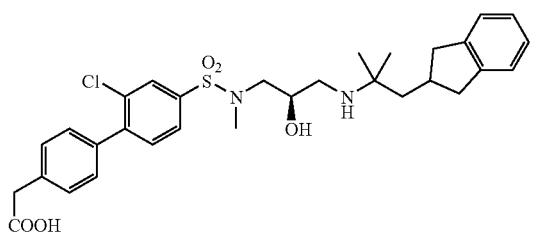
Exp. 3-143
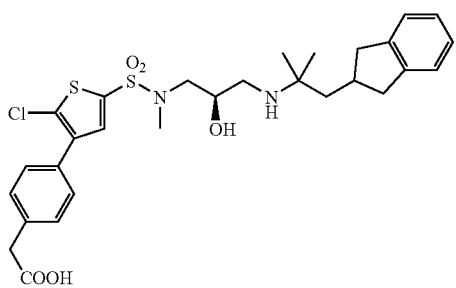

-continued
Exp. 3-144
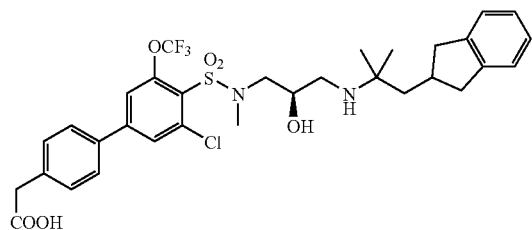
Exp. 3-145
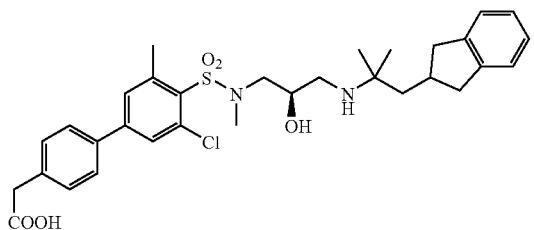
Exp. 3-146
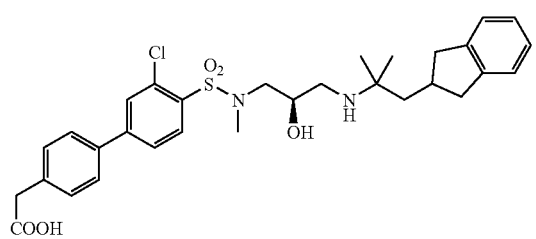
Exp. 3-147
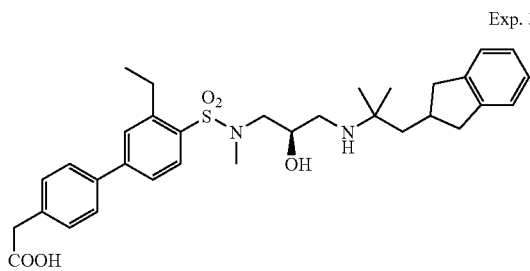
Exp. 3-148
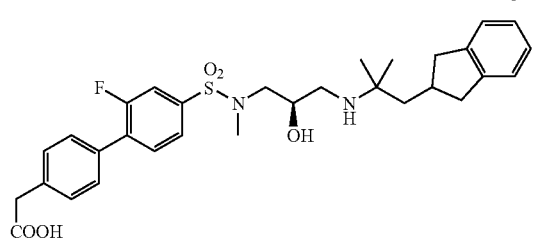
Exp. 3-149
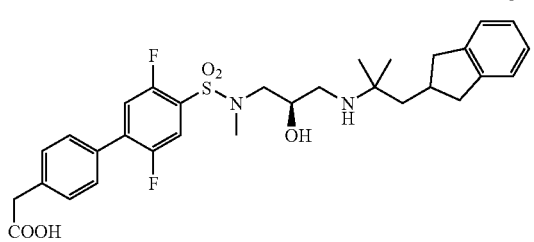
Exp. 3-150
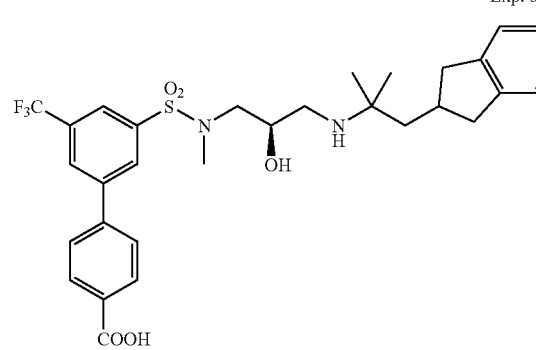
Exp. 3-151
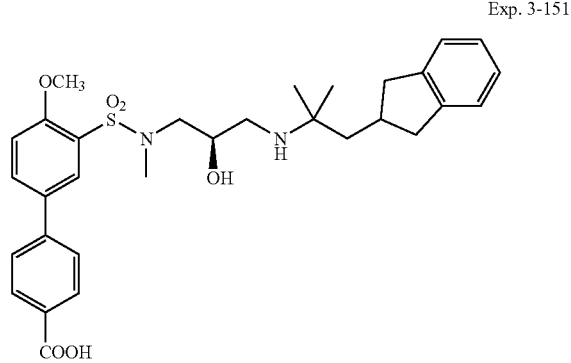
Exp. 3-152
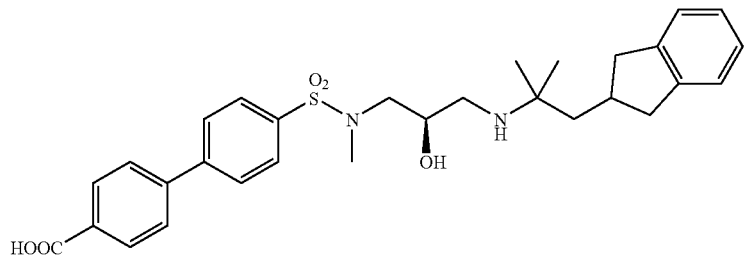

-continued
Exp. 3-153
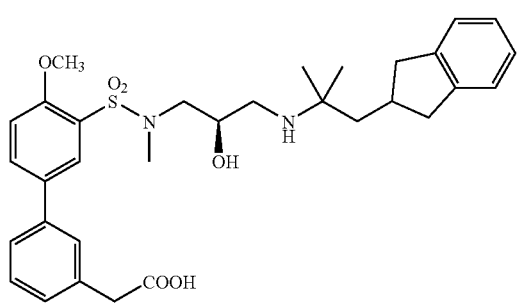
Exp. 3-154
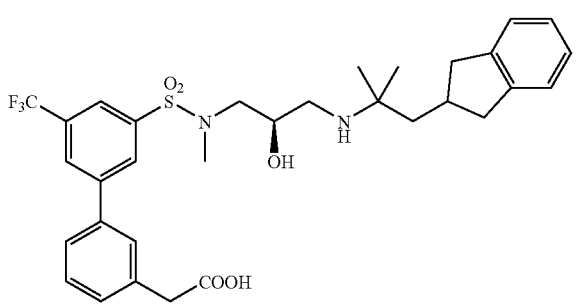
Exp. 3-155
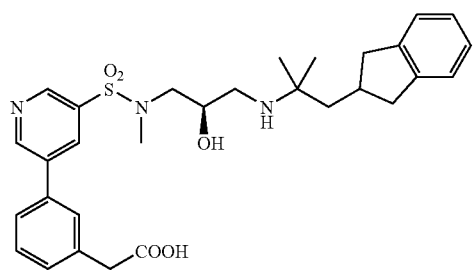
Exp. 3-156
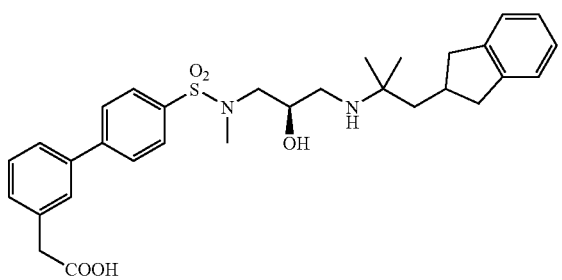
Exp. 3-157
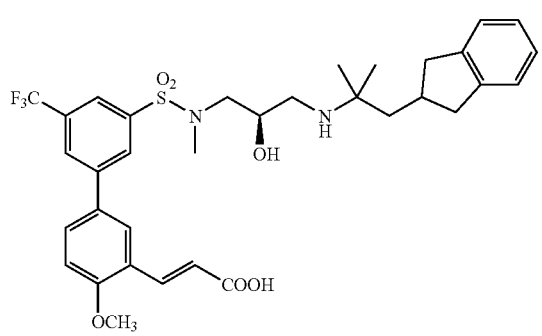
Exp. 3-158
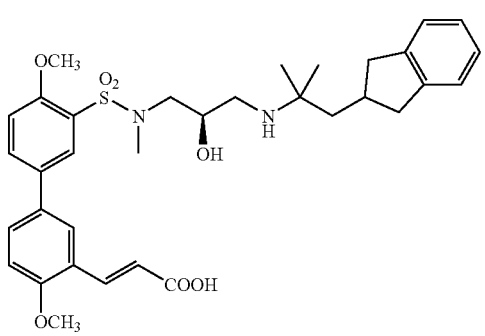
Exp. 3-159
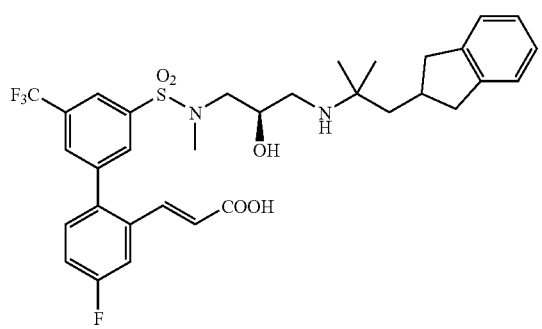
Exp. 3-160
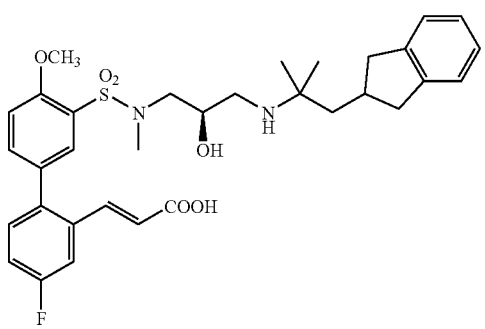
Exp. 3-161
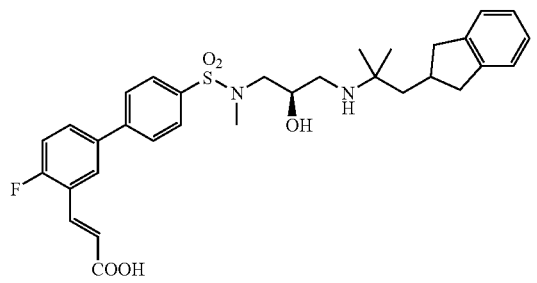
Exp. 3-162
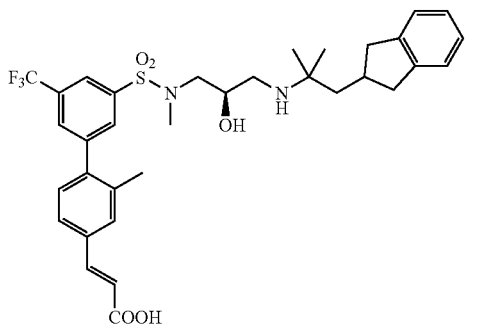

Exp. 3-163 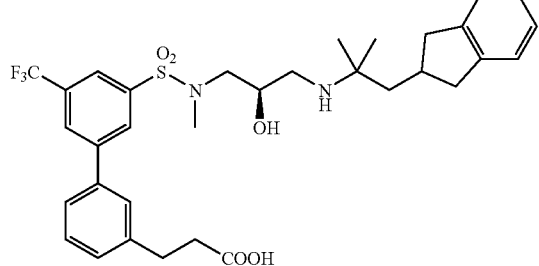
Exp. 3-164 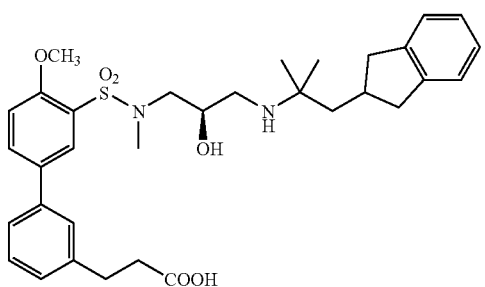
Exp. 3-165 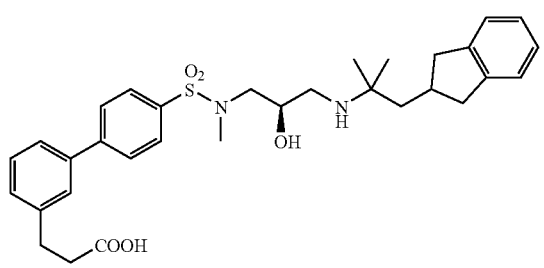
Exp. 3-166 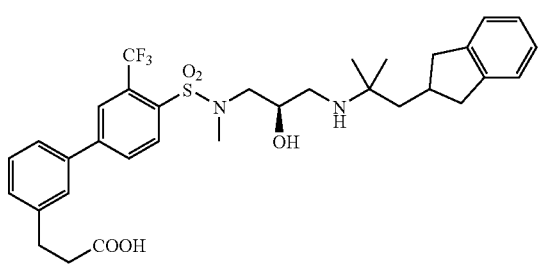
Exp. 3-167 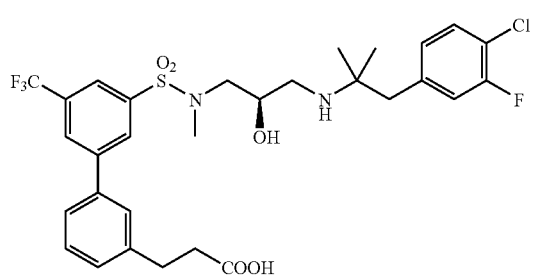
Exp. 3-168 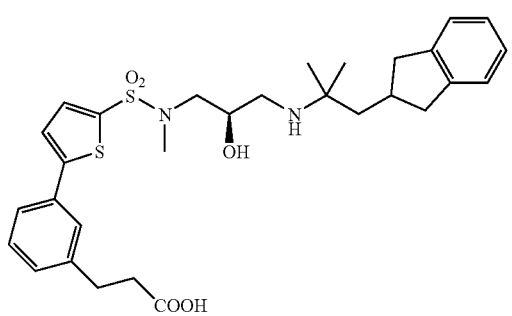
Exp. 3-169 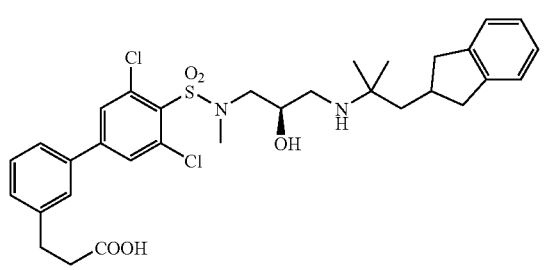
Exp. 3-170 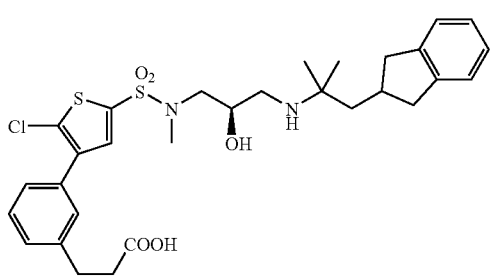
Exp. 3-171 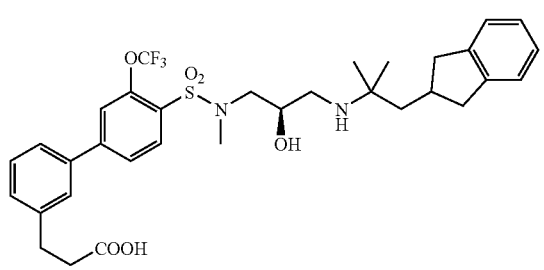
Exp. 3-172 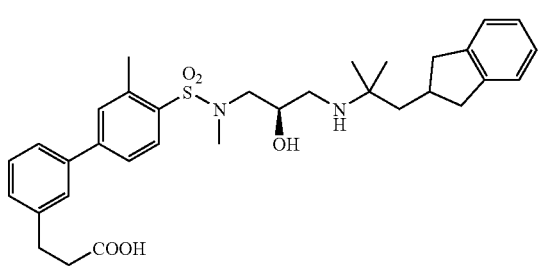

-continued
Exp. 3-173
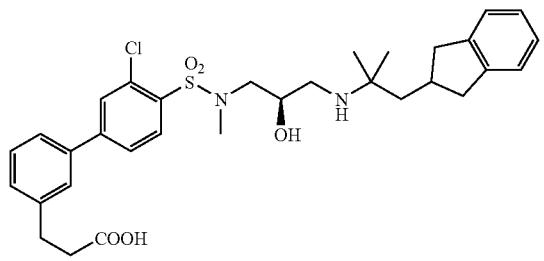
Exp. 3-174
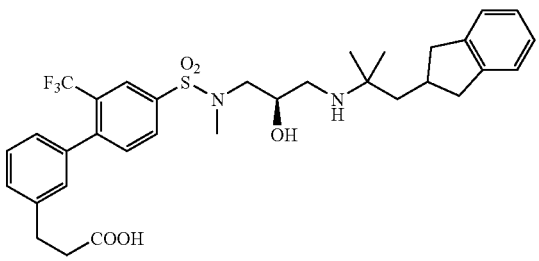
Exp. 3-175
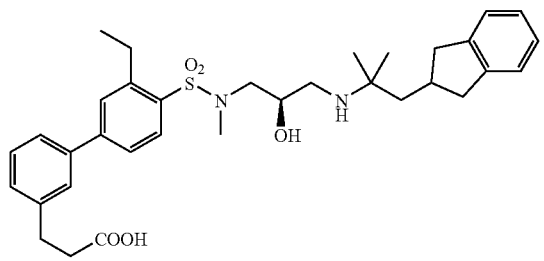
Exp. 3-176
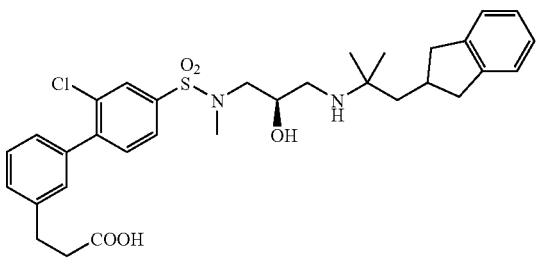
Exp. 3-177
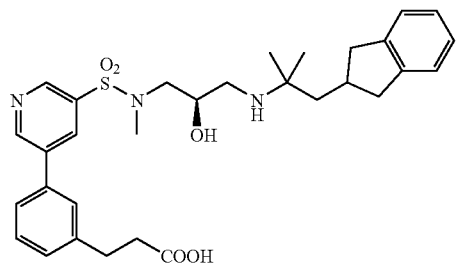
Exp. 3-178
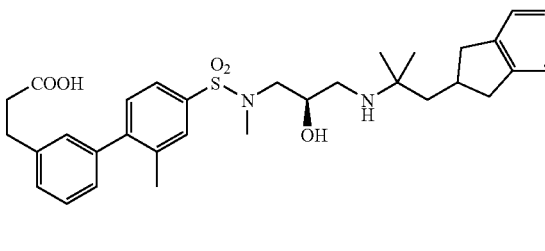
Exp. 3-179
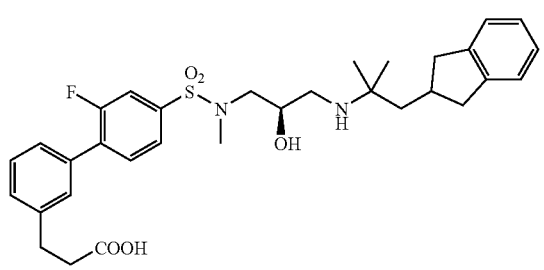
Exp. 3-180
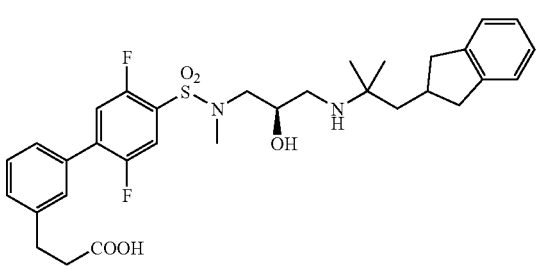
Exp. 3-181
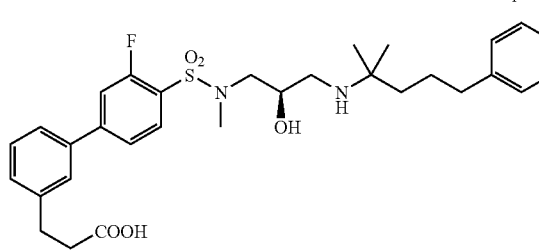
Exp. 3-182
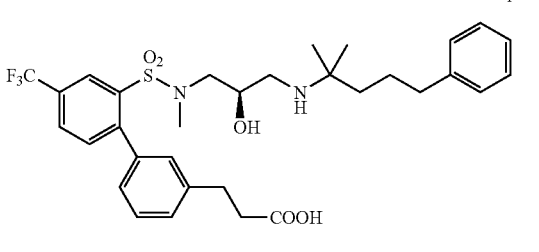
Exp. 3-183
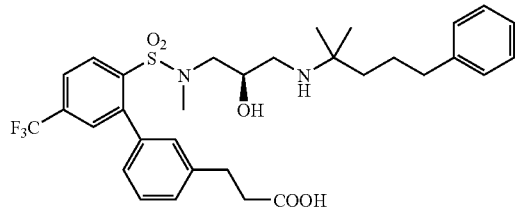
Exp. 3-184
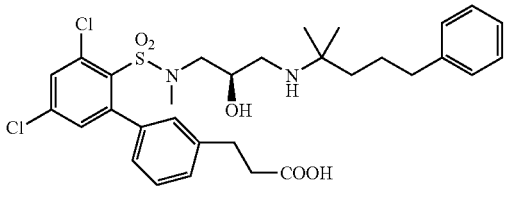

-continued
Exp. 3-185
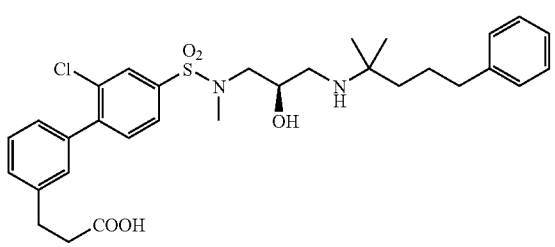
Exp. 3-186
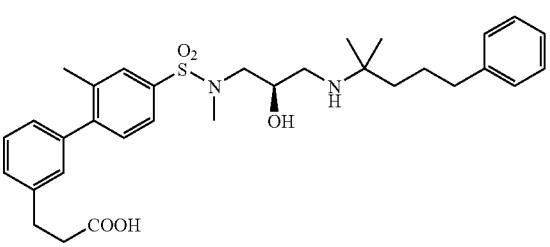
Exp. 3-187
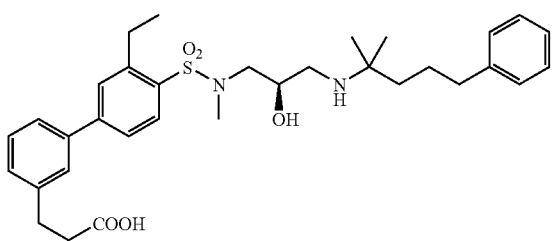
Exp. 3-188
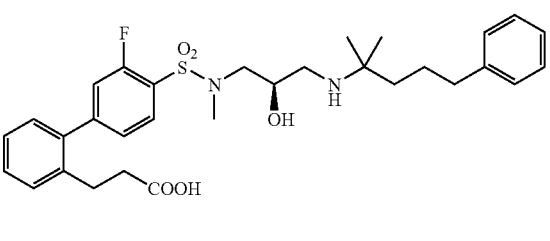
Exp. 3-189
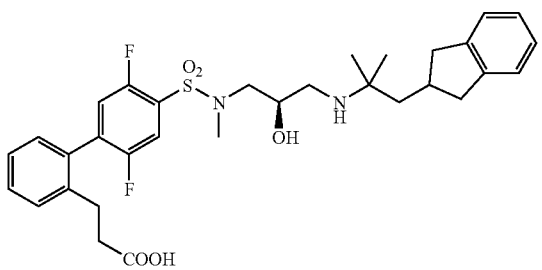
Exp. 3-190
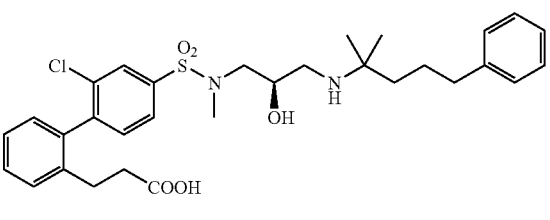
Exp. 3-191
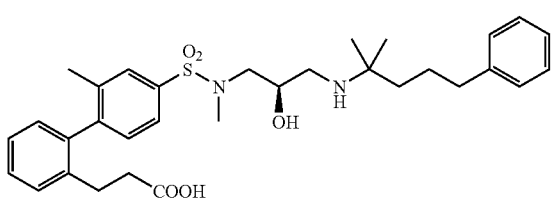
Exp. 3-192
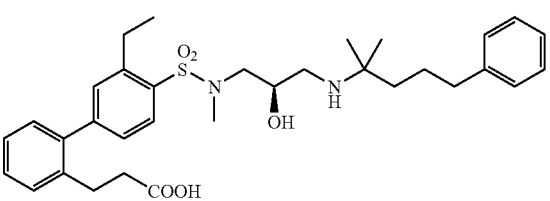
Exp. 3-193
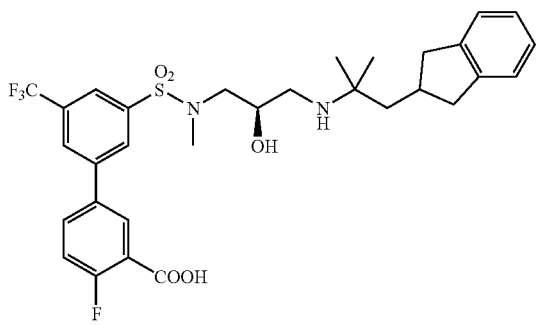
Exp. 3-194
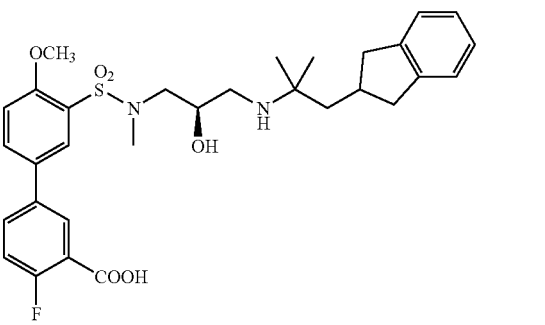
Exp. 3-195
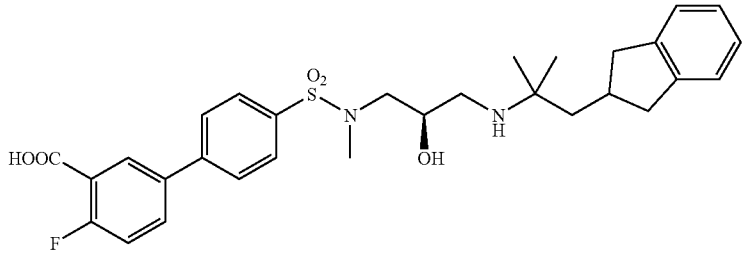

-continued
Exp. 3-196
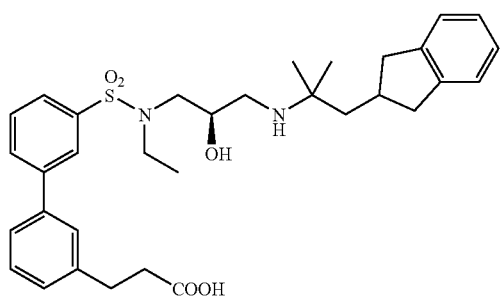
Exp. 3-197
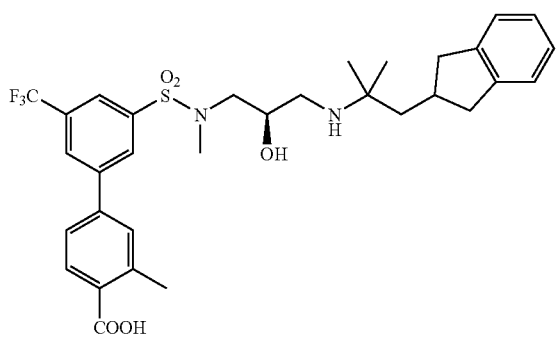
Exp. 3-198
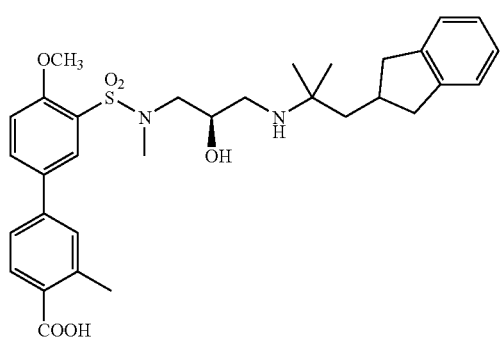
Exp. 3-199
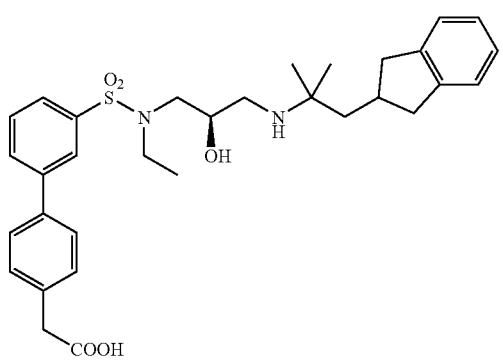
Exp. 3-200
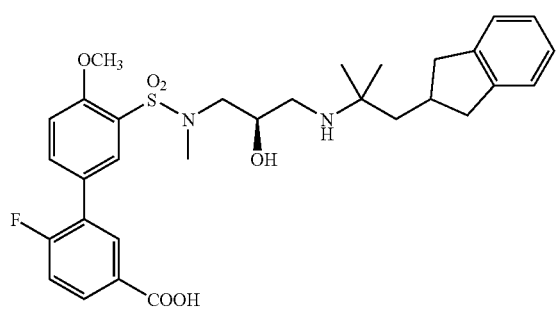
Exp. 3-201
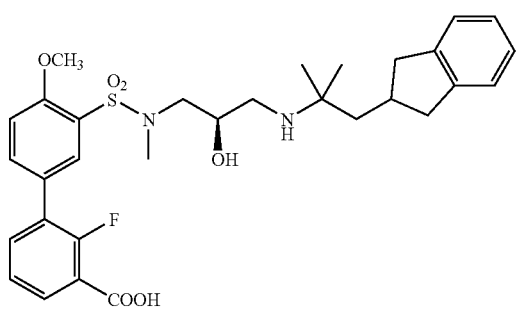
Exp. 3-202
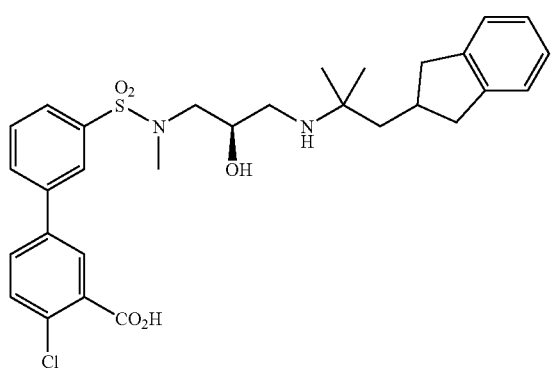
Exp. 3-203
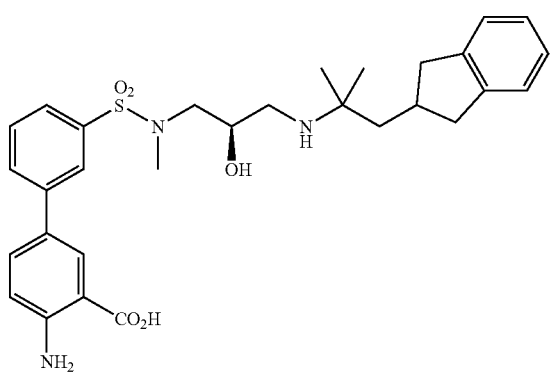

-continued
Exp. 3-204
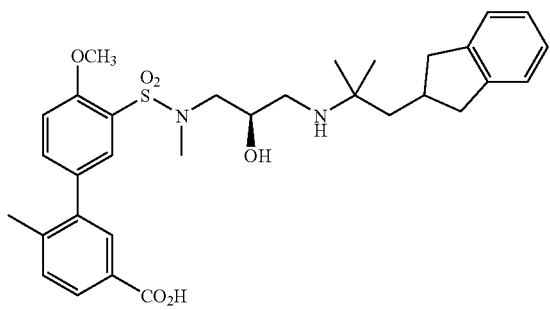
Exp. 3-205
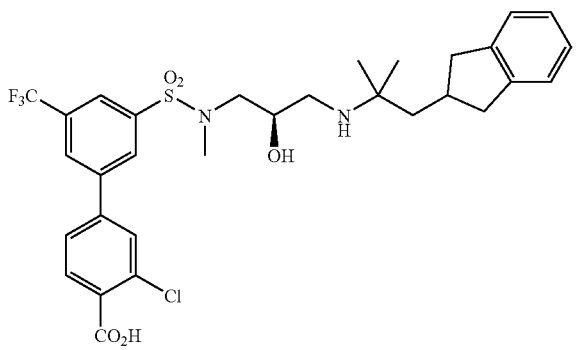
Exp. 3-206
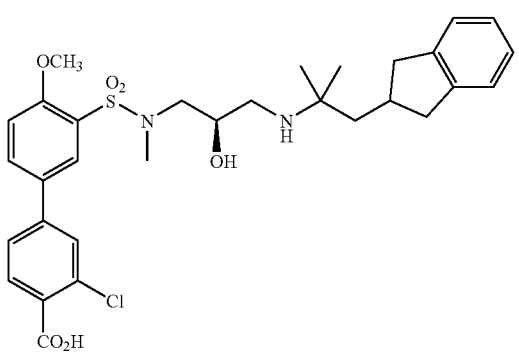
Exp. 3-207
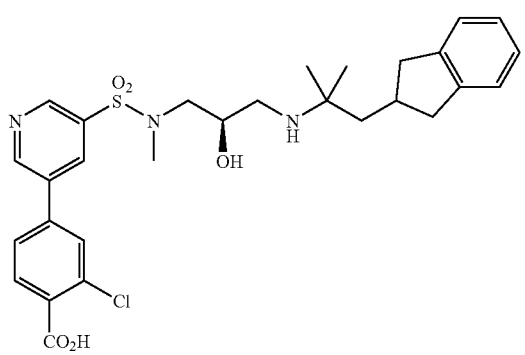
Exp. 3-208
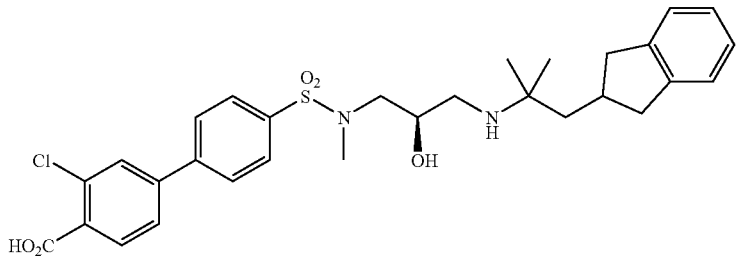
Exp. 3-209
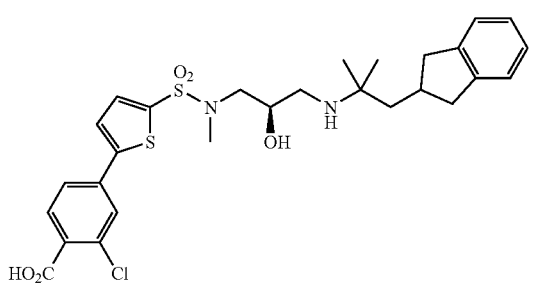
Exp. 3-210
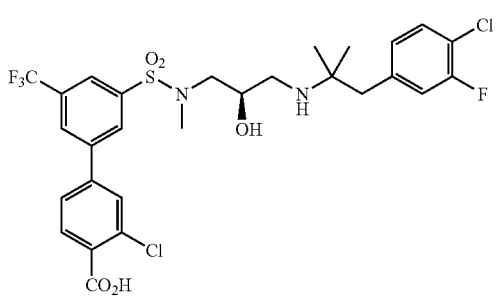
Exp. 3-210
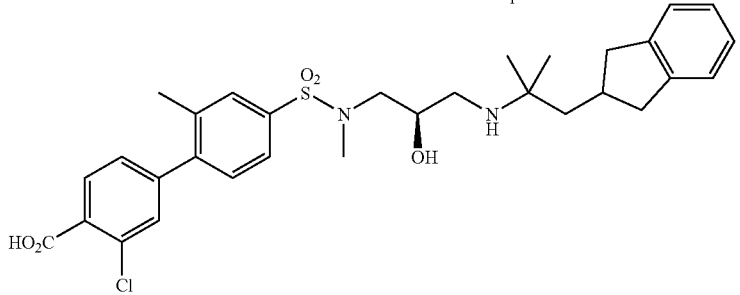
Exp. 3-211

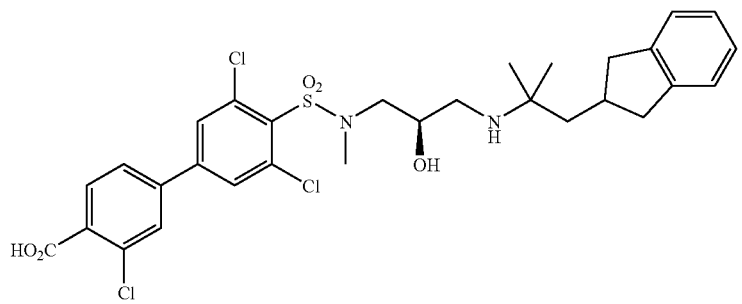
Exp. 3-212
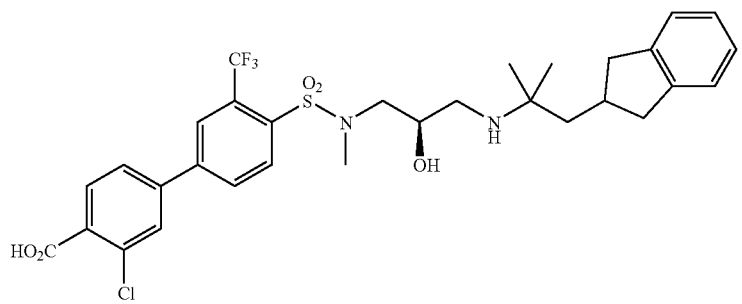
Exp. 3-213
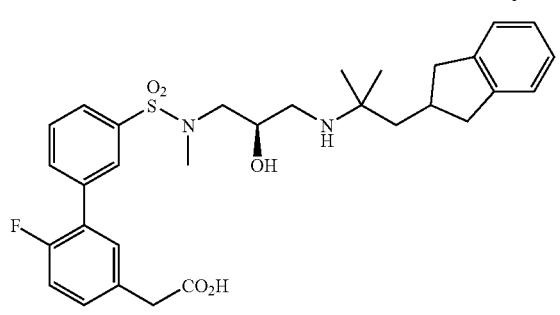
Exp. 3-214
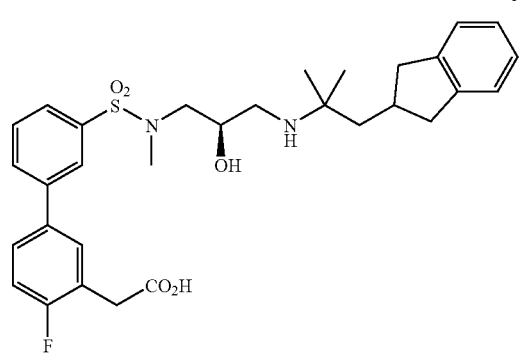
Exp. 3-215
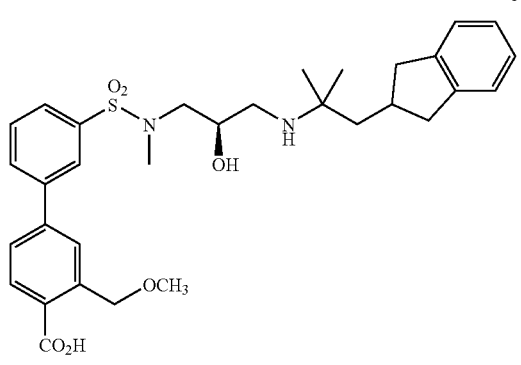
Exp. 3-216
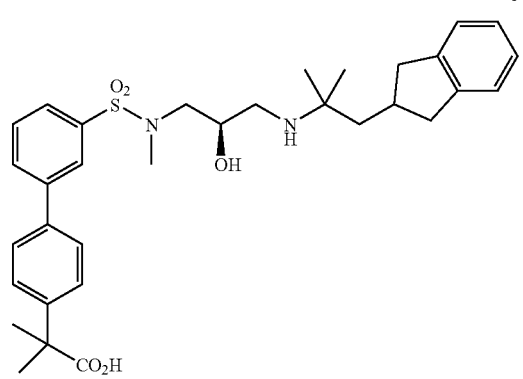
Exp. 3-217

-continued
Exp. 3-218
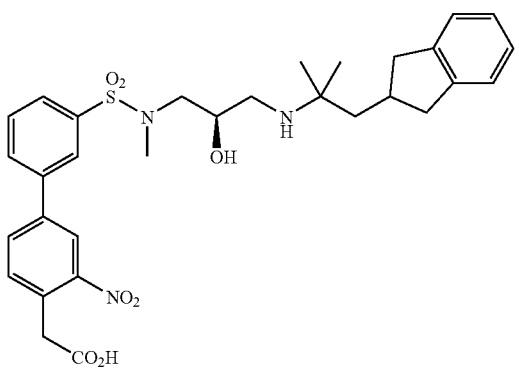
Exp. 3-219
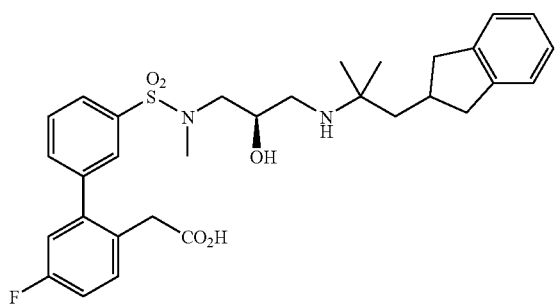
Exp. 3-220
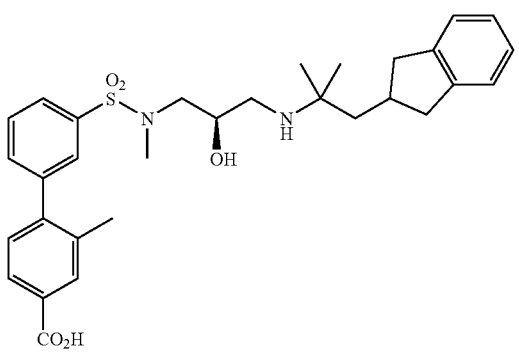
Exp. 3-221
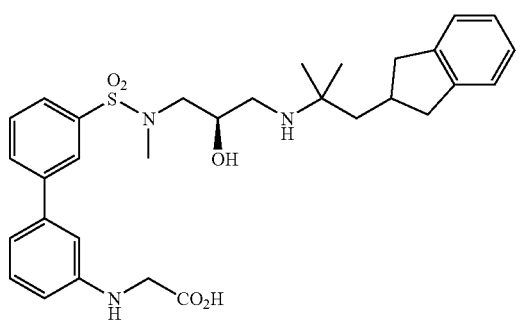
Exp. 3-222
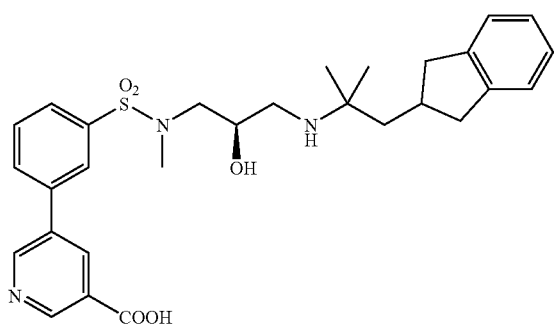
Exp. 3-223
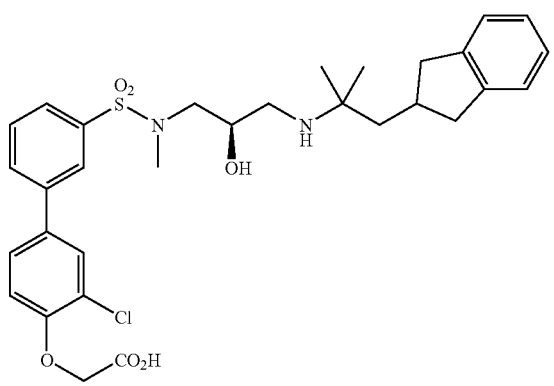
Exp. 3-224
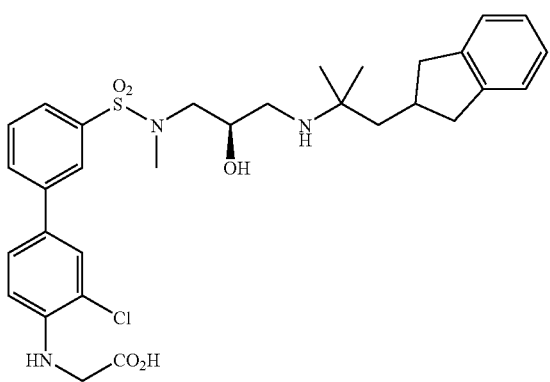
Exp. 3-225
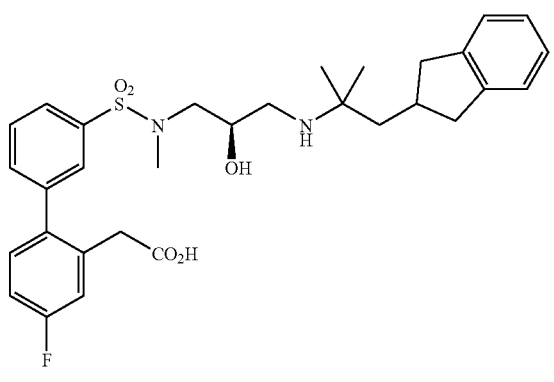

Exp. 3-226
Exp. 3-227
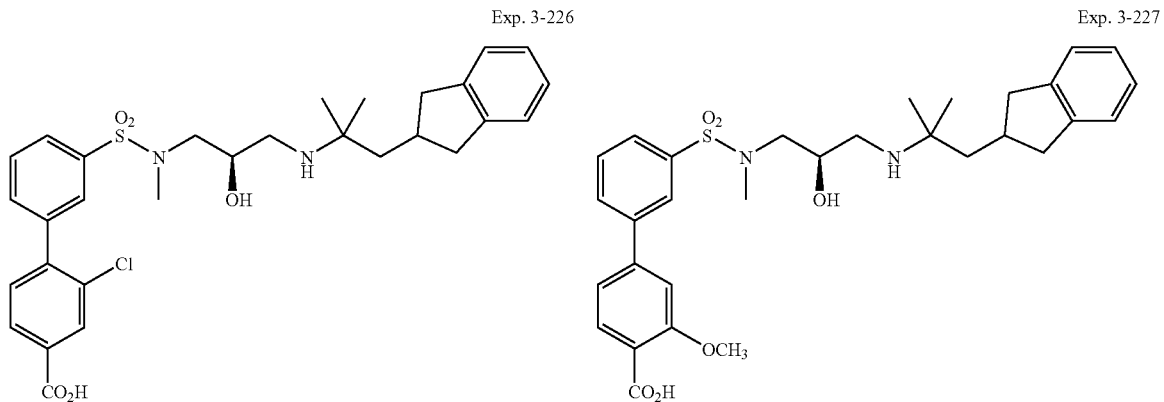
Exp. 3-228
Exp. 3-229
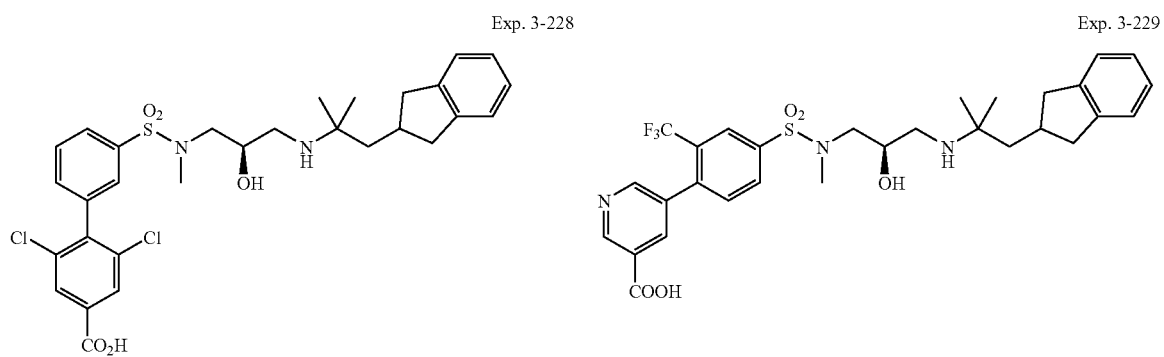
Exp. 3-230
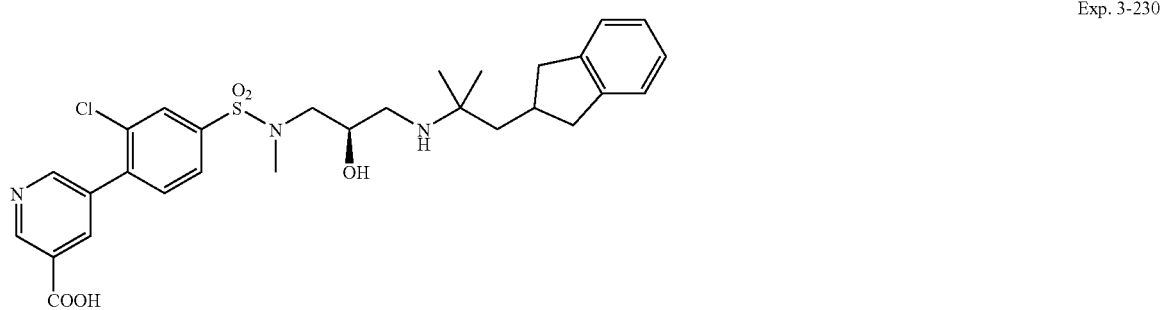
Exp. 3-231
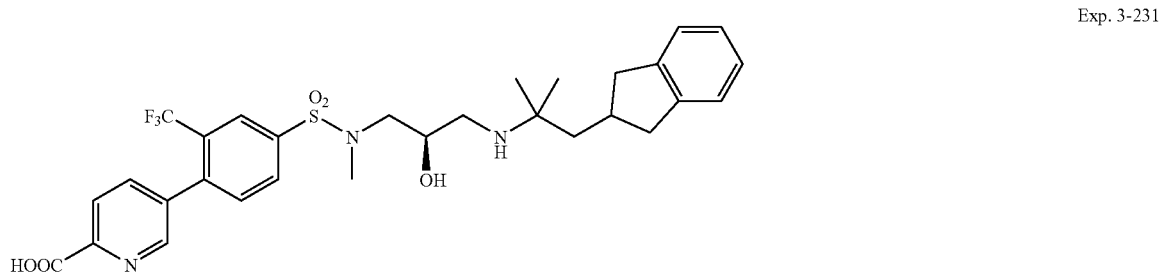

-continued

Exp. 3-232

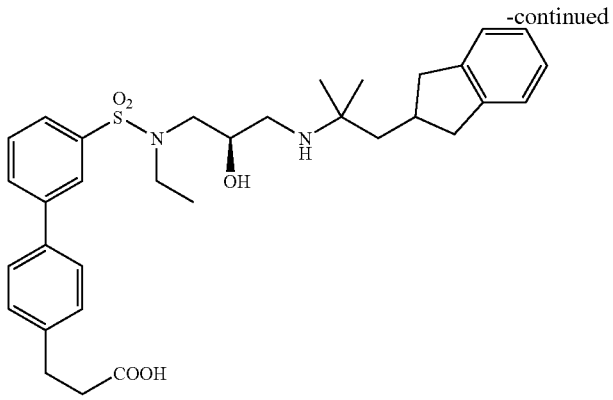

EXAMPLE 3-92

(R)-3'-(N-(3-(1-(2,3-dihydro-1H-inden-2-yl)-2-methylpropan-2-ylamino)-2-hydroxypropyl)-N-methylsulfamoyl)-2-methylbiphenyl-3-carboxylic acid

EXAMPLE 3-93

(R)-3-(3'-(N-(3-(1-(2,3-dihydro-1H-inden-2-yl)-2-methylpropan-2-ylamino)-2-hydroxypropyl)-N-methylsulfamoyl)-5'-(trifluoromethyl)biphenyl-4-yl)propionic acid

EXAMPLE 3-94

(R)-3-(3'-(N-(3-(1-(2,3-dihydro-1H-inden-2-yl)-2-methylpropan-2-ylamino)-2-hydroxypropyl)-N-methylsulfamoyl)-4'-methoxybiphenyl-4-yl)propionic acid

EXAMPLE 3-95

(R)-3-(3'-(N-(3-(1-(4-chloro-3-fluorophenyl)-2-methylpropan-2-ylamino)-2-hydroxypropyl)-N-methylsulfamoyl)-5'-(trifluoromethyl)biphenyl-4-yl)propionic acid

EXAMPLE 3-96

(R)-3-(4-(5-(N-(3-(1-(2,3-dihydro-1H-inden-2-yl)-2-methylpropan-2-ylamino)-2-hydroxypropyl)-N-methylsulfamoyl)thiophen-2-yl)phenyl)propionic acid

EXAMPLE 3-97

(R)-3-(3',5'-dichloro-4'-(N-(3-(1-(2,3-dihydro-1H-inden-2-yl)-2-methylpropan-2-ylamino)-2-hydroxypropyl)-N-methylsulfamoyl)biphenyl-4-yl)propionic acid

EXAMPLE 3-98

(R)-3-(4'-(N-(3-(1-(2,3-dihydro-1H-inden-2-yl)-2-methylpropan-2-ylamino)-2-hydroxypropyl)-N-methylsulfamoyl)-3'-(trifluoromethyl)biphenyl-4-yl)propionic acid

EXAMPLE 3-99

(R)-3-(4-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)phenyl)propionic acid

EXAMPLE 3-100

(R)-3-(4'-(N-(3-(1-(2,3-dihydro-1H-inden-2-yl)-2-methylpropan-2-ylamino)-2-hydroxypropyl)-N-methylsulfamoyl)-3'-(trifluoromethoxy)biphenyl-4-yl)propionic acid

EXAMPLE 3-101

(R)-3-(4'-(N-(3-(1-(2,3-dihydro-1H-inden-2-yl)-2-methylpropan-2-ylamino)-2-hydroxypropyl)-N-methylsulfamoyl)-3'-methylbiphenyl-4-yl)propionic acid

EXAMPLE 3-102

(R)-3-(4'-(N-(3-(1-(2,3-dihydro-1H-inden-2-yl)-2-methylpropan-2-ylamino)-2-hydroxypropyl)-N-methylsulfamoyl)-3'-ethylbiphenyl-4-yl)propionic acid

EXAMPLE 3-103

(R)-3-(4-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)propionic acid

EXAMPLE 3-104

(R)-3-(3'-chloro-4'-(N-(3-(1-(2,3-dihydro-1H-inden-2-yl)-2-methylpropan-2-ylamino)-2-hydroxypropyl)-N-methylsulfamoyl)biphenyl-4-yl)propionic acid

EXAMPLE 3-105

(R)-3-(4'-(N-(3-(1-(2,3-dihydro-1H-inden-2-yl)-2-methylpropan-2-ylamino)-2-hydroxypropyl)-N-methylsulfamoyl)-2'-(trifluoromethyl)biphenyl-4-yl)propionic acid

EXAMPLE 3-106

(R)-3-(2'-chloro-4'-(N-(3-(1-(2,3-dihydro-1H-inden-2-yl)-2-methylpropan-2-ylamino)-2-hydroxypropyl)-N-methylsulfamoyl)biphenyl-4-yl)propionic acid

EXAMPLE 3-107

(R)-3-(4'-(N-(3-(1-(2,3-dihydro-1H-inden-2-yl)-2-methylpropan-2-ylamino)-2-hydroxypropyl)-N-methylsulfamoyl)-2'-methylbiphenyl-4-yl)propionic acid

EXAMPLE 3-108

(R)-3-(4'-(N-(3-(1-(2,3-dihydro-1H-inden-2-yl)-2-methylpropan-2-ylamino)-2-hydroxypropyl)-N-methylsulfamoyl)-2',5'-difluorobiphenyl-4-yl)propionic acid

EXAMPLE 3-109

(R)-3-(4'-(N-(3-(1-(2,3-dihydro-1H-inden-2-yl)-2-methylpropan-2-ylamino)-2-hydroxypropyl)-N-methylsulfamoyl)-2'-fluorobiphenyl-4-yl)propionic acid

EXAMPLE 3-110

(R)-3-(3'-fluoro-4'-(N-(2-hydroxy-3-(2-methyl-5-phenylpentan-2-ylamino)propyl)-N-methylsulfamoyl)biphenyl-4-yl)propionic acid

EXAMPLE 3-111

(R)-3-(2'-(N-(2-hydroxy-3-(2-methyl-5-phenylpentan-2-ylamino)propyl)-N-methylsulfamoyl)-4'-(trifluoromethyl)biphenyl-4-yl)propionic acid

EXAMPLE 3-112

(R)-3-(3',5'-dichloro-2'-(N-(2-hydroxy-3-(2-methyl-5-phenylpentan-2-ylamino)propyl)-N-methylsulfamoyl)biphenyl-4-yl)propionic acid

EXAMPLE 3-113

(R)-3-(2'-(N-(2-hydroxy-3-(2-methyl-5-phenylpentan-2-ylamino)propyl)-N-methylsulfamoyl)-5'-(trifluoromethyl)biphenyl-4-yl)propionic acid

EXAMPLE 3-114

(R)-3-(2'-chloro-4'-(N-(2-hydroxy-3-(2-methyl-5-phenylpentan-2-ylamino)propyl)-N-methylsulfamoyl)biphenyl-4-yl)propionic acid

EXAMPLE 3-115

(R)-3-(4'-(N-(2-hydroxy-3-(2-methyl-5-phenylpentan-2-ylamino)propyl)-N-methylsulfamoyl)-2'-methylbiphenyl-4-yl)propionic acid

EXAMPLE 3-116

(R)-3-(3'-ethyl-4'-(N-(2-hydroxy-3-(2-methyl-5-phenylpentan-2-ylamino)propyl)-N-methylsulfamoyl)biphenyl-4-yl)propionic acid

EXAMPLE 3-117

(R)-3-(4'-(N-(3-(1-(2,3-dihydro-1H-inden-2-yl)-2-methylpropan-2-ylamino)-2-hydroxypropyl)-N-methylsulfamoyl)biphenyl-3-yl)acrylic acid

EXAMPLE 3-118

(R)-3'-(N-(3-(1-(2,3-dihydro-1H-inden-2-yl)-2-methylpropan-2-ylamino)-2-hydroxypropyl)-N-methylsulfamoyl)-5'-(trifluoromethyl)biphenyl-3-carboxylic acid

EXAMPLE 3-119

(R)-3'-(N-(3-(1-(2,3-dihydro-1H-inden-2-yl)-2-methylpropan-2-ylamino)-2-hydroxypropyl)-N-methylsulfamoyl)-4'-methoxybiphenyl-3-carboxylic acid

EXAMPLE 3-120

(R)-4'-(N-(3-(1-(2,3-dihydro-1H-inden-2-yl)-2-methylpropan-2-ylamino)-2-hydroxypropyl)-N-methylsulfamoyl)biphenyl-3-carboxylic acid

EXAMPLE 3-121

(R)-3-(5-(N-(3-(1-(2,3-dihydro-1H-inden-2-yl)-2-methylpropan-2-ylamino)-2-hydroxypropyl)-N-methylsulfamoyl)pyridin-3-yl)benzoic acid

EXAMPLE 3-122

(R)-3-(5-(N-(3-(1-(2,3-dihydro-1H-inden-2-yl)-2-methylpropan-2-ylamino)-2-hydroxypropyl)-N-methylsulfamoyl)thiophen-2-yl)benzoic acid

EXAMPLE 3-123

(R)-4'-(N-(3-(1-(2,3-dihydro-1H-inden-2-yl)-2-methylpropan-2-ylamino)-2-hydroxypropyl)-N-methylsulfamoyl)-2'-methylbiphenyl-3-carboxylic acid

EXAMPLE 3-124

(R)-4'-(N-(3-(1-(2,3-dihydro-1H-inden-2-yl)-2-methylpropan-2-ylamino)-2-hydroxypropyl)-N-methylsulfamoyl)-3'-(trifluoromethyl)biphenyl-3-carboxylic acid

EXAMPLE 3-125

(R)-3'-(N-(3-(1-(4-chloro-3-fluorophenyl)-2-methylpropan-2-ylamino)-2-hydroxypropyl)-N-methylsulfamoyl)-5'-(trifluoromethyl)biphenyl-3-carboxylic acid

EXAMPLE 3-126

(R)-3',5'-dichloro-4'-(N-(3-(1-(2,3-dihydro-1H-inden-2-yl)-2-methylpropan-2-ylamino)-2-hydroxypropyl)-N-methylsulfamoyl)biphenyl-3-carboxylic acid

EXAMPLE 3-127

(R)-3'-(N-(3-(1-(2,3-dihydro-1H-inden-2-yl)-2-methylpropan-2-ylamino)-2-hydroxypropyl)-N-methylsulfamoyl)-5-fluoro-4'-methoxybiphenyl-3-carboxylic acid

EXAMPLE 3-128

(R)-3'-(N-(3-(1-(2,3-dihydro-1H-inden-2-yl)-2-methylpropan-2-ylamino)-2-hydroxypropyl)-N-methylsulfamoyl)-5-fluoro-5'-(trifluoromethyl)biphenyl-3-carboxylic acid

EXAMPLE 3-129

(R)-3-(3'-(N-(3-(1-(2,3-dihydro-1H-inden-2-yl)-2-methylpropan-2-ylamino)-2-hydroxypropyl)-N-methylsulfamoyl)-3-fluorobiphenyl-4-yl)acrylic acid

EXAMPLE 3-130

(R)-5-(3-(N-(3-(1-(2,3-dihydro-1H-inden-2-yl)-2-methylpropan-2-ylamino)-2-hydroxypropyl)-N-methylsulfamoyl)phenyl)thiophen-2-carboxylic acid

EXAMPLE 3-131

(R)-2-(3'-(N-(3-(1-(2,3-dihydro-1H-inden-2-yl)-2-methylpropan-2-ylamino)-2-hydroxypropyl)-N-methylsulfamoyl)-4'-methoxybiphenyl-4-yl)acetic acid

EXAMPLE 3-132

(R)-2-(3-(5-(N-(3-(1-(2,3-dihydro-1H-inden-2-yl)-2-methylpropan-2-ylamino)-2-hydroxypropyl)-N-methylsulfamoyl)thiophen-2-yl)phenyl)acetic acid

EXAMPLE 3-133

(R)-2-(3'-(N-(3-(1-(2,3-dihydro-1H-inden-2-yl)-2-methylpropan-2-ylamino)-2-hydroxypropyl)-N-methylsulfamoyl)-5'-(trifluoromethyl)biphenyl-4-yl)acetic acid

EXAMPLE 3-134

(R)-2-(4'-(N-(3-(1-(2,3-dihydro-1H-inden-2-yl)-2-methylpropan-2-ylamino)-2-hydroxypropyl)-N-methylsulfamoyl)biphenyl-4-yl)acetic acid

EXAMPLE 3-135

(R)-2-(4'-(N-(3-(1-(2,3-dihydro-1H-inden-2-yl)-2-methylpropan-2-ylamino)-2-hydroxypropyl)-N-methylsulfamoyl)-2'-methylbiphenyl-4-yl)acetic acid

EXAMPLE 3-136

(R)-2-(3'-(N-(3-(1-(4-chloro-3-fluorophenyl)-2-methylpropan-2-ylamino)-2-hydroxypropyl)-N-methylsulfamoyl)-5'-(trifluoromethyl)biphenyl-4-yl)acetic acid

EXAMPLE 3-137

(R)-2-(4'-(N-(3-(1-(2,3-dihydro-1H-inden-2-yl)-2-methylpropan-2-ylamino)-2-hydroxypropyl)-N-methylsulfamoyl)-3'-(trifluoromethyl)biphenyl-4-yl)acetic acid

EXAMPLE 3-138

(R)-2-(4-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)acetic acid

EXAMPLE 3-139

(R)-2-(4-(5-(N-(3-(1-(2,3-dihydro-1H-inden-2-yl)-2-methylpropan-2-ylamino)-2-hydroxypropyl)-N-methylsulfamoyl)thiophen-2-yl)phenyl)acetic acid

EXAMPLE 3-140

(R)-2-(3',5'-dichloro-4'-(N-(3-(1-(2,3-dihydro-1H-inden-2-yl)-2-methylpropan-2-ylamino)-2-hydroxypropyl)-N-methylsulfamoyl)biphenyl-4-yl)acetic acid

EXAMPLE 3-141

(R)-2-(4'-(N-(3-(1-(2,3-dihydro-1H-inden-2-yl)-2-methylpropan-2-ylamino)-2-hydroxypropyl)-N-methylsulfamoyl)-2'-(trifluoromethyl)biphenyl-4-yl)acetic acid

EXAMPLE 3-142

(R)-2-(2'-chloro-4'-(N-(3-(1-(2,3-dihydro-1H-inden-2-yl)-2-methylpropan-2-ylamino)-2-hydroxypropyl)-N-methylsulfamoyl)biphenyl-4-yl)acetic acid

EXAMPLE 3-143

(R)-2-(4-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)phenyl)acetic acid

EXAMPLE 3-144

(R)-2-(4'-(N-(3-(1-(2,3-dihydro-1H-inden-2-yl)-2-methylpropan-2-ylamino)-2-hydroxypropyl)-N-methylsulfamoyl)-3'-(trifluoromethoxy)biphenyl-4-yl)acetic acid

EXAMPLE 3-145

(R)-2-(4'-(N-(3-(1-(2,3-dihydro-1H-inden-2-yl)-2-methylpropan-2-ylamino)-2-hydroxypropyl)-N-methylsulfamoyl)-3'-methylbiphenyl-4-yl)acetic acid

EXAMPLE 3-146

(R)-2-(3'-chloro-4'-(N-(3-(1-(2,3-dihydro-1H-inden-2-yl)-2-methylpropan-2-ylamino)-2-hydroxypropyl)-N-methylsulfamoyl)biphenyl-4-yl)acetic acid

EXAMPLE 3-147

(R)-2-(4'-(N-(3-(1-(2,3-dihydro-1H-inden-2-yl)-2-methylpropan-2-ylamino)-2-hydroxypropyl)-N-methylsulfamoyl)-3'-ethylbiphenyl-4-yl)acetic acid

EXAMPLE 3-148

(R)-2-(4'-(N-(3-(1-(2,3-dihydro-1H-inden-2-yl)-2-methylpropan-2-ylamino)-2-hydroxypropyl)-N-methylsulfamoyl)-2'-fluorobiphenyl-4-yl)acetic acid

EXAMPLE 3-149

(R)-2-(4'-(N-(3-(1-(2,3-dihydro-1H-inden-2-yl)-2-methylpropan-2-ylamino)-2-hydroxypropyl)-N-methylsulfamoyl)-2',5'-difluorobiphenyl-4-yl)acetic acid

EXAMPLE 3-150

(R)-3'-(N-(3-(1-(2,3-dihydro-1H-inden-2-yl)-2-methylpropan-2-ylamino)-2-hydroxypropyl)-N-methylsulfamoyl)-5'-(trifluoromethyl)biphenyl-4-carboxylic acid

EXAMPLE 3-151

(R)-3'-(N-(3-(1-(2,3-dihydro-1H-inden-2-yl)-2-methylpropan-2-ylamino)-2-hydroxypropyl)-N-methylsulfamoyl)-4'-methoxybiphenyl-4-carboxylic acid

EXAMPLE 3-152

(R)-4'-(N-(3-(1-(2,3-dihydro-1H-inden-2-yl)-2-methylpropan-2-ylamino)-2-hydroxypropyl)-N-methylsulfamoyl)biphenyl-4-carboxylic acid

EXAMPLE 3-153

(R)-2-(3'-(N-(3-(1-(2,3-dihydro-1H-inden-2-yl)-2-methylpropan-2-ylamino)-2-hydroxypropyl)-N-methylsulfamoyl)-4'-methoxybiphenyl-3-yl)acetic acid

EXAMPLE 3-154

(R)-2-(3'-(N-(3-(1-(2,3-dihydro-1H-inden-2-yl)-2-methylpropan-2-ylamino)-2-hydroxypropyl)-N-methylsulfamoyl)-5'-(trifluoromethyl)biphenyl-3-yl)acetic acid

EXAMPLE 3-155

(R)-2-(3-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)acetic acid

EXAMPLE 3-156

(R)-2-(4'-(N-(3-(1-(2,3-dihydro-1H-inden-2-yl)-2-methylpropan-2-ylamino)-2-hydroxypropyl)-N-methylsulfamoyl)biphenyl-3-yl)acetic acid

EXAMPLE 3-157

(R)-3-(3'-(N-(3-(1-(2,3-dihydro-1H-inden-2-yl)-2-methylpropan-2-ylamino)-2-hydroxypropyl)-N-methylsulfamoyl)-4-methoxy-5'-(trifluoromethyl)biphenyl-3-yl)acrylic acid

EXAMPLE 3-158

(R)-3-(3'-(N-(3-(1-(2,3-dihydro-1H-inden-2-yl)-2-methylpropan-2-ylamino)-2-hydroxypropyl)-N-methylsulfamoyl)-4,4'-dimethoxybiphenyl-3-yl)acrylic acid

EXAMPLE 3-159

(R)-3-(3'-(N-(3-(1-(2,3-dihydro-1H-inden-2-yl)-2-methylpropan-2-ylamino)-2-hydroxypropyl)-N-methylsulfamoyl)-4-fluoro-5'-(trifluoromethyl)biphenyl-2-yl)acrylic acid

EXAMPLE 3-160

(R)-3-(3'-(N-(3-(1-(2,3-dihydro-1H-inden-2-yl)-2-methylpropan-2-ylamino)-2-hydroxypropyl)-N-methylsulfamoyl)-4-fluoro-4'-methoxybiphenyl-3-yl)acrylic acid

EXAMPLE 3-161

(R)-3-(4'-(N-(3-(1-(2,3-dihydro-1H-inden-2-yl)-2-methylpropan-2-ylamino)-2-hydroxypropyl)-N-methylsulfamoyl)-4-fluorobiphenyl-3-yl)acrylic acid

EXAMPLE 3-162

(R)-3-(3'-(N-(3-(1-(2,3-dihydro-1H-inden-2-yl)-2-methylpropan-2-ylamino)-2-hydroxypropyl)-N-methylsulfamoyl)-2-methyl-5'-(trifluoromethyl)biphenyl-4-yl)acrylic acid

EXAMPLE 3-163

(R)-3-(3'-(N-(3-(1-(2,3-dihydro-1H-inden-2-yl)-2-methylpropan-2-ylamino)-2-hydroxypropyl)-N-methylsulfamoyl)-5'-(trifluoromethyl)biphenyl-3-yl)propionic acid

EXAMPLE 3-164

(R)-3-(3'-(N-(3-(1-(2,3-dihydro-1H-inden-2-yl)-2-methylpropan-2-ylamino)-2-hydroxypropyl)-N-methylsulfamoyl)-4'-methoxybiphenyl-3-yl)propionic acid

EXAMPLE 3-165

(R)-3-(4'-(N-(3-(1-(2,3-dihydro-1H-inden-2-yl)-2-methylpropan-2-ylamino)-2-hydroxypropyl)-N-methylsulfamoyl)biphenyl-3-yl)propionic acid

EXAMPLE 3-166

(R)-3-(4'-(N-(3-(1-(2,3-dihydro-1H-inden-2-yl)-2-methylpropan-2-ylamino)-2-hydroxypropyl)-N-methylsulfamoyl)-3'-(trifluoromethyl)biphenyl-3-yl)propionic acid

EXAMPLE 3-167

(R)-3-(3'-(N-(3-(1-(4-chloro-3-fluorophenyl)-2-methylpropan-2-ylamino)-2-hydroxypropyl)-N-methylsulfamoyl)-5'-(trifluoromethyl)biphenyl-3-yl)propionic acid

EXAMPLE 3-168

(R)-3-(3-(5-(N-(3-(1-(2,3-dihydro-1H-inden-2-yl)-2-methylpropan-2-ylamino)-2-hydroxypropyl)-N-methylsulfamoyl)thiophen-2-yl)phenyl)propionic acid

EXAMPLE 3-169

(R)-3-(3',5'-dichloro-4'-(N-(3-(1-(2,3-dihydro-1H-inden-2-yl)-2-methylpropan-2-ylamino)-2-hydroxypropyl)-N-methylsulfamoyl)biphenyl-3-yl)propionic acid

EXAMPLE 3-170

(R)-3-(3-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)phenyl)propionic acid

EXAMPLE 3-171

(R)-3-(4'-(N-(3-(1-(2,3-dihydro-1H-inden-2-yl)-2-methylpropan-2-ylamino)-2-hydroxypropyl)-N-methylsulfamoyl)-3'-(trifluoromethoxy)biphenyl-3-yl)propionic acid

EXAMPLE 3-172

(R)-3-(4'-(N-(3-(1-(2,3-dihydro-1H-inden-2-yl)-2-methylpropan-2-ylamino)-2-hydroxypropyl)-N-methylsulfamoyl)-3'-methylbiphenyl-3-yl)propionic acid

EXAMPLE 3-173

(R)-3-(3'-chloro-4'-(N-(3-(1-(2,3-dihydro-1H-inden-2-yl)-2-methylpropan-2-ylamino) 2-hydroxypropyl)-N-methylsulfamoyl)biphenyl-3-yl)propionic acid

EXAMPLE 3-174

(R)-3-(4'-(N-(3-(1-(2,3-dihydro-1H-inden-2-yl)-2-methylpropan-2-ylamino)-2-hydroxypropyl)-N-methylsulfamoyl)-2'-(trifluoromethyl)biphenyl-3-yl)propionic acid

EXAMPLE 3-175

(R)-3-(4'-(N-(3-(1-(2,3-dihydro-1H-inden-2-yl)-2-methylpropan-2-ylamino)-2-hydroxypropyl)-N-methylsulfamoyl)-3'-ethylbiphenyl-3-yl)propionic acid

EXAMPLE 3-116

(R)-3-(2'-chloro-4'-(N-(3-(1-(2,3-dihydro-1H-inden-2-yl)-2-methylpropan-2-ylamino)-2-hydroxypropyl)-N-methylsulfamoyl)biphenyl-3-yl)propionic acid

EXAMPLE 3-177

(R)-3-(3-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)propionic acid

EXAMPLE 3-178

(R)-3-(4'-(N-(3-(1-(2,3-dihydro-1H-inden-2-yl)-2-methylpropan-2-ylamino)-2-hydroxypropyl)-N-methylsulfamoyl) 2'-methylbiphenyl-3-yl)propionic acid

EXAMPLE 3-179

(R)-3-(4'-(N-(3-(1-(2,3-dihydro-1H-inden-2-yl)-2-methylpropan-2-ylamino)-2-hydroxypropyl)-N-methylsulfamoyl)-2'-fluorobiphenyl-3-yl)propionic acid

EXAMPLE 3-180

(R)-3-(4'-(N-(3-(1-(2,3-dihydro-1H-inden-2-yl)-2-methylpropan-2-ylamino)-2-hydroxypropyl)-N-methylsulfamoyl)-2',5'-difluorobiphenyl-3-yl)propionic acid

EXAMPLE 3-181

(R)-3-(3'-fluoro-4'-(N-(2-hydroxy-3-(2-methyl-5-phenylpentan-2-ylamino)propyl)-N-methylsulfamoyl)biphenyl-3-yl)propionic acid

EXAMPLE 3-182

(R)-3-(2'-(N-(2-hydroxy-3-(2-methyl-5-phenylpentan-2-ylamino)propyl)-N-methylsulfamoyl)-4'-(trifluoromethyl)biphenyl-3-yl)propionic acid

EXAMPLE 3-183

(R)-3-(2'-(N-(2-hydroxy-3-(2-methyl-5-phenylpentan-2-ylamino)propyl)-N-methylsulfamoyl)-5'-(trifluoromethyl)biphenyl-3-yl)propionic acid

EXAMPLE 3-184

(R)-3-(3',5'-dichloro-2'-(N-(2-hydroxy-3-(2-methyl-5-phenylpentan-2-ylamino)propyl)-N-methylsulfamoyl)biphenyl-3-yl)propionic acid

EXAMPLE 3-185

(R)-3-(2'-chloro-4'-(N-(2-hydroxy-3-(2-methyl-5-phenylpentan-2-ylamino)propyl)-N-methylsulfamoyl)biphenyl-3-yl)propionic acid

EXAMPLE 3-186

(R)-3-(4'-(N-(2-hydroxy-3-(2-methyl-5-phenylpentan-2-ylamino)propyl)-N-methylsulfamoyl)-2'-methylbiphenyl-3-yl)propionic acid

EXAMPLE 3-187

(R)-3-(3'-ethyl-4'-(N-(2-hydroxy-3-(2-methyl-5-phenylpentan-2-ylamino)propyl)-N-methylsulfamoyl)biphenyl-3-yl)propionic acid

EXAMPLE 3-188

(R)-3-(3'-fluoro-4'-(N-(2-hydroxy-3-(2-methyl-5-phenylpentan-2-ylamino)propyl)-N-methylsulfamoyl)biphenyl-2-yl)propionic acid

EXAMPLE 3-189

(R)-3-(4'-(N-(3-(1-(2,3-dihydro-1H-inden-2-yl)-2-methylpropan-2-ylamino)-2-hydroxypropyl)-N-methylsulfamoyl)-2',5'-difluorobiphenyl-2-yl)propionic acid

EXAMPLE 3-190

(R)-3-(2'-chloro-4'-(N-(2-hydroxy-3-(2-methyl-5-phenylpentan-2-ylamino)propyl)-N-methylsulfamoyl)biphenyl-2-yl)propionic acid

EXAMPLE 3-191

(R)-3-(4'-(N-(2-hydroxy-3-(2-methyl-5-phenylpentan-2-ylamino)propyl)-N-methylsulfamoyl)-2'-methylbiphenyl-2-yl)propionic acid

EXAMPLE 3-192

(R)-3-(3'-ethyl-4'-(N-(2-hydroxy-3-(2-methyl-5-phenylpentan-2-ylamino)propyl)-N-methylsulfamoyl)biphenyl-2-yl)propionic acid

EXAMPLE 3-193

(R)-3'-(N-(3-(1-(2,3-dihydro-1H-inden-2-yl)-2-methylpropan-2-ylamino)-2-hydroxypropyl)-N-methylsulfamoyl)-4-fluoro-5'-(trifluoromethyl)biphenyl-3-carboxylic acid

EXAMPLE 3-194

(R)-3'-(N-(3-(1-(2,3-dihydro-1H-inden-2-yl)-2-methylpropan-2-ylamino)-2-hydroxypropyl)-N-methylsulfamoyl)-4-fluoro-4'-methoxybiphenyl-3-carboxylic acid

EXAMPLE 3-195

(R)-4'-(N-(3-(1-(2,3-dihydro-1H-inden-2-yl)-2-methylpropan-2-ylamino)-2-hydroxypropyl)-N-methylsulfamoyl)-4-fluorobiphenyl-3-carboxylic acid

EXAMPLE 3-196

(R)-3-(3'-(N-(3-(1-(2,3-dihydro-1H-inden-2-yl)-2-methylpropan-2-ylamino)-2-hydroxypropyl)-N-ethylsulfamoyl)biphenyl-3-yl)propionic acid

EXAMPLE 3-197

(R)-3'-(N-(3-(1-(2,3-dihydro-1H-inden-2-yl)-2-methylpropan-2-ylamino)-2-hydroxypropyl)-N-methylsulfamoyl)-3-methyl-5'-(trifluoromethyl)biphenyl-4-carboxylic acid

EXAMPLE 3-198

(R)-3'-(N-(3-(1-(2,3-dihydro-1H-inden-2-yl)-2-methylpropan-2-ylamino)-2-hydroxypropyl)-N-methylsulfamoyl)-4'-methoxy-3-methylbiphenyl-4-carboxylic acid

EXAMPLE 3-199

(R)-2-(3'-(N-(3-(1-(2,3-dihydro-1H-inden-2-yl)-2-methylpropan-2-ylamino)-2-hydroxypropyl)-N-ethylsulfamoyl)biphenyl-4-yl)acetic acid

EXAMPLE 3-200

(R)-3'-(N-(3-(1-(2,3-dihydro-1H-inden-2-yl)-2-methylpropan-2-ylamino)-2-hydroxypropyl)-N-methylsulfamoyl)-6-fluoro-4'-methoxybiphenyl-3-carboxylic acid

EXAMPLE 3-201

(R)-3'-(N-(3-(1-(2,3-dihydro-1H-inden-2-yl)-2-methylpropan-2-ylamino)-2-hydroxypropyl)-N-methylsulfamoyl)-2-fluorobiphenyl-3-carboxylic acid

EXAMPLE 3-202

(R)-4-chloro-3'-(N-(3-(1-(2,3-dihydro-1H-inden-2-yl)-2-methylpropan-2-ylamino) 2-hydroxypropyl)-N-methylsulfamoyl)biphenyl-3-carboxylic acid

EXAMPLE 3-203

(R)-4-amino-3'-(N-(3-(1-(2,3-dihydro-1H-inden-2-yl)-2-methylpropan-2-ylamino)-2-hydroxypropyl)-N-methylsulfamoyl)biphenyl-3-carboxylic acid

EXAMPLE 3-204

(R)-3'-(N-(3-(1-(2,3-dihydro-1H-inden-2-yl)-2-methylpropan-2-ylamino)-2-hydroxypropyl)-N-methylsulfamoyl)-6-methylbiphenyl-3-carboxylic acid

EXAMPLE 3-205

(R)-3-chloro-3'-(N-(3-(1-(2,3-dihydro-1H-inden-2-yl)-2-methylpropan-2-ylamino)-2-hydroxypropyl)-N-methylsulfamoyl)-5'-(trifluoromethyl)biphenyl-4-carboxylic acid

EXAMPLE 3-206

(R)-3-chloro-3'-(N-(3-(1-(2,3-dihydro-1H-inden-2-yl)-2-methylpropan-2-ylamino)-2-hydroxypropyl)-N-methylsulfamoyl)-4'-methoxybiphenyl-4-carboxylic acid

EXAMPLE 3-207

(R)-2-chloro-4-(5-(N-(3-(1-(2,3-dihydro-1H-inden-2-yl)-2-methylpropan-2-ylamino)-2-hydroxypropyl)-N-methylsulfamoyl)pyridin-3-yl)benzoic acid

EXAMPLE 3-208

(R)-3-chloro-4'-(N-(3-(1-(2,3-dihydro-1H-inden-2-yl)-2-methylpropan-2-ylamino)-2-hydroxypropyl)-N-methylsulfamoyl)biphenyl-4-carboxylic acid

EXAMPLE 3-209

(R)-2-chloro-4-(5-(N-(3-(1-(2,3-dihydro-1H-inden-2-yl)-2-methylpropan-2-ylamino)-2-hydroxypropyl)-N-methylsulfamoyl)thiophen-2-yl)benzoic acid

EXAMPLE 3-210

(R)-3-chloro-3'-(N-(3-(1-(4-chloro-3-fluorophenyl)-2-methylpropan-2-ylamino)-2-hydroxypropyl)-N-methylsulfamoyl)-5'-(trifluoromethyl)biphenyl-4-carboxylic acid

EXAMPLE 3-211

(R)-3-chloro-4'-(N-(3-(1-(2,3-dihydro-1H-inden-2-yl)-2-methylpropan-2-ylamino)-2-hydroxypropyl)-N-methylsulfamoyl)-2'-methylbiphenyl-4-carboxylic acid

EXAMPLE 3-212

(R)-3,3',5'-trichloro-4'-(N-(3-(1-(2,3-dihydro-1H-inden-2-yl)-2-methylpropan-2-ylamino)-2-hydroxypropyl)-N-methylsulfamoyl)biphenyl-4-carboxylic acid

EXAMPLE 3-213

(R)-3-chloro-4'-(N-(3-(1-(2,3-dihydro-1H-inden-2-yl)-2-methylpropan-2-ylamino)-2-hydroxypropyl)-N-methylsulfamoyl)-3'-(trifluoromethyl)biphenyl-4-carboxylic acid

EXAMPLE 3-214

(R)-2-(3'-(N-(3-(1-(2,3-dihydro-1H-inden-2-yl)-2-methylpropan-2-ylamino)-2-hydroxypropyl)-N-methylsulfamoyl)-6-fluorobiphenyl-3-yl)acetic acid

EXAMPLE 3-215

(R)-2-(3'-(N-(3-(1-(2,3-dihydro-1H-inden-2-yl)-2-methylpropan-2-ylamino)-2-hydroxypropyl)-N-methylsulfamoyl)-4-fluorobiphenyl-3-yl)acetic acid

EXAMPLE 3-216

(R)-3'-(N-(3-(1-(2,3-dihydro-1H-inden-2-yl)-2-methylpropan-2-ylamino)-2-hydroxypropyl)-N-methylsulfamoyl)-3-(methoxymethyl)biphenyl-4-carboxylic acid

EXAMPLE 3-217

(R)-2-(3'-(N-(3-(1-(2,3-dihydro-1H-inden-2-yl)-2-methylpropan-2-ylamino)-2-hydroxypropyl)-N-methylsulfamoyl)biphenyl-4-yl)-2-methylpropionic acid

EXAMPLE 3-218

(R)-2-(3'-(N-(3-(1-(2,3-dihydro-1H-inden-2-yl)-2-methyl-propan-2-ylamino)-2-hydroxypropyl)-N-methylsulfamoyl)-3-nitrobiphenyl-4-yl)acetic acid

EXAMPLE 3-219

(R)-2-(3'-(N-(3-(1-(2,3-dihydro-1H-inden-2-yl)-2-methyl-propan-2-ylamino)-2-hydroxypropyl)-N-methylsulfamoyl)-5-fluorobiphenyl-2-yl)acetic acid

EXAMPLE 3-220

(R)-3'-(N-(3-(1-(2,3-dihydro-1H-inden-2-yl)-2-methylpropan-2-ylamino)-2-hydroxypropyl)-N-methylsulfamoyl)-2-methylbiphenyl-4-carboxylic acid

EXAMPLE 3-221

(R)-2-(3'-(N-(3-(1-(2,3-dihydro-1H-inden-2-yl)-2-methyl-propan-2-ylamino)-2-hydroxypropyl)-N-methylsulfamoyl)biphenyl-3-ylamino)acetic acid

EXAMPLE 3-222

(R)-5-(3-(N-(3-(1-(2,3-dihydro-1H-inden-2-yl)-2-methyl-propan-2-ylamino)-2-hydroxypropyl)-N-methylsulfamoyl)phenyl)nicotinic acid

EXAMPLE 3-223

(R)-2-(3-chloro-3'-(N-(3-(1-(2,3-dihydro-1H-inden-2-yl)-2-methylpropan-2-ylamino)-2-hydroxypropyl)-N-methylsulfamoyl)biphenyl-4-yloxy)acetic acid

EXAMPLE 3-224

(R)-2-(3-chloro-3'-(N-(3-(1-(2,3-dihydro-1H-inden-2-yl)-2-methylpropan-2-ylamino)-2-hydroxypropyl)-N-methylsulfamoyl)biphenyl-4-ylamino)acetic acid

EXAMPLE 3-225

(R)-2-(3'-(N-(3-(1-(2,3-dihydro-1H-inden-2-yl)-2-methyl-propan-2-ylamino)-2-hydroxypropyl)-N-methylsulfamoyl)-4-fluorobiphenyl-2-yl)acetic acid

EXAMPLE 3-226

(R)-2-chloro-3'-(N-(3-(1-(2,3-dihydro-1H-inden-2-yl)-2-methylpropan-2-ylamino)-2-hydroxypropyl)-N-methylsulfamoyl)biphenyl-4-carboxylic acid

EXAMPLE 3-227

(R)-3'-(N-(3-(1-(2,3-dihydro-1H-inden-2-yl)-2-methylpropan-2-ylamino)-2-hydroxypropyl)-N-methylsulfamoyl)-3-methoxybiphenyl-4-carboxylic acid

EXAMPLE 3-228

(R)-2,6-dichloro-3'-(N-(3-(1-(2,3-dihydro-1H-inden-2-yl)-2-methylpropan-2-ylamino)-2-hydroxypropyl)-N-methylsulfamoyl)biphenyl-4-carboxylic acid

EXAMPLE 3-229

(R)-5-(4-(N-(3-(1-(2,3-dihydro-1H-inden-2-yl)-2-methyl-propan-2-ylamino)-2-hydroxypropyl)-N-methylsulfamoyl)-2-(trifluoromethyl)phenyl)nicotinic acid

EXAMPLE 3-230

(R)-5-(2-chloro-4-(N-(3-(1-(2,3-dihydro-1H-inden-2-yl)-2-methylpropan-2-ylamino)-2-hydroxypropyl)-N-methyl-sulfamoyl)phenyl)nicotinic acid

EXAMPLE 3-231

(R)-5-(4-(N-(3-(1-(2,3-dihydro-1H-inden-2-yl)-2-methyl-propan-2-ylamino)-2-hydroxypropyl)-N-methylsulfamoyl)-2-(trifluoromethyl)phenyl)picolinic acid

EXAMPLE 3-232

(R)-3-(3'-(N-(3-(1-(2,3-dihydro-1H-inden-2-yl)-2-methyl-propan-2-ylamino)-2-hydroxypropyl)-N-ethylsulfamoyl)biphenyl-4-yl)propionic acid

EXAMPLES 4-1 TO 10

By using SM2 instead of Exp. 2-1 and using BA instead of ba13, the reaction was carried out in combination described in the Table 5 according to Step A of Example 3-1 to obtain crude products, which were then purified by the above described purification method to obtain the target compounds.

TABLE 5

| Exp. | SM2 | BA | LCMS method | RTime | Mass |
|---|---|---|---|---|---|
| 4-1 | Exp. 2-2 | ba1 | A | 3.6 | 575 |
| 4-2 | Exp. 2-2 | ba5 | A | 3.74 | 575 |
| 4-3 | Exp. 2-2 | ba20 | B | 2.14 | 593 |
| 4-4 | Exp. 2-2 | ba27 | B | 1.31 | 646 |
| 4-5 | Exp. 2-2 | ba28 | B | 1.43 | 604 |
| 4-6 | Exp. 2-5 | ba2 | B | 1.61 | 565 |
| 4-7 | Exp. 2-5 | ba12 | B | 1.65 | 593 |
| 4-8 | Exp. 2-5 | ba20 | B | 2.14 | 583 |
| 4-9 | Exp. 2-5 | ba28 | B | 1.27 | 594 |
| 4-10 | Exp. 2-5 | ba29 | B | 1.54 | 579 |

Further, structure of the compounds of Example 4-1 to Example 4-10 (Exp. 4-1 to Exp. 4-10) are shown below.

Exp. 4-1

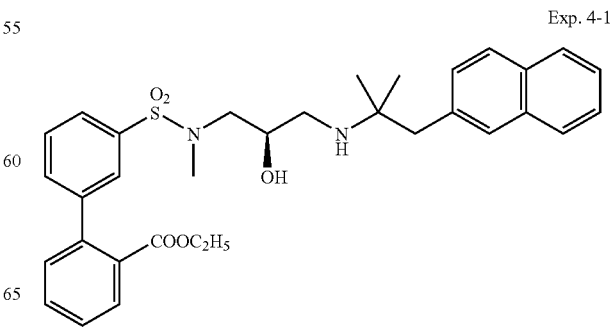

Exp. 4-2
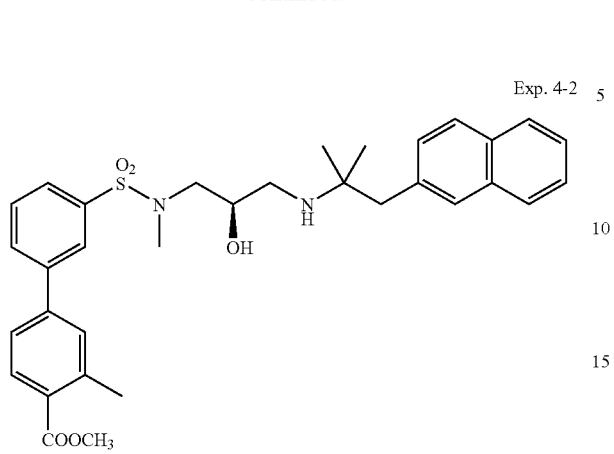
Exp. 4-6
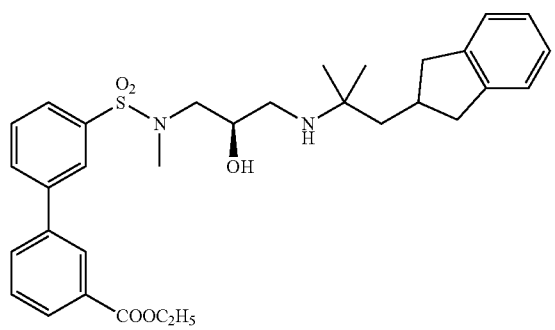
Exp. 4-3
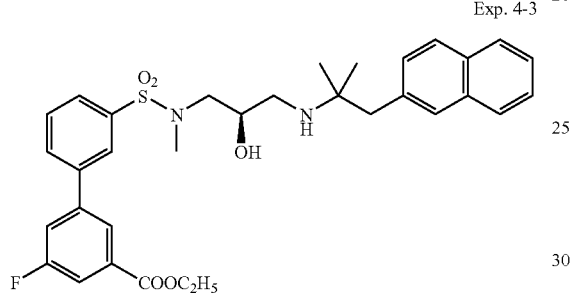
Exp. 4-7
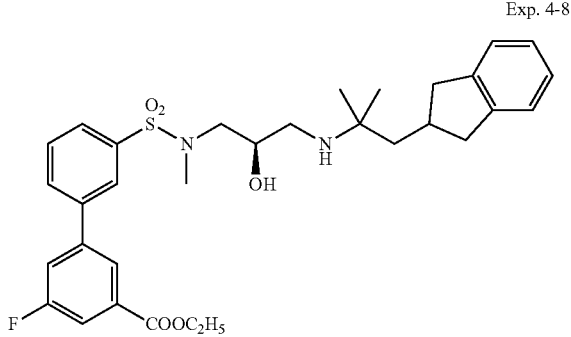
Exp. 4-4
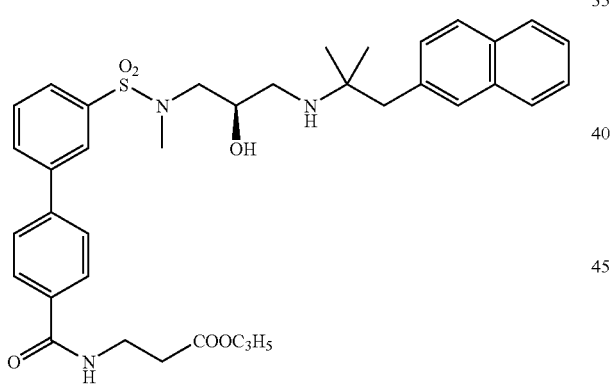
Exp. 4-8
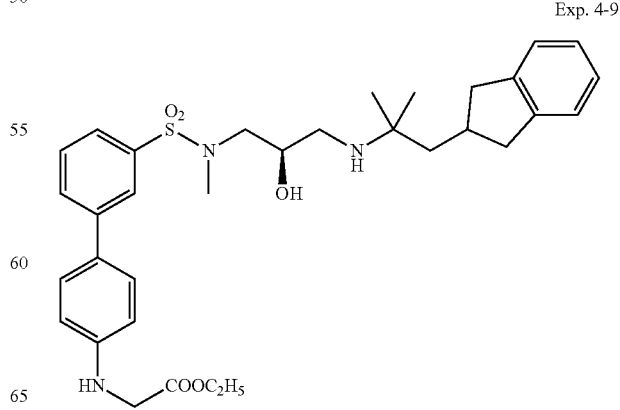
Exp. 4-5
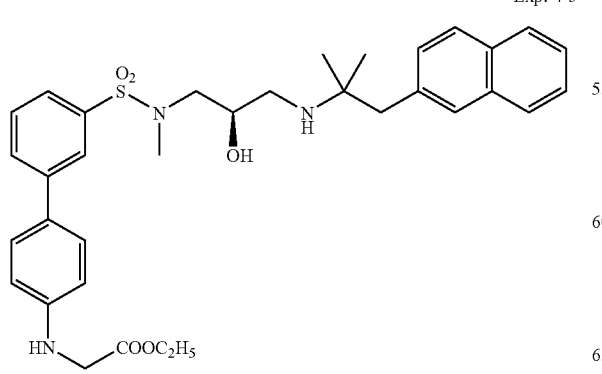
Exp. 4-9

-continued

Exp. 4-10

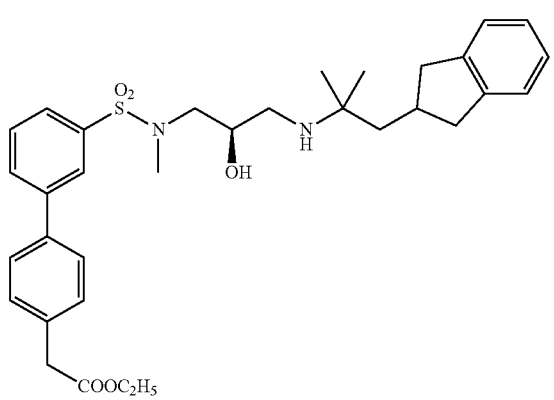

EXAMPLE 4-1

Ethyl (R)-3'-(N-(2-hydroxy-3-(2-methyl-1-(naphthalen-2-yl)propan-2-ylamino)propyl)-N-methylsulfamoyl)biphenyl-2-carboxylate

EXAMPLE 4-2

Methyl (R)-3'-(N-(2-hydroxy-3-(2-methyl-1-(naphthalen-2-yl)propan-2-ylamino)propyl)-N-methylsulfamoyl)-3-methylbiphenyl-4-carboxylate

EXAMPLE 4-3

Ethyl (R)-5-fluoro-3'-(N-(2-hydroxy-3-(2-methyl-1-(naphthalen-2-yl)propan-2-ylamino)propyl)-N-methylsulfamoyl)biphenyl-3-carboxylate

EXAMPLE 4-4

Ethyl (R)-3-(3'-(N-(2-hydroxy-3-(2-methyl-1-(naphthalen-2-yl)propan-2-ylamino)propyl)-N-methylsulfamoyl)biphenyl-4-ylcarboxamide)propionate

EXAMPLE 4-5

Ethyl (R)-2-(3'-(N-(2-hydroxy-3-(2-methyl-1-(naphthalen-2-yl)propan-2-ylamino)propyl)-N-methylsulfamoyl)biphenyl-4-ylamino)acetate

EXAMPLE 4-6

Ethyl (R)-3'-(N-(3-(1-(2,3-dihydro-1H-inden-2-yl)-2-methylpropan-2-ylamino)-2-hydroxypropyl)-N-methylsulfamoyl)biphenyl-3-carboxylate

EXAMPLE 4-7

Ethyl (R)-3-(3'-(N-(3-(1-(2,3-dihydro-1H-inden-2-yl)-2-methylpropan-2-ylamino)-2-hydroxypropyl)-N-methylsulfamoyl)biphenyl-4-yl)propionate

EXAMPLE 4-8

Ethyl (R)-3'-(N-(3-(1-(2,3-dihydro-1H-inden-2-yl)-2-methylpropan-2-ylamino)-2-hydroxypropyl)-N-methylsulfamoyl)-5-fluorobiphenyl-3-carboxylate

EXAMPLE 4-9

Ethyl (R)-2-(3'-(N-(3-(1-(2,3-dihydro-1H-inden-2-yl)-2-methylpropan-2-ylamino)-2-hydroxypropyl)-N-methylsulfamoyl)biphenyl-4-ylamino)acetate

EXAMPLE 4-10

Ethyl (R)-2-(3'-(N-(3-(1-(2,3-dihydro-1H-inden-2-yl)-2-methylpropan-2-ylamino)-2-hydroxypropyl)-N-methylsulfamoyl)biphenyl-4-yl)acetate

EXAMPLE 5-1

(R)-3-(2-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)propionic acid (Step A) Synthesis of methyl (R)-3-(2-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)acrylate A target compound was obtained in the same manner as Example 3-1 Step A except that Exp. 2-41 and ba21 were used instead of Exp. 2-1 and ba13, respectively.

(Step B) Synthesis of methyl (R)-3-(2-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)propionate The compound obtained from the Step A was dissolved in methanol, and added with 10% palladium carbon powder and the mixture was stirred under hydrogen atmosphere at room temperature. After the filtration of the reaction solution, the residue was concentrated to obtain the target compound.

(Step C) Synthesis of (R)-3-(2-(5-(N-(3-(1-(2,3-dihydro-1H-inden-2-yl)-2-methylpropan-2-ylamino)-2-hydroxypropyl)-N-methylsulfamoyl)pyridin-3-yl)phenyl)propionic acid The reaction was carried out according to Example 3-1 Step B to obtain a crude product, which was then purified according to the above described purification method to obtain a target compound.

EXAMPLES 5-2 TO 85

The target compounds were obtained in the same manner as Example 5-1 Step A to C with combinations shown in Table except that SM2 and BA were used instead of Exp. 2-41 and ba21, respectively.

TABLE 6

| Exp. | SM2 | BA | LCMS method | Rtime | Mass |
|---|---|---|---|---|---|
| 5-1 | Exp. 2-41 | ba21 | B | 1.29 | 566 |
| 5-2 | Exp. 2-26 | ba21 | B | 1.46 | 633 |
| 5-3 | Exp. 2-40 | ba21 | B | 1.39 | 571 |
| 5-4 | Exp. 2-21 | ba21 | B | 1.46 | 579 |
| 5-5 | Exp. 2-18 | ba21 | B | 1.48 | 633 |
| 5-6 | Exp. 2-28 | ba21 | B | 1.53 | 649 |
| 5-7 | Exp. 2-24 | ba21 | B | 1.50 | 599 |
| 5-8 | Exp. 2-16 | ba21 | B | 1.50 | 593 |

TABLE 6-continued

| Exp. | SM2 | BA | LCMS method | Rtime | Mass |
|---|---|---|---|---|---|
| 5-9 | Exp. 2-20 | ba21 | B | 1.48 | 579 |
| 5-10 | Exp. 2-23 | ba21 | B | 1.46 | 599 |
| 5-11 | Exp. 2-39 | ba21 | B | 1.62 | 605 |
| 5-12 | Exp. 2-27 | ba21 | B | 1.57 | 633 |
| 5-13 | Exp. 2-24 | ba31 | B | 1.43 | 633 |
| 5-14 | Exp. 2-39 | ba31 | B | 1.56 | 639 |
| 5-15 | Exp. 2-28 | ba31 | B | 1.53 | 683 |
| 5-16 | Exp. 2-16 | ba31 | B | 1.56 | 627 |
| 5-17 | Exp. 2-21 | ba31 | B | 1.51 | 613 |
| 5-18 | Exp. 2-26 | ba32 | B | 1.45 | 651 |
| 5-19 | Exp. 2-35 | ba32 | B | 1.49 | 651 |
| 5-20 | Exp. 2-24 | ba32 | B | 1.43 | 617 |
| 5-21 | Exp. 2-16 | ba32 | B | 1.45 | 611 |
| 5-22 | Exp. 2-39 | ba32 | B | 1.50 | 623 |
| 5-23 | Exp. 2-31 | ba32 | B | 1.54 | 601 |
| 5-24 | Exp. 2-18 | ba32 | B | 1.83 | 651 |
| 5-25 | Exp. 2-5 | ba33 | B | 1.43 | 595 |
| 5-26 | Exp. 2-35 | ba33 | B | 1.54 | 663 |
| 5-27 | Exp. 2-24 | ba33 | B | 1.45 | 629 |
| 5-28 | Exp. 2-16 | ba33 | B | 1.45 | 623 |
| 5-29 | Exp. 2-39 | ba33 | B | 1.54 | 635 |
| 5-30 | Exp. 2-17 | ba33 | B | 1.45 | 611 |
| 5-31 | Exp. 2-25 | ba33 | B | 1.64 | 617 |
| 5-32 | Exp. 2-22 | ba33 | B | 1.62 | 597 |
| 5-33 | Exp. 2-40 | ba34 | B | 1.40 | 589 |
| 5-34 | Exp. 2-18 | ba34 | B | 1.44 | 651 |
| 5-35 | Exp. 2-16 | ba34 | B | 1.44 | 611 |
| 5-36 | Exp. 2-24 | ba34 | B | 1.61 | 617 |
| 5-37 | Exp. 2-31 | ba34 | B | 1.59 | 601 |
| 5-38 | Exp. 2-39 | ba34 | B | 2.02 | 623 |
| 5-39 | Exp. 2-22 | ba34 | B | 1.50 | 585 |
| 5-40 | Exp. 2-25 | ba34 | B | 1.67 | 605 |
| 5-41 | Exp. 2-17 | ba34 | B | 1.65 | 599 |
| 5-42 | Exp. 2-35 | ba35 | B | 1.46 | 693 |
| 5-43 | Exp. 2-26 | ba35 | B | 1.43 | 693 |
| 5-44 | Exp. 2-16 | ba35 | B | 1.36 | 653 |
| 5-45 | Exp. 2-24 | ba35 | B | 1.53 | 659 |
| 5-46 | Exp. 2-31 | ba35 | B | 1.48 | 643 |
| 5-47 | Exp. 2-18 | ba35 | B | 1.72 | 693 |
| 5-48 | Exp. 2-24 | ba36 | B | 1.65 | 617 |
| 5-49 | Exp. 2-31 | ba36 | B | 1.62 | 601 |
| 5-50 | Exp. 2-18 | ba36 | B | 1.50 | 651 |
| 5-51 | Exp. 2-39 | ba36 | B | 1.87 | 623 |
| 5-52 | Exp. 2-16 | ba36 | B | 1.69 | 611 |
| 5-53 | Exp. 2-17 | ba36 | B | 1.56 | 599 |
| 5-54 | Exp. 2-25 | ba36 | B | 1.69 | 605 |
| 5-55 | Exp. 2-22 | ba36 | B | 1.51 | 585 |
| 5-56 | Exp. 2-5 | ba37 | B | 1.41 | 583 |
| 5-57 | Exp. 2-31 | ba37 | B | 1.66 | 601 |
| 5-58 | Exp. 2-16 | ba37 | B | 1.64 | 611 |
| 5-59 | Exp. 2-24 | ba37 | B | 1.73 | 617 |
| 5-60 | Exp. 2-5 | ba38 | B | 1.42 | 583 |
| 5-61 | Exp. 2-35 | ba38 | B | 1.50 | 651 |
| 5-62 | Exp. 2-26 | ba38 | B | 1.48 | 651 |
| 5-63 | Exp. 2-31 | ba39 | B | 1.54 | 597 |
| 5-64 | Exp. 2-16 | ba39 | B | 1.55 | 607 |
| 5-65 | Exp. 2-39 | ba39 | B | 2.06 | 619 |
| 5-66 | Exp. 2-25 | ba39 | B | 1.73 | 601 |
| 5-67 | Exp. 2-22 | ba39 | B | 1.70 | 581 |
| 5-68 | Exp. 2-17 | ba39 | B | 1.76 | 595 |
| 5-69 | Exp. 2-22 | ba40 | B | 1.54 | 581 |
| 5-70 | Exp. 2-25 | ba40 | B | 1.69 | 601 |
| 5-71 | Exp. 2-17 | ba40 | B | 1.71 | 595 |
| 5-72 | Exp. 2-22 | ba41 | B | 1.68 | 603 |
| 5-73 | Exp. 2-17 | ba41 | B | 1.70 | 617 |
| 5-74 | Exp. 2-17 | ba42 | B | 1.48 | 599 |
| 5-75 | Exp. 2-25 | ba42 | B | 1.53 | 605 |
| 5-76 | Exp. 2-17 | ba43 | B | 1.53 | 595 |
| 5-77 | Exp. 2-17 | ba44 | B | 1.53 | 595 |
| 5-78 | Exp. 2-17 | ba31 | B | 1.63 | 615 |
| 5-79 | Exp. 2-30 | ba42 | B | 1.53 | 589 |
| 5-80 | Exp. 2-35 | ba43 | B | 1.62 | 647 |
| 5-81 | Exp. 2-35 | ba36 | B | 1.60 | 651 |
| 5-82 | Exp. 2-5 | ba34 | B | 1.46 | 583 |
| 5-83 | Exp. 2-5 | ba72 | B | 1.49 | 601 |
| 5-84 | Exp. 2-5 | ba45 | B | 1.43 | 593 |
| 5-85 | Exp. 2-5 | ba65 | B | 1.45 | 579 |

Hereinbelow, structures of the compounds of Example to 5-85 (Exp. 5-1 to Exp. 5-85) are shown.

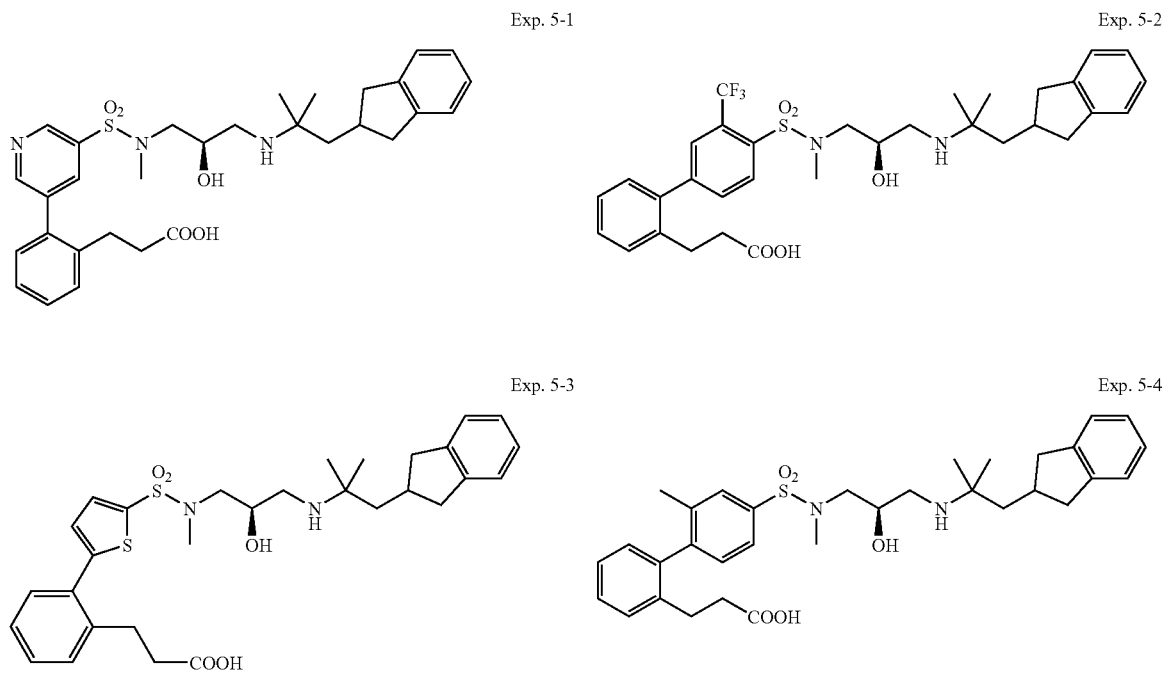

-continued
Exp. 5-5
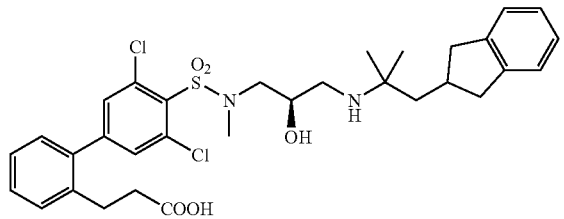
Exp. 5-6
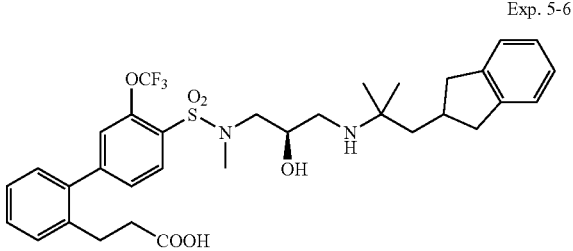
Exp. 5-7
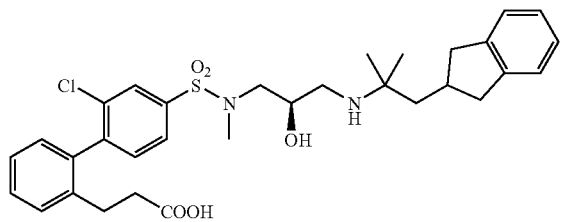
Exp. 5-8
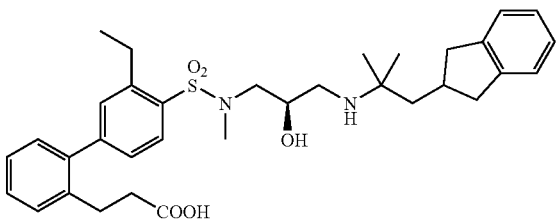
Exp. 5-9
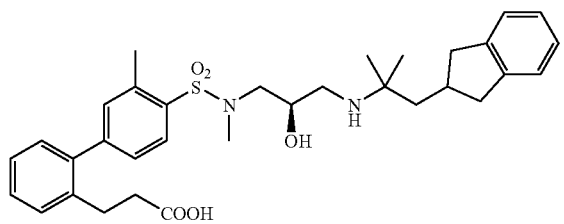
Exp. 5-10
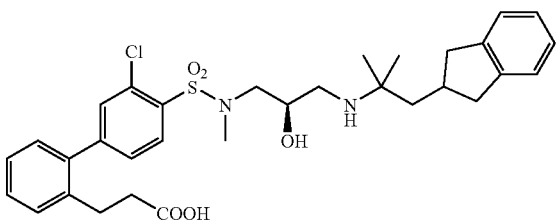
Exp. 5-11
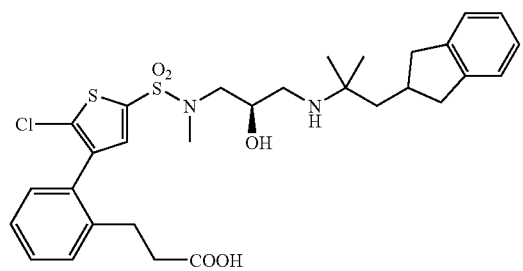
Exp. 5-12
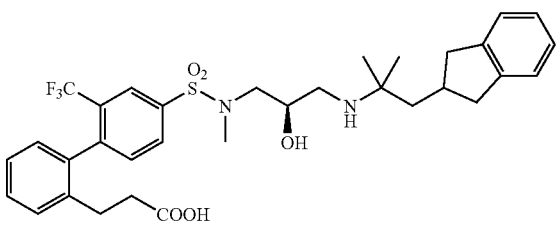
Exp. 5-13
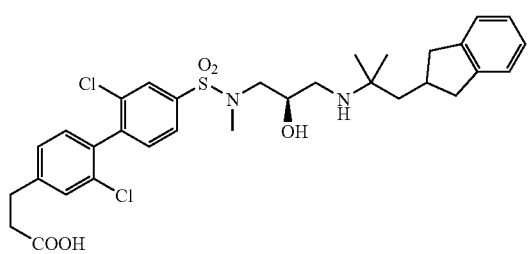
Exp. 5-14
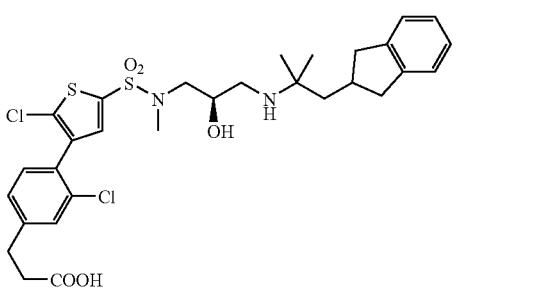
Exp. 5-15
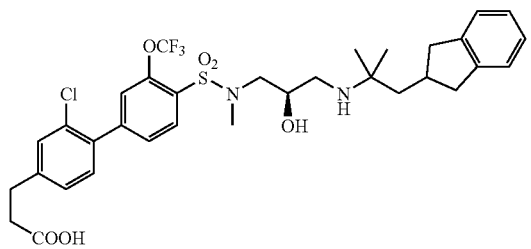
Exp. 5-16
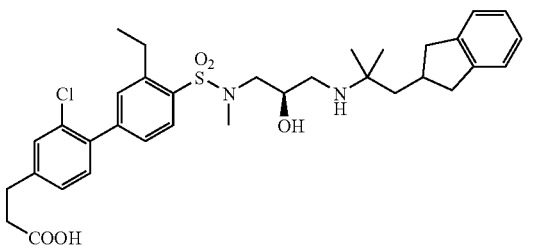

-continued
Exp. 5-17
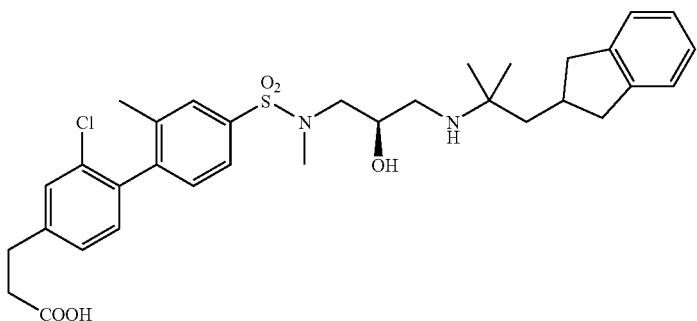
Exp. 5-18
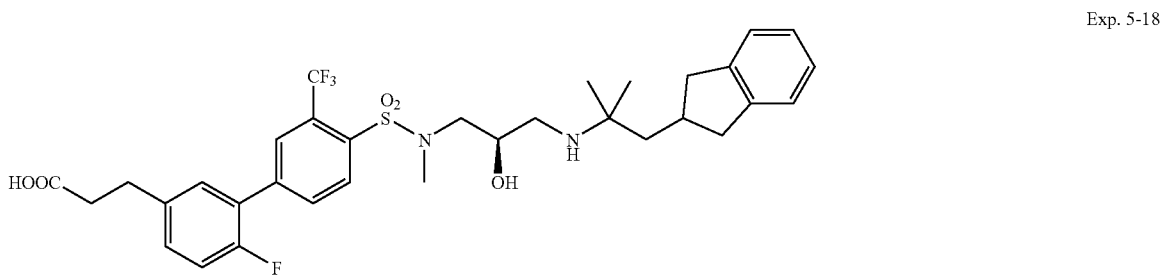
Exp. 5-19
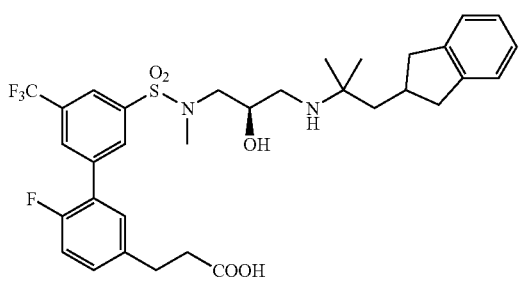
Exp. 5-20
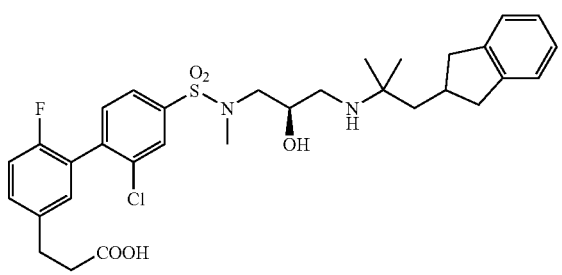
Exp. 5-21
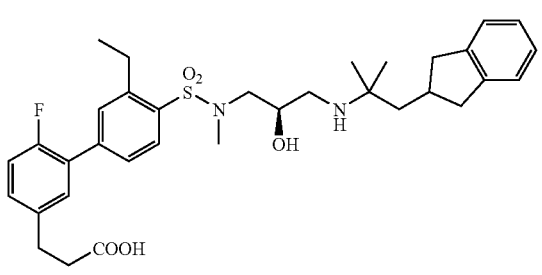
Exp. 5-22
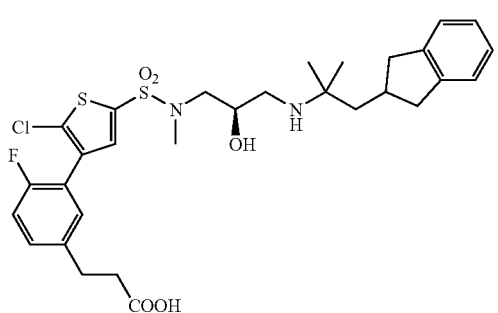
Exp. 5-23
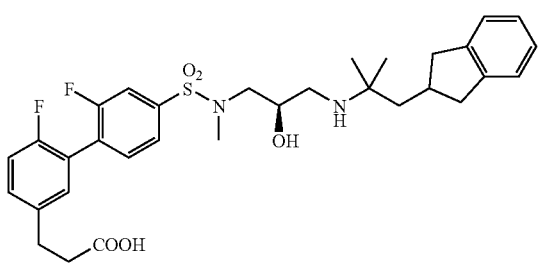
Exp. 5-24
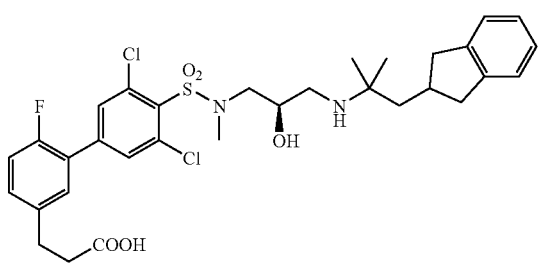

-continued
Exp. 5-25
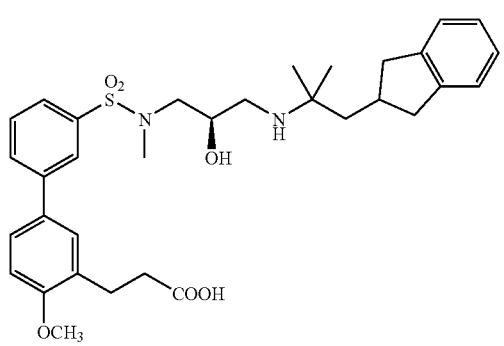
Exp. 5-26
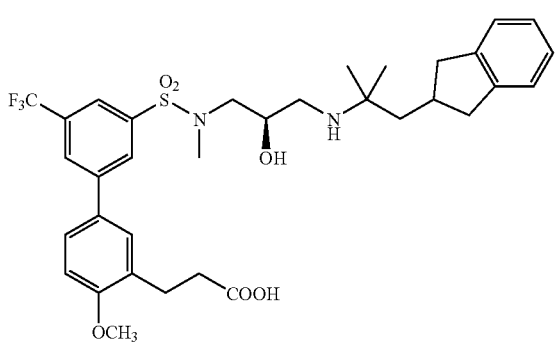
Exp. 5-27
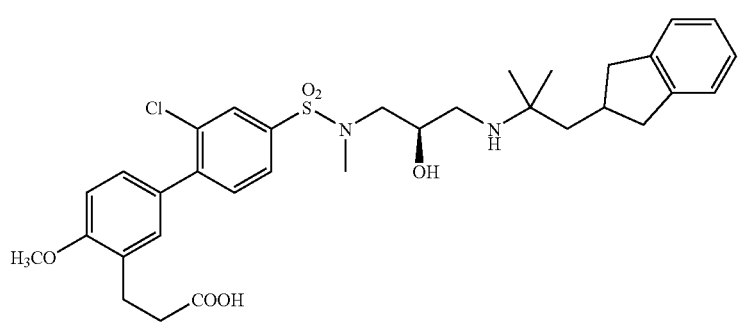
Exp. 5-28
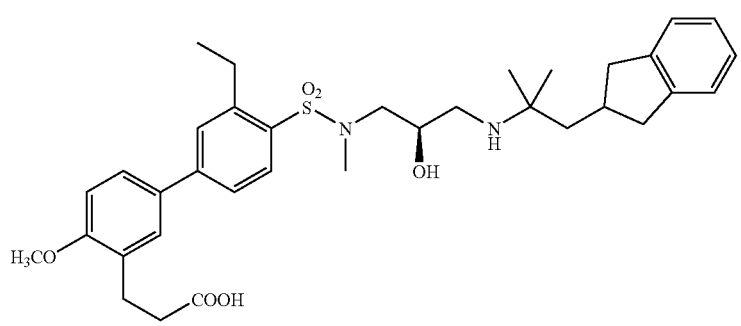
Exp. 5-29
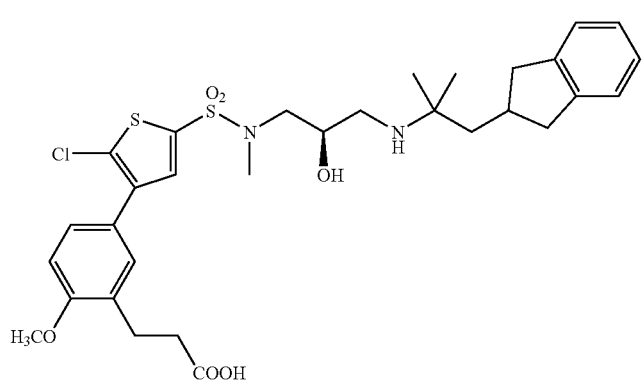
Exp. 5-30
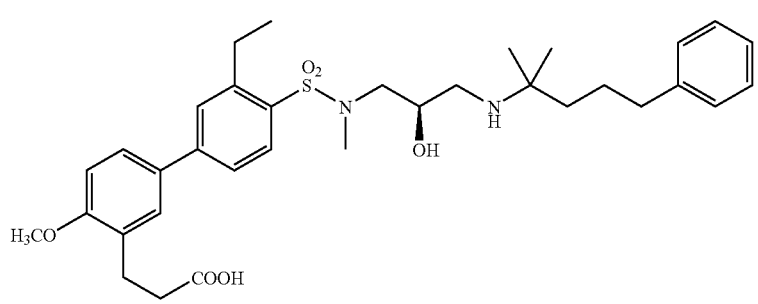

Exp. 5-31
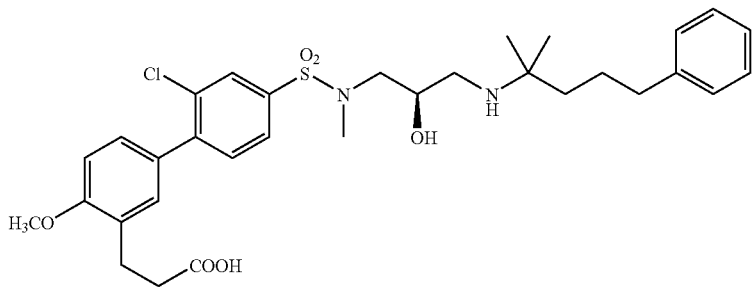
Exp. 5-32
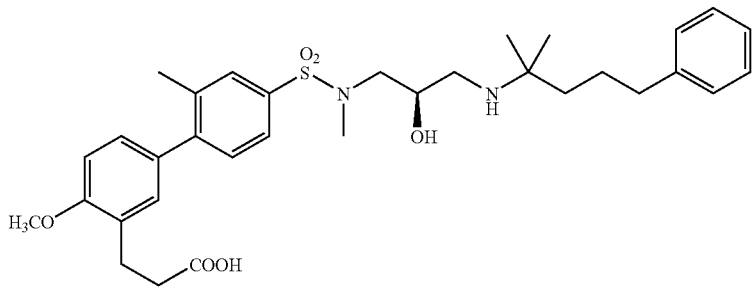
Exp. 5-33 Exp. 5-34
Exp. 5-35 Exp. 5-36
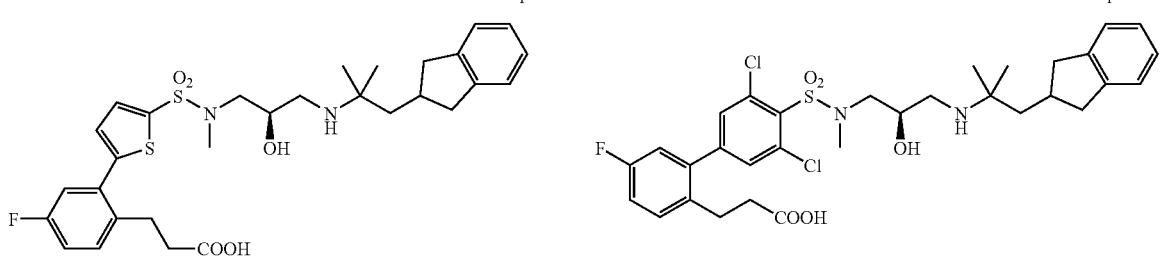
Exp. 5-35 Exp. 5-36
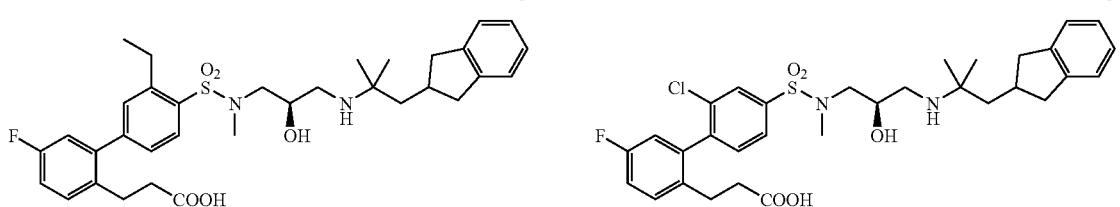
Exp. 5-37 Exp. 5-38
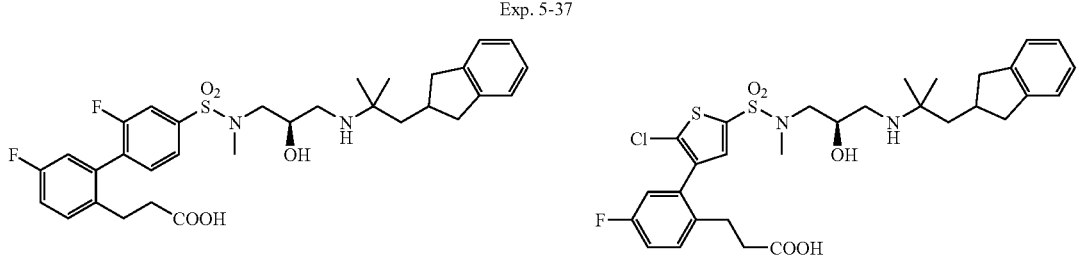
Exp. 5-39 Exp. 5-40
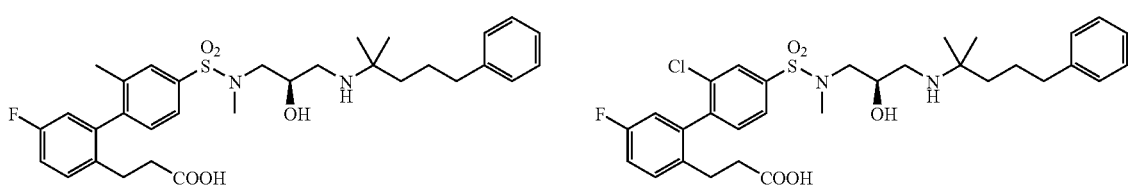

-continued
Exp. 5-41
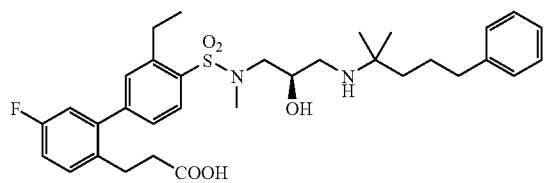
Exp. 5-42
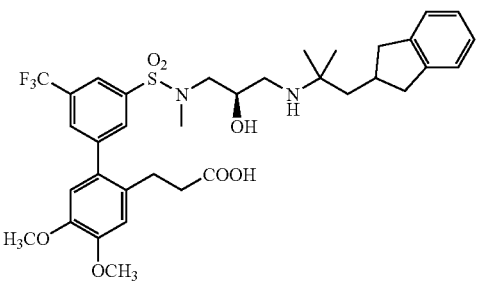
Exp. 5-43
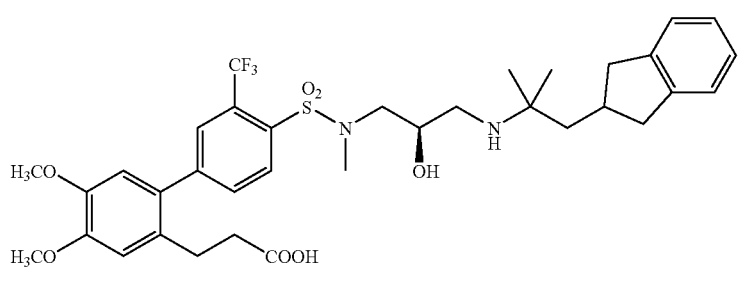
Exp. 5-44
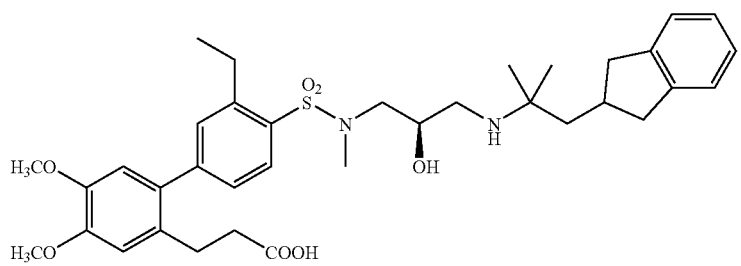
Exp. 5-45
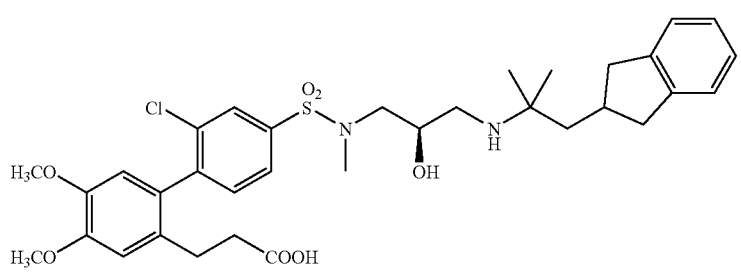
Exp. 5-46
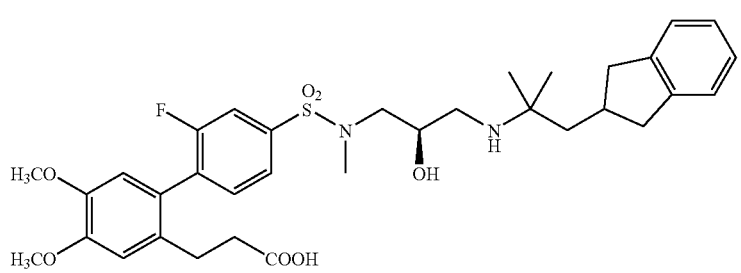
Exp. 5-47
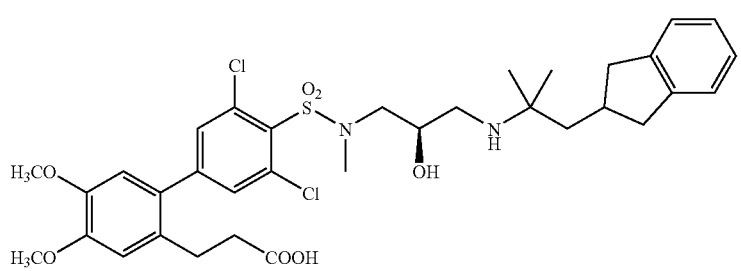

-continued
Exp. 5-48
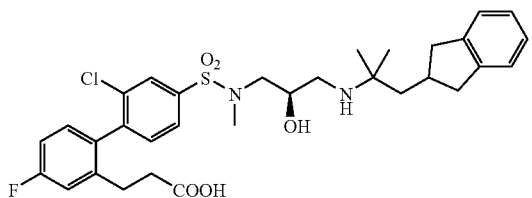
Exp. 5-49
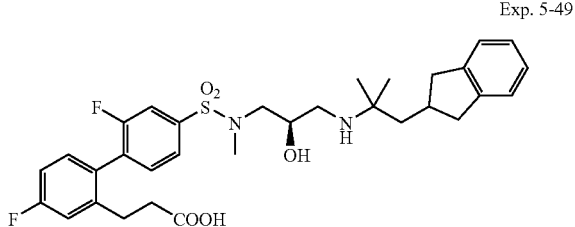
Exp. 5-50
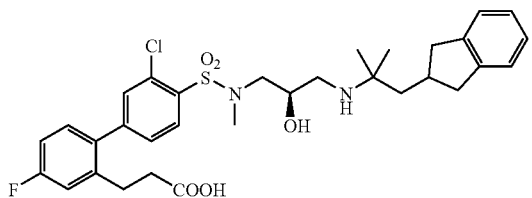
Exp. 5-51
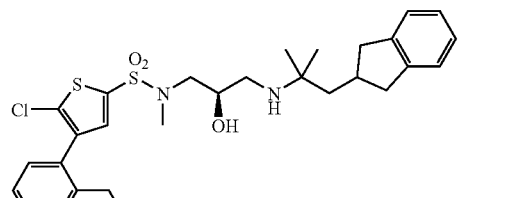
Exp. 5-52
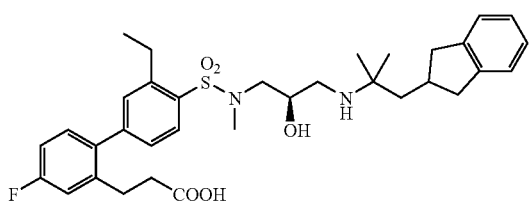
Exp. 5-53
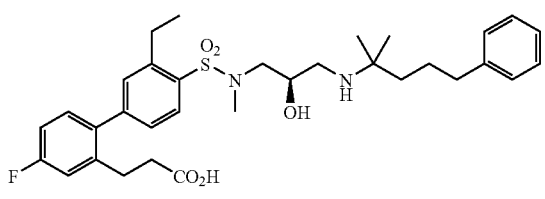
Exp. 5-54
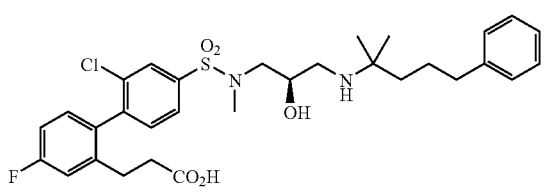
Exp. 5-55
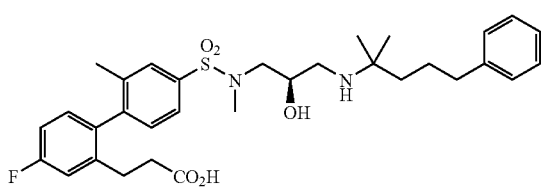
Exp. 5-56
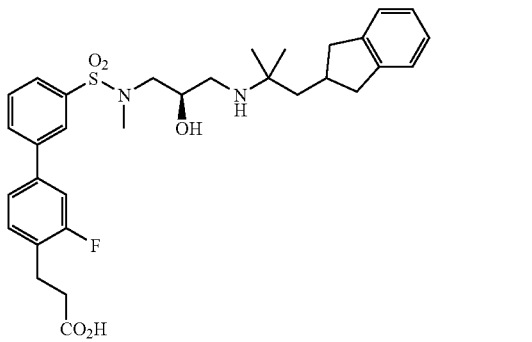
Exp. 5-57
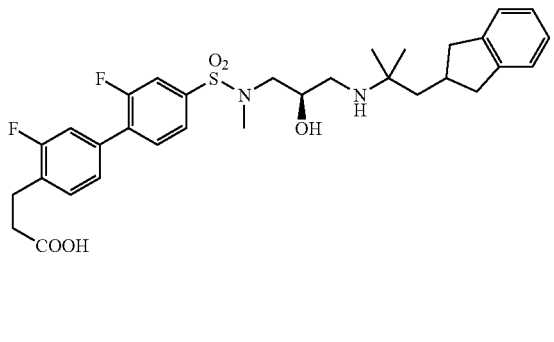
Exp. 5-58
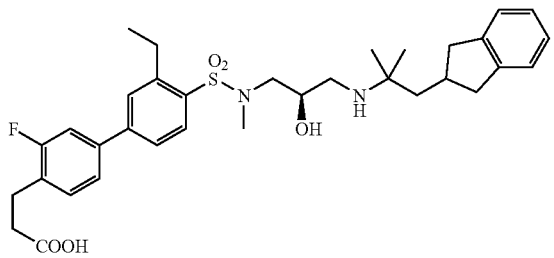
Exp. 5-59
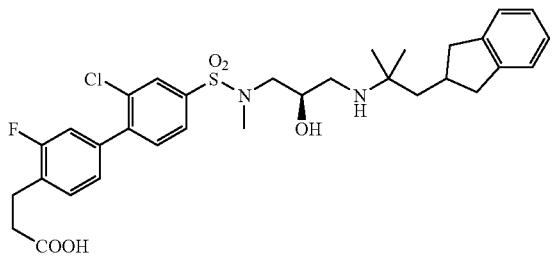

-continued
Exp. 5-60
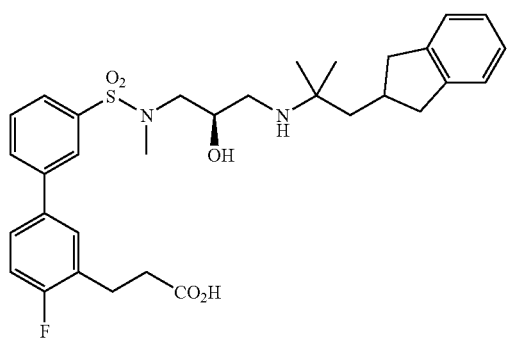
Exp. 5-61
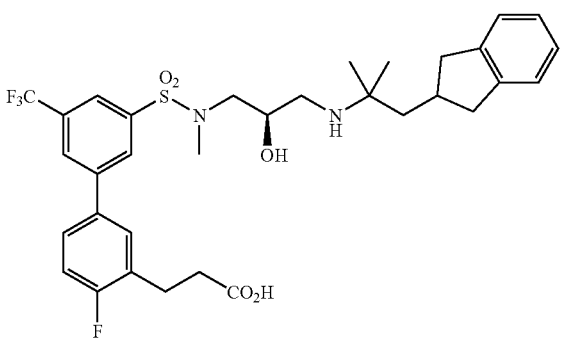
Exp. 5-62
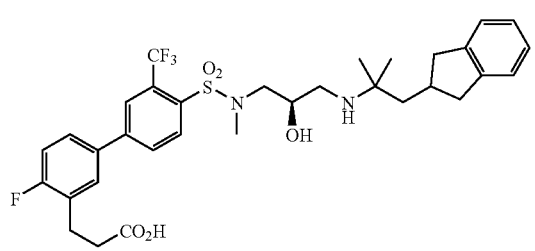
Exp. 5-53
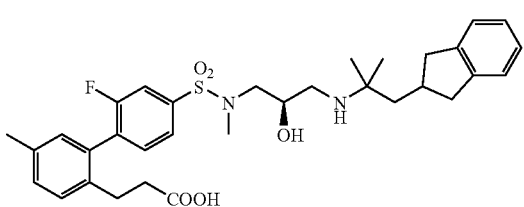
Exp. 5-64
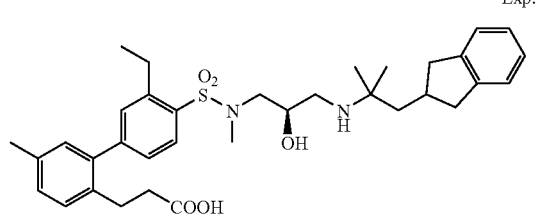
Exp. 5-65
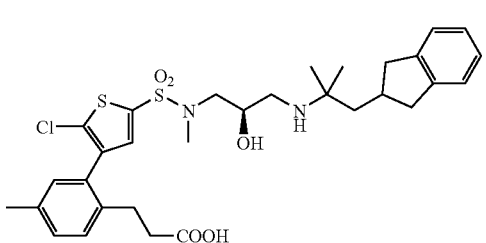
Exp. 5-66
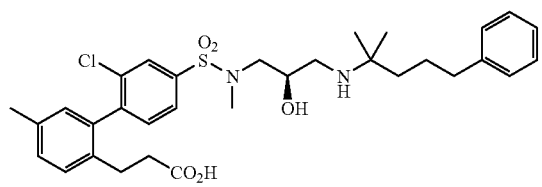
Exp. 5-67
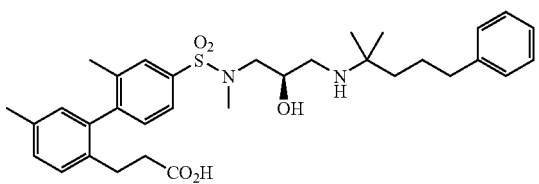
Exp. 5-68
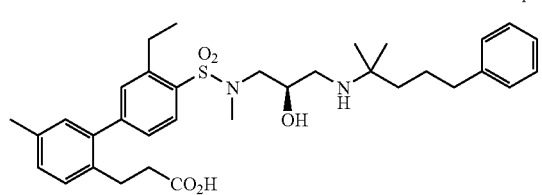
Exp. 5-69
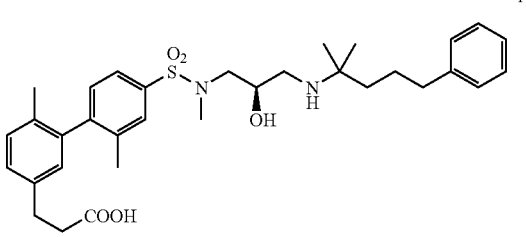
Exp. 5-70
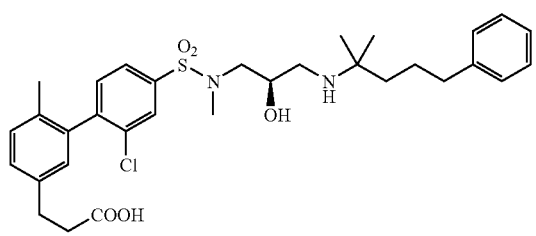
Exp. 5-71
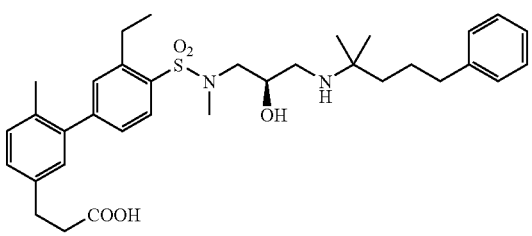

-continued
Exp. 5-72
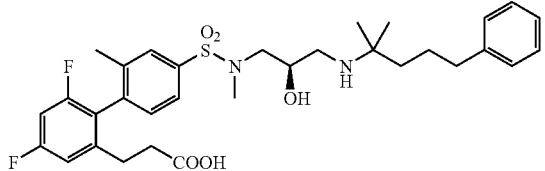
Exp. 5-73
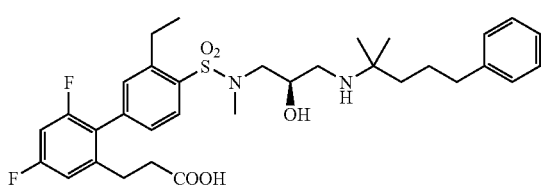
Exp. 5-74
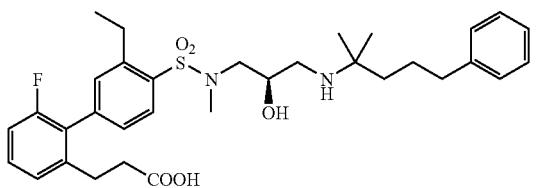
Exp. 5-75
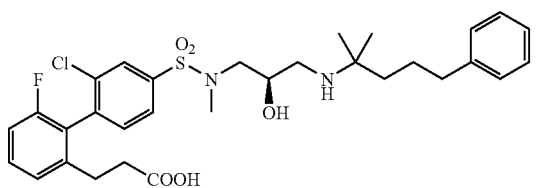
Exp. 5-76
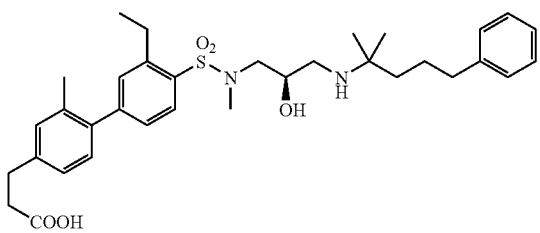
Exp. 5-77
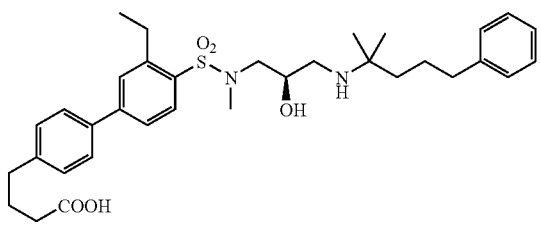
Exp. 5-78
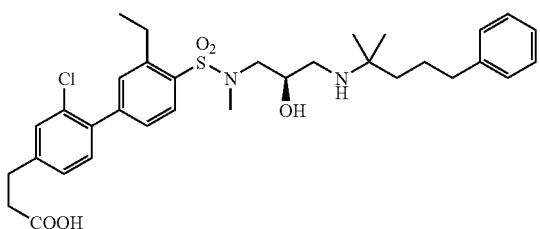
Exp. 5-79
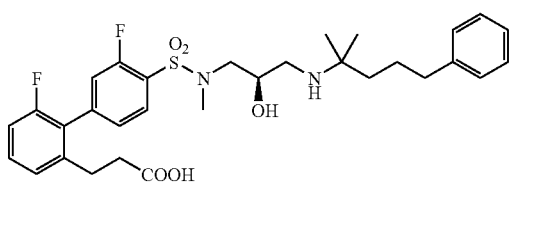
Exp. 5-80
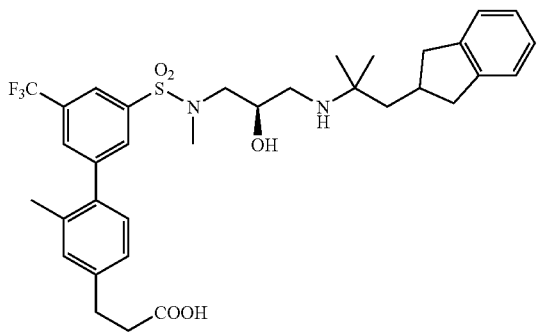
Exp. 5-81
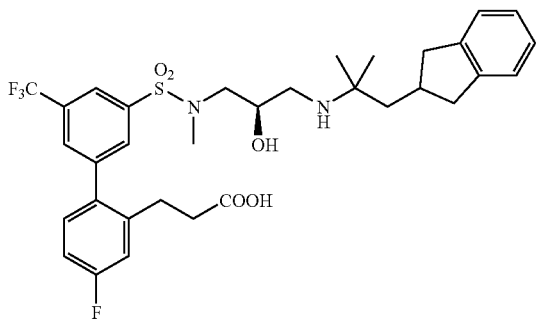
Exp. 5-82
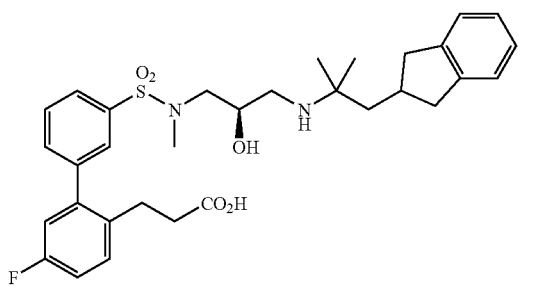
Exp. 5-83
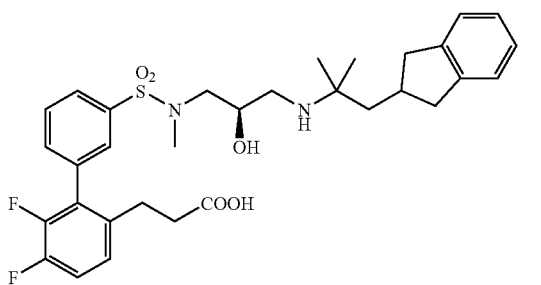

-continued

Exp. 5-84

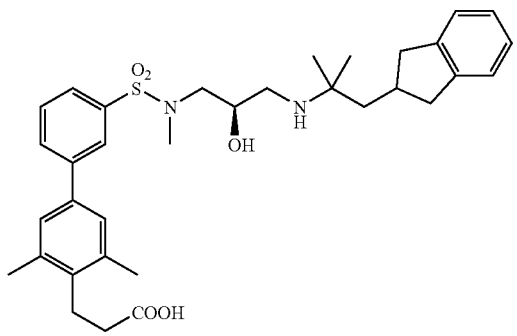

Exp. 5-85

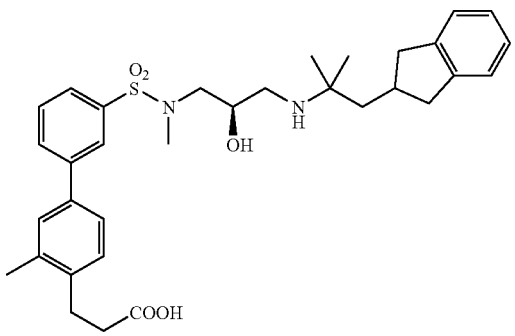

EXAMPLE 5-2

(R)-3-(4'-(N-(3-(1-(2,3-dihydro-1H-inden-2-yl)-2-methylpropan-2-ylamino)-2-hydroxypropyl)-N-methylsulfamoyl)-3'-(trifluoromethyl)biphenyl-2-yl)propionic acid

EXAMPLE 5-3

(R)-3-(2-(5-(N-(3-(1-(2,3-dihydro-1H-inden-2-yl)-2-methylpropan-2-ylamino)-2-hydroxypropyl)-N-methylsulfamoyl)thiophen-2-yl)phenyl)propionic acid

EXAMPLE 5-4

(R)-3-(4'-(N-(3-(1-(2,3-dihydro-1H-inden-2-yl)-2-methylpropan-2-ylamino)-2-hydroxypropyl)-N-methylsulfamoyl)-2'-methylbiphenyl-2-yl)propionic acid

EXAMPLE 5-5

(R)-3-(3',5'-dichloro-4'-(N-(3-(1-(2,3-dihydro-1H-inden-2-yl)-2-methylpropan-2-ylamino)-2-hydroxypropyl)-N-methylsulfamoyl)biphenyl-2-yl)propionic acid

EXAMPLE 5-6

(R)-3-(4'-(N-(3-(1-(2,3-dihydro-1H-inden-2-yl)-2-methylpropan-2-ylamino)-2-hydroxypropyl)-N-methylsulfamoyl)-3'-(trifluoromethoxy)biphenyl-2-yl)propionic acid

EXAMPLE 5-7

(R)-3-(2'-chloro-4'-(N-(3-(1-(2,3-dihydro-1H-inden-2-yl)-2-methylpropan-2-ylamino)-2-hydroxypropyl)-N-methylsulfamoyl)biphenyl-2-yl)propionic acid

EXAMPLE 5-8

(R)-3-(4'-(N-(3-(1-(2,3-dihydro-1H-inden-2-yl)-2-methylpropan-2-ylamino)-2-hydroxypropyl)-N-methylsulfamoyl)-3'-ethylbiphenyl-2-yl)propionic acid

EXAMPLE 5-9

(R)-3-(4'-(N-(3-(1-(2,3-dihydro-1H-inden-2-yl)-2-methylpropan-2-ylamino)-2-hydroxypropyl)-N-methylsulfamoyl)-3'-methylbiphenyl-2-yl)propionic acid

EXAMPLE 5-10

(R)-3-(3'-chloro-4'-(N-(3-(1-(2,3-dihydro-1H-inden-2-yl)-2-methylpropan-2-ylamino)-2-hydroxypropyl)-N-methylsulfamoyl)biphenyl-2-yl)propionic acid

EXAMPLE 5-11

(R)-3-(2-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)phenyl)propionic acid

EXAMPLE 5-12

(R)-3-(4'-(N-(3-(1-(2,3-dihydro-1H-inden-2-yl)-2-methylpropan-2-ylamino)-2-hydroxypropyl)-N-methylsulfamoyl)-2'-(trifluoromethyl)biphenyl-2-yl)propionic acid

EXAMPLE 5-13

(R)-3-(2,2'-dichloro-4'-(N-(3-(1-(2,3-dihydro-1H-inden-2-yl)-2-methylpropan-2-ylamino)-2-hydroxypropyl)-N-methylsulfamoyl)biphenyl-4-yl)propionic acid

EXAMPLE 5-14

(R)-3-(3-chloro-4-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)phenyl)propionic acid

EXAMPLE 5-15

(R)-3-(2-chloro-4'-(N-(3-(1-(2,3-dihydro-1H-inden-2-yl)-2-methylpropan-2-ylamino)-2-hydroxypropyl)-N-methylsulfamoyl)-3'-(trifluoromethoxy)biphenyl-4-yl)propionic acid

EXAMPLE 5-16

(R)-3-(2-chloro-4'-(N-(3-(1-(2,3-dihydro-1H-inden-2-yl)-2-methylpropan-2-ylamino)-2-hydroxypropyl)-N-methylsulfamoyl)-3'-ethylbiphenyl-4-yl)propionic acid

EXAMPLE 5-17

(R)-3-(2-chloro-4'-(N-(3-(1-(2,3-dihydro-1H-inden-2-yl)-2-methylpropan-2-ylamino)-2-hydroxypropyl)-N-methylsulfamoyl)-2'-methylbiphenyl-4-yl)propionic acid

EXAMPLE 5-18

(R)-3-(4'-(N-(3-(1-(2,3-dihydro-1H-inden-2-yl)-2-methylpropan-2-ylamino)-2-hydroxypropyl)-N-methylsulfamoyl)-6-fluoro-3'-(trifluoromethyl)biphenyl-3-yl)propionic acid

EXAMPLE 5-19

(R)-3-(3'-(N-(3-(1-(2,3-dihydro-1H-inden-2-yl)-2-methylpropan-2-ylamino)-2-hydroxypropyl)-N-methylsulfamoyl)-6-fluoro-5'-(trifluoromethyl)biphenyl-3-yl)propionic acid

EXAMPLE 5-20

(R)-3-(2'-chloro-4'-(N-(3-(1-(2,3-dihydro-1H-inden-2-yl)-2-methylpropan-2-ylamino)-2-hydroxypropyl)-N-methylsulfamoyl)-6-fluorobiphenyl-3-yl)propionic acid

EXAMPLE 5-21

(R)-3-(4'-(N-(3-(1-(2,3-dihydro-1H-inden-2-yl)-2-methylpropan-2-ylamino)-2-hydroxypropyl)-N-methylsulfamoyl)-3'-ethyl-6-fluorobiphenyl-3-yl)propionic acid

EXAMPLE 5-22

(R)-3-(3-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)-4-fluorophenyl)propionic acid

EXAMPLE 5-23

(R)-3-(4'-(N-(3-(1-(2,3-dihydro-1H-inden-2-yl)-2-methylpropan-2-ylamino)-2-hydroxypropyl)-N-methylsulfamoyl)-2',6-difluorobiphenyl-3-yl)propionic acid

EXAMPLE 5-24

(R)-3-(3',5'-dichloro-4'-(N-(3-(1-(2,3-dihydro-1H-inden-2-yl)-2-methylpropan-2-ylamino)-2-hydroxypropyl)-N-methylsulfamoyl)-6-fluorobiphenyl-3-yl)propionic acid

EXAMPLE 5-25

(R)-3-(3'-(N-(3-(1-(2,3-dihydro-1H-inden-2-yl)-2-methylpropan-2-ylamino)-2-hydroxypropyl)-N-methylsulfamoyl)-4-methoxybiphenyl-3-yl)propionic acid

EXAMPLE 5-26

(R)-3-(3'-(N-(3-(1-(2,3-dihydro-1H-inden-2-yl)-2-methylpropan-2-ylamino)-2-hydroxypropyl)-N-methylsulfamoyl)-4-methoxy-5'-(trifluoromethyl)biphenyl-3-yl)propionic acid

EXAMPLE 5-27

(R)-3-(2'-chloro-4'-(N-(3-(1-(2,3-dihydro-1H-inden-2-yl)-2-methylpropan-2-ylamino)-2-hydroxypropyl)-N-methylsulfamoyl)-4-methoxybiphenyl-3-yl)propionic acid

EXAMPLE 5-28

(R)-3-(4'-(N-(3-(1-(2,3-dihydro-1H-inden-2-yl)-2-methylpropan-2-ylamino)-2-hydroxypropyl)-N-methylsulfamoyl)-3'-ethyl-4-methoxybiphenyl-3-yl)propionic acid

EXAMPLE 5-29

(R)-3-(5-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)-2-methoxyphenyl)propionic acid

EXAMPLE 5-30

(R)-3-(3'-ethyl-4'-(N-(2-hydroxy-3-(2-methyl-5-phenylpentan-2-ylamino)propyl)-N-methylsulfamoyl)-4-methoxybiphenyl-3-yl)propionic acid

EXAMPLE 5-31

(R)-3-(2'-chloro-4'-(N-(2-hydroxy-3-(2-methyl-5-phenylpentan-2-ylamino)propyl)-N-methylsulfamoyl)-4-methoxybiphenyl-3-yl)propionic acid

EXAMPLE 5-32

(R)-3-(4'-(N-(2-hydroxy-3-(2-methyl-5-phenylpentan-2-ylamino)propyl)-N-methylsulfamoyl)-4-methoxy-2'-methylbiphenyl-3-yl)propionic acid

EXAMPLE 5-33

(R)-3-(2-(5-(N-(3-(1-(2,3-dihydro-1H-inden-2-yl)-2-methylpropan-2-ylamino)-2-hydroxypropyl)-N-methylsulfamoyl)thiophen-2-yl)-4-fluorophenyl)propionic acid

EXAMPLE 5-34

(R)-3-(3',5'-dichloro-4'-(N-(3-(1-(2,3-dihydro-1H-inden-2-yl)-2-methylpropan-2-ylamino)-2-hydroxypropyl)-N-methylsulfamoyl)-5-fluorobiphenyl-2-yl)propionic acid

EXAMPLE 5-35

(R)-3-(4'-(N-(3-(1-(2,3-dihydro-1H-inden-2-yl)-2-methylpropan-2-ylamino)-2-hydroxypropyl)-N-methylsulfamoyl)-3'-ethyl-5-fluorobiphenyl-2-yl)propionic acid

EXAMPLE 5-36

(R)-3-(2'-chloro-4'-(N-(3-(1-(2,3-dihydro-1H-inden-2-yl)-2-methylpropan-2-ylamino)-2-hydroxypropyl)-N-methylsulfamoyl)-5-fluorobiphenyl-2-yl)propionic acid

EXAMPLE 5-37

(R)-3-(4'-(N-(3-(1-(2,3-dihydro-1H-inden-2-yl)-2-methylpropan-2-ylamino)-2-hydroxypropyl)-N-methylsulfamoyl)-2',5-difluorobiphenyl-2-yl)propionic acid

EXAMPLE 5-38

(R)-3-(2-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)-4-fluorophenyl)propionic acid

EXAMPLE 5-39

(R)-3-(5-fluoro-4'-(N-(2-hydroxy-3-(2-methyl-5-phenyl-pentan-2-ylamino)propyl)-N-methylsulfamoyl)-2'-methylbiphenyl-2-yl)propionic acid

EXAMPLE 5-40

(R)-3-(2'-chloro-5-fluoro-4'-(N-(2-hydroxy-3-(2-methyl-5-phenylpentan-2-ylamino)propyl)-N-methylsulfamoyl)biphenyl-2-yl)propionic acid

EXAMPLE 5-41

(R)-3-(3'-ethyl-5-fluoro-4'-(N-(2-hydroxy-3-(2-methyl-5-phenylpentan-2-ylamino)propyl)-N-methylsulfamoyl)biphenyl-2-yl)propionic acid

EXAMPLE 5-42

(R)-3-(3'-(N-(3-(1-(2,3-dihydro-1H-inden-2-yl)-2-methylpropan-2-ylamino)-2-hydroxypropyl)-N-methylsulfamoyl)-4,5-dimethoxy-5'-(trifluoromethyl)biphenyl-2-yl)propionic acid

EXAMPLE 5-43

(R)-3-(4'-(N-(3-(1-(2,3-dihydro-1H-inden-2-yl)-2-methylpropan-2-ylamino)-2-hydroxypropyl)-N-methylsulfamoyl)-4,5-dimethoxy-3'-(trifluoromethyl)biphenyl-2-yl)propionic acid

EXAMPLE 5-44

(R)-3-(4'-(N-(3-(1-(2,3-dihydro-1H-inden-2-yl)-2-methylpropan-2-ylamino)-2-hydroxypropyl)-N-methylsulfamoyl)-3'-ethyl-4,5-dimethoxybiphenyl-2-yl)propionic acid

EXAMPLE 5-45

(R)-3-(2'-chloro-4'-(N-(3-(1-(2,3-dihydro-1H-inden-2-yl)-2-methylpropan-2-ylamino)-2-hydroxypropyl)-N-methylsulfamoyl)-4,5-dimethoxybiphenyl-2-yl)propionic acid

EXAMPLE 5-46

(R)-3-(4'-(N-(3-(1-(2,3-dihydro-1H-inden-2-yl)-2-methylpropan-2-ylamino)-2-hydroxypropyl)-N-methylsulfamoyl)-2'-fluoro-4,5-dimethoxybiphenyl-2-yl)propionic acid

EXAMPLE 5-47

(R)-3-(3',5'-dichloro-4'-(N-(3-(1-(2,3-dihydro-1H-inden-2-yl)-2-methylpropan-2-ylamino)-2-hydroxypropyl)-N-methylsulfamoyl)-4,5-dimethoxybiphenyl-2-yl)propionic acid

EXAMPLE 5-48

(R)-3-(2'-chloro-4'-(N-(3-(1-(2,3-dihydro-1H-inden-2-yl)-2-methylpropan-2-ylamino)-2-hydroxypropyl)-N-methylsulfamoyl)-4-fluorobiphenyl-2-yl)propionic acid

EXAMPLE 5-49

(R)-3-(4'-(N-(3-(1-(2,3-dihydro-1H-inden-2-yl)-2-methylpropan-2-ylamino)-2-hydroxypropyl)-N-methylsulfamoyl)-2',4-difluorobiphenyl-2-yl)propionic acid

EXAMPLE 5-50

(R)-3-(3',5'-dichloro-4'-(N-(3-(1-(2,3-dihydro-1H-inden-2-yl)-2-methylpropan-2-ylamino)-2-hydroxypropyl)-N-methylsulfamoyl)-4-fluorobiphenyl-2-yl)propionic acid

EXAMPLE 5-51

(R)-3-(2-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)-5-fluorophenyl)propionic acid

EXAMPLE 5-52

(R)-3-(4'-(N-(3-(1-(2,3-dihydro-1H-inden-2-yl)-2-methylpropan-2-ylamino)-2-hydroxypropyl)-N-methylsulfamoyl)-3'-ethyl-4-fluorobiphenyl-2-yl)propionic acid

EXAMPLE 5-53

(R)-3-(3'-ethyl-4-fluoro-4'-(N-(2-hydroxy-3-(2-methyl-5-phenylpentan-2-ylamino)propyl)-N-methylsulfamoyl)biphenyl-2-yl)propionic acid

EXAMPLE 5-54

(R)-3-(2'-chloro-4-fluoro-4'-(N-(2-hydroxy-3-(2-methyl-5-phenylpentan-2-ylamino)propyl)-N-methylsulfamoyl)biphenyl-2-yl)propionic acid

EXAMPLE 5-55

(R)-3-(4-fluoro-4'-(N-(2-hydroxy-3-(2-methyl-5-phenyl-pentan-2-ylamino)propyl)-N-methylsulfamoyl)-2'-methylbiphenyl-2-yl)propionic acid

EXAMPLE 5-56

(R)-3-(3'-(N-(3-(1-(2,3-dihydro-1H-inden-2-yl)-2-methylpropan-2-ylamino)-2-hydroxypropyl)-N-methylsulfamoyl)-3-fluorobiphenyl-4-yl)propionic acid

EXAMPLE 5-57

(R)-3-(4'-(N-(3-(1-(2,3-dihydro-1H-inden-2-yl)-2-methylpropan-2-ylamino)-2-hydroxypropyl)-N-methylsulfamoyl)-2',3-difluorobiphenyl-4-yl)propionic acid

EXAMPLE 5-58

(R)-3-(4'-(N-(3-(1-(2,3-dihydro-1H-inden-2-yl)-2-methylpropan-2-ylamino)-2-hydroxypropyl)-N-methylsulfamoyl)-3'-ethyl-3-fluorobiphenyl-4-yl)propionic acid

EXAMPLE 5-59

(R)-3-(2'-chloro-4'-(N-(3-(1-(2,3-dihydro-1H-inden-2-yl)-2-methylpropan-2-ylamino)-2-hydroxypropyl)-N-methylsulfamoyl)-3-fluorobiphenyl-4-yl)propionic acid

EXAMPLE 5-60

(R)-3-(3'-(N-(3-(1-(2,3-dihydro-1H-inden-2-yl)-2-methylpropan-2-ylamino)-2-hydroxypropyl)-N-methylsulfamoyl)-4-fluorobiphenyl-3-yl)propionic acid

EXAMPLE 5-61

(R)-3-(3'-(N-(3-(1-(2,3-dihydro-1H-inden-2-yl)-2-methylpropan-2-ylamino)-2-hydroxypropyl)-N-methylsulfamoyl)-4-fluoro-5'-(trifluoromethyl)biphenyl-3-yl)propionic acid

EXAMPLE 5-62

(R)-3-(4'-(N-(3-(1-(2,3-dihydro-1H-inden-2-yl)-2-methylpropan-2-ylamino)-2-hydroxypropyl)-N-methylsulfamoyl)-4-fluoro-3'-(trifluoromethyl)biphenyl-3-yl)propionic acid

EXAMPLE 5-63

(R)-3-(4'-(N-(3-(1-(2,3-dihydro-1H-inden-2-yl)-2-methylpropan-2-ylamino)-2-hydroxypropyl)-N-methylsulfamoyl)-2'-fluoro-5-methylbiphenyl-2-yl)propionic acid

EXAMPLE 5-64

(R)-3-(4'-(N-(3-(1-(2,3-dihydro-1H-inden-2-yl)-2-methylpropan-2-ylamino)-2-hydroxypropyl)-N-methylsulfamoyl)-3'-ethyl-5-methylbiphenyl-2-yl)propionic acid

EXAMPLE 5-65

(R)-3-(2-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)-4-methylphenyl)propionic acid

EXAMPLE 5-66

(R)-3-(2'-chloro-4'-(N-(2-hydroxy-3-(2-methyl-5-phenylpentan-2-ylamino)propyl)-N-methylsulfamoyl)-5-methylbiphenyl-2-yl)propionic acid

EXAMPLE 5-67

(R)-3-(4'-(N-(2-hydroxy-3-(2-methyl-5-phenylpentan-2-ylamino)propyl)-N-methylsulfamoyl)-2',5-dimethylbiphenyl-2-yl)propionic acid

EXAMPLE 5-68

(R)-3-(3'-ethyl-4'-(N-(2-hydroxy-3-(2-methyl-5-phenylpentan-2-ylamino)propyl)-N-methylsulfamoyl)-5-methylbiphenyl-2-yl)propionic acid

EXAMPLE 5-69

(R)-3-(4'-(N-(2-hydroxy-3-(2-methyl-5-phenylpentan-2-ylamino)propyl)-N-methylsulfamoyl)-2',6-dimethylbiphenyl-3-yl)propionic acid

EXAMPLE 5-70

(R)-3-(2'-chloro-4'-(N-(2-hydroxy-3-(2-methyl-5-phenylpentan-2-ylamino)propyl)-N-methylsulfamoyl)-6-methylbiphenyl-3-yl)propionic acid

EXAMPLE 5-71

(R)-3-(3'-ethyl-4'-(N-(2-hydroxy-3-(2-methyl-5-phenylpentan-2-ylamino)propyl)-N-methylsulfamoyl)-6-methylbiphenyl-3-yl)propionic acid

[Example 5-72] 3-(4,6-difluoro-4'-(N—((R)-2-hydroxy-3-(2-methyl-5-phenylpentan-2-ylamino)propyl)-N-methylsulfamoyl)-2'-methylbiphenyl-2-yl)propionic acid

EXAMPLE 5-73

(R)-3-(3'-ethyl-4,6-difluoro-4'-(N-(2-hydroxy-3-(2-methyl-5-phenylpentan-2-ylamino)propyl)-N-methylsulfamoyl)biphenyl-2-yl)propionic acid

EXAMPLE 5-74

(R)-3-(3'-ethyl-6-fluoro-4'-(N-(2-hydroxy-3-(2-methyl-5-phenylpentan-2-ylamino)propyl)-N-methylsulfamoyl)biphenyl-2-yl)propionic acid

[Example 5-75] 3-(2'-chloro-6-fluoro-4'-(N—((R)-2-hydroxy-3-(2-methyl-5-phenylpentan-2-ylamino)propyl)-N-methylsulfamoyl)biphenyl-2-yl)propionic acid

EXAMPLE 5-76

(R)-3-(3'-ethyl-4'-(N-(2-hydroxy-3-(2-methyl-5-phenylpentan-2-ylamino)propyl)-N-methylsulfamoyl)-2-methylbiphenyl-4-yl)propionic acid

EXAMPLE 5-77

(R)-4-(3'-ethyl-4'-(N-(2-hydroxy-3-(2-methyl-5-phenylpentan-2-ylamino)propyl)-N-methylsulfamoyl)biphenyl-4-yl)butanoic acid

EXAMPLE 5-78

(R)-3-(2-chloro-3'-ethyl-4'-(N-(2-hydroxy-3-(2-methyl-5-phenylpentan-2-ylamino)propyl)-N-methylsulfamoyl)biphenyl-4-yl)propionic acid

EXAMPLE 5-79

(R)-3-(3',6-difluoro-4'-(N-(2-hydroxy-3-(2-meth-yl-5-phenylpentan-2-ylamino)propyl)-N-methylsulfamoyl)biphenyl-2-yl)propionic acid

EXAMPLE 5-80

(R)-3-(3'-(N-(3-(1-(2,3-dihydro-1H-inden-2-yl)-2-methylpropan-2-ylamino)-2-hydroxypropyl)-N-methylsulfamoyl)-2-methyl-5'-(trifluoromethyl)biphenyl-4-yl)propionic acid

EXAMPLE 5-81

(R)-3-(3'-(N-(3-(1-(2,3-dihydro-1H-inden-2-yl)-2-methylpropan-2-ylamino)-2-hydroxypropyl)-N-methylsulfamoyl)-4-fluoro-5'-(trifluoromethyl)biphenyl-2-yl)propionic acid

EXAMPLE 5-82

(R)-3-(3'-(N-(3-(1-(2,3-dihydro-1H-inden-2-yl)-2-methylpropan-2-ylamino)-2-hydroxypropyl)-N-methylsulfamoyl)-5-fluorobiphenyl-2-yl)propionic acid

EXAMPLE 5-83

(R)-3-(3'-(N-(3-(1-(2,3-dihydro-1H-inden-2-yl)-2-methylpropan-2-ylamino)-2-hydroxypropyl)-N-methylsulfamoyl)-5,6-difluorobiphenyl-3-yl)propionic acid

EXAMPLE 5-84

(R)-3-(3'-(N-(3-(1-(2,3-dihydro-1H-inden-2-yl)-2-methylpropan-2-ylamino)-2-hydroxypropyl)-N-methylsulfamoyl)-3,5-dimethylbiphenyl-4-yl)propionic acid

EXAMPLE 5-85

(R)-3-(3'-(N-(3-(1-(2,3-dihydro-1H-inden-2-yl)-2-methylpropan-2-ylamino)-2-hydroxypropyl)-N-methylsulfamoyl)-3-methylbiphenyl-4-yl)propionic acid

EXAMPLE 6-1

(R)-3-(5-(3-(N-(2-hydroxy-3-(2-methyl-5-phenylpentan-2-ylamino)propyl)-N-methylsulfamoyl)-5-(trifluoromethyl)phenyl)-4-methylthiophen-2-yl)propionic acid (Step A) Synthesis of ethyl (R)-3-(5-(3-(N-(2-hydroxy-3-(2-methyl-5-phenylpentan-2-ylamino)propyl)-N-methylsulfamoyl)-5-(trifluoromethyl)phenyl)-4-methylthiophen-2-yl)acrylate According to the method of the patent document (WO03/070686), the target compound was obtained as a crude product from (R)-3-bromo-N-(2-hydroxy-3-(2-methyl-5-phenylpentan-2-ylamino)propyl)-N-methyl-5-(trifluoromethyl)benzenesulfoneamide (Exp. 2-37, 172 mg) and ethyl 3-(5-bromo-4-methylthiophen-2-yl)propionate.

(Step B) Synthesis of ethyl (R)-3-(S-(3-(N-(2-hydroxy-3-(2-methyl-5-phenylpentan-2-ylamino)propyl)-N-methylsulfamoyl)-5-(trifluoromethyl)phenyl)-4-methylthiophen-2-yl)propionate According to the method of Example 5-1 Step B, the target compound was obtained from the compound synthesized from Example 6-1 Step A.

(Step C) Synthesis of (R)-3-(5-(3-(N-(2-hydroxy-3-(2-methyl-5-phenylpentan-2-ylamino)propyl)-N-methylsulfamoyl)-5-(trifluoromethyl)phenyl)-4-methylthiophen-2-yl)propionic acid According to the method of Example 3-1 Step B, the target compound was obtained from the compound synthesized from Example 6-1 Step B.

EXAMPLES 6-2 TO 3

The target compound was obtained in the same manner as Example 6-1 except that ethyl 3-(5-bromo-4-methylthiophen-2-yl)propionate and SM2, which is described in Table 7, were used instead of Exp. 2-37.

EXAMPLE 6-2

(R)-3-(5-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)-4-methylthiophen-2-yl)propionic acid

EXAMPLE 6-3

(R)-3-(5-(3-(N-(3-(1-(2,3-dihydro-1H-inden-2-yl)-2-methylpropan-2-ylamino)-2-hydroxypropyl)-N-methylsulfamoyl)phenyl)-4-methylthiophen-2-yl)propionic acid

EXAMPLE 6-4 TO 7

The target compound was obtained in the same manner as Example 6-1 except that SM2 described in Table 7 was used instead of Exp. 2-37 and ethyl 3-(2-bromopyridin-3-yl)propionate, ethyl 3-(2-bromophenyl)propionic acid, ethyl 3-(3-bromophenyl)propionate, or ethyl 3-(6-bromopyridin-2-yl)propionate was used instead of ethyl 3-(5-bromo-4-methylthiophen-2-yl)propionate.

EXAMPLE 6-4

(R)-3-(2-(3,5-dichloro-4-(N-(2-hydroxy-3-(2-methyl-5-phenylpentan-2-ylamino)propyl)-N-methylsulfamoyl)phenyl)pyridin-3-yl)propionic acid

EXAMPLE 6-5

(R)-3-(3',5'-dichloro-4'-(N-(2-hydroxy-3-(2-methyl-5-phenylpentan-2-ylamino)propyl)-N-methylsulfamoyl)biphenyl-2-yl)propionic acid

EXAMPLE 6-6

(R)-3-(3',5'-dichloro-4'-(N-(2-hydroxy-3-(2-methyl-5-phenylpentan-2-ylamino)propyl)-N-methylsulfamoyl)biphenyl-3-yl)propionic acid

EXAMPLE 6-7

(R)-3-(6-(3,5-dichloro-4-(N-(2-hydroxy-3-(2-methyl-5-phenylpentan-2-ylamino)propyl)-N-methylsulfamoyl)phenyl)pyridin-2-yl)propionic acid Hereinbelow, structures of the compounds of Example 6-1 to 6-7 (Exp. 6-1 to Exp. 6-7) are shown.

Exp. 6-1

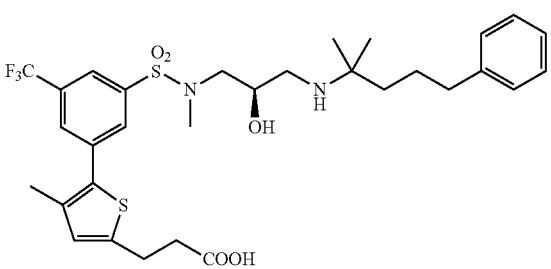

Exp. 6-2

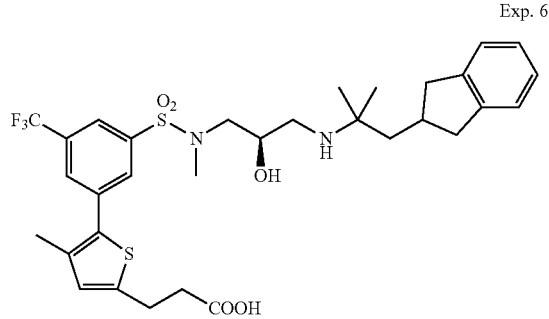

Exp. 6-3

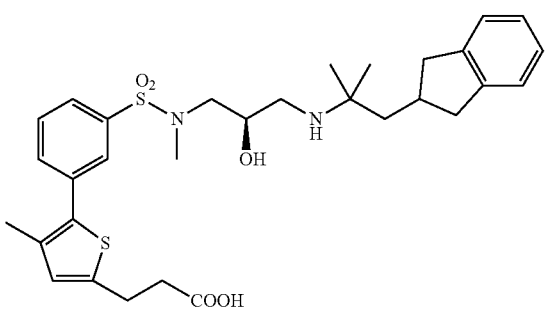

Exp. 6-4

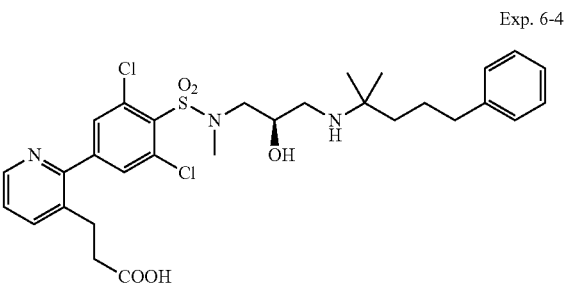

Exp. 6-5

Exp. 6-6

Exp. 6-7

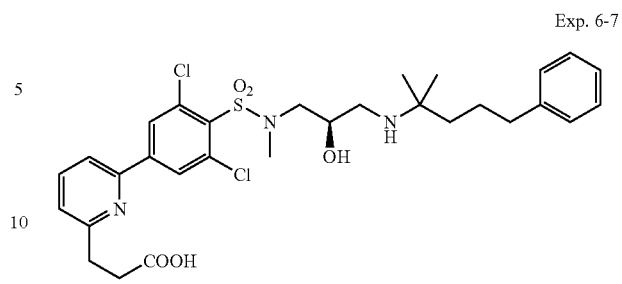

EXAMPLES 7-1 TO 2

The target compound was obtained in the same manner as Example 6-1 Step A and Step C except that SM2 described in Table 7 was used instead of Exp. 2-37 and ethyl 3-(3-methyl-2-(trifluoromethylsulfonyloxy)phenyl)propionate was used instead of ethyl 3-(5-bromo-4-methylthiophen-2-yl)propionate.

TABLE 7

| Exp. | SM2 | LCMS | | |
| | | method | Rtime | Mass |
| --- | --- | --- | --- | --- |
| 6-1 | Exp. 2-37 | B | 1.48 | 641 |
| 6-2 | Exp. 2-35 | B | 1.54 | 653 |
| 6-3 | Exp. 2-5 | B | 1.43 | 585 |
| 6-4 | Exp. 2-19 | B | 1.40 | 622 |
| 6-5 | Exp. 2-19 | A | 3.55 | 621 |
| 6-6 | Exp. 2-19 | A | 3.45 | 621 |
| 6-7 | Exp. 2-19 | B | 1.56 | 622 |
| 7-1 | Exp. 2-16 | B | 1.90 | 607 |
| 7-2 | Exp. 2-17 | B | 1.58 | 595 |

Hereinbelow, structures of the compounds of Example to 7-2 (Exp. 7-1 to Exp. 7-2) are shown.

Exp. 7-1

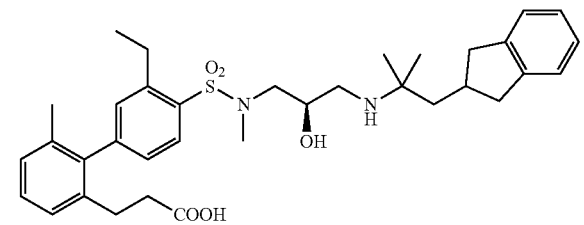

Exp. 7-2

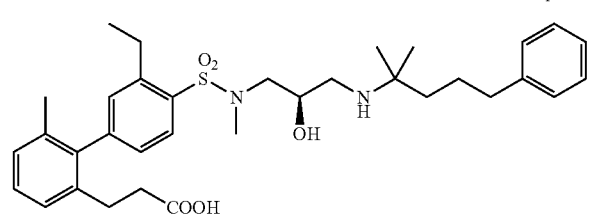

EXAMPLE 7-1

(R)-3-(4'-(N-(3-(1-(2,3-dihydro-1H-inden-2-yl)-2-methyl-propan-2-ylamino)-2-hydroxypropyl)-N-methylsulfamoyl)-3'-ethyl-6-methylbiphenyl-2-yl)propionic acid

EXAMPLE 7-2

(R)-3-(3'-ethyl-4'-(N-(2-hydroxy-3-(2-methyl-5-phenylpentan-2-ylamino)propyl)-N-methylsulfamoyl)-6-methylbiphenyl-2-yl)propionic acid

EXAMPLE 8-1

(R)-3-(5-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)thiophen-2-yl)propionic acid (Step A) Synthesis of ethyl (R)-3-(5-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)thiophen-2-yl)acrylate The target compound was obtained in the same manner as Example 2-1 except that Exp. 1-56 and am2 were used instead of Exp. 1-1 and am1, respectively.

(Step B) Synthesis of ethyl (R)-3-(5-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)thiophen-2-yl)propionate According to the method of Example 5-1 Step B, the target compound was obtained from the compound synthesized from Example 8-1 Step A.

(Step C) Synthesis of (R)-3-(5-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)thiophen-2-yl)propionic acid According to the method of Example 3-1 Step B, the target compound was obtained from the compound synthesized from Example 8-1 Step B.

EXAMPLES 8-2 TO 24

The target compound was obtained in the same manner as Example 8-1 with combinations shown in Table 8 except that SM1 and AM were used instead of Exp. 1-56 and am2, respectively.

TABLE 8

| Exp. | SM1 | AM | LCMS method | Rtime | Mass |
|---|---|---|---|---|---|
| 8-1 | Exp. 1-56 | am2 | B | 1.47 | 639 |
| 8-2 | Exp. 1-54 | am2 | B | 1.40 | 634 |
| 8-3 | Exp. 1-54 | am5 | B | 1.40 | 622 |
| 8-4 | Exp. 1-57 | am2 | B | 1.40 | 571 |
| 8-5 | Exp. 1-34 | am5 | B | 1.40 | 545 |
| 8-6 | Exp. 1-34 | am14 | B | 1.40 | 551 |
| 8-7 | Exp. 1-34 | am22 | B | 1.56 | 559 |
| 8-8 | Exp. 1-34 | am4 | B | 1.34 | 535 |
| 8-9 | Exp. 1-34 | am9 | B | 1.45 | 564 |
| 8-10 | Exp. 1-34 | am10 | B | 1.45 | 564 |

TABLE 8-continued

| Exp. | SM1 | AM | LCMS method | Rtime | Mass |
|---|---|---|---|---|---|
| 8-11 | Exp. 1-34 | am11 | B | 1.45 | 564 |
| 8-12 | Exp. 1-34 | am15 | B | 1.40 | 552 |
| 8-13 | Exp. 1-43 | am15 | B | 1.42 | 605 |
| 8-14 | Exp. 1-43 | am9 | B | 1.48 | 617 |
| 8-15 | Exp. 1-52 | am2 | B | 1.48 | 634 |
| 8-16 | Exp. 1-43 | am20 | B | 1.28 | 618 |
| 8-17 | Exp. 1-43 | am33 | B | 1.24 | 619 |
| 8-18 | Exp. 1-43 | am27 | B | 1.18 | 618 |
| 8-19 | Exp. 1-43 | am19 | B | 1 | 601 |
| 8-20 | Exp. 1-50 | am20 | B | 1.24 | 658 |
| 8-21 | Exp. 1-50 | am33 | B | 1.24 | 658 |
| 8-22 | Exp. 1-50 | am27 | B | 1.19 | 658 |
| 8-23 | Exp. 1-50 | am19 | B | 0.94 | 640 |
| 8-24 | Exp. 1-43 | am14 | B | 1.41 | 605 |

Hereinbelow, structures of the compounds of Example to 8-24 (Exp. 8-1 to Exp. 8-24) are shown.

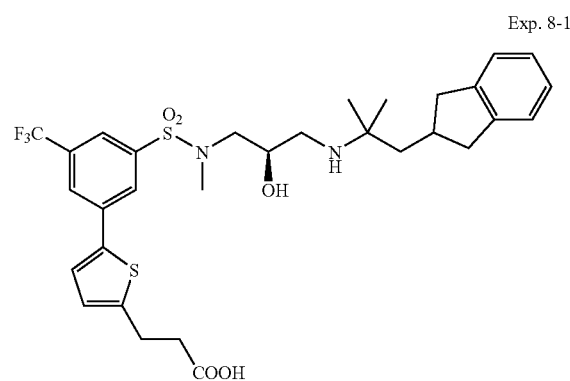

Exp. 8-4
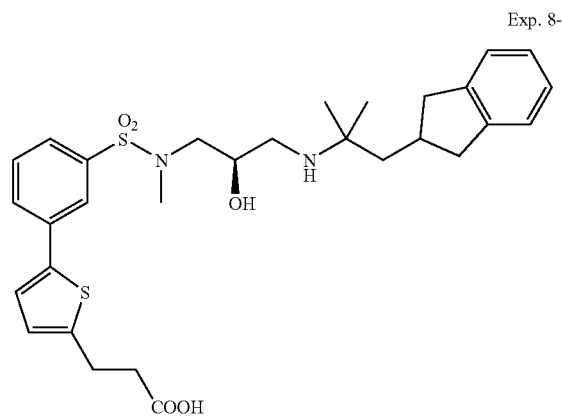
Exp. 8-5
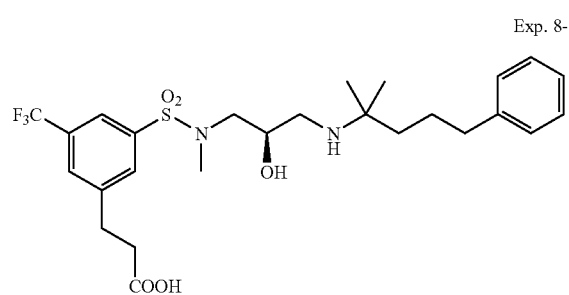
Exp. 8-6
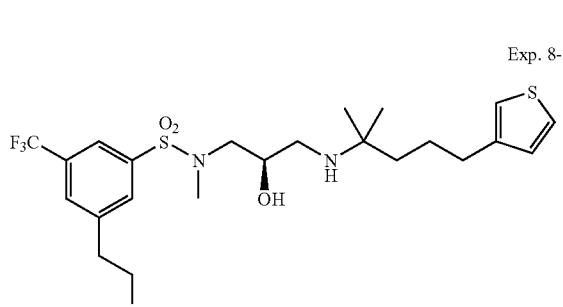
Exp. 8-7
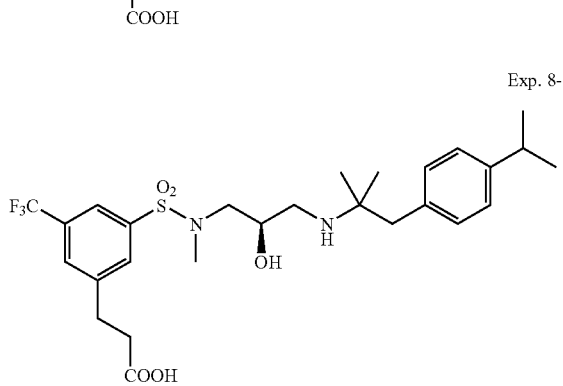
Exp. 8-8
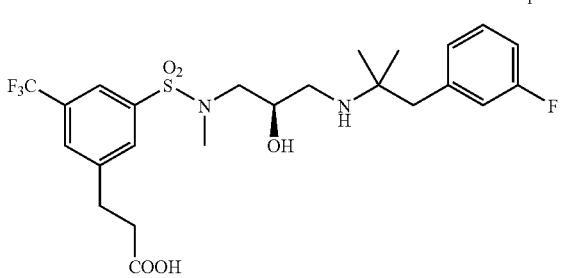
Exp. 8-9
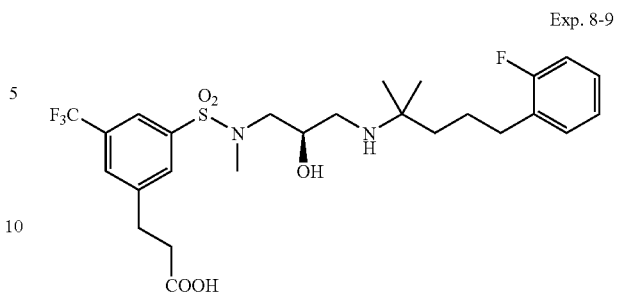
Exp. 8-10
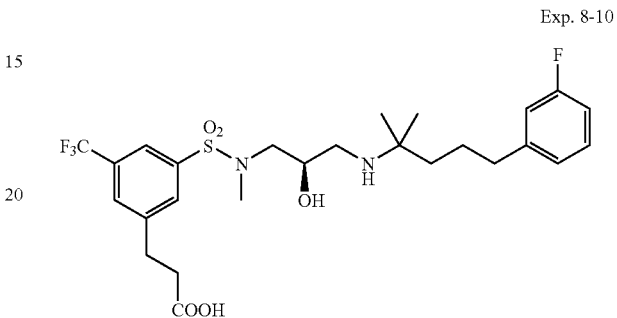
Exp. 8-11
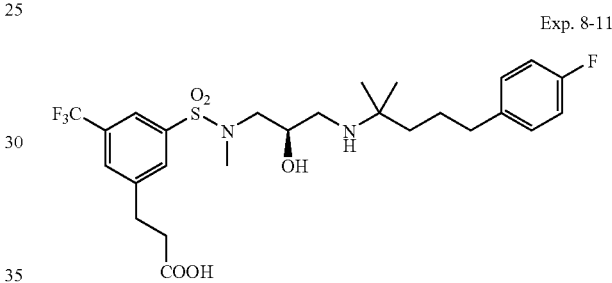
Exp. 8-12
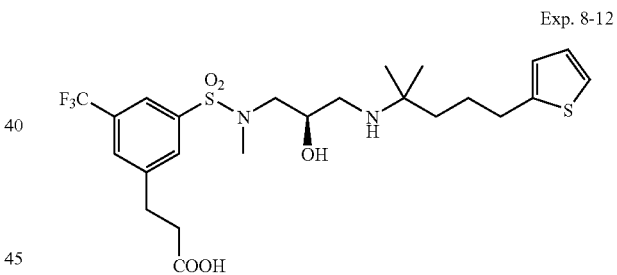
Exp. 8-13
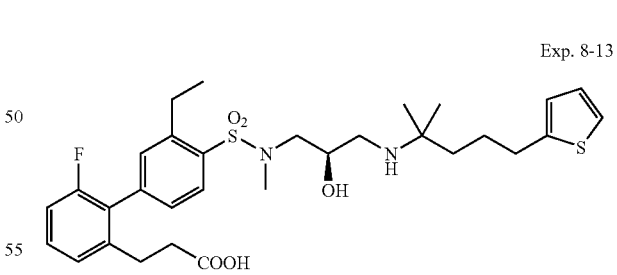
Exp. 8-14
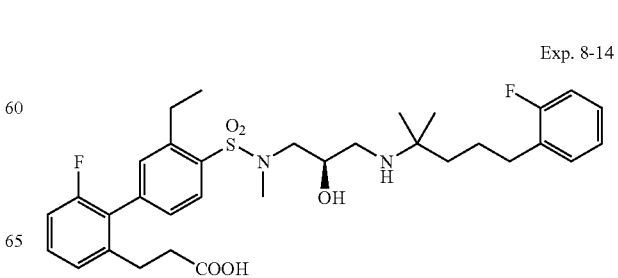

Exp. 8-15
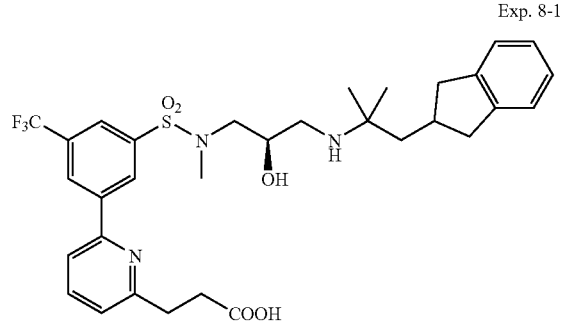

Exp. 8-16
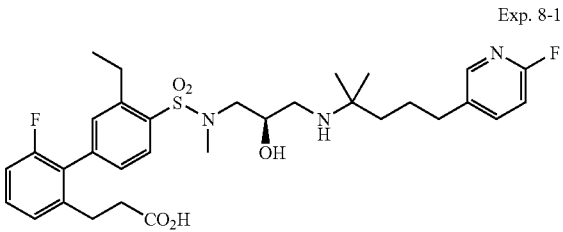

Exp. 8-17
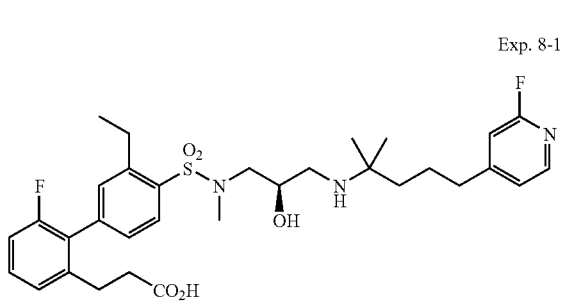

Exp. 8-18
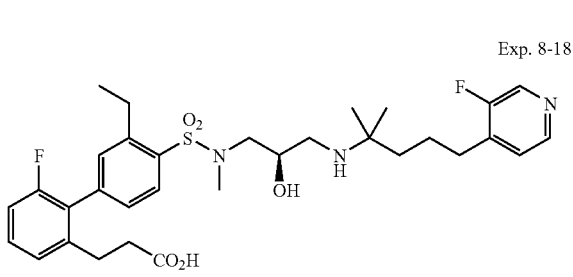

Exp. 8-19
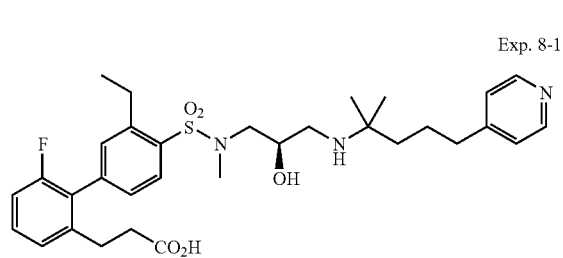

Exp. 8-20
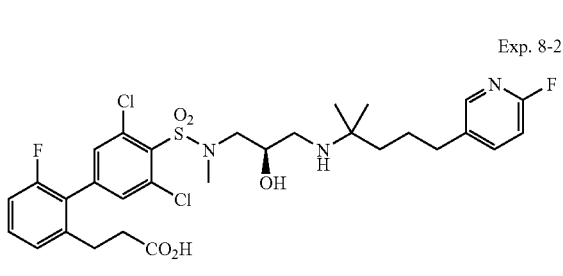

Exp. 8-21
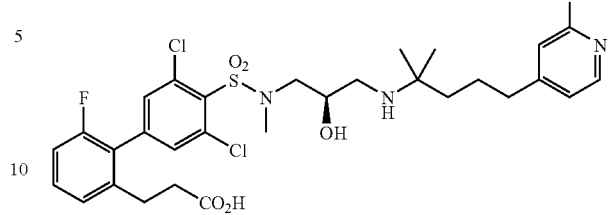

Exp. 8-22

Exp. 8-23

Exp. 8-24

EXAMPLE 8-2

(R)-3-(2-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)pyridin-3-yl)propionic acid

EXAMPLE 8-3

(R)-3-(2-(3-(N-(2-hydroxy-3-(2-methyl-5-phenylpentan-2-ylamino)propyl)-N-methylsulfamoyl)-5-(trifluoromethyl)phenyl)pyridin-3-yl)propionic acid

EXAMPLE 8-4

(R)-3-(5-(3-(N-(3-(1-(2,3-dihydro-1H-inden-2-yl)-2-methylpropan-2-ylamino)-2-hydroxypropyl)-N-methylsulfamoyl)phenyl)thiophen-2-yl)propionic acid

EXAMPLE 8-5

(R)-3-(3-(N-(2-hydroxy-3-(2-methyl-5-phenylpentan-2-ylamino)propyl)-N-methylsulfamoyl)-5-(trifluoromethyl)phenyl)propionic acid

EXAMPLE 8-6

(R)-3-(3-(N-(2-hydroxy-3-(2-methyl-5-(thiophen-3-yl)pentan-2-ylamino)propyl)-N-methylsulfamoyl)-5-(trifluoromethyl)phenyl)propionic acid

EXAMPLE 8-7

(R)-3-(3-(N-(2-hydroxy-3-(1-(4-isopropylphenyl)-2-methylpropan-2-ylamino)propyl)-N-methylsulfamoyl)-5-(trifluoromethyl)phenyl)propionic acid

EXAMPLE 8-8

(R)-3-(3-(N-(3-(1-(3-fluorophenyl)-2-methylpropan-2-ylamino)-2-hydroxypropyl)-N-methylsulfamoyl)-5-(trifluoromethyl-)phenyl)propionic acid

EXAMPLE 8-9

(R)-3-(3-(N-(3-(5-(2-fluorophenyl)-2-methylpentan-2-ylamino)-2,hydroxypropyl)-N-methylsulfamoyl)-5-(trifluoromethyl)phenyl)propionic acid

EXAMPLE 8-10

(R)-3-(3-(N-(3-(5-(3-fluorophenyl)-2-methylpentan-2-ylamino)-2-hydroxypropyl)-N-methylsulfamoyl)-5-(trifluoromethyl)phenyl)propionic acid

EXAMPLE 8-11

(R)-3-(3-(N-(3-(5-(4-fluorophenyl)-2-methylpentan-2-ylamino)-2-hydroxypropyl)-N-methylsulfamoyl)-5-(trifluoromethyl)phenyl)propionic acid

EXAMPLE 8-12

(R)-3-(3-(N-(2-hydroxy-3-(2-methyl-5-(thiophen-2-yl)pentan-2-ylamino)propyl)-N-methylsulfamoyl)-5-(trifluoromethyl)phenyl)propionic acid

EXAMPLE 8-13

(R)-3-(3'-ethyl-6-fluoro-4'-(N-(2-hydroxy-3-(2-methyl-5-(thiophen-2-yl)pentan-2-ylamino)propyl)-N-methylsulfamoyl)biphenyl-2-yl)propionic acid

EXAMPLE 8-14

(R)-3-(3'-ethyl-6-fluoro-4'-(N-(3-(5-(2-fluorophenyl)-2-methylpentan-2-ylamino)-2-hydroxypropyl)-N-methylsulfamoyl)biphenyl-2-yl)propionic acid

EXAMPLE 8-15

(R)-3-(6-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)pyridin-2-yl)propionic acid

EXAMPLE 8-16

(R)-3-(3'-ethyl-6-fluoro-4'-(N-(3-(5-(6-fluoropyridin-3-yl)-2-methylpentan-2-ylamino)-2-hydroxypropyl)-N-methylsulfamoyl)biphenyl-2-yl)propionic acid

EXAMPLE 8-17

(R)-3-(3'-ethyl-6-fluoro-4'-(N-(3-(5-(2-fluoropyridin-4-yl)-2-methylpentan-2-ylamino)-2-hydroxypropyl)-N-methylsulfamoyl)biphenyl-2-yl)propionic acid

EXAMPLE 8-18

(R)-3-(3'-ethyl-6-fluoro-4'-(N-(3-(5-(3-fluoropyridin-4-yl)-2-methylpentan-2-ylamino)-2-hydroxypropyl)-N-methylsulfamoyl)biphenyl-2-yl)propionic acid

EXAMPLE 8-19

(R)-3-(3'-ethyl-6-fluoro-4'-(N-(2-hydroxy-3-(2-methyl-5-(pyridin-4-yl)pentan-2-ylamino)propyl)-N-methylsulfamoyl)biphenyl-2-yl)propionic acid

EXAMPLE 8-20

(R)-3-(3',5'-dichloro-6-fluoro-4'-(N-(3-(5-(6-fluoropyridin-3-yl)-2-methylpentan-2-ylamino)-2-hydroxypropyl)-N-methylsulfamoyl)biphenyl-2-yl)propionic acid

EXAMPLE 8-21

(R)-3-(3',5'-dichloro-6-fluoro-4'-(N-(3-(5-(2-fluoropyridin-4-yl)-2-methylpentan-2-ylamino)-2-hydroxypropyl)-N-methylsulfamoyl)biphenyl-2-yl)propionic acid

EXAMPLE 8-22

(R)-3-(3',5'-dichloro-6-fluoro-4'-(N-(3-(5-(3-fluoropyridin-4-yl)-2-methylpentan-2-ylamino)-2-hydroxypropyl)-N-methylsulfamoyl)biphenyl-2-yl)propionic acid

EXAMPLE 8-23

(R)-3-(3',5'-dichloro-6-fluoro-4'-(N-(2-hydroxy-3-(2-methyl-5-(pyridin-4-yl)pentan-2-ylamino)propyl)-N-methylsulfamoyl)biphenyl-2-yl)propionic acid

EXAMPLE 8-24

(R)-3-(3'-ethyl-6-fluoro-4'-(N-(2-hydroxy-3-(2-methyl-5-(thiophen-3-yl)pentan-2-ylamino)propyl)-N-methylsulfamoyl)biphenyl-2-yl)propionic acid

EXAMPLES 9-1 TO 180

The target compound was obtained in the same manner as Example 8-1 Step A and Step C with combinations shown in Table 9 except that SM1 and AM were used instead of Exp. 1-56 and am2, respectively.

TABLE 9

| Exp. | SM1 | AM | LCMS method | Rtime | Mass |
|---|---|---|---|---|---|
| 9-1 | Exp. 1-60 | am5 | B | 1.78 | 627 |
| 9-2 | Exp. 1-60 | am2 | B | 1.78 | 639 |
| 9-3 | Exp. 1-59 | am5 | B | 1.72 | 627 |
| 9-4 | Exp. 1-59 | am2 | B | 1.75 | 639 |
| 9-5 | Exp. 1-58 | am5 | B | 1.34 | 582 |
| 9-6 | Exp. 1-58 | am14 | B | 1.31 | 588 |
| 9-7 | Exp. 1-58 | am2 | B | 1.35 | 594 |
| 9-8 | Exp. 1-38 | am14 | B | 1.45 | 565 |

TABLE 9-continued

| Exp. | SM1 | AM | method | Rtime | Mass |
|---|---|---|---|---|---|
| 9-9 | Exp. 1-38 | am5 | B | 1.53 | 559 |
| 9-10 | Exp. 1-38 | am13 | B | 1.56 | 593 |
| 9-11 | Exp. 1-38 | am17 | B | 1.04 | 560 |
| 9-12 | Exp. 1-38 | am9 | B | 1.44 | 578 |
| 9-13 | Exp. 1-38 | am10 | B | 1.44 | 578 |
| 9-14 | Exp. 1-38 | am11 | B | 1.47 | 578 |
| 9-15 | Exp. 1-38 | am15 | B | 1.42 | 565 |
| 9-16 | Exp. 1-38 | am18 | B | 1.03 | 560 |
| 9-17 | Exp. 1-38 | am19 | B | 0.98 | 560 |
| 9-18 | Exp. 1-39 | am9 | B | 1.44 | 549 |
| 9-19 | Exp. 1-39 | am11 | B | 1.43 | 549 |
| 9-20 | Exp. 1-39 | am15 | B | 1.36 | 537 |
| 9-21 | Exp. 1-39 | am14 | B | 1.36 | 537 |
| 9-22 | Exp. 1-38 | am12 | B | 1.32 | 595 |
| 9-23 | Exp. 1-38 | am20 | B | 1.21 | 578 |
| 9-24 | Exp. 1-41 | am5 | B | 1.36 | 560 |
| 9-25 | Exp. 1-41 | am15 | B | 1.32 | 565 |
| 9-26 | Exp. 1-41 | am2 | B | 1.35 | 571 |
| 9-27 | Exp. 1-41 | am9 | B | 1.35 | 577 |
| 9-28 | Exp. 1-27 | am4 | B | 1.32 | 518 |
| 9-29 | Exp. 1-28 | am5 | B | 1.31 | 532 |
| 9-30 | Exp. 1-51 | am24 | B | 1.31 | 525 |
| 9-31 | Exp. 1-51 | am22 | B | 1.39 | 539 |
| 9-32 | Exp. 1-51 | am5 | B | 1.29 | 525 |
| 9-33 | Exp. 1-51 | am30 | B | 1.36 | 565 |
| 9-34 | Exp. 1-46 | am24 | B | 1.35 | 553 |
| 9-35 | Exp. 1-46 | am22 | B | 1.42 | 567 |
| 9-36 | Exp. 1-46 | am5 | B | 1.32 | 553 |
| 9-37 | Exp. 1-46 | am30 | B | 1.39 | 593 |
| 9-38 | Exp. 1-48 | am28 | B | 1.31 | 593 |
| 9-39 | Exp. 1-48 | am29 | B | 1.30 | 593 |
| 9-40 | Exp. 1-48 | am8 | B | 1.28 | 567 |
| 9-41 | Exp. 1-44 | am28 | B | 1.28 | 579 |
| 9-42 | Exp. 1-44 | am29 | B | 1.28 | 579 |
| 9-43 | Exp. 1-44 | am8 | B | 1.32 | 553 |
| 9-44 | Exp. 1-46 | am28 | B | 1.32 | 593 |
| 9-45 | Exp. 1-46 | am29 | B | 1.30 | 593 |
| 9-46 | Exp. 1-46 | am8 | B | 1.35 | 567 |
| 9-47 | Exp. 1-48 | am21 | B | 1.46 | 553 |
| 9-48 | Exp. 1-48 | am23 | B | 1.53 | 581 |
| 9-49 | Exp. 1-48 | am25 | B | 1.29 | 555 |
| 9-50 | Exp. 1-48 | am26 | B | 1.38 | 571 |
| 9-51 | Exp. 1-44 | am21 | B | 1.39 | 539 |
| 9-52 | Exp. 1-44 | am23 | B | 1.48 | 567 |
| 9-53 | Exp. 1-44 | am25 | B | 1.23 | 541 |
| 9-54 | Exp. 1-44 | am26 | B | 1.31 | 557 |
| 9-55 | Exp. 1-47 | am5 | B | 1.45 | 621 |
| 9-56 | Exp. 1-49 | am5 | B | 1.46 | 621 |
| 9-57 | Exp. 1-48 | am14 | B | 1.25 | 559 |
| 9-58 | Exp. 1-44 | am14 | B | 1.17 | 545 |
| 9-59 | Exp. 1-48 | am6 | B | 1.58 | 567 |
| 9-60 | Exp. 1-48 | am7 | B | 1.56 | 567 |
| 9-61 | Exp. 1-44 | am6 | B | 1.50 | 553 |
| 9-62 | Exp. 1-44 | am7 | B | 1.53 | 553 |
| 9-63 | Exp. 1-48 | am16 | B | 1.39 | 573 |
| 9-64 | Exp. 1-48 | am9 | B | 1.37 | 571 |
| 9-65 | Exp. 1-48 | am10 | B | 1.37 | 571 |
| 9-66 | Exp. 1-48 | am11 | B | 1.43 | 571 |
| 9-67 | Exp. 1-48 | am15 | B | 1.32 | 559 |
| 9-68 | Exp. 1-44 | am16 | B | 1.29 | 559 |
| 9-69 | Exp. 1-44 | am9 | B | 1.32 | 557 |
| 9-70 | Exp. 1-44 | am10 | B | 1.31 | 557 |
| 9-71 | Exp. 1-44 | am11 | B | 1.32 | 557 |
| 9-72 | Exp. 1-44 | am15 | B | 1.26 | 545 |
| 9-73 | Exp. 1-47 | am14 | B | 1.61 | 627 |
| 9-74 | Exp. 1-47 | am22 | B | 1.70 | 635 |
| 9-75 | Exp. 1-49 | am14 | B | 1.67 | 627 |
| 9-76 | Exp. 1-49 | am22 | B | 1.69 | 635 |
| 9-77 | Exp. 1-48 | am5 | B | 1.45 | 553 |
| 9-78 | Exp. 1-44 | am5 | B | 1.40 | 539 |
| 9-79 | Exp. 1-48 | am13 | B | 1.45 | 587 |
| 9-80 | Exp. 1-44 | am13 | B | 1.39 | 573 |
| 9-81 | Exp. 1-49 | am13 | B | 1.58 | 655 |
| 9-82 | Exp. 1-49 | am9 | B | 1.51 | 639 |
| 9-83 | Exp. 1-49 | am10 | B | 1.48 | 639 |
| 9-84 | Exp. 1-49 | am11 | B | 1.51 | 639 |
| 9-85 | Exp. 1-49 | am15 | B | 1.47 | 627 |
| 9-86 | Exp. 1-49 | am18 | B | 1.15 | 622 |
| 9-87 | Exp. 1-49 | am19 | B | 1.11 | 622 |
| 9-88 | Exp. 1-45 | am13 | B | 1.51 | 615 |
| 9-89 | Exp. 1-45 | am9 | B | 1.47 | 599 |
| 9-90 | Exp. 1-45 | am10 | B | 1.45 | 599 |
| 9-91 | Exp. 1-45 | am11 | B | 1.50 | 599 |
| 9-92 | Exp. 1-45 | am15 | B | 1.42 | 588 |
| 9-93 | Exp. 1-45 | am18 | B | 1.06 | 582 |
| 9-94 | Exp. 1-45 | am17 | B | 1.11 | 582 |
| 9-95 | Exp. 1-45 | am14 | B | 1.47 | 587 |
| 9-96 | Exp. 1-49 | am17 | B | 1.29 | 622 |
| 9-97 | Exp. 1-45 | am19 | B | 1.09 | 582 |
| 9-98 | Exp. 1-40 | am5 | B | 1.32 | 565 |
| 9-99 | Exp. 1-40 | am9 | B | 1.33 | 583 |
| 9-100 | Exp. 1-40 | am2 | B | 1.32 | 577 |
| 9-101 | Exp. 1-40 | am12 | B | 1.32 | 601 |
| 9-102 | Exp. 1-31 | am5 | B | 1.16 | 496 |
| 9-103 | Exp. 1-31 | am9 | B | 1.18 | 514 |
| 9-104 | Exp. 1-31 | am2 | B | 1.18 | 508 |
| 9-105 | Exp. 1-31 | am12 | B | 1.18 | 532 |
| 9-106 | Exp. 1-31 | am31 | B | 1.19 | 519 |
| 9-107 | Exp. 1-35 | am5 | B | 1.21 | 510 |
| 9-108 | Exp. 1-35 | am9 | B | 1.21 | 528 |
| 9-109 | Exp. 1-35 | am2 | B | 1.24 | 521 |
| 9-110 | Exp. 1-35 | am14 | B | 1.18 | 515 |
| 9-111 | Exp. 1-35 | am15 | B | 1.18 | 515 |
| 9-112 | Exp. 1-35 | am12 | B | 1.23 | 545 |
| 9-113 | Exp. 1-29 | am5 | B | 1.24 | 511 |
| 9-114 | Exp. 1-29 | am9 | B | 1.23 | 529 |
| 9-115 | Exp. 1-29 | am2 | B | 1.25 | 523 |
| 9-116 | Exp. 1-29 | am14 | B | 1.21 | 517 |
| 9-117 | Exp. 1-29 | am15 | B | 1.21 | 517 |
| 9-118 | Exp. 1-29 | am12 | B | 1.24 | 547 |
| 9-119 | Exp. 1-29 | am31 | B | 1.26 | 535 |
| 9-120 | Exp. 1-30 | am5 | B | 1.27 | 525 |
| 9-121 | Exp. 1-30 | am9 | B | 1.27 | 543 |
| 9-122 | Exp. 1-30 | am2 | B | 1.31 | 537 |
| 9-123 | Exp. 1-30 | am14 | B | 1.24 | 531 |
| 9-124 | Exp. 1-30 | am15 | B | 1.24 | 531 |
| 9-125 | Exp. 1-30 | am12 | B | 1.28 | 561 |
| 9-126 | Exp. 1-37 | am9 | B | 1.25 | 538 |
| 9-127 | Exp. 1-37 | am2 | B | 1.25 | 532 |
| 9-128 | Exp. 1-37 | am14 | B | 1.21 | 525 |
| 9-129 | Exp. 1-37 | am15 | B | 1.22 | 525 |
| 9-130 | Exp. 1-37 | am12 | B | 1.25 | 555 |
| 9-131 | Exp. 1-37 | am31 | B | 1.26 | 543 |
| 9-132 | Exp. 1-32 | am5 | B | 1.32 | 561 |
| 9-133 | Exp. 1-32 | am9 | B | 1.31 | 579 |
| 9-134 | Exp. 1-32 | am2 | B | 1.32 | 573 |
| 9-135 | Exp. 1-32 | am14 | B | 1.28 | 567 |
| 9-136 | Exp. 1-32 | am15 | B | 1.28 | 567 |
| 9-137 | Exp. 1-32 | am12 | B | 1.32 | 597 |
| 9-138 | Exp. 1-32 | am31 | B | 1.32 | 585 |
| 9-139 | Exp. 1-36 | am5 | B | 1.33 | 575 |
| 9-140 | Exp. 1-36 | am9 | B | 1.33 | 593 |
| 9-141 | Exp. 1-36 | am2 | B | 1.34 | 587 |
| 9-142 | Exp. 1-36 | am14 | B | 1.31 | 581 |
| 9-143 | Exp. 1-36 | am15 | B | 1.31 | 581 |
| 9-144 | Exp. 1-36 | am12 | B | 1.33 | 611 |
| 9-145 | Exp. 1-33 | am12 | B | 1.28 | 582 |
| 9-146 | Exp. 1-33 | am31 | B | 1.28 | 569 |
| 9-147 | Exp. 1-33 | am32 | B | 1.32 | 581 |
| 9-148 | Exp. 1-63 | am5 | B | 1.31 | 622 |
| 9-149 | Exp. 1-63 | am9 | B | 1.27 | 640 |
| 9-150 | Exp. 1-63 | am2 | B | 1.3 | 634 |
| 9-151 | Exp. 1-63 | am14 | B | 1.25 | 628 |
| 9-152 | Exp. 1-63 | am15 | B | 1.25 | 628 |
| 9-153 | Exp. 1-63 | am12 | B | 1.3 | 658 |
| 9-154 | Exp. 1-63 | am19 | B | 0.86 | 623 |
| 9-155 | Exp. 1-64 | am5 | B | 1.36 | 622 |
| 9-156 | Exp. 1-64 | am9 | B | 1.36 | 641 |
| 9-157 | Exp. 1-64 | am2 | B | 1.37 | 634 |
| 9-158 | Exp. 1-64 | am15 | B | 1.37 | 628 |
| 9-159 | Exp. 1-62 | am5 | B | 1.24 | 588 |
| 9-160 | Exp. 1-62 | am9 | B | 1.25 | 606 |

TABLE 9-continued
| | | | LCMS | | |
|---|---|---|---|---|---|
| Exp. | SM1 | AM | method | Rtime | Mass |
| 9-161 | Exp. 1-62 | am2 | B | 1.28 | 600 |
| 9-162 | Exp. 1-62 | am15 | B | 1.24 | 594 |
| 9-163 | Exp. 1-65 | am5 | B | 1.22 | 622 |
| 9-164 | Exp. 1-65 | am9 | B | 1.22 | 640 |
| 9-165 | Exp. 1-42 | am5 | B | 1.35 | 573 |
| 9-166 | Exp. 1-42 | am9 | B | 1.36 | 591 |
| 9-167 | Exp. 1-42 | am2 | B | 1.37 | 585 |
| 9-168 | Exp. 1-58 | am9 | B | 1.31 | 600 |
| 9-169 | Exp. 1-61 | am14 | B | 1.32 | 628 |
| 9-170 | Exp. 1-61 | am2 | B | 1.36 | 634 |
| 9-171 | Exp. 1-53 | am2 | B | 1.43 | 606 |
| 9-172 | Exp. 1-53 | am5 | B | 1.42 | 594 |
| 9-173 | Exp. 1-67 | am5 | B | 1.25 | 529 |
| 9-174 | Exp. 1-67 | am9 | B | 1.24 | 547 |
| 9-175 | Exp. 1-67 | am2 | B | 1.27 | 541 |
| 9-176 | Exp. 1-67 | am14 | B | 1.22 | 535 |
| 9-177 | Exp. 1-67 | am15 | B | 1.21 | 535 |
| 9-178 | Exp. 1-67 | am12 | B | 1.27 | 565 |
| 9-179 | Exp. 1-55 | am5 | B | 1.34 | 547 |
| 9-180 | Exp. 1-68 | am5 | A | 3.27 | 546 |
Hereinbelow, structures of the compounds of Example to 9-180 (Exp. 9-1 to Exp. 9-180) are shown.
Exp. 9-1
Exp. 9-2
Exp. 9-3
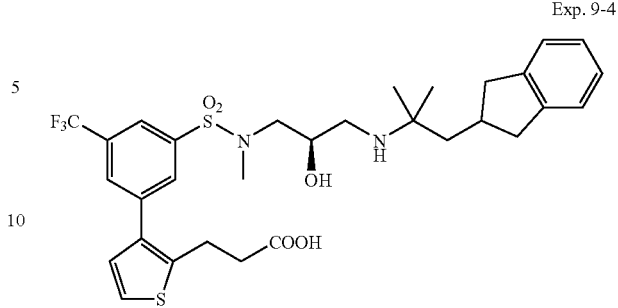
Exp. 9-4
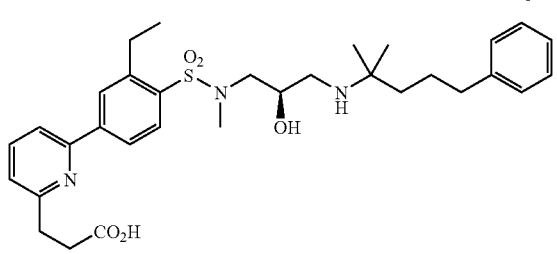
Exp. 9-5
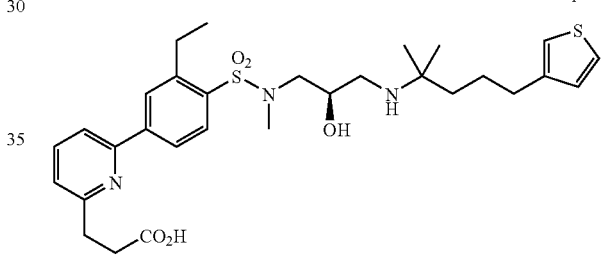
Exp. 9-6
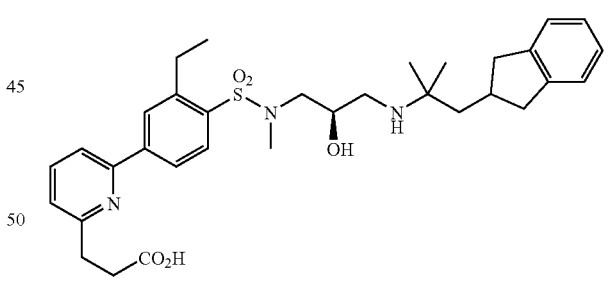
Exp. 9-7
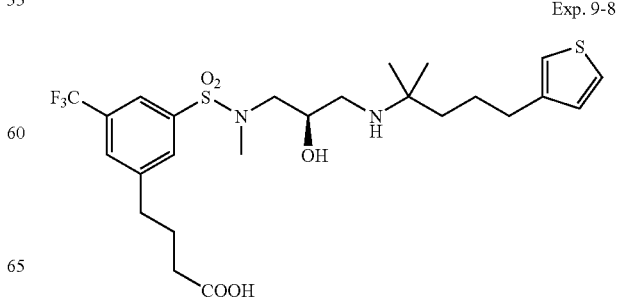
Exp. 9-8

Exp. 9-9
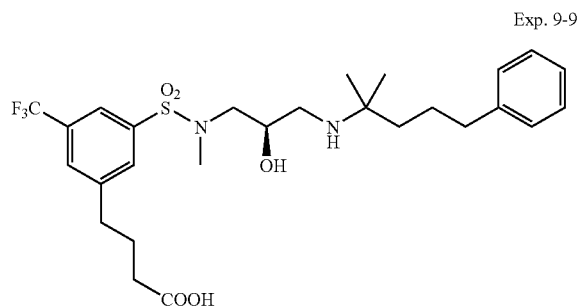
Exp. 9-10
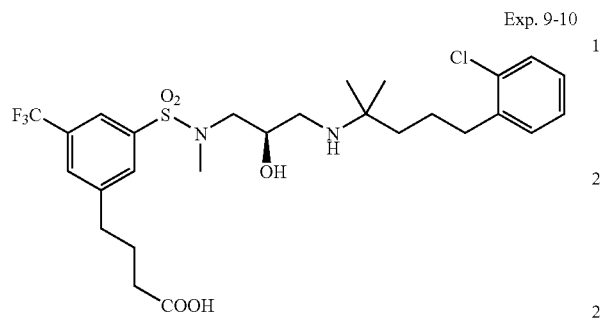
Exp. 9-11
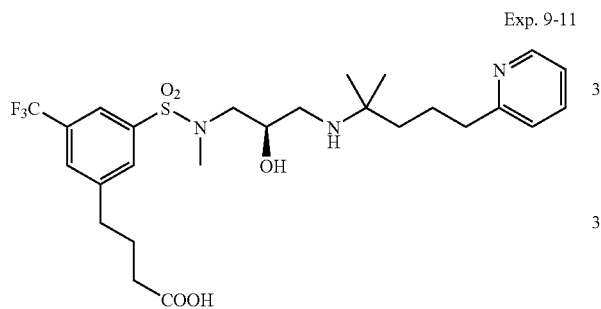
Exp. 9-12
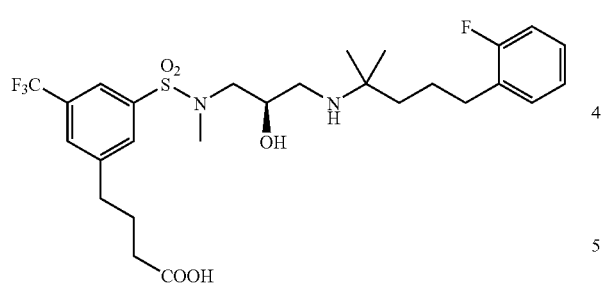
Exp. 9-13
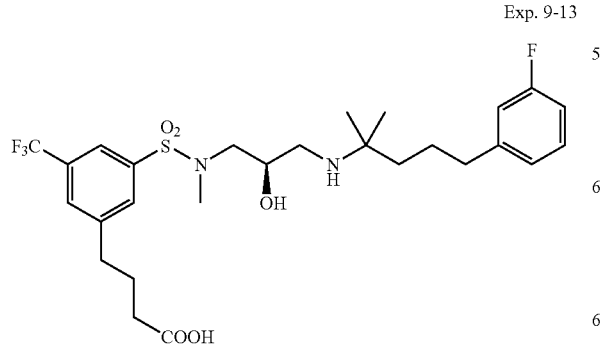
Exp. 9-14
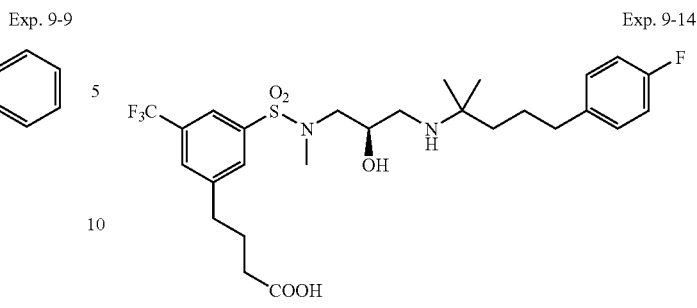
Exp. 9-15
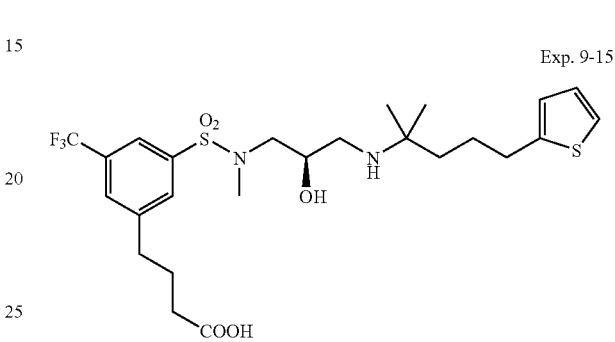
Exp. 9-16
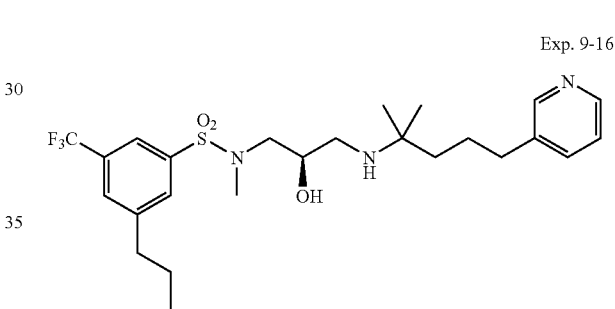
Exp. 9-17
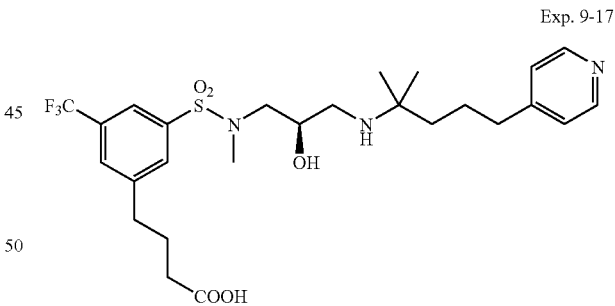
Exp. 9-18
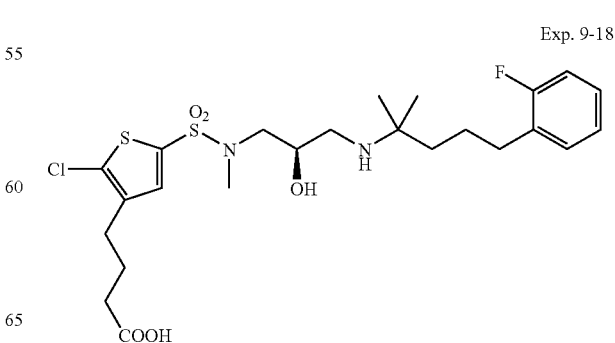

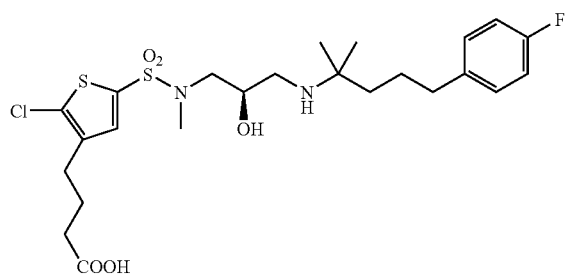
Exp. 9-19
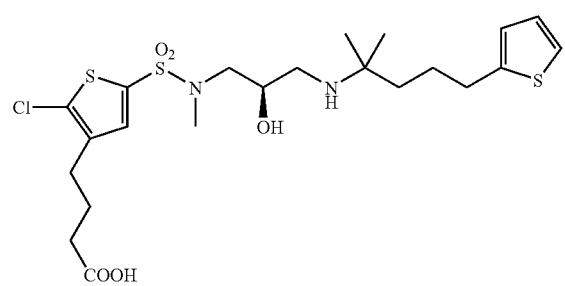
Exp. 9-20
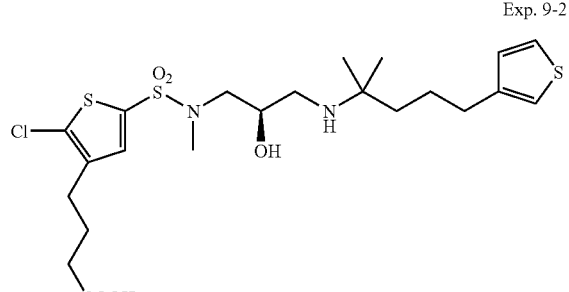
Exp. 9-21
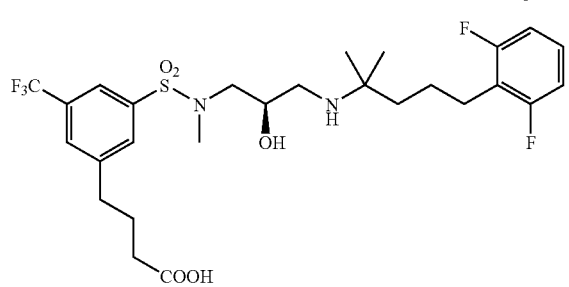
Exp. 9-22
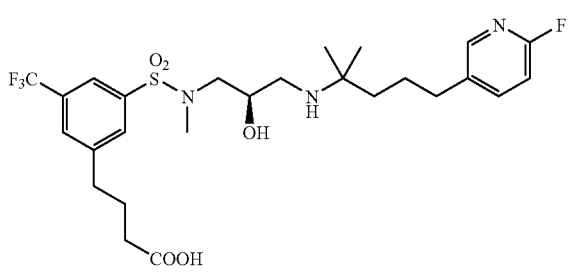
Exp. 9-23
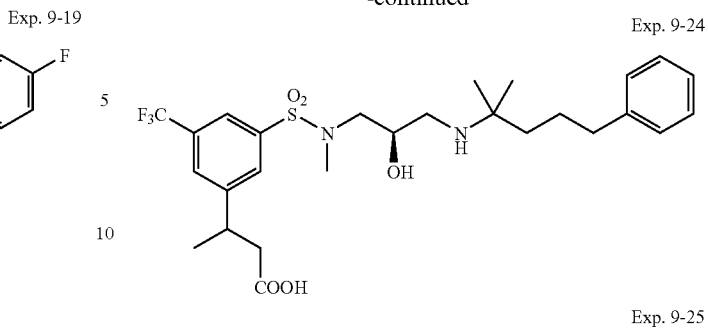
Exp. 9-24
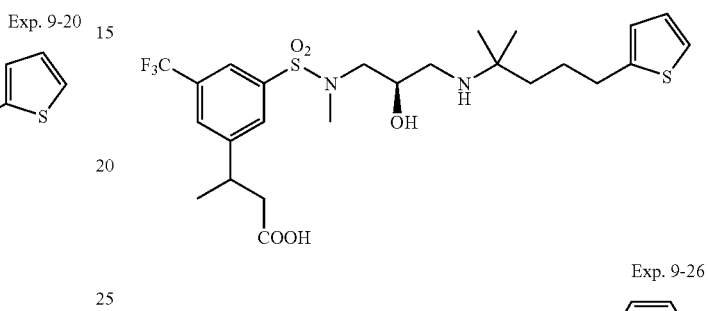
Exp. 9-25
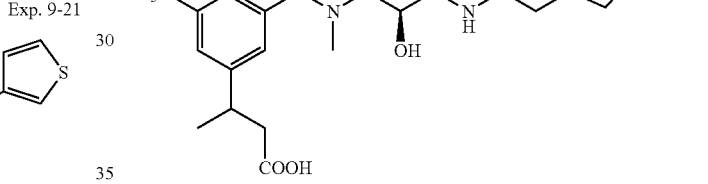
Exp. 9-26
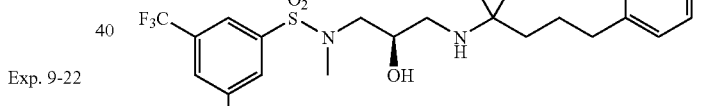
Exp. 9-27
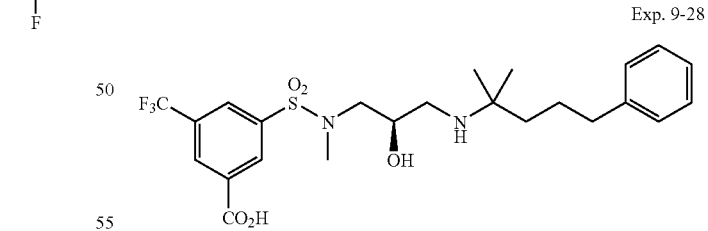
Exp. 9-28
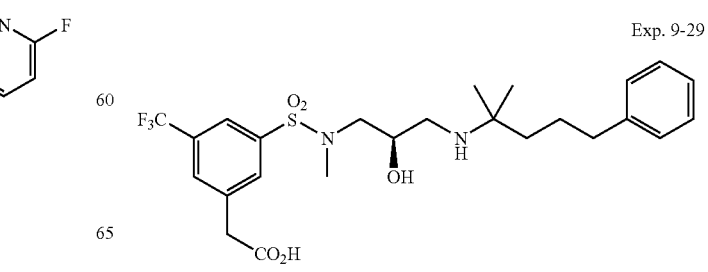
Exp. 9-29

-continued
Exp. 9-30
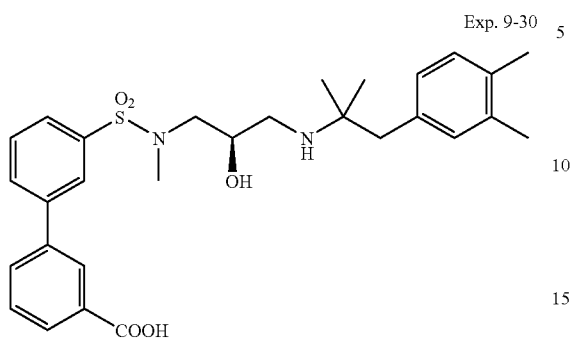
Exp. 9-34
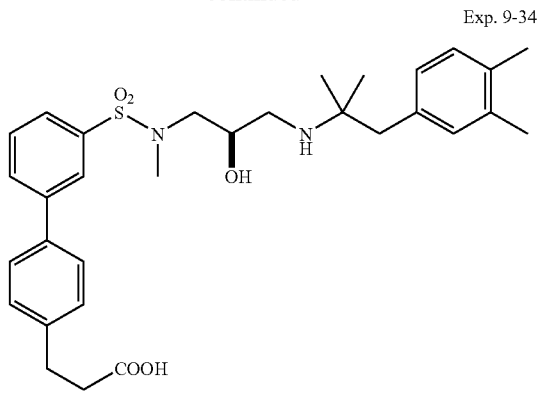
Exp. 9-31
Exp. 9-35
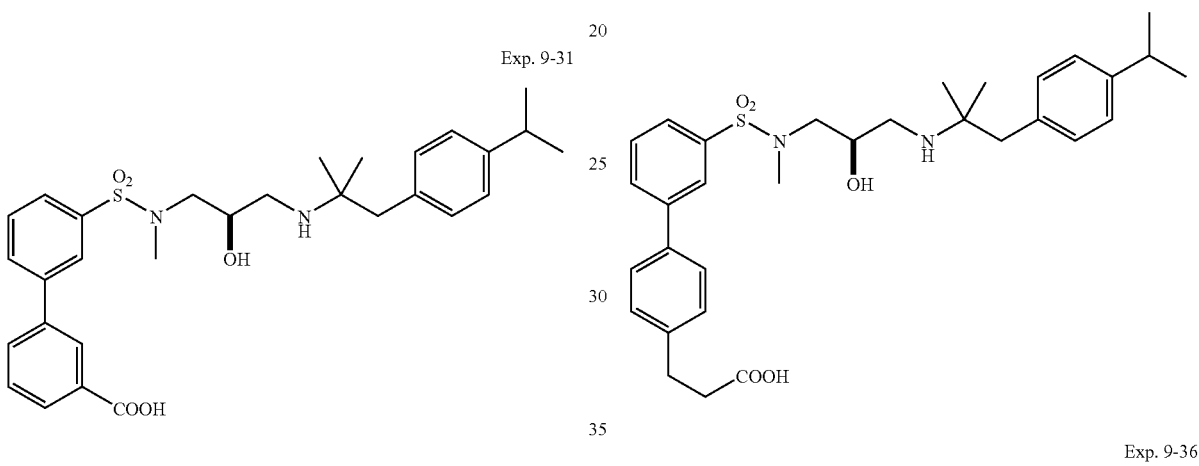
Exp. 9-32
Exp. 9-36
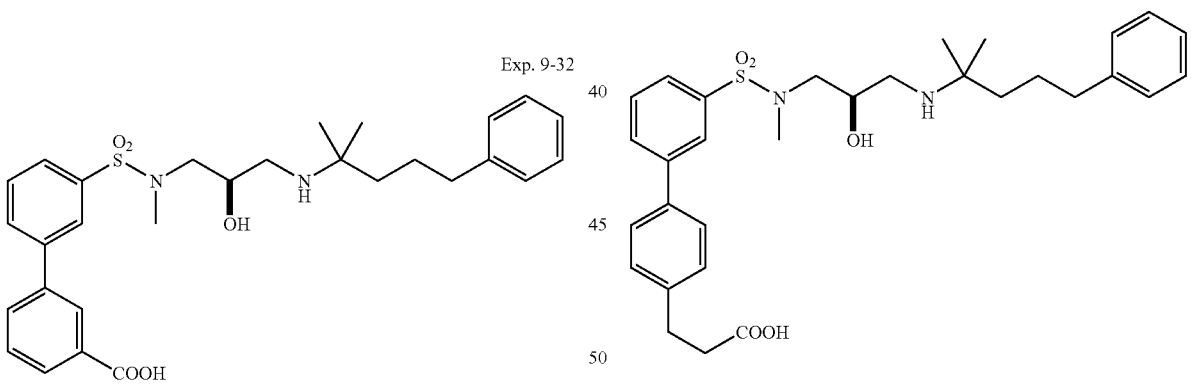
Exp. 9-33
Exp. 9-37
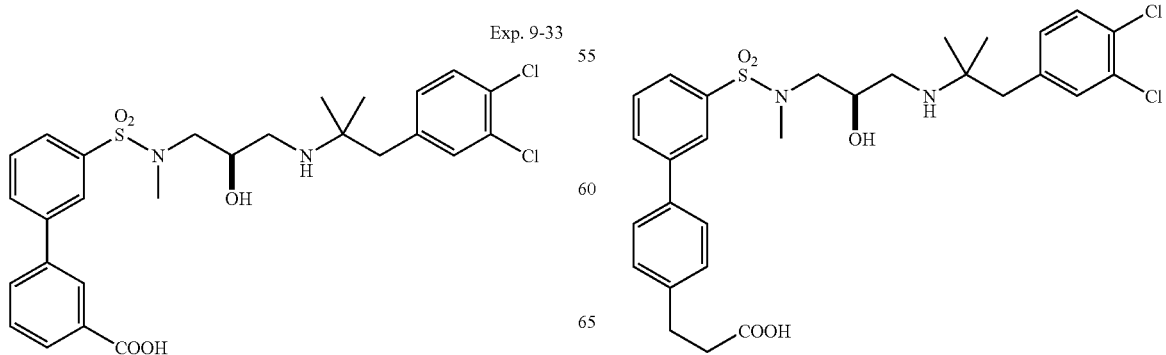

Exp. 9-38
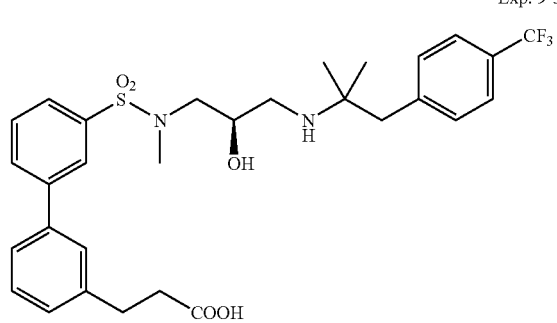
Exp. 9-39
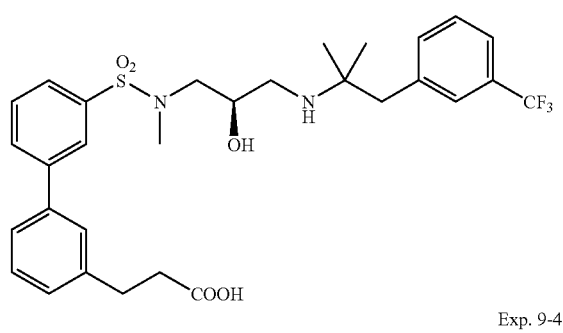
Exp. 9-40
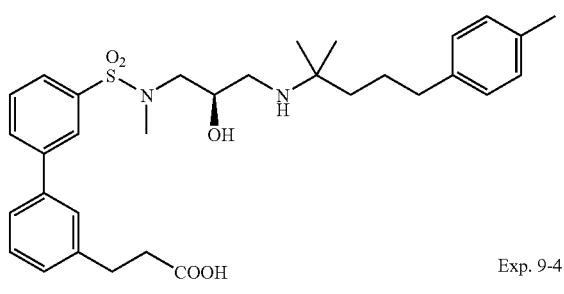
Exp. 9-41
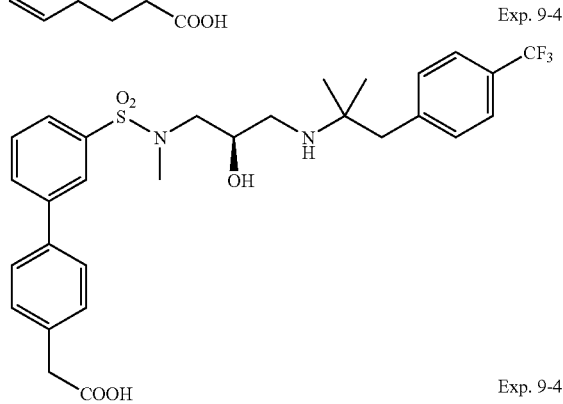
Exp. 9-42
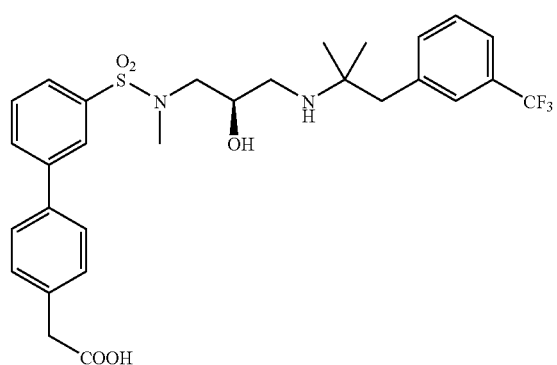
Exp. 9-43
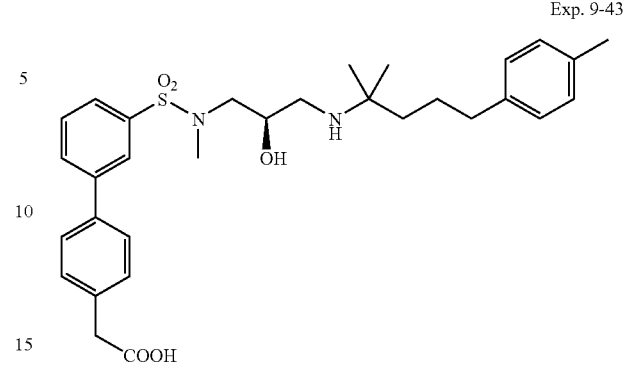
Exp. 9-44
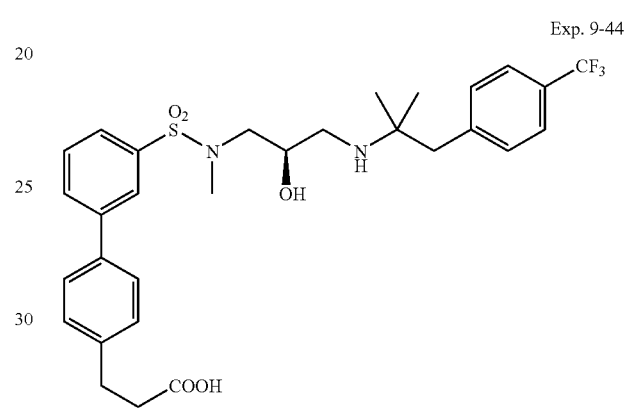
Exp. 9-45
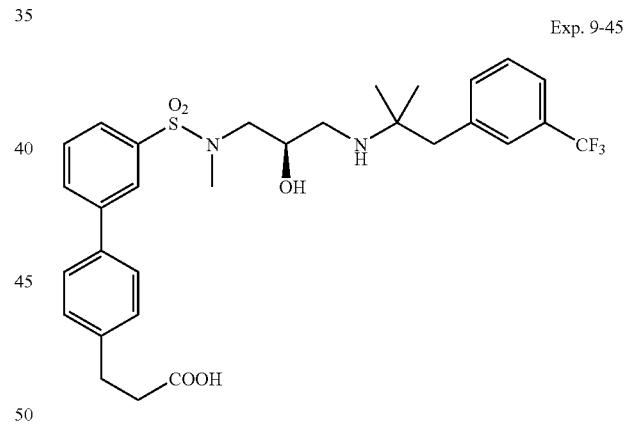
Exp. 9-46
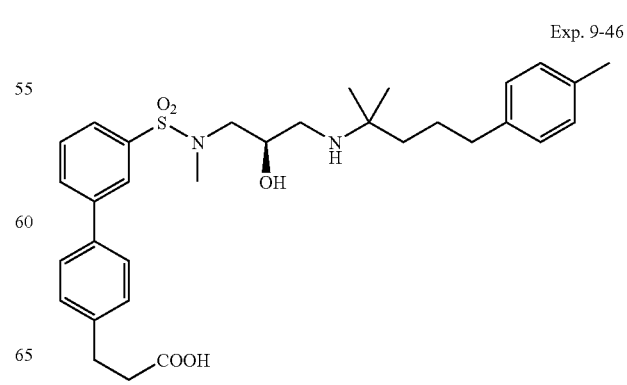

215
-continued
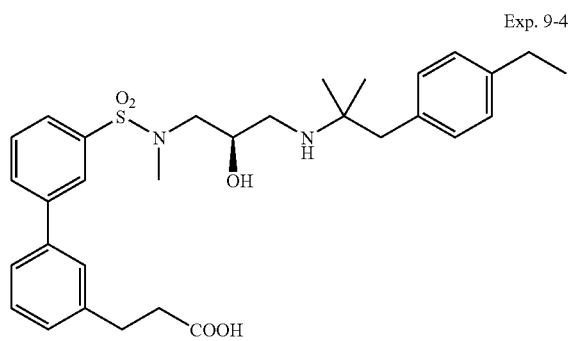
Exp. 9-47
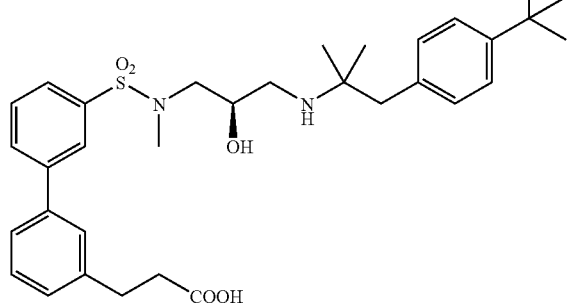
Exp. 9-48
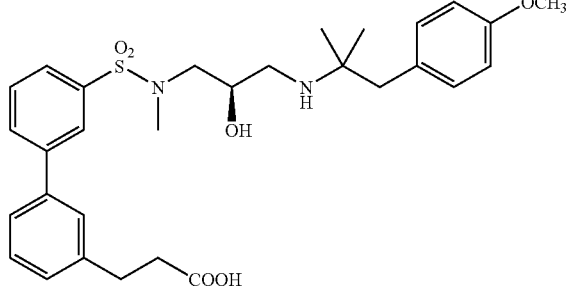
Exp. 9-49
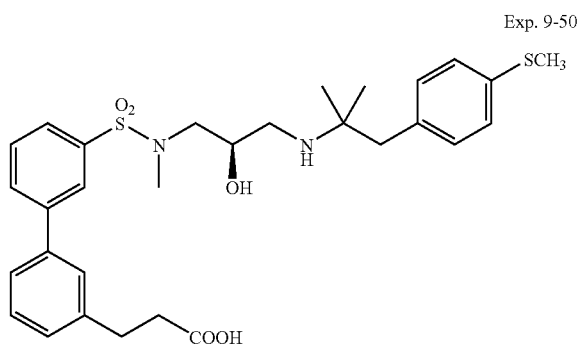
Exp. 9-50
216
-continued
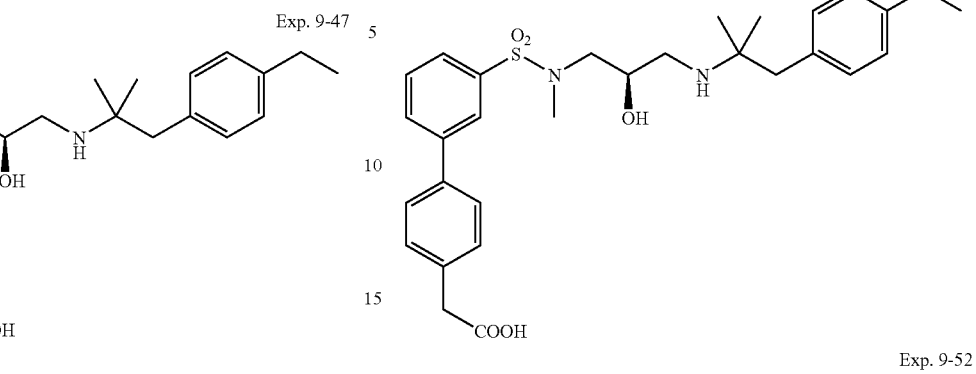
Exp. 9-51
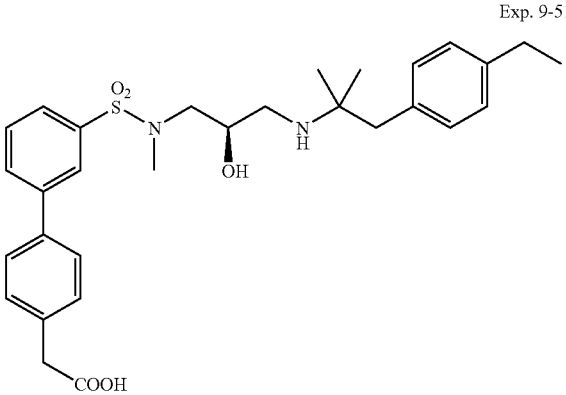
Exp. 9-52
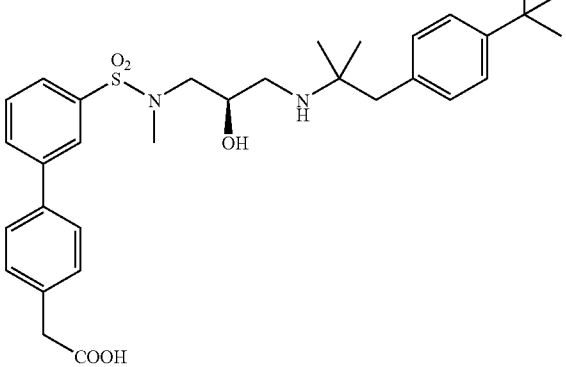
Exp. 9-53
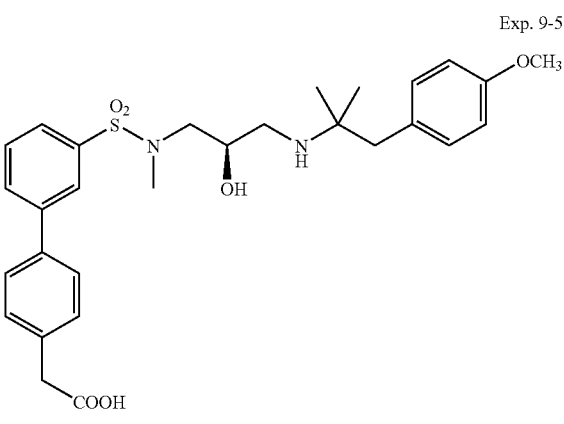
Exp. 9-54

217
-continued
Exp. 9-55
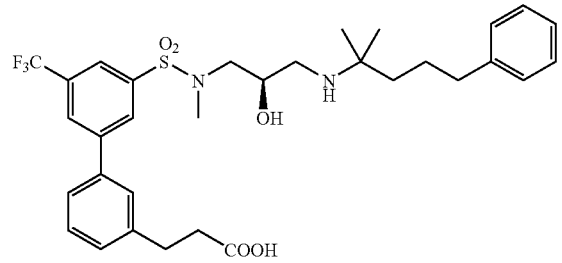
Exp. 9-56
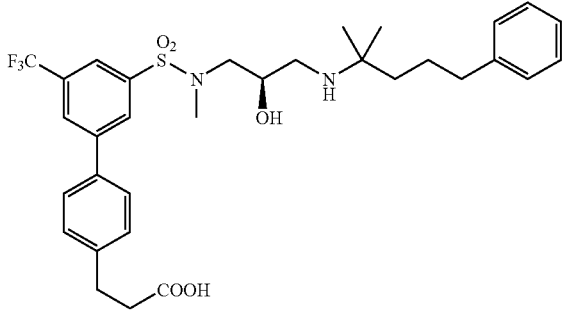
Exp. 9-57
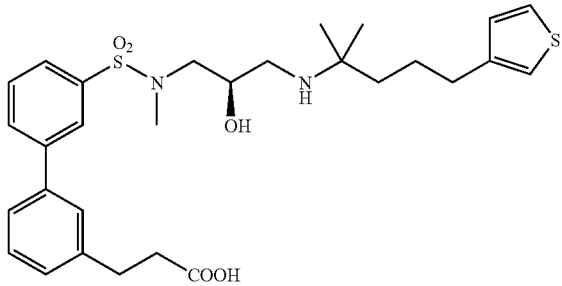
Exp. 9-58
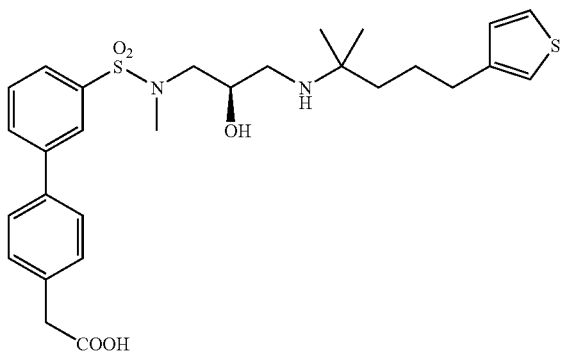
Exp. 9-59
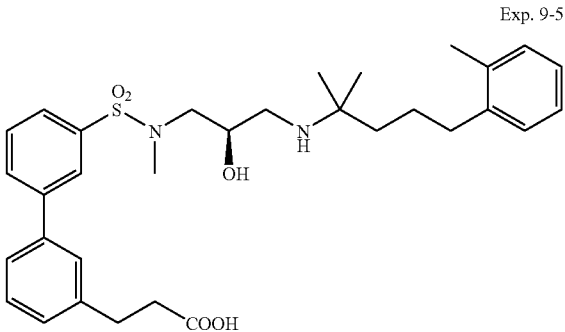
218
-continued
Exp. 9-60
Exp. 9-61
Exp. 9-62
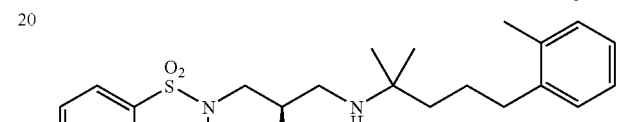
Exp. 9-63
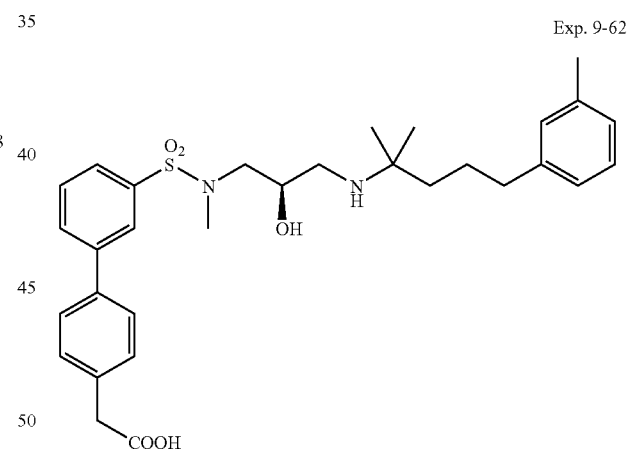

Exp. 9-64
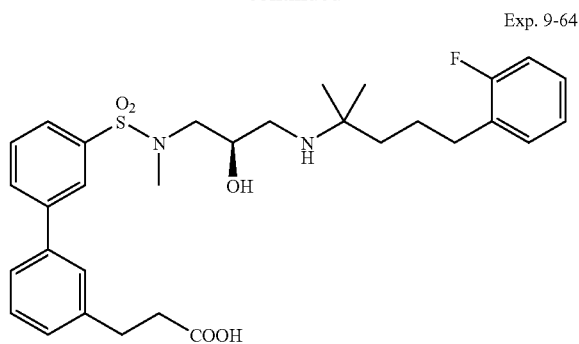
Exp. 9-65
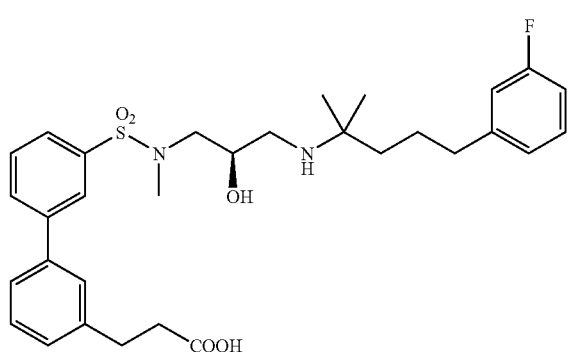
Exp. 9-66
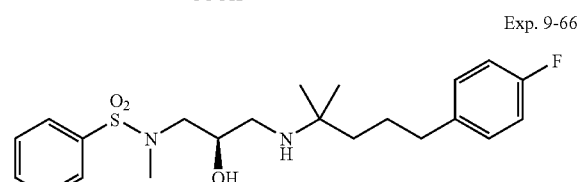
Exp. 9-67
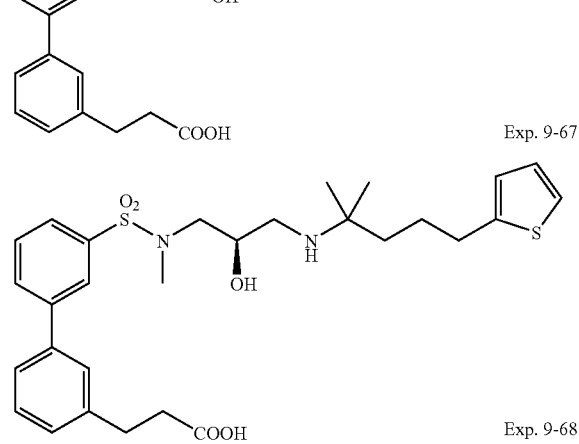
Exp. 9-68
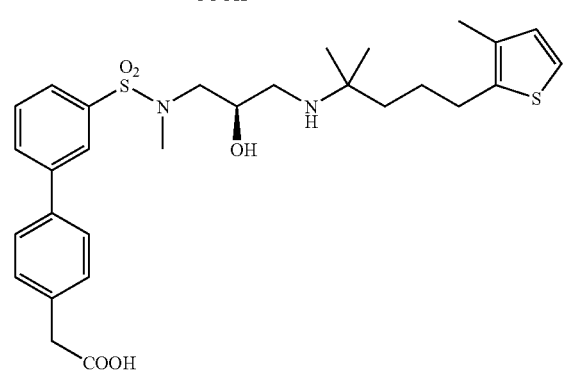
Exp. 9-69
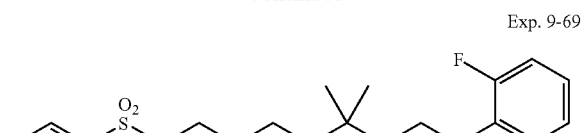
Exp. 9-70
Exp. 9-71
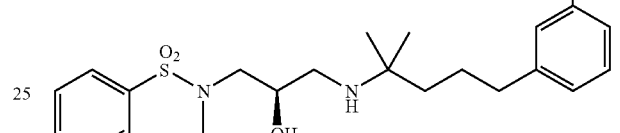
Exp. 9-72
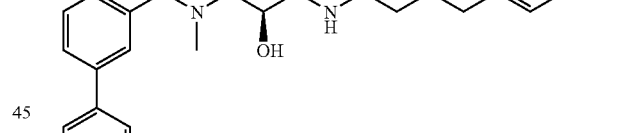

Exp. 9-73
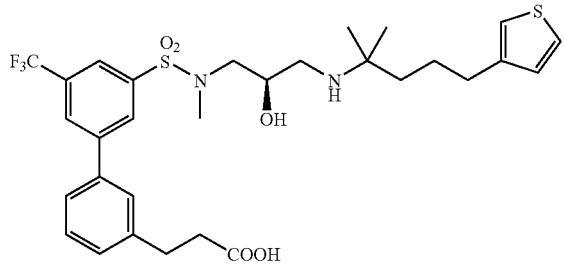
Exp. 9-74
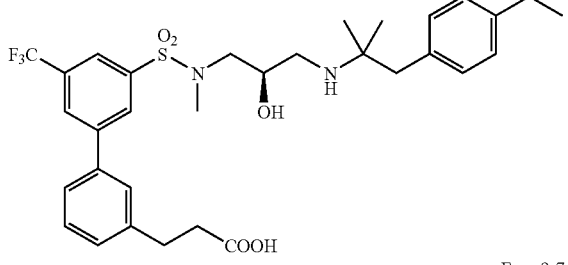
Exp. 9-75
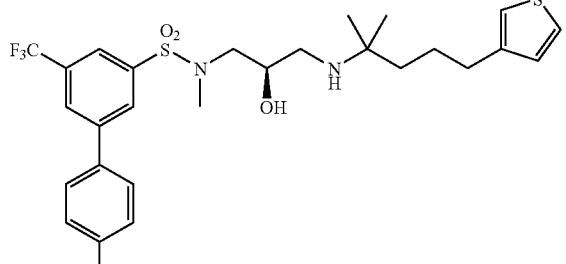
Exp. 9-76
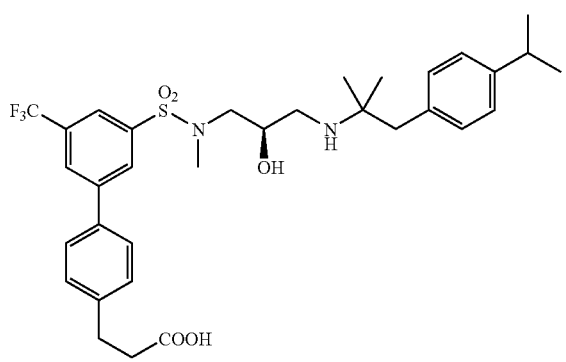
Exp. 9-77
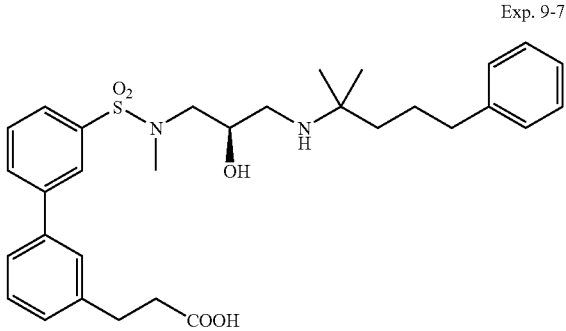
Exp. 9-78
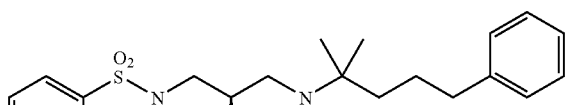
Exp. 9-79
Exp. 9-80
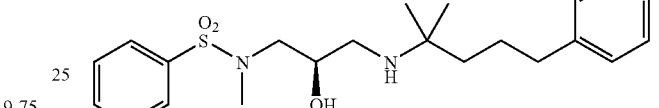
Exp. 9-81
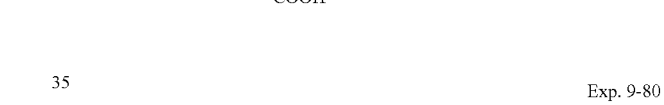

Exp. 9-82
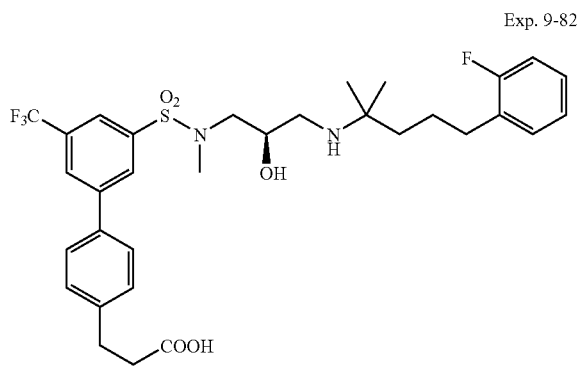
Exp. 9-86
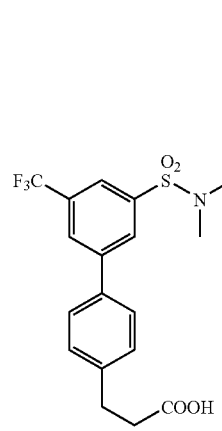
Exp. 9-83
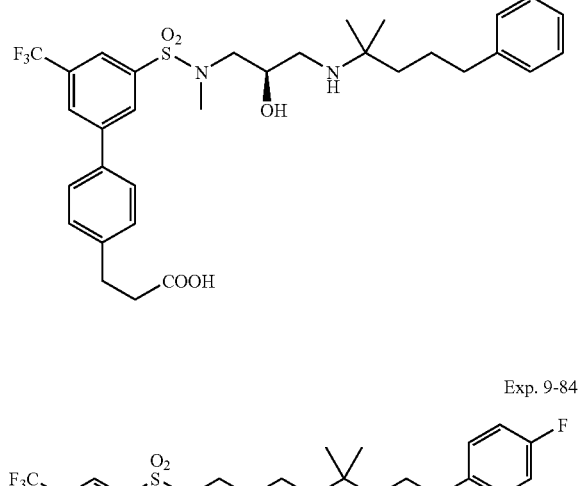
Exp. 9-87
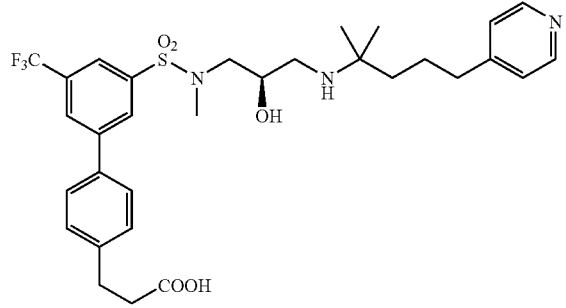
Exp. 9-84
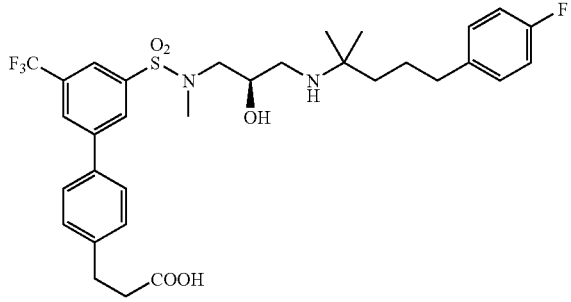
Exp. 9-88
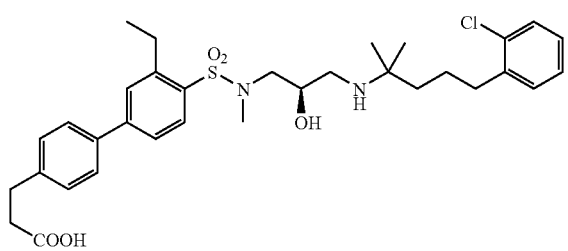
Exp. 9-85
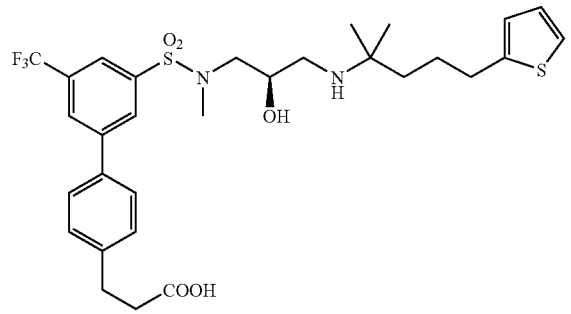
Exp. 9-89
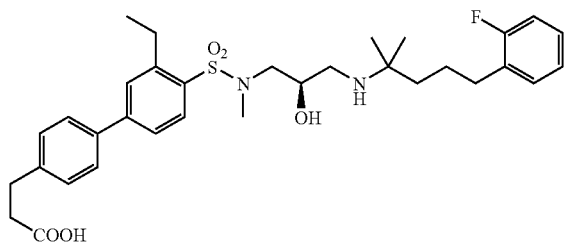
Exp. 9-90

225
-continued
Exp. 9-91
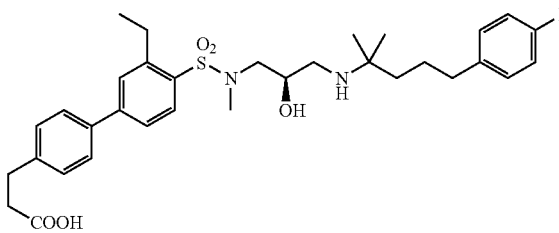
Exp. 9-92
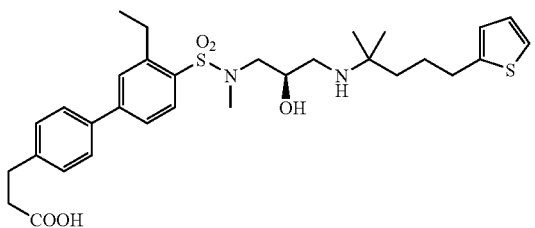
Exp. 9-93
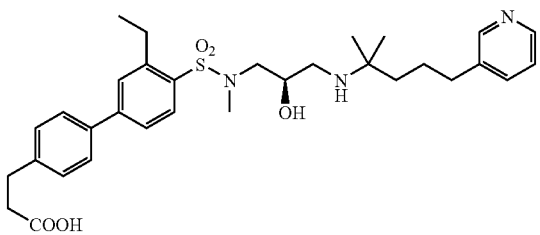
Exp. 9-94
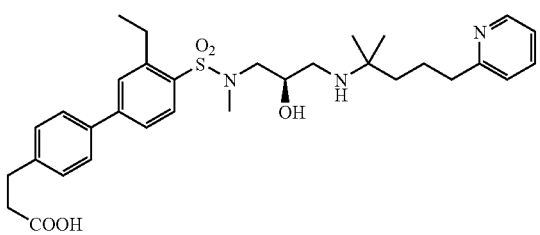
Exp. 9-95
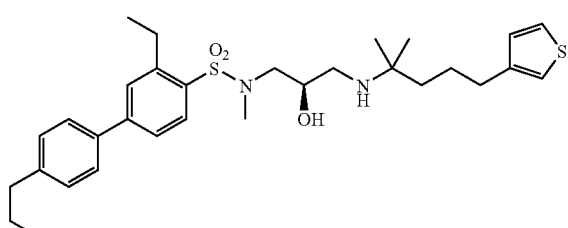
Exp. 9-96
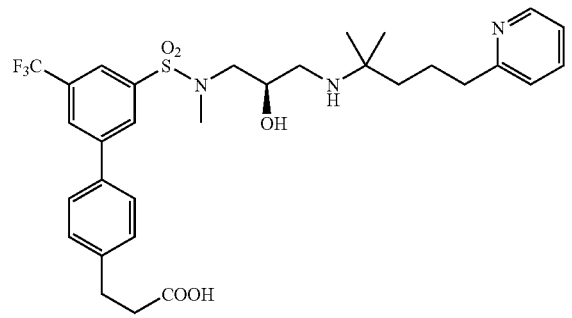
226
-continued
Exp. 9-97
Exp. 9-98
Exp. 9-99
Exp. 9-100
Exp. 9-101
Exp. 9-102

-continued
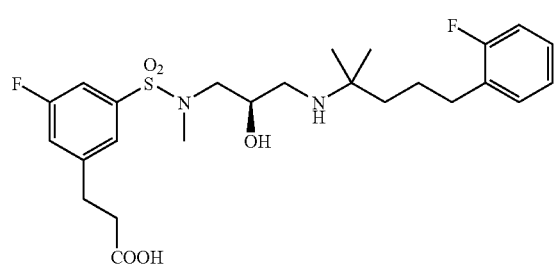
Exp. 9-103
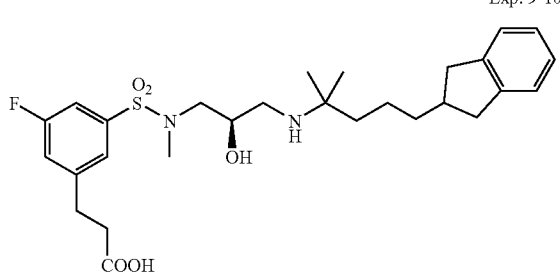
Exp. 9-104
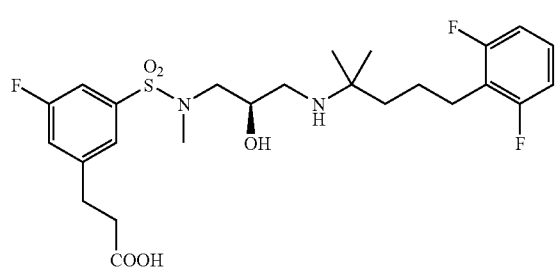
Exp.-9-105
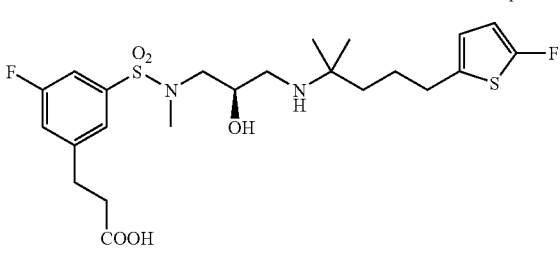
Exp. 9-106
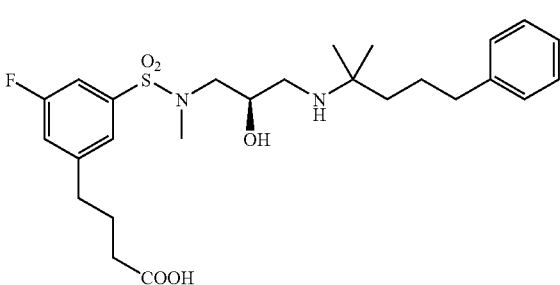
Exp. 9-107
-continued
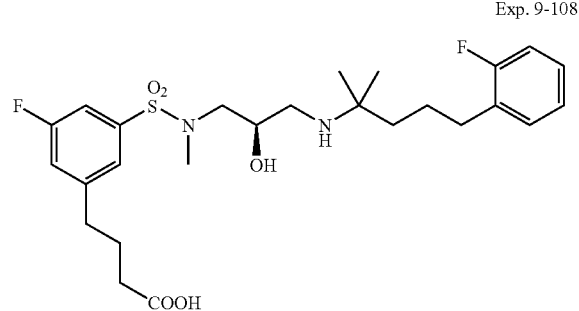
Exp. 9-108
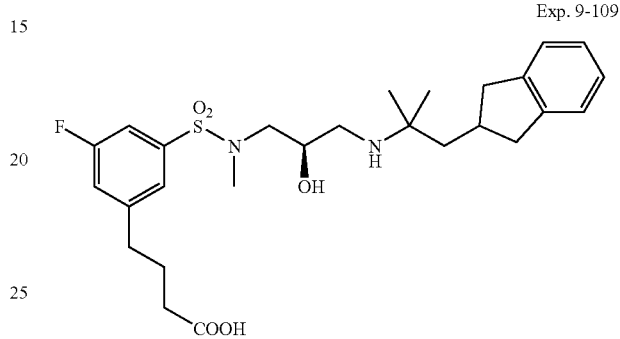
Exp. 9-109
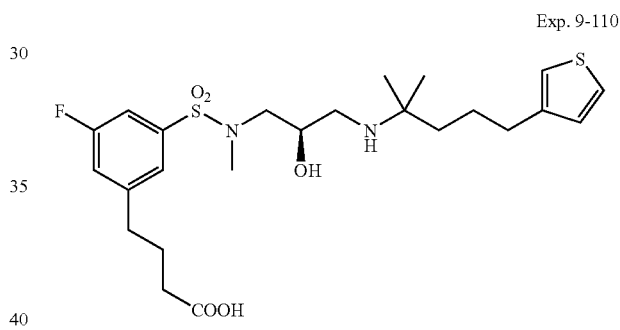
Exp. 9-110
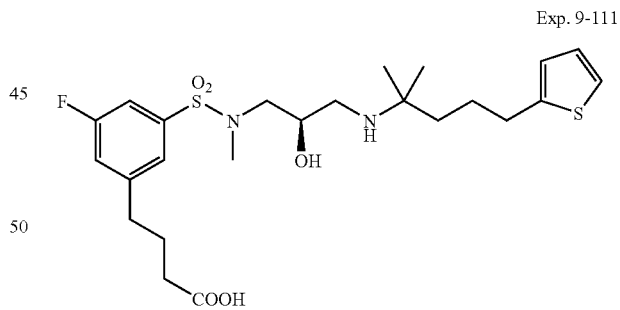
Exp. 9-111
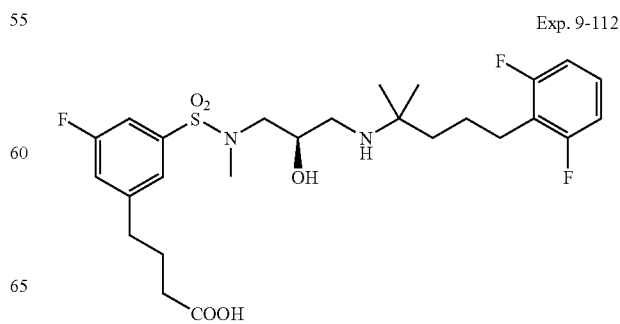
Exp. 9-112

Exp. 9-113
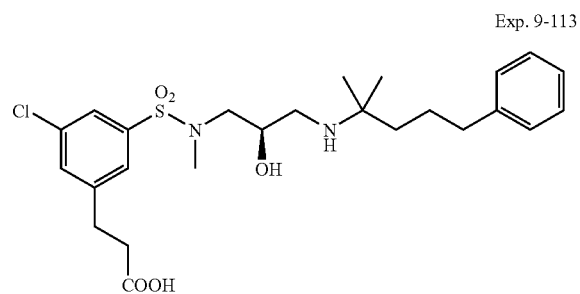
Exp. 9-118
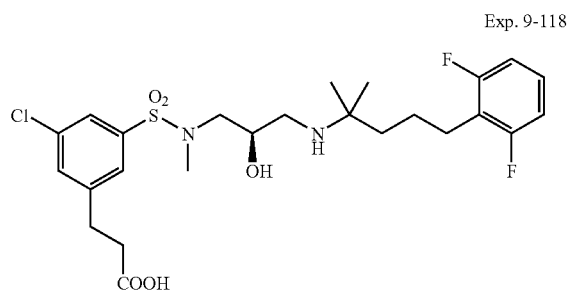
Exp. 9-114
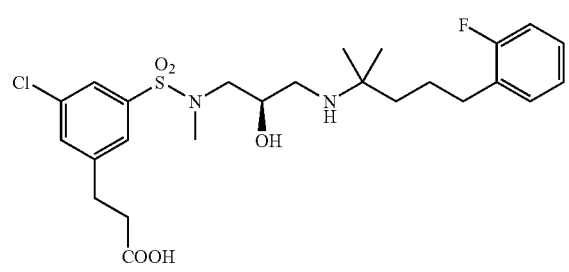
Exp. 9-119
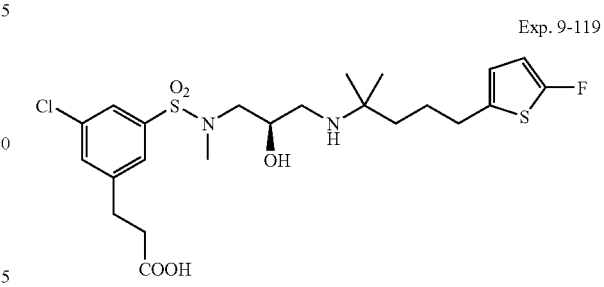
Exp. 9-115
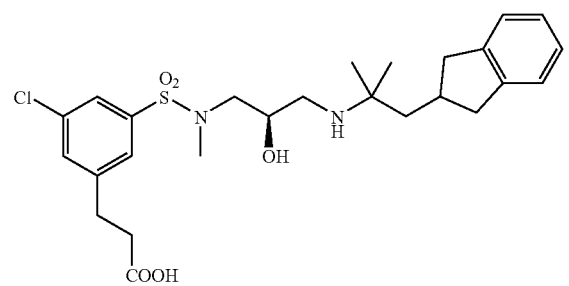
Exp. 9-120
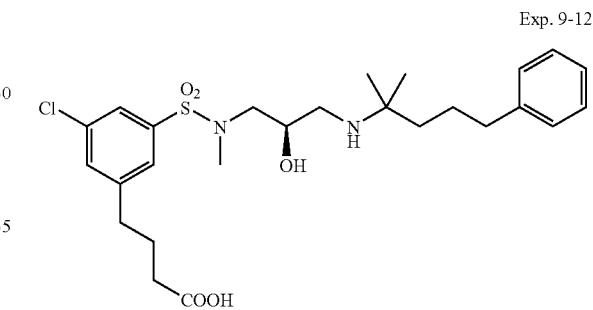
Exp. 9-116
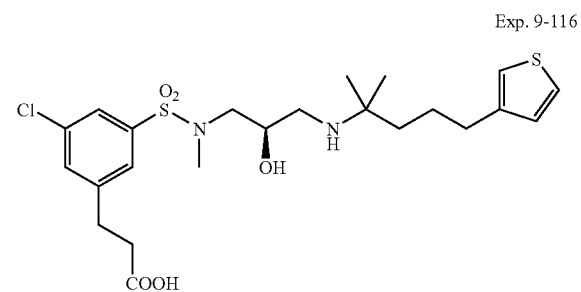
Exp. 9-121
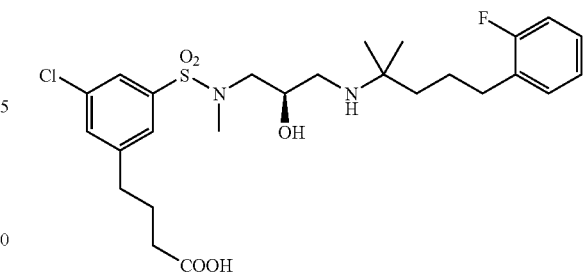
Exp. 9-117
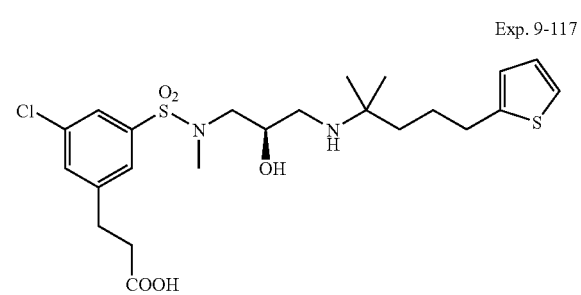
Exp. 9-122
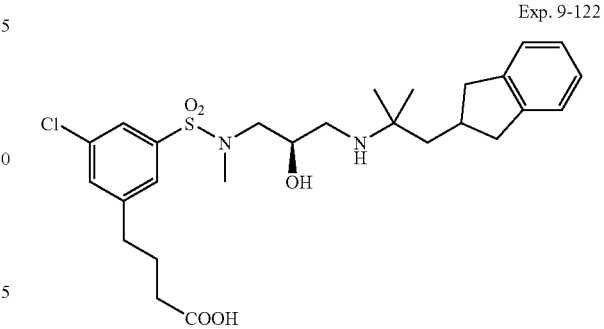

Exp. 9-123
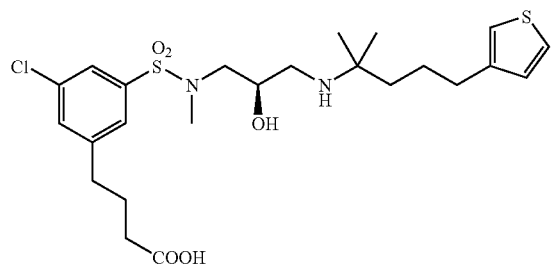
Exp. 9-124
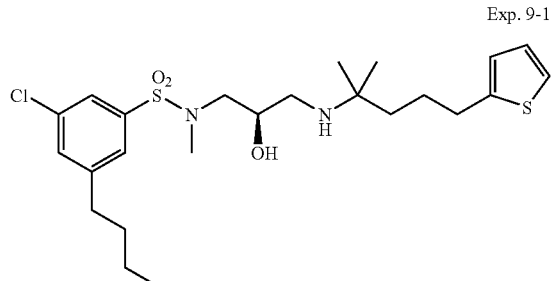
Exp. 9-125
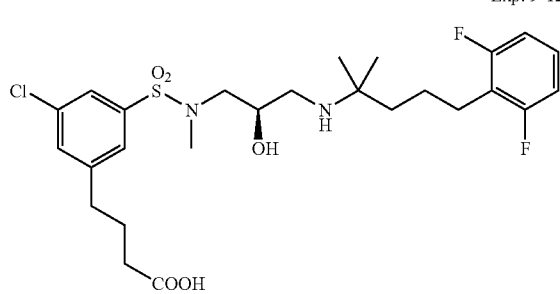
Exp. 9-126
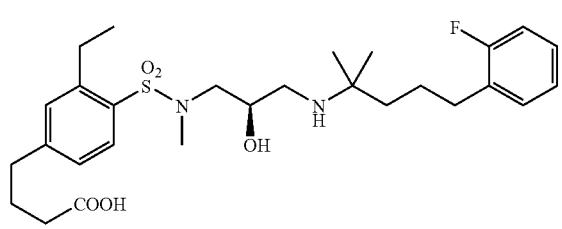
Exp. 9-127
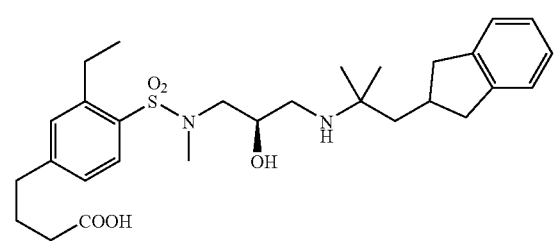
Exp. 9-128
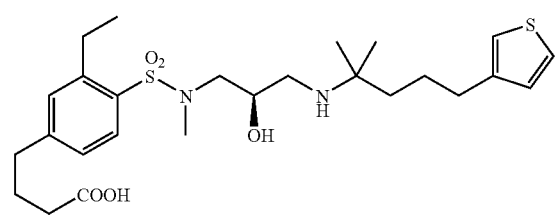
Exp. 9-129
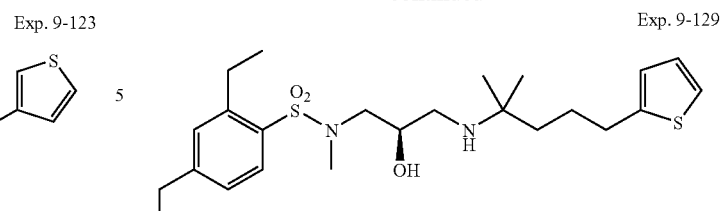
Exp. 9-130
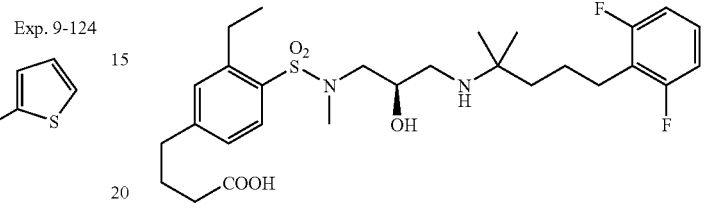
Exp. 9-131
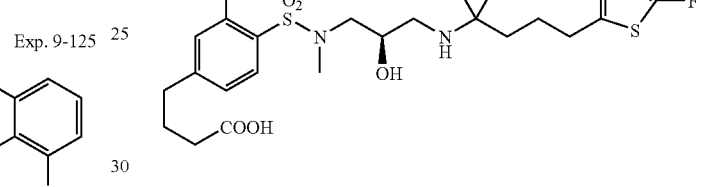
Exp. 9-132
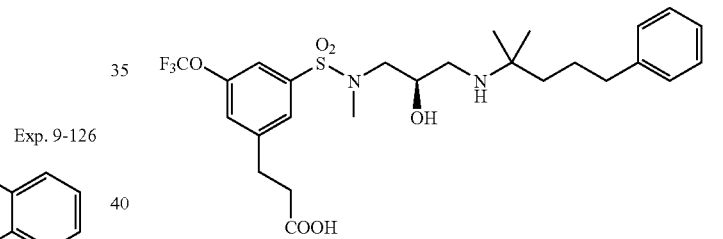
Exp. 9-133
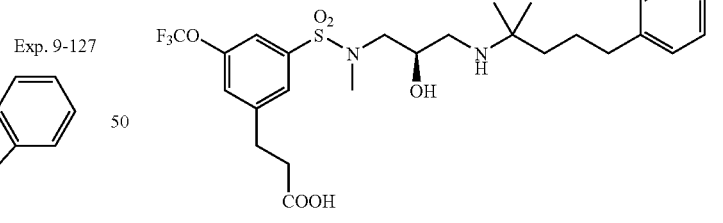
Exp. 9-134
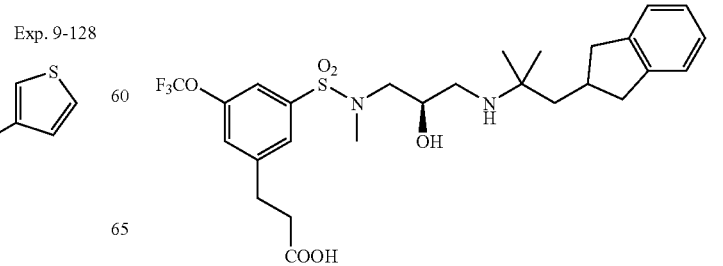

Exp. 9-135
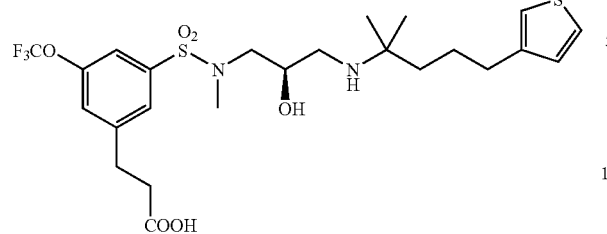
Exp. 9-136
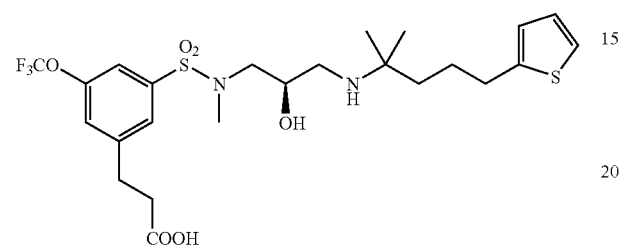
Exp. 9-137
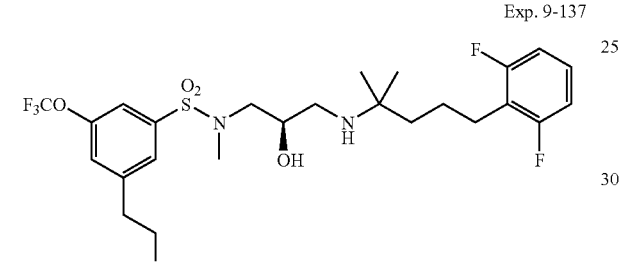
Exp. 9-138
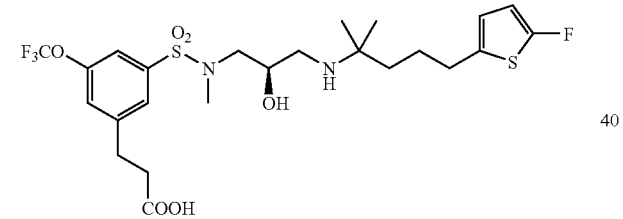
Exp. 9-139
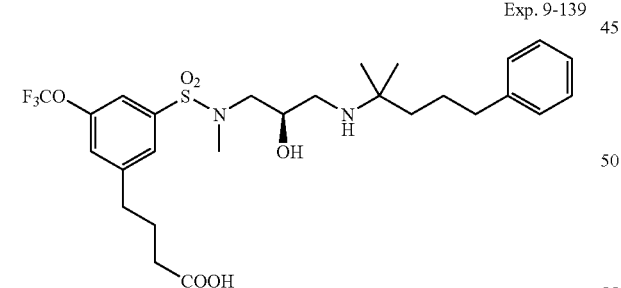
Exp. 9-140
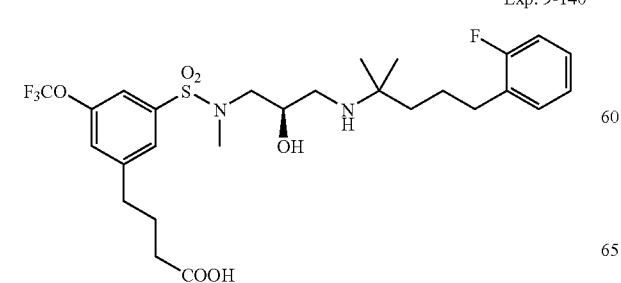
Exp. 9-141
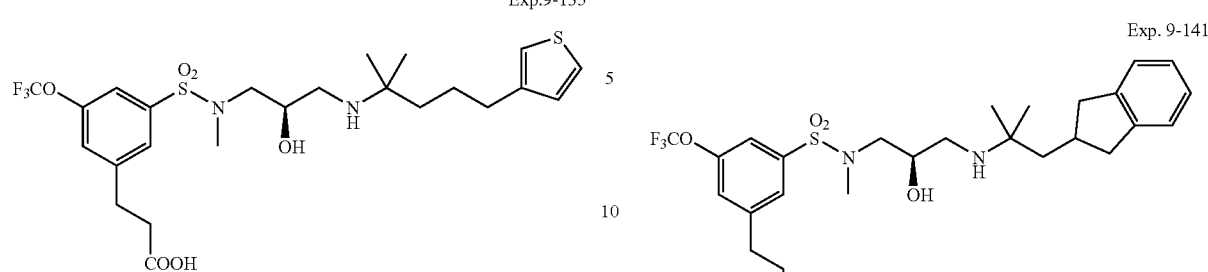
Exp. 9-142
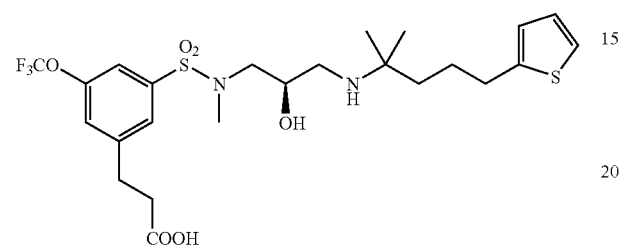
Exp. 9-143
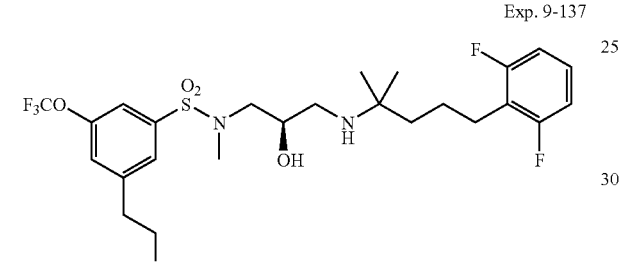
Exp. 9-144
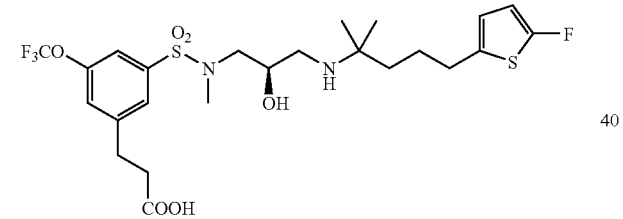
Exp. 9-145
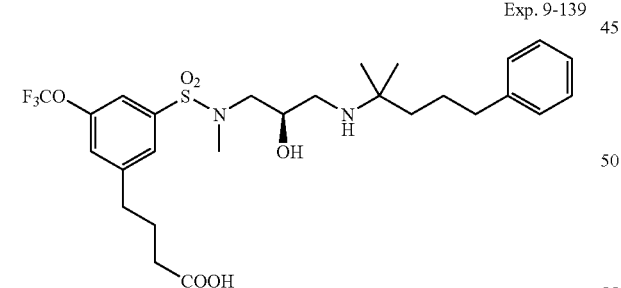

Exp. 9-146
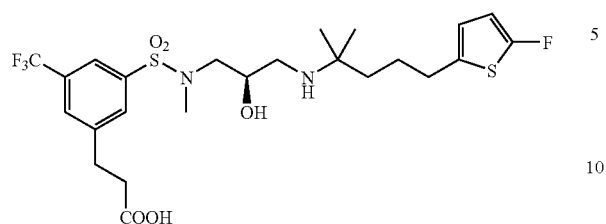
Exp. 9-147
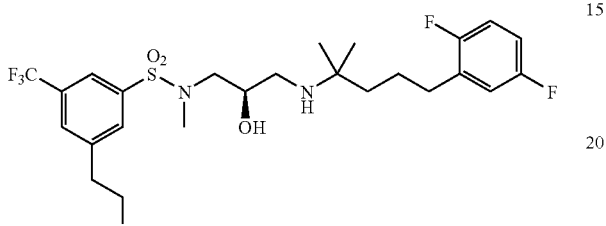
Exp. 9-148
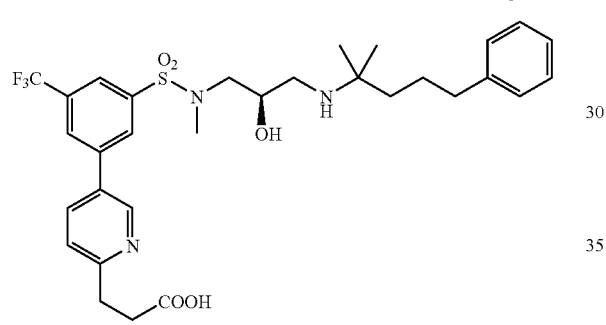
Exp. 9-149
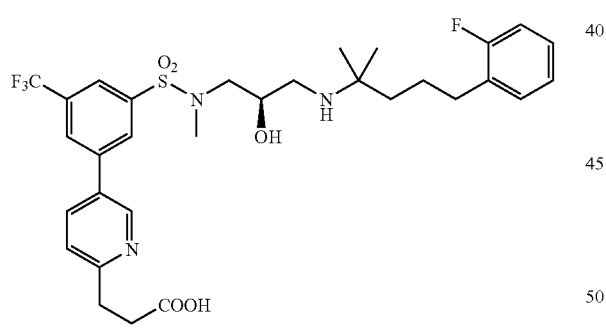
Exp. 9-150
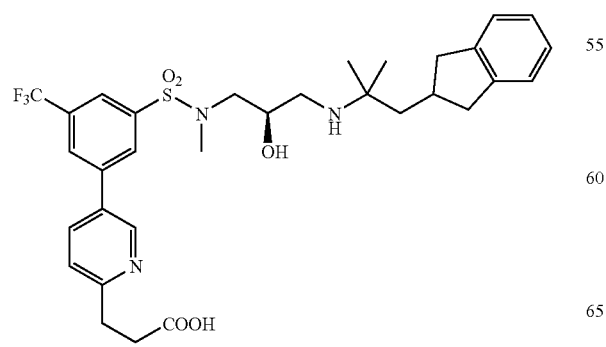
Exp. 9-151
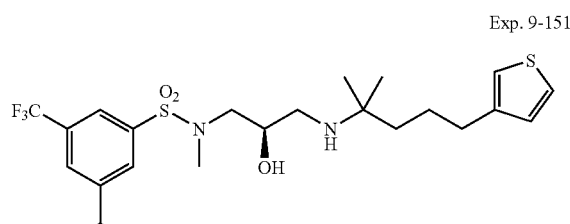
Exp. 9-152
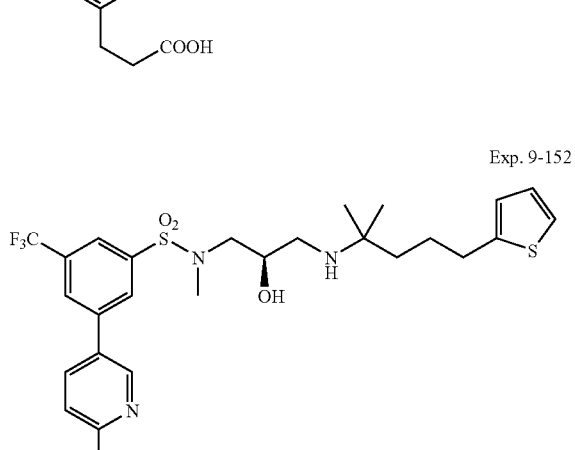
Exp. 9-153
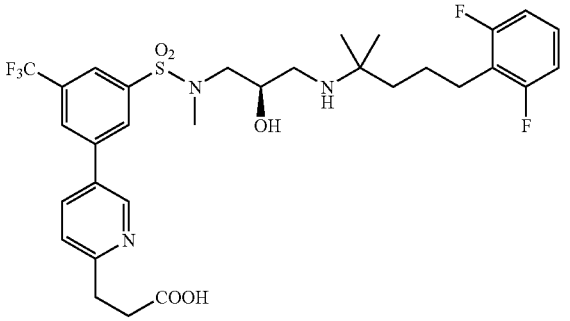
Exp. 9-154
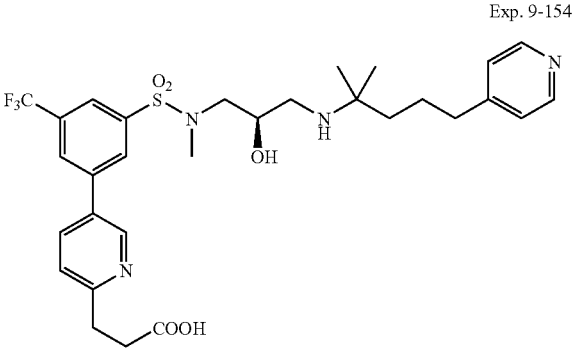

Exp. 9-155
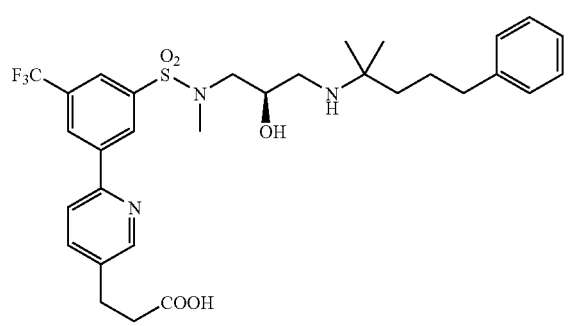
Exp. 9-156
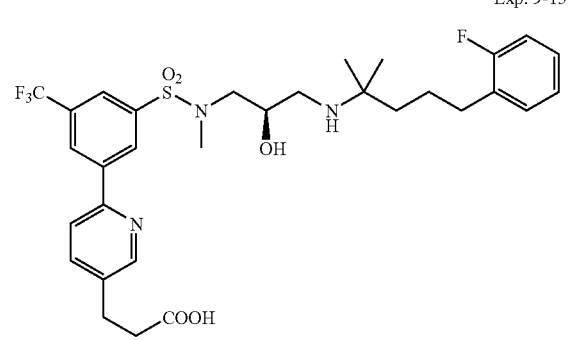
Exp. 9-157
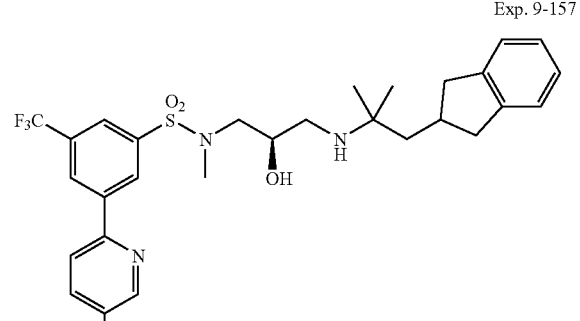
Exp. 9-158
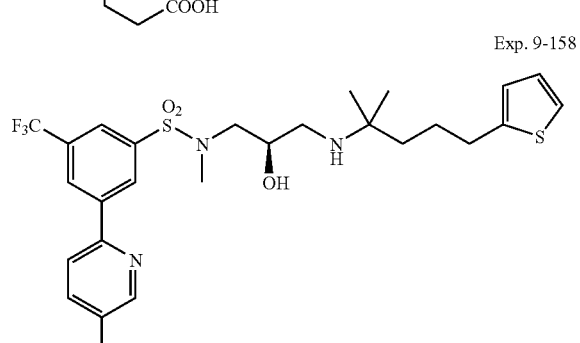
Exp. 9-159
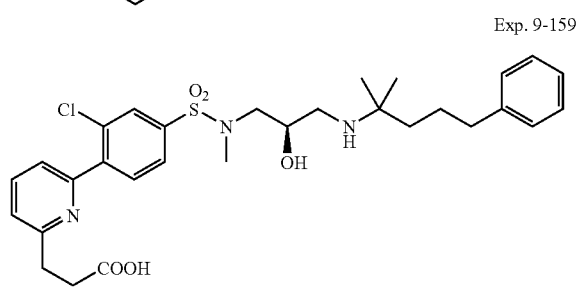
Exp. 9-160
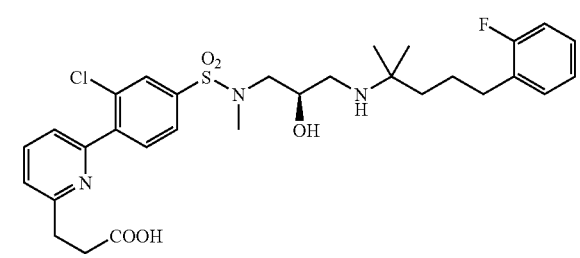
Exp. 9-161
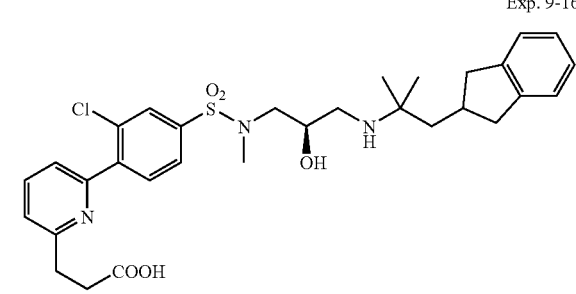
Exp. 9-162
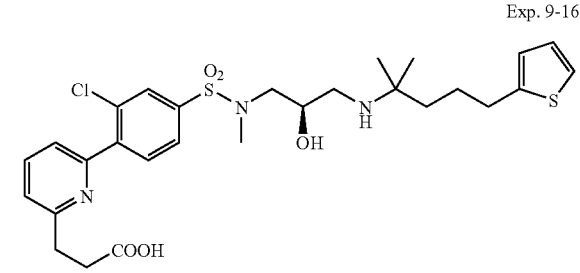
Exp. 9-163
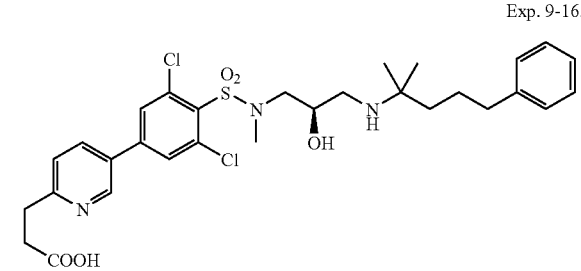
Exp. 9-164
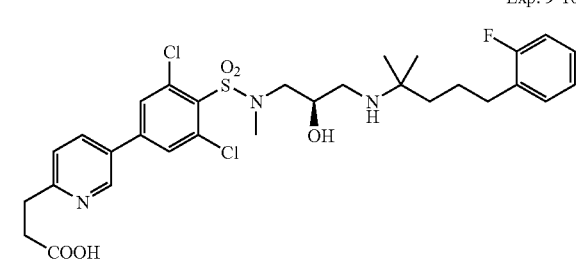
Exp. 9-165
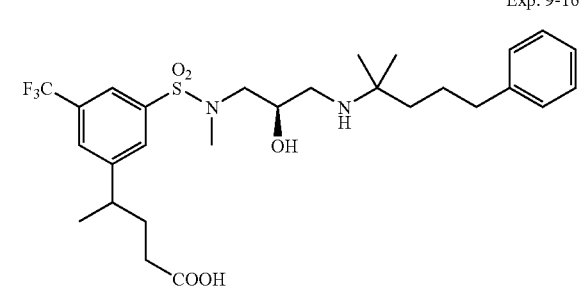

Exp. 9-166
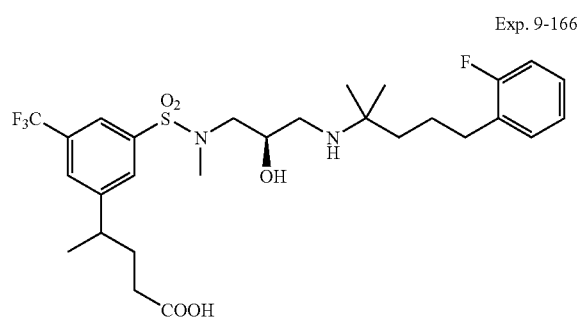
Exp. 9-171
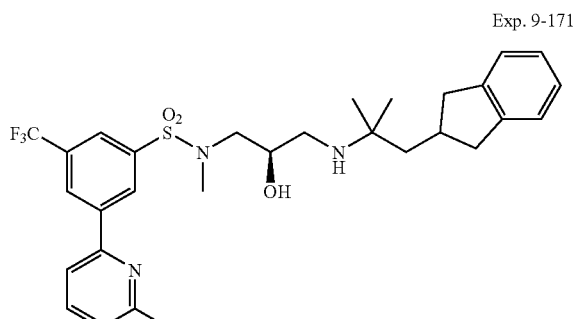
Exp. 9-167
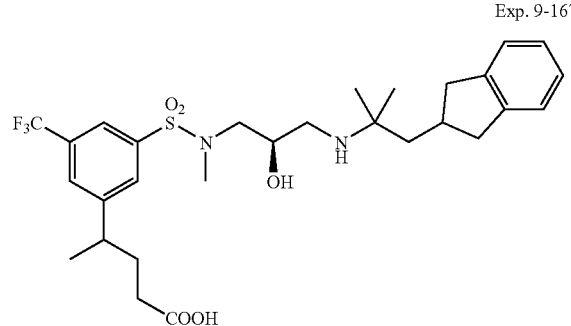
Exp. 9-172
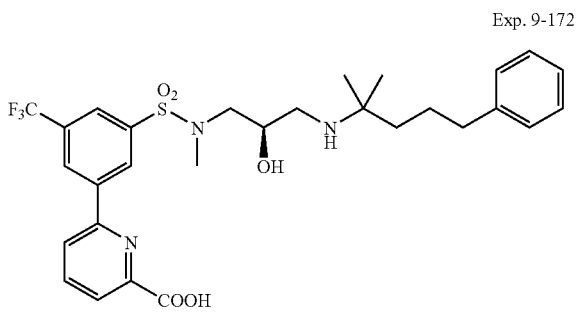
Exp. 9-168
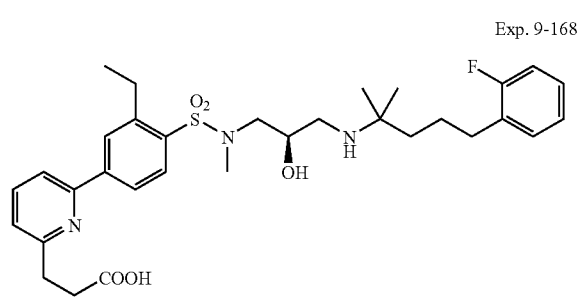
Exp. 9-173
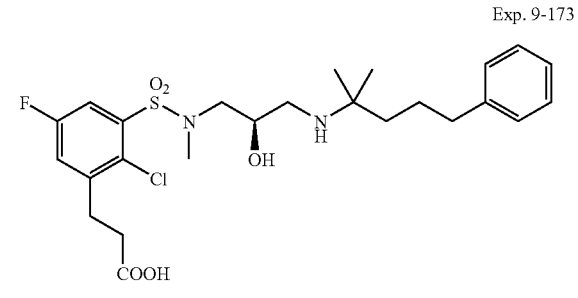
Exp. 9-169
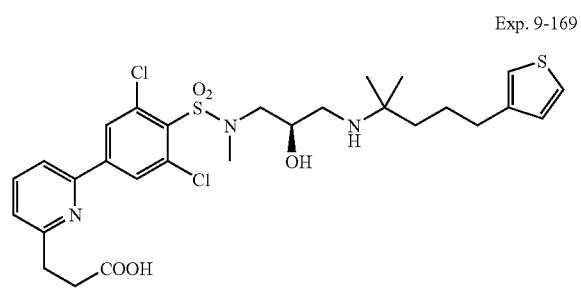
Exp. 9-174
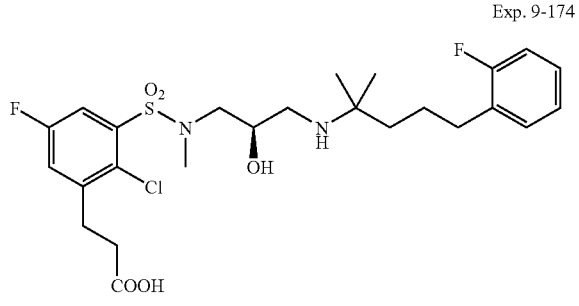
Exp. 9-170
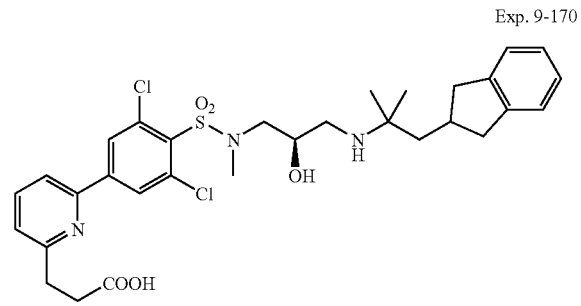
Exp. 9-175
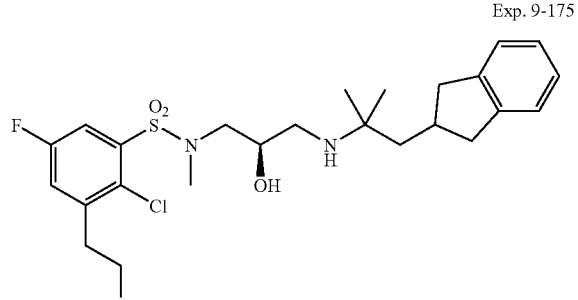

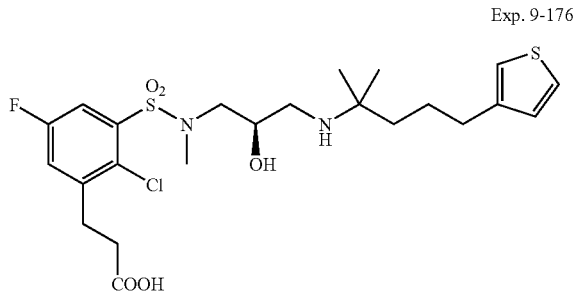

Exp. 9-176

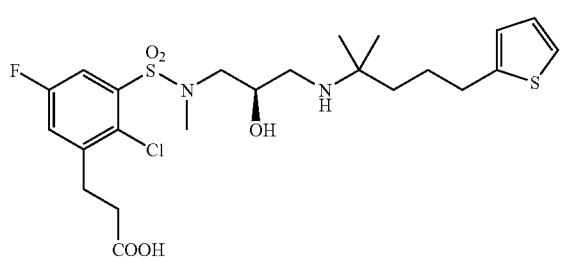

Exp. 9-177

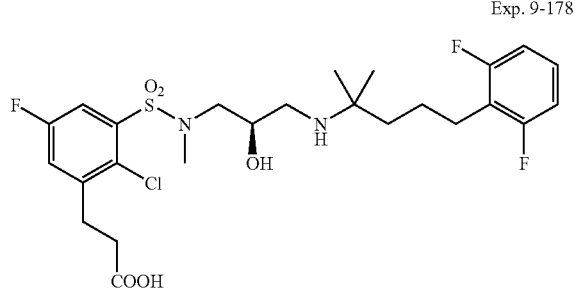

Exp. 9-178

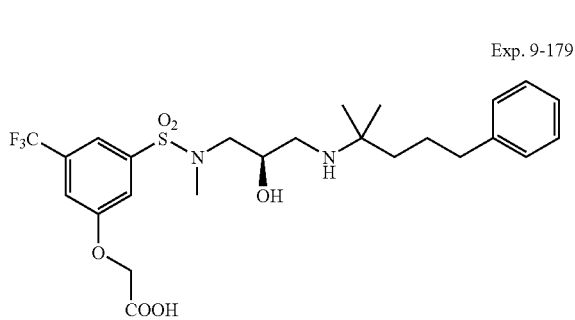

Exp. 9-179

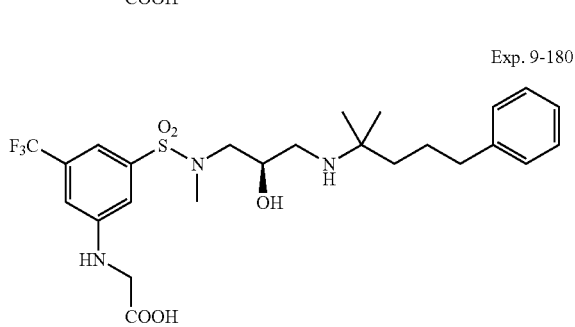

Exp. 9-180

EXAMPLE 9-1

(R)-3-(2-(3-(N-(2-hydroxy-3-(2-methyl-5-phenylpentan-2-ylamino)propyl)-N-methylsulfamoyl)-5-(trifluoromethyl)phenyl)thiophen-3-yl)propionic acid

EXAMPLE 9-2

(R)-3-(2-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)thiophen-3-yl)propionic acid

EXAMPLE 9-3

(R)-3-(3-(3-(N-(2-hydroxy-3-(2-methyl-5-phenylpentan-2-ylamino)propyl)-N-methylsulfamoyl)-5-(trifluoromethyl)phenyl)thiophen-2-yl)propionic acid

EXAMPLE 9-4

(R)-3-(3-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)thiophen-2-yl)propionic acid

EXAMPLE 9-5

(R)-3-(6-(3-ethyl-4-(N-(2-hydroxy-3-(2-methyl-5-phenylpentan-2-ylamino)propyl)-N-methylsulfamoyl)phenyl)pyridin-2-yl)propionic acid

EXAMPLE 9-6

(R)-3-(6-(3-ethyl-4-(N-(2-hydroxy-3-(2-methyl-5-(thiophen-3-yl)pentan-2-ylamino)propyl)-N-methylsulfamoyl)phenyl)pyridin-2-yl)propionic acid

EXAMPLE 9-7

(R)-3-(6-(4-(N-(3-(1-(2,3-dihydro-1H-inden-2-yl)-2-methylpropan-2-ylamino)-2-hydroxypropyl)-N-methylsulfamoyl)-3-ethylphenyl)pyridin-2-yl)propionic acid

EXAMPLE 9-8

(R)-4-(3-(N-(2-hydroxy-3-(2-methyl-5-(thiophen-3-yl)pentan-2-ylamino)propyl)-N-methylsulfamoyl)-5-(trifluoromethyl)phenyl)butanoic acid

EXAMPLE 9-9

(R)-4-(3-(N-(2-hydroxy-3-(2-methyl-5-phenylpentan-2-ylamino)propyl)-N-methylsulfamoyl)-5-(trifluoromethyl)phenyl)butanoic acid

EXAMPLE 9-10

(R)-4-(3-(N-(3-(5-(2-chlorophenyl)-2-methylpentan-2-ylamino)-2-hydroxypropyl)-N-methylsulfamoyl)-5-(trifluoromethyl)phenyl)butanoic acid

EXAMPLE 9-11

(R)-4-(3-(N-(2-hydroxy-3-(2-methyl-5-(pyridin-2-yl)pentan-2-ylamino)propyl)-N-methylsulfamoyl)-5-(trifluoromethyl)phenyl)butanoic acid

EXAMPLE 9-12

(R)-4-(3-(N-(3-(5-(2-fluorophenyl)-2-methylpentan-2-ylamino)-2-hydroxypropyl)-N-methylsulfamoyl)-5-(trifluoro methyl)phenyl)butanoic acid

EXAMPLE 9-13

(R)-4-(3-(N-(3-(S-(3-fluorophenyl)-2-methylpentan-2-ylamino)-2-hydroxypropyl)-N-methylsulfamoyl)-5-(trifluoromethyl)phenyl)butanoic acid

EXAMPLE 9-14

(R)-4-(3-(N-(3-(5-(4-fluorophenyl)-2-methylpentan-2-ylamino)-2-hydroxypropyl)-N-methylsulfamoyl)-5-(trifluoromethyl)phenyl)butanoic acid

EXAMPLE 9-15

(R)-4-(3-(N-(2-hydroxy-3-(2-methyl-5-(thiophen-2-yl)pentan-2-ylamino)propyl)-N-methylsulfamoyl)-5-(trifluoromethyl)phenyl)butanoic acid

EXAMPLE 9-16

(R)-4-(3-(N-(2-hydroxy-3-(2-methyl-5-(pyridin-3-yl)pentan-2-ylamino)propyl)-N-methylsulfamoyl)-5-(trifluoromethyl)phenyl)butanoic acid

EXAMPLE 9-17

(R)-4-(3-(N-(2-hydroxy-3-(2-methyl-5-(pyridin-4-yl)pentan-2-ylamino)propyl)-N-methylsulfamoyl)-5-(trifluoromethyl)phenyl)butanoic acid

EXAMPLE 9-18

(R)-4-(2-chloro-5-(N-(3-(5-(2-fluorophenyl)-2-methylpentan-2-ylamino)-2-hydroxypropyl)-N-methylsulfamoyl)thiophen-3-yl)butanoic acid

EXAMPLE 9-19

(R)-4-(2-chloro-5-(N-(3-(5-(4-fluorophenyl)-2-methylpentan-2-ylamino)-2-hydroxypropyl)-N-methylsulfamoyl)thiophen-3-yl)butanoic acid

EXAMPLE 9-20

(R)-4-(2-chloro-5-(N-(2-hydroxy-3-(2-methyl-5-(thiophen-2-yl)pentan-2-ylamino)propyl)-N-methylsulfamoyl)thiophen-3-yl)butanoic acid

EXAMPLE 9-21

(R)-4-(2-chloro-5-(N-(2-hydroxy-3-(2-methyl-5-(thiophen-3-yl)pentan-2-ylamino)propyl)-N-methylsulfamoyl)thiophen-3-yl)butanoic acid

EXAMPLE 9-22

(R)-4-(3-(N-(3-(5-(2,6-difluorophenyl)-2-methylpentan-2-ylamino)-2-hydroxypropyl)-N-methylsulfamoyl)-5-(trifluoromethyl)phenyl)butanoic acid

EXAMPLE 9-23

(R)-4-(3-(N-(3-(5-(6-fluoropyridin-3-yl)-2-methylpentan-2-ylamino)-2-hydroxypropyl)-N-methylsulfamoyl)-5-(trifluoromethyl)phenyl)butanoic acid

EXAMPLE 9-24

(R)-3-(3-(N-(2-hydroxy-3-(2-methyl-5-phenylpentan-2-ylamino)propyl)-N-methylsulfamoyl)-5-(trifluoromethyl)phenyl)butanoic acid

EXAMPLE 9-25

(R)-3-(3-(N-(2-hydroxy-3-(2-methyl-5-(thiophen-2-yl)pentan-2-ylamino)propyl)-N-methylsulfamoyl)-5-(trifluoromethyl)phenyl)butanoic acid

[Example 9-26] 3-(3-(N—((R)-3-(1-(2,3-dihydro-1H-inden-2-yl)-2-methylpropan-2-ylamino)-2-hydroxypropyl)-N-methylsulfamoyl)-5-(trifluoromethyl)phenyl)butanoic acid

EXAMPLE 9-27

(R)-3-(3-(N-(3-(5-(2-fluorophenyl)-2-methylpentan-2-ylamino)-2-hydroxypropyl)-N-methylsulfamoyl)-5-(trifluoromethyl)phenyl)butanoic acid

EXAMPLE 9-28

(R)-3-(N-(2-hydroxy-3-(2-methyl-5-phenylpentan-2-ylamino)propyl)-N-methylsulfamoyl)-5-(trifluoromethyl)benzoic acid

EXAMPLE 9-29

(R)-2-(3-(N-(2-hydroxy-3-(2-methyl-5-phenylpentan-2-ylamino)propyl)-N-methylsulfamoyl)-5-(trifluoromethyl)phenyl)acetic acid

EXAMPLE 9-30

(R)-3'-(N-(3-(1-(3,4-dimethylphenyl)-2-methylpropan-2-ylamino)-2-hydroxypropyl)-N-methylsulfamoyl-)biphenyl-3-carboxylic acid

EXAMPLE 9-31

(R)-3'-(N-(2-hydroxy-3-(1-(4-isopropylphenyl)-2-methylpropan-2-ylamino)propyl)-N-methylsulfamoyl)biphenyl-3-carboxylic acid

EXAMPLE 9-32

(R)-3'-(N-(2-hydroxy-3-(2-methyl-5-phenylpentan-2-ylamino)propyl)-N-methylsulfamoyl)biphenyl-3-carboxylic acid

EXAMPLE 9-33

(R)-3'-(N-(3-(1-(3,4-dichlorophenyl)-2-methylpropan-2-ylamino)-2-hydroxypropyl)-N-methylsulfamoyl)biphenyl-3-carboxylic acid

EXAMPLE 9-34

(R)-3-(3'-(N-(3-(1-(3,4-dimethylphenyl)-2-methylpropan-2-ylamino)-2-hydroxypropyl)-N-methylsulfamoyl)biphenyl-4-yl)propionic acid

EXAMPLE 9-35

(R)-3-(3'-(N-(2-hydroxy-3-(1-(4-isopropylphenyl)-2-methylpropan-2-ylamino)propyl)-N-methylsulfamoyl)biphenyl-4-yl)propionic acid

EXAMPLE 9-36

(R)-3-(3'-(N-(2-hydroxy-3-(2-methyl-5-phenylpentan-2-ylamino)propyl)-N-methylsulfamoyl)biphenyl-4-yl)propionic acid

EXAMPLE 9-37

(R)-3-(3'-(N-(3-(1-(3,4-dichlorophenyl)-2-methylpropan-2-ylamino)-2-hydroxypropyl)-N-methylsulfamoyl)biphenyl-4-yl)propionic acid

EXAMPLE 9-38

(R)-3-(3'-(N-(2-hydroxy-3-(2-methyl-1-(4-trifluoromethylphenyl)propan-2-ylamino)propyl)-N-methylsulfamoyl)biphenyl-3-yl)propionic acid

EXAMPLE 9-39

(R)-3-(3'-(N-(2-hydroxy-3-(2-methyl-1-(3-trifluoromethylphenyl)propan-2-ylamino)propyl)-N-methylsulfamoyl)biphenyl-3-yl)propionic acid

EXAMPLE 9-40

(R)-3-(3'-(N-(2-hydroxy-3-(2-methyl-5-(4-methylphenyl)pentan-2-ylamino)propyl)-N-methylsulfamoyl)biphenyl-3-yl)propionic acid

EXAMPLE 9-41

(R)-2-(3'-(N-(2-hydroxy-3-(2-methyl-1-(4-trifluoromethylphenyl)propan-2-ylamino)propyl)-N-methylsulfamoyl)biphenyl-4-yl)acetic acid

EXAMPLE 9-42

(R)-2-(3'-(N-(2-hydroxy-3-(2-methyl-1-(3-trifluoromethylphenyl)propan-2-ylamino)propyl)-N-methylsulfamoyl)biphenyl-4-yl)acetic acid

EXAMPLE 9-43

(R)-2-(3'-(N-(2-hydroxy-3-(2-methyl-5-(4-methylphenyl)pentan-2-ylamino)propyl)-N-methylsulfamoyl)biphenyl-4-yl)acetic acid

EXAMPLE 9-44

(R)-3-(3'-(N-(2-hydroxy-3-(2-methyl-1-(4-trifluoromethylphenyl)propan-2-ylamino)propyl)-N-methylsulfamoyl)biphenyl-4-yl)propionic acid

EXAMPLE 9-45

(R)-3-(3'-(N-(2-hydroxy-3-(2-methyl-1-(3-trifluoromethylphenyl)propan-2-ylamino)propyl)-N-methylsulfamoyl)biphenyl-4-yl)propionic acid

EXAMPLE 9-46

(R)-3-(3'-(N-(2-hydroxy-3-(2-methyl-5-(4-methylphenyl)pentan-2-ylamino)propyl)-N-methylsulfamoyl)biphenyl-4-yl)propionic acid

EXAMPLE 9-47

(R)-3-(3'-(N-(3-(1-(4-ethylphenyl)-2-methylpropan-2-ylamino)-2-hydroxypropyl)-N-methylsulfamoyl)biphenyl-3-yl)propionic acid

EXAMPLE 9-48

(R)-3-(3'-(N-(3-(1-(4-tert-butylphenyl)-2-methylpropan-2-ylamino)-2-hydroxypropyl)-N-methylsulfamoyl)biphenyl-3-yl)propionic acid

EXAMPLE 9-49

(R)-3-(3'-(N-(2-hydroxy-3-(1-(4-methoxyphenyl)-2-methylpropan-2-ylamino)propyl)-N-methylsulfamoyl)biphenyl-3-yl)propionic acid

EXAMPLE 9-50

(R)-3-(3'-(N-(2-hydroxy-3-(2-methyl-1-(4-methylthiophenyl)propan-2-ylamino)propyl)-N-methylsulfamoyl)biphenyl-3-yl)propionic acid

EXAMPLE 9-51

(R)-2-(3'-(N-(3-(1-(4-ethylphenyl)-2-methylpropan-2-ylamino)-2-hydroxypropyl)-N-methylsulfamoyl)biphenyl-4-yl)acetic acid

EXAMPLE 9-52

(R)-2-(3'-(N-(3-(1-(4-tert-butylphenyl)-2-methylpropan-2-ylamino)-2-hydroxypropyl)-N-methylsulfamoyl)biphenyl-4-yl)acetic acid

EXAMPLE 9-53

(R)-2-(3'-(N-(2-hydroxy-3-(1-(4-methoxyphenyl)-2-methylpropan-2-ylamino)propyl)-N-methylsulfamoyl)biphenyl-4-yl)acetic acid

EXAMPLE 9-54

(R)-2-(3'-(N-(2-hydroxy-3-(2-methyl-1-(4-methylthiophenyl)propan-2-ylamino)propyl)-N-methylsulfamoyl)biphenyl-4-yl)acetic acid

EXAMPLE 9-55

(R)-3-(3'-(N-(2-hydroxy-3-(2-methyl-5-phenylpentan-2-ylamino)propyl)-N-methylsulfamoyl)-5'-(trifluoromethyl)biphenyl-3-yl)propionic acid

EXAMPLE 9-56

(R)-3-(3'-(N-(2-hydroxy-3-(2-methyl-5-phenylpentan-2-ylamino)propyl)-N-methylsulfamoyl)-5'-(trifluoromethyl)biphenyl-4-yl)propionic acid

EXAMPLE 9-57

(R)-3-(3'-(N-(2-hydroxy-3-(2-methyl-5-(thiophen-3-yl)pentan-2-ylamino)propyl)-N-methylsulfamoyl)biphenyl-3-yl)propionic acid

EXAMPLE 9-58

(R)-2-(3'-(N-(2-hydroxy-3-(2-methyl-5-(thiophen-3-yl)pentan-2-ylamino)propyl)-N-methylsulfamoyl)biphenyl-4-yl)acetic acid

EXAMPLE 9-59

(R)-3-(3'-(N-(2-hydroxy-3-(2-methyl-5-(2-methylphenyl)pentan-2-ylamino)propyl)-N-methylsulfamoyl)biphenyl-3-yl)propionic acid

EXAMPLE 9-60

(R)-3-(3'-(N-(2-hydroxy-3-(2-methyl-5-(3-methylphenyl)pentan-2-ylamino)propyl)-N-methylsulfamoyl)biphenyl-3-yl)propionic acid

EXAMPLE 9-61

(R)-2-(3'-(N-(2-hydroxy-3-(2-methyl-5-(2-methylphenyl)pentan-2-ylamino)propyl)-N-methylsulfamoyl)biphenyl-4-yl)acetic acid

EXAMPLE 9-62

(R)-2-(3'-(N-(2-hydroxy-3-(2-methyl-5-(3-methylphenyl)pentan-2-ylamino)propyl)-N-methylsulfamoyl)biphenyl-4-yl)acetic acid

EXAMPLE 9-63

(R)-3-(3'-(N-(2-hydroxy-3-(2-methyl-5-(3-methylthiophen-2-yl)pentan-2-ylamino)propyl)-N-methylsulfamoyl)biphenyl-3-yl)propionic acid

EXAMPLE 9-64

(R)-3-(3'-(N-(3-(5-(2-fluorophenyl)-2-methylpentan-2-ylamino)-2-hydroxypropyl)-N-methylsulfamoyl)biphenyl-3-yl)propionic acid

EXAMPLE 9-65

(R)-3-(3'-(N-(3-(5-(3-fluorophenyl)-2-methylpentan-2-ylamino)-2-hydroxypropyl)-N-methylsulfamoyl)biphenyl-3-yl)propionic acid

EXAMPLE 9-66

(R)-3-(3'-(N-(3-(5-(4-fluorophenyl)-2-methylpentan-2-ylamino)-2-hydroxypropyl)-N-methylsulfamoyl)biphenyl-3-yl)propionic acid

EXAMPLE 9-67

(R)-3-(3'-(N-(2-hydroxy-3-(2-methyl-5-(thiophen-2-yl)pentan-2-ylamino)propyl)-N-methylsulfamoyl)biphenyl-3-yl)propionic acid

EXAMPLE 9-68

(R)-2-(3'-(N-(2-hydroxy-3-(2-methyl-5-(3-methylthiophen-2-yl)pentan-2-ylamino)propyl)-N-methylsulfamoyl)biphenyl-4-yl)acetic acid

EXAMPLE 9-69

(R)-2-(3'-(N-(3-(5-(2-fluorophenyl)-2-methylpentan-2-ylamino)-2-hydroxypropyl)-N-methylsulfamoyl)biphenyl-4-yl)acetic acid

EXAMPLE 9-70

(R)-2-(3'-(N-(3-(5-(3-fluorophenyl)-2-methylpentan-2-ylamino)-2-hydroxypropyl)-N-methylsulfamoyl)biphenyl-4-yl)acetic acid

EXAMPLE 9-71

(R)-2-(3'-(N-(3-(5-(4-fluorophenyl)-2-methylpentan-2-ylamino)-2-hydroxypropyl)-N-methylsulfamoyl)biphenyl-4-yl)acetic acid

EXAMPLE 9-72

(R)-2-(3'-(N-(2-hydroxy-3-(2-methyl-5-(thiophen-2-yl)pentan-2-ylamino)propyl)-N-methylsulfamoyl)biphenyl-4-yl)acetic acid

EXAMPLE 9-73

(R)-3-(3'-(N-(2-hydroxy-3-(2-methyl-5-(thiophen-3-yl)pentan-2-ylamino)propyl)-N-methylsulfamoyl)-5'-(trifluoromethyl)biphenyl-3-yl)propionic acid

EXAMPLE 9-74

(R)-3-(3'-(N-(2-hydroxy-3-(1-(4-isopropylphenyl)-2-methylpropan-2-ylamino)propyl)-N-methylsulfamoyl)-5'-(trifluoromethyl)biphenyl-3-yl)propionic acid

EXAMPLE 9-75

(R)-3-(3'-(N-(2-hydroxy-3-(2-methyl-5-(thiophen-3-yl)pentan-2-ylamino)propyl)-N-methylsulfamoyl)-5'-(trifluoromethyl)biphenyl-4-yl)propionic acid

EXAMPLE 9-76

(R)-3-(3'-(N-(2-hydroxy-3-(1-(4-isopropylphenyl)-2-methylpropan-2-ylamino)propyl)-N-methylsulfamoyl)-5'-(trifluoromethyl)biphenyl-4-yl)propionic acid

EXAMPLE 9-77

(R)-3-(3'-(N-(2-hydroxy-3-(2-methyl-5-phenylpentan-2-ylamino)propyl)-N-methylsulfamoyl)biphenyl-3-yl)propionic acid

EXAMPLE 9-78

(R)-2-(3'-(N-(2-hydroxy-3-(2-methyl-5-phenylpentan-2-ylamino)propyl)-N-methylsulfamoyl)biphenyl-4-yl)acetic acid

EXAMPLE 9-79

(R)-3-(3'-(N-(3-(5-(2-chlorophenyl)-2-methylpentan-2-ylamino)-2-hydroxypropyl)-N-methylsulfamoyl)biphenyl-3-yl)propionic acid

EXAMPLE 9-80

(R)-2-(3'-(N-(3-(5-(2-chlorophenyl)-2-methylpentan-2-ylamino)-2-hydroxypropyl)-N-methylsulfamoyl)biphenyl-4-yl)acetic acid

EXAMPLE 9-81

(R)-3-(3'-(N-(3-(5-(2-chlorophenyl)-2-methylpentan-2-ylamino)-2-hydroxypropyl)-N-methylsulfamoyl)-5'-(trifluoromethyl)biphenyl-4-yl)propionic acid

EXAMPLE 9-82

(R)-3-(3'-(N-(3-(5-(2-fluorophenyl)-2-methylpentan-2-ylamino)-2-hydroxypropyl)-N-methylsulfamoyl)-5'-(trifluoromethyl)biphenyl-4-yl)propionic acid

EXAMPLE 9-83

(R)-3-(3'-(N-(3-(5-(3-fluorophenyl)-2-methylpentan-2-ylamino)-2-hydroxypropyl)-N-methylsulfamoyl)-5'-(trifluoromethyl)biphenyl-4-yl)propionic acid

EXAMPLE 9-84

(R)-3-(3'-(N-(3-(5-(4-fluorophenyl)-2-methylpentan-2-ylamino)-2-hydroxypropyl)-N-methylsulfamoyl)-5'-(trifluoromethyl)biphenyl-4-yl)propionic acid

EXAMPLE 9-85

(R)-3-(3'-(N-(2-hydroxy-3-(2-methyl-5-(thiophen-2-yl)pentan-2-ylamino)propyl)-N-methylsulfamoyl)-5'-(trifluoromethyl)biphenyl-4-yl)propionic acid

EXAMPLE 9-86

(R)-3-(3'-(N-(2-hydroxy-3-(2-methyl-5-(pyridin-3-yl)pentan-2-ylamino)propyl)-N-methylsulfamoyl)-5'-(trifluoromethyl)biphenyl-4-yl)propionic acid

EXAMPLE 9-87

(R)-3-(3'-(N-(2-hydroxy-3-(2-methyl-5-(pyridin-4-yl)pentan-2-ylamino)propyl)-N-methylsulfamoyl)-5'-(trifluoromethyl)biphenyl-4-yl)propionic acid

EXAMPLE 9-88

(R)-3-(4'-(N-(3-(5-(2-chlorophenyl)-2-methylpentan-2-ylamino)-2-hydroxypropyl)-N-methylsulfamoyl)-3'-ethylbiphenyl-4-yl)propionic acid

EXAMPLE 9-89

(R)-3-(3'-ethyl-4'-(N-(3-(5-(2-fluorophenyl)-2-methylpentan-2-ylamino)-2-hydroxypropyl)-N-methylsulfamoyl)biphenyl-4-yl)propionic acid

EXAMPLE 9-90

(R)-3-(3'-ethyl-4'-(N-(3-(5-(3-fluorophenyl)-2-methylpentan-2-ylamino)-2-hydroxypropyl)-N-methylsulfamoyl)biphenyl-4-yl)propionic acid

EXAMPLE 9-91

(R)-3-(3'-ethyl-4'-(N-(3-(5-(4-fluorophenyl)-2-methylpentan-2-ylamino)-2-hydroxypropyl)-N-methylsulfamoyl)biphenyl-4-yl)propionic acid

EXAMPLE 9-92

(R)-3-(3'-ethyl-4'-(N-(2-hydroxy-3-(2-methyl-5-(thiophen-2-yl)pentan-2-ylamino)propyl)-N-methylsulfamoyl)biphenyl-4-yl)propionic acid

EXAMPLE 9-93

(R)-3-(3'-ethyl-4'-(N-(2-hydroxy-3-(2-methyl-5-(pyridin-3-yl)pentan-2-ylamino)propyl)-N-methylsulfamoyl)biphenyl-4-yl)propionic acid

EXAMPLE 9-94

(R)-3-(3'-ethyl-4'-(N-(2-hydroxy-3-(2-methyl-5-(pyridin-2-yl)pentan-2-ylamino)propyl)-N-methylsulfamoyl)biphenyl-4-yl)propionic acid

EXAMPLE 9-95

(R)-3-(3'-ethyl-4'-(N-(2-hydroxy-3-(2-methyl-5-(thiophen-3-yl)pentan-2-ylamino)propyl)-N-methylsulfamoyl)biphenyl-4-yl)propionic acid

EXAMPLE 9-96

(R)-3-(3'-(N-(2-hydroxy-3-(2-methyl-5-(pyridin-2-yl)pentan-2-ylamino)propyl)-N-methylsulfamoyl)-5'-(trifluoromethyl)biphenyl-4-yl)propionic acid

EXAMPLE 9-97

(R)-3-(3'-ethyl-4'-(N-(2-hydroxy-3-(2-methyl-5-(pyridin-4-yl)pentan-2-ylamino)propyl)-N-methylsulfamoyl)biphenyl-4-yl)propionic acid

[Example 9-98] (R)-4-(5-(N-(2-hydroxy-3-(2-methyl-5-phenylpentan-2-ylamino)propyl)-N-methylsulfamoyl)-2-(trifluoromethyl)thiophen-3-yl)butanoic acid

EXAMPLE 9-99

(R)-4-(5-(N-(3-(5-(2-fluorophenyl)-2-methylpentan-2-ylamino)-2-hydroxypropyl)-N-methylsulfamoyl)-2-(trifluoromethyl)thiophen-3-yl)butanoic acid

EXAMPLE 9-100

(R)-4-(5-(N-(3-(1-(2,3-dihydro-1H-inden-2-yl)-2-methylpropan-2-ylamino)-2-hydroxypropyl)-N-methylsulfamoyl)-2-(trifluoromethyl)thiophen-3-yl)butanoic acid

EXAMPLE 9-101

(R)-4-(5-(N-(3-(5-(2,6-difluorophenyl)-2-methylpentan-2-ylamino)-2-hydroxypropyl)-N-methylsulfamoyl)-2-(trifluoromethyl)thiophen-3-yl)butanoic acid

EXAMPLE 9-102

(R)-3-(3-fluoro-5-(N-(2-hydroxy-3-(2-methyl-5-phenylpentan-2-ylamino)propyl)-N-methylsulfamoyl)phenyl)propionic acid

EXAMPLE 9-103

(R)-3-(3-fluoro-5-(N-(3-(5-(2-fluorophenyl)-2-methylpentan-2-ylamino)-2-hydroxypropyl)-N-methylsulfamoyl)phenyl)propionic acid

EXAMPLE 9-104

(R)-3-(3-(N-(3-(1-(2,3-dihydro-1H-inden-2-yl)-2-methylpropan-2-ylamino)-2-hydroxypropyl)-N-methylsulfamoyl)-5-fluorophenyl)propionic acid

EXAMPLE 9-105

(R)-3-(3-(N-(3-(5-(2,6-difluorophenyl)-2-methylpentan-2-ylamino)-2-hydroxypropyl)-N-methylsulfamoyl)-5-fluorophenyl)propionic acid

EXAMPLE 9-106

(R)-3-(3-fluoro-5-(N-(3-(5-(5-fluorothiophen-2-yl)-2-methylpentan-2-ylamino)-2-hydroxypropyl)-N-methylsulfamoyl)phenyl)propionic acid

EXAMPLE 9-107

(R)-4-(3-fluoro-5-(N-(2-hydroxy-3-(2-methyl-5-phenylpentan-2-ylamino)propyl)-N-methylsulfamoyl)phenyl)butanoic acid

EXAMPLE 9-108

(R)-4-(3-fluoro-5-(N-(3-(5-(2-fluorophenyl)-2-methylpentan-2-ylamino)-2-hydroxypropyl)-N-methylsulfamoyl)phenyl)butanoic acid

EXAMPLE 9-109

(R)-4-(3-(N-(3-(1-(2,3-dihydro-1H-inden-2-yl)-2-methylpropan-2-ylamino)-2-hydroxypropyl)-N-methylsulfamoyl)-5-fluorophenyl)butanoic acid
(Example 9-110] (R)-4-(3-fluoro-5-(N-(2-hydroxy-3-(2-methyl-5-(thiophen-3-yl)pentan-2-ylamino)propyl)-N-methylsulfamoyl)phenyl)butanoic acid

EXAMPLE 9-111

(R)-4-(3-fluoro-5-(N-(2-hydroxy-3-(2-methyl-5-(thiophen-2-yl)pentan-2-ylamino)propyl)-N-methylsulfamoyl)phenyl)butanoic acid

EXAMPLE 9-112

(R)-4-(3-(N-(3-(5-(2,6-difluorophenyl)-2-methylpentan-2-ylamino)-2-hydroxypropyl)-N-methylsulfamoyl)-5-fluorophenyl)butanoic acid

EXAMPLE 9-113

(R)-3-(3-chloro-5-(N-(2-hydroxy-3-(2-methyl-5-phenylpentan-2-ylamino)propyl)-N-methylsulfamoyl)phenyl)propionic acid

EXAMPLE 9-114

(R)-3-(3-chloro-5-(N-(3-(5-(2-fluorophenyl)-2-methylpentan-2-ylamino)-2-hydroxypropyl)-N-methylsulfamoyl)phenyl)propionic acid

EXAMPLE 9-115

(R)-3-(3-chloro-5-(N-(3-(1-(2,3-dihydro-1H-inden-2-yl)-2-methylpropan-2-ylamino)-2-hydroxypropyl)-N-methylsulfamoyl)phenyl)propionic acid

EXAMPLE 9-116

(R)-3-(3-chloro-5-(N-(2-hydroxy-3-(2-methyl-5-(thiophen-3-yl)pentan-2-ylamino)propyl)-N-methylsulfamoyl)phenyl)propionic acid

EXAMPLE 9-117

(R)-3-(3-chloro-5-(N-(2-hydroxy-3-(2-methyl-5-(thiophen-2-yl)pentan-2-ylamino)propyl)-N-methylsulfamoyl)phenyl)propionic acid

EXAMPLE 9-118

(R)-3-(3-chloro-5-(N-(3-(5-(2,6-difluorophenyl)-2-methylpentan-2-ylamino)-2-hydroxypropyl)-N-methylsulfamoyl)phenyl)propionic acid

EXAMPLE 9-119

(R)-3-(3-chloro-5-(N-(3-(5-(5-fluorothiophen-2-yl)-2-methylpentan-2-ylamino)-2-hydroxypropyl)-N-methylsulfamoyl)phenyl)propionic acid

EXAMPLE 9-120

(R)-4-(3-chloro-5-(N-(2-hydroxy-3-(2-methyl-5-phenylpentan-2-ylamino)propyl)-N-methylsulfamoyl)phenyl)butanoic acid

EXAMPLE 9-121

(R)-4-(3-chloro-5-(N-(3-(5-(2-fluorophenyl)-2-methylpentan-2-ylamino)-2-hydroxypropyl)-N-methylsulfamoyl)phenyl)butanoic acid

EXAMPLE 9-122

(R)-4-(3-chloro-5-(N-(3-(1-(2,3-dihydro-1H-inden-2-yl)-2-methylpropan-2-ylamino)-2-hydroxypropyl)-N-methylsulfamoyl)phenyl)butanoic acid

EXAMPLE 9-123

(R)-4-(3-chloro-5-(N-(2-hydroxy-3-(2-methyl-5-(thiophen-3-yl)pentan-2-ylamino)propyl)-N-methylsulfamoyl)phenyl)butanoic acid

EXAMPLE 9-124

(R)-4-(3-chloro-5-(N-(2-hydroxy-3-(2-methyl-5-(thiophen-2-yl)pentan-2-ylamino)propyl)-N-methylsulfamoyl)phenyl)butanoic acid

EXAMPLE 9-125

(R)-4-(3-chloro-5-(N-(3-(5-(2,6-difluorophenyl)-2-methylpentan-2-ylamino)-2-hydroxypropyl)-N-methylsulfamoyl)phenyl)butanoic acid

EXAMPLE 9-126

(R)-4-(3-ethyl-4-(N-(3-(5-(2-fluorophenyl)-2-methylpentan-2-ylamino)-2-hydroxypropyl)-N-methylsulfamoyl)phenyl)butanoic acid

EXAMPLE 9-127

(R)-4-(4-(N-(3-(1-(2,3-dihydro-1H-inden-2-yl)-2-methylpropan-2-ylamino)-2-hydroxypropyl)-N-methylsulfamoyl)-3-ethylphenyl)butanoic acid

EXAMPLE 9-128

(R)-4-(3-ethyl-4-(N-(2-hydroxy-3-(2-methyl-5-(thiophen-3-yl)pentan-2-ylamino)propyl)-N-methylsulfamoyl)phenyl)butanoic acid

EXAMPLE 9-129

(R)-4-(3-ethyl-4-(N-(2-hydroxy-3-(2-methyl-5-(thiophen-2-yl)pentan-2-ylamino)propyl)-N-methylsulfamoyl)phenyl)butanoic acid

EXAMPLE 9-130

(R)-4-(4-(N-(3-(5-(2,6-difluorophenyl)-2-methylpentan-2-ylamino)-2-hydroxypropyl)-N-methylsulfamoyl)-3-ethylphenyl)butanoic acid

EXAMPLE 9-131

(R)-4-(3-ethyl-4-(N-(3-(5-(5-fluorothiophen-2-yl)-2-methylpentan-2-ylamino)-2-hydroxypropyl)-N-methylsulfamoyl)phenyl)butanoic acid

EXAMPLE 9-132

(R)-3-(3-(N-(2-hydroxy-3-(2-methyl-5-phenylpentan-2-ylamino)propyl)-N-methylsulfamoyl)-5-(trifluoromethoxy)phenyl)propionic acid

EXAMPLE 9-133

(R)-3-(3-(N-(3-(5-(2-fluorophenyl)-2-methylpentan-2-ylamino)-2-hydroxypropyl)-N-methylsulfamoyl)-5-(trifluoromethoxy)phenyl)propionic acid

EXAMPLE 9-134

(R)-3-(3-(N-(3-(1-(2,3-dihydro-1H-inden-2-yl)-2-methylpropan-2-ylamino)-2-hydroxypropyl)-N-methylsulfamoyl)-5-(trifluoromethoxy)phenyl)propionic acid

EXAMPLE 9-135

(R)-3-(3-(N-(2-hydroxy-3-(2-methyl-5-(thiophen-3-yl)pentan-2-ylamino)propyl)-N-methylsulfamoyl)-5-(trifluoromethoxy)phenyl)propionic acid

EXAMPLE 9-136

(R)-3-(3-(N-(2-hydroxy-3-(2-methyl-5-(thiophen-2-yl)pentan-2-ylamino)propyl)-N-methylsulfamoyl)-5-(trifluoromethoxy)phenyl)propionic acid

EXAMPLE 9-137

(R)-3-(3-(N-(3-(5-(2,6-difluorophenyl)-2-methylpentan-2-ylamino)-2-hydroxypropyl)-N-methylsulfamoyl)-5-(trifluoromethoxy)phenyl)propionic acid

EXAMPLE 9-138

(R)-3-(3-(N-(3-(5-(5-fluorothiophen-2-yl)-2-methylpentan-2-ylamino)-2-hydroxypropyl)-N-methylsulfamoyl)-5-(trifluoromethoxy)phenyl)propionic acid

EXAMPLE 9-139

(R)-4-(3-(N-(2-hydroxy-3-(2-methyl-5-phenylpentan-2-ylamino)propyl)-N-methylsulfamoyl)-5-(trifluoromethoxy)phenyl)butanoic acid

EXAMPLE 9-140

(R)-4-(3-(N-(3-(5-(2-fluorophenyl)-2-methylpentan-2-ylamino)-2-hydroxypropyl)-N-methylsulfamoyl)-5-(trifluoromethoxy)phenyl)butanoic acid

EXAMPLE 9-141

(R)-4-(3-(N-(3-(1-(2,3-dihydro-1H-inden-2-yl)-2-methylpropan-2-ylamino)-2-hydroxypropyl)-N-methylsulfamoyl)-5-(trifluoromethoxy)phenyl)butanoic acid

EXAMPLE 9-142

(R)-4-(3-(N-(2-hydroxy-3-(2-methyl-5-(thiophen-3-yl)pentan-2-ylamino)propyl)-N-methylsulfamoyl)-5-(trifluoromethoxy)phenyl)butanoic acid

EXAMPLE 9-143

(R)-4-(3-(N-(2-hydroxy-3-(2-methyl-5-(thiophen-2-yl)pentan-2-ylamino)propyl)-N-methylsulfamoyl)-5-(trifluoromethoxy)phenyl)butanoic acid

EXAMPLE 9-144

(R)-4-(3-(N-(3-(5-(2,6-difluorophenyl)-2-methylpentan-2-ylamino)-2-hydroxypropyl)-N-methylsulfamoyl)-5-(trifluoromethoxy)phenyl)butanoic acid

EXAMPLE 9-145

(R)-3-(3-(N-(3-(5-(2,6-difluorophenyl)-2-methylpentan-2-ylamino)-2-hydroxypropyl)-N-methylsulfamoyl)-5-(trifluoromethyl)phenyl)propionic acid

EXAMPLE 9-146

(R)-3-(3-(N-(3-(5-(5-fluorothiophen-2-yl)-2-methylpentan-2-ylamino)-2-hydroxypropyl)-N-methylsulfamoyl)-5-(trifluoromethyl)phenyl)propionic acid

EXAMPLE 9-147

(R)-3-(3-(N-(3-(5-(2,5-difluorophenyl)-2-methylpentan-2-ylamino)-2-hydroxypropyl)-N-methylsulfamoyl)-5-(trifluoromethyl)phenyl)propionic acid

EXAMPLE 9-148

(R)-3-(5-(3-(N-(2-hydroxy-3-(2-methyl-5-phenylpentan-2-ylamino)propyl)-N-methylsulfamoyl)-5-(trifluoromethyl)phenyl)pyridin-2-yl)propionic acid

EXAMPLE 9-149

(R)-3-(5-(3-(N-(3-(5-(2-fluorophenyl)-2-methylpentan-2-ylamino)-2-hydroxypropyl)-N-methylsulfamoyl)-5-(trifluoromethyl)phenyl)pyridin-2-yl)propionic acid

EXAMPLE 9-150

(R)-3-(5-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)pyridin-2-yl)propionic acid

EXAMPLE 9-151

(R)-3-(5-(3-(N-(2-hydroxy-3-(2-methyl-5-(thiophen-3-yl)pentan-2-ylamino)propyl)-N-methylsulfamoyl)-5-(trifluoromethyl)phenyl)pyridin-2-yl)propionic acid

EXAMPLE 9-152

(R)-3-(5-(3-(N-(2-hydroxy-3-(2-methyl-5-(thiophen-2-yl)pentan-2-ylamino)propyl)-N-methylsulfamoyl)-5-(trifluoromethyl)phenyl)pyridin-2-yl)propionic acid

EXAMPLE 9-153

(R)-3-(5-(3-(N-(3-(5-(2,6-difluorophenyl)-2-methylpentan-2-ylamino)-2-hydroxypropyl)-N-methylsulfamoyl)-5-(trifluoromethyl)phenyl)pyridin-2-yl)propionic acid

EXAMPLE 9-154

(R)-3-(5-(3-(N-(2-hydroxy-3-(2-methyl-5-(pyridin-4-yl)pentan-2-ylamino)propyl)-N-methylsulfamoyl)-5-(trifluoromethyl)phenyl)pyridin-2-yl)propionic acid

EXAMPLE 9-155

(R)-3-(6-(3-(N-(2-hydroxy-3-(2-methyl-5-phenylpentan-2-ylamino)propyl)-N-methylsulfamoyl)-5-(trifluoromethyl)phenyl)pyridin-3-yl)propionic acid

EXAMPLE 9-156

(R)-3-(6-(3-(N-(3-(5-(2-fluorophenyl)-2-methylpentan-2-ylamino)-2-hydroxypropyl)-N-methylsulfamoyl)-5-(trifluoromethyl)phenyl)pyridin-3-yl)propionic acid

EXAMPLE 9-157

(R)-3-(6-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)pyridin-3-yl)propionic acid

EXAMPLE 9-158

(R)-3-(6-(3-(N-(2-hydroxy-3-(2-methyl-5-(thiophen-2-yl)pentan-2-ylamino)propyl)-N-methylsulfamoyl)-5-(trifluoromethyl)phenyl)pyridin-3-yl)propionic acid

EXAMPLE 9-159

(R)-3-(6-(2-chloro-4-(N-(2-hydroxy-3-(2-methyl-5-phenylpentan-2-ylamino)propyl)-N-methylsulfamoyl)phenyl)pyridin-2-yl)propionic acid

EXAMPLE 9-160

(R)-3-(6-(2-chloro-4-(N-(3-(5-(2-fluorophenyl)-2-methylpentan-2-ylamino)-2-hydroxypropyl)-N-methylsulfamoyl)phenyl)pyridin-2-yl)propionic acid

EXAMPLE 9-161

(R)-3-(6-(2-chloro-4-(N-(3-(1-(2,3-dihydro-1H-inden-2-yl)-2-methylpropan-2-ylamino)-2-hydroxypropyl)-N-methylsulfamoyl)phenyl)pyridin-2-yl)propionic acid

EXAMPLE 9-162

(R)-3-(6-(2-chloro-4-(N-(2-hydroxy-3-(2-methyl-5-(thiophen-2-yl)pentan-2-ylamino)propyl)-N-methylsulfamoyl)phenyl)pyridin-2-yl)propionic acid

EXAMPLE 9-163

(R)-3-(5-(3,5-dichloro-4-(N-(2-hydroxy-3-(2-methyl-5-phenylpentan-2-ylamino)propyl)-N-methylsulfamoyl)phenyl)pyridin-2-yl)propionic acid

EXAMPLE 9-164

(R)-3-(5-(3,5-dichloro-4-(N-(3-(5-(2-fluorophenyl)-2-methylpentan-2-ylamino)-2-hydroxypropyl)-N-methylsulfamoyl)phenyl)pyridin-2-yl)propionic acid

[Example 9-165] 4-(3-(N—((R)-2-hydroxy-3-(2-methyl-5-phenylpentan-2-ylamino)propyl)-N-methylsulfamoyl)-5-(trifluoromethyl)phenyl)pentanoic acid

[Example 9-166] 4-(3-(N—((R)-3-(5-(2-fluorophenyl)-2-methylpentan-2-ylamino)-2-hydroxypropyl)-N-methylsulfamoyl)-5-(trifluoromethyl)phenyl)pentanoic acid

[Example 9-167] 4-(3-(N—((R)-3-(1-(2,3-dihydro-1H-inden-2-yl)-2-methylpropan-2-ylamino)-2-hydroxypropyl)-N-methylsulfamoyl)-5-(trifluoromethyl)phenyl)pentanoic acid

EXAMPLE 9-168

(R)-3-(6-(3-ethyl-4-(N-(3-(5-(2-fluorophenyl)-2-methylpentan-2-ylamino)-2-hydroxypropyl)-N-methylsulfamoyl)phenyl)pyridin-2-yl)propionic acid

EXAMPLE 9-169

(R)-3-(6-(3,5-dichloro-4-(N-(2-hydroxy-3-(2-methyl-5-(thiophen-3-yl)pentan-2-ylamino)propyl)-N-methylsulfamoyl)phenyl)pyridin-2-yl)propionic acid

EXAMPLE 9-170

(R)-3-(6-(3,5-dichloro)4-(N-(3-(1-(2,3-dihydro-1H-inden-2-yl)-2-methylpropan-2-ylamino)-2-hydroxypropyl)-N-methylsulfamoyl)phenyl)pyridin-2-yl)propionic acid

EXAMPLE 9-171

(R)-6-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)picolinic acid

EXAMPLE 9-172

(R)-6-(3-(N-(2-hydroxy-3-(2-methyl-5-phenylpentan-2-ylamino)propyl)-N-methylsulfamoyl)-5-(trifluoromethyl)phenyl)picolinic acid

EXAMPLE 9-173

(R)-3-(2-chloro-5-fluoro-3-(N-(2-hydroxy-3-(2-methyl-5-phenylpentan-2-ylamino)propyl)-N-methylsulfamoyl)phenyl)propionic acid

EXAMPLE 9-174

(R)-3-(2-chloro-5-fluoro-3-(N-(3-(5-(2-fluorophenyl)-2-methylpentan-2-ylamino)-2-hydroxypropyl)-N-methylsulfamoyl)phenyl)propionic acid

EXAMPLE 9-175

(R)-3-(2-chloro-3-(N-(3-(1-(2,3-dihydro-1H-inden-2-yl)-2-methylpropan-2-ylamino)-2-hydroxypropyl)-N-methylsulfamoyl)-5-fluorophenyl)propionic acid

EXAMPLE 9-176

(R)-3-(2-chloro-5-fluoro-3-(N-(2-hydroxy-3-(2-methyl-5-(thiophen-3-yl)pentan-2-ylamino)propyl)-N-methylsulfamoyl)phenyl)propionic acid

EXAMPLE 9-177

(R)-3-(2-chloro-5-fluoro-3-(N-(2-hydroxy-3-(2-methyl-5-(thiophen-2-yl)pentan-2-ylamino)propyl)-N-methylsulfamoyl)phenyl)propionic acid

EXAMPLE 9-178

(R)-3-(2-chloro-3-(N-(3-(5-(2,6-difluorophenyl)-2-methylpentan-2-ylamino)-2-hydroxypropyl)-N-methylsulfamoyl)-5-fluorophenyl)propionic acid

EXAMPLE 9-179

(R)-2-(3-(N-(2-hydroxy-3-(2-methyl-5-phenylpentan-2-ylamino)propyl)-N-methylsulfamoyl)-5-(trifluoromethyl)phenyloxy)acetic acid

EXAMPLE 9-180

(R)-2-(3-(N-(2-hydroxy-3-(2-methyl-5-phenylpentan-2-ylamino)propyl)-N-methylsulfamoyl)-5-(trifluoromethyl)phenylamino)acetic acid

EXAMPLE 10-1

(R)-3-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)propionic acid (Step A) Synthesis of ethyl (R)-3-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)acrylate 0.1M toluene solution (4 mL) comprising (R)-3-bromo-N-(3-(1-(2,3-dihydro-1H-inden-2-yl)-2-methylpropan-2-ylamino)-2-hydroxypropyl)-N-methyl-5-(trifluoromethyl)benzenesulfoneamide (Exp. 2-35) was dissolved in dioxane (4 mL), and added with trisdibenzylideneacetonepalladium (0) (Ald, 55 mg), tri-tert-butylphosphinetetrafluoroborate (Ald, 46.4 mg), cesium carbonate (WAKO, 312.8 mg), and ethyl acrylate (es1, Ald, 1.164 mL) followed by stirring at 100° C. for 9 hours. After subjecting the mixture to a ChemElute column (manufactured by VARIAN), the solvent was distilled off under reduced pressure. The residue was subjected to distillation under reduced pressure to remove the solvent, and therefore the target compound (372.4 mg) was obtained as a crude product.

LCMS: Method B, retention time 1.57 minutes, (ES+) 583

(Step B) Synthesis of ethyl (R)-3-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)propionate The compound obtained from the Example 10-1 Step A (372.4 mg) was dissolved in methanol (3 mL), and added with 10% palladium-activated carbon (MERCK, 20 mg) and the mixture was stirred under hydrogen atmosphere for 1 day at room temperature. With purification by filtering, the target compound (348.8 mg) was obtained.

LCMS: Method B, retention time 1.54 minutes, (ES+) 585

(Step C) Synthesis of (R)-3-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)propionic acid According to the method of Example 3-1 Step B, the target compound was obtained from the compound obtained from Example 10-1 Step B.

EXAMPLES 10-2 TO 33

The target compound was obtained in the same manner as Example 10-1 with combinations shown in Table 10 [in the table, es1 indicates ethyl acrylate, es2 indicates isobutyl 3-butenoate, es3 indicates ethyl 4-pentenoate, es4 indicates methyl 5-hexenoate, and es5 indicates methyl 3,3-dimethyl 4-petenoate] except that SM2 and ES were used instead of Exp. 2-35 and es1, respectively.

TABLE 10

| Exp. | SM2 | ES | LCMS method | Rtime | Mass |
|---|---|---|---|---|---|
| 10-1 | Exp. 2-35 | es1 | B | 1.43 | 557 |
| 10-2 | Exp. 2-38 | es1 | B | 1.24 | 519 |

TABLE 10-continued
| | | | LCMS | | |
|---|---|---|---|---|---|
| Exp. | SM2 | ES | method | Rtime | Mass |
| 10-3 | Exp. 2-4 | es1 | B | 1.23 | 489 |
| 10-4 | Exp. 2-6 | es1 | B | 1.25 | 489 |
| 10-5 | Exp. 2-27 | es1 | B | 1.25 | 557 |
| 10-6 | Exp. 2-18 | es1 | B | 1.21 | 557 |
| 10-7 | Exp. 2-23 | es1 | B | 1.17 | 523 |
| 10-8 | Exp. 2-24 | es1 | B | 1.26 | 523 |
| 10-9 | Exp. 2-26 | es1 | B | 1.24 | 557 |
| 10-10 | Exp. 2-20 | es1 | B | 1.21 | 503 |
| 10-11 | Exp. 2-21 | es1 | B | 1.20 | 503 |
| 10-12 | Exp. 2-16 | es1 | B | 1.26 | 517 |
| 10-13 | Exp. 2-27 | es3 | B | 1.40 | 585 |
| 10-14 | Exp. 2-27 | es4 | B | 1.48 | 599 |
| 10-15 | Exp. 2-6 | es3 | B | 1.34 | 517 |
| 10-16 | Exp. 2-27 | es5 | B | 1.60 | 613 |
| 10-17 | Exp. 2-28 | es1 | B | 1.25 | 573 |
| 10-18 | Exp. 2-31 | es1 | B | 1.22 | 507 |
| 10-19 | Exp. 2-29 | es1 | B | 1.25 | 525 |
| 10-20 | Exp. 2-33 | es1 | B | 1.33 | 545 |
| 10-21 | Exp. 2-34 | es1 | B | 1.34 | 545 |
| 10-22 | Exp. 2-30 | es1 | B | 1.12 | 495 |
| 10-23 | Exp. 2-27 | es2 | B | 1.26 | 571 |
| 10-24 | Exp. 2-39 | es1 | B | 1.37 | 529 |
| 10-25 | Exp. 2-35 | es2 | A | 3.17 | 571 |
| 10-26 | Exp. 2-17 | es1 | B | 1.33 | 505 |
| 10-27 | Exp. 2-25 | es1 | B | 1.43 | 511 |
| 10-28 | Exp. 2-22 | es1 | B | 1.36 | 491 |
| 10-29 | Exp. 2-25 | es2 | B | 1.46 | 525 |
| 10-30 | Exp. 2-17 | es2 | B | 1.43 | 519 |
| 10-31 | Exp. 2-42 | es2 | B | 1.34 | 531 |
| 10-32 | Exp. 2-42 | es1 | B | 1.45 | 517 |
| 10-33 | Exp. 2-19 | es1 | B | 1.24 | 545 |
Hereinbelow, structures of the compounds of Example to 10-33 (Exp. 10-1 to 10-33) are shown.
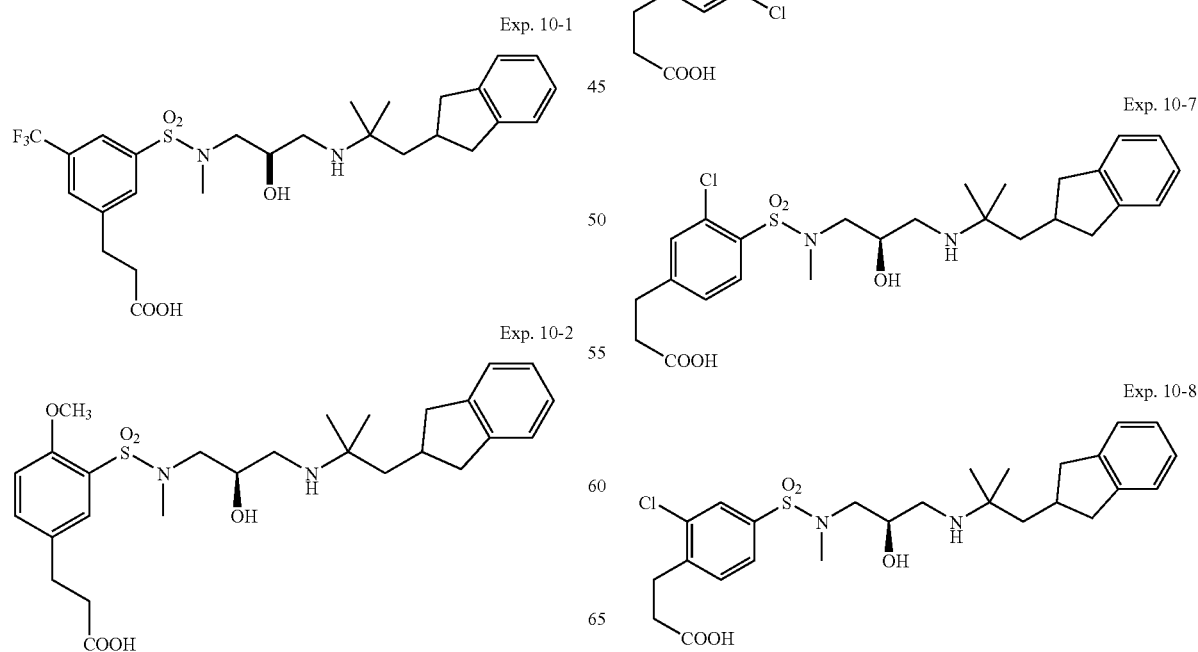

Exp. 10-9
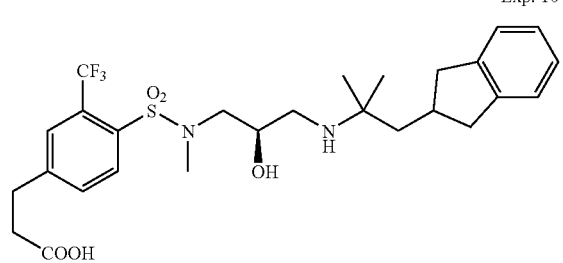
Exp. 10-10
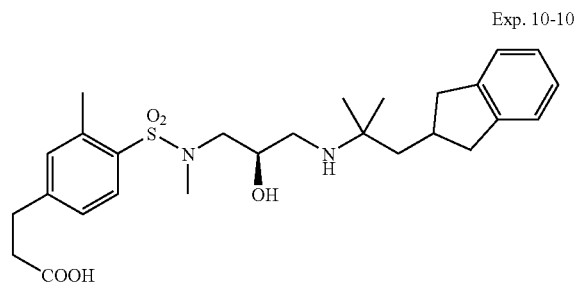
Exp. 10-11
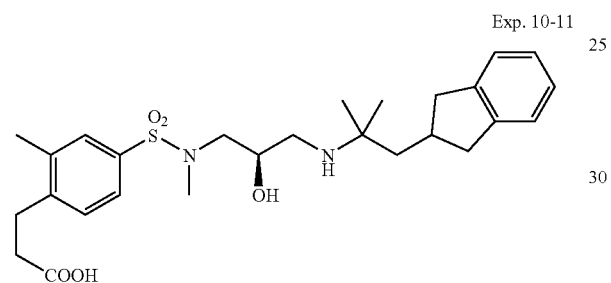
Exp. 10-12
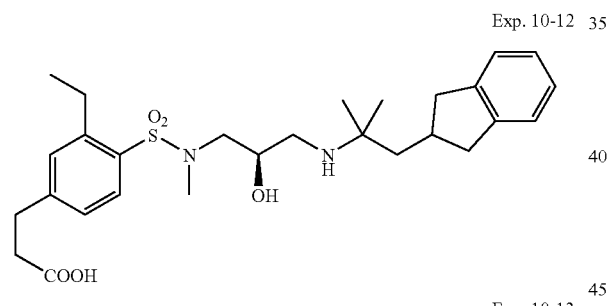
Exp. 10-13
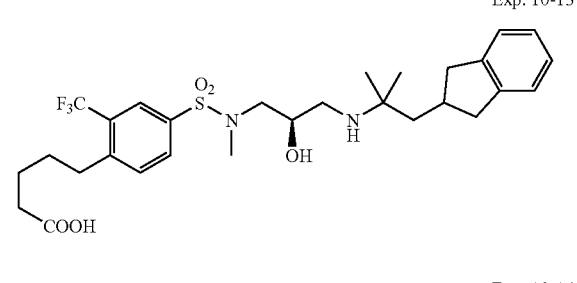
Exp. 10-14
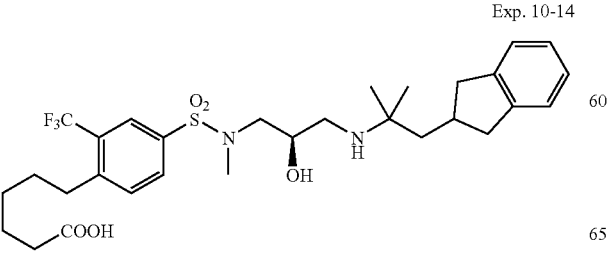
Exp. 10-15
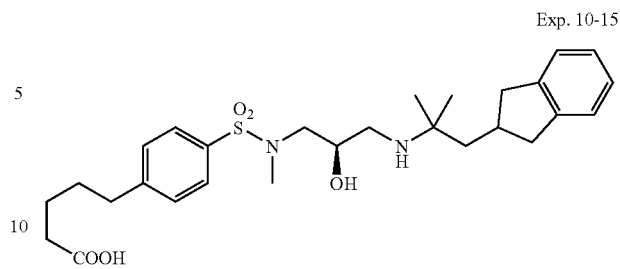
Exp. 10-16
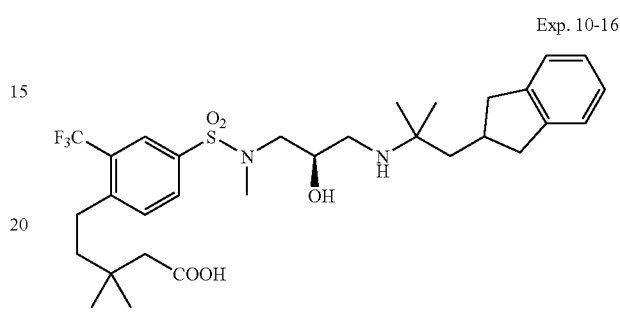
Exp. 10-17
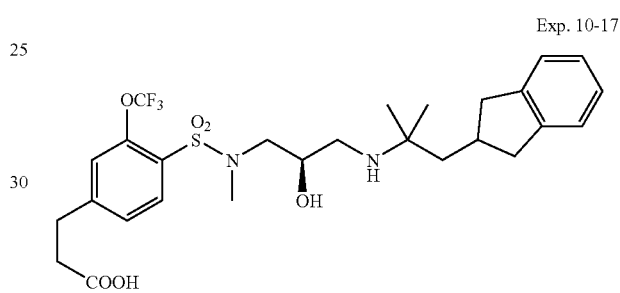
Exp. 10-18
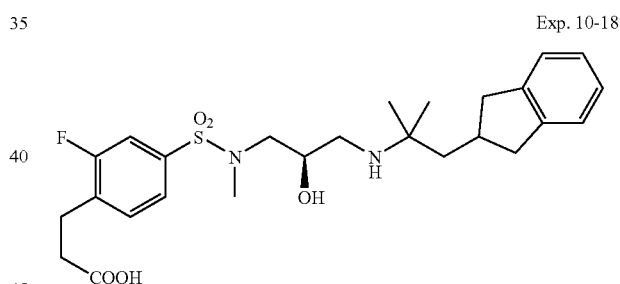
Exp. 10-19
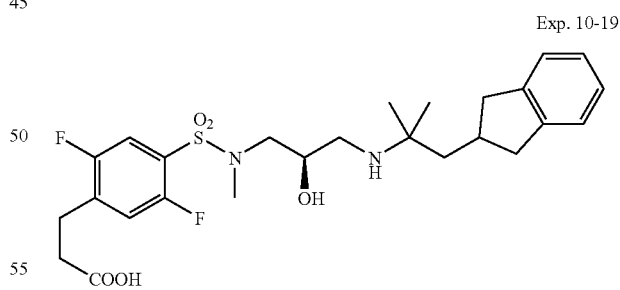
Exp. 10-20
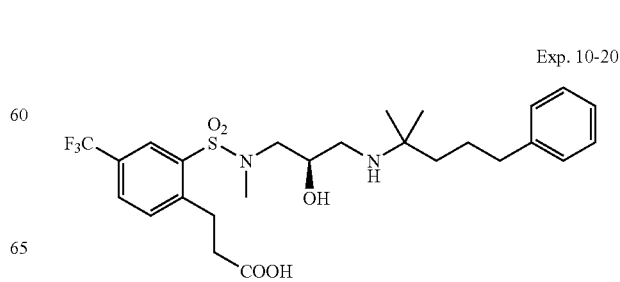

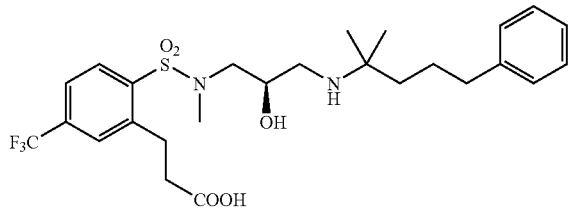
Exp. 10-21
Exp. 10-27
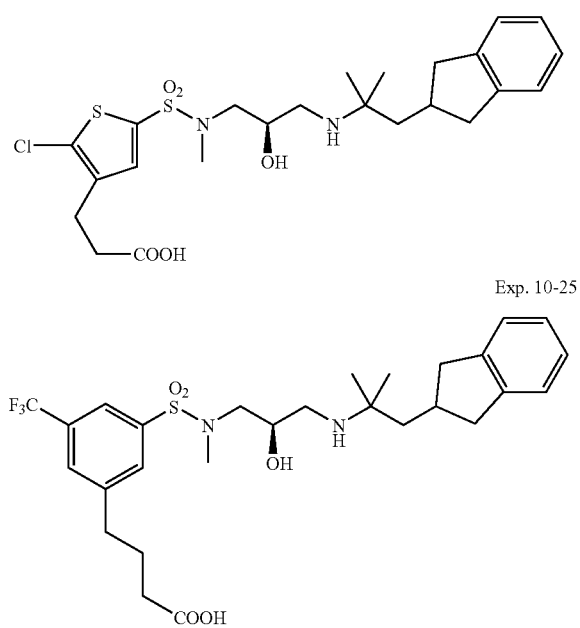
Exp. 10-22
Exp. 10-23
Exp. 10-24
Exp. 10-25
Exp. 10-26
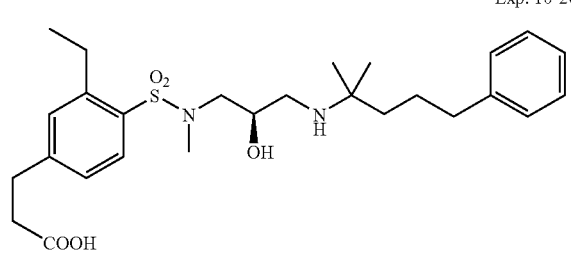
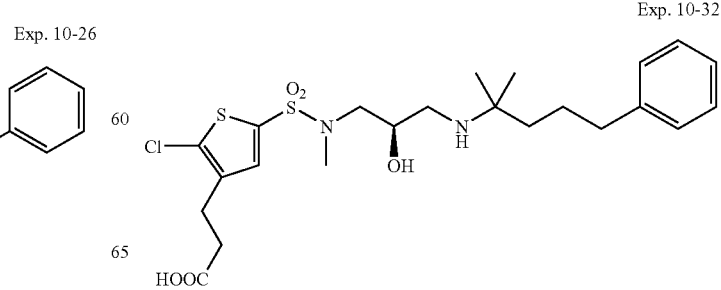
Exp. 10-28
Exp. 10-29
Exp. 10-30
Exp. 10-31
Exp. 10-32

-continued

Exp. 10-33

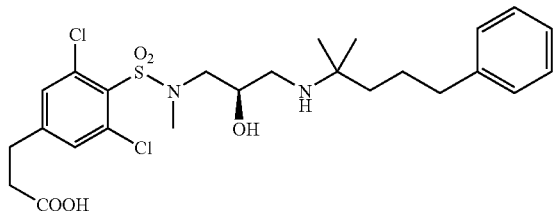

EXAMPLE 10-2

(R)-3-(3-(N-(3-(1-(2,3-dihydro-1H-inden-2-yl)-2-methyl-propan-2-ylamino)-2-hydroxypropyl)-N-methylsulfamoyl)-4-methoxyphenyl)propionic acid

EXAMPLE 10-3

(R)-3-(2-(N-(3-(1-(2,3-dihydro-1H-inden-2-yl)-2-methyl-propan-2-ylamino)-2-hydroxypropyl)-N-methylsulfamoyl)phenyl)propionic acid

EXAMPLE 10-4

(R)-3-(4-(N-(3-(1-(2,3-dihydro-1H-inden-2-yl)-2-methyl-propan-2-ylamino)-2-hydroxypropyl)-N-methylsulfamoyl)phenyl)propionic acid

EXAMPLE 10-5

(R)-3-(4-(N-(3-(1-(2,3-dihydro-1H-inden-2-yl)-2-methyl-propan-2-ylamino)-2-hydroxypropyl)-N-methylsulfamoyl)-2-(trifluoromethyl)phenyl)propionic acid

EXAMPLE 10-6

(R)-3-(3,5-dichloro-4-(N-(3-(1-(2,3-dihydro-1H-inden-2-yl)-2-methylpropan-2-ylamino)-2-hydroxypropyl)-N-methylsulfamoyl)phenyl)propionic acid

EXAMPLE 10-7

(R)-3-(3-chloro-4-(N-(3-(1-(2,3-dihydro-1H-inden-2-yl)-2-methylpropan-2-ylamino)-2-hydroxypropyl)-N-methylsulfamoyl)phenyl)propionic acid

EXAMPLE 10-8

(R)-3-(2-chloro-4-(N-(3-(1-(2,3-dihydro-1H-inden-2-yl)-2-methylpropan-2-ylamino)-2-hydroxypropyl)-N-methylsulfamoyl)phenyl)propionic acid

EXAMPLE 10-9

(R)-3-(4-(N-(3-(1-(2,3-dihydro-1H-inden-2-yl)-2-methyl-propan-2-ylamino)-2-hydroxypropyl)-N-methylsulfamoyl)-3-(trifluoromethyl)phenyl)propionic acid

EXAMPLE 10-10

(R)-37(4-(N-(3-(1-(2,3-dihydro-1H-inden-2-yl)-2-methyl-propan-2-ylamino)-2-hydroxypropyl)-N-methylsulfamoyl)-3-methylphenyl)propionic acid

EXAMPLE 10-11

(R)-3-(4-(N-(3-(1-(2,3-dihydro-1H-inden-2-yl)-2-methyl-propan-2-ylamino)-2-hydroxypropyl)-N-methylsulfamoyl)-2-methylphenyl)propionic acid

EXAMPLE 10-12

(R)-3-(4-(N-(3-(1-(2,3-dihydro-1H-inden-2-yl)-2-methyl-propan-2-ylamino)-2-hydroxypropyl)-N-methylsulfamoyl)-3-ethylphenyl)propionic acid

EXAMPLE 10-13

(R)-5-(4-(N-(3-(1-(2,3-dihydro-1H-inden-2-yl)-2-methyl-propan-2-ylamino)-2-hydroxypropyl)-N-methylsulfamoyl)-2-(trifluoromethyl)phenyl)pentanoic acid

EXAMPLE 10-14

(R)-6-(4-(N-(3-(1-(2,3-dihydro-1H-inden-2-yl)-2-methyl-propan-2-ylamino)-2-hydroxypropyl)-N-methylsulfamoyl)-2-(trifluoromethyl)phenyl)hexanoic acid

EXAMPLE 10-15

(R)-5-(4-(N-(3-(1-(2,3-dihydro-1H-inden-2-yl)-2-methyl-propan-2-ylamino)-2-hydroxypropyl)-N-methylsulfamoyl)phenyl)pentanoic acid

EXAMPLE 10-16

(R)-5-(4-(N-(3-(1-(2,3-dihydro-1H-inden-2-yl)-2-methyl-propan-2-ylamino)-2-hydroxypropyl)-N-methylsulfamoyl)-2-(trifluoromethyl)phenyl)-3,3-dimethylpentanoic acid

EXAMPLE 10-17

(R)-3-(4-(N-(3-(1-(2,3-dihydro-1H-inden-2-yl)-2-methyl-propan-2-ylamino)-2-hydroxypropyl)-N-methylsulfamoyl)-3-(trifluoromethoxy)phenyl)propionic acid

EXAMPLE 10-18

(R)-3-(4-(N-(3-(1-(2,3-dihydro-1H-inden-2-yl)-2-methyl-propan-2-ylamino)-2-hydroxypropyl)-N-methylsulfamoyl)-2-fluorophenyl)propionic acid

EXAMPLE 10-19

(R)-3-(4-(N-(3-(1-(2,3-dihydro-1H-inden-2-yl)-2-methyl-propan-2-ylamino)-2-hydroxypropyl)-N-methylsulfamoyl)-2,5-difluorophenyl)propionic acid

EXAMPLE 10-20

(R)-3-(2-(N-(2-hydroxy-3-(2-methyl-5-phenylpentan-2-ylamino)propyl)-N-methylsulfamoyl)-4-(trifluoromethyl)phenyl)propionic acid

EXAMPLE 10-21

(R)-3-(2-(N-(2-hydroxy-3-(2-methyl-5-phenylpentan-2-ylamino)propyl)-N-methylsulfamoyl)-5-(trifluoromethyl)phenyl)propionic acid

EXAMPLE 10-22

(R)-3-(3-fluoro-4-(N-(2-hydroxy-3-(2-methyl-5-phenylpentan-2-ylamino)propyl)-N-methylsulfamoyl)phenyl)propionic acid

EXAMPLE 10-23

(R)-4-(4-(N-(3-(1-(2,3-dihydro-1H-inden-2-yl)-2-methylpropan-2-ylamino)-2-hydroxypropyl)-N-methylsulfamoyl)-2-(trifluoromethyl)phenyl)butanoic acid

EXAMPLE 10-24

(R)-3-(2-chloro-5-(N-(3-(1-(2,3-dihydro-1H-inden-2-yl)-2-methylpropan-2-ylamino)-2-hydroxypropyl)-N-methylsulfamoyl)thiophen-3-yl)propionic acid

EXAMPLE 10-25

(R)-4-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)butanoic acid

EXAMPLE 10-26

(R)-3-(3-ethyl-4-(N-(2-hydroxy-3-(2-methyl-5-phenylpentan-2-ylamino)propyl)-N-methylsulfamoyl)phenyl)propionic acid

EXAMPLE 10-27

(R)-3-(2-chloro-4-(N-(2-hydroxy-3-(2-methyl-5-phenylpentan-2-ylamino)propyl)-N-methylsulfamoyl)phenyl)propionic acid

EXAMPLE 10-28

(R)-3-(4-(N-(2-hydroxy-3-(2-methyl-5-phenylpentan-2-ylamino)propyl)-N-methylsulfamoyl)-2-methylphenyl)propionic acid

EXAMPLE 10-29

(R)-4-(2-chloro-4-(N-(2-hydroxy-3-(2-methyl-5-phenylpentan-2-ylamino)propyl)-N-methylsulfamoyl)phenyl)butanoic acid

EXAMPLE 10-30

(R)-4-(3-ethyl-4-(N-(2-hydroxy-3-(2-methyl-5-phenylpentan-2-ylamino)propyl)-N-methylsulfamoyl)phenyl)butanoic acid

EXAMPLE 10-31

(R)-4-(2-chloro-5-(N-(2-hydroxy-3-(2-methyl-5-phenylpentan-2-ylamino)propyl)-N-methylsulfamoyl)thiophen-3-yl)butanoic acid

EXAMPLE 10-32

(R)-3-(2-chloro-5-(N-(2-hydroxy-3-(2-methyl-5-phenylpentan-2-ylamino)propyl)-N-methylsulfamoyl)thiophen-3-yl)propionic acid

EXAMPLE 10-33

(R)-3-(3,5-dichloro-4-(N-(2-hydroxy-3-(2-methyl-5-phenylpentan-2-ylamino)propyl)-N-methylsulfamoyl)phenyl)propionic acid

EXAMPLES 11-1 TO 14

The target compound was obtained in the same manner as Example 10-1 Step A and C with combinations shown in Table 11 except that SM2 and ES were used instead of Exp. and es1, respectively.

TABLE 11

| Exp. | SM2 | ES | LCMS method | Rtime | Mass |
|---|---|---|---|---|---|
| 11-1 | Exp. 2-35 | es1 | B | 1.43 | 555 |
| 11-2 | Exp. 2-38 | es1 | B | 1.24 | 517 |
| 11-3 | Exp. 2-4 | es1 | B | 1.28 | 487 |
| 11-4 | Exp. 2-6 | es1 | B | 1.28 | 487 |
| 11-5 | Exp. 2-20 | es1 | B | 1.24 | 501 |
| 11-6 | Exp. 2-21 | es1 | B | 1.28 | 501 |
| 11-7 | Exp. 2-16 | es1 | B | 1.34 | 515 |
| 11-8 | Exp. 2-27 | es3 | B | 1.40 | 583 |
| 11-9 | Exp. 2-27 | es4 | B | 1.45 | 597 |
| 11-10 | Exp. 2-6 | es3 | B | 1.31 | 515 |
| 11-11 | Exp. 2-27 | es5 | B | 1.51 | 611 |
| 11-12 | Exp. 2-27 | es1 | B | 1.39 | 555 |
| 11-13 | Exp. 2-26 | es1 | B | 1.37 | 555 |
| 11-14 | Exp. 2-27 | es2 | B | 1.39 | 569 |

Hereinbelow, structures of the compounds of Example to 11-14 (Exp. 11-1 to 11-14) are shown.

Exp. 11-1

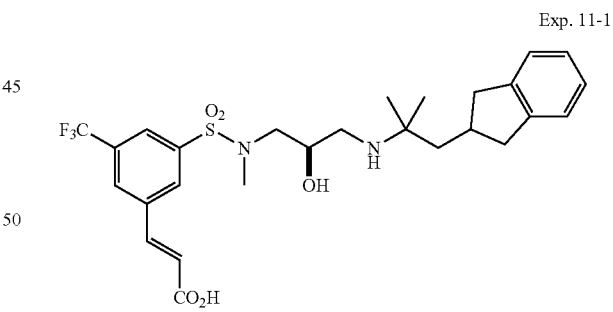

Exp. 11-2

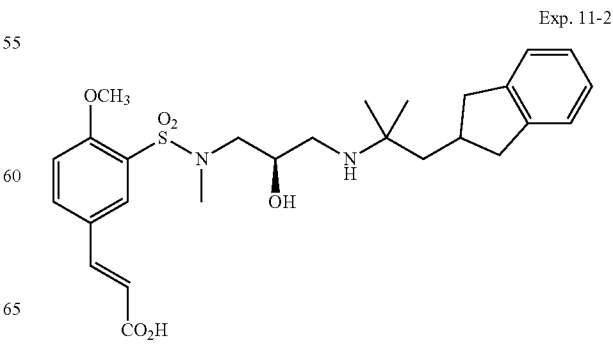

Exp. 11-3
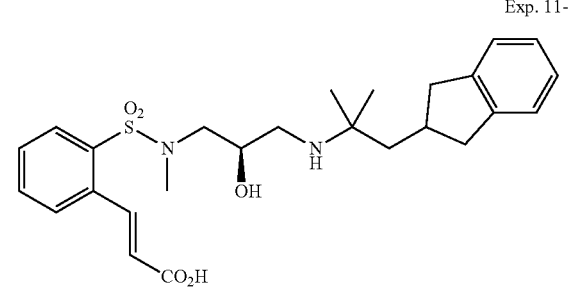

Exp. 11-4
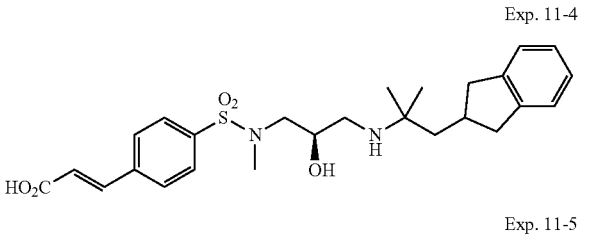

Exp. 11-5
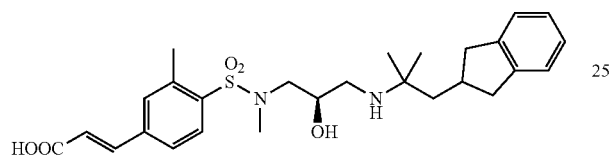

Exp. 11-6
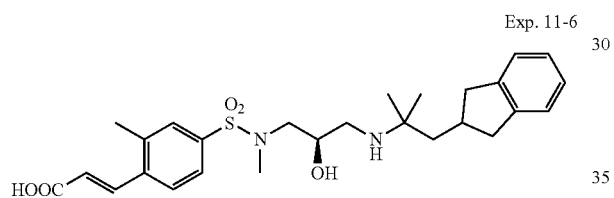

Exp. 11-7
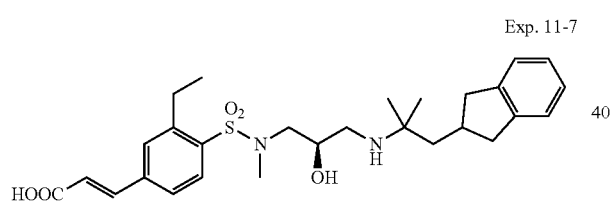

Exp. 11-8
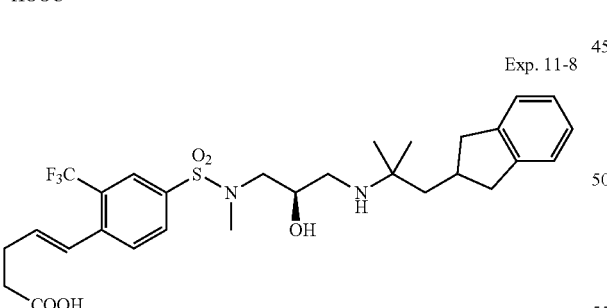

Exp. 11-9
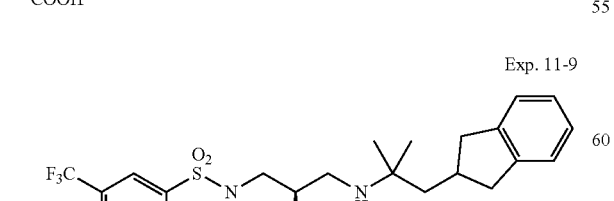

Exp. 11-10
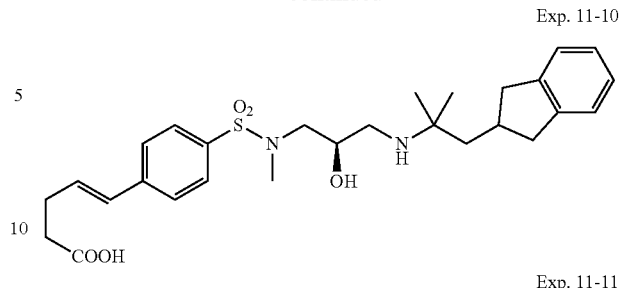

Exp. 11-11
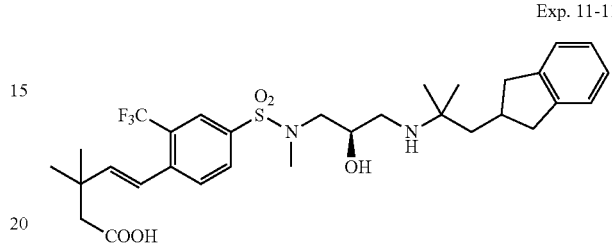

Exp. 11-12
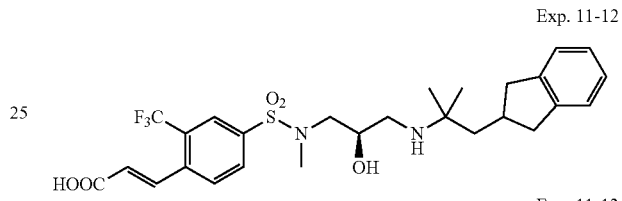

Exp. 11-13
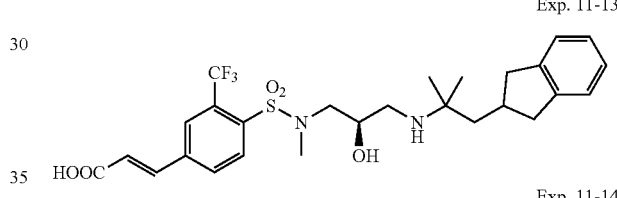

Exp. 11-14
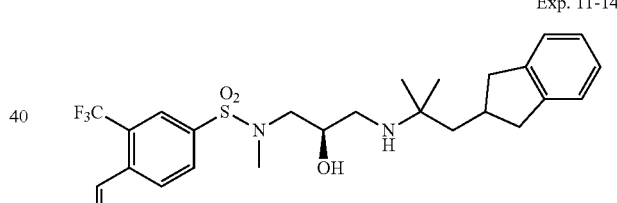

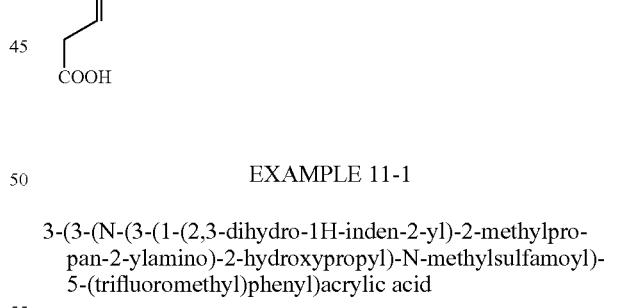

EXAMPLE 11-1

3-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenyl)acrylic acid

EXAMPLE 11-2

3-(3-(N-(3-(1-(2,3-dihydro-1H-inden-2-yl)-2-methylpropan-2-ylamino)-2-hydroxypropyl)-N-methylsulfamoyl)-4-methoxyphenyl)acrylic acid

EXAMPLE 11-3

3-(2-(N-(3-(1-(2,3-dihydro-1H-inden-2-yl)-2-methylpropan-2-ylamino)-2-hydroxypropyl)-N-methylsulfamoyl)phenyl)acrylic acid

EXAMPLE 11-4

3-(4-(N-(3-(1-(2,3-dihydro-1H-inden-2-yl)-2-methylpropan-2-ylamino)-2-hydroxypropyl)-N-methylsulfamoyl)phenyl)acrylic acid

EXAMPLE 11-5

3-(4-(N-(3-(1-(2,3-dihydro-1H-inden-2-yl)-2-methylpropan-2-ylamino)-2-hydroxypropyl)-N-methylsulfamoyl)-3-methylphenyl)acrylic acid

EXAMPLE 11-6

3-(4-(N-(3-(1-(2,3-dihydro-1H-inden-2-yl)-2-methylpropan-2-ylamino)-2-hydroxypropyl)-N-methylsulfamoyl)-2-methylphenyl)acrylic acid

EXAMPLE 11-7

3-(4-(N-(3-(1-(2,3-dihydro-1H-inden-2-yl)-2-methylpropan-2-ylamino)-2-hydroxypropyl)-N-methylsulfamoyl)-3-ethylphenyl)acrylic acid

EXAMPLE 11-8

(R)-5-(4-(N-(3-(1-(2,3-dihydro-1H-inden-2-yl)-2-methylpropan-2-ylamino)-2-hydroxypropyl)-N-methylsulfamoyl)-2-(trifluoromethyl)phenyl)pent-4-enoic acid

EXAMPLE 11-9

(R)-6-(4-(N-(3-(1-(2,3-dihydro-1H-inden-2-yl)-2-methylpropan-2-ylamino)-2-hydroxypropyl)-N-methylsulfamoyl)-2-(trifluoromethyl)phenyl)hex-5-enoic acid

EXAMPLE 11-10

(R)-5-(4-(N-(3-(1-(2,3-dihydro-1H-inden-2-yl)-2-methylpropan-2-ylamino)-2-hydroxypropyl)-N-methylsulfamoyl)phenyl)pent-4-enoic acid

EXAMPLE 11-11

(R)-5-(4-(N-(3-(1-(2,3-dihydro-1H-inden-2-yl)-2-methylpropan-2-ylamino)-2-hydroxypropyl)-N-methylsulfamoyl)-2-(trifluoromethyl)phenyl)-3,3-dimethylpent-4-enoic acid

EXAMPLE 11-12

(R)-3-(4-(N-(3-(1-(2,3-dihydro-1H-inden-2-yl)-2-methylpropan-2-ylamino)-2-hydroxypropyl)-N-methylsulfamoyl)-2-(trifluoromethyl)phenyl)acrylic acid

EXAMPLE 11-13

(R)-3-(4-(N-(3-(1-(2,3-dihydro-1H-inden-2-yl)-2-methylpropan-2-ylamino)-2-hydroxypropyl)-N-methylsulfamoyl)-3-(trifluoromethyl)phenyl)acrylic acid

EXAMPLE 11-14

(R)-4-(4-(N-(3-(1-(2,3-dihydro-1H-inden-2-yl)-2-methylpropan-2-ylamino)-2-hydroxypropyl)-N-methylsulfamoyl)-2-(trifluoromethyl)phenyl)but-3-enoic acid

EXAMPLE 12-1

(R)-2-(3-(N-(2-hydroxy-3-(2-methyl-5-phenylpentan-2-ylamino)propyl)-N-methylsulfamoyl)-5-(trifluoromethyl)phenylthio)acetic acid (Step A) Synthesis of methyl (R)-2-(3-(N-(2-hydroxy-3-(2-methyl-5-phenylpentan-2-ylamino)propyl)-N-methylsulfamoyl)-5-(trifluoromethyl)phenylthio)acetate According to the method described in the literature (Org. Lett., 2004, 6(24), 4587-4590), the target compound (43.5 mg) was obtained from (R)-3-bromo-N-(2-hydroxy-3-(2-methyl-5-phenylpentan-2-ylamino)propyl)-N-methyl-5-(trifluoromethyl)benzenesulfoneamide (Exp. 2-37, 49.1 mg) and methyl 2-mercaptoacetate.

(Step B) Synthesis of (R)-2-(3-(N-(2-hydroxy-3-(2-methyl-5-phenylpentan-2-ylamino)propyl)-N-methylsulfamoyl)-5-(trifluoromethyl)phenylthio)acetic acid According to the method of Example 3-1 Step B, the target compound was obtained from the compound synthesized from Example 12-1 Step A.
LCMS: Method B, retention time 1.48 minutes, (ES+)

EXAMPLE 12-2

(R)-2-(3-(N-(3-(1-(2,3-dihydro-1H-inden-2-yl)-2-methylpropan-2-ylamino)-2-hydroxypropyl)-N-methylsulfamoyl)-5-(trifluoromethyl)phenylthio)acetic acid The target compound was obtained in the same manner as Example 12-1 except that Exp. 2-35 was used instead of Exp. 2-37.
LCMS: Method B, retention time 1.46 minutes, (ES+)

EXAMPLE 13-1

(R)-6-(3-(N-(2-hydroxy-3-(2-methyl-5-phenylpentan-2-ylamino)propyl)-N-methylsulfamoyl)-5-(trifluoromethyl)phenyl)hex-5-ynoic acid (Step A) Synthesis of methyl (R)-6-(3-(N-(2-hydroxy-3-(2-methyl-5-phenylpentan-2-ylamino)propyl)-N-methylsulfamoyl)-5-(trifluoromethyl)phenyl)hex-5-ynoate Under nitrogen atmosphere, (R)-3-bromo-N-(2-hydroxy-3-(2-methyl-5-phenylpentan-2-ylamino)propyl)-N-methyl-5-(trifluoromethyl)benzenesulfoneamide (Exp. 2-37, 20 mg) and methyl 5-hexynoate (WAKO, 5.4 mg) were dissolved in dichloromethane (KANTO, 122 µL) and triethylamine (WAKO, 14 µL), followed by stirring at room temperature for 15 minutes. Dichloro(triphenylphosphine)palladium(II) dichloride (KANTO, 1.0 mg) and copper iodide (WAKO, 1.0 mg) were added thereto and stirred overnight at 45° C. To the reaction mixture, methyl 5-hexynoate (5.4 mg), triethylamine (14 µL) and dichloro(triphenylphosphine)palladium(II) dichloride (1.0 mg) were further added and stirred overnight at 45° C. Dichloromethane was added to the reaction mixture. The organic layer was washed with water and brine, and concentrated under reduced pressure to obtain the target compound as a crude product (46.9 mg).

(Step B) According to the Method of Example 3-1 Step B, the Target Compound was Obtained from the Compound Synthesized from Example 13-1 Step A LCMS: Method B, retention time 1.39 minutes, (ES+)

EXAMPLE 13-2

(R)-5-(3-(N-(2-hydroxy-3-(2-methyl-5-phenylpentan-2-ylamino)propyl)-N-methylsulfamoyl)-5-(trifluoromethyl)phenyl)pent-4-ynoic acid The target compound was obtained in the same manner as Example 13-1 except that methyl 4-pentynate was used instead of methyl 5-hexynate.
LCMS: Method B, retention time 1.35 minutes, (ES+)

EXAMPLE 14-1

(R)-3-(3'-(N-(3-(1-(2,3-dihydro-1H-inden-2-yl)-2-methylpropan-2-ylamino)-2-hydroxypropyl)sulfamoyl)biphenyl-4-yl)propionic acid (Step A) Synthesis of tert-butyl 3-bromophenylsulfonyl carbamate 3-Bromobenzenesulfoneamide (1 g), dimethylaminopyridine (51.6 mg), and triethylamine (513.6 mg) were dissolved in chloromethylene (20 mL), and chloromethylene solution comprising di-tert-butyl bicarbonate (WAKO, 1.107 g) was added dropwise to the resulting mixture at room temperature, followed by stirring overnight. The reaction solution was concentrated, added with ethyl acetate, washed with 1N hydrochloric acid solution, and brine. The solvent was concentrated under reduced pressure to obtain the target compound.

(Step B) Synthesis of (S)-tert-butyl 3-bromophenylsulfonyl(oxiran-2-yl)carbamate The compound synthesized from the Example 14-1 Step A (1.28 g), (S)-glycidol (283 mg), and triphenylphosphine (1 g) were dissolved in tetrahydrofuran (20 mL), and added with diisopropylazodicarboxylic acid (772 mg) followed by stirring at room temperature. The reaction solution was concentrated, and the residue was dissolved in ethyl acetate and then washed with water and brine. The organic layer was dried, the solvent was concentrated and purified by silica gel column chromatography to obtain the target compound (1.30 g).

(Step C) Synthesis of (R)-3-bromo-N-(3-(1-(2,3-dihydro-1H-inden-2-yl)-2-methylpropan-2-ylamino)-2-hydroxypropyl)benzenesulfoneamide The compound synthesized from the Example 14-1 Step B (0.27 g) and am2 (130 mg) were stirred overnight at 90° C. under nitrogen atmosphere. The reaction solution was cooled to room temperature, and 4N HCl-dioxane solution (2 mL) was added, and stirred for 2 hours and 30 minutes at room temperature. The reaction solution was concentrated, added with ethyl acetate, washed with saturated sodium bicarbonate water, and brine. The organic layer was dried, and the solvent was concentrated under reduced pressure to obtain the target compound.

(Step D) Synthesis of methyl (R)-3-(3'-(N-(3-(1-(2,3-dihydro-1H-inden-2-yl)-2-methylpropan-2-ylamino)-2-hydroxypropyl)sulfamoyl)biphenyl-4-yl)propionate According to the method of Example 3-1 Step A, the target compound was obtained from the compound (96.3 mg) synthesized from Example 14-1 Step C and ba12 (62.4 mg).

(Step E) Synthesis of (R)-3-(3'-(N-(3-(1-(2,3-dihydro-1H-inden-2-yl)-2-methylpropan-2-ylamino)-2-hydroxypropyl)sulfamoyl)biphenyl-4-yl)propionic acid The compound synthesized from the Example 14-1 Step D was dissolved in methanol (2 mL) and added with 2N sodium hydroxide solution (1 mL), followed by stirring at room temperature for 105 minutes. The reaction solution was concentrated and then extracted with ethyl acetate and 1N hydrochloric acid. The organic layer was washed with brine and dried, and the solvent was concentrated under reduced pressure. The residue was purified to obtain the target compound.
LCMS Method A, retention time 3.13 minutes, (ES+) 551
[Example 14-2] (R)-3'-(N-(3-(1-(2,3-dihydro-1H-inden-2-yl)-2-methylpropan-2-ylamino)-2-hydroxypropyl)sulfamoyl)biphenyl-3-carboxylic acid
According to the method of Example 14-1 Step D and Step E, the target compound was obtained from the compound of Example 14-1 Step C and ba2.
LCMS Method A, retention time 3.04 minutes, (ES+) 523
Hereinbelow, structures of the compounds of Example 12-1 (Exp. 12-1) and 12-2 (Exp. 12-2), Example 13-1 (Exp. 13-1) and 13-2 (Exp. 13-2), Example 14-1 (Exp. 14-1) and 14-2 (Exp. 14-2) are shown.

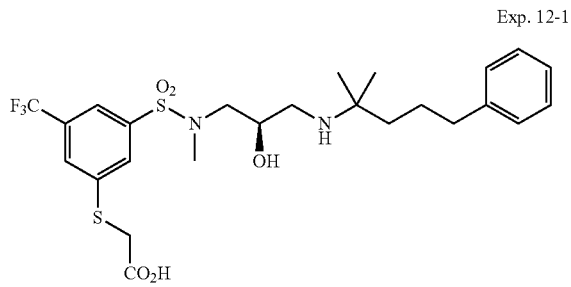

Exp. 12-1

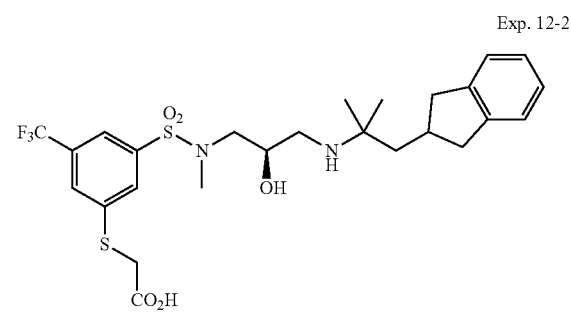

Exp. 12-2

-continued

Exp. 13-1
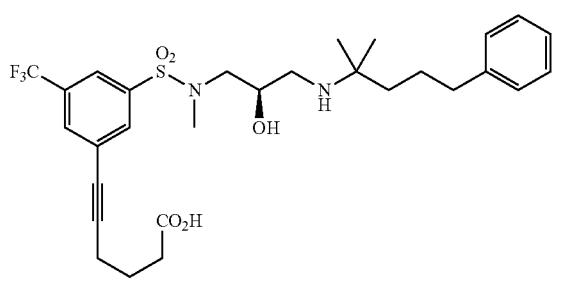

Exp. 13-2
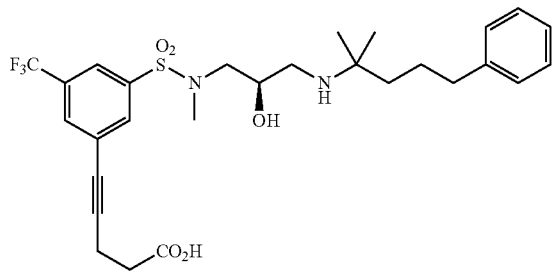

Exp. 14-1
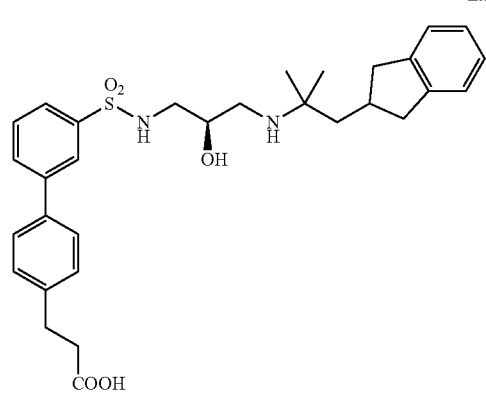

Exp. 14-2
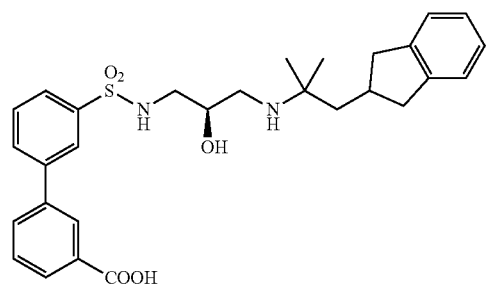

REFERENCE EXAMPLE 1-1

1-(2,3-Dihydro-1H-inden-2-yl)-2-methylpropan-2-amine (Step A) Synthesis of methyl 2-(2,3-dihydro-1H-inden-2-yl)acetate Under nitrogen atmosphere, 2-(2,3-dihydro-1H-inden-2-yl)acetic acid (Lanc, 19.6 g, 111 mmol) was dissolved in methanol (100 mL) and cooled in an ice bath. Thionyl chloride (9.7 mL, 133 mmol) was slowly added dropwise thereto under stirring. After completing the dropwise addition, the ice bath was removed and the reaction solution was additionally stirred for 30 minutes. Upon the completion of the reaction, the reaction solution was added in small portions to ice-cold sodium bicarbonate solution under stirring. The reaction mixture was extracted twice with ethyl acetate, and the obtained organic layer was washed once with water, dried over anhydrous magnesium sulfate, and the reaction solution was concentrated to obtain the target compound (21.2 g, Yield 100%).

$^1$H-NMR (CDCl$_3$): δ (ppm) 2.50 (2H, d, J=7.4 Hz), 2.65 (2H, dd, J=7.2 Hz, 15.4 Hz), 2.88 (1H, m), 3.14 (2H, dd, 7.8 Hz, 15.4 Hz), 3.69 (3H, s), 7.1-7.2 (4H, m)

(Step B) Synthesis of 1-(2,3-dihydro-1H-inden-2-yl)-2-methylpropan-2-ol

Under nitrogen atmosphere, to 3.0M methyl lithium dimethoxyethane solution (Ald, 89 mL, 267 mmol) cooled in an ice bath, compound of Reference example 1-1 Step A (21.2 g, 111 mmol) which had been dissolved in tetrahydrofuran (100 mL) was slowly added dropwise under stirring. After completing the dropwise addition, the ice bath was removed followed by stirring for 45 minutes. Upon the completion of the reaction, saturated ammonium chloride was slowly added dropwise under stirring. The reaction mixture was extracted once with ethyl acetate, and the obtained organic layer was washed twice with water, dried over anhydrous magnesium sulfate, and the reaction solution was concentrated to obtain the target compound (21.0 g, Yield 100%).

$^1$H-NMR (CDCl$_3$): δ (ppm) 1.30 (6H, s), 1.79 (2H, d, J=5.9 Hz), 2.5-2.7 (3H, m), 3.0-3.2 (2H, m), 7.1-7.2 (4H, m)

(Step C) Synthesis of N-(1-(2,3-dihydro-1H-inden-2-yl)-2-methylpropan-2-yl)acetamide Under nitrogen atmosphere, to acetonitrile (38 mL) cooled in an ice bath, concentrated sulfuric acid (11 mL) was added under stirring followed by further stirring for 45 minutes. While continuously stirring the reaction solution under ice cooling, the compound of Reference example 1-1 Step B (21.0 g, 110 mmol) dissolved in glacial acetic acid (32 mL) was added dropwise to the mixture for about 10 minutes. After completing the dropwise addition, the ice bath was removed followed by stirring for 45 minutes. Upon the completion of the reaction, ice water was added to the reaction solution. The reaction solution was extracted twice with ethyl acetate, and the obtained organic layer was washed once with water, once with 5N sodium hydroxide solution, and three times with brine. The organic layer was dried over anhydrous magnesium sulfate, and the reaction solution was concentrated to obtain a crude product, which was then purified by silica gel flash column chromatography (ethyl acetate: hexane=1:2) to obtain the target compound (20.9 g, Yield 82.3%).

LCMS Method B, retention time 1.56 minutes, (ES+) 232.2

(Step D) Synthesis of 1-(2,3-dihydro-1H-inden-2-yl)-2-methylpropan-2-amine

A mixture comprising the compound of Reference example 1-1 Step C (20.9 g, 90.3 mmol), potassium hydroxide (40.5 g, 722 mmol), and ethylene glycol (220 mL) was stirred at 190° C. for about 1 day under heating. Upon the completion of the reaction, the mixture was cooled to room temperature and added with water. The reaction mixture was extracted twice with ethyl acetate, and the obtained organic layer was washed once with water, and then extracted twice with 1N hydrochloric acid. The resulting aqueous layer was washed twice with ethyl acetate. To the aqueous layer, 5N sodium hydroxide solution was added, extracted twice with ethyl acetate, and the obtained organic layer was washed twice with brine. And then it was dried over anhydrous magnesium sulfate, and the reaction solution was concentrated to obtain the target compound (14.3 g, Yield 83.6%).

$^1$H-NMR (CDCl$_3$): δ (ppm) 1.17 (6H, s), 1.71 (2H, d, J=9.2 Hz), 2.5-2.7 (3H, m), 3.05-3.15 (2H, m), 7.1-7.2 (4H, m)

REFERENCE EXAMPLES 1-2 TO 8

According to Reference example 1-1, the compounds were synthesized from the corresponding carboxylic acids. In addition, Reference example 6 was synthesized from the corresponding ester according to Reference example 1-1 Step B to D.

REFERENCE EXAMPLE 1-9

5-(2-Fluorophenyl)-2-methylpentan-2-amine (Step A) Synthesis of 2-(2-fluorophenyl)acetaldehyde 2-(2-Fluorophenyl)ethanol (Ald, 1.0 g) was dissolved in dichloromethane (KANTO, 20 mL) under nitrogen atmosphere and added with Dess-Martin reagent (Alfa Aesar, 3.64 g), followed by stirring at room temperature for 3 hours. Saturated sodium thiosulfate solution was added to the reaction mixture and then extracted with ethyl acetate. The organic layer was washed with saturated sodium hydrogencarbonate solution and brine, and then dried over anhydrous magnesium sulfate. The reaction solution was concentrated under reduced pressure to obtain the target compound as a crude product.

(Step B) Synthesis of ethyl 4-(2-fluorophenyl)-2-butenoate

The crude compound synthesized from Reference example 1-9 Step A was dissolved in ethanol (KANTO, 11 mL) under nitrogen atmosphere and added with diethylphsphonoethyl acetate (TCI, 1.7 mL) and sodium ethoxide (WAKO, 3.34 mL), followed by stirring at room temperature for 1 hour. Water was added to the reaction mixture and then extracted with ethyl acetate. The organic layer was washed with brine, dried over anhydrous magnesium sulfate. The reaction solution was concentrated under reduced pressure to obtain a crude product, which was then purified by silica gel column chromatography to obtain the target compound (957.4 mg).

(Step C) Synthesis of ethyl 4-(2-fluorophenyl)butanoate

The compound synthesized from the Reference example 1-9 Step B (957.4 mg) was dissolved in ethanol (KANTO, 30 mL), and added with 10% palladium-activated carbon (MERCK, 176 mg) and the mixture was stirred under hydrogen atmosphere for 2 hours and 30 minutes at room temperature. The reaction mixture was filtered and concentrated under reduced pressure, the target compound was obtained as a crude product (964.1 mg).

(Step D) Synthesis of 5-(2-fluorophenyl)-2-methyl-2-pentanol

According to Reference example 1-1 Step B, a crude product (862.8 mg) of the target compound was obtained from the compound that was synthesized from Reference example 1-9 Step C.

(Step E) Synthesis of 2-chloro-N-(5-(2-fluorophenyl)-2-methylpentan-2-yl)acetamide The crude product synthesized from the Reference example 1-9 Step D (862.8 mg) was dissolved in chloroacetonitrile (TCI, 1.04 mL) and acetic acid (KANTO, 0.84 mL), and conc. sulfuric acid (WAKO, 0.25 mL) was added dropwise thereto under stirring with ice cooling. After stirring overnight at room temperature, saturated sodium hydrogencarbonate solution was added to the reaction solution, and the extraction was carried out with ethyl acetate. The organic layer was washed with water and brine, dried over anhydrous magnesium sulfate, and the reaction solution was concentrated under reduced pressure to obtain a crude product, which was then purified by silica gel column chromatography to obtain the target compound (1.11 g).

(Step F) Synthesis of 5-(2-fluorophenyl)-2-methylpentan-2-amine 2-chloro-N-(5-(2-fluorophenyl)-2-methylpentan-2-yl)acetamide (1.11 g) obtained from the Step F was dissolved in acetic acid (KANTO, 1.6 mL) and ethanol (KANTO, 8.0 mL), and thiourea (WAKO, 372 mg) was added thereto and stirred overnight at 100° C. After cooling to room temperature, 5N NaOH solution was added to the reaction solution, and the extraction was carried out with ethyl acetate. Subsequently, the organic layer was washed with water, and extracted with 1N HCl solution. The aqueous layer was washed with ethyl acetate and added with 5N NaOH solution to obtain a basic solution. Extraction was carried out with ethyl acetate. The organic layer was washed with brine, dried over anhydrous magnesium sulfate, and the reaction solution was concentrated to obtain the target compound (167.3 mg).

REFERENCE EXAMPLES 1-10 TO 12

According to Reference example 1-9, the compounds were synthesized from the corresponding alcohols.

REFERENCE EXAMPLE 1-13

According to Reference example 1-1 Step B to D, the compound was synthesized from the corresponding ester.

REFERENCE EXAMPLES 1-14 TO 16

According to Reference example 1-1, the compounds were synthesized from the corresponding carboxylic acids.

REFERENCE EXAMPLE 1-17

2-Methyl-5-(pyridin-2-yl)pentan-2-amine

According to the literatures (J. Med. Chem., 1987, Vol. 30, No. 1, 185-193, and J. Med. Chem., 1989, Vol. 32, No. 8, 1820-1835), the target compound (530.6 mg) was obtained from 2-bromopyridine (WAKO, 2.0 g).

REFERENCE EXAMPLES 1-18 TO 20

According to Reference example 1-17, the compounds were synthesized from the corresponding pyridine derivatives.

REFERENCE EXAMPLE 1-21

1-(4-Ethylphenyl)-2-methylpropan-2-amine (Step A) Synthesis of 1-ethyl-4-(2-methylallyl)benzene Under nitrogen atmosphere, tetrahydrofuran (KANTO, 8.1 mL) was added to magnesium (WAKO, 263 mg) and iodide (WAKO, 1 mg), followed with addition of tetrahydrofuran (KANTO, 5.5 mL) solution comprising 1-bromo-4-ethylbenzene (TCI, 2.0 g). The mixture was stirred at room temperature for 30 minutes. The reaction solution was cooled to 0° C. and added with copper iodide (WAKO, 205 mg) and 3-chloro-2-methyl-1-propene (WAKO, 1.32 mL) followed by stirring at room temperature for 1 hour and 30 minutes. The reaction solution was cooled and added with saturated ammonium chloride solution, and further added with sodium sulfate. The reaction mixture was filtered, and concentrated under reduced pressure to obtain a crude product, which was then purified by silica gel column chromatography to obtain the target compound (500 mg).

(Step B) Synthesis of 1-(4-ethylphenyl)-2-methylpropan-2-amine

According to the method of Reference example 1-1 Step C and Step D, the target compound was obtained from the compound obtained from Reference example 1-21 Step A.

REFERENCE EXAMPLE 1-22

According to Reference example 1-1, the compound was synthesized from the corresponding carboxylic acid.

REFERENCE EXAMPLE 1-23

According to Reference example 1-21, the compound was synthesized from 1-bromo-4-tert-butylbenzene.

REFERENCE EXAMPLES 1-24 TO 26

According to Reference example 1-1, the compounds were obtained from the corresponding carboxylic acids.

REFERENCE EXAMPLE 1-27

According to Reference example 1-17, the compound was synthesized from the corresponding pyridine derivative.

REFERENCE EXAMPLES 1-28 TO 30

According to Reference example 1-1, the compounds were obtained from the corresponding carboxylic acids.

REFERENCE EXAMPLE 1-31

(Step A) Synthesis of 5-(5-fluorothiophen-2-yl)-2-methyl-2-pentanol

According to the literature (J. Fluorine Chem., 2003, 124, 159-168), the target compound (221.6 mg) was obtained from 2-methyl-5-(thiophen-2-yl)-2-pentanol (2.0 g).

(Step B) Synthesis of 5-(5-fluorothiophen-2-yl)-2-methylpentan-2-amine

According to the method of Reference example 1-9 Step E and Step F, the target compound was obtained from the compound obtained from Reference example 1-31 Step A.

REFERENCE EXAMPLE 1-32

According to Reference example 1-9, the compound was obtained from the corresponding alcohol.

REFERENCE EXAMPLE 1-33

According to Reference example 1-17, the compound was synthesized from the corresponding pyridine derivative.

Structure of the compounds of Reference example 1-1 to 33 are shown in Table 12 and Table 13. (In Table 12, Reference example 1-1 to Reference example 1-4 are respectively indicated as am1 to am4, and in Table 13 Reference example 1-5 to Reference example 1-33 are respectively indicated as am5 to am33.)

TABLE 12

| AM | Str. |
|---|---|
| am1 | (structure) |
| am2 | (structure) |
| am3 | (structure) |
| am4 | (structure) |

TABLE 13

| AM | Str. |
|---|---|
| am5 | (structure) |

TABLE 13-continued
| AM | Str. |
|---|---|
| am6 | 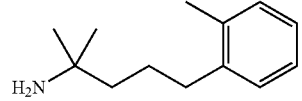 |
| am7 | 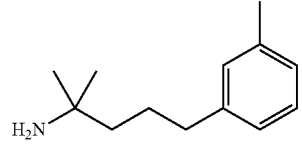 |
| am8 | 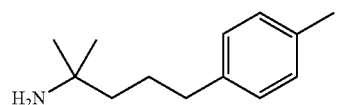 |
| am9 | 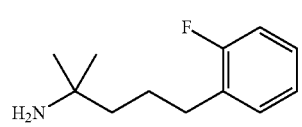 |
| am10 | 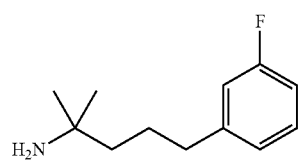 |
| am11 | 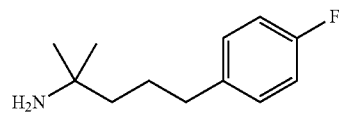 |
| am12 | 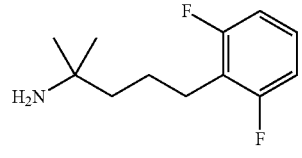 |
| am13 | 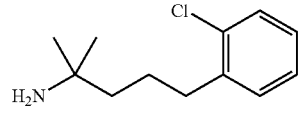 |
| am14 | 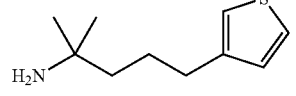 |
| am15 | 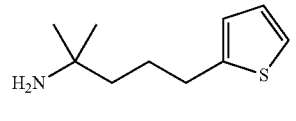 |
| am16 | 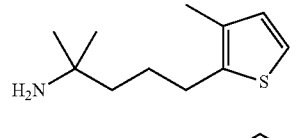 |
| am17 | 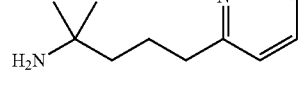 |
| am18 | 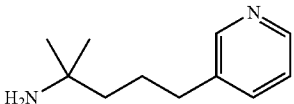 |
| am19 | 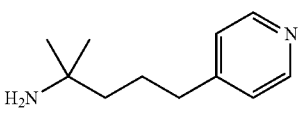 |
| am20 | 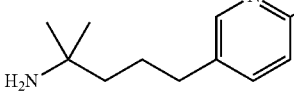 |
| am21 | 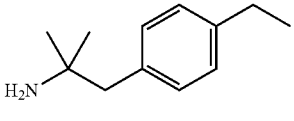 |
| am22 | 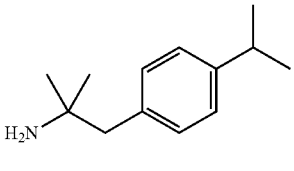 |
| am23 | 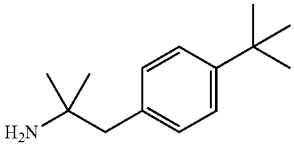 |
| am24 | 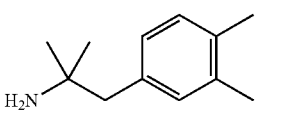 |
| am25 | 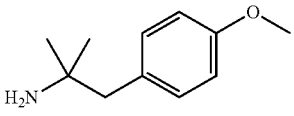 |
| am26 | 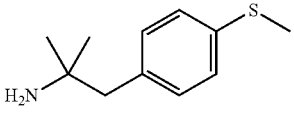 |
| am27 | 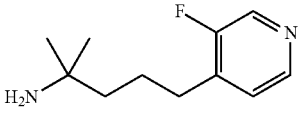 |
| am28 | 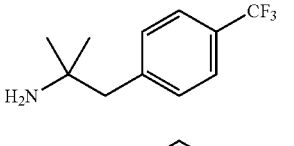 |
| am29 | 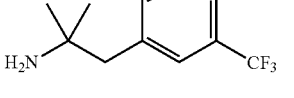 |

TABLE 13-continued

| AM | Str. |
|---|---|
| am30 | H₂N–C(CH₃)₂–CH₂–C₆H₃(Cl)(Cl) (3,4-dichloro) |
| am31 | H₂N–C(CH₃)₂–CH₂CH₂CH₂–(2-thienyl)-5-F |
| am32 | H₂N–C(CH₃)₂–CH₂CH₂CH₂–C₆H₃(2-F)(5-F) |
| am33 | H₂N–C(CH₃)₂–CH₂CH₂CH₂–(4-pyridyl)-2-F |

REFERENCE EXAMPLE 2-1

Methyl 3-fluoro-4-(4,4,5,5-tetramethyl-1,3,2-dioxaborolan-2-yl)benzoic acid (ba9)

(Step A) Synthesis of methyl 4-bromo-3-fluorobenzoic acid

4-Bromo-3-fluorobenzoic acid (WAKO, 1.0 g) was dissolved in methanol (10 mL), followed by addition of concentrated sulfuric acid (10 drops). The mixture was refluxed for three hours. After cooling to room temperature, water was added and the extraction was carried out with ethyl acetate. The organic layer was washed with brine, dried over anhydrous sodium sulfate, and the solvent was distilled off under reduced pressure to obtain the target compound (618 mg).

(Step B) Synthesis of methyl 3-fluoro-4-(4,4,5,5-tetramethyl-1,3,2-dioxaborolan 2-yl)benzoic acid Methyl 4-bromo-3-fluorobenzoic acid (618 mg) that is synthesized from Reference example 2-1 Step A was dissolved in dimethylsulfoxide (15 mL), and bis(pinacolato)diborane (Ald, 673 mg), bis1,1'-bis(diphenylphosphinoferrocene)palladium(II)dichloride-dichloromethane complex (Ald, 216 mg), and potassium acetate (WAKO, 780 mg) were added thereto followed by stirring at 80° C. for three hours. After cooling the reaction solution, water was added and the extraction was carried out with ethyl acetate. The organic layer was washed with brine, dried over anhydrous sodium sulfate, and the solvent was distilled off under reduced pressure. The residue was purified by silica gel column chromatography to obtain the target compound (377 mg).

Among the boronic acid esters shown in Table 14 and Table 15 (i.e., ba1 to ba72), those described as "IM2-11" for column Spl were prepared from the corresponding carboxylic acids or esters, according to Reference example 2-1 Step A and B.

TABLE 14

| BA | Str. | Spl |
|---|---|---|
| ba1 | 2-(pinacolboronate)-C₆H₄–COOC₂H₅ | WAKO |
| ba2 | 3-B(OH)₂-C₆H₄–COOC₂H₅ | WAKO |
| ba3 | 4-B(OH)₂-C₆H₄–COOCH₃ (H₃COOC–) | WAKO |
| ba4 | 4-(pinacolboronate)-3-methyl-C₆H₃–COOCH₃ | IM2-1 |
| ba5 | 4-(pinacolboronate)-2-methyl-C₆H₃–COOCH₃ (H₃COOC–) | IM2-1 |
| ba6 | 4-(pinacolboronate)-2-F-C₆H₃–COOCH₃ (H₃COOC–) | IM2-1 |
| ba7 | 4-(pinacolboronate)-2-NH₂-C₆H₃–COOCH₃ (H₃COOC–) | IM2-1 |

TABLE 14-continued

| BA | Str. | Spl |
|---|---|---|
| ba8 | 4-(4,4,5,5-tetramethyl-1,3,2-dioxaborolan-2-yl)-2-chloro-benzoic acid methyl ester | IM2-1 |
| ba9 | 4-(4,4,5,5-tetramethyl-1,3,2-dioxaborolan-2-yl)-3-fluoro-benzoic acid methyl ester | IM2-1 |
| ba10 | 4-(4,4,5,5-tetramethyl-1,3,2-dioxaborolan-2-yl)-2,3-dihydrobenzofuran-7-carboxylic acid methyl ester | IM2-1 |
| ba11 | methyl (E)-3-(4-boronophenyl)acrylate | Combi |
| ba12 | methyl 3-(4-boronophenyl)propanoate | Combi |
| ba13 | ethyl (E)-3-(3-boronophenyl)acrylate | Combi |
| ba14 | 3-amino-5-(4,4,5,5-tetramethyl-1,3,2-dioxaborolan-2-yl)benzoic acid methyl ester | IM2-1 |
| ba15 | 3-nitro-5-(4,4,5,5-tetramethyl-1,3,2-dioxaborolan-2-yl)benzoic acid methyl ester | IM2-1 |
| ba16 | 3-amino-4-(4,4,5,5-tetramethyl-1,3,2-dioxaborolan-2-yl)benzoic acid methyl ester | IM2-1 |
| ba17 | 3-nitro-4-(4,4,5,5-tetramethyl-1,3,2-dioxaborolan-2-yl)benzoic acid methyl ester | IM2-1 |
| ba18 | ethyl 4-((4-(4,4,5,5-tetramethyl-1,3,2-dioxaborolan-2-yl)phenyl)amino)-4-oxobutanoate | IM2-1 |
| ba19 | 2-(methoxymethyl)-4-(4,4,5,5-tetramethyl-1,3,2-dioxaborolan-2-yl)benzoic acid methyl ester | IM2-1 |
| ba20 | ethyl 3-fluoro-5-(4,4,5,5-tetramethyl-1,3,2-dioxaborolan-2-yl)benzoate | IM2-1 |
| ba21 | methyl (E)-3-(2-boronophenyl)acrylate | Combi |
| ba22 | ethyl (E)-3-(2-fluoro-4-(4,4,5,5-tetramethyl-1,3,2-dioxaborolan-2-yl)phenyl)acrylate | IM2-1 |

TABLE 14-continued

| BA | Str. | Spl |
|---|---|---|
| ba23 | 4-(4,4,5,5-tetramethyl-1,3,2-dioxaborolan-2-yl)-2-hydroxybenzoic acid methyl ester (H3COOC, OH) | IM2-1 |
| ba24 | 4-(4,4,5,5-tetramethyl-1,3,2-dioxaborolan-2-yl)phenylthio acetic acid ethyl ester (C2H5O2C-CH2-S-) | IM2-1 |
| ba25 | 3,5-difluoro-4-(ethoxycarbonyl)phenyl pinacol boronate (C2H5OOC, F, F) | IM2-1 |
| ba26 | HOOC-thiophene-B(OH)2 | Frontier |
| ba27 | N-(3-ethoxy-3-oxopropyl)-4-(4,4,5,5-tetramethyl-1,3,2-dioxaborolan-2-yl)benzamide (C2H5O2C-CH2CH2-NH-C(O)-) | IM2-1 |
| ba28 | N-[4-(4,4,5,5-tetramethyl-1,3,2-dioxaborolan-2-yl)phenyl]glycine ethyl ester (C2H5OOC-CH2-NH-) | IM2-1 |
| ba29 | [4-(4,4,5,5-tetramethyl-1,3,2-dioxaborolan-2-yl)phenyl]acetic acid ethyl ester (C2H5OOC-CH2-) | IM2-1 |

TABLE 14-continued

| BA | Str. | Spl |
|---|---|---|
| ba30 | [3-(4,4,5,5-tetramethyl-1,3,2-dioxaborolan-2-yl)phenyl]acetic acid ethyl ester (C2H5OOC-CH2-) | IM2-1 |

TABLE 15

| BA | Str. | Spl |
|---|---|---|
| ba31 | (E)-3-[3-chloro-4-(4,4,5,5-tetramethyl-1,3,2-dioxaborolan-2-yl)phenyl]acrylic acid ethyl ester (Cl, C2H5OOC-CH=CH-) | IM2-1 |
| ba32 | (E)-3-[4-fluoro-3-(4,4,5,5-tetramethyl-1,3,2-dioxaborolan-2-yl)phenyl]acrylic acid ethyl ester (F, COOC2H5) | IM2-1 |
| ba33 | (E)-3-[4-methoxy-3-(4,4,5,5-tetramethyl-1,3,2-dioxaborolan-2-yl)phenyl]acrylic acid ethyl ester (H3CO, COOC2H5) | IM2-1 |
| ba34 | (E)-3-[4-fluoro-2-(4,4,5,5-tetramethyl-1,3,2-dioxaborolan-2-yl)phenyl]acrylic acid ethyl ester (F) | IM2-1 |

TABLE 15-continued

| BA | Str. | Spl |
|---|---|---|
| ba35 | | IM2-1 |
| ba36 | | IM2-1 |
| ba37 | | IM2-1 |
| ba38 | | IM2-1 |
| ba39 | | IM2-1 |
| ba40 | | IM2-1 |
| ba41 | | IM2-1 |
| ba42 | | IM2-1 |
| ba43 | | IM2-1 |
| ba44 | | IM2-1 |
| ba45 | | IM2-1 |
| ba46 | | Combi |
| ba47 | | IM2-1 |

TABLE 15-continued

| BA | Str. | Spl |
|---|---|---|
| ba48 | 4-fluoro-3-(ethoxycarbonyl)phenylboronic acid pinacol ester | IM2-1 |
| ba49 | 5-(ethoxycarbonyl)pyridine-3-boronic acid pinacol ester | Frontier |
| ba50 | 6-(methoxycarbonyl)pyridine-3-boronic acid | Combi |
| ba51 | 4-fluoro-3-(ethoxycarbonyl)phenylboronic acid pinacol ester | IM2-1 |
| ba52 | 2-fluoro-3-(ethoxycarbonyl)phenylboronic acid pinacol ester | IM2-1 |
| ba53 | 4-chloro-3-(ethoxycarbonyl)phenylboronic acid pinacol ester | IM2-1 |
| ba54 | 4-amino-3-(methoxycarbonyl)phenylboronic acid pinacol ester | IM2-1 |
| ba55 | 2-methyl-5-(methoxycarbonyl)phenylboronic acid pinacol ester | IM2-1 |
| ba56 | 2-methyl-3-(ethoxycarbonyl)phenylboronic acid pinacol ester | IM2-1 |
| ba57 | 3-(ethoxycarbonylmethyl)-6-fluorophenylboronic acid pinacol ester | IM2-1 |
| ba58 | 3-(ethoxycarbonylmethyl)-4-fluorophenylboronic acid pinacol ester | IM2-1 |
| ba59 | 4-(methoxycarbonyl)-3-(methoxymethyl)phenylboronic acid pinacol ester | IM2-1 |

TABLE 15-continued
| BA | Str. | Spl |
|---|---|---|
| ba60 | 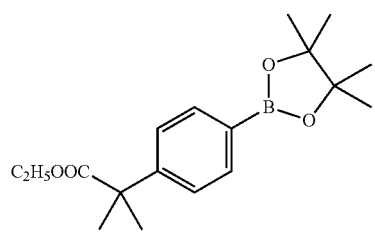 | IM2-1 |
| ba61 | | IM2-1 |
| ba62 | 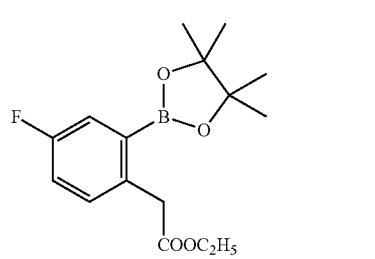 | IM2-1 |
| ba63 | 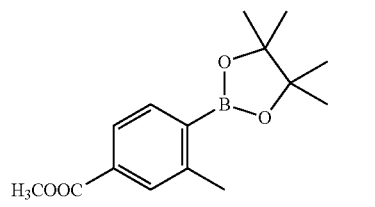 | IM2-1 |
| ba64 | 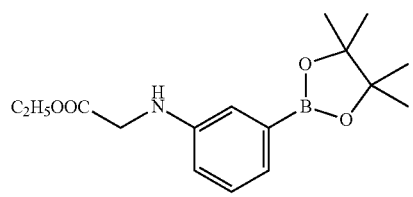 | IM2-1 |
| ba65 | 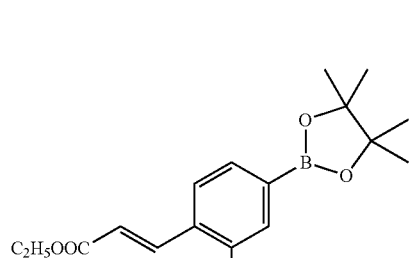 | IM2-1 |
TABLE 15-continued
| BA | Str. | Spl |
|---|---|---|
| ba66 | 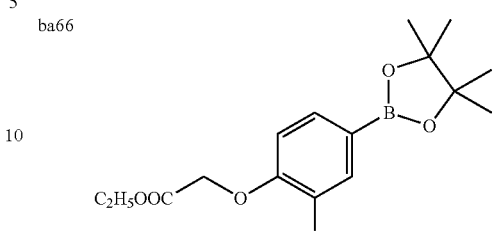 | IM2-1 |
| ba67 | 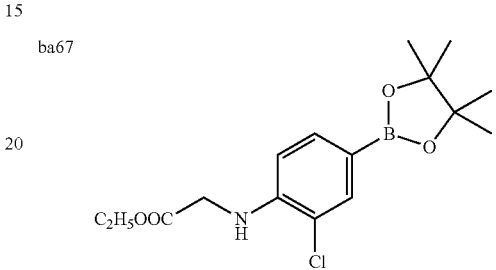 | IM2-1 |
| ba68 | 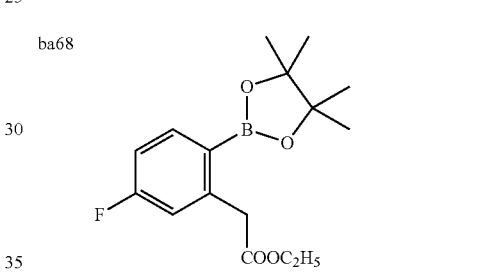 | IM2-1 |
| ba69 | 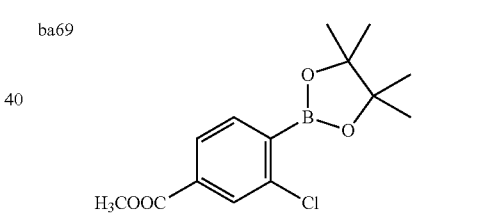 | IM2-1 |
| ba70 | 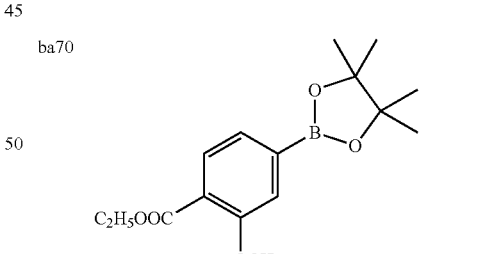 | IM2-1 |
| ba71 | 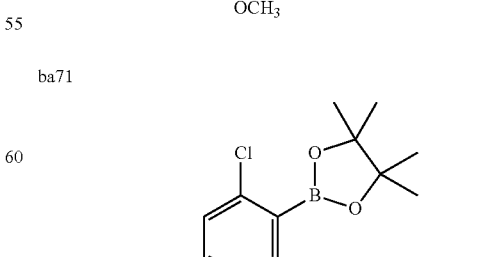 | IM2-1 |

TABLE 15-continued

| BA | Str. | Spl |
|---|---|---|
| ba72 |  | IM2-1 |

TEST EXAMPLE 1

HEK293 cells stably expressing human calcium-sensing receptor (CaSR) (termed HEK293/hCaSR cells) were used. HEK293/hCaSR cells were cultured in a culture medium [DMEM medium containing 0.5 mg/mL Geneticin, 50 Unit/mL penicillin, 50 μg/mL streptomycin and 10% fetal bovine serum (FBS), all manufactured by Invitrogen] to semiconfluent in an incubator at 37° C. under 5% carbon dioxide atmosphere.

Cultured cells were washed with phosphate buffered saline (PBS(−), manufactured by Dainippon Sumitomo Pharmaceutical Company) which had been prewarmed to 37° C., added with PBS(−) containing 10 mM ethylenediamine tetraacetic acid (EDTA), and then incubated in an incubator at 37° C. for 10 minutes. After adding the culture medium to separate the cells, cell suspension was transferred to a centrifuge tube. Cells were collected by centrifuge at 1,500 rpm for 3 minutes, and resuspended in Ca assay buffer [20 mM HEPES buffer (pH 7.4), 115 mM sodium chloride, 5.4 mM potassium chloride, 0.8 mM magnesium chloride, 0.8 mM calcium chloride, 13.8 mM D(+)-glucose (all manufactured by Wako Pure Chemicals) and 0.1% bovine serum albumin (manufactured by SIGMA)] containing 0.2% Pluronic F-127 (manufactured by Molecular Probes) and 5 KM Fura2-AM (manufactured by DOJINDO LABORATORIES) to obtain a cell suspension of $5 \times 10^6$ cells/mL. After incubating at 37° C. for 30 minutes, the cells were washed twice with the Ca assay buffer and suspended in the same buffer to obtain a cell suspension of $1 \times 10^6$ cells/60 μL. 60 μL of the cell suspension was aliquoted to each well of a 96 well UV microplate (manufactured by Corning Co.) to give a cell plate.

The test compound was diluted with the Ca assay buffer to five times the final concentration and then 80 μL of the diluted compound was applied to each well of a 96 well round bottomed microplate (manufactured by Corning Co.) to give a sample plate. 80 μL of the Ca assay buffer containing 7.5 mM calcium chloride (i.e., ligand solution) was applied to each well of a 96 well round bottomed microplate to give a ligand plate. Then, thus prepared sample plate, ligand plate, and the cell plate were placed in Functional Drug Screening System (FDSS) 4000 (manufactured by Hamamatsu Photonics K.K.) which had been preswitched on and prewarmed to 37° C. Measurements were then carried out as follows. After incubating the cell plate for 180 seconds, fluorescence intensity was measured every two seconds (excitation wavelength; 340 nm and 380 nm, measurement wavelength; 500 nm). After the measurement for 40 seconds, 20 μL of the test compound solution from the sample plate was added to the cell plate, followed by continuous measurement for 160 seconds. Then, 20 μL of the ligand solution from the ligand plate was added to the cell plate, followed by continuous measurement for 100 seconds.

Amount of change in intracellular Ca concentration is indicated as a peak height of the ratio of the fluorescence intensity with excitation of 340 nm and 380 nm (i.e., fluorescence intensity with excitation at 340 nm/fluorescence intensity with excitation at 380 nm) that is obtained from the difference between the maximum ratio after adding the ligand solution and the ratio before adding the ligand solution. Further, when the peak height obtained from the Ca assay buffer containing no test compound has inhibition ratio of 0% while the peak height obtained from the Ca assay buffer containing no calcium chloride as a ligand solution has inhibition ratio of 100%, inhibition ratio for each test compound (i.e., CaSR antagonist activity) was calculated.

Test compounds (compound No.: Exp. 3-5, Exp. 3-8, Exp. 3-10, Exp. 3-23, Exp. 3-30, Exp. 3-48, Exp. 3-49, Exp. 3-50, Exp. 3-53, Exp. 3-54, Exp. 3-55, Exp. 3-58, Exp. 3-59, Exp. 3-60) have $IC_{50}$ values of 0.3 μM or less according to the intracellular Ca assay. Other test compounds (compound No.: Exp. 3-1, Exp. 3-6, Exp. 3-7, Exp. 3-9, Exp. 3-11, Exp. 3-12, Exp. 3-14, Exp. 3-15, Exp. 3-17, Exp. 3-19, Exp. 3-21, Exp. 3-22, Exp. 3-24, Exp. 3-25, Exp. 3-26, Exp. 3-27, Exp. 3-28, Exp. 3-29, Exp. 3-31, Exp. 3-33, Exp. 3-35, Exp. 3-39, Exp. 3-40, Exp. 3-46, Exp. 3-47, Exp. 3-51, Exp. 3-52, Exp. 3-56, Exp. 3-57, Exp. 3-67, Exp. 3-81, Exp. 3-86) have $IC_{50}$ values of 1.0-0.3 μM according to the intracellular Ca assay. Still other test compounds (compound No.: Exp. 3-13, Exp. 3-16, Exp. 3-18, Exp. 3-20, Exp. 3-32, Exp. 3-34, Exp. 3-36, Exp. 3-43, Exp. 3-44, Exp. 3-63, Exp. 3-71, Exp. 3-76, Exp. 3-78, Exp. 3-84, Exp. 3-85, Exp. 3-87, Exp. 3-90, Exp. 3-91) have $IC_{50}$ values of 3.0-1.0 μM according to the intracellular Ca assay.

The test compounds (Compound No.: Exp. 3-92, Exp. 3-93, Exp. 3-106, Exp. 3-114, Exp. 3-116, Exp. 3-124, Exp. 3-126, Exp. 3-128, Exp. 3-130, Exp. 3-133, Exp. 3-140, Exp. 3-147, Exp. 3-154, Exp. 3-178, Exp. 3-180, Exp. 3-185, Exp. 3-187, Exp. 3-193, Exp. 3-197, Exp. 3-201, Exp. 3-203 to 205, Exp. 3-213, Exp. 3-220, Exp. 3-223, Exp. 3-228, Exp. 3-231, Exp. 5-16, Exp. 5-18, Exp. 5-21, Exp. 5-23, Exp. 5-29, Exp. 5-30, Exp. 5-58, Exp. 5-59, Exp. 5-62, Exp. 5-74, Exp. 5-77, Exp. 6-1, Exp. 6-6, Exp. 8-1, Exp. 8-5, Exp. 8-24, Exp. 9-55, Exp. 9-56, Exp. 9-73, Exp. 9-75, Exp. 9-82 to 85, Exp. 9-89, Exp. 9-90, Exp. 9-92, Exp. 9-98 to 101, Exp. 9-113 to 115, Exp. 9-118 to 121, Exp. 9-123 to 125, Exp. 9-132 to 134, Exp. 9-138 to 140, Exp. 9-142 to 146, Exp. 9-148 to 153, Exp. 9-155 to 159, Exp. 9-161, Exp. 9-163 to 168, Exp. 9-173, Exp. 9-179, Exp. 9-180, Exp. 10-14, Exp. 11-1, Exp. 14-2) have $IC_{50}$ value of 0.3 μM or less according to intracellular Ca assay. Another test compounds (Compound No.: Exp. 3-98, Exp. 3-99, Exp. 3-101, Exp. 3-102, Exp. 3-105, Exp. 3-108, Exp. 3-113, Exp. 3-115, Exp. 3-117, Exp. 3-118, Exp. 3-120, Exp. 3-122, Exp. 3-123, Exp. 3-127, Exp. 3-129, Exp. 3-132, Exp. 3-135, Exp. 3-136, Exp. 3-138, Exp. 3-139, Exp. 3-141 to 146, Exp. 3-148 to 150, Exp. 3-157, Exp. 3-160 to 164, Exp. 3-166, Exp. 3-168 to 176, Exp. 3-179, Exp. 3-186, Exp. 3-195, Exp. 3-202, Exp. 3-207, Exp. 3-209, Exp. 3-210, Exp. 3-212, Exp. 3-214 to 217, Exp. 3-222, Exp. 3-224, Exp. 3-226, Exp. 3-227, Exp. 3-229, Exp. 3-230, Exp. 5-13 to 15, Exp. 5-19, Exp. 5-20, Exp. 5-22, Exp. 5-24 to 28, Exp. 5-31, Exp. 5-32, Exp. 5-36, Exp. 5-37, Exp. 5-39 to 41, Exp. 5-45, Exp. 5-53, Exp. 5-55 to 57, Exp. 5-60, Exp. 5-61, Exp. 5-63, Exp. 5-66, Exp. 5-68, Exp. 5-69, Exp. 5-71, Exp. 5-73, Exp. 5-76, Exp. 5-80, Exp. 5-82 to 85, Exp. 6-2, Exp. 6-3, Exp. 6-5, Exp. 6-7, Exp. 7-2, Exp. 8-3, Exp. 8-4, Exp. 8-6, Exp. 8-9 to 12, Exp. 8-15, Exp. 8-16, Exp. 8-18, Exp. 8-24, Exp. 9-1, Exp. 9-3, Exp. 9-4, Exp. 9-8, Exp. 9-9, Exp. 9-12 to 15, Exp. 9-18 to 20, Exp. 9-28, Exp. 9-29, Exp. 9-32, Exp. 9-36, Exp. 9-57, Exp. 9-58, Exp. 9-64 to 67, Exp. 9-69 to 72, Exp. 9-77, Exp. 9-78, Exp. 9-81, Exp. 9-91, Exp. 9-95, Exp. 9-96, Exp. 9-103, Exp. 9-106 to 108, Exp. 9-111, Exp. 9-112, Exp. 9-116, Exp. 9-117, Exp. 9-122, Exp. 9-126 to 131, Exp. 9-135 to 137, Exp. 9-141, Exp. 9-160, Exp. 9-162, Exp. 9-171, Exp. 9-172, Exp. 9-174, Exp. 10-1, Exp. 10-5, Exp. 10-8, Exp. 10-13, Exp. 10-16, Exp. 10-23 to 25, Exp. 10-29 to 32, Exp. 11-8, Exp. 11-9, Exp. 11-11 to 14, Exp. 14-1) have $IC_{50}$ value of 1.0 to 0.3 μM according to intracellular Ca assay. Still another test compounds (Compound No.: Exp. 3-95 to 97, Exp. 3-100, Exp. 3-103, Exp. 3-109, Exp. 3-112, Exp. 3-119, Exp. 3-121, Exp. 3-125, Exp. 3-131, Exp. 3-137, Exp. 3-151, Exp. 3-153, Exp. 3-155, Exp. 3-156, Exp. 3-165, Exp. 3-177, Exp. 3-183, Exp. 3-189, Exp. 3-191, Exp. 3-192, Exp. 3-194, Exp. 3-199, Exp. 3-200, Exp. 3-208, Exp. 3-211, Exp. 3-218, Exp. 3-221, Exp. 5-2 to 9, Exp. 5-11 to 12, Exp. 5-17, Exp. 5-33 to 35, Exp. 5-38, Exp. 5-42 to 44, Exp. 5-46 to 52, Exp. 5-54, Exp. 5-64, Exp. 5-65, Exp. 5-67, Exp. 5-81, Exp. 7-1, Exp. 8-2, Exp. 8-19, Exp. 9-2, Exp. 9-31, Exp. 9-76, Exp. 9-86, Exp. 9-87, Exp. 9-94, Exp. 9-97, Exp. 9-102, Exp. 9-104, Exp. 9-105, Exp. 9-110, Exp. 9-173, Exp. 9-175 to 178, Exp. 10-9, Exp. 10-12, Exp. 10-21, Exp. 10-26, Exp. 10-27, Exp. 11-7) have $IC_{50}$ value of 3.0 to 1.0 μM according to intracellular Ca assay.

TEST EXAMPLE 2

Cell toxicity of the compounds was evaluated by using human promyelocytic leukemia HL-60 cells.

HL-60 cells were subcultured in RPMI1640 medium (GIBCO) containing 10% fetal bovine serum (GIBCO) and 30 mg/L kanamycin (GIBCO). At the time of testing, a suspension of HL-60 cells adjusted to $6-4 \times 10^5$ cells/mL, was added to a 96 well plate (50 μL per each well).

Compounds of Exp. 3-5, Exp. 3-6, Exp. 3-8, Exp. 3-30, Exp. 3-31, Exp. 3-49, and Exp. 3-57 were respectively dissolved in DMSO to 10 mM solution and diluted to twice the final concentration with RPMI1640 medium containing 10% fetal bovine serum and 30 mg/L kanamycin. This diluted solution was added to the suspension of HL-60 cells (50 μL per each well), mixed well and incubated in a 5% $CO_2$ incubator. Final concentration of the test compounds was 10-100 μM.

Twenty-four hours after the addition of the compounds, Alamar Blue reagent (BIOSOURCE) was added (10 μL per each well) and then incubated again for four hours.

Fluorescence intensity of each sample was measured using a fluorescence plate reader (excitation wavelength: 544 nm, measurement wavelength: 590 nm). Survival ratio of the cells was calculated according to the following equation.

Survival ratio of the cells (%)=$(S-B)/(N-B) \times 100$

S=Fluorescence intensity of the cells that are treated with the compounds
N=Fluorescence intensity of the cells that are treated only with DMSO
B=Fluorescence intensity of the blank Next, among the survival ratios of the cells for each concentration of the compound, the survival ratio of the cells for the two concentrations that are just next to the 50% inhibition concentration ($IC_{50}$) was taken to establish a two-point standard curve. From Excel graph (Microsoft Company), 50% inhibition concentration ($IC_{50}$) was calculated. All of the test compounds evaluated as above have high $IC_{50}$ values of at least 30 μM, indicating low cell toxicity. As such, the compounds of the present invention are proven to be safe to use.

TEST EXAMPLE 3

Compounds of Exp. 3-49, Exp. 3-57, Exp. 3-93, Exp. 3-95, Exp. 3-102, Exp. 3-106, Exp. 8-5, Exp. 10-1 and Exp. 10-25 were chosen as a test compound. Each of them was either dissolved or suspended in physiological saline or distilled water containing 1-20% DMSO, 5% CremophorEL, 10-40% PEG300, etc. and administered intravenously (tail vein or femoral vein) or orally administered to a 7 week to 10 week old male SD-IGS rat (Nippon Charles-River) with dosage of 0.1-100 mg/kg. After that, blood sample was taken from subclavian vein over the time and serum was separated. Concentration of PTH in blood was measured using Rat Intact PTH ELISA Kit (manufactured by Immutopics) to evaluate an activity of increasing PTH concentration in blood. The compounds evaluated as above, PTH concentration was increased at least twice the normal value 5 minutes after the intravenous administration. However, it is returned to a normal value after 30 minutes. PTH concentration increase is dependent on the administration amount of the compound. Further, for the rat administered with the compounds, no death or abnormality was found. Therefore, the safety of these compounds was confirmed again.

The invention claimed is:

1. A compound represented by Formula (1) or a salt thereof:

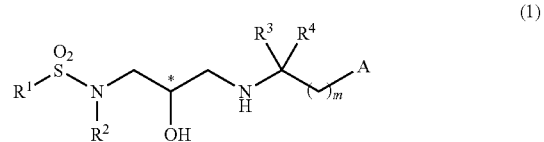
(1)

wherein,

A represents an optionally substituted aryl group;

$R^1$ represents the following Formula ($R^{1a}$) or ($R^{1b}$):

($R^{1a}$)

($R^{1b}$)

[in the Formulae ($R^{1a}$) and ($R^{1b}$), $Ar^1$ represents the following Formula ($Ar^{1a}$), ($Ar^{1b}$) or ($Ar^{1c}$):

($Ar^{1a}$)

-continued

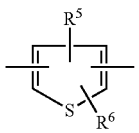 (Ar¹ᵇ)

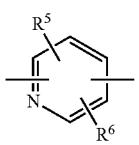 (Ar¹ᶜ)

($R^5$ and $R^6$ each independently represents a hydrogen atom, a halogen atom, an optionally substituted lower alkyl group, an optionally substituted lower alkoxy group, or a cyano group);

$Ar^2$ represents the following Formula ($Ar^{2a}$), ($Ar^{2b}$) or ($Ar^{2c}$):

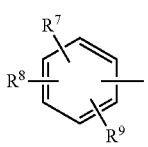 ($Ar^{2a}$)

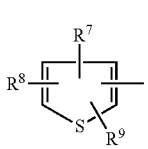 ($Ar^{2b}$)

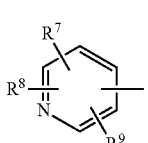 ($Ar^{2c}$)

($R^7$ and $R^8$ each independently represents a hydrogen atom, a hydroxyl group, a halogen atom, an optionally substituted lower alkyl group, an optionally substituted lower alkoxy group, an optionally substituted amino group, a nitro group, a cyano group, $SOCH_3$ group, $SO_2CH_3$ group, a lower acyl group, or $R^7$ and $R^8$ together form -$COOCH_2$- or -$CH_2CH_2O$- ;

$R^9$ represents a hydrogen atom or -J-$COOR^{10}$;

J represents a covalent bond, an optionally substituted alkylene having 1 to 5 carbon atoms, an optionally substituted alkenylene having 2 to 5 carbon atoms, or an optionally substituted alkynylene having 2 to 5 carbon atoms, wherein one carbon atom in said alkylene, alkenylene and alkynylene groups may be replaced by an oxygen atom, a sulfur atom, $NR^{11}$, $CONR^{11}$, or $NR^{11}CO$ at any chemically allowable position;

$R^{11}$ represents a hydrogen atom or a lower alkyl group; and $R^{10}$ represents a hydrogen atom or a lower alkyl group); and p represents 0 or 1];

$R^2$ represents a hydrogen atom or a lower alkyl group;

$R^3$ and $R^4$ each independently represents a lower alkyl group, or $R^3$ and $R^4$ together form an alkylene having 2 to 6 carbon atoms;

* represents an asymmetric carbon atom; and m represents an integer of 1 to 3.

2. The compound according to claim 1 or a salt thereof, wherein A is optionally substituted phenyl, optionally substituted thiophen-yl, naphthalen-2-yl, or 2,3-dihydroinden-2-yl;

$R^2$, $R^3$ and $R^4$ are a methyl group; and m=1.

3. The compound according to claim 1 or a salt thereof, wherein A is phenyl, optionally substituted phenyl, optionally substituted thiophen-yl, or optionally substituted pyridin-yl; $R^2$, $R^3$ and $R^4$ are a methyl group; and m=3.

4. The compound according to claim 1 or a salt thereof, wherein each of $R^7$ and $R^8$ is independently a hydrogen atom, a fluorine atom, a chlorine atom, a methyl group, an ethyl group, a trifluoromethyl group, a methoxy group or a trifluoromethoxy group.

5. The compound according to claim 1 or a salt thereof, wherein $R^9$ is $CH_2CH_2COOR^{10}$, $CH_2CH_2CH_2COOR^{10}$ or $CH=CHCOOR^{10}$.

6. The compound according to claim 1 or a salt thereof, wherein $R^1$ is ($R^{1a}$); p=0; $Ar^1$ is ($Ar^{1a}$) or ($Ar^{1b}$); $R^5$ is a hydrogen atom or a chlorine atom; and $R^6$ is a fluorine atom, a chlorine atom, a methyl group, an ethyl group, a trifluoromethyl group, or a trifluoromethoxy group.

7. The compound according to claim 1 or a salt thereof, wherein $R^1$ is ($R^{1b}$); p=0; $Ar^2$ is ($Ar^{2a}$) or ($Ar^{2b}$); $R^7$ is a hydrogen atom, a chlorine atom, or a fluorine atom;

and $R^8$ is a fluorine atom, a chlorine atom, a methyl group, an ethyl group, a trifluoromethyl group, or a trifluoromethoxy group.

8. Compound represented by the following Formula (A) or (B), or a salt thereof:

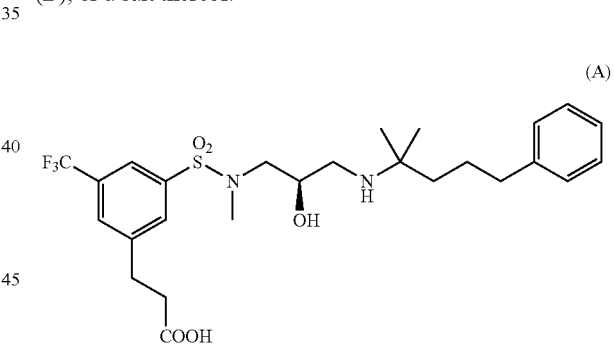

(A)

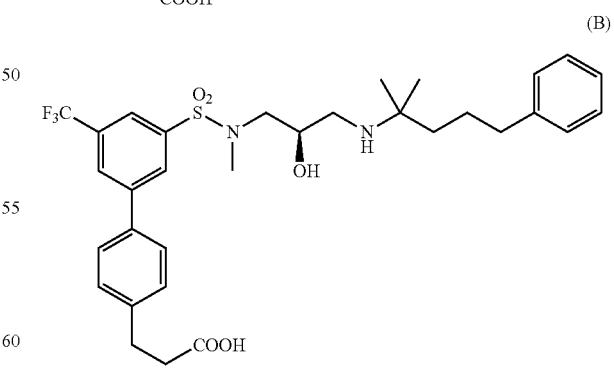

(B)

9. A medicament comprising, as an effective component, a compound according to claim 1 or 8, or a pharmaceutically acceptable salt thereof.

* * * * *